US012605451B2

(12) United States Patent
Allan et al.

(10) Patent No.: US 12,605,451 B2
(45) Date of Patent: Apr. 21, 2026

(54) TARGETED PLASMA PROTEIN DEGRADATION

(71) Applicant: Novartis AG, Basel (CH)

(72) Inventors: Martin Allan, Worcester, MA (US); Jeffrey T. Bagdanoff, Quincy, MA (US); David Weninger Barnes, Waban, MA (US); Kevin Clairmont, Acton, MA (US); Thomas Smith, Arlington, MA (US); Shuangxi Wang, Auburndale, MA (US)

(73) Assignee: NOVARTIS AG, Basel (CH)

( * ) Notice: Subject to any disclaimer, the term of this patent is extended or adjusted under 35 U.S.C. 154(b) by 913 days.

(21) Appl. No.: 17/760,081

(22) PCT Filed: Feb. 4, 2021

(86) PCT No.: PCT/IB2021/050922

§ 371 (c)(1),
(2) Date: Aug. 3, 2022

(87) PCT Pub. No.: WO2021/156792

PCT Pub. Date: Aug. 12, 2021

(65) Prior Publication Data

US 2023/0398224 A1 Dec. 14, 2023

Related U.S. Application Data

(60) Provisional application No. 62/971,684, filed on Feb. 7, 2020.

(51) Int. Cl.
*A61K 47/54* (2017.01)
*C07K 7/64* (2006.01)

(52) U.S. Cl.
CPC .............. *A61K 47/549* (2017.08); *C07K 7/64* (2013.01)

(58) Field of Classification Search
None
See application file for complete search history.

(56) References Cited

U.S. PATENT DOCUMENTS

| | | | |
|---|---|---|---|
| 8,759,501 B2 | 6/2014 | Zhu et al. | |
| 9,617,293 B2 | 4/2017 | Liras et al. | |
| 10,039,778 B2 | 8/2018 | Liras et al. | |

FOREIGN PATENT DOCUMENTS

| | | | |
|---|---|---|---|
| WO | 2012082618 A2 | 6/2012 | |
| WO | WO-2019199634 A1 * | 10/2019 | ........... A61K 47/549 |
| WO | 2020110008 A1 | 6/2020 | |
| WO | 2020110011 A1 | 6/2020 | |

OTHER PUBLICATIONS

Bergeron, et al., Proprotein Convertase Subtilisin/Kexin Type 9 Inhibition: A New Therapeutic Mechanism for Reducing Cardiovascular Disease Risk, Circulation, 132(17), 1648-1666, Oct. 27, 2015.

Xu, et al., Small molecules as inhibitors of PCSK9: Current status and future challenges, European Journal of Medicinal Chemistry, 162, 212-233, 2019.

* cited by examiner

*Primary Examiner* — Sergio Coffa
(74) *Attorney, Agent, or Firm* — Daniel E. Raymond

(57) ABSTRACT

The present invention is directed to the bifunctional compounds and the use of such bifunctional compounds to lower plasma levels of extracellular target molecules by lysosomal degradation. Such bifunctional compounds have a cell surface receptor ligand covalently linked to a ligand that is capable of binding to an extracellular target molecule (such as a ligand for a growth factor, a cytokine, a chemokine, a hormone, a neurotransmitter, a capsid, a soluble receptor, an extracellular secreted protein, an antibody, a lipoprotein, an exosome, a virus, a cell, or a plasma membrane protein), where the cell surface receptor is associated with receptor mediated endocytosis, including asialoglycoprotein receptor (ASGPR) mediated lysosomal degradation and mannose-6-phosphate (M6PR) mediated lysosomal degradation. Pharmaceutical compositions comprising such bifunctional compounds and methods of treating a disease or disorder mediated by an extracellular molecule using such bifunctional compounds are also provided herein.

3 Claims, 8 Drawing Sheets

Specification includes a Sequence Listing.

TARGETED PLASMA PROTEIN DEGRADATION

CROSS-REFERENCE TO RELATED APPLICATIONS

This application is the U.S. National Stage of International Application No. PCT/IB2021/050922, filed Feb. 4, 2021, which claims the benefit of priority to U.S. Provisional Application No. 62/971,684, filed Feb. 7, 2020, the contents of which are incorporated herein by reference.

SEQUENCE LISTING

The instant application contains Sequence Listings which have been submitted electronically in text format and are hereby incorporated by reference in their entirety. Said text copy, created on, Mar. 9, 2021, is named PAT058752 Sequence listing and is 4.53 kilobytes in size.

FIELD OF THE INVENTION

The invention relates to the field of receptor mediated endocytosis or lysosomal degradation of target molecules that are present in the cell membrane or are extracellular.

BACKGROUND OF THE INVENTION

Conventional protein-directed therapeutics treat diseases by obstructing protein function, for example enzyme inhibitors and receptor antagonists, or by recruiting immune effectors, as in the case of many monoclonal antibody drugs. However, potential therapeutic protein targets such as transcription factors, scaffolding proteins, aggregate-forming proteins, lipid carriers, mucins, orphan receptors, and polyfunctional molecules, which have molecular functions that are either incompletely understood or not readily inhibited, are not druggable by conventional therapeutic approaches. Targeted protein degradation (TPD) is a therapeutic approach to the treatment of these undruggable disease-causing proteins and signaling pathways by controlling the amount of a target protein via the degradation of the target protein rather than inhibiting its function.

Examples of targeted protein degradation systems include proteolysis targeting chimeras (PROTACs) (K. M. Sakamoto et al., Proc. Natl. Acad. Sci. 98, 8554-8559, (2001) and G. E. Winter et al., Science. 348, 1376-1381 (2015)), dTAGs (B. Nabet et al., Nat. Chem. Biol. 14, 431 (2018)), Trim-Away (D. Clift et al., Cell., 171, 1692-1706.e18 (2017)), chaperone mediated autophagy targeting (X. Fan et al., Nat. Neurosci., 17, 471-480 (2014)) and SNIPERs (M. Naito et al., Drug Discov. Today Technol., (2019). PROTACs form a bridge between an E3 ubiquitin ligase and their target of interest, thereby facilitating ubiquitination and degradation by the proteasome (G. M. Burslem et. al., Chem. Rev., 117, 11269-11301 (2017). These degradation systems utilize the proteosomal pathway to degrade intracellular proteins. Additionally, degradation systems utilizing the lysosomal pathway for the degradation of extracellular proteins (secreted and plasma membrane proteins) have been reported (S. Banik et al., ChemRxiv, 2019 and P. C. N. Rensen et al., J. Med. Chem., 47, 5798-5808, 2004), although strategies for the degradation of extracellular targets, such as growth factors, cytokines, chemokines, hormones, neurotransmitters, capsids, soluble receptors, extracellular secreted proteins, antibodies, lipoproteins, exosomes, viruses, cells and plasma membrane proteins, remains an unmet need.

SUMMARY OF THE INVENTION

The present invention is directed to bifunctional compounds and the use of such bifunctional compounds to lower plasma levels of extracellular target molecules in patients by receptor mediated endocytosis followed by lysosomal degradation, and thereby find use as pharmaceutical agents in the treatment of disease states and/or conditions that are mediated by such extracellular molecules. Thus, the invention provides bifunctional compounds and their use in the targeted degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, by lysosomal degradation. The invention further provides bifunctional compounds and their use in the targeted degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, by asialoglycoprotein receptor (ASGPR) mediated lysosomal degradation. The invention also provides bifunctional compounds and their use in the targeted degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, by mannose-6-phosphate (M6PR) mediated lysosomal degradation.

The bifunctional compounds of the invention may offer important clinical benefits to patients, in particular for the treatment of disease states and conditions modulated by the extracellular target of interest.

The bifunctional compounds of the invention comprise a cell surface receptor ligand covalently linked to a ligand that is capable of binding to an extracellular target molecule (such as a growth factor, a cytokine, a chemokine, a hormone, a neurotransmitter, a capsid, a soluble receptor, an extracellular secreted protein, an antibody, a lipoprotein, an exosome, a virus, a cell, or a plasma membrane protein), where the cell surface receptor is associated with receptor mediated endocytosis.

The invention further provides bifunctional compounds having the structure of Formula (I):

$$R_L\text{-}L_A\text{-}T_L \quad \text{(I)}$$

wherein:

$R_L$ is a moiety that binds to a cell surface receptor associated with receptor mediated endocytosis;

$L_A$ is a linker, and $T_L$ is a moiety that binds an extracellular target.

The invention further provides a pharmaceutical composition comprising a therapeutically effective amount of a bifunctional compound of Formula (I) and a pharmaceutically acceptable carrier.

In another aspect, the invention provides a pharmaceutical composition comprising a therapeutically effective amount of a compound of the present invention and one or more pharmaceutically acceptable carriers.

The invention further provides a pharmaceutical composition comprising a bifunctional compound of Formula (I) and a pharmaceutically acceptable carrier.

In another aspect, the invention provides a pharmaceutical composition comprising a compound of the present invention and one or more pharmaceutically acceptable carriers.

In another aspect, the invention provides a combination, in particular a pharmaceutical combination, comprising a therapeutically effective amount of compound of the present invention and one or more therapeutically active agents.

The invention provides methods for the targeted lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, by the administration of a bifunctional compound of the invention. The invention also provides methods for the targeted asialoglycoprotein receptor (ASGPR) mediated lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, by the administration of a bifunctional compound of the invention. The invention further provides methods for the targeted mannose-6-phosphate (M6PR) mediated lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, by the administration of a bifunctional compound of the invention.

These methods can be utilized in the treatment of a variety of diseases, conditions or clinical situations that are often treated via therapeutic apheresis, such as cardiovascular diseases, liver diseases, renal diseases, autoimmune diseases, neurological diseases, hematological diseases, skin diseases, medicinal poisoning and vasculitis. By way of example such diseases include, but are not limited to, hypercholesterolemia, familial hypercholesterolemia, hyperlipidemia, hypertriglyceridemia, sitosterolemia, atherosclerosis, arteriosclerosis, arteriosclerosis obliterans, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, xanthoma, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, membranous nephropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease.

These methods can also be utilized in the treatment of nephropathy, age-related macular degeneration, atypical hemolytic uremic syndrome and hepatocellular carcinoma (HCC).

In another aspect, the invention further provides a method for treating a disease or condition which is modulated by an extracellular target molecule by administering a therapeutically effective amount of a bifunctional compound of Formula (I), or sub-formulae thereof to a subject in need thereof.

In another aspect, the invention also provides the use of a bifunctional compound of Formula (I), or sub-formulae thereof, for treating a disease or condition which is modulated by a targeted extracellular molecule described herein.

In another aspect, the invention also provides the use of a bifunctional compound of Formula (I), or sub-formulae thereof, in the manufacture of a medicament for treating a disease or condition which is modulated by a targeted extracellular molecule described herein.

In another aspect, the invention also provides an intracorporeal therapeutic plasmapheresis method, wherein the method comprises administering to a subject a bifunctional compound of Formula (I), or sub-formulae thereof. The invention also provides a method for performing intracorporeal therapeutic plasmapheresis, wherein the method comprises administering to a subject a bifunctional compound of the invention.

In another aspect, the invention also provides an intracorporeal therapeutic plasmapheresis method for the treatment of a cardiovascular disease, a liver disease, a renal disease, an autoimmune disease, a neurological disease, a hematological disease, a skin disease, medicinal poisoning or vasculitis, wherein the method comprises administering to a subject a bifunctional compound of the invention. In certain embodiments such diseases are hypercholesterolemia, familial hypercholesterolemia, hyperlipidemia, hypertriglyceridemia, sitosterolemia, atherosclerosis, arteriosclerosis, arteriosclerosis obliterans, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, xanthoma, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, membranous nephropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease.

In another aspect, the invention also provides an intracorporeal therapeutic plasmapheresis method for the treatment of nephropathy, age-related macular degeneration, atypical hemolytic uremic syndrome and hepatocellular carcinoma (HCC) In another aspect, the invention also provides therapies based upon depression of the extracellulalar levels of extracellular target molecules by lysosomal degradation mediated by a bifunctional compound of Formula (I), or sub-formulae thereof.

In another aspect, the invention also provides therapies for the treatment of cardiovascular diseases based upon depression of the extracellular levels of the protein proprotein convertase subtilisin/kexin type 9 (PCSK9) by lysosomal degradation mediated by a bifunctional compound of Formula (Ia).

In another aspect, the invention also provides therapies for the treatment of a disease or disorder associated with complement factor H-related protein 3 gene (CFHR3) based upon depression of the extracellular levels of the protein complement factor H-related protein 3 (FHR3) by lysosomal degradation mediated by a bifunctional compound of Formula (Ib).

In another aspect, the invention also provides therapies for the treatment of a disease or disorder associated with complement factor H-related protein 3 (FHR3) based upon depression of the levels of extracellular complement factor H-related protein 3 (FHR3) by lysosomal degradation mediated by a bifunctional compound of Formula (Ib).

In another aspect, the invention also provides a bifunctional compound of Formula (Ia) for use in the treatment of a PCSK9 mediated disease or disorder. In another aspect, the invention also provides a pharmaceutical composition comprising a bifunctional compound of Formula (Ia), for use in the treatment of a PCSK9 mediated disease or disorder. In certain embodiments of such uses the PCSK9 mediated disease or disorder is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, triglyceride-rich lipoproteins (TRL), elevated triglycerides, sepsis and xanthoma.

In another aspect, the invention also provides a bifunctional compound of Formula (Ib) for use in the treatment of a CFHR3 mediated disease or disorder. In another aspect, the invention also provides a pharmaceutical composition comprising a bifunctional compound of Formula (Ib), for use in the treatment of a CFHR3 mediated disease or disorder. In certain embodiments of such uses the CFHR3 mediated disease or disorder is selected from nephropathy, age-related macular degeneration, atypical hemolytic uremic syndrome and hepatocellular carcinoma (HCC).

In another aspect, the invention also provides a bifunctional compound of Formula (Ib) for use in the treatment of a FHR3 mediated disease or disorder. In another aspect, the invention also provides a pharmaceutical composition comprising a bifunctional compound of Formula (Ib), for use in the treatment of a FHR3 mediated disease or disorder. In certain embodiments of such uses the FHR3 mediated disease or disorder is selected from nephropathy, age-related macular degeneration, atypical hemolytic uremic syndrome and hepatocellular carcinoma (HCC).

In another aspect, the invention also provides the use of a bifunctional compound of Formula (Ia) in the treatment of a PCSK9 mediated disease or disorder. In another aspect, the invention also provides the use of a bifunctional compound of Formula (Ia) in the manufacture of a medicament for the treatment of a PCSK9 mediated disease or disorder. In another aspect, the invention also provides the use of a pharmaceutical composition comprising a bifunctional compound of Formula (Ia) in the treatment of a PCSK9 mediated disease or disorder. In certain embodiments of such uses the PCSK9 mediated disease or disorder is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, triglyceride-rich lipoproteins (TRL), elevated triglycerides, sepsis and xanthoma.

In another aspect, the invention also provides the use of a bifunctional compound of Formula (Ib) in the treatment of a CFHR3 mediated disease or disorder. In another aspect, the invention also provides the use of a bifunctional compound of Formula (Ib) in the manufacture of a medicament for the treatment of a CFHR3 mediated disease or disorder. In another aspect, the invention also provides the use of a pharmaceutical composition comprising a bifunctional compound of Formula (Ib) in the treatment of a CFHR3 mediated disease or disorder. In certain embodiments of such uses the CFHR3 mediated disease or disorder is selected from nephropathy, age-related macular degeneration, atypical hemolytic uremic syndrome and hepatocellular carcinoma (HCC).

In another aspect, the invention also provides the use of a bifunctional compound of Formula (Ib) in the treatment of a FHR3 mediated disease or disorder. In another aspect, the invention also provides the use of a bifunctional compound of Formula (Ib) in the manufacture of a medicament for the treatment of a FHR3 mediated disease or disorder. In another aspect, the invention also provides the use of a pharmaceutical composition comprising a bifunctional compound of Formula (Ib) in the treatment of a FHR3 mediated disease or disorder. In certain embodiments of such uses the FHR3 mediated disease or disorder is selected from nephropathy, age-related macular degeneration, atypical hemolytic uremic syndrome and hepatocellular carcinoma (HCC).

In another aspect, the invention also provides a method for treating a PCSK9 mediated disease or disorder comprising the step of administering to a patient in need thereof a therapeutically effective amount of a bifunctional compound of Formula (Ia). In certain embodiments of this method the PCSK9 mediated disease or disorder is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, triglyceride-rich lipoproteins (TRL), elevated triglycerides, sepsis and xanthoma.

In another aspect, the invention also provides a method for treating a CFHR3 mediated disease or disorder comprising the step of administering to a patient in need thereof a therapeutically effective amount of a bifunctional compound of Formula (Ib). In certain embodiments of this method the CFHR3 mediated disease or disorder is selected from nephropathy, age-related macular degeneration, atypical hemolytic uremic syndrome and hepatocellular carcinoma (HCC).

In another aspect, the invention also provides a method for treating a FHR3 mediated disease or disorder comprising the step of administering to a patient in need thereof a therapeutically effective amount of a bifunctional compound of Formula (Ib). In certain embodiments of this method the FHR3 mediated disease or disorder is selected from nephropathy, age-related macular degeneration, atypical hemolytic uremic syndrome and hepatocellular carcinoma (HCC).

In another aspect, the invention also provides a method for the targeted lysosomal degradation of an extracellular target molecule, comprising administering a bifunctional compound of Formula (Ia), wherein the extracellular target molecule is PCSK9.

In another aspect, the invention also provides a method for the targeted lysosomal degradation of an extracellular target molecule, comprising administering a bifunctional compound of Formula (Ib), wherein the extracellular target molecule is FHR3.

In another aspect, the invention also provides a method for the removal of an extracellular target molecule from the plasma of a patient in need thereof, comprising administering a bifunctional compound of Formula (Ia), wherein the extracellular target molecule is PCSK9.

In another aspect, the invention also provides a method for the removal of an extracellular target molecule from the plasma of a patient in need thereof, comprising administering a bifunctional compound of Formula (Ib), wherein the extracellular target molecule is FHR3.

In another aspect, the invention also provides a bifunctional compound of Formula (Ia) for use in therapy for the treatment of cardiovascular disease, wherein the therapy is based upon depression of the extracellular levels of PCSK9 by lysosomal degradation mediated by a bifunctional compound of Formula (Ia).

In another aspect, the invention also provides a bifunctional compound of Formula (Ib) for use in therapy for the treatment of nephropathy, age-related macular degeneration, atypical hemolytic uremic syndrome or hepatocellular carcinoma (HCC), wherein the therapy is based upon depression of the extracellular levels of FHR3 by lysosomal degradation mediated by a bifunctional compound of Formula (Ib).

BRIEF DESCRIPTION OF THE DRAWINGS

i) iv bolus administration of vehicle+3.3 μg hPCSK9
ii) iv bolus administration of 0.1 mg/kg bifunctional compound (BFC-1)+3.3 μg hPCSK9
iii) iv bolus administration of 0.1 mg/kg bifunctional compound (BFC-12)+3.3 μg hPCSK9
iv) iv bolus administration of 0.1 mg/kg bifunctional compound (BFC-12) followed by iv bolus administration of 3.3 μg hPCSK9 70 minutes later
v) po administration of 30 mg/kg bifunctional compound (BFC-12) followed by iv bolus administration of 3.3 μg hPCSK9 70 minutes later

Stats by Ordinary one-way ANOVA vs vehicle:
* p=0.0005;  p<0.0001;  p=0.0027

Figure 7A:
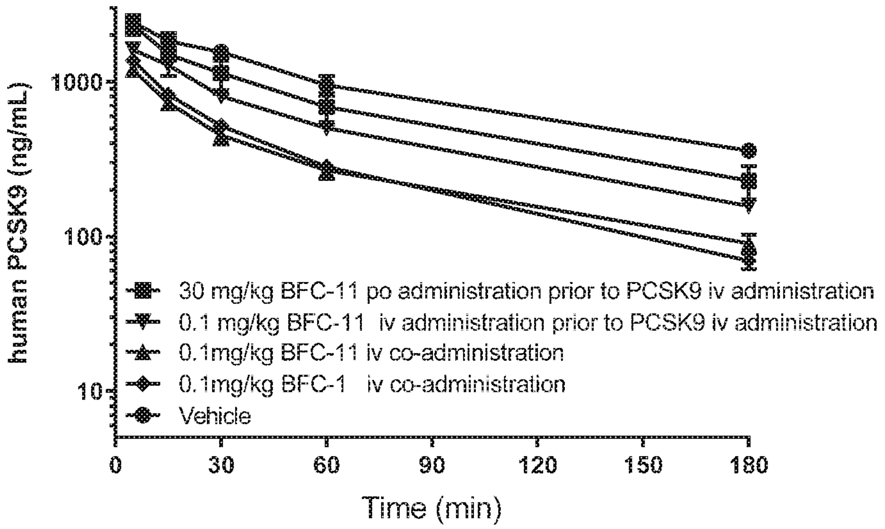

FIG. 7A: Co-administration vs pre-dosing of bifunctional compound study: clearance of human PCSK9 from LDLR (−/−) mice after:

i) iv bolus administration of vehicle+3.3 μg hPCSK9
ii) iv bolus administration of 0.1 mg/kg bifunctional compound (BFC-1)+3.3 μg hPCSK9
iii) iv bolus administration of 0.1 mg/kg bifunctional compound (BFC-11)+3.3 μg hPCSK9
iv) iv bolus administration of 0.1 mg/kg bifunctional compound (BFC-11) followed by iv bolus administration of 3.3 μg hPCSK9 40 minutes later
v) po administration of 30 mg/kg bifunctional compound (BFC-11) followed by iv bolus administration of 3.3 μg hPCSK9 40 minutes later FIG. 7B: Co-administration vs pre-dosing of bifunctional compound study: -AUC plot of clearance data depicted in FIG. 7A.

Figure 8A:
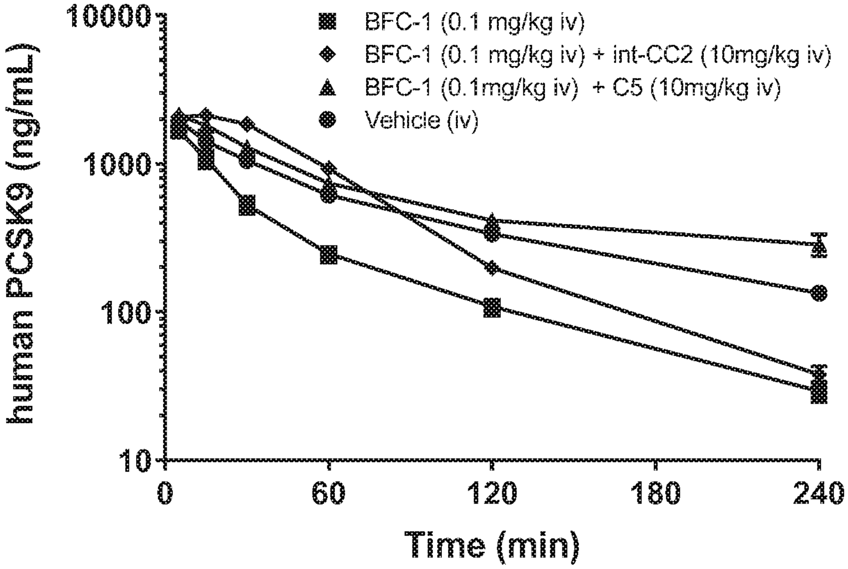

Stats by Ordinary one-way ANOVA vs Vehicle with Dunnett's multiple comparisons test FIG. 8A: Competition study: clearance of human PCSK9 from LDLR(−/−) mice after:

i) iv bolus administration of vehicle+3.3 μg hPCSK9
ii) iv bolus administration of 0.1 mg/kg bifunctional compound (BFC-1)+3.3 μg hPCSK9
iii) iv bolus administration of 0.1 mg/kg bifunctional compound (BFC-1)+3.3 μg hPCSK9+10 mg/kg ASGPR ligand (int-CC2)
iv) iv bolus administration of 0.1 mg/kg bifunctional compound (BFC-1)+3.3 μg hPCSK9+10 mg/kg PCSK9 ligand (C5)

Figure 8B:
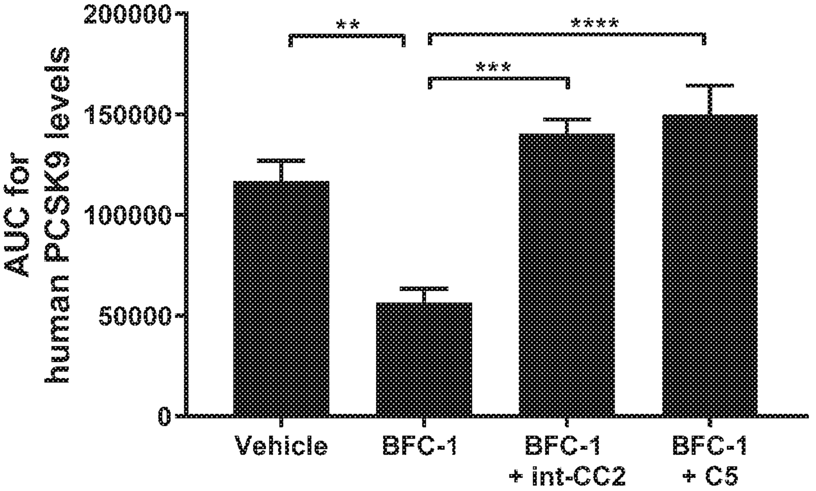

FIG. 8B: Competition study: AUC plot of clearance data depicted in FIG. 8A.

Stats by Ordinary one-way ANOVA vs bifuntional compound (BFC-1):  p=0.0033; * p=0.0003; **** p<0.0001

DETAILED DESCRIPTION OF THE INVENTION

Definitions

The term "alkyl", as used herein, refers to a straight or branched hydrocarbon chain radical consisting solely of carbon and hydrogen atoms, containing no unsaturation. The term "$C_1$-$C_6$alkyl", as used herein, refers to a straight or branched hydrocarbon chain radical consisting solely of carbon and hydrogen atoms, containing no unsaturation, having from one to six carbon atoms, and which is attached to the rest of the molecule by a single bond. Non-limiting examples of "$C_1$-$C_6$alkyl" groups include methyl (a $C_1$alkyl), ethyl (a $C_2$alkyl), 1-methylethyl (a $C_3$alkyl), n-propyl (a $C_3$alkyl), isopropyl (a $C_3$alkyl), n-butyl (a $C_4$alkyl), isobutyl (a $C_4$alkyl), sec-butyl (a $C_4$alkyl), tert-butyl (a $C_4$alkyl), n-pentyl (a $C_5$alkyl), isopentyl (a $C_5$alkyl), neopentyl (a $C_5$alkyl) and hexyl (a $C_6$alkyl).

The term "alkenyl", as used herein, refers to a straight or branched hydrocarbon chain radical group consisting solely of carbon and hydrogen atoms, containing at least one double bond. The term "$C_2$-$C_6$alkenyl", as used herein, refers to a straight or branched hydrocarbon chain radical group consisting solely of carbon and hydrogen atoms, containing at least one double bond, having from two to six carbon atoms, which is attached to the rest of the molecule by a single bond. Non-limiting examples of "$C_2$-$C_6$alkenyl" groups include ethenyl (a $C_2$alkenyl), prop-1-enyl (a $C_3$alkenyl), but-1-enyl (a $C_4$alkenyl), pent-1-enyl (a $C_5$alkenyl), pent-4-enyl (a $C_5$alkenyl), penta-1,4-dienyl (a $C_5$alkenyl), hexa-1-enyl (a $C_5$alkenyl), hexa-2-enyl (a $C_6$alkenyl), hexa-3-enyl (a $C_6$alkenyl), hexa-1-, 4-dienyl (a $C_6$alkenyl), hexa-1-, 5-dienyl (a $C_6$alkenyl) and hexa-2-, 4-dienyl (a $C_6$alkenyl). The term "$C_2$-$C_6$alkenyl", as used herein, refers to a straight or branched hydrocarbon chain radical group consisting solely of carbon and hydrogen atoms, containing at least one double bond, having from two to three carbon atoms, which is attached to the rest of the molecule by a single bond. Non-limiting examples of "$C_2$-$C_3$alkenyl" groups include ethenyl (a $C_2$alkenyl) and prop-1-enyl (a $C_3$alkenyl).

The term "alkylene", as used herein, refers to a bivalent straight or branched hydrocarbon chain radical consisting solely of carbon and hydrogen atoms and containing no unsaturation. The term "$C_1$-$C_6$alkylene", as used herein, refers to a bivalent straight or branched hydrocarbon chain radical consisting solely of carbon and hydrogen atoms, containing no unsaturation, having from one to six carbon atoms. Non-limiting examples of "$C_1$-$C_6$alkylene" groups include methylene (a $C_1$alkylene), ethylene (a $C_2$alkylene), 1-methylethylene (a $C_3$alkylene), n-propylene (a $C_5$alkylene), isopropylene (a $C_3$alkylene), n-butylene (a $C_4$alkylene), isobutylene (a $C_4$alkylene), sec-butylene (a $C_4$alkylene), tert-butylene (a $C_4$alkylene), n-pentylene (a $C_5$alkylene), isopentylene (a $C_5$alkylene), neopentylene (a $C_5$alkylene), and hexylene (a $C_6$alkylene).

The term "alkenylene", as used herein, refers to a bivalent straight or branched hydrocarbon chain radical consisting solely of carbon and hydrogen atoms and containing at least one double bond. The term "$C_2$-$C_6$alkenylene", as used herein, refers to a bivalent straight or branched hydrocarbon chain radical group consisting solely of carbon and hydrogen atoms, containing at least one double bond, and having from two to six carbon atoms. Non-limiting examples of "$C_2$-$C_6$alkenylene" groups include ethenylene (a $C_2$alkenylene), prop-1-enylene (a $C_3$alkenylene), but-1-enylene (a $C_4$alkenylene), pent-1-enylene (a $C_5$alkenylene), pent-4-enylene (a $C_5$alkenylene), penta-1,4-dienylene (a $C_5$alkenylene), hexa-1-enylene (a $C_6$alkenylene), hexa-2-enylene (a $C_6$alkenylene), hexa-3-enylene (a $C_6$alkenylene), hexa-1-, 4-dienylene (a $C_6$alkenylene), hexa-1-, 5-dienylene (a $C_6$alkenylene) and hexa-2-, 4-dienylene (a $C_6$alkenylene). The term "$C_2$-$C_6$alkenylene", as used herein, refers to a bivalent straight or branched hydrocarbon chain radical group consisting solely of carbon and hydrogen atoms, containing at least one double bond, and having from two to three carbon atoms. Non-limiting examples of "$C_2$-$C_5$alkenylene" groups include ethenylene (a $C_2$alkenylene) and prop-1-enylene (a $C_3$alkenylene).

The term "alkoxy", as used herein, refers to —O-alkyl or -alkyl-O—, wherein the "alkyl" group is as defined herein. In certain embodiments an alkoxy group is a "$C_1$-$C_2$alkoxy", "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" or "$C_1$-$C_{10}$alkoxy", wherein the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" and "$C_1$-$C_{10}$alkoxy", as used herein refer to —O—$C_1$-$C_2$alkyl, —O—$C_1$-$C_8$alkyl, —O—$C_1$-$C_4$alkyl, —O—$C_1$-$C_5$alkyl, —O—$C_1$-$C_6$alkyl, —O—$C_1$-$C_7$alkyl, —O—$C_1$-$C_6$alkyl, —O—$C_1$-$C_5$alkyl or —O—$C_1$-$C_{10}$alkyl, respectively. Non-limiting examples of "alkoxy" groups include methoxy, ethoxy, n-propoxy, isopropoxy, n-butoxy, isobutoxy, sec-butoxy, tert-butoxy, n-pentoxy, isopentoxy, hexoxy, heptoxy, octoxy, nonoxy, decoxy and the like.

The term "aryl," as used herein, refers to an aromatic monocyclic ring system having 6 carbon atoms as ring members, an aromatic fused bicyclic ring system having 9-10 carbon atoms as ring members, or an aromatic fused tricyclic ring systems having 14 carbon atoms as ring members. Non-limiting examples of an aryl group, as used herein, include phenyl, naphthalenyl, fluorenyl, indenyl, azulenyl, anthracenyl, phenanthrenyl and the like. In certain embodiments such aryl groups are optionally substituted. In preferred embodiments an aryl group is a phenyl.

The term "cycloalkyl," or "$C_3$-$C_8$cycloalkyl," as used herein, refers to a saturated, monocyclic, fused bicyclic, fused tricyclic or bridged polycyclic ring system. Non-limiting examples of fused bicyclic or bridged polycyclic ring systems include bicyclo[1.1.1]pentane, bicyclo[2.1.1]hexane, bicyclo[2.2.1]heptane, bicyclo[3.1.1]heptane, bicyclo[3.2.1]octane, bicyclo[2.2.2]octane and adamantanyl. Non-limiting examples monocyclic $C_3$-$C_8$cycloalkyl groups include cyclopropyl, cyclobutyl, cyclopentyl, cyclohexyl, cycloheptyl and cyclooctyl groups.

The term "haloalkyl" as used herein, refers to an alkyl as defined herein, wherein at least one of the hydrogen atoms of the alkyl is replaced by a halo group as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g., trifluoromethyl. Representative haloalkyl groups, unless specified otherwise, include methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CH(CF_3)$— or $CF_3CF_2CF_2CF_2$—.

The term "$C_1$-$C_6$haloalkyl" as used herein, refers to the respective "$C_1$-$C6_3$alkyl", as defined herein, wherein at least one of the hydrogen atoms of the "$C_1$-$C_6$alkyl" is replaced by a halo atom. The $C_1$-$C_6$haloalkyl groups can be mono$C_1$-$C_6$haloalkyl, wherein such $C_1$-$C_6$haloalkyl groups have one iodo, one bromo, one chloro or one fluoro. Additionally, the $C_1$-$C_6$haloalkyl groups can be di$C_1$-$C_6$haloalkyl wherein such $C_1$-$C_6$haloalkyl groups can have two halo atoms independently selected from iodo, bromo, chloro or fluoro. Furthermore, the $C_1$-$C_6$haloalkyl groups can be poly$C_1$-$C_6$haloalkyl wherein such $C_1$-$C_6$haloalkyl groups can have two or more of the same halo atoms or a combination of two or more different halo atoms. Such poly$C_1$-$C_6$haloalkyl can be perhaloC-$C_6$haloalkyl where all the hydrogen atoms of the respective $C_1$-$C_6$alkyl have been replaced with halo atoms and the halo atoms can be the same or a combination of different halo atoms. Non-limiting examples of "$C_1$-$C_6$haloalkyl" groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, fluoroethyl, difluoroethyl, trifluoroethyl, difluoropropyl, dichloroethyl and dichloropropyl.

The term "haloalkoxy" as used herein, refers to an alkoxy as defined herein, wherein at least one of the hydrogen atoms of the alkyl is replaced by a halo group as defined herein. The haloalkyl can be monohaloalkoxy, dihaloalkoxy, trihaloalkoxy, or polyhaloalkoxy including perhaloalkoxy. A monohaloalkoxy can have one iodo, bromo, chloro or fluoro within the alkyl group. Dihaloalkoxy and polyhaloalkoxy groups can have two or more of the same halo atoms or a combination of different halo groups within the alkyl. Typically the polyhaloalkoxy contains up to 6, or 4, or 3, or 2 halo groups. Non-limiting examples of haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy. A perhalo-alkoxy refers to an alkoxy having all hydrogen atoms replaced with halo atoms, e.g., trifluoromethoxy. Representative haloalkoxy groups, unless specified otherwise, include methoxy, ethoxy, propoxy, isopropoxy, butoxy, isobutoxy, sec-butoxy and tert-butoxy that have at least one hydrogen substituted with halogen, such as where the halogen is fluorine: $CF_3CF_2O$—, $(CF_3)_2CHO$—, $CH_3$—$CF_2O$—, $CF_3CF_2O$—, —$OCF_3$, —$OCHF_2$—, $CF_3CF_2CH(CF_3)O$— or $CF_3CF_2CF_2CF_2O$—.

The term "$C_1$-$C_6$haloalkoxy" as used herein, refers to the respective "$C_1$-$C_{63}$alkoxy", as defined herein, wherein at least one of the hydrogen atoms of the "$C_1$-$C_6$alkyl" is replaced by a halo atom. The $C_1$-$C_6$haloalkoxy groups can be mono$C_1$-$C_6$haloalkoxy, wherein such $C_1$-$C_6$haloalkoxy groups have one iodo, one bromo, one chloro or one fluoro. Additionally, the $C_1$-$C_6$haloalkoxy groups can be di$C_1$-$C_6$haloalkoxy wherein such $C_1$-$C_6$haloalkoxy groups can have two halo atoms independently selected from iodo, bromo, chloro or fluoro. Furthermore, the $C_1$-$C_6$haloalkoxy groups can be poly$C_1$-$C_6$haloalkoxy wherein such $C_1$-$C_6$haloalkoxy groups can have two or more of the same halo atoms or a combination of two or more different halo atoms. Such poly$C_1$-$C_6$haloalkoxy can be perhaloC-$C_6$haloalkoxy where all the hydrogen atoms of the respective $C_1$-$C_6$alkyl have been replaced with halo atoms and the halo atoms can be the same or a combination of different halo atoms. Non-limiting examples of "$C_1$-$C_6$haloalkoxy" groups include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, fluoroethoxy, difluoroethoxy, trifluoroethoxy, difluoropropoxy, dichloroethoxy and dichloropropoxy.

The terms "halo" or "halogen" as used herein, refer to fluoro (F), chloro (Cl), bromo (Br) or iodo (1).

The term "heteroaryl," as used herein, refers to an aromatic ring system containing one or more heteroatoms. Heteroaryl groups containing more than one heteroatom may contain different heteroatoms. Heteroaryl groups may be optionally substituted with one or more substituents as defined in Formula (I). Heteroaryl groups may be monocyclic ring systems or fused bicyclic ring systems. Monocyclic heteroaryl rings have from 5 to 6 ring atoms. Bicyclic heteroaryl rings have from 8 to 10 member atoms. Bicyclic heteroaryl rings include those ring systems wherein a heteroaryl ring is fused to a phenyl ring. Non-limiting examples of heteroaryl groups, as used herein, include benzofuranyl, benzo[c]thiophenyl, benzothiophenyl, benzoxazolyl, benzthiazolyl, benzimidazolyl, cinnolinyl, furazanyl, furyl, imidazolyl, indolyl, indolizinyl, indazolyl, isoindolyl, isoquinolinyl, isoxazolyl, isothiazolyl, oxazolyl, oxaindolyl, oxadiazolyl (including 1,3,4-oxadiazolyl and 1,2,4-oxadiazolyl), purinyl, pyrazolyl, pyrrolyl, phthalazinyl, pyridinyl (including 2-, 3-, and 4-pyridinyl), pyridazinyl, pyrazinyl, pyrimidinyl, quinoxalinyl, quinolinyl, quinazolinyl, tetrazinyl, tetrazolyl, tetrazolo[1,5-a]pyridinyl, thiazolyl, thiadiazolyl (including 1,3,4-thiadiazolyl), thienyl, triazinyl, and triazolyl.

The term "5-, or 6-membered heteroaryl comprising 1-4 heteroatoms selected from N, O, and S", refers to an aromatic, 5-6 membered monocyclic ring system having 1 to 4 heteroatoms independently selected from the heteroatoms N, O and S as ring members.

The term "5-, or 6-membered heteroaryl comprising 1-3 heteroatoms selected from N, O, and S", refers to an aromatic, 5-6 membered monocyclic ring system having 1 to 3 heteroatoms independently selected from the heteroatoms N, O and S as ring members.

The term "heteroatom", as used herein, refers to a nitrogen, oxygen, or sulfur atom.

The term "heterocycloalkyl," as used herein refers to a cycloalkyl group as defined herein having one to two carbon atoms in the ring structure being replaced with one to two groups independently selected from N, NH, $N^{12}$, O or S, wherein $R^{12}$ is H or $C_1$-$C_6$alkyl. The term "4 to 6 membered heterocycloalkyl having one to two ring members independently selected from N, NH, $NR^{12}$, O or S", as used herein refers to a 4 to 6 ring membered heterocycloalkyl which is a fully saturated, monocyclic hydrocarbon ring structure having 4 to 6 ring members, wherein one to two of the ring members are independently selected from N, NH, $NR^{12}$, O or —S—, wherein $R^{12}$ is H or $C_1$-$C_6$alkyl. Non-limiting examples of heterocycloalkyl groups, as used herein, include azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4-yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrazolidinyl, pyrazolidin-1-yl, pyrazolidin-2-yl, pyrazolidin-3-yl, pyrazolidin-4-yl and pyrazolidin-5-yl.

The term "heterocyclyl", as used herein, refers to a saturated (e.g., heterocycloalkyl ring) or partially unsaturated monocyclic or polycyclic ring containing carbon and at least one heteroatom selected from oxygen, nitrogen, or sulfur (O, N, or S) and wherein there is not delocalized n electrons (aromaticity) shared among the ring carbon or heteroatoms.

The term "hydroxyalkyl", as used herein, refers to an alkyl group substituted with one or more —OH groups. Examples of hydroxyalkyl groups include HO—$CH_2$—, HO—$CH_2CH_2$—, and $CH_2$—CH(OH)—.

The terms "spirocycloalkyl" or "spirocyclyl", as used herein, refers to a carbogenic bicyclic ring systems with both rings connected through a single atom. The rings can be different in size and nature, or identical in size and nature. Examples include spiropentane, spirohexane, spiroheptane, spirooctane, spirononane, or spirodecane. One or both of the rings in a spirocycle can be fused to another ring carbocyclic, heterocyclic, aromatic, or heteroaromatic ring. A ($C_3$-$C_{12}$)spirocycloalkyl is a spirocycle containing between 3 and 12 carbon atoms.

The terms "spiroheterocycloalkyl" or "spiroheterocyclyl", as used herein, refers to a spirocycle wherein at least one of the rings is a heterocycle one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

The term "intracorporeal therapeutic plasmapheresis", as used herein, refers to the removal of undesired extracellular target molecules from the plasma withinin the body. Examples of such extracellular target molecules include growth factors, cytokines, chemokines, hormones, neurotransmitters, capsids, soluble receptors, extracellular secreted proteins, antibodies, lipoproteins, exosomes, viruses, cell and plasma membrane proteins. Specific examples of such target molecules include, but are not limited to, LDL (ApoB), Lp(a), ApoCIII, ANGPTL3, ANGPTL4, ANGPTL8, Factor 11, GDF15, LPL, PCSK9, IL1β, IL17, Complement Factor B, Complement Factor D, MPO, IgE, IL7, IL12A, IL23, TNFA, CXCR4, MAPT, FHR3, TIMP1, Apelin, BMP6, BMP9/GDF2, CSF-1, EPO, IL5, MFGE8, TSLP, TSP, C5, CXCL10, FGF23, IGF1, IL10, IL13, IL2, IL6, VEGFA, NKG2D, ZNFR3, ADA2, suPAR, TGF-β1, IL4 receptor, sToll receptor, histamine, Tau, proglanulin, Alpha-synuclein, toxins, venoms, HBV soluble antigen, viral antigens, prion protein, scFV, AAV and anti-AAV antibodies.

The term "polyethylene glycol" or "PEG", as used herein, refers to a linear chain, a branched chain or a star shaped configuration comprised of ($OCH_2CH_2$) groups. In certain embodiments a polyethylene or PEG group is —$(OCH_2CH_2)_t$*—, where t is 4-40, and where the "-" indicates the end directed toward the self-immolative spacer and the "*-" indicates the point of attachment to a terminal end group R' where R' is OH, $OCH_3$ or $OCH_2CH_2C$(═O)OH. In other embodiments a polyethylene or PEG group is —$(CH_2CH_2O)_t$*—, where t is 4-40, and where the "-" indicates the end directed toward the self-immolative spacer and the "indicates the point of attachment to a terminal end group R" where R" is H, $CH_3$ or $CH_2CH_2C$(═O)OH.

The term "polyalkylene glycol", as used herein, refers to a linear chain, a branched chain or a star shaped configuration comprised of $(O(CH_2)_m)_t$ groups. In certain embodiments a polyethylene or PEG group is —$(O(CH_2)_m)_t$*—, where m is 1-10, t is 4-40, and where the "-" indicates the end directed toward the self-immolative spacer and the "*-" indicates the point of attachment to a terminal end group R' where R' is OH, $OCH_3$ or $OCH_2CH_2C$(═O)OH. In other embodiments a polyethylene or PEG group is —$((CH_2)_mO)_t$*—, where m is 1-10, t is 4-40, and where the "-" indicates the end directed toward the self-immolative spacer and the "indicates the point of attachment to a terminal end group R" where R" is H, $CH_3$ or $CH_2CH_2C$(═O)OH.

The term "extracellular", as used herein, refers to the space outside the plasma membrane of a cell or cells.

The terms "depression of the extracellular level" or "depression of the extracellular levels", as used herein, refers to decreasing or lowering the concentration of a target molecule located in the space outside the plasma membrane of a cell or cells.

The terms "PCSK9", "hPCSK9" or "proprotein convertase subtilisin/kexin type 9" interchangeably refer to a naturally occurring human proprotein convertase belonging to the proteinase K subfamily of the secretory subtilase family. PCSK9 is synthesized as a soluble zymogen that undergoes autocatalytic intramolecular processing in the endoplasmic reticulum, and is thought to function as a proprotein convertase. PCSK9 plays a role in cholesterol homeostasis and may have a role in the differentiation of cortical neurons. Mutations in the PCSK9 gene are a cause of autosomal dominant familial hypercholesterolemia. (Burnett and Hooper, Clin. Biochem. Rev. (2008) 29(1):11-26)

The terms "PCSK9 mediated disease or disorder" or "disease or disorder associated with PCSK9", as used herein, refers to a disease or disorder associated with the activity of PCSK9, which include hypercholesterolemia, hyperlipidemia, hypertriglyceridemia, sitosterolemia, atherosclerosis, arteriosclerosis, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, and xanthoma The term "hypercholesterolemia" or "dyslipidemia" includes, e.g., familial and non-familial hypercholesterolemia. Familial hypercholesterolemia (FH) is an autosomal dominant disorder characterized by elevation of serum cholesterol bound to low density lipoprotein (LDL). Familial hypercholesterolemia includes both heterozygous FH and homozygous FH. Hypercholesterolemia (or dyslipidemia) is the presence of high levels of cholesterol in the blood. It is a form of hyperlipidemia (elevated levels of lipids in the blood) and hyperlipoproteinemia (elevated levels of lipoproteins in the blood).

Hyperlipidemia is an elevation of lipids in the bloodstream. These lipids include cholesterol, cholesterol esters, phospholipids and triglycerides. Hyperlipidemia includes for example, type I, IIa, IIb, III, IV and V.

Hypertriglyceridemia denotes high blood levels of triglycerides. Elevated levels of triglycerides are associated with atherosclerosis, even in the absence of hypercholesterolemia, and predispose to cardiovascular disease.

"Sitosterolemia" or "phytosterolemia" is a rare autosomal recessively inherited lipid metabolic disorder characterized by hyperabsorption of sitosterol from the gastrointestinal tract and decreased biliary excretion of dietary sterols (i.e., leading to hypercholesterolemia, tendon and tuberous xanthomas, premature development of atherosclerosis) and altered cholesterol synthesis.

"Atherosclerosis" includes hardening of arteries associated with deposition of fatty substances, cholesterol, cellular waste products, calcium and fibrin in the inner lining of an artery. The buildup that results is called plaque.

"Atherosclerosis" or "arteriosclerotic vascular disease (ASVD)" is a specific form of arteriosclerosis involving thickening, hardening and loss of elasticity of the walls of arteries as a result of invasion and accumulation of white blood cells, containing both living, active white blood cells (producing inflammation) and remnants of dead cells, including cholesterol and triglycerides. Atherosclerosis is therefore a syndrome affecting arterial blood vessels due to a chronic inflammatory response of white blood cells in the walls of arteries.

"Coronary heart disease," also known as atherosclerotic artery disease, atherosclerotic cardiovascular disease, coronary heart disease or ischemic heart disease is the most common type of heart disease and cause of heart attacks. The disease is caused by plaque building up along the inner walls of the arteries of the heart, which narrows the lumen of arteries and reduces blood flow to the heart.

"Xanthoma" is a cutaneous manifestation of lipidosis in which lipids accumulate in large foam cells within the skin. Xanthomas are associated with hyperlipidemias.

The term "elevated Lp(a) concentration", as used herein, refers to a serum Lp(a) concentration above 30 mg/dl (75 nmol/L). "Elevated serum Lp(a)" means a serum Lp(a) level greater than about 14 mg/dL. In certain embodiments, a patient is considered to exhibit elevated serum Lp(a) if the level of serum Lp(a) measured in the patient is greater than about 15 mg/dL, about 20 mg/dL, about 25 mg/dL, about 30 mg/dL, about 35 mg/dL, about 40 mg/dL, about 45 mg/dL, about 50 mg/dL, about 60 mg/dL, about 70 mg/dL, about 80 mg/dL, about 90 mg/dL, about 100 mg/dL, about 20 mg/dL, about 140 mg/dL, about 150 mg dL, about 180 mg/dL, or about 200 mg/dL The serum Lp(a) level can be measured in a patient post-prandial. In some embodiments, the Lp(a) level is measured after a period of time of fasting (e.g., after fasting for 8 hrs, 8 hrs, 10 hrs, 12 hrs or more). Exemplary methods for measuring serum Lp(a) in a patient include, but are not limited to, rate immunonephelometry, ELISA, nephelometry, immunoturbidimetry, and dissociation-enhanced lanthanide fluorescent immunoassay, although any clinically acceptable diagnostic method can be used in the context of the disclosure.

By "elevated triglyceride levels" or "ETL" is meant any degree of triglyceride levels that is determined to be undesirable or is targeted for modulation.

"Sepsis" is a systemic reaction characterized by arterial hypotension, metabolic acidosis, decreased systemic vascular resistance, tachypnea, and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

The term "CFHR3" or "complement factor H-related protein 3 gene" interchangeably refer to the gene that encodes the human protein complement factor H-related protein 3 (FHR3).

The term "FHR3" or "complement factor H-related protein 3" interchangeably refer to a naturally occurring human complement factor H-related protein 3 which is a secreted protein, belonging to the complement factor H-related protein family.

The terms "CFHR3 mediated disease or disorder" or disease or disorder associated with CFHR3', as used herein, refer to a disease or disorder associated with the abherent activity of CFHR3, which include nephropathy, age-related macular degeneration, atypical hemolytic uremic syndrome and hepatocellular carcinoma (HCC).

The terms "FHR3 mediated disease or disorder" or disease or disorder associated with FHR3", as used herein, refer to a disease or disorder associated with the activity of FHR3, which include nephropathy, age-related macular degeneration, atypical hemolytic uremic syndrome and hepatocellular carcinoma (HCC).

The term "nephropathy", as used herein, refers disease or damage of the kidney(s).

The term "age-related macular degeneration", as used herein, refers an eye disease which affects the macula of the eye causing blindness over time.

The term "atypical hemolytic uremic syndrome", as used herein, refers a disease which affects kidney function due to abnormal blood clotting in the kidney. Atypical hemolytic-uremic syndrome is characterized by three major features related to abnormal clotting: hemolytic anemia, thrombocytopenia, and kidney failure.

The term ""hemolytic anemia, as used herein, refers to the premature break down of red blood cells.

The term "thrombocytopenia", as used herein, refers to the reduced level of circulating platelets used in assisting clotting.

The term "hepatocellular carcinoma (HCC)", as used herein, refers cancer of the liver. The term "reactive group", as used herein, is a functional group capable of forming a covalent bond with a functional group of an antibody or antibody fragment. Non limiting examples of such functional groups include reactive groups of Table 1 provided herein.

The term "coupling group", as used herein, refers to a bivalent moiety which links the bridging spacer to the antibody or fragment thereof. The coupling group is a bivalent moiety formed by the reaction between a reaction group and a functional group on the antibody or fragment thereof. Non limiting examples of such bivalent moieties include the bivalent chemical moieties given in Table 1 and Table 2 provided herein.

As used herein, when partial structures of the compounds are illustrated a wavy line (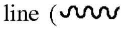) indicates the point of attachment of the partial structure to the rest of the molecule.

The terms "composition" or "pharmaceutical composition," as used herein, refers to a mixture of a compound of the invention with at least one and optionally more than one other pharmaceutically acceptable chemical components, such as carriers, stabilizers, diluents, dispersing agents, suspending agents, thickening agents, and/or excipients.

The term "an optical isomer" or "a stereoisomer", as used herein, refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "subject", as used herein, encompasses mammals and non-mammals. Examples of mammals include, but are not limited to, humans, chimpanzees, apes, monkeys, cattle, horses, sheep, goats, swine; rabbits, dogs, cats, rats, mice, guinea pigs, and the like. Examples of non-mammals include, but are not limited to, birds, fish and the like. Frequently the subject is a human.

The term "a subject in need of such treatment", refers to a subject which would benefit biologically, medically or in quality of life from such treatment.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both.

As used herein, the term "prevent", "preventing" or "prevention" of any disease or disorder refers to the prophylactic treatment of the disease or disorder; or delaying the onset or progression of the disease or disorder.

The term "therapeutically effective amount" or "therapeutically effective dose" interchangeably refers to an amount sufficient to effect the desired result (i.e., reduction or inhibition of an enzyme or a protein activity, amelioration of symptoms, alleviation of symptoms or conditions, delay of disease progression, a reduction in tumor size, inhibition of tumor growth, prevention of metastasis, inhibition or prevention of viral, bacterial, fungal or parasitic infection). In some embodiments, a therapeutically effective amount does not induce or cause undesirable side effects. In some embodiments, a therapeutically effective amount induces or causes side effects but only those that are acceptable by the healthcare providers in view of a patient's condition. A therapeutically effective amount can be determined by first administering a low dose, and then incrementally increasing that dose until the desired effect is achieved. A "prophylactically effective dose" or a "prophylactically effect amount", of the molecules of the invention can prevent the onset of disease symptoms, including symptoms associated with cancer. A "therapeutically effective dose" or a "therapeutically effective amount" of the molecules of the invention can result in a decrease in severity of disease symptoms, including symptoms associated with cancer.

The compound names provided herein were obtained using ChemBioDraw Ultra version 14.0.

As used herein, the term "a," "an," "the" and similar terms used in the context of the present invention (especially in the context of the claims) are to be construed to cover both the singular and plural unless otherwise indicated herein or clearly contradicted by the context.

Unless specified otherwise, the term "bifunctional compound of the invention", "bifunctional compounds of the invention", "bifunctional compound of the present invention" or "bifunctional compounds of the present invention" refers to a bifunctional compound or bifunctional compounds of formula (I), subformulae thereof (such as formula (Ia) and formula (Ib)) and exemplified compounds, and salts thereof, as well as all stereoisomers (including diastereoisomers and enantiomers), rotamers, tautomers and isotopically labeled compounds (including deuterium substitutions).

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

As used herein, the terms "polypeptide" and "peptide" are used interchangeably to refer to two or more amino acids linked together. Except for the abbreviations for the uncommon or unnatural amino acids set forth in Table A below and the abbreviations for protected amino acids set forth in Table B below, the art-recognized three letter or one letter abbreviations are used to represent amino acid residues that constitute the peptides and polypeptides of the disclosure. When preceded with "D," the amino acid is an D-amino acid.

When preceded with "L," the amino acid is an L-amino acid. When the one letter abbreviation is a capital letter, it refers to the L-amino acid. When the one letter abbreviation is a lower case letter, it refers to the D-amino acid. Groups or strings of amino acid abbreviations are used to represent peptides. Peptides are indicated with the N-terminus on the left and the sequence is written from the N-terminus to the C-terminus.

The cyclic peptides described herein contain non-natural amino acids (i.e., compounds that do not occur in nature) and other amino acid analogs as are known in the art may alternatively be employed.

One of ordinary skill in the art will appreciate that various amino acid substitutions, e.g., conservative amino acid substitutions, may be made in the sequence of any of the cyclic polypeptides described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols, a code listed in Table A or Table B, or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or lie), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582).

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

Peptides are defined herein as organic compounds comprising two or more amino acids covalently joined by peptide bonds. Peptides may be referred to with respect to the number of constituent amino acids, i.e., a dipeptide or dimer contains two amino acid residues, a tripeptide or trimer contains three, etc. Peptides containing ten or fewer amino acids may be referred to as oligopeptides, while those with more than ten amino acid residues are polypeptides.

The term "peptide" as used herein means two or more amino acids that are linked together via a peptide bond.

TABLE A

Examples of un-natural or non-natural Amino Acids as described in the disclosure:

| Symbol | Chemical Name | Structure |
|---|---|---|
| (p-Cl)F or (4-Cl)F or (4-Cl)Phe | 2-amino-3-(4-chlorophenyl)propanoic acid or 4-chloro-phenylalanine | 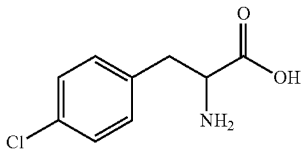 [SMILES: NC(Cc1ccc(Cl)cc1)C(=O)O] |
| (p-F)F or (3-F)F or (3-F)Phe | 2-amino-3-(3-fluorophenyl)propanoic acid or 3-fluoro-phenylalanine | 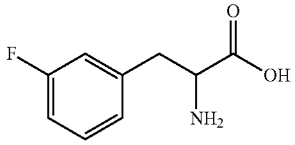 [SMILES: NC(Cc1cccc(F)c1)C(=O)O] |

TABLE A-continued

| Examples of un-natural or non-natural Amino Acids as described in the disclosure: | | |
|---|---|---|
| Symbol | Chemical Name | Structure |
| (p-$CF_3$)F or (4-$CF_3$)F or (4-$CF_3$)Phe | 2-amino-3-(4-(trifluoromethyl)phenyl)propanoic acid or 4-trifluoromethyl-phenylalanine | 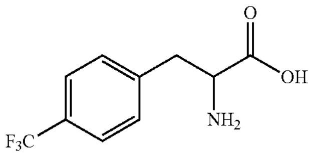 [SMILES: NC(Cc1ccc(C(F)(F)F)cc1)C(=O)O] |
| (3,4-diCl)F or (3,4-diCl)Phe | 2-amino-3-(3,4-dichlorophenyl)propanoic acid or 3,4-dichloro-phenylalanine | 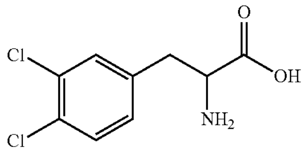 [SMILES: NC(Cc1ccc(Cl)c(Cl)c1)C(=O)O] |
| B or Bip | 3-([1,1'-biphenyl]-4-yl)-2-aminopropanoic acid or 4-phenyl-phenylalanine | 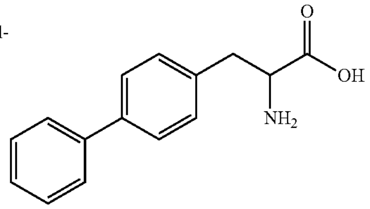 |
| (N-Me)A | N-methylalanine | 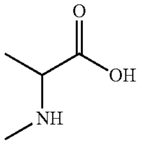 |
| (N-Me)E | N-Methylglutamic acid | 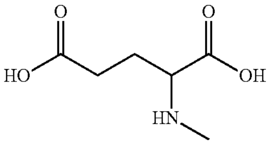 |
| (N-Me)F | N-methylphenylalanine | 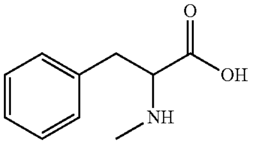 |
| HomoSer or Hse | homoserine | 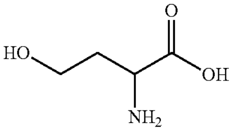 |

TABLE B

| Examples of Protected Amino Acids as described in the disclosure: | | |
|---|---|---|
| Symbol | Name | Structure |
| S(tBu) | O-(tert-butyl)serine | 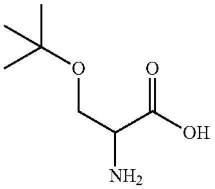 |

TABLE B-continued

| Examples of Protected Amino Acids as described in the disclosure: | | |
|---|---|---|
| Symbol | Name | Structure |
| D(tBu) | 2-amino-4-(tert-butoxy)-4-oxobutanoic acid | 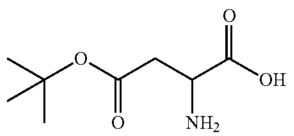 |
| C(Trt) | Trityl-cysteine | 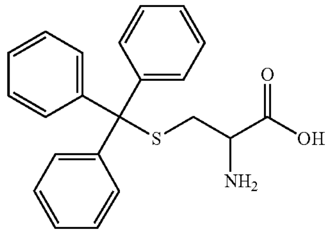 [SMILES: NC(CSC(c1ccccc1)(c1ccccc1)c1ccccc1)C(=O)O] |
| K(Boc) or Lys(Boc) | $N^6$-(tert-butoxycarbonyl)lysine | 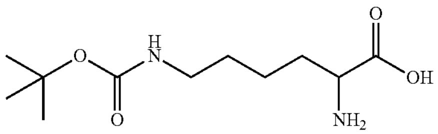 [SMILES: CC(C)(C)OC(=O)NCCCCC(N)C(=O)O] |

Bifunctional Compounds of the Invention

The bifunctional compounds of the invention are compounds that comprise a moiety that binds an extracellular target ($T_L$), such as a growth factor, a cytokine, a chemokine, a hormone, a neurotransmitter, a capsid, a soluble receptor, an extracellular secreted protein, an antibody, a lipoprotein, an exosomes, a virus, a cell, or a plasma membrane protein. This target molecule ligand ($T_L$) is linked to a moiety that binds to a cell surface receptor ($R_L$), wherein the cell surface receptor is associated with receptor mediated endocytosis. The bifunctional compounds of the invention have the structure of Formula (I):

$$R_L\text{-}L_A\text{-}T_L \qquad (1)$$

wherein:

$R_L$ is a moiety that binds to a cell surface receptor associated with receptor mediated endocytosis;

$L_A$ is a linker, and $T_L$ is a moiety that binds an extracellular target.

Certain aspects and examples of the bifunctional compounds of the invention are provided in the enumerated embodiments provided herein. It will be recognized that features specified in each embodiment may be combined with other specified features to provide further embodiments of the present invention.

A. Target Binding Moiety ($T_L$)

The Target binding moiety ($T_L$) of the bifunctional compound of the invention, is a moiety that binds to an extracellular target molecule, such as a growth factor, a cytokine, a chemokine, a hormone, a neurotransmitter, a capsid, a soluble receptor, an extracellular secreted protein, an antibody, a lipoprotein, an exosome, a virus, a cell, or a plasma membrane protein, wherein the bifunctional compounds of the invention can then be used to direct the extracellular target molecule to lysosomes for degradation. Examples of such target molecules which can be directed for degradation using the bifunctional compound of the invention include, but are not limited to, LDL (ApoB), Lp(a), ApoCIII, ANGPTL3, ANGPTL4, ANGPTL8, Factor 11, GDF15, LPL, PCSK9, IL1β, IL17, Complement Factor B, Complement Factor D, MPO, IgE, IL7, IL12A, IL23, TNFA, CXCR4, MAPT, FHR3, TIMP1, Apelin, BMP6, BMP9/GDF2, CSF-1, EPO, IL5, MFGE8, TSLP, TSP, C5, CXCL10, FGF23, IGF1, I10, IL13, IL2, IL6, VEGFA, NKG2D, ZNFR3, ADA2, suPAR, TGF-β1, IL4 receptor, sToll receptor, histamine, Tau, proglanulin, Alpha-synuclein, toxins, venoms, HBV soluble antigen, viral antigens, prion protein, scFV, AAV and anti-AAV antibodies. In certain embodimenst, the extracellular target molecules which can be directed for degradation using the bifunctional compound of the invention are PCSK9 and FHR3.

Embodiment 1. The bifunctional compound of Formula (I), wherein $T_L$ is a moiety which bind to PCSK9 or FHR3.

Embodiment 2. The bifunctional compound of Formula (I), wherein $T_L$ is a moiety which binds to PCSK9.

Embodiment 3. The bifunctional compound of Formula (I), or any one of Embodiments 1 to 2, having the structure of Formula (Ia):

$$R_L\text{-}L_A\text{-}PSK9_L \qquad (Ia)$$

wherein:

$R_L$ is a moiety that binds to a cell surface receptor associated with receptor mediated endocytosis;

$L_A$ is a linker, and $PCSK9_L$ is a moiety that binds to PCSK9.

Embodiment 4. The bifunctional compound of Formula (I), or any one of Embodiments 1 to 3, wherein the Target binding moiety ($T_L$) is a compound of Formula (A), or a pharmaceutically acceptable salt or stereoisomer thereof, which bind to PCSK9:

Formula (A)
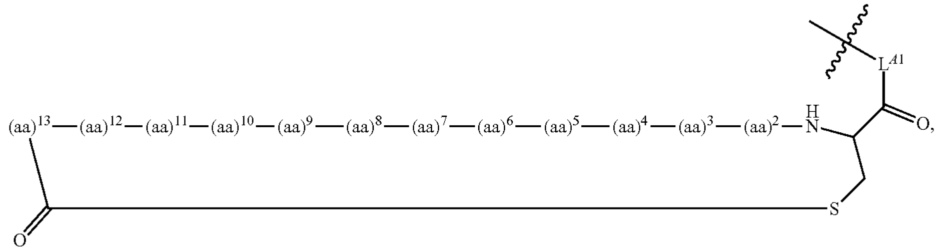
wherein:
$L^{A1}$ is selected from
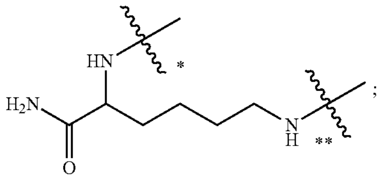
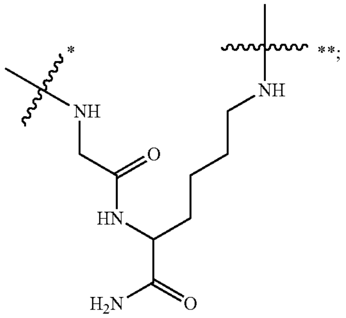
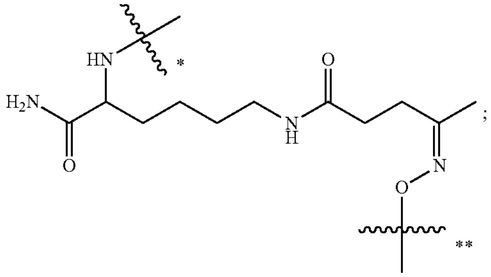
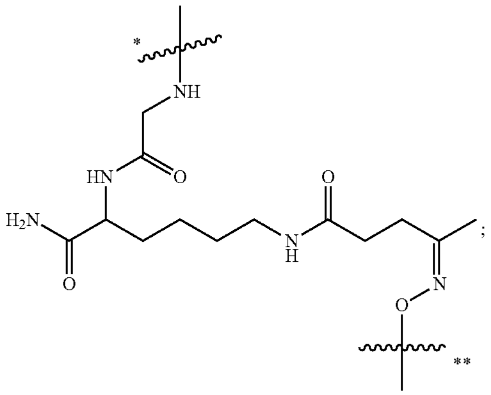
-continued
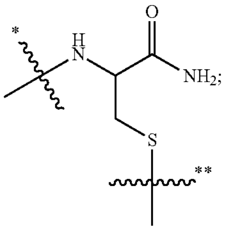
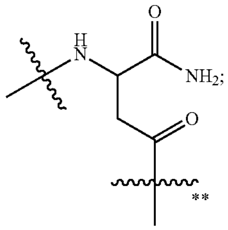
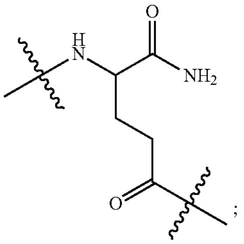
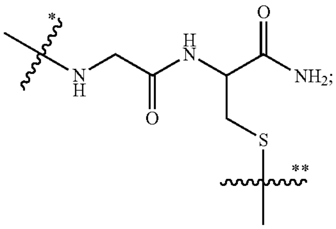
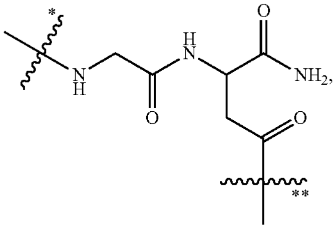
and
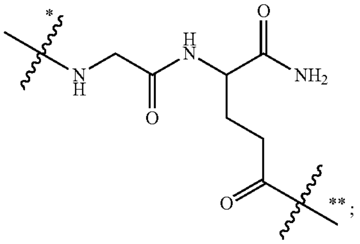
where the ** of $L^{A1}$ indicates the point of attachment to Linker ($L_A$) and the * of $L^{A1}$ indicates the point of attachment to the —C(═O)— group attached to $L_{A1}$;

$(aa)^2$ is an amino acid residue selected from an L-proline residue and a D-proline residue, where the C-terminus of $(aa)^2$ is the point of attachment to the —NH— group;

$(aa)^3$ is an amino acid residue selected from an L-arginine residue, a D-arginine residue, an L-serine residue, a D-serine residue, an L-histidine residue, a D-histidine residue, an L-alanine residue and a D-alanine residue, where the C-terminus of $(aa)^3$ is the point of attachment to $(aa)^2$;

$(aa)^4$ is an amino acid residue selected from an L-aspartic acid residue, a D-aspartic acid residue, an L-asparagine residue, a D-asparagine residue, an L-glutamic acid residue, a D-glutamic acid residue, an L-lysine residue, a D-lysine residue, an L-glutamine residue, a D-glutamine residue, an L-proline residue, a D-proline residue, an L-alanine residue, a D-alanine residue, an L-(N-Me)glutamic acid residue and a D-(N-Me)glutamic acid residue, where the C-terminus of $(aa)^4$ is the point of attachment to $(aa)^3$;

$(aa)^5$ is an amino acid residue selected from an L-(N-Me)alanine residue, a D-(N-Me)alanine residue, an L-(N-Me)glutamic acid residue and a D-(N-Me) glutamic acid residue, where the C-terminus of $(aa)^5$ is the point of attachment to $(aa)^4$;

$(aa)^6$ is an amino acid residue selected from an L-(4-phenyl-phenylalanine) (Bip) residue, a D-(4-phenyl-phenylalanine) (Bip) residue, an L-(4-trifluoromethyl-phenylalanine) residue, a D-(4-trifluoromethyl-phenylalanine) residue, an L-(3,4-dichloro-phenylalanine) residue, a D-(3,4-dichloro-phenylalanine) residue, an L-(3-fluoro-phenylalanine) residue, a D-(3-fluoro-phenylalanine) residue, an L-(4-chloro-phenylalanine) residue and a D-(4-chloro-phenylalanine) residue, where the C-terminus of $(aa)^6$ is the point of attachment to $(aa)^5$;

$(aa)^7$ is an amino acid residue selected from an L-(N-Me)alanine residue, a D-(N-Me)alanine residue, an L-(N-Me)phenylalanine residue and a D-(N-Me) phenylalanine residue, where the C-terminus of $(aa)^7$ is the point of attachment to $(aa)^6$;

$(aa)^8$ is an amino acid residue selected from an L-(4-phenyl-phenylalanine) (Bip) residue, a D-(4-phenyl-phenylalanine) (Bip) residue, an L-serine residue, a D-serine residue, an L-tyrosine residue, a D-tyrosine residue, an L-(4-trifluoromethyl-phenylalanine) residue, a D-(4-trifluoromethyl-phenylalanine) residue, an L-alanine residue, a D-alanine residue, an L-phenylalanine residue, a D-phenylalanine residue, an L-valine residue and a D-valine residue, where the C-terminus of $(aa)^8$ is the point of attachment to $(aa)^7$;

$(aa)^9$ is an amino acid residue selected from an L-threonine residue and a D-threonine residue, where the C-terminus of $(aa)^9$ is the point of attachment to $(aa)^8$;

$(aa)^{10}$ is an amino acid residue selected from an L-threonine residue, a D-threonine residue, an L-serine residue and a D-serine residue, where the C-terminus of $(aa)^{10}$ is the point of attachment to $(aa)^9$;

$(aa)^{11}$ is an amino acid residue selected from an L-serine residue, a D-serine residue, an L-aspartic acid residue, a D-aspartic acid residue, an L-asparagine residue, a D-asparagine residue, an L-proline residue, a D-proline residue, an L-alanine residue, a D-alanine residue, an L-homoserine residue and a D-homoserine residue, where the C-terminus of $(aa)^{11}$ is the point of attachment to $(aa)^{10}$;

$(aa)^{12}$ is an amino acid residue selected from an L-valine residue, a D-valine residue, an L-glutamic acid residue and a D-glutamic acid residue, where the C-terminus of $(aa)^{12}$ is the point of attachment to $(aa)^{11}$; and $(aa)^{13}$ is an amino acid residue selected from an L-phenylalanine residue and a D-phenylalanine residue, where the C-terminus of $(aa)^{13}$ is the point of attachment to $(aa)^{12}$.

Embodiment 5. The bifunctional compound of Embodiment 4, wherein $(aa)^2$ is an amino acid residue selected from an L-proline residue and a D-proline residue, where the C-terminus of $(aa)^2$ is the point of attachment to the —NH— group.

Embodiment 6. The bifunctional compound of Embodiment 4 or Embodiment 5, wherein $(aa)^2$ is an L-proline residue, where the C-terminus of $(aa)^2$ is the point of attachment to the —NH— group depicted in Formula (A).

Embodiment 7. The bifunctional compound of any one of Embodiments 4 to 6, wherein $(aa)^3$ is an amino acid residue selected from an L-arginine residue, a D-arginine residue, an L-serine residue, a D-serine residue, an L-histidine residue, a D-histidine residue, an L-alanine residue and a D-alanine residue, where the C-terminus of $(aa)^3$ is the point of attachment to $(aa)^2$.

Embodiment 8. The bifunctional compound of any one of Embodiments 4 to 7, wherein $(aa)^3$ is an amino acid residue selected from an L-arginine residue, an L-serine residue, an L-histidine residue and an L-alanine residue, where the C-terminus of $(aa)^3$ is the point of attachment to $(aa)^2$.

Embodiment 9. The bifunctional compound of any one of Embodiments 4 to 8, wherein $(aa)^3$ is an L-alanine residue, where the C-terminus of $(aa)^3$ is the point of attachment to $(aa)^2$.

Embodiment 10. The bifunctional compound of any one of Embodiments 4 to 9, wherein $(aa)^4$ is an amino acid residue selected from an L-aspartic acid residue, a D-aspartic acid residue, an L-asparagine residue, a D-asparagine residue, an L-glutamic acid residue, a D-glutamic acid residue, an L-lysine residue, a D-lysine residue, an L-glutamine residue, a D-glutamine residue, an L-proline residue, a D-proline residue, an L-alanine residue, a D-alanine residue, an L-(N-Me) glutamic acid residue and a D-(N-Me)glutamic acid residue, where the C-terminus of $(aa)^4$ is the point of attachment to $(aa)^3$.

Embodiment 11. The bifunctional compound of any one of Embodiments 4 to 10, wherein $(aa)^4$ is an amino acid residue selected from an L-aspartic acid residue, an L-asparagine residue, an L-glutamic acid residue, an L-lysine residue, an L-glutamine residue, an L-proline residue, an L-alanine residue and an L-(N-Me)glutamic acid residue, where the C-terminus of $(aa)^4$ is the point of attachment to $(aa)^3$.

Embodiment 12. The bifunctional compound of any one of Embodiments 4 to 11, wherein $(aa)^4$ is an L-glutamic acid residue, where the C-terminus of $(aa)^4$ is the point of attachment to $(aa)^3$.

Embodiment 13. The bifunctional compound of any one of Embodiments 4 to 12, wherein $(aa)^5$ is an amino acid residue selected from an L-(N-Me) alanine residue, a D-(N-Me)alanine residue, an L-(N-Me)glutamic acid residue and a D-(N-Me)glutamic acid residue, where the C-terminus of $(aa)^5$ is the point of attachment to $(aa)^4$.

Embodiment 14. The bifunctional compound of any one of Embodiments 4 to 13, wherein $(aa)^5$ is an amino acid residue selected from an L-(N-Me) alanine residue and an L-(N-Me)glutamic acid residue, where the C-terminus of $(aa)^5$ is the point of attachment to $(aa)^4$.

Embodiment 15. The bifunctional compound of any one of Embodiments 4 to 14, wherein $(aa)^5$ is an L-(N-Me)alanine residue, where the C-terminus of $(aa)^5$ is the point of attachment to $(aa)^4$.

Embodiment 16. The bifunctional compound of any one of Embodiments 4 to 15, wherein $(aa)^6$ is an amino acid residue selected from an L-(4-phenyl-phenylalanine) (Bip) residue, a D-(4-phenyl-phenylalanine) (Bip) residue, an L-(4-trifluoromethyl-phenylalanine) residue, a D-(4-trifluoromethyl-phenylalanine) residue, an L-(3,4-dichloro-phenylalanine) residue, a D-(3,4-dichloro-phenylalanine) residue, an L-(3-fluoro-phenylalanine) residue, a D-(3-fluoro-phenylalanine) residue, an L-(4-chloro-phenylalanine) residue and a D-(4-chloro-phenylalanine) residue, where the C-terminus of $(aa)^6$ is the point of attachment to $(aa)^5$.

Embodiment 17. The bifunctional compound of any one of Embodiments 4 to 16, wherein $(aa)^6$ is an amino acid residue selected from an L-(4-phenyl-phenylalanine) (Bip) residue, an L-(4-trifluoromethyl-phenylalanine) residue, an L-(3,4-dichloro-phenylalanine) residue, an L-(3-fluoro-phenylalanine) residue and an L-(4-chloro-phenylalanine) residue, where the C-terminus of $(aa)^6$ is the point of attachment to $(aa)^5$.

Embodiment 18. The bifunctional compound of any one of Embodiments 4 to 17, wherein $(aa)^6$ is an L-(4-phenyl-phenylalanine) (Bip) residue, where the C-terminus of $(aa)^6$ is the point of attachment to $(aa)^5$.

Embodiment 19. The bifunctional compound of any one of Embodiments 4 to 18, wherein $(aa)^7$ is an amino acid residue selected from an L-(N-Me) alanine residue, a D-(N-Me)alanine residue, an L-(N-Me)phenylalanine residue and a D-(N-Me)phenylalanine residue, where the C-terminus of $(aa)^7$ is the point of attachment to $(aa)^6$.

Embodiment 20. The bifunctional compound of any one of Embodiments 4 to 19, wherein $(aa)^7$ is an amino acid residue selected from an L-(N-Me) alanine residue, and an L-(N-Me)phenylalanine residue, where the C-terminus of $(aa)^7$ is the point of attachment to $(aa)^6$.

Embodiment 21. The bifunctional compound of any one of Embodiments 4 to 20, wherein $(aa)^7$ is an L-(N-Me)alanine residue, where the C-terminus of $(aa)^7$ is the point of attachment to $(aa)^6$.

Embodiment 22. The bifunctional compound of any one of Embodiments 4 to 21, wherein $(aa)^8$ is an amino acid residue selected from an L-(4-phenyl-phenylalanine) (Bip) residue, a D-(4-phenyl-phenylalanine) (Bip) residue, an L-serine residue, a D-serine residue, an L-tyrosine residue, a D-tyrosine residue, an L-(4-trifluoromethyl-phenylalanine) residue, a D-(4-trifluoromethyl-phenylalanine) residue, an L-alanine residue, a D-alanine residue, an L-phenylalanine residue, a D-phenylalanine residue, an L-valine residue and a D-valine residue, where the C-terminus of $(aa)^8$ is the point of attachment to $(aa)^7$.

Embodiment 23. The bifunctional compound of any one of Embodiments 4 to 22, wherein $(aa)^8$ is an amino acid residue selected from an L-(4-phenyl-phenylalanine) (Bip) residue, an L-serine residue, an L-tyrosine residue, an L-(4-trifluoromethyl-phenylalanine) residue, an L-alanine residue, an L-phenylalanine residue and an L-valine residue, where the C-terminus of $(aa)^8$ is the point of attachment to $(aa)^7$.

Embodiment 24. The bifunctional compound of any one of Embodiments 4 to 23, wherein $(aa)^8$ is an L-(4-phenyl-phenylalanine) (Bip) residue, where the C-terminus of $(aa)^8$ is the point of attachment to $(aa)^7$.

Embodiment 25. The bifunctional compound of any one of Embodiments 4 to 24, wherein $(aa)^9$ is an amino acid residue selected from an L-threonine residue and a D-threonine residue, where the C-terminus of $(aa)^9$ is the point of attachment to $(aa)^8$.

Embodiment 26. The bifunctional compound of any one of Embodiments 4 to 25, wherein $(aa)^9$ is an L-threonine residue, where the C-terminus of $(aa)^9$ is the point of attachment to $(aa)^8$.

Embodiment 27. The bifunctional compound of any one of Embodiments 4 to 26, wherein $(aa)^{10}$ is an amino acid residue selected from an L-threonine residue, a D-threonine residue, an L-serine residue and a D-serine residue, where the C-terminus of $(aa)^{10}$ is the point of attachment to $(aa)^9$.

Embodiment 28. The bifunctional compound of any one of Embodiments 4 to 27, wherein $(aa)^{10}$ is an L-threonine residue, where the C-terminus of $(aa)^{10}$ is the point of attachment to $(aa)^9$.

Embodiment 29. The bifunctional compound of Embodiment any one of Embodiments 4 to 28, wherein $(aa)^{11}$ is an amino acid residue selected from an L-serine residue, a D-serine residue, an L-aspartic acid residue, a D-aspartic acid residue, an L-asparagine residue, a D-asparagine residue, an L-proline residue, a D-proline residue, an L-alanine residue, a D-alanine residue, an L-homoserine residue and a D-homoserine residue, where the C-terminus of $(aa)^{11}$ is the point of attachment to $(aa)^{10}$.

Embodiment 30. The bifunctional compound of Embodiment any one of Embodiments 4 to 29, wherein $(aa)^{11}$ is an amino acid residue selected from an L-serine residue, an L-aspartic acid residue, an L-asparagine residue, an L-proline residue, an L-alanine residue, and an L-homoserine residue, where the C-terminus of $(aa)^{11}$ is the point of attachment to $(aa)^{10}$.

Embodiment 31. The bifunctional compound of Embodiment any one of Embodiments 4 to 30, wherein $(aa)^{11}$ is an L-proline residue, where the C-terminus of $(aa)^{11}$ is the point of attachment to $(aa)^{10}$.

Embodiment 32. The bifunctional compound of any one of Embodiments 4 to 31, wherein $(aa)^{12}$ is an amino acid residue selected from an L-valine residue, a D-valine residue, an L-glutamic acid residue and a D-glutamic acid residue, where the C-terminus of $(aa)^{12}$ is the point of attachment to $(aa)^{11}$.

Embodiment 33. The bifunctional compound of any one of Embodiments 4 to 32, wherein $(aa)^{12}$ is an amino acid residue selected from an L-valine residue and an L-glutamic acid residue, where the C-terminus of $(aa)^{12}$ is the point of attachment to $(aa)^{11}$.

Embodiment 34. The bifunctional compound of any one of Embodiments 4 to 33, wherein $(aa)^{12}$ is an an L-valine residue, where the C-terminus of $(aa)^{12}$ is the point of attachment to $(aa)^{11}$.

Embodiment 35. The bifunctional compound of any one of Embodiments 4 to 34, wherein $(aa)^{13}$ is an amino acid residue selected from an L-phenylalanine residue and a D-phenylalanine residue, where the C-terminus of $(aa)^{13}$ is the point of attachment to $(aa)^{12}$.

Embodiment 36. The bifunctional compound of any one of Embodiments 4 to 35, wherein $(aa)^{13}$ is an L-phenylalanine, where the C-terminus of $(aa)^{13}$ is the point of attachment to $(aa)^{12}$.

Embodiment 37. The bifunctional compound of Embodiment 4, wherein $T_L$ is a compound of Formula (A), or pharmaceutically acceptable salts or stereoisomers, selected from the following:

| $T_L$ Structure |
|---|
| 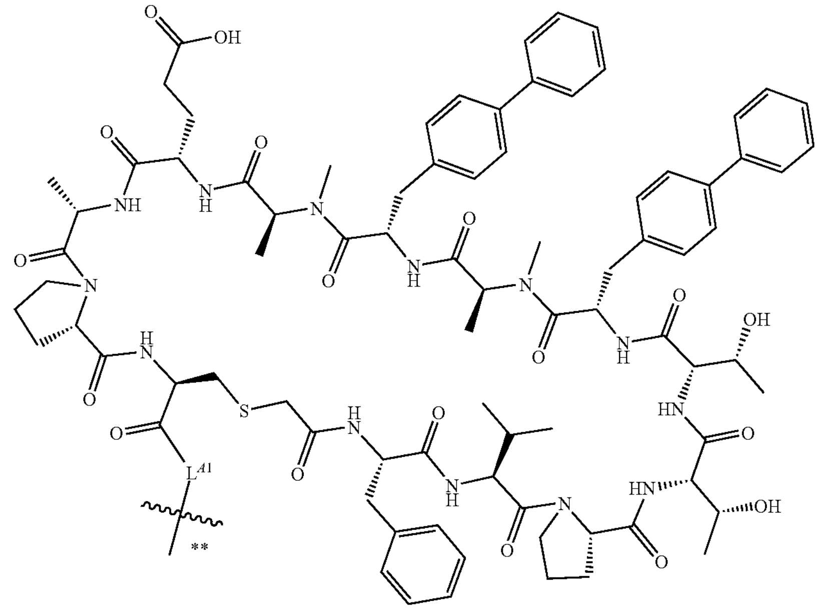 |

which can be represented by the following:

Ac*-F-V-P-T-T-B-(N-Me)A-B-(N-Me)A-E-A-P-C*-$L^{A1}$-**; or

Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Glu)-(L-Ala)-(L-Pro)-(L-Cys)*-$L^{A1}$-**; or

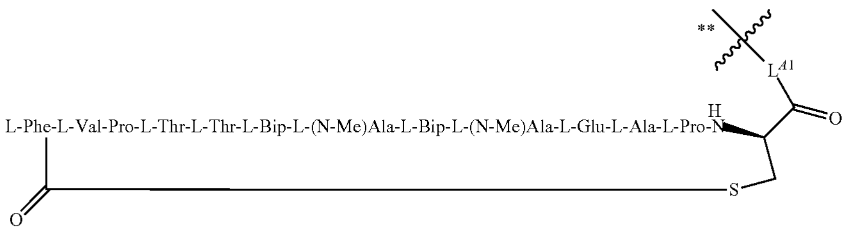

-continued
| $T_L$ Structure |
| --- |
| 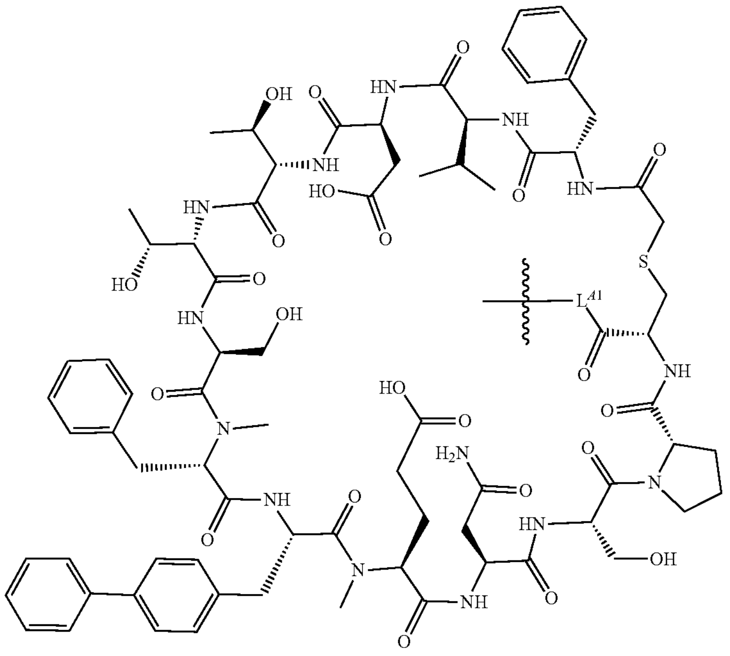 |
| which can be represented by the following:<br>Ac*-F-V-D-T-T-S-(N-Me)F-B-(N-Me)E-N-S-P-C*-$L^{A1}$-**; or<br>Ac*-(L-Phe)-(L-Val)-(L-Asp)-(L-Thr)-(L-Thr)-(L-Ser)-(L-(N-Me)Phe)-(L-Bip)-(L-(N-Me)Glu)-(L-Asn)-(L-Ser)-(L-Pro)-(L-Cys)*-$L^{A1}$-**; or |
| 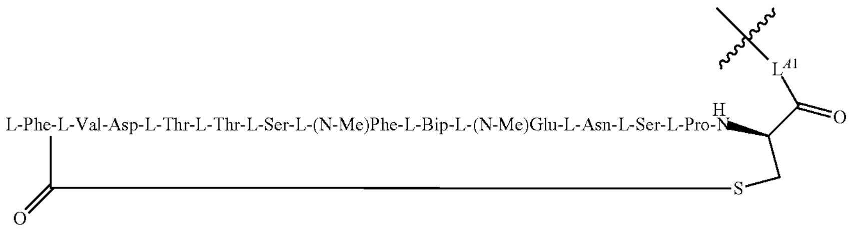 |

-continued
| $T_L$ Structure |
| --- |
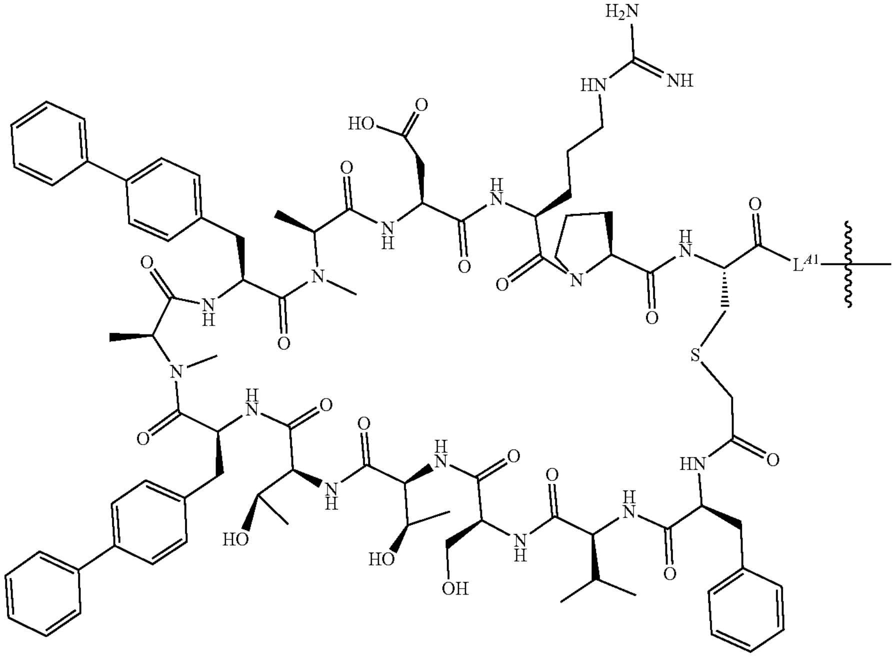
which can be represented by the following:
Ac*-F-V-S-T-T-B-(N-Me)A-B-(N-Me)A-D-R-P-C*-$L^{A1}$-**; or
Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Asp)-(L-Arg)-(L-Pro)-(L-Cys)*-$L^{A1}$-**; or
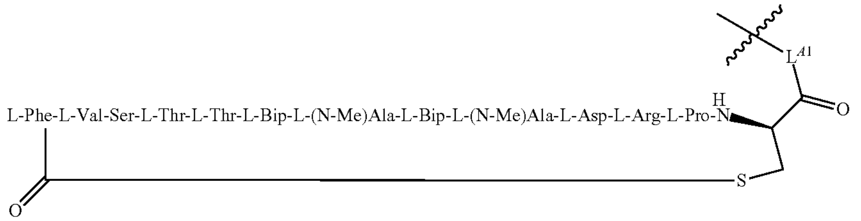
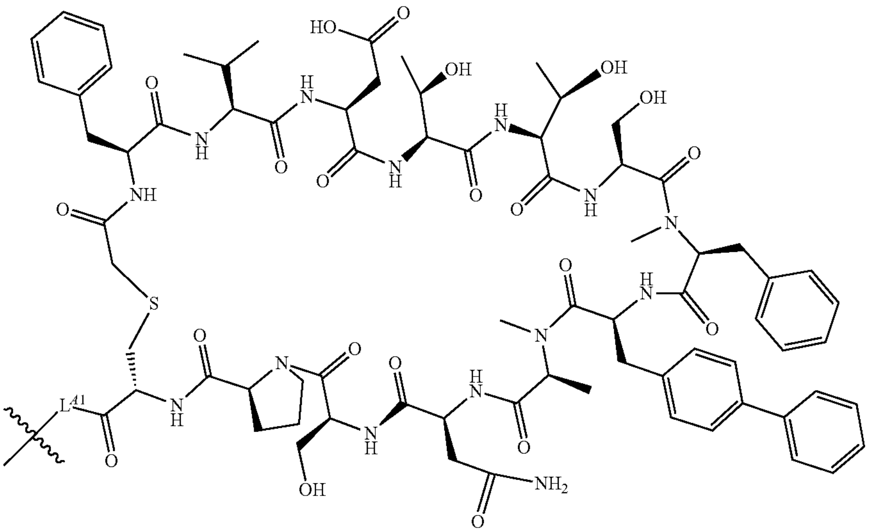
which can be represented by the following:
Ac*-F-V-D-T-T-S-(N-Me)F-B-(N-Me)A-N-S-P-C*-$L^{A1}$-**; or
Ac*-(L-Phe)-(L-Val)-(L-Asp)-(L-Thr)-(L-Thr)-(L-Ser)-(L-(N-Me)Phe)-(L-Bip)-(L-(N-Me)Ala)-(L-Asn)-(L-Ser)-(L-Pro)-(L-Cys)*-$L^{A1}$-**; or -continued
| $T_L$ Structure |
| --- |
| 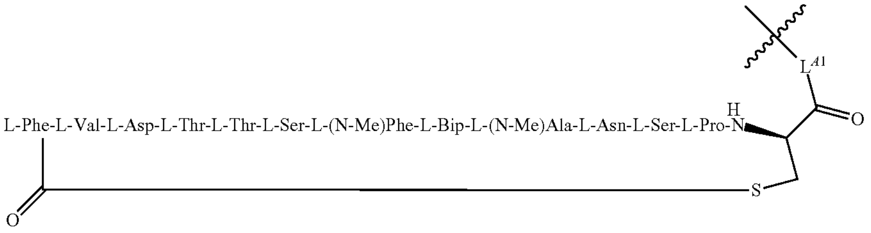 |
| 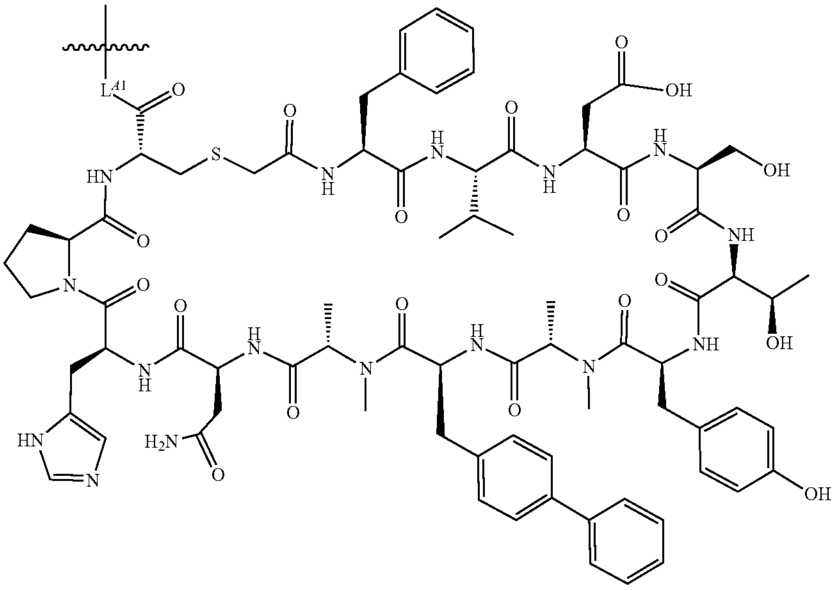 |
| which can be represented by the following: Ac*-F-V-D-S-T-Y-(N-Me)A-B-(N-Me)A-N-H-P-C*-$L^{A1}$-**; or Ac*-(L-Phe)-(L-Val)-(L-Asp)-(L-Ser)-(L-Thr)-(L-Tyr)-(L-(N-Me)Ala)-(L-Bip)-(L-(N-Me)Ala)-(L-Asn)-(L-His)-(L-Pro)-(L-Cys)*-$L^{A1}$-**; or |
| 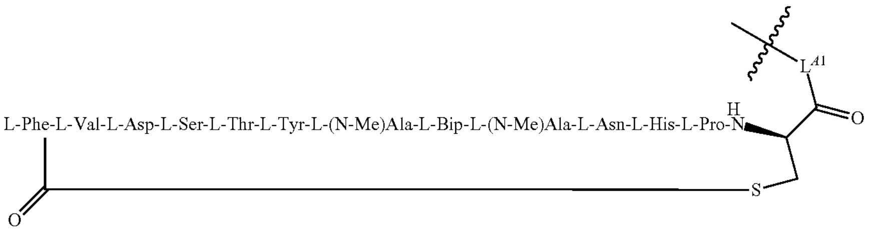 |

-continued
| $T_L$ Structure |
|---|
| 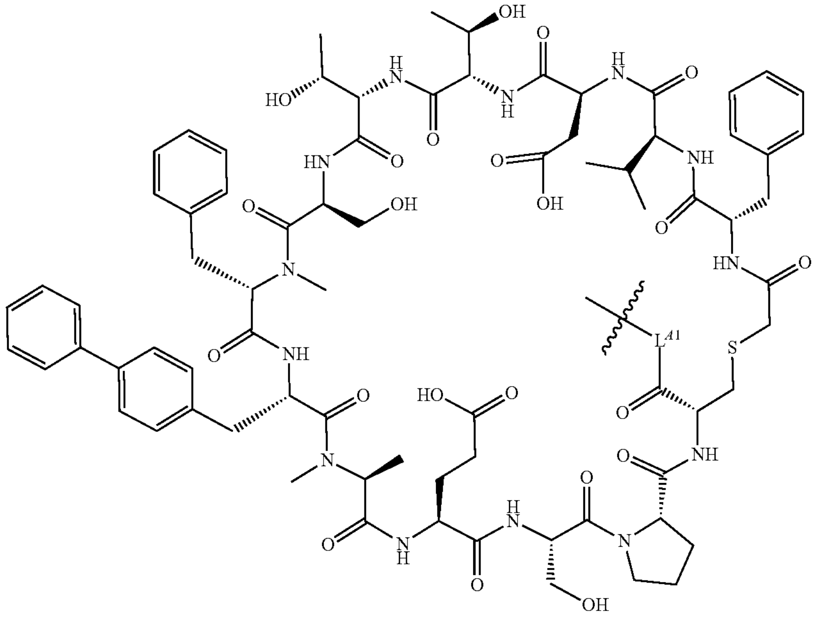 |
| which can be represented by the following:<br>Ac*-F-V-D-T-T-S-(N-Me)F-B-(N-Me)A-E-S-P-C*-$L^{A1}$-**; or<br>Ac*-(L-Phe)-(L-Val)-(L-Asp)-(L-Thr)-(L-Thr)-(L-Ser)-(L-(N-Me)Phe)-(L-Bip)-(L-(N-Me)Ala)-(L-Glu)-(L-Ser)-(L-Pro)-(L-Cys)*-$L^{A1}$-**; or |
| 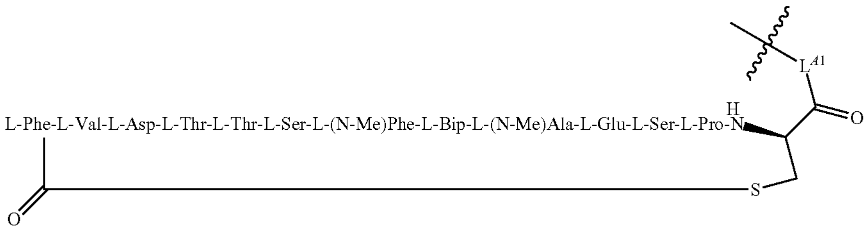 |
| 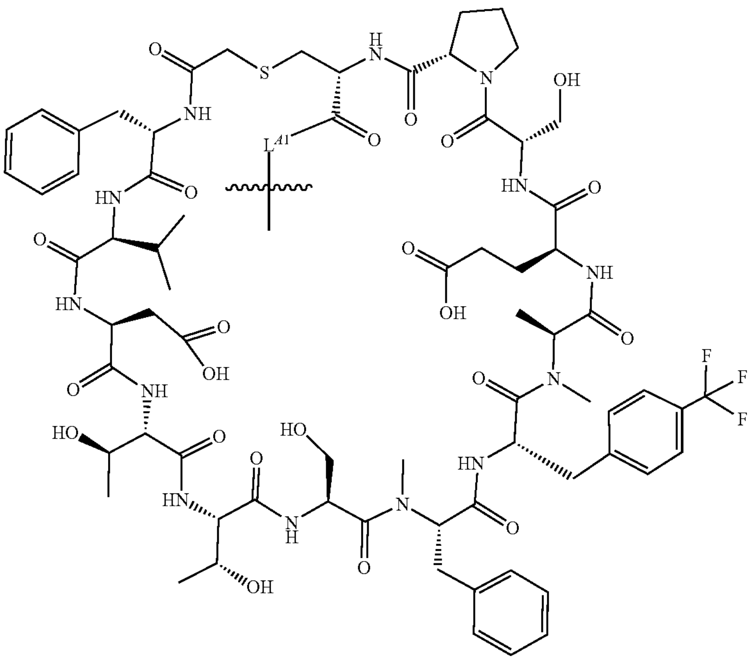 |

-continued
| $T_L$ Structure |
| --- |
which can be represented by the following:
Ac*-F-V-D-T-T-S-(N-Me)F-(p-$CF_3$)F-(N-Me)A-E-S-P-C*-$L^{A1}$-**; or
Ac*-(L-Phe)-(L-Val)-(L-Asp)-(L-Thr)-(L-Thr)-(L-Ser)-(L-(N-Me)Phe)-(L-(4-$CF_3$)Phe)-(L-(N-Me)Ala)-(L-Glu)-(L-Ser)-(L-Pro)-(L-Cys)*-$L^{A1}$-**; or
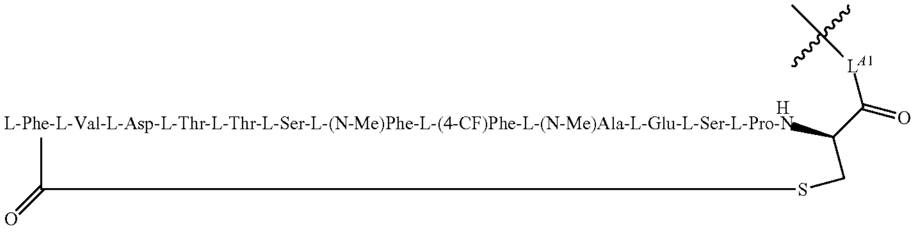
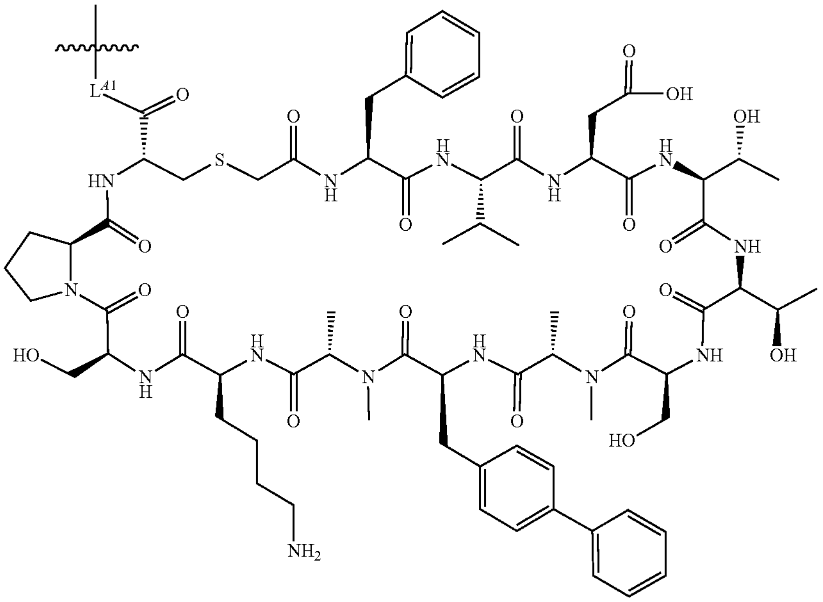
which can be represented by the following:
Ac*-F-V-D-T-T-S-(N-Me)A-B-(N-Me)A-K-S-P-C*-$L^{A1}$-**; or
Ac*-(L-Phe)-(L-Val)-(L-Asp)-(L-Thr)-(L-Thr)-(L-Ser)-(N-Me)Ala)-(L-Bip)-(N-Me)Ala)-(L-Lys)-(L-Ser)-(L-Pro)-(L-Cys)*-$L^{A1}$-**; or
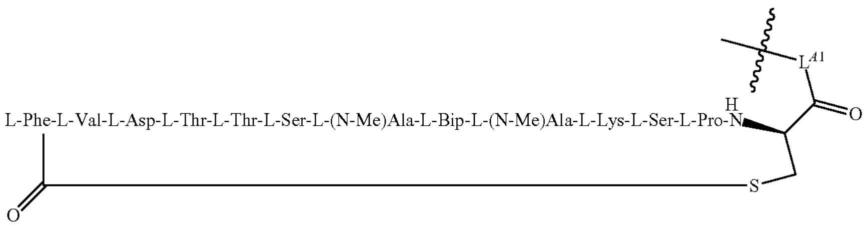

-continued
| $T_L$ Structure |
|---|
| 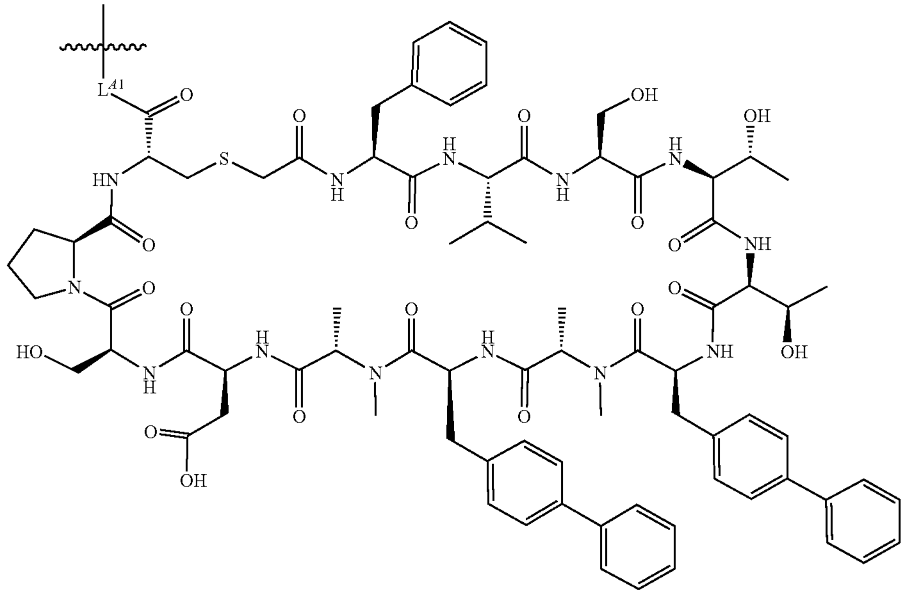 |
| which can be represented by the following:<br>Ac*-F-V-S-T-T-B-(N-Me)A-B-(N-Me)A-D-S-P-C*-$L^{A1}$-**; or<br>Ac*-(L-Phe)-(L-Val)-(L-Ser)-(L-Thr)-(L-Thr)-(L-Bip)-(L-(N-Me)Ala)-(L-Bip)-(L-(N-Me) Ala)-(L-Asp)-(L-Ser)-(L-Pro)-(L-Cys)*-$L^{A1}$-**; or |
| 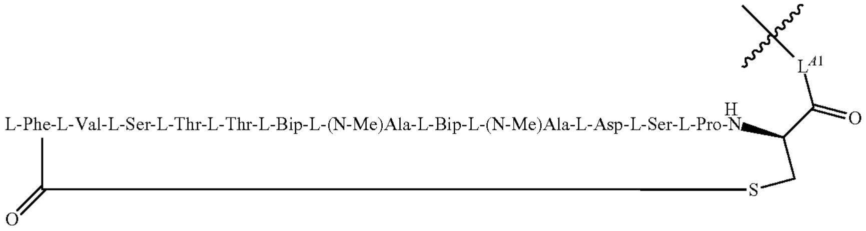 |
| 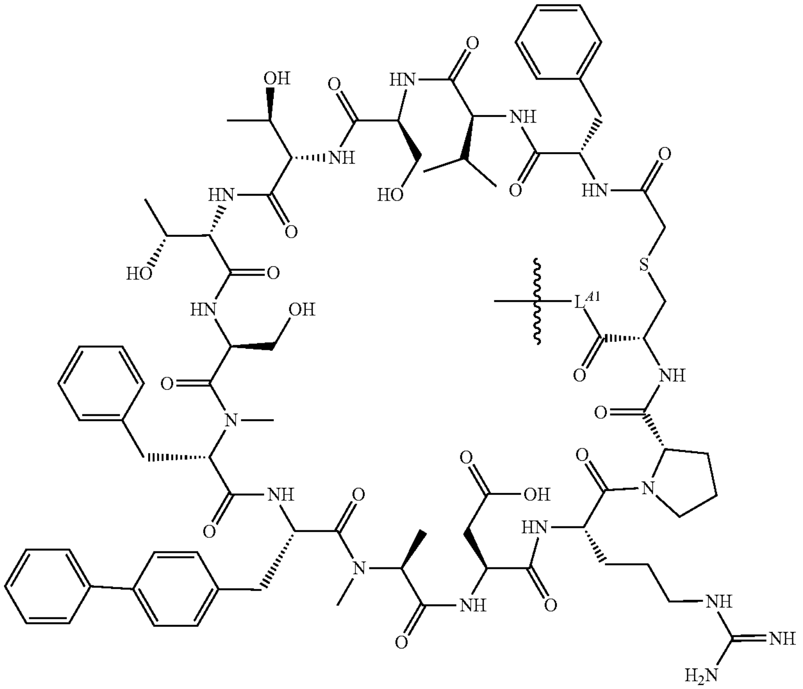 |

-continued
| $T_L$ Structure |
| --- |
which can be represented by the following:
Ac*-F-V-S-T-T-S-(N-Me)F-B-(N-Me)A-D-R-P-C*-$L^{A1}$-**; or
Ac*-(L-Phe)-(L-Val)-(L-Ser)-(L-Thr)-(L-Thr)-(L-Ser)-(L-(N-Me)Phe)-(L-Bip)-(L-(N-Me) Ala)-(L-Asp)-(L-Arg)-(L-Pro)-(L-Cys)*-$L^{A1}$-**; or
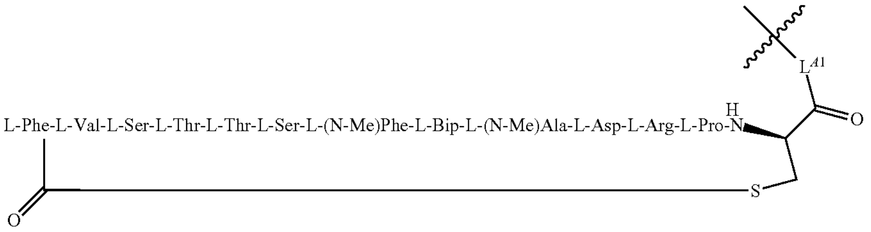
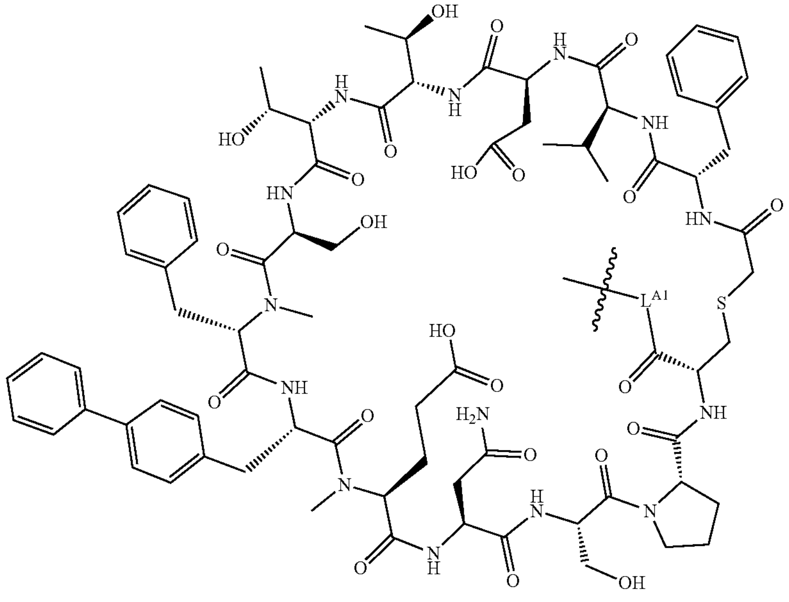
which can be represented by the following:
Ac*-F-V-D-T-T-B-(N-Me)A-B-(N-Me)A-E-S-P-C*-$L^{A1}$-**; or
Ac*-(L-Phe)-(L-Val)-(L-Asp)-(L-Thr)-(L-Thr)-(L-Bip)-(L-(N-Me)Ala)-(L-Bip)-(L-(N-Me)Ala)-(L-Glu)-(L-Ser)-(L-Pro)-(L-Cys)*-$L^{A1}$-**; or
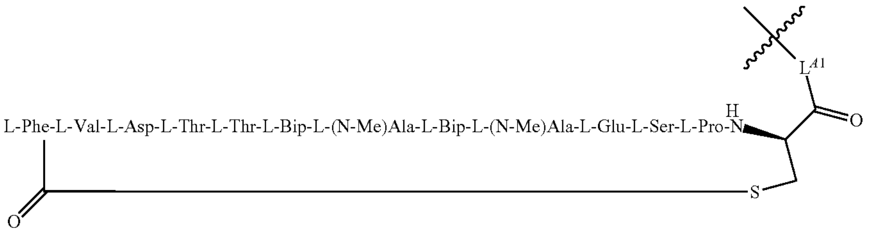

-continued
| $T_L$ Structure |
|---|
| 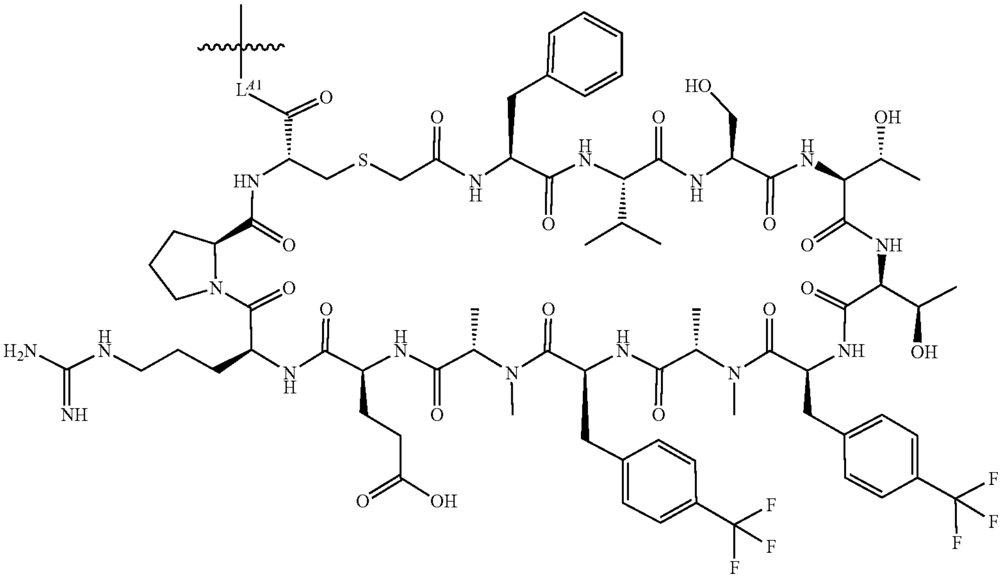 |
which can be represented by the following:
Ac*-F-V-S-T-T-(p-$CF_3$) F-(N-Me)A-(p-$CF_3$)F-(N-Me)A-E-R-P-C*-$L^{A1}$-**; or
Ac*-(L-Phe)-(L-Val)-(L-Ser)-(L-Thr)-(L-Thr)-(L-(4-$CF_3$)Phe)-(L-(N-Me)Ala)-(L-(4-$CF_3$)Phe)-(L-(N-Me)Ala)-(L-Glu)-(L-Arg)-(L-Pro)-(L-Cys)*-$L^{A1}$-**; or
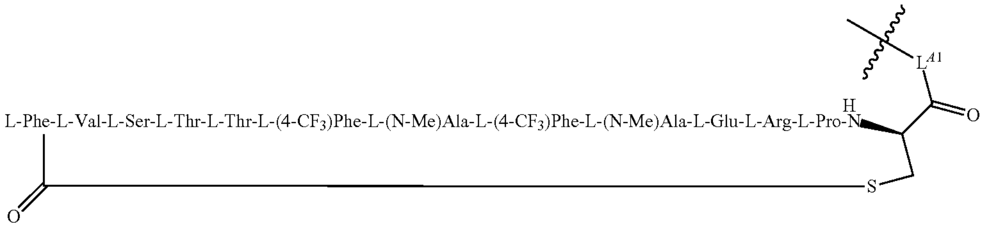
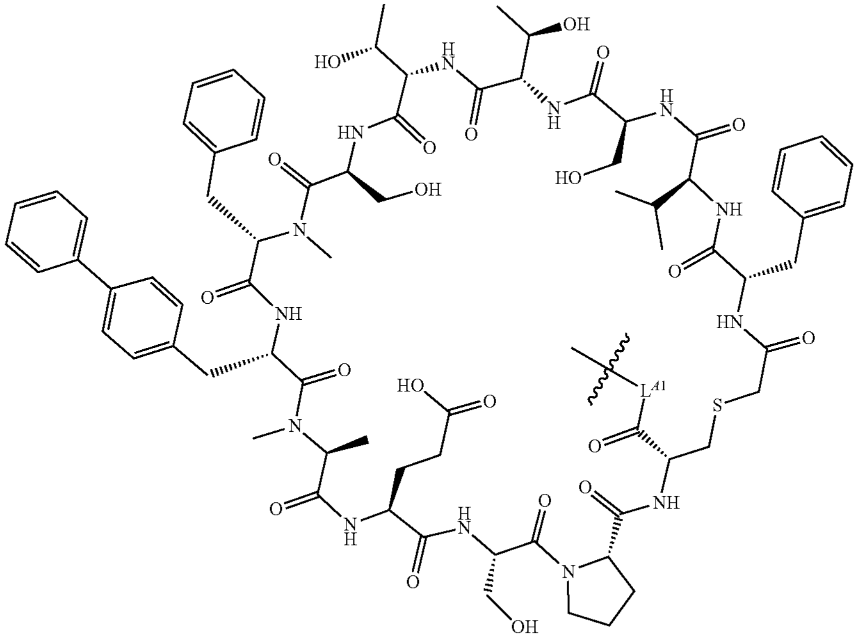

-continued
| $T_L$ Structure |
|---|
which can be represented by the following:
Ac*-F-V-S-T-T-S-(N-Me)F-B-(N-Me)A-E-S-P-C*-$L^{A1}$-**; or
Ac*-(L-Phe)-(L-Val)-(L-Ser)-(L-Thr)-(L-Thr)-(L-Ser)-(L-(N-Me)Phe)-(L-Bip)-(L-(N-Me) Ala)-(L-Glu)-(L-Ser)-(L-Pro)-(L-Cys)*-$L^{A1}$-**; or
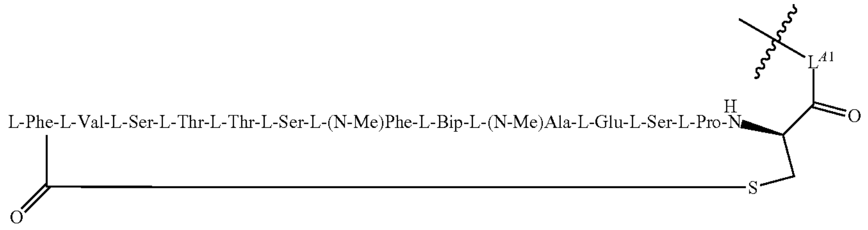
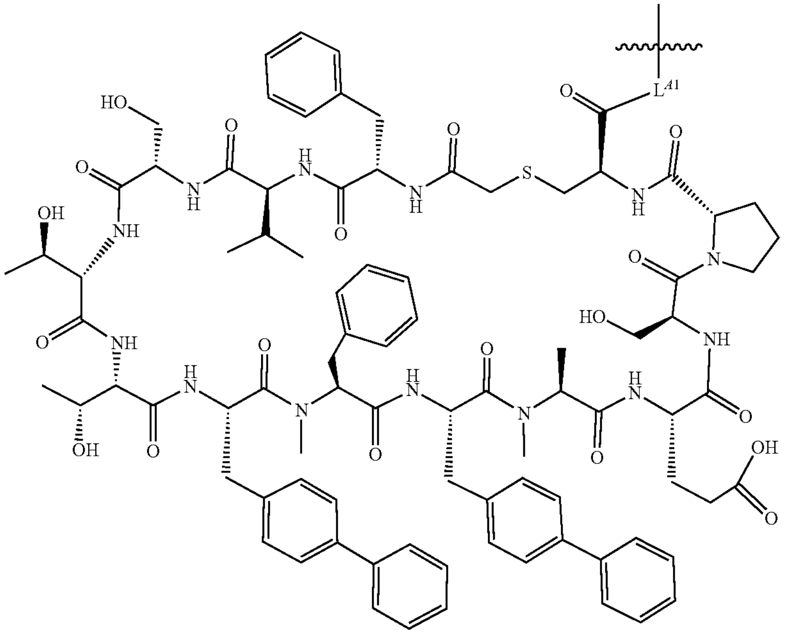
which can be represented by the following:
Ac*-F-V-S-T-T-B-(N-Me)F-B-(N-Me)A-E-S-P-C*-$L^{A1}$-**; or
Ac*-(L-Phe)-(L-Val)-(L-Ser)-(L-Thr)-(L-Thr)-(L-Bip)-(L-(N-Me)Phe)-(L-Bip)-(L-(N-Me) Ala)-(L-Glu)-(L-Ser)-(L-Pro)-(L-Cys)*-$L^{A1}$-**; or
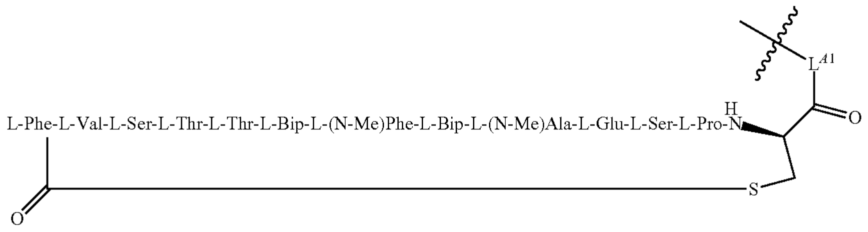

-continued
| $T_L$ Structure |
|---|
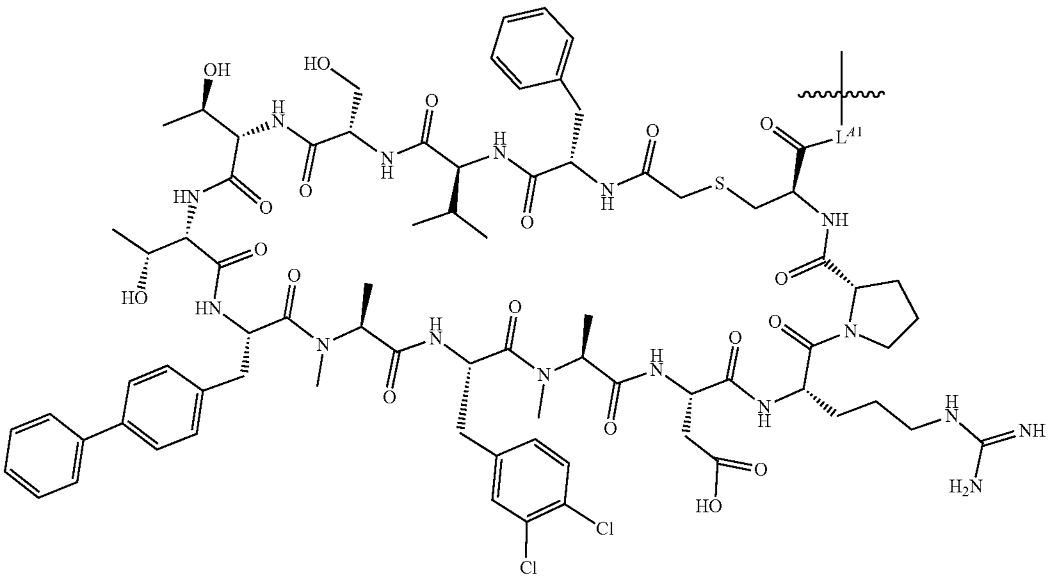
which can be represented by the following:
Ac*-F-V-S-T-T-B-(N-Me)A-(3,4-diCl)F-(N-Me)A-D-R-P-C*-$L^{A1}$-** , or
Ac*-(L-Phe)-(L-Val)-(L-Ser)-(L-Thr)-(L-Thr)-(L-Bip)-(L-(N-Me)Ala)-(L-(3,4-diCl)Phe)-(L-(N-Me)Ala)-(L-Asp)-(L-Arg)-(L-Pro)-(L-Cys)*-$L^{A1}$-**; or
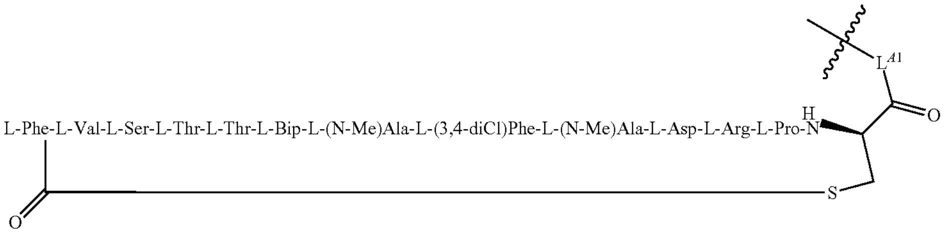
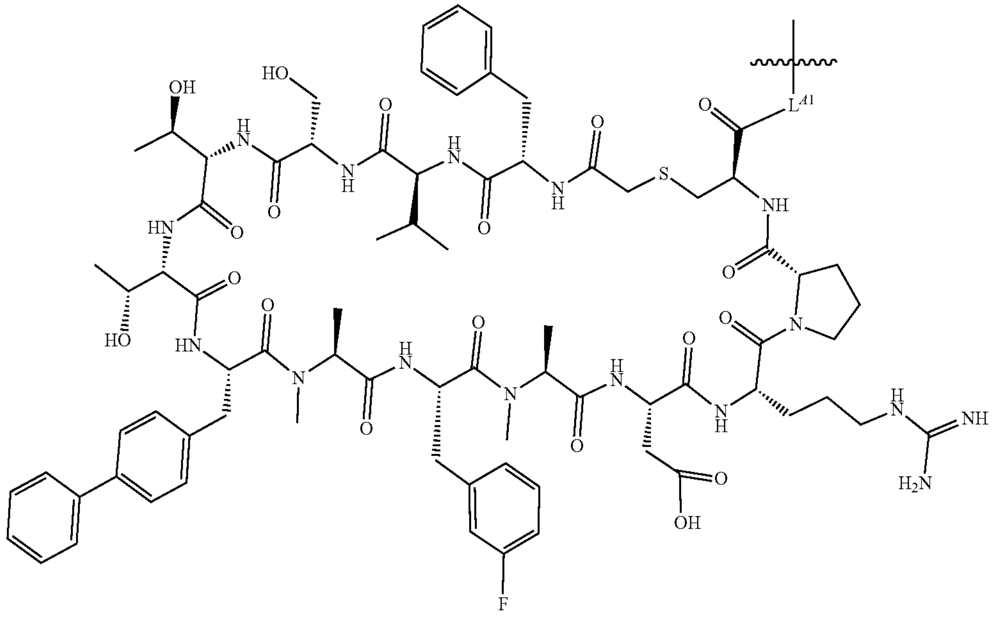

-continued
| $T_L$ Structure |
| --- |
which can be represented by the following:
Ac*-F-V-S-T-T-B-(N-Me)A-(3-F)F-(N-Me)A-D-R-P-C*-$L^{A1}$-**; or
Ac*-(L-Phe)-(L-Val)-(L-Ser)-(L-Thr)-(L-Thr)-(L-Bip)-(L-(N-Me)Ala)-(L-(3-F)Phe)-(L-(N-Me) Ala)-(L-Asp)-(L-Arg)-(L-Pro)-(L-Cys)*-$L^{A1}$-**; or
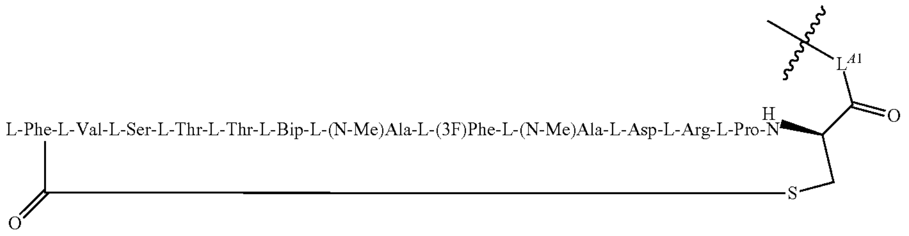
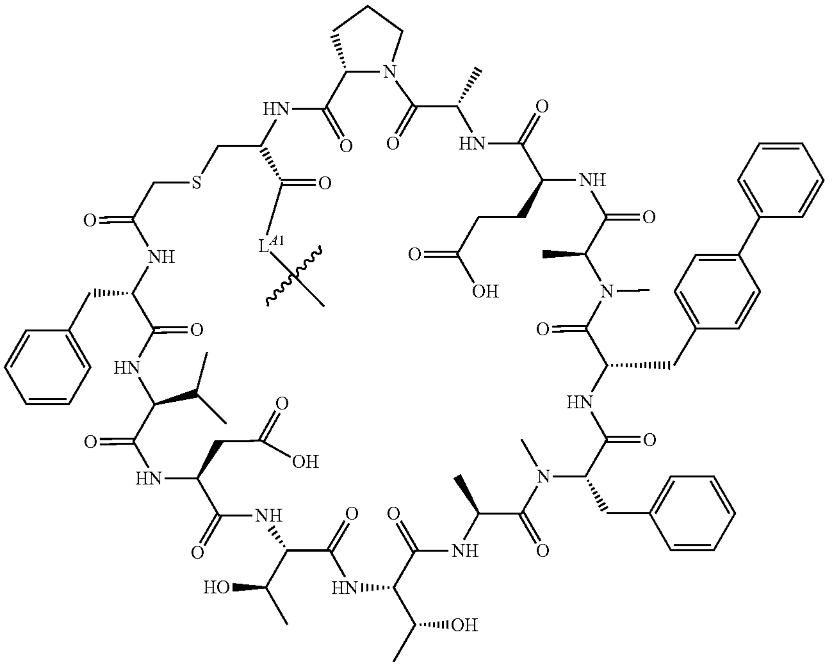
which can be represented by the following:
Ac*-F-V-D-T-T-A-(N-Me)F-B-(N-Me)A-E-A-P-C*-$L^{A1}$-**; or
Ac*-(L-Phe)-(L-Val)-(L-Asp)-(L-Thr)-(L-Thr)-(L-Ala)-(L-(N-Me)Phe)-(L-Bip)-(L-(N-Me)Ala)-(L-Glu)-(L-Ala)-(L-Pro)-(L-Cys)*-$L^{A1}$-**; or
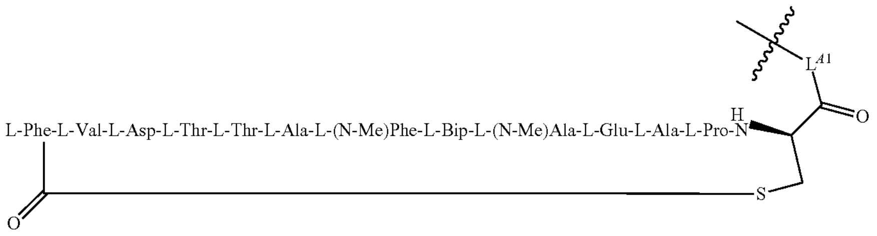

-continued
| $T_L$ Structure |
| --- |
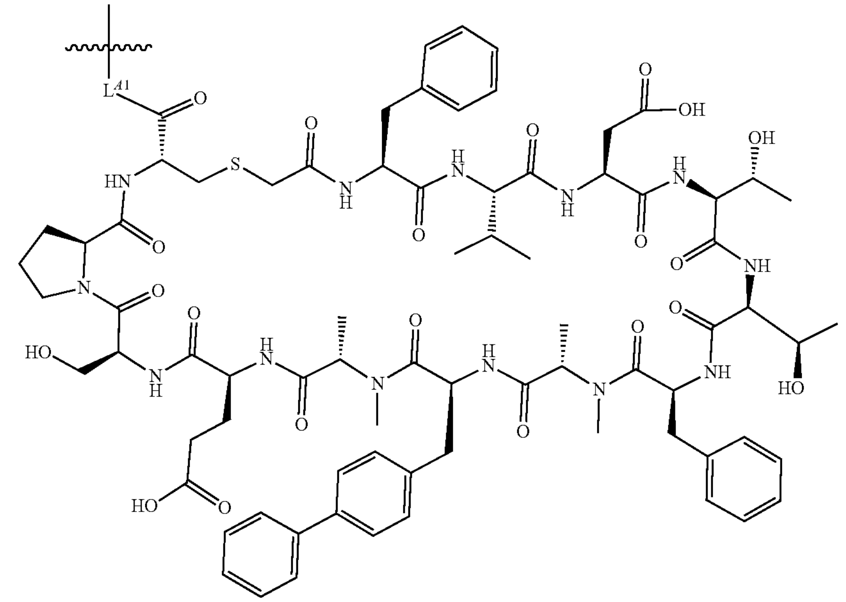
which can be represented by the following:
Ac*-F-V-D-T-T-F-(N-Me)A-B-(N-Me)A-E-S-P-C*-$L^{A1}$-**; or
Ac*-(L-Phe)-(L-Val)-(L-Asp)-(L-Thr)-(L-Thr)-(L-Phe)-(L-(N-Me)Ala)-(L-Bip)-(L-(N-Me)Ala)-(L-Glu)-(L-Ser)-(L-Pro)-(L-Cys)*-$L^{A1}$-**; or
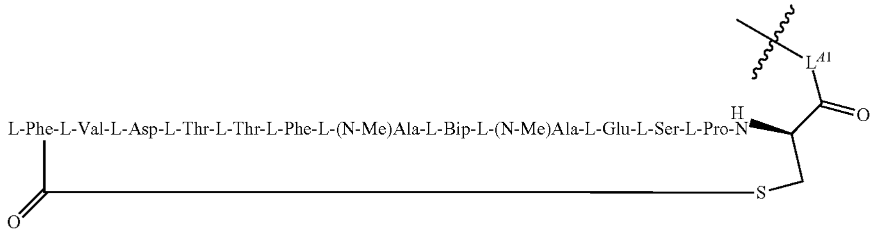
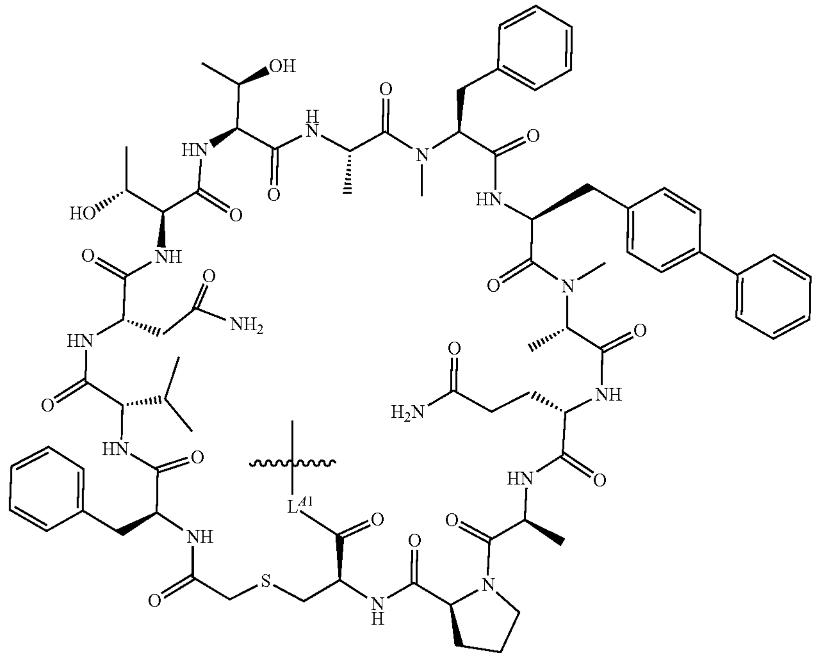

-continued
| $T_L$ Structure |
| --- |
which can be represented by the following:
Ac*-F-V-N-T-T-A-(N-Me)F-B-(N-Me)A-Q-A-P-C*-$L^{A1}$-**; or
Ac*-(L-Phe)-(L-Val)-(L-Asn)-(L-Thr)-(L-Thr)-(L-Ala)-(L-(N-Me)Phe)-(L-Bip)-(L-(N-Me)Ala)-(L-Gln)-(L-Ala)-(L-Pro)-(L-Cys)*-$L^{A1}$-**; or
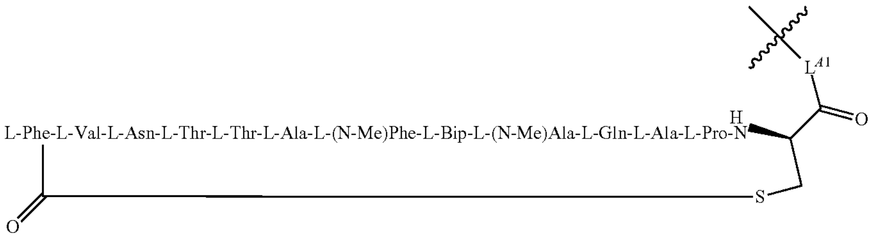
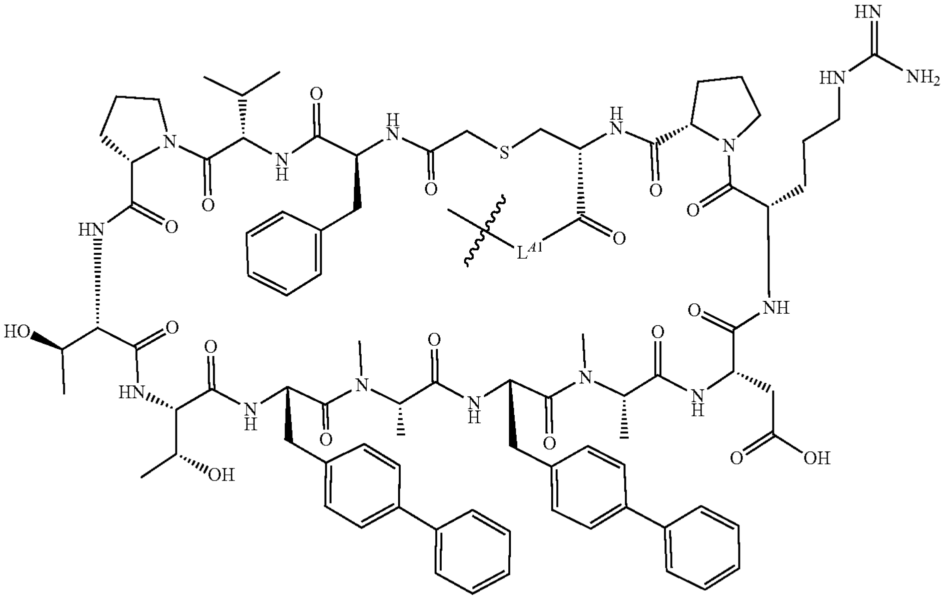
which can be represented by the following:
Ac*-F-V-P-T-T-B-(N-Me)A-B-(N-Me)A-D-R-P-C*-$L^{A1}$-**; or
Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Asp)-(L-Arg)-(L-Pro)-(L-Cys)*-$L^{A1}$-**; or
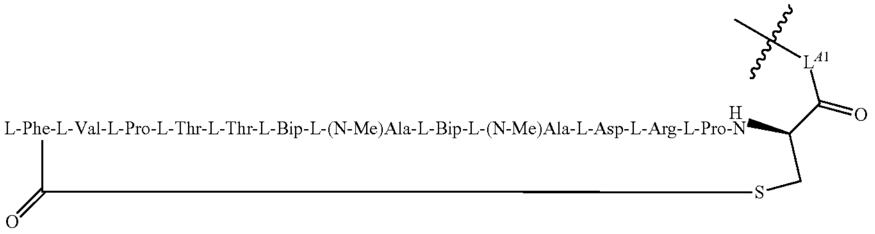

-continued
| $T_L$ Structure |
| --- |
| 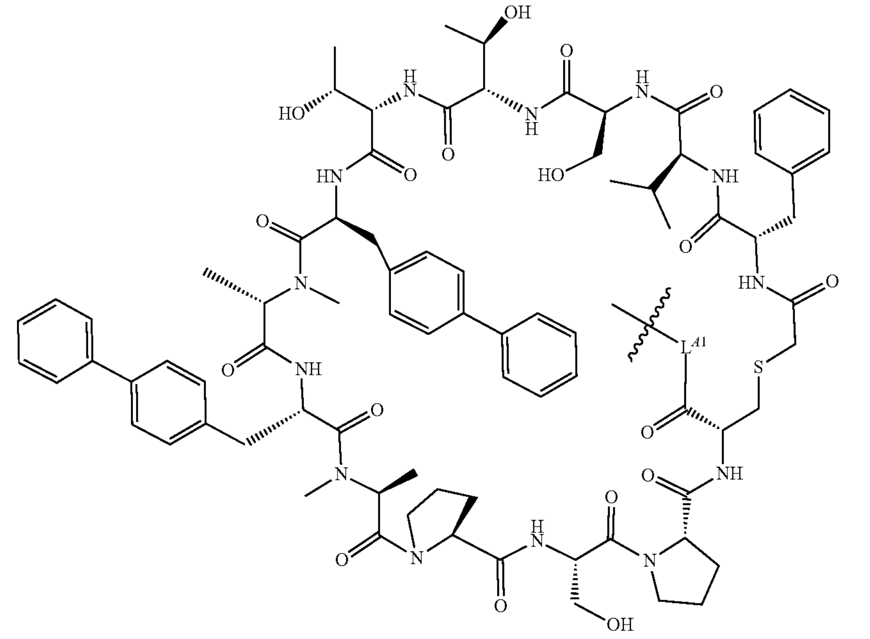 |
| which can be represented by the following:<br>Ac*-F-V-S-T-T-B-(N-Me)A-B-(N-Me)A-P-S-P-C*-$L^{A1}$-**; or<br>Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Pro)-(L-Ser)-(L-Pro)-(L-Cys)*-$L^{A1}$-**; or |
| 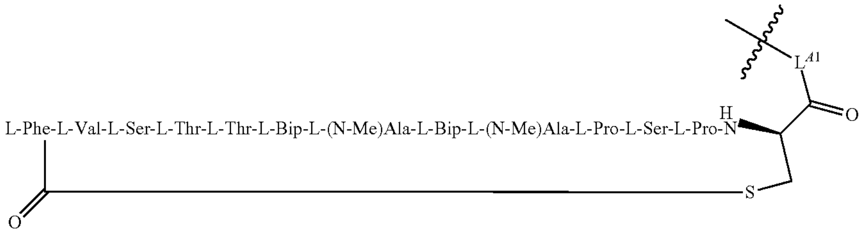 |
| 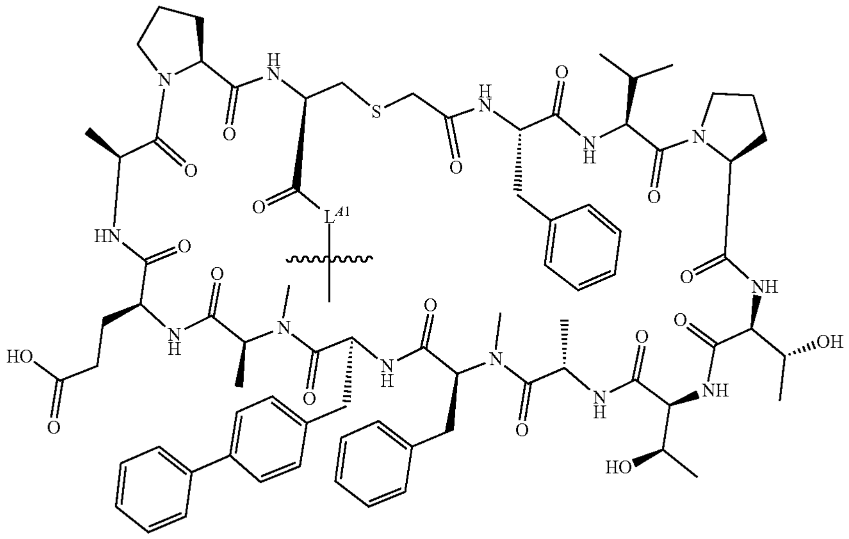 |
| which can be represented by the following:<br>Ac*-F-V-P-T-T-A-(N-Me)F-B-(N-Me)A-E-A-P-C*-$L^{A1}$-**; or<br>Ac*-(L-Phe)-(L-Val)-(L-Pro)-(L-Thr)-(L-Thr)-(L-Ala)-(L-(N-Me)Phe)-(L-Bip)-(L-(N-Me)Ala)-(L-Glu)-(L-Ala)-(L-Pro)-(L-Cys)*-$L^{A1}$-**; or |

-continued
| $T_L$ Structure |
| --- |
| 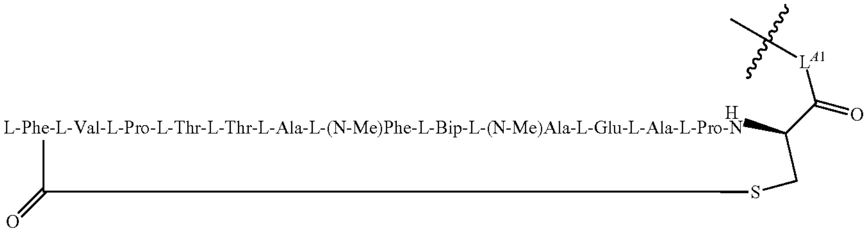 |
| 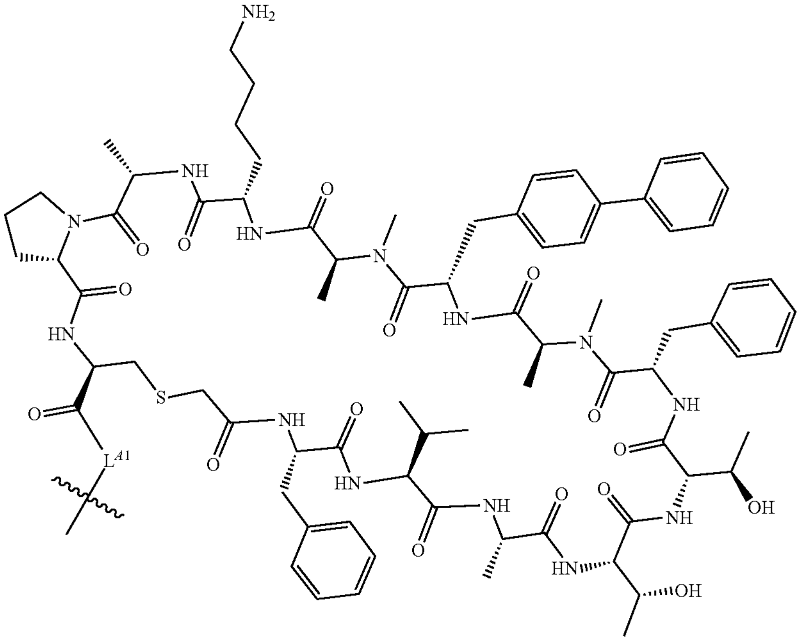 which can be represented by the following: Ac*-F-V-A-T-T-F-(N-Me)A-B-(N-Me)A-K-A-P-C*-$L^{A1}$-**; or Ac*-(L-Phe)-(L-Val)-(L-Ala)-(L-Thr)-(L-Thr)-(L-Phe)-(L-(N-Me)Ala)-(L-Bip)-(L-(N-Me)Ala)-(L-Lys)-(L-Ala)-(L-Pro)-(L-Cys)*-$L^{A1}$-**; or |
| 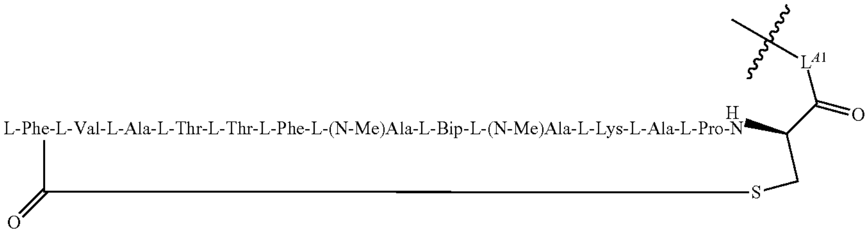 |

-continued
| $T_L$ Structure |
| --- |
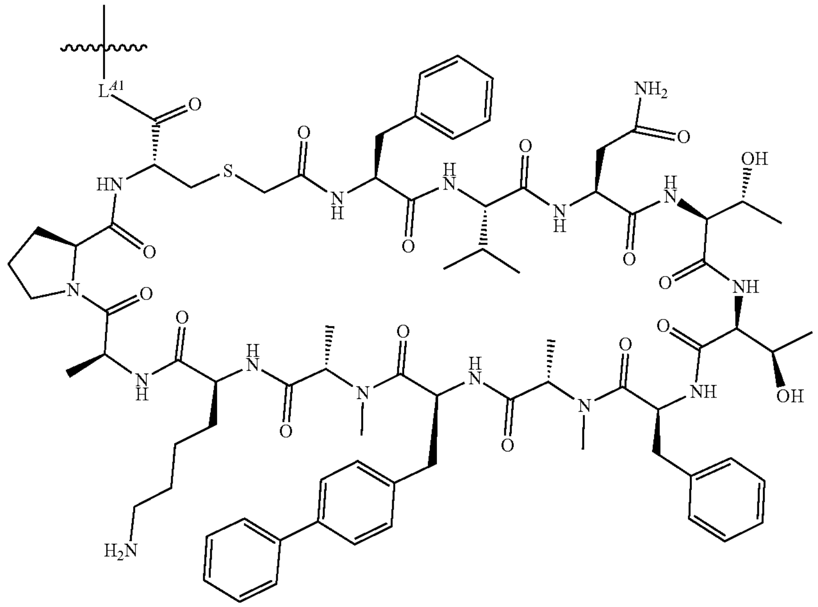
which can be represented by the following:
Ac*-F-V-N-T-T-F-(N-Me)A-B-(N-Me)A-K-A-P-C*-$L^{A1}$-**; or
Ac*-(L-Phe)-(L-Val)-(L-Asn)-(L-Thr)-(L-Thr)-(L-Phe)-(L-(N-Me)Ala)-(L-Bip)-(L-(N-Me)Ala)-(L-Lys)-(L-Ala)-(L-Pro)-(L-Cys)*-$L^{A1}$-**; or
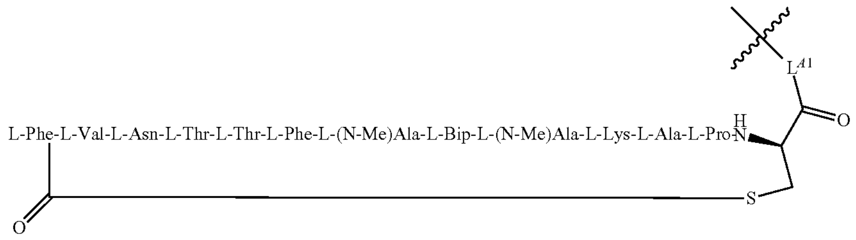
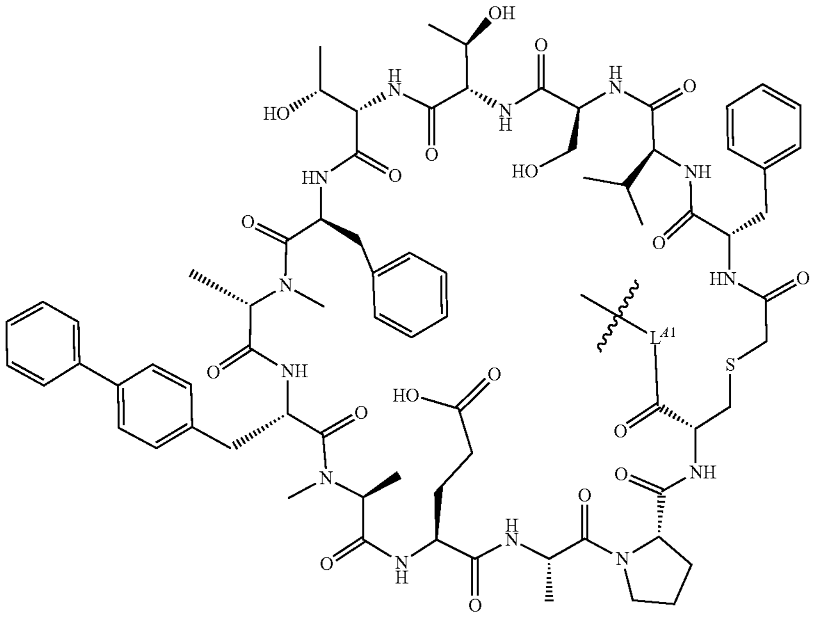

-continued
| $T_L$ Structure |
|---|
| which can be represented by the following:<br>Ac*-F-V-S-T-T-F-(N-Me)A-B-(N-Me)A-E-A-P-C*-$L^{A1}$-**; or<br>Ac*-(L-Phe)-(L-Val)-(L-Ser)-(L-Thr)-(L-Thr)-(L-Phe)-(L-(N-Me)Ala)-(L-Bip)-(L-(N-Me)Ala)-(L-Glu)-(L-Ala)-(L-Pro)-(L-Cys)*-$L^{A1}$-**; or |
| 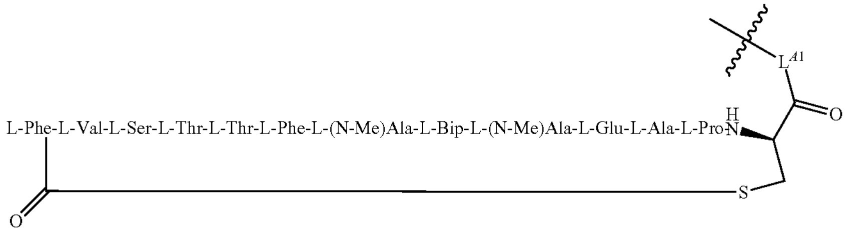 |
| 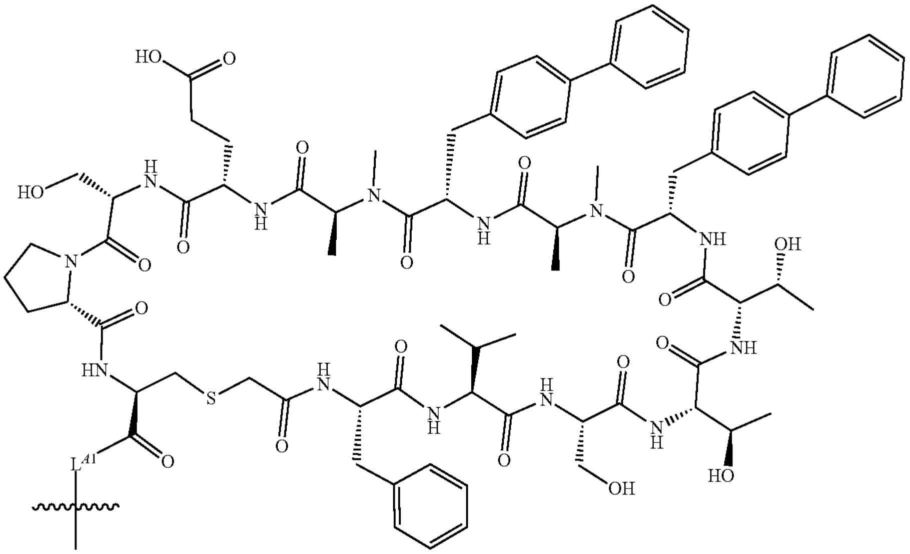 |
| which can be represented by the following:<br>Ac*-F-V-S-T-T-B-(N-Me)A-B-(N-Me)A-E-S-P-C*-$L^{A1}$-**; or<br>Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Glu)-(L-Ser)-(L-Pro)-(L-Cys)*-$L^{A1}$-**; or |
| 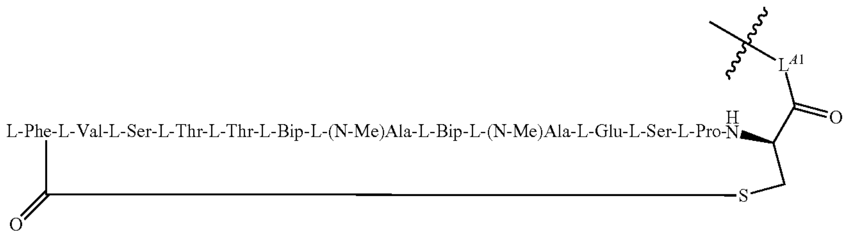 |

-continued
| $T_L$ Structure |
| --- |
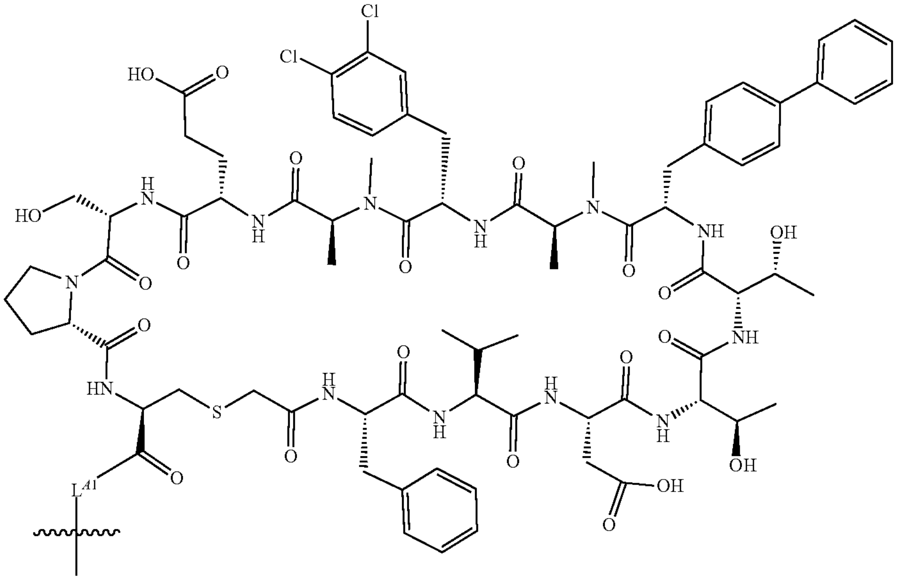
which can be represented by the following:
Ac*-F-V-D-T-T-B-(N-Me)A-(3,4-diCl)F-(N-Me)A-E-S-P-C*-$L^{A1}$-**; or
Ac*-(L-Phe)-(L-Val)-(L-Asp)-(L-Thr)-(L-Thr)-(L-Bip)-(L-(N-Me)Ala)-(L-(3,4-diCl)Phe)-(L-(N-Me)Ala)-(L-Glu)-(L-Ser)-(L-Pro)-(L-Cys)*-$L^{A1}$-**; or
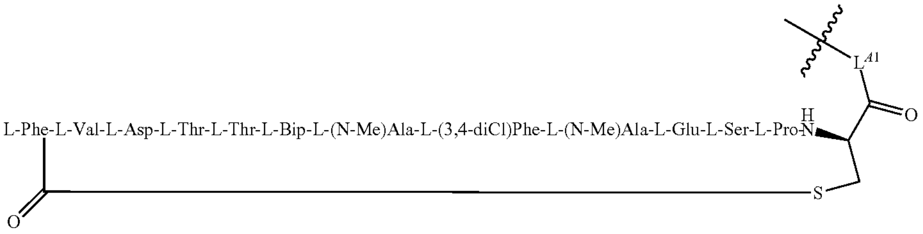
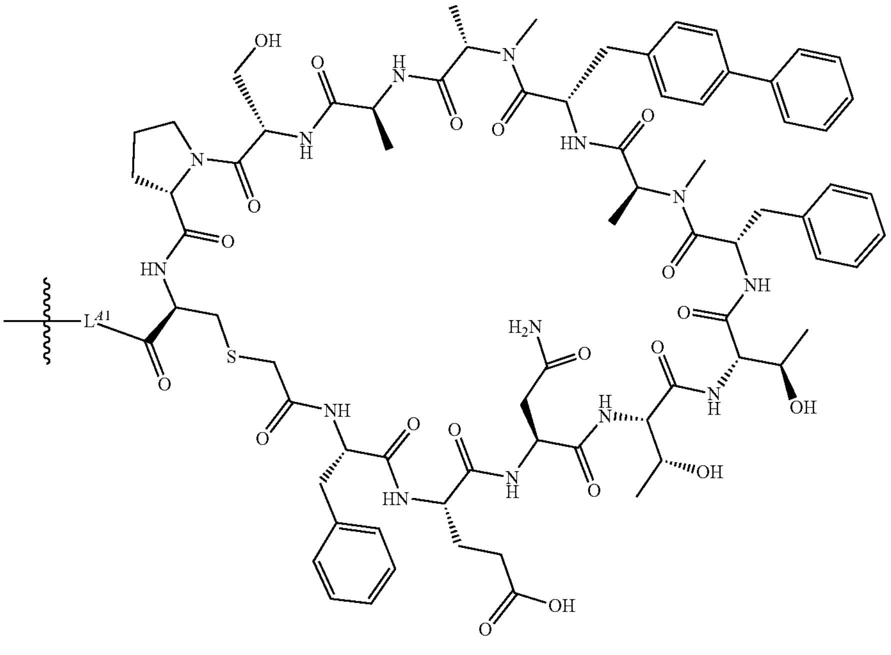

-continued

| $T_L$ Structure |
| --- |
| which can be represented by the following:<br>Ac*-F-E-N-T-T-F-(N-Me)A-B-(N-Me)A-A-S-P-C*-$L^{A1}$-**; or<br>Ac*-(L-Phe)-(L-Glu)-(L-Asn)-(L-Thr)-(L-Thr)-(L-Phe)-(L-(N-Me)Ala)-(L-Bip)-<br>(L-(N-Me)Ala)-(L-Ala)-(L-Ser)-(L-Pro)-(L-Cys)*-$L^{A1}$-**; or |
| 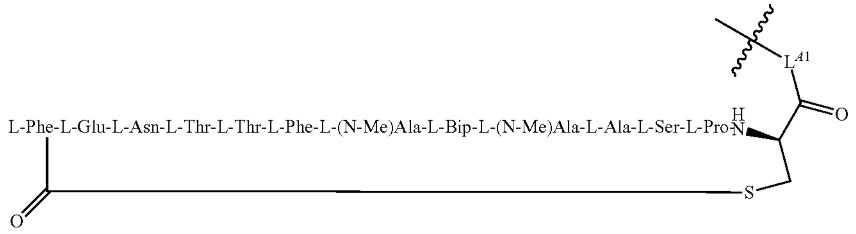 |
| 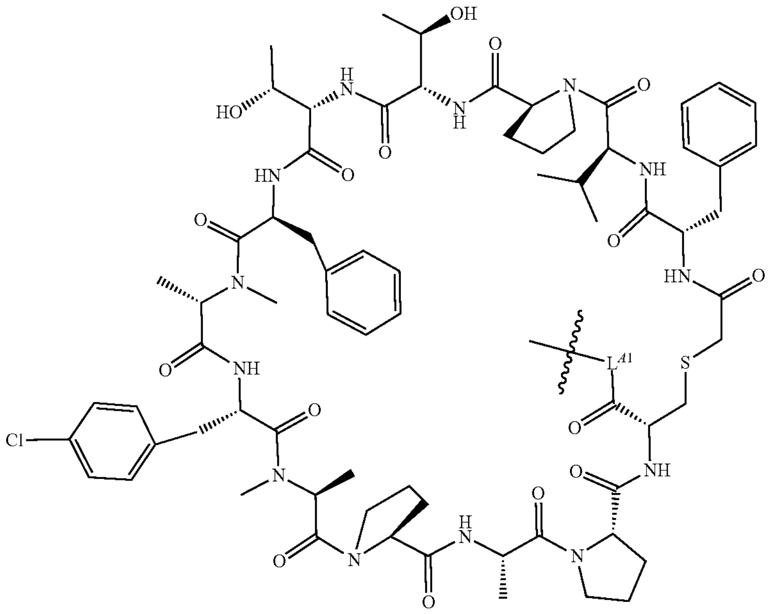 |
| which can be represented by the following:<br>Ac*-F-V-P-T-T-F-(N-Me)A-(p-Cl)F-(N-Me)A-P-A-P-C*-$L^{A1}$-**; or<br>Ac*-(L-Phe)-(L-Val)-(L-Pro)-(L-Thr)-(L-Thr)-(L-Phe)-(L-(N-Me)Ala)-(L-(4-<br>Cl)Phe)-(L-(N-Me)Ala)-(L-Pro)-(L-Ala)-(L-Pro)-(L-Cys)*-$L^{A1}$-**; or |
| 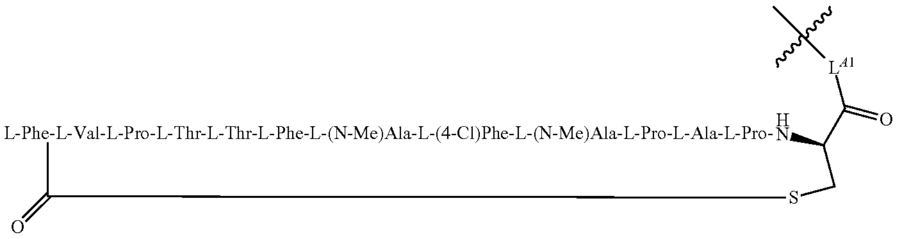 |

-continued
| $T_L$ Structure |
| --- |
| 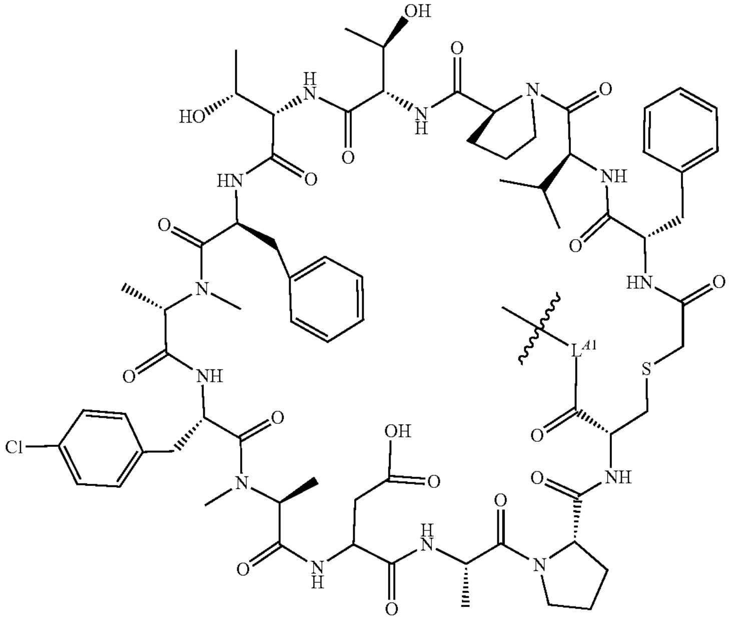 |
| which can be represented by the following:<br>Ac*-F-V-P-T-T-F-(N-Me)A-(p-Cl)F-(N-Me)A-D-A-P-C*-$L^{A1}$-**; or<br>Ac*-(L-Phe)-(L-Val)-(L-Pro)-(L-Thr)-(L-Thr)-(L-Phe)-(L-(N-Me)Ala)-(L-(4-Cl)Phe)-(L-(N-Me)Ala)-(L-Asp)-(L-Ala)-(L-Pro)-(L-Cys)*-$L^{A1}$-**; or |
| 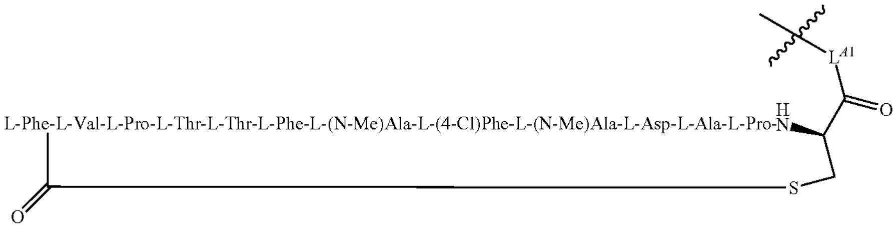 |
| 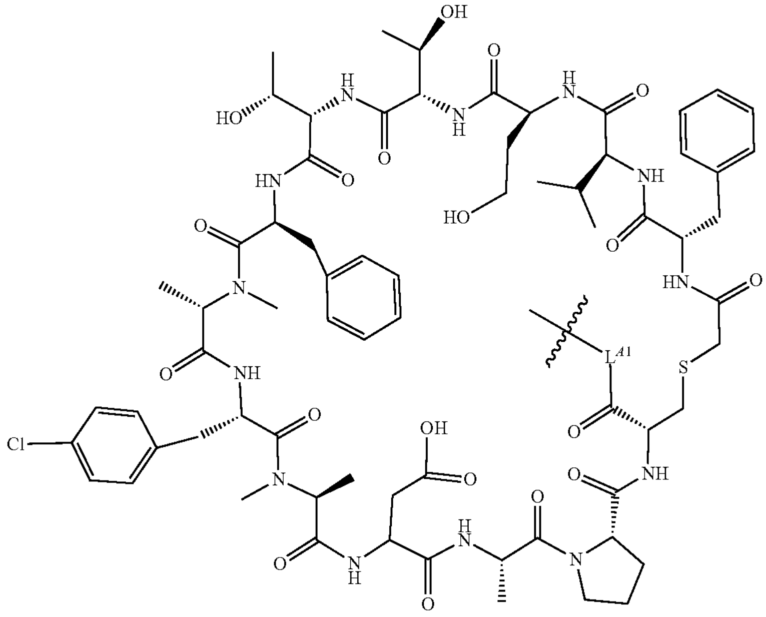 |

-continued
| $T_L$ Structure |
| --- |
| which can be represented by the following: |
| Ac*-F-V-HomoSer-T-T-F-(N-Me)A-(p-Cl)F-(N-Me)A-D-A-P-C*-$L^{A1}$-**; or |
| Ac*-(L-Phe)-(L-Val)-(L-Hse)-(L-Thr)-(L-Thr)-(L-Phe)-(L-(N-Me)Ala)-(L-(4-Cl)Phe)-(L-(N-Me)Ala)-(L-Asp)-(L-Ala)-(L-Pro)-(L-Cys)*-$L^{A1}$-**; or |
| 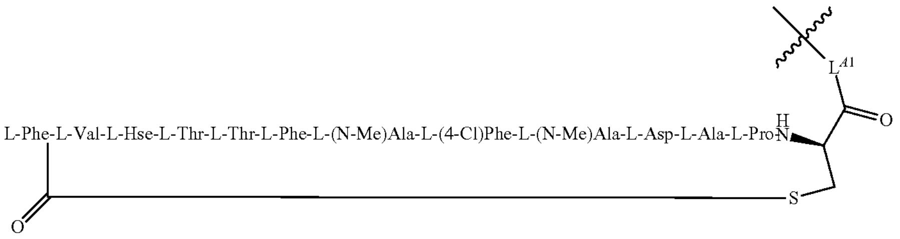 |
| 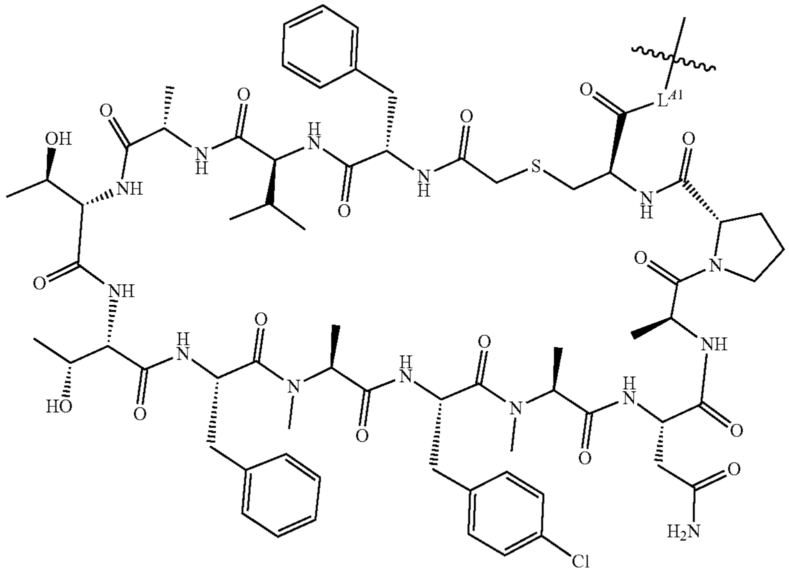 |
| which can be represented by the following: |
| Ac*-F-V-A-T-T-F-(N-Me)A-(p-Cl)F-(N-Me)A-N-A-P-C*-$L^{A1}$-**; or |
| Ac*-(L-Phe)-(L-Val)-(L-Ala)-(L-Thr)-(L-Thr)-(L-Phe)-(L-(N-Me)Ala)-(L-(4-Cl)Phe)-(L-(N-Me)Ala)-(L-Asn)-(L-Ala)-(L-Pro)-(L-Cys)*-$L^{A1}$-**; or |
| 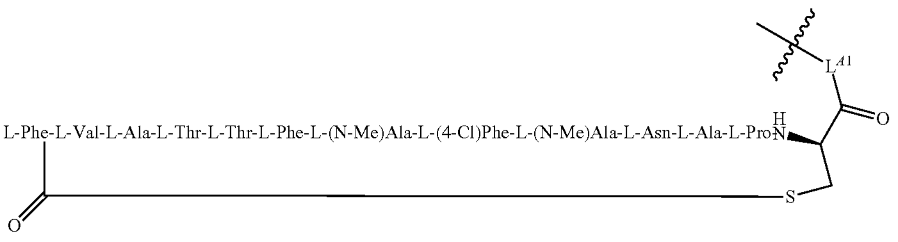 |

-continued

| $T_L$ Structure |
|---|
| 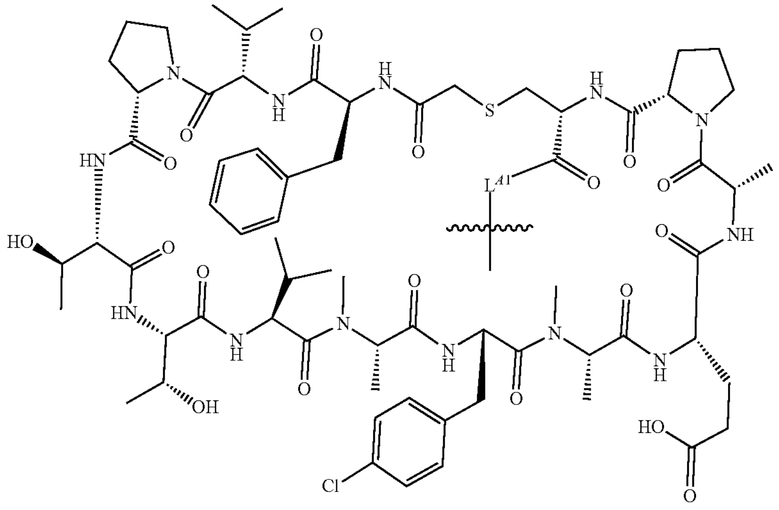 |
| which can be represented by the following:<br>Ac*-F-V-P-T-T-V-(N-Me)A-(p-Cl)F-(N-Me)A-E-A-P-C*-$L^{A1}$-**; or<br>Ac*-(L-Phe)-(L-Val)-(L-Pro)-(L-Thr)-(L-Thr)-(L-Val)-(L-(N-Me)Ala)-(L-(4-Cl)Phe)-(L-(N-Me)Ala)-(L-Glu)-(L-Ala)-(L-Pro)-(L-Cys)*-$L^{A1}$-**; or |
| 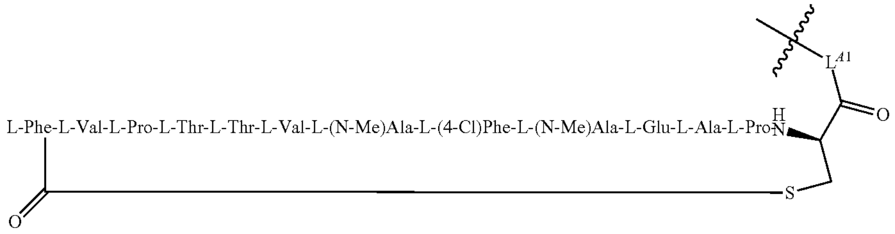 |
| 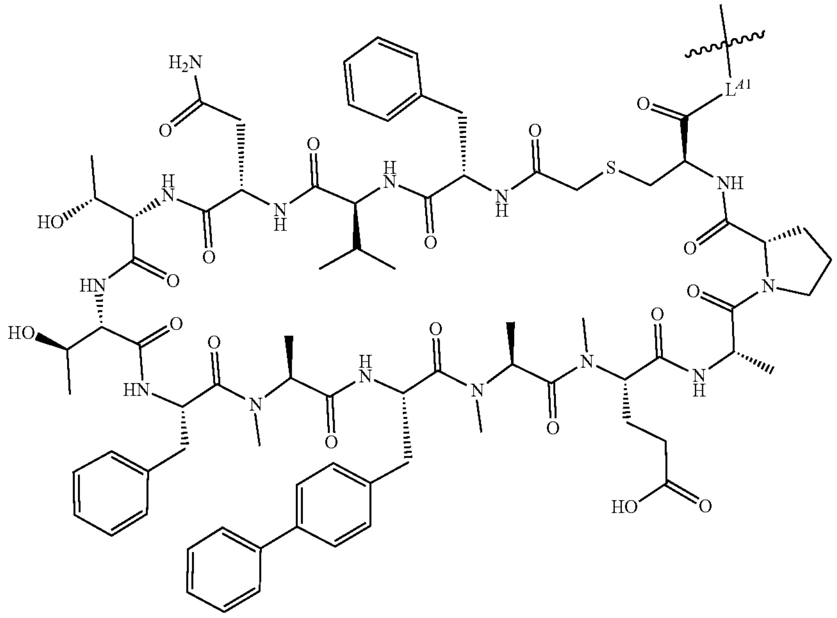 |
| which can be represented by the following:<br>Ac*-F-V-N-T-T-F-(N-Me)A-B-(N-Me)A-(N-Me)E-A-P-C*-$L^{A1}$-**; or<br>Ac*-(L-Phe)-(L-Val)-(L-Asn)-(L-Thr)-(L-Thr)-(L-Phe)-(L-(N-Me)Ala)-(L-Bip)-(L-(N-Me)Ala)-(L-(N-Me)Glu)-(L-Ala)-(L-Pro)-(L-Cys)*-$L^{A1}$-**; or |

-continued
| $T_L$ Structure |
| --- |
| 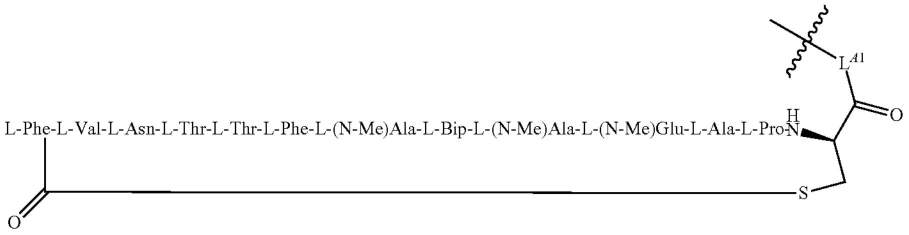 |
| 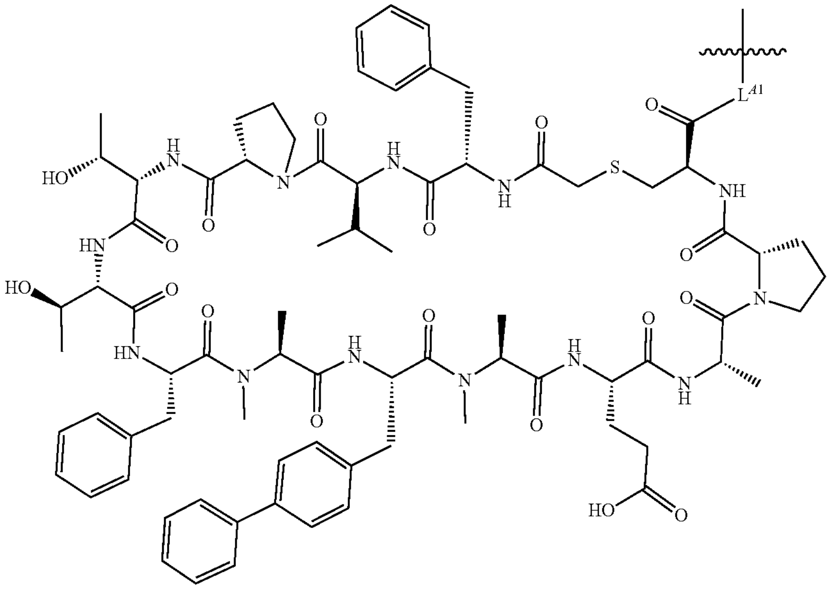 |
| which can be represented by the following:<br>Ac*-F-V-P-T-T-F-(N-Me)A-B-(N-Me)A-E-A-P-C*-$L^{A1}$-**; or<br>Ac*-(L-Phe)-(L-Val)-(L-Pro)-(L-Thr)-(L-Thr)-(L-Phe)-(L-(N-Me)Ala)-(L-Bip)-(L-(N-Me)Ala)-(L-Glu)-(L-Ala)-(L-Pro)-(L-Cys)*-$L^{A1}$-**; or |
| 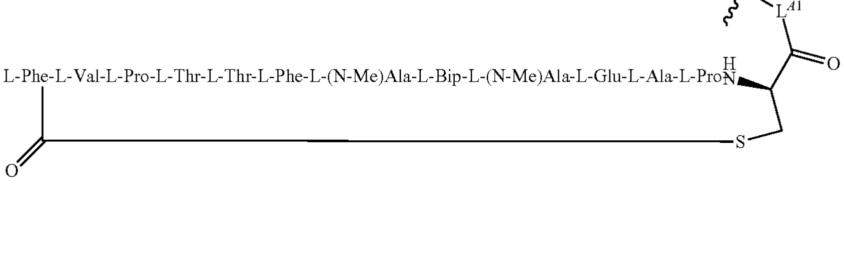 |

-continued

| $T_L$ Structure |
|---|
| 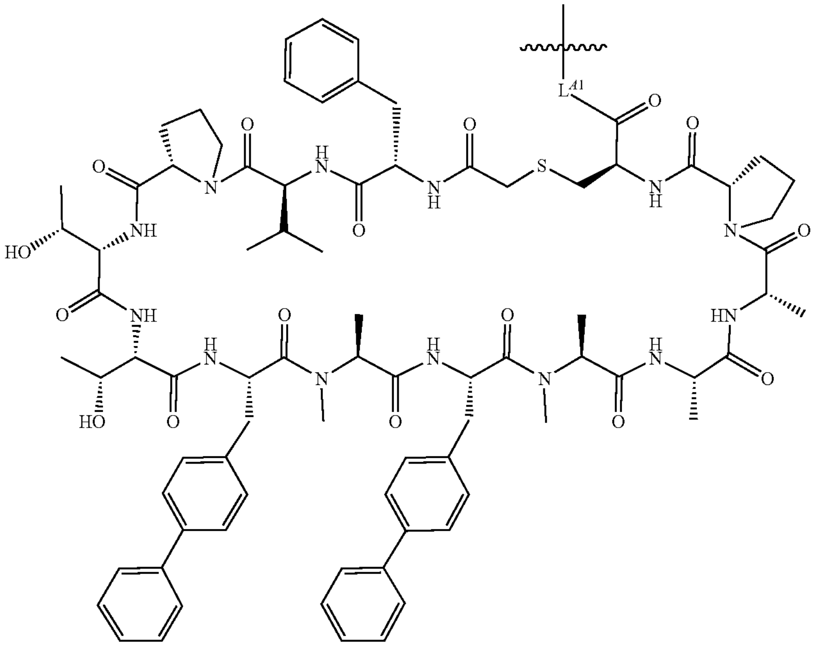 |
| which can be represented by the following:<br>Ac*-F-V-P-T-T-B-(N-Me)A-B-(N-Me)A-A-A-P-C*-$L^{A1}$-**; or<br>Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Ala)-(L-Ala)-(L-Pro)-(L-Cys)*-$L^{A1}$-**; or |
| 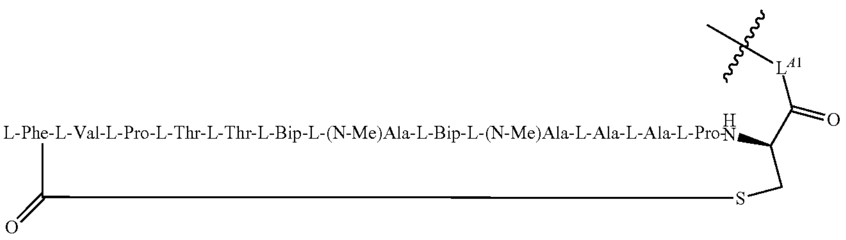 |

wherein:

Ac is acetyl and wherein acetyl labeled with the "*" and the (L-Cys) labeled with the are linked via a sulfide bond formed via their side chain or terminus, and $L^{A1}$ is as defined herein and the ** of $L^{A1}$ indicates the point of attachment to Linker ($L_A$).

Embodiment 38. The bifunctional compound of any one of Embodiments 4 to 37, wherein $L^{A1}$ is

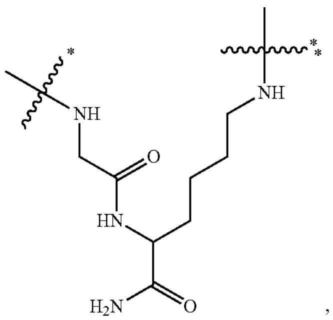 [SMILES: *NCCCCC(NC(=O)CN*)C(N)=O]

, or

-continued

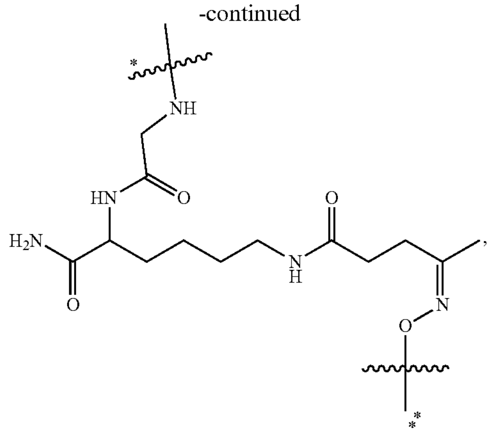

where the ** of $L^{A1}$ indicates the point of attachment to Linker ($L_A$) and the * of $L^{A1}$ indicates the point of attachment to the —C(═O)— group.

Embodiment 39. The bifunctional compound of any one of Embodiments 4 to 38, wherein $L^{A1}$ is

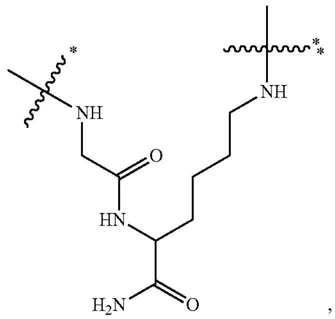

, where the ** of $L^{A1}$ indicates the point of attachment to Linker ($L_A$) and the * of $L^{A1}$ indicates the point of attachment to the —C(═O)— group.

Embodiment 40. The bifunctional compound of any one of Embodiments 4 to 38, wherein $L^{A1}$ is

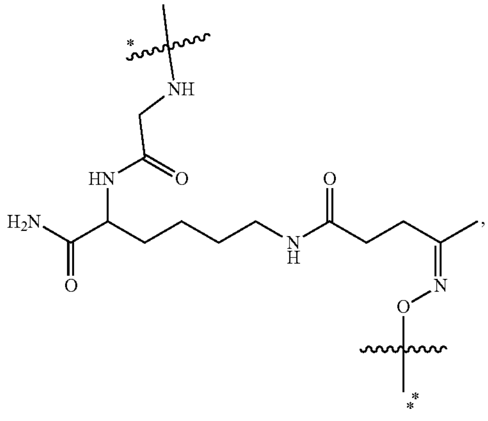

, where the ** of $L^{A1}$ indicates the point of attachment to Linker ($L_A$) and the * of $L^{A1}$ indicates the point of attachment to the —C(═O)— group.

Embodiment 41. The bifunctional compound of any one of Embodiments 4 to 38, wherein $T_L$ is a compound of Formula (A), or pharmaceutically acceptable salts or stereoisomers, selected from the following:

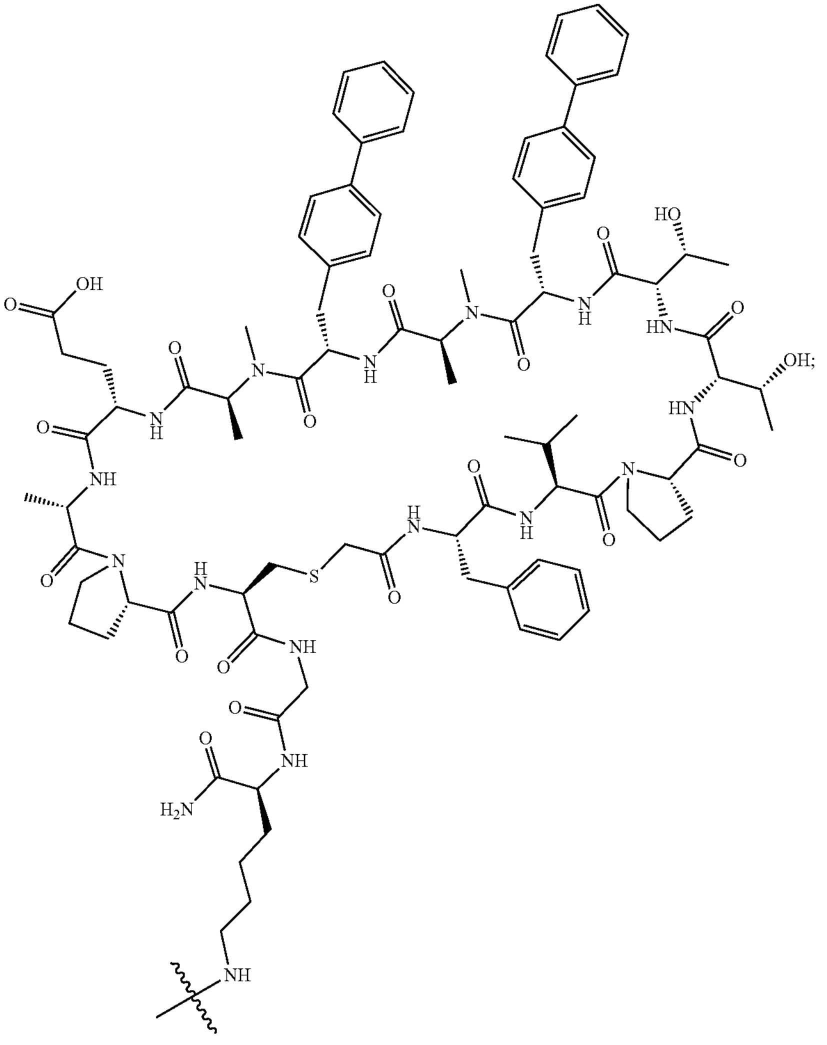

;

-continued
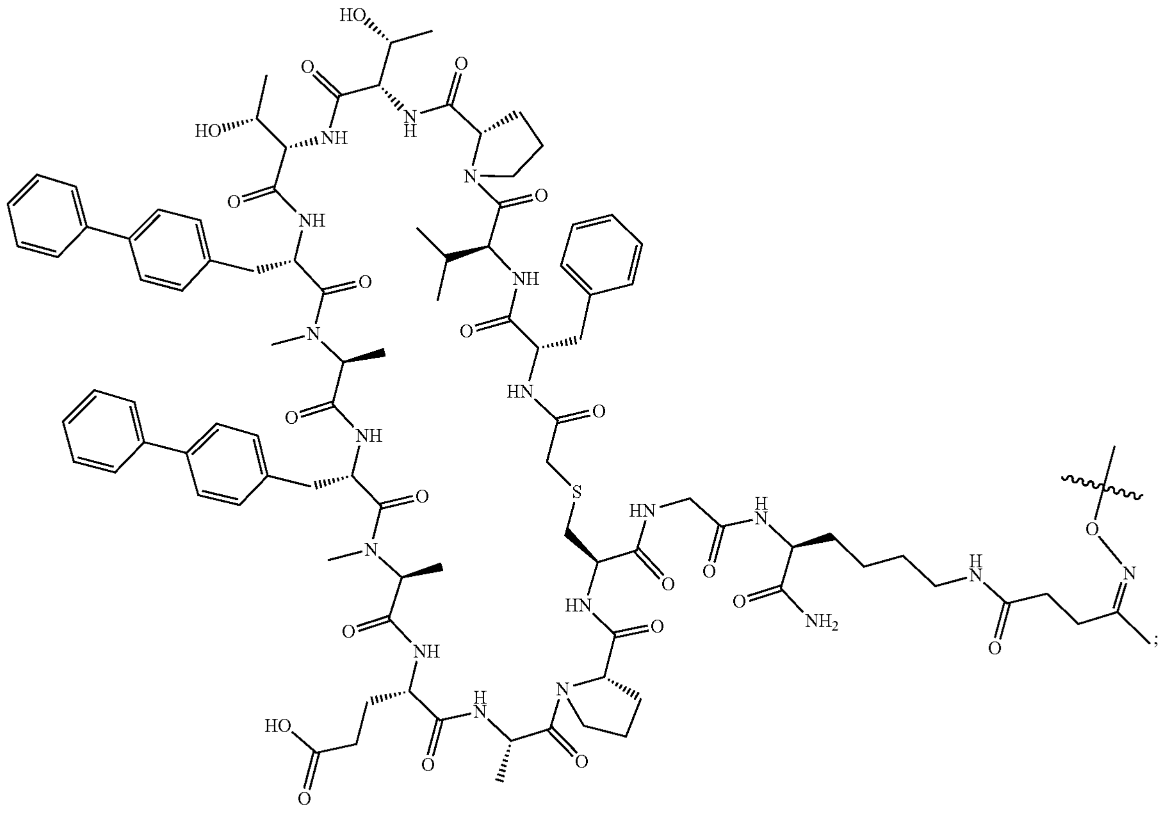
;
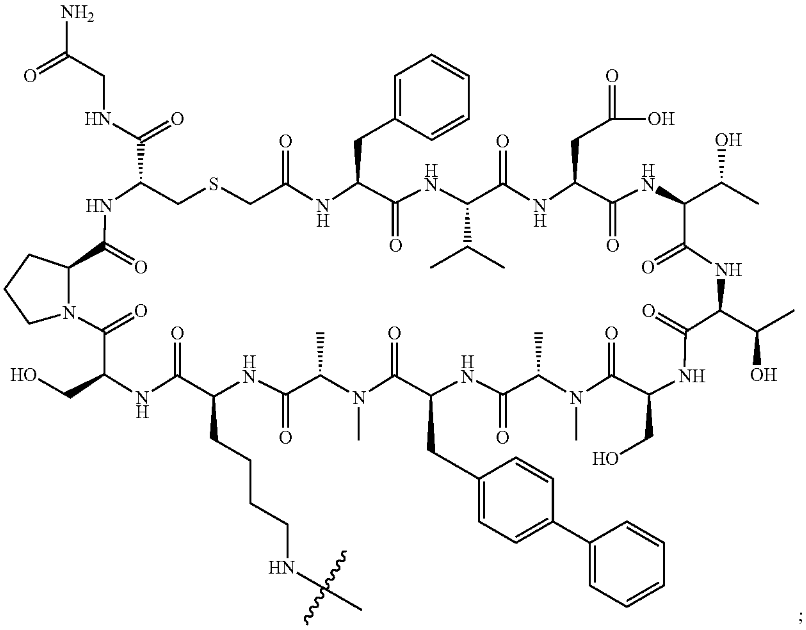
;

-continued
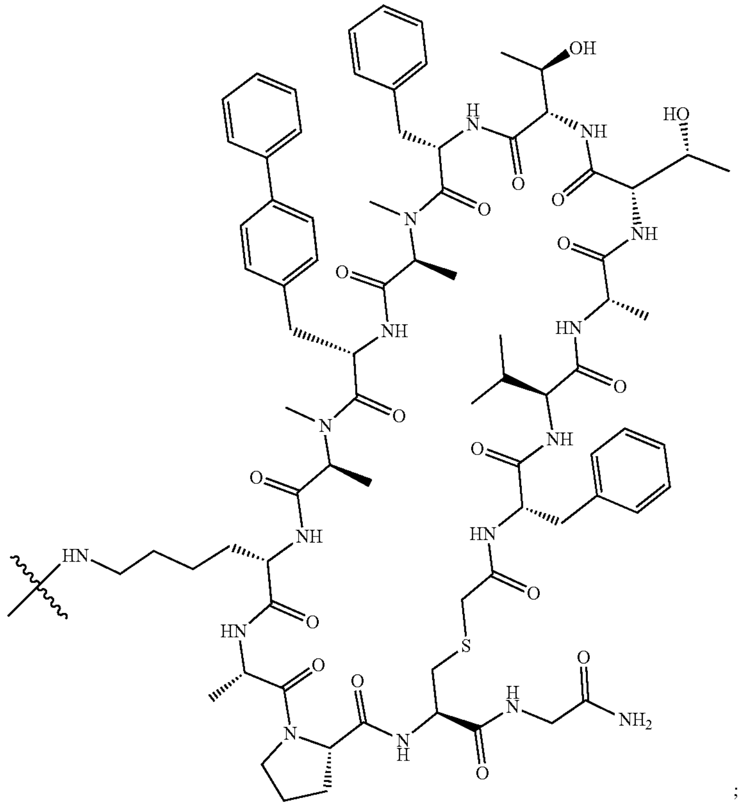
; and
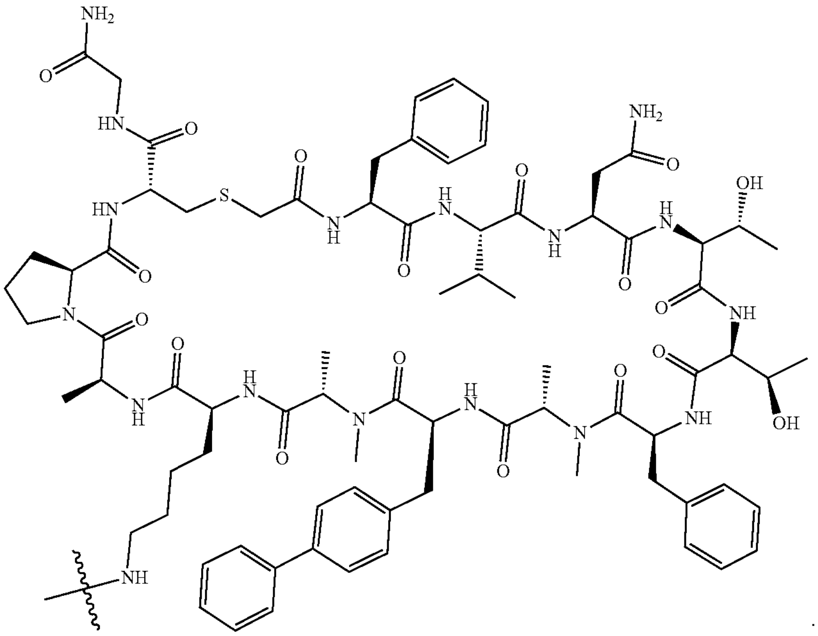 [SMILES: *NCCCC[C@@H]1NC(=O)[C@H](C)N(C)C(=O)[C@H](Cc2ccc(-c3ccccc3)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](CC(N)=O)NC(=O)[C@H](C(C)C)NC(=O)[C@H](Cc2ccccc2)NC(=O)CSC[C@@H](C(=O)NCC(N)=O)NC(=O)[C@@H]2CCCN2C(=O)[C@H](C)NC1=O]
.

Embodiment 42. The bifunctional compound of any one of Embodiments 4 to 38, wherein $T_L$ is

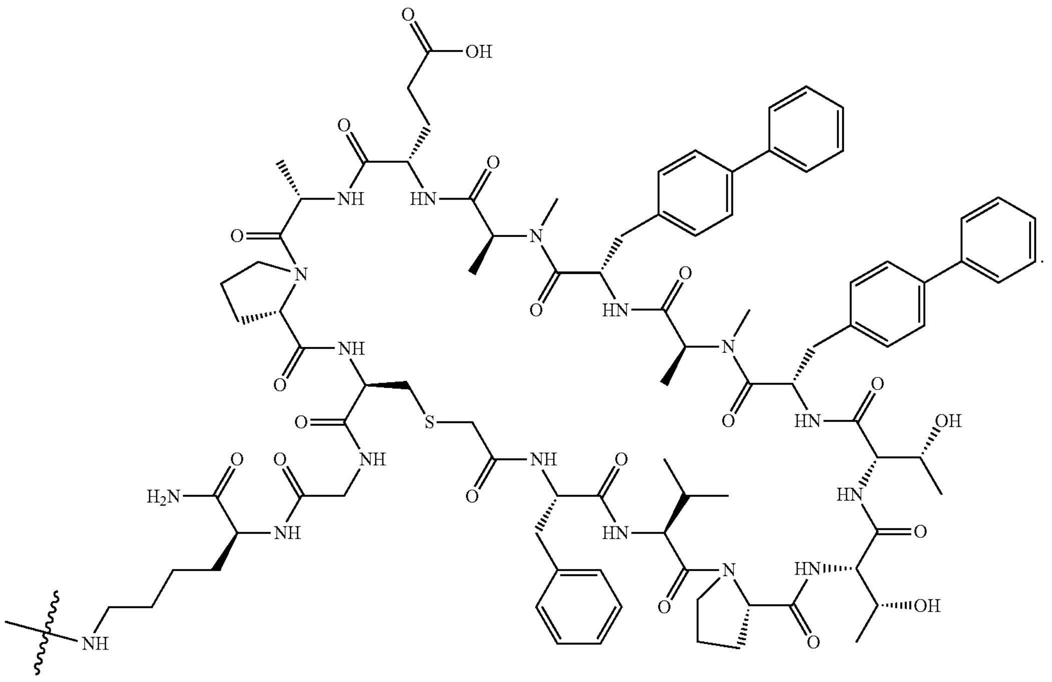 [SMILES: *NCCCC[C@H](NC(=O)CNC(=O)[C@@H]1CSCC(=O)N[C@@H](Cc2ccccc2)C(=O)N[C@@H](C(C)C)C(=O)N2CCC[C@H]2C(=O)N[C@@H]([C@@H](C)O)C(=O)N[C@@H]([C@@H](C)O)C(=O)N[C@@H](Cc2ccc(-c3ccccc3)cc2)C(=O)N(C)[C@@H](C)C(=O)N[C@@H](Cc2ccc(-c3ccccc3)cc2)C(=O)N(C)[C@@H](C)C(=O)N[C@@H](CCC(=O)O)C(=O)N[C@@H](C)C(=O)N2CCC[C@H]2C(=O)N1)C(N)=O]

Embodiment 43. The bifunctional compound of Formula (I), or any one of Embodiments 1 to 3, wherein $T_L$ is a compound of Formula (B), or a pharmaceutically acceptable salt or stereoisomer thereof, which bind to PCSK9:

Formula (B)

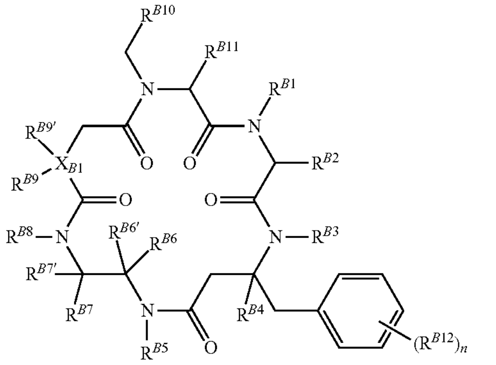

wherein:

$X_{B1}$ is C or N;

$R^{B1}$ is H, $(C_1$-$C_6)$alkyl, or $(C_1$-$C_6)$haloalkyl;

or $R^{B1}$ and $R^{B11}$ together with the atoms to which they are attached form a 5- to 7-membered heterocyclyl ring comprising 1-3 heteroatoms selected from N, O, and S optionally substituted with one or more substituents each independently selected from =(O), $(C_1$-$C_6)$alkyl, and $(C_1$-$C_6)$haloalkyl;

$R^{B2}$ is $(C_1$-$C_6)$alkoxy, $(C_1$-$C_6)$alkyl, -$L^{B1}$-, $(C_1$-$C_6)$haloalkyl, $(C_1$-$C_6)$hydroxyalkyl, $(C_3$-$C_7)$cycloalkyl, or 4- to 7-membered heterocyclyl comprising 1-3 heteroatoms selected from N, O, and S, wherein the alkyl is optionally substituted with one or more substituents each independently selected from $(C_1$-$C_6)$alkoxy, $(C_1$-$C_6)$haloalkoxy, —C(=O)$(C_1$-$C_6)$alkyl, —C(=O)OH, —C(=O)O$(C_1$-$C_6)$alkyl, —OC(=O)$(C_1$-$C_6)$alkyl, —C(=O)$NR^{B17}R^{B18}$, —$NR^{B17}$C(=O)$R^{B18}$, $(C_6$-$C_{10})$aryl, and 5- or 6-membered heteroaryl comprising 1-4 heteroatoms selected from N, O, and S;

$R^{B3}$ is H, $(C_1$-$C_6)$alkyl, or $(C_1$-$C_6)$haloalkyl;

$R^{B4}$ is H, $(C_1$-$C_6)$alkyl, or $(C_1$-$C_6)$haloalkyl;

$R^{B5}$ is H, $(C_1$-$C_6)$alkyl, or $(C_1$-$C_6)$haloalkyl;

$R^{B6}$ is H, $(C_1$-$C_6)$alkyl, -$L^{B1}$-, $(C_1$-$C_6)$haloalkyl, or $(C_1$-$C_6)$hydroxyalkyl, wherein the alkyl is optionally substituted with one or more substituents each independently selected from $(C_1$-$C_6)$alkoxy, —C(=O)OH, —C(=O)O$(C_1$-$C_6)$alkyl, —$NR^{B17}R^{B18}$, —C(=O)$NR^{B17}R^{B18}$, —$NR^{B17}$C(=O)$R^{B18}$, $(C_3$-$C_7)$cycloalkyl, and 4- to 7-membered heterocyclyl comprising 1-3 heteroatoms selected from N, O, and S;

$R^{B6'}$ is H, $(C_1$-$C_6)$alkyl, -$L^{B1}$-, $(C_1$-$C_6)$haloalkyl, or $(C_1$-$C_6)$hydroxyalkyl, wherein the alkyl is optionally substituted with one or more substituents each independently selected from $(C_1$-$C_6)$alkoxy, —C(=O)OH, —C(=O)O$(C_1$-$C_6)$alkyl, —$NR^{B17}R^{B18}$, —C(=O)$NR^{B17}R^{B18}$, —$NR^{B17}$C(=O)$R^{B18}$, $(C_3$-$C_7)$cycloalkyl, and 4- to 7-membered heterocyclyl comprising 1-3 heteroatoms selected from N, O, and S;

$R^{B7}$ is H, $(C_1$-$C_6)$alkyl, -$L^{B1}$-, $(C_1$-$C_6)$haloalkyl, or $(C_1$-$C_6)$hydroxyalkyl, wherein the alkyl is optionally substituted with one or more substituents each independently selected from $(C_1$-$C_6)$alkoxy, —C(=O)OH, —C(=O)O$(C_1$-$C_6)$alkyl, —$NR^{B17}R^{B18}$, —C(=O)$NR^{B17}R^{B18}$, —$NR^{B17}$C(=O)$R^{B18}$, $(C_3$-$C_7)$cycloalkyl, and 4- to 7-membered heterocyclyl comprising 1-3 heteroatoms selected from N, O, and S;

$R^{B7'}$ is H, $(C_1$-$C_6)$alkyl, -$L^{B1}$-, $(C_1$-$C_6)$haloalkyl, or $(C_1$-$C_6)$hydroxyalkyl, wherein the alkyl is optionally substituted with one or more substituents each independently selected from $(C_1\text{-}C_6)$alkoxy, —C(═O)OH, —C(═O)O$(C_1\text{-}C_6)$alkyl, —NR$^{B17}$R$^{B18}$, —C(═O)NR$^{B17}$R$^{B18}$, —NR$^{B17}$C(═O)R$^{B18}$, $(C_3\text{-}C_7)$cycloalkyl, and 4- to 7-membered heterocyclyl comprising 1-3 heteroatoms selected from N, O, and S;

or R$^{B6}$ and R$^{B7}$ together with the carbon atoms to which they are attached form a $(C_3\text{-}C_7)$cycloalkyl or a 4- to 7-membered heterocyclyl ring comprising 1-3 heteroatoms selected from N, O, and S;

or R$^{B7}$ and R$^{B7'}$ together with the carbon atom to which they are attached form a $(C_3\text{-}C_7)$cycloalkyl or a 4- to 7-membered heterocyclyl ring comprising 1-3 heteroatoms selected from N, O, and S; or R$^{B7}$ and R$^{B9}$ together with the atoms to which they are attached form a 5- to 7-membered heterocyclyl ring comprising 1-3 heteroatoms selected from N, O, and S optionally substituted with one or more substituents independently selected from $(C_1\text{-}C_6)$alkyl, $(C_1\text{-}C_6)$haloalkyl, and ═(O);

R$^{B8}$ is H or $(C_1\text{-}C_6)$alkyl;

R$^{B9}$ is H, $(C_1\text{-}C_6)$alkyl, $(C_2\text{-}C_6)$alkenyl, $(C_1\text{-}C_6)$haloalkyl, $(C_2\text{-}C_6)$haloalkenyl, $(C_1\text{-}C_6)$alkoxy, $(C_1\text{-}C_6)$haloalkoxy, $(C_1\text{-}C_6)$hydroxyalkyl, $(C_3\text{-}C_7)$cycloalkyl, or 4- to 7-membered heterocyclyl comprising 1-3 heteroatoms selected from N, O, and S, wherein the alkyl is optionally substituted with one or more R$^{B27}$;

R$^{B9'}$ is H, $(C_1\text{-}C_6)$alkyl, $(C_2\text{-}C_6)$alkenyl, $(C_1\text{-}C_6)$haloalkyl, $(C_2\text{-}C_6)$haloalkenyl, $(C_1\text{-}C_6)$alkoxy, $(C_1\text{-}C_6)$haloalkoxy, $(C_1\text{-}C_6)$hydroxyalkyl, $(C_3\text{-}C_7)$cycloalkyl, or 4- to 7-membered heterocyclyl comprising 1-3 heteroatoms selected from N, O, and S, wherein the alkyl is optionally substituted with one or more R$^{B27}$; or R$^{B9'}$ is absent when $X_{B1}$ is N;

or R$^{B9}$ and R$^{B9'}$ together with the carbon atom to which they are attached form a $(C_3\text{-}C_7)$cycloalkyl or a 4- to 7-membered heterocyclyl ring comprising 1-3 heteroatoms selected from N, O, and S;

or R$^{B7}$ and R$^{B9}$ together with the atoms to which they are attached form a 5- to 7-membered heterocyclyl ring comprising 1-3 heteroatoms selected from N, O, and S optionally substituted with one or more substituents independently selected from $(C_1\text{-}C_6)$alkyl, $(C_1\text{-}C_6)$haloalkyl, and ═(O);

R$^{B10}$ is $(C_6\text{-}C_{10})$aryl, 5- or 6-membered heteroaryl comprising 1-3 heteroatoms selected from N, O, and S, $(C_3\text{-}C_7)$cycloalkyl, or 4- to 7-membered heterocyclyl comprising 1-3 heteroatoms selected from N, O, and S, wherein the cycloalkyl, heterocyclyl, aryl and heteroaryl are substituted with —OR$^{B13}$ or —NR$^{B23}$R$^{B13}$, and optionally substituted with one or more R$^{B14}$;

R$^{B11}$ is -L$^{B1}$-, $(C_1\text{-}C_6)$alkyl, $(C_1\text{-}C_6)$haloalkyl, or $(C_1\text{-}C_6)$hydroxyalkyl, wherein the alkyl is optionally substituted with one or more R$^{B15}$;

or R$^{B1}$ and R$^{B11}$ together with the atoms to which they are attached form a 5- to 7-membered heterocyclyl ring comprising 1-3 heteroatoms selected from N, O, and S optionally substituted with one or more substituents each independently selected from ═(O), $(C_1\text{-}C_6)$alkyl, and $(C_1\text{-}C_6)$haloalkyl;

R$^{B12}$ is halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

R$^{B13}$ is $(C_6\text{-}C_{10})$aryl, or 5- or 6-membered heteroaryl comprising 1-3 heteroatoms selected from N, O, and S, wherein the aryl and heteroaryl are substituted with $R_{16}$ and optionally substituted with one or more R$^{B16'}$;

each R$^{B14}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, oxo, —OH, or CN;

or when R$^{B10}$ is cycloalkyl or heterocyclyl, two R$^{B14}$ together, when attached to the same carbon atom, together form ═(O);

each R$^{B15}$ is independently at each occurrence $(C_1\text{-}C_6)$alkoxy, $(C_1\text{-}C_6)$haloalkoxy, —C(═O)R$^{B19}$, S(O)$_q$$(C_1\text{-}C_6)$alkyl, —C(═O)OH, —C(═O)O$(C_1\text{-}C_6)$alkyl, —OC(═O)$(C_1\text{-}C_6)$alkyl, —NR$^{B17}$R$^{B18}$, —C(═O)NR$^{B17}$R$^{B18}$, —NR$^{B17}$C(═O)R$^{B20}$, —NR$^{B17}$C(═O)OR$^{B18}$, $(C_3\text{-}C_7)$cycloalkyl, or 4- to 7-membered heterocyclyl comprising 1-3 heteroatoms selected from N, O, and S, wherein the cycloalkyl and heterocyclyl are optionally substituted with one or more R$^{B21}$;

R$^{B16}$ is —C(═O)NR$^{B31}$R$^{B32}$, $(C_6\text{-}C_{10})$aryl, or 5- to 7-membered heteroaryl comprising 1-3 heteroatoms selected from N, O, and S, wherein the aryl and heteroaryl are optionally substituted with one or more R$^{B26}$;

each R$^{B16'}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

or R$^{B16}$ and R$^{B16'}$ together with the atoms to which they are attached form a 5- to 7-membered heterocyclyl ring optionally substituted with one or more substituents independently selected from ═(O) and R$^{B34}$;

R$^{B17}$ is H or $(C_1\text{-}C_6)$alkyl optionally substituted with one or more substituents each independently selected from $(C_1\text{-}C_6)$alkoxy and —C(═O)O$(C_1\text{-}C_6)$alkyl;

R$^{B18}$ is H or $(C_1\text{-}C_6)$alkyl optionally substituted with one or more substituents each independently selected from $(C_1\text{-}C_6)$alkoxy and —C(═O)O$(C_1\text{-}C_6)$alkyl;

R$^{B19}$ is $(C_3\text{-}C_7)$cycloalkyl or 4- to 7-membered heterocyclyl comprising 1-3 heteroatoms selected from N, O, and S, optionally substituted with one or more R$^{B22}$;

R$^{B20}$ is —$(CH_2CH_2O)_m CH_2CH_2ONH_2$, —$(CH_2CH_2O)_m CH_2CH_2ONH(C_1\text{-}C_6)$alkyl, or $(C_1\text{-}C_6)$alkyl optionally substituted with one or more —NR$^{B23}$C(═O)R$^{B24}$;

each R$^{B21}$ is independently at each occurrence $(C_1\text{-}C_6)$alkyl, $(C_1\text{-}C_6)$alkoxy, $(C_1\text{-}C_6)$haloalkyl, $(C_1\text{-}C_6)$haloalkoxy, halogen, ═(O), or —OH;

each R$^{B22}$ is independently at each occurrence $(C_1\text{-}C_6)$alkyl, $(C_1\text{-}C_6)$haloalkyl, halogen, or —OH;

or two $R_{22}$, when on the same atom, together with the atom to which they are attached form a $(C_3\text{-}C_7)$spirocycloalkyl or a 4- to 7-membered spiroheterocyclyl ring comprising 1-3 heteroatoms selected from N, O, and S;

R$^{B23}$ is H or $(C_1\text{-}C_6)$alkyl;

R$^{B24}$ is H or $(C_1\text{-}C_6)$alkyl optionally substituted with one or more R$^{B25}$;

each R$^{B25}$ is independently at each occurrence $(C_3\text{-}C_7)$cycloalkyl or 4- to 10-membered mono or bicyclic heterocyclyl comprising 1-4 heteroatoms selected from N, O, and S, wherein the cycloalkyl and heterocyclyl are optionally substituted with one or more substituents independently selected from $(C_1\text{-}C_6)$alkyl, $(C_1\text{-}C_6)$haloalkyl, and ═(O);

each R$^{B26}$ is independently at each occurrence $(C_1\text{-}C_6)$alkyl optionally substituted with one or more R$^{B29}$, $(C_2\text{-}C_6)$alkenyl, $(C_2\text{-}C_6)$alkynyl, $(C_1\text{-}C_6)$alkoxy, $(C_1\text{-}C_6)$haloalkyl, $(C_1\text{-}C_6)$haloalkoxy, $(C_1\text{-}C_6)$hydroxyalkyl, —NR$^{B31}$R$^{B32}$, —C(═O)NR$^{B31}$R$^{B32}$, —C(═O)O$(C_1\text{-}C_6)$alkyl, $(C_3\text{-}C_7)$cycloalkyl, 4- to 7-membered heterocyclyl comprising 1-3 heteroatoms selected from N, O, and S, $(C_6\text{-}C_{10})$aryl, or 5- or 6-membered heteroaryl comprising 1-3 heteroatoms selected from N, O, and S, wherein the cycloalkyl, heterocyclyl, aryl and heteroaryl are optionally substituted with one or more substituents each independently selected from $(C_1\text{-}C_6)$alkyl, $(C_1\text{-}C_6)$haloalkyl, —$NH_2$, —N(H)$(C_1\text{-}C_6)$alkyl, —N($(C_1\text{-}C_6)$alkyl$)_2$, —N(H)$(C_1\text{-}C_6)$haloalkyl, —N($(C_1\text{-}C_6)$haloalkyl$)_2$, halogen, and —OH;

or two $R^{B26}$, when on adjacent atoms, together with the atoms to which they are attached form a $(C_3\text{-}C_7)$cycloalkyl or a 4- to 7-membered heterocyclyl ring comprising 1-3 heteroatoms selected from N, O, and S, optionally substituted with one or more $R^{B33}$;

each $R^{B27}$ is independently at each occurrence CN, $(C_6\text{-}C_{10})$aryl, 5- to 7-membered heteroaryl comprising 1-3 heteroatoms selected from N, O, and S, $(C_3\text{-}C_7)$cycloalkyl, or 4- to 7-membered heterocyclyl comprising 1-3 heteroatoms selected from N, O, and S, wherein the aryl, heteroaryl, cycloalkyl and heterocyclyl are optionally substituted with one or more $R^{B28}$;

each $R^{B28}$ is independently at each occurrence $(C_1\text{-}C_6)$alkyl, $(C_1\text{-}C_6)$haloalkyl, $(C_1\text{-}C_6)$alkoxy, $(C_1\text{-}C_6)$haloalkoxy, $(C_1\text{-}C_6)$hydroxyalkyl, halogen, oxo, or CN; or when $R^{B27}$ is cycloalkyl or heterocyclyl, two $R^{B28}$ together with the atoms to which they are attached form a $(C_4\text{-}C_7)$cycloalkyl or a 4- to 7-membered heterocyclyl ring comprising 1-3 heteroatoms selected from N, O, and S;

or when $R^{B27}$ is cycloalkyl or heterocyclyl, two $R^{B28}$ together, when attached to the same carbon atom, together form =(O);

each $R^{B29}$ is independently at each occurrence —$NR^{B31}R^{B32}$ or 4- to 7-membered heterocyclyl comprising 1-3 heteroatoms selected from N, O, and S optionally substituted with one or more $R^{B30}$;

each $R^{B30}$ is independently at each occurrence —OH, halogen, $(C_1\text{-}C_6)$alkyl, or $(C_1\text{-}C_6)$haloalkyl;

or two $R^{B30}$, when on the same atom, together with the atom to which they are attached form a $(C_3\text{-}C_7)$spirocycloalkyl or 4- to 7-membered spiroheterocyclyl ring comprising 1-3 heteroatoms selected from N, O, and S;

each $R^{B31}$ is independently selected from H, $(C_1\text{-}C_6)$alkyl, $(C_1\text{-}C_6)$hydroxyalkyl, $(C_3\text{-}C_7)$ cycloalkyl, or 4- to 7-membered heterocyclyl comprising 1-3 heteroatoms selected from N, O, and S, wherein the alkyl is optionally substituted with one or more D, and the cycloalkyl and heterocyclyl are optionally substituted with one or more substituents each independently selected from $(C_1\text{-}C_6)$alkyl, $(C_1\text{-}C_6)$haloalkyl, halogen, and —OH;

each $R^{B32}$ is independently selected from H, $(C_1\text{-}C_6)$alkyl, $(C_1\text{-}C_6)$hydroxyalkyl, $(C_3\text{-}C_7)$ cycloalkyl, and 4- to 7-membered heterocyclyl comprising 1-3 heteroatoms selected from N, O, and S, wherein the alkyl is optionally substituted with one or more D, and the cycloalkyl and heterocyclyl are optionally substituted with one or more substituents each independently selected from $(C_1\text{-}C_6)$alkyl, $(C_1\text{-}C_6)$haloalkyl, halogen, and —OH;

each $R^{B33}$ is independently at each occurrence $(C_1\text{-}C_6)$alkyl, $(C_1\text{-}C_6)$haloalkyl, or —C(=O)R, wherein R is $(C_1\text{-}C_6)$haloalkyl, $(C_3\text{-}C_7)$cycloalkyl, 4- to 7-membered heterocyclyl comprising 1-3 heteroatoms selected from N, O, and S, or $(C_1\text{-}C_6)$alkyl optionally substituted with one or more $(C_1\text{-}C_6)$alkoxy;

or two $R^{B33}$, when on the same atom, together with the atom to which they are attached form a $(C_3\text{-}C_7)$spirocycloalkyl or a 4- to 7-membered spiroheterocyclyl ring comprising 1-3 heteroatoms selected from N, O, and S;

each $R^{B34}$ is independently at each occurrence $(C_3\text{-}C_7)$cycloalkyl or 4- to 10-membered mono or bicyclic heterocyclyl comprising 1-4 heteroatoms selected from N, O, and S, wherein the cycloalkyl and heterocyclyl are optionally substituted with $(C_1\text{-}C_6)$alkyl optionally substituted with one or more substituents each independently selected from $(C_3\text{-}C_7)$cycloalkyl and 4- to 10-membered mono or bicyclic heterocyclyl comprising 1-4 heteroatoms selected from N, O, and S;

$L^{B1}$ is —$(CH_2)_p$NH—*, where the * of $L^{B1}$ indicates the point of attachment to Linker ($L_A$), and where at least one of $R^{B11}$, $R^{B2}$, $R^{B6}$ or $R^{B7}$ is -$L^{B1}$-;

m is an integer selected from 1 to 13;

n is 1, 2, 3, or 4;

q is 0, 1, or 2, and p is 1, 2, 3, 4, 5 or 6.

Embodiment 44. The bifunctional compound of Embodiment 43, wherein $X_{B1}$ is C;

$R^{B1}$ is H;

$R^{B2}$ is $(C_1\text{-}C_6)$alkoxy, -$L^{B1}$-, or $(C_1\text{-}C_6)$alkyl, substituted with —C(=O)OH;

$R^{B3}$ is H or $(C_1\text{-}C_6)$alkyl;

$R^{B4}$ is H or $(C_1\text{-}C_6)$alkyl;

$R^{B5}$ is H or $(C_1\text{-}C_6)$alkyl;

$R^{B6}$ is H, $(C_1\text{-}C_6)$alkyl or -$L^{B1}$-;

$R^{B6'}$ is H;

$R^{B7}$ is H, $(C_1\text{-}C_6)$alkyl or -$L^{B1}$-; $R^{B7'}$ is H;

or $R^{B6}$ and $R^{B7}$ together with the carbon atoms to which they are attached form a $(C_3\text{-}C_7)$cycloalkyl;

$R^{B8}$ is H or $(C_1\text{-}C_6)$alkyl;

$R^{B9}$ is H or $(C_1\text{-}C_6)$alkyl optionally substituted with one or more $R^{B27}$;

$R^{B9'}$ is H or $(C_1\text{-}C_6)$alkyl;

$R^{B10}$ is $(C_6\text{-}C_{10})$aryl substituted with —$OR^{B13}$ and optionally substituted with one or more $R^{B14}$.

$R^{B11}$ is -$L^{B1}$- or $(C_1\text{-}C_6)$alkyl;

$R^{B12}$ is halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

$R^{B13}$ is $(C_6\text{-}C_{10})$aryl substituted with $R_{16}$ and optionally substituted with one or more $R^{B16'}$;

each $R^{B14}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, oxo, —OH, or CN;

$R^{B16}$ is 5- to 7-membered heteroaryl comprising 1-3 heteroatoms selected from N, O, and S, optionally substituted with one or more $R^{B26}$;

each $R^{B16'}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

each $R^{B26}$ is independently at each occurrence $(C_1\text{-}C_6)$alkyl optionally substituted with one or more $R^{B29}$;

each $R^{B27}$ is independently at each occurrence $(C_6\text{-}C_{10})$aryl;

each $R^{B29}$ is independently at each occurrence —$NR^{B31}R^{B32}$ or 4- to 7-membered heterocyclyl comprising 1-3 heteroatoms selected from N, O, and S;

each $R^{B31}$ is independently selected from H and $(C_1\text{-}C_6)$alkyl;

each $R^{B32}$ is independently selected from H and $(C_1\text{-}C_6)$alkyl; $L^{B1}$ is —$(CH_2)_p$NH—*, where the * of $L^{B1}$ indicates the point of attachment to Linker ($L_A$), and where at least one of $R^{B11}$, $R^{B6}$ or $R^{B7}$ is -$L^{B1}$-;

n is 1; and p is 1, 2, 3, 4, 5 or 6.

Embodiment 45. The bifunctional compound of Embodiment 43, wherein the compound of Formula (B) have the structure of Formula (B-1):

(B-1)

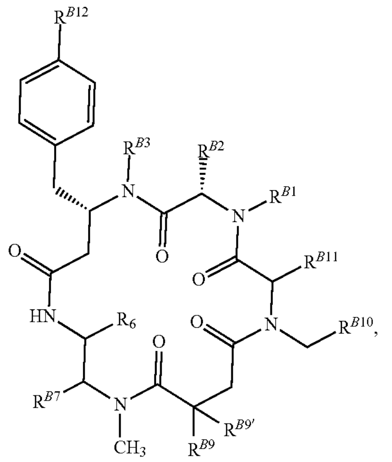

or a pharmaceutically acceptable salt or stereoisomer thereof.

Embodiment 46. The bifunctional compound of any one of Embodiments 43 to 45, wherein $R^{B1}$ is H;

$R^{B2}$ is $(C_1\text{-}C_6)$alkoxy, $\text{-}L^{B1}\text{-}$, or $(C_1\text{-}C_6)$alkyl, substituted with —C(═O)OH;

$R^{B3}$ is H or $(C_1\text{-}C_6)$alkyl;

$R^{B6}$ is H, $(C_1\text{-}C_6)$alkyl or $\text{-}L^{B1}\text{-}$;

$R^{B7}$ is H, $(C_1\text{-}C_6)$alkyl or $\text{-}L^{B1}\text{-}$;

or $R^{B6}$ and $R^{B7}$ together with the carbon atoms to which they are attached form a $(C_3\text{-}C_7)$cycloalkyl;

$R^{B9}$ is H or $(C_1\text{-}C_6)$alkyl optionally substituted with one or more $R^{B27}$;

$R^{B9'}$ is H or $(C_1\text{-}C_6)$alkyl;

$R^{B10}$ is $(C_6\text{-}C_{10})$aryl substituted with —$OR^{B13}$ and optionally substituted with one or more $R^{B14}$.

$R^{B11}$ is $\text{-}L^{B1}\text{-}$ or $(C_1\text{-}C_6)$alkyl;

$R^{B12}$ is halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

$R^{B13}$ is $(C_6\text{-}C_{10})$aryl substituted with $R_{16}$;

each $R^{B14}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, oxo, —OH, or CN;

$R^{B16}$ is 5- to 7-membered heteroaryl comprising 1-3 heteroatoms selected from N, O, and S, optionally substituted with one or more $R^{B26}$;

each $R^{B26}$ is independently at each occurrence $(C_1\text{-}C_6)$alkyl optionally substituted with one or more $R^{B29}$;

each $R^{B27}$ is independently at each occurrence $(C_6\text{-}C_{10})$aryl;

each $R^{B29}$ is independently at each occurrence —$NR^{B31}R^{B32}$ or 4- to 7-membered heterocyclyl comprising 1-3 heteroatoms selected from N, O, and S;

each $R^{B31}$ is independently selected from H and $(C_1\text{-}C_6)$alkyl;

each $R^{B32}$ is independently selected from H and $(C_1\text{-}C_6)$alkyl;

$L^{B1}$ is —$(CH_2)_p$NH—*, where the * of $L^{B1}$ indicates the point of attachment to Linker ($L_A$), and where at least one of $R^{B11}$, $R^{B6}$ or $R^{B7}$ is $\text{-}L^{B1}\text{-}$;

n is 1; and p is 1, 2, 3, 4, 5 or 6.

Embodiment 47. The bifunctional compound of Embodiment 43, wherein $T_L$ is selected from:

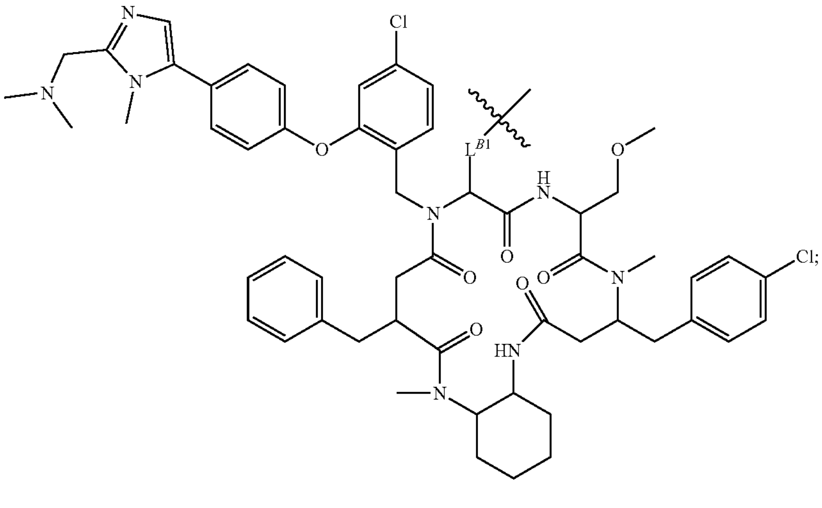

-continued
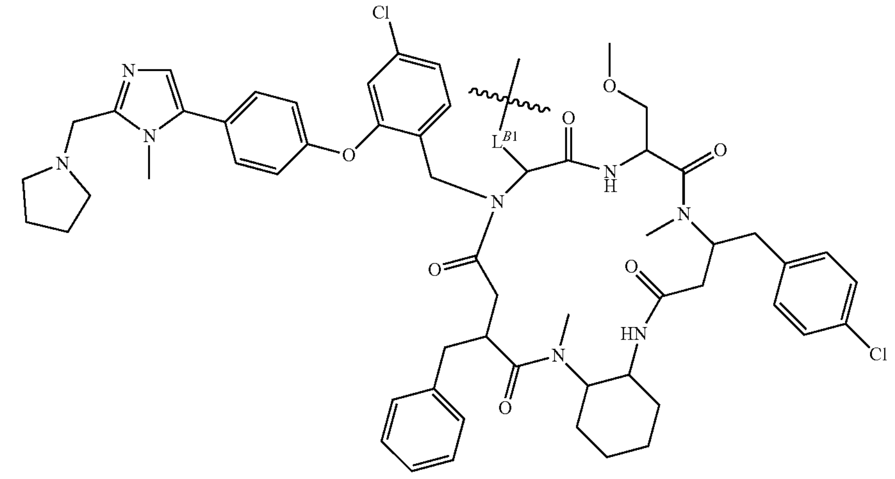
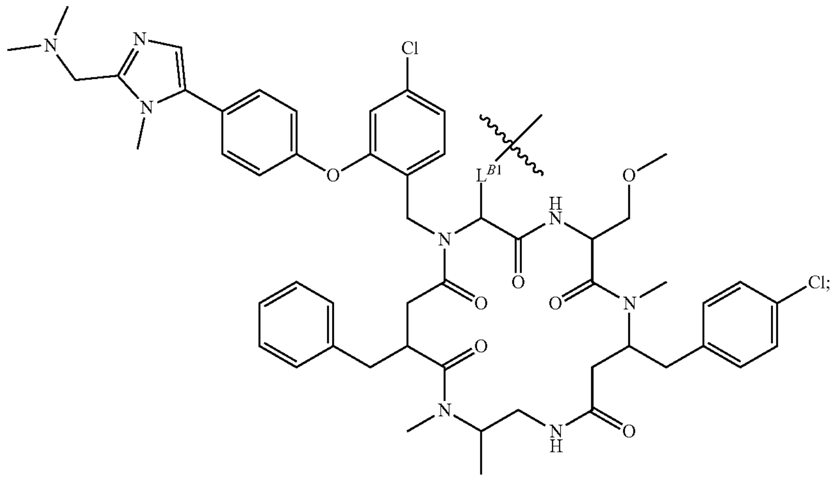
;
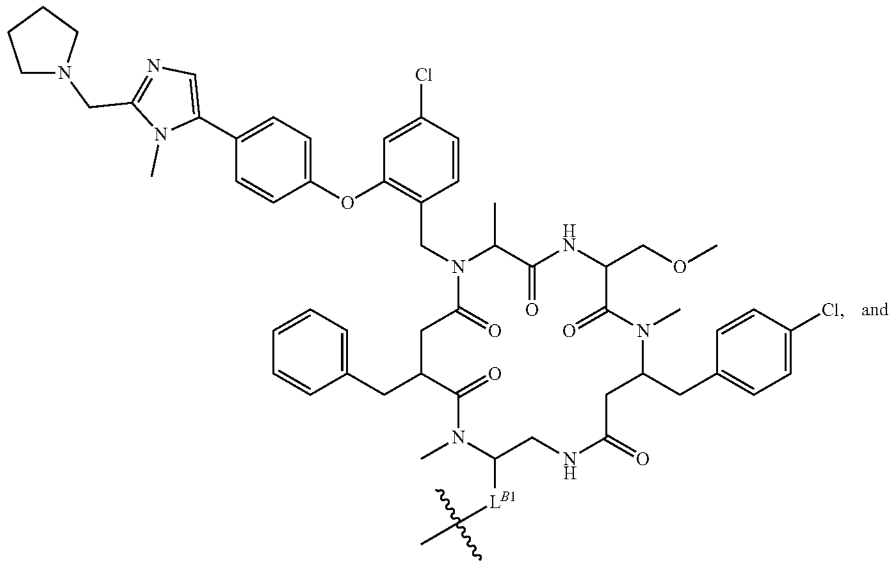
, and

-continued
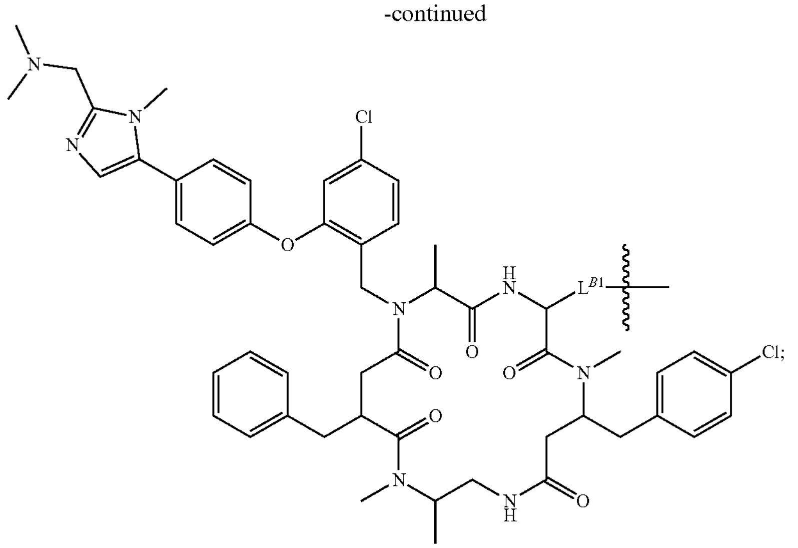
or pharmaceutically acceptable salt or stereoisomer thereof, wherein:
$L^{B1}$ is —$(CH_2)_p$NH—*, where the * of $L^{B1}$ indicates the point of attachment to Linker ($L_A$).
Embodiment 48. The bifunctional compound of any one of Embodiments 43 to 47, wherein $T_L$ is a compound of Formula (B), or pharmaceutically acceptable salts or stereoisomers, selected from:
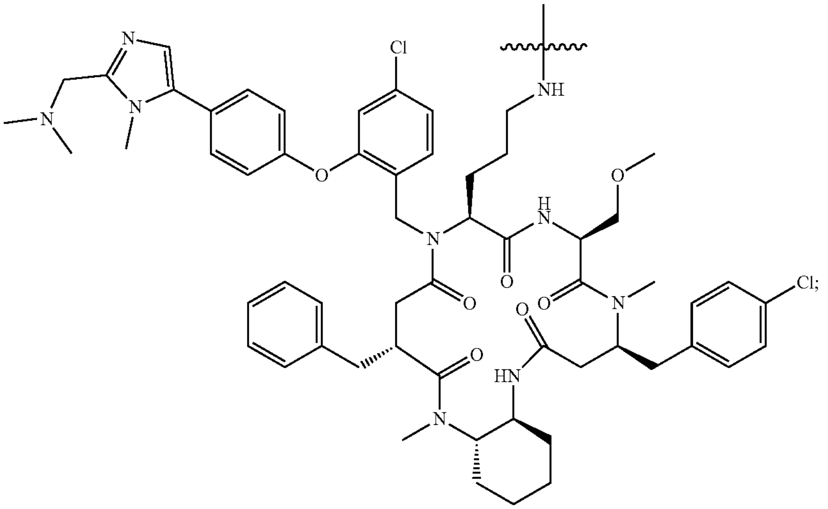
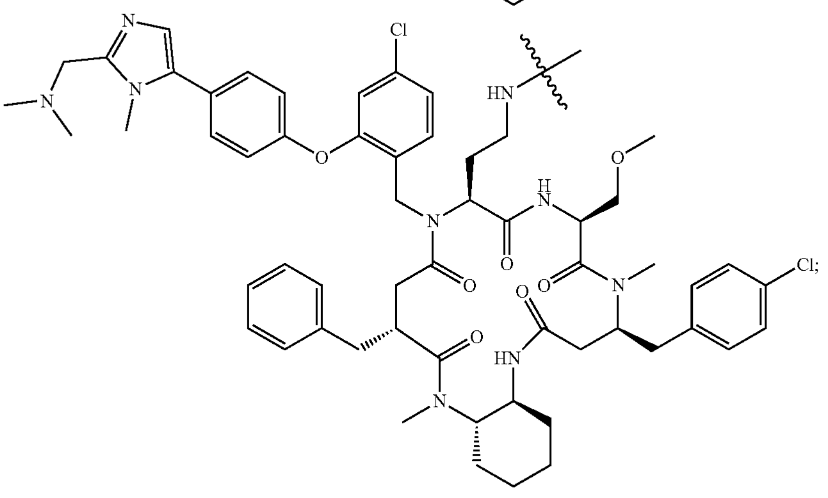

-continued
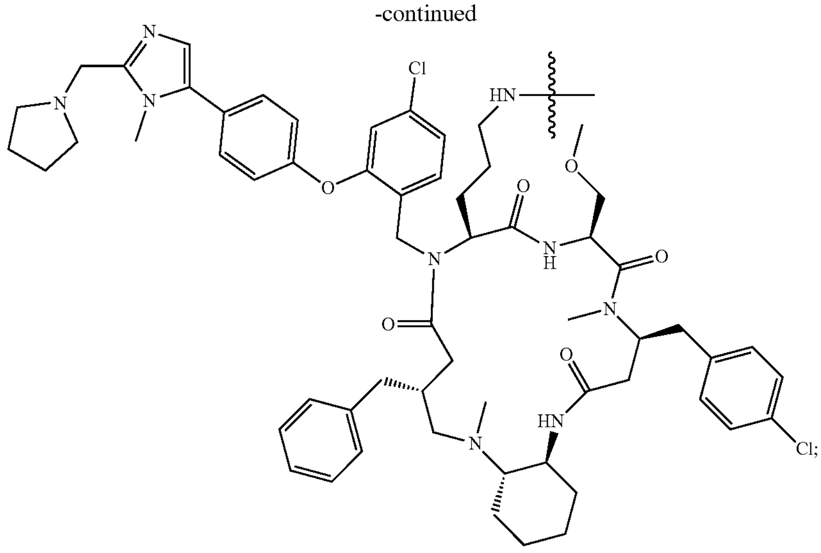
Cl;
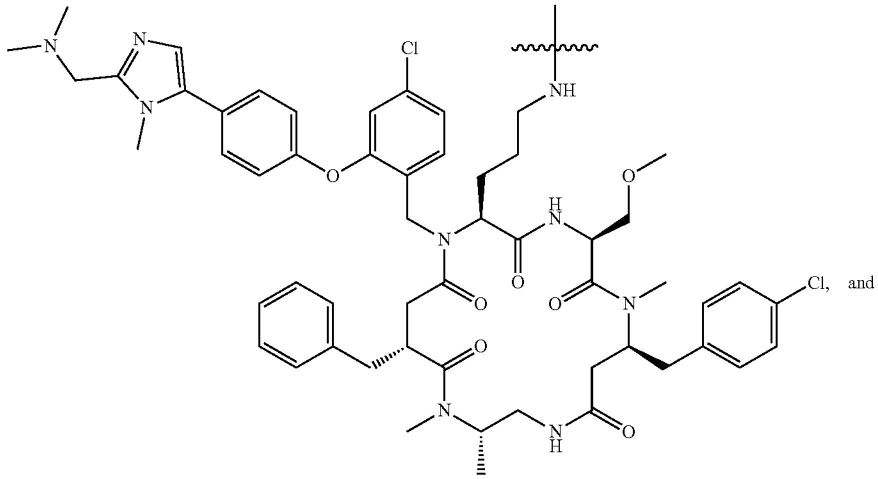
Cl, and
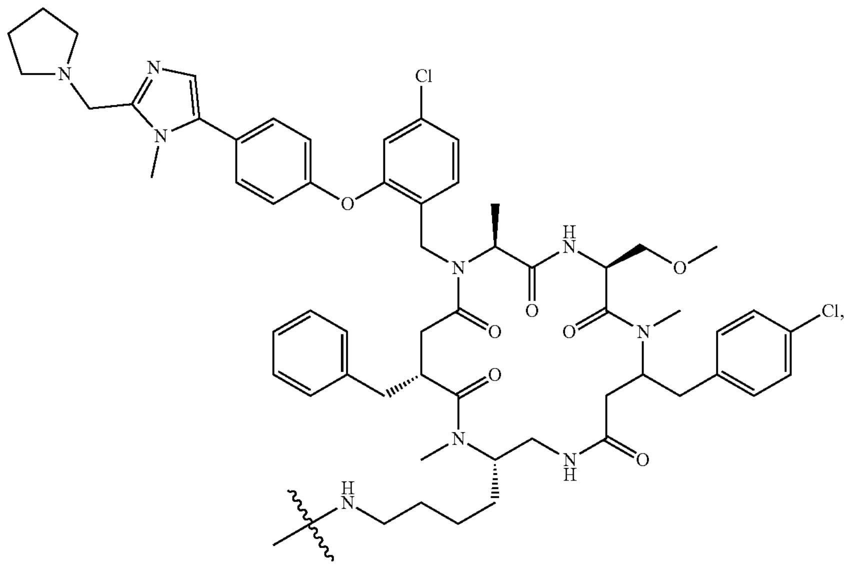
Cl, or a pharmaceutically acceptable salt or stereoisomer thereof.

Embodiment 49. The bifunctional compound of any one of Embodiments 43 to 48, wherein $T_L$ is

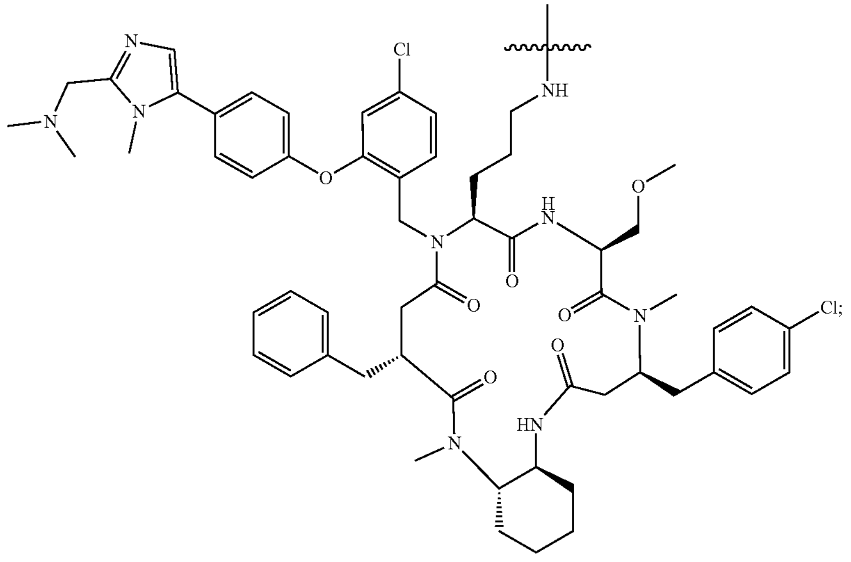 [SMILES: *NCCC[C@H]1C(=O)N[C@@H](COC)C(=O)N(C)[C@@H](Cc2ccc(Cl)cc2)CC(=O)N[C@H]2CCCC[C@@H]2N(C)C(=O)[C@H](Cc2ccccc2)CC(=O)N1Cc1ccc(Cl)cc1Oc1ccc(-c2cnc(CN(C)C)n2C)cc1]

or pharmaceutically acceptable salts or stereoisomers thereof.

Embodiment 50. The bifunctional compound of Formula (I), or any one of Embodiments 1 to 3, wherein $T_L$ is a compound of Formula (C), or a pharmaceutically acceptable salt or stereoisomer thereof, which bind to PCSK9:

Formula (C)

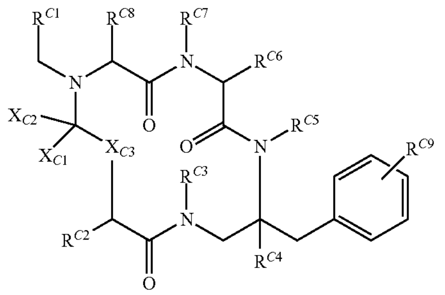

wherein:

$X_{C1}$ is H or $(C_1\text{-}C_6)$alkyl;

$X_{C2}$ is H or $(C_1\text{-}C_6)$alkyl;

or $X_{C1}$ and $X_{C2}$ together with the carbon atom to which they are attached form =(O);

$X_{C3}$ is —$CH_2$— when $X_{C1}$ and $X_{C2}$ are each independently H or $(C_1\text{-}C_6)$alkyl, or $X_{C1}$ and $X_{C2}$ together with the carbon atom to which they are attached form =(O);

or $X_{C3}$ is —O—, —NH— or —$N(C_1\text{-}C_6)$alkyl-, when $X_{C1}$ and $X_{C2}$ together with the carbon atom to which they are attached form =(O);

$R^{C1}$ is $(C_6\text{-}C_{10})$aryl or 5- or 6-membered heteroaryl comprising 1-3 heteroatoms selected from N, O, and S, wherein the aryl and heteroaryl are substituted with —$OR^{C10}$ or —$NR^{C21}R^{C10}$ and optionally substituted with one or more $R^{C1}$;

$R^{C2}$ is H, $(C_1\text{-}C_6)$alkyl, -$L^{C1}$-, $(C_2\text{-}C_6)$alkenyl, $(C_1\text{-}C_6)$haloalkyl, —$NR^{C12}R^{C13}$, $(C_3\text{-}C_9)$carbocyclyl, $(C_3\text{-}C_7)$cycloalkenyl, 5- to 7-membered heterocyclyl comprising 1-3 heteroatoms selected from N, O, and S, $(C_6\text{-}C_{10})$aryl, or 5- or 6-membered heteroaryl comprising 1-3 heteroatoms selected from N, O, and S, wherein the alkyl is optionally substituted with one or more $R^{C18}$, and the carbocyclyl, $(C_3\text{-}C_7)$cycloalkenyl, heterocyclyl, aryl and heteroaryl are optionally substituted with one or more $R^{C19}$ $R^{C3}$ is H, D, $(C_1\text{-}C_6)$alkyl, $(C_1\text{-}C_6)$alkoxy, $(C_1\text{-}C_6)$haloalkyl, $(C_1\text{-}C_6)$haloalkoxy, or $(C_1\text{-}C_6)$hydroxyalkyl, wherein the alkyl is optionally substituted with one or more $R^{C14}$;

$R^{C4}$ is H or $(C_1\text{-}C_6)$alkyl;

or $R^{C3}$ and $R^{C4}$ together with the atoms to which they are attached form a 5- to 7-membered heterocyclyl ring comprising 1-3 heteroatoms selected from N, O, and S;

$R^{C5}$ is H, D, $(C_1\text{-}C_6)$alkyl, $(C_1\text{-}C_6)$alkoxy, $(C_1\text{-}C_6)$haloalkyl, $(C_1\text{-}C_6)$haloalkoxy, or $(C_1\text{-}C_6)$hydroxyalkyl, wherein the $(C_1\text{-}C_6)$alkyl is optionally substituted with one or more D;

$R^{C6}$ is $(C_1\text{-}C_6)$alkyl, $(C_1\text{-}C_6)$alkoxy, -$L^{C1}$-, $(C_1\text{-}C_6)$haloalkyl, $(C_1\text{-}C_6)$haloalkoxy, or $(C_1\text{-}C_6)$hydroxyalkyl, wherein the alkyl is optionally substituted with one or more substituents each independently selected from —OH, $(C_1\text{-}C_6)$alkoxy, $(C_1\text{-}C_6)$haloalkoxy, —$C(O)(C_1\text{-}C_6)$alkyl, —C(O)OH, and —$C(O)O(C_1\text{-}C_6)$alkyl;

$R^{C7}$ is H, D, $(C_1\text{-}C_6)$alkyl, $(C_1\text{-}C_6)$alkoxy, $(C_1\text{-}C_6)$haloalkyl, $(C_1\text{-}C_6)$haloalkoxy, or $(C_1\text{-}C_6)$hydroxyalkyl, wherein the $(C_1\text{-}C_6)$alkyl is optionally substituted with one or more D;

$R^{C8}$ is H, $(C_1\text{-}C_6)$alkyl, -$L^{C1}$- or $(C_1\text{-}C_6)$haloalkyl, wherein the alkyl is optionally substituted with one or more substituents each independently selected from $(C_3\text{-}C_7)$carbocyclyl, 4- to 7-membered heterocyclyl comprising 1-3 heteroatoms selected from N, O, and S, —C(O)OH, —$NR^{C16}R^{C17}$, and —$C(O)NR^{C16}R^{C17}$;

$R^{C9}$ is halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

$R^{C10}$ is $(C_6\text{-}C_{10})$aryl or 5- or 6-membered heteroaryl comprising 1-3 heteroatoms selected from N, O, and S, wherein the aryl and heteroaryl are optionally substituted with one or more $R^{C22}$;

each $R^{C11}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

$R^{C12}$ and $R^{C13}$ are each independently H or $(C_1\text{-}C_6)$alkyl;

each $R^{14}$ is independently at each occurrence D, $NR^{C15}R^{C15'}$, $(C_3\text{-}C_7)$carbocyclyl, or 3- to 7-membered heterocyclyl comprising 1-3 heteroatoms selected from N, O, and S, wherein the carbocyclyl and heterocyclyl are optionally substituted with one or more substituents each independently selected from halogen, $(C_1\text{-}C_6)$alkyl, $(C_1\text{-}C_6)$alkoxy, $(C_1\text{-}C_6)$haloalkyl, and $(C_1\text{-}C_6)$haloalkoxy;

$R^{C15}$ and $R^{C15'}$ are each independently H or $(C_1\text{-}C_6)$alkyl;

$R^{C16}$ and $R^{C17}$ are each independently H or $(C_1\text{-}C_6)$alkyl, or $R^{C16}$ and $R^{C17}$ together with the nitrogen atom to which they are attached form a 4- to 7-membered heterocyclyl ring comprising 1-2 additional heteroatoms selected from N, O, and S;

each $R^{C18}$ is independently at each occurrence $(C_3\text{-}C_7)$carbocyclyl, 5- to 7-membered heterocyclyl comprising 1-3 heteroatoms selected from N, O, and S, $(C_6\text{-}C_{10})$aryl, or 5- or 6-membered heteroaryl comprising 1-3 heteroatoms selected from N, O, and S, wherein the carbocyclyl, heterocyclyl, aryl and heteroaryl are optionally substituted with one or more $R^{C20}$;

each $R^{C19}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

or two $R^{C19}$ together, when on adjacent atoms, form a $(C_6\text{-}C_{10})$aryl or 5- or 6-membered heteroaryl ring comprising 1-3 heteroatoms selected from N, O, and S, wherein the aryl and heteroaryl are optionally substituted with one or more substituents each independently selected from halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, and CN;

each $R^{C20}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, oxo, —OH, or CN; or or when $R^{C18}$ is a carbocyclyl or a heterocyclyl, then two $R^{C20}$, when attached to the same carbon atom, together form =(O);

$R^{C21}$ is H or $(C_1\text{-}C_6)$alkyl;

each $R^{C22}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, CN, $(C_6\text{-}C_{10})$aryl, or 5- or 6-membered heteroaryl comprising 1-3 heteroatoms selected from N, O, and S, wherein the aryl and heteroaryl are optionally substituted with one or more $R^{C23}$;

each $R^{C23}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, $—CH_2(OCH_2CH_2)_nOCH_2CH_3$, —OH, CN, or 4- to 7-membered heterocyclyl comprising 1-3 heteroatoms selected from N, O, and S, wherein the heterocyclyl is optionally substituted with one or more substituents each independently selected from halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, $—C(O)R^{C24}R^{C25}$, $—NR^{C24}C(O)R^{C25}$, $—NH_2$, $—NH(C_1\text{-}C_6)$alkyl, and $—N((C_1\text{-}C_6)$alkyl$)_2$, and the alkyl is optionally substituted with $—NR^{C24}R^{C25}$ or a 4- to 7-membered heterocyclyl comprising 1-3 heteroatoms selected from N, O, and S optionally substituted with one or more substituents each independently selected from halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, $—NH_2$, $—NH(C_1\text{-}C_6)$alkyl, and $—N((C_1\text{-}C_6)$alkyl$)_2$;

$R^{C24}$ is H, $(C_1\text{-}C_6)$alkyl, or $(C_3\text{-}C_7)$carbocyclyl;

$R^{C25}$ is H, $(C_1\text{-}C_6)$alkyl, or $(C_3\text{-}C_7)$carbocyclyl; and $L^{C1}$ is $—(CH_2)_pNH—*$, where the * of $L^{C1}$ indicates the point of attachment to Linker ($L_A$), and where at least one of $R^{C2}$, $R^{C6}$ or $R^{C8}$ is $-L^{C1}-$.

Embodiment 51. The bifunctional compound of Embodiment 50, wherein the compound of Formula (C) have the structure of Formula (C-1):

(C-1)

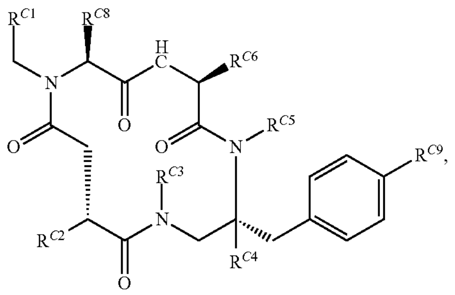

or a pharmaceutically acceptable salt or stereoisomer thereof.

Embodiment 52. The bifunctional compound of Embodiment 50 or Embodiment 51, wherein $X_{C1}$ and $X_{C2}$ together with the carbon atom to which they are attached form =(O);

$X_{C3}$ is $—CH_2—$;

$R^{C1}$ is $(C_6\text{-}C_{10})$aryl substituted with $—OR^{C10}$ and one or more $R^{C11}$;

$R^{C2}$ is H, $(C_1\text{-}C_6)$alkyl, $-L^{C1}-$ or $(C_3\text{-}C_9)$carbocyclyl, wherein the alkyl is substituted with one $R^{C18}$, and the carbocyclyl is substituted with one or more $R^{C19}$;

$R^{C3}$ is H or $(C_1\text{-}C_6)$alkyl;

$R^{C4}$ is H or $(C_1\text{-}C_6)$alkyl;

or $R^{C3}$ and $R^{C4}$ together with the atoms to which they are attached form a 5- to 7-membered heterocyclyl ring comprising 1-3 heteroatoms selected from N, O, and S;

$R^{C5}$ is H or $(C_1\text{-}C_6)$alkyl;

$R^{C6}$ is $(C_1\text{-}C_6)$alkyl or $-L^{C1}-$, wherein the alkyl is optionally substituted with one or more substituents each independently selected from —OH or $(C_1\text{-}C_6)$alkoxy;

$R^{C7}$ is H or $(C_1\text{-}C_6)$alkyl;

$R^{C8}$ is H, $(C_1\text{-}C_6)$alkyl or $-L^{C1}-$;

$R^{C9}$ is halogen;

$R^{C10}$ is $(C_6\text{-}C_{10})$aryl substituted with one $R^{C22}$;

each $R^{C11}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

$R^{C1}$ is $(C_6\text{-}C_{10})$aryl;

each $R^{C19}$ is independently at each occurrence halogen, $(C_1\text{-}C_6)$alkyl, $(C_1\text{-}C_6)$alkoxy, $(C_1\text{-}C_6)$haloalkyl, $(C_1\text{-}C_6)$haloalkoxy, —OH, or CN;

$R^{C22}$ is 5- or 6-membered heteroaryl comprising 1-3 heteroatoms selected from N, O, and S, substituted with one or more $R^{C23}$;

each $R^{C23}$ is independently at each occurrence $(C_1\text{-}C_6)$alkyl optionally substituted with $—NR^{C24}R^{C25}$ or a 4- to 7-membered heterocyclyl comprising 1-3 heteroatoms selected from N, O, and S;

$R^{C24}$ is H, $(C_1\text{-}C_6)$alkyl;

$R^{C25}$ is H, ($C_1$-$C_6$)alkyl, and $L^{C1}$ is —$(CH_2)_p$NH—*, where the * of $L^{C1}$ indicates the point of attachment to Linker ($L_A$), and where at least one of $R^{C2}$, $R^{C6}$ or $R^{C8}$ is -$L^{C1}$-.

Embodiment 53. The bifunctional compound of any one of Embodiments 50 to 52, wherein $R^{C1}$ is ($C_6$-$C_{10}$)aryl substituted with —$OR^{C10}$ and one or more $R^{C11}$;

$R^{C2}$ is ($C_1$-$C_6$)alkyl, -$L^{C1}$- or ($C_3$-$C_9$)carbocyclyl, wherein the alkyl is substituted with one $R^{C18}$, and the carbocyclyl is substituted with one or more $R^{C19}$;

$R^{C3}$ is ($C_1$-$C_6$)alkyl;

$R^{C4}$ is H;

or $R^{C3}$ and $R^{C4}$ together with the atoms to which they are attached form a 5- to 7-membered heterocyclyl ring comprising 1-3 heteroatoms selected from N, O, and S;

$R^{C5}$ is H or ($C_1$-$C_6$)alkyl;

$R^{C6}$ is ($C_1$-$C_6$)alkyl or -$L^{C1}$-, wherein the alkyl is optionally substituted with one or more substituents each independently selected from —OH or ($C_1$-$C_6$)alkoxy;

$R^{C7}$ is H;

$R^{C8}$ is ($C_1$-$C_6$)alkyl or -$L^{C1}$-;

$R^{C9}$ is halogen;

$R^{C10}$ is ($C_6$-$C_{10}$)aryl substituted with one $R^{C22}$;

each $R^{C11}$ is independently at each occurrence halogen;

$R^{C18}$ is ($C_6$-$C_{10}$)aryl;

each $R^{C19}$ is independently at each occurrence ($C_1$-$C_6$) alkyl;

$R^{C22}$ is 5- or 6-membered heteroaryl comprising 1-3 heteroatoms selected from N, O, and S, substituted with one or more $R^{C23}$;

each $R^{C23}$ is independently at each occurrence ($C_1$-$C_6$) alkyl optionally substituted with —$NR^{C24}R^{C25}$ or a 4- to 7-membered heterocyclyl comprising 1-3 heteroatoms selected from N, O, and S;

$R^{C24}$ is ($C_1$-$C_6$)alkyl;

$R^{C25}$ is $C_1$-$C_6$)alkyl, and $L^{C1}$ is —$(CH_2)_p$NH—*, where the * of $L^{C1}$ indicates the point of attachment to Linker ($L_A$), and where at least one of $R^{C2}$, $R^{C6}$ or $R^{C8}$ is -$L^{C1}$-.

Embodiment 54. The bifunctional compound of Embodiment 50, wherein $T_L$ is selected from:

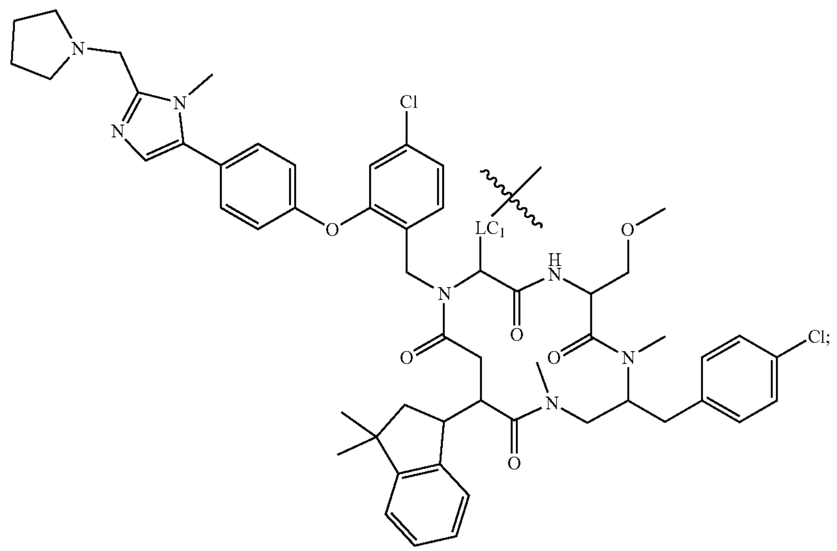

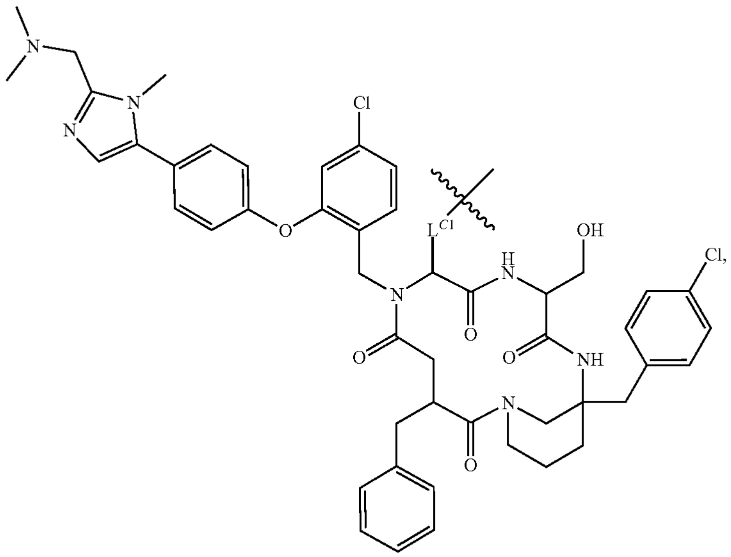

and

-continued

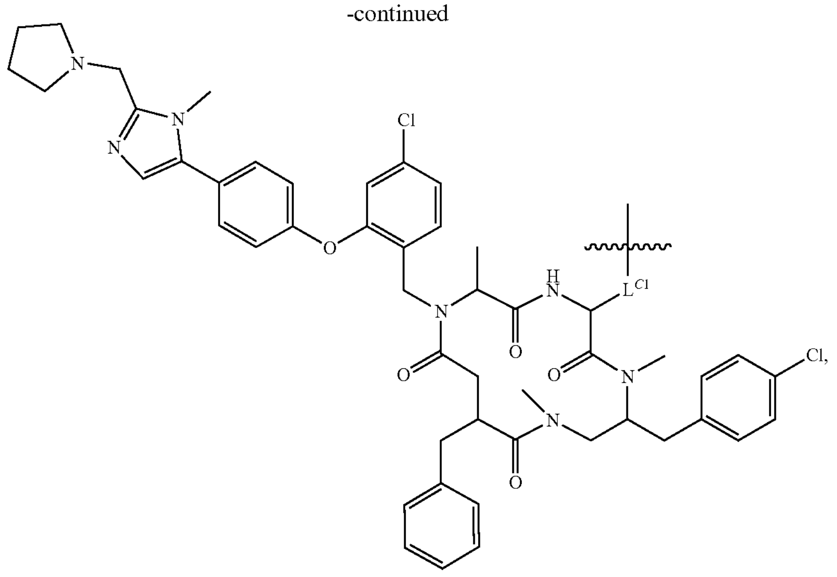

$L^{C1}$ is —$(CH_2)_p$NH—*, where the * of $L^{C1}$ indicates the point of attachment to Linker ($L_A$).

Embodiment 55. The bifunctional compound of any one of Embodiments 50 to 54, wherein $T_L$ is a compound of Formula (C), or pharmaceutically acceptable salts or stereoisomers, selected from:

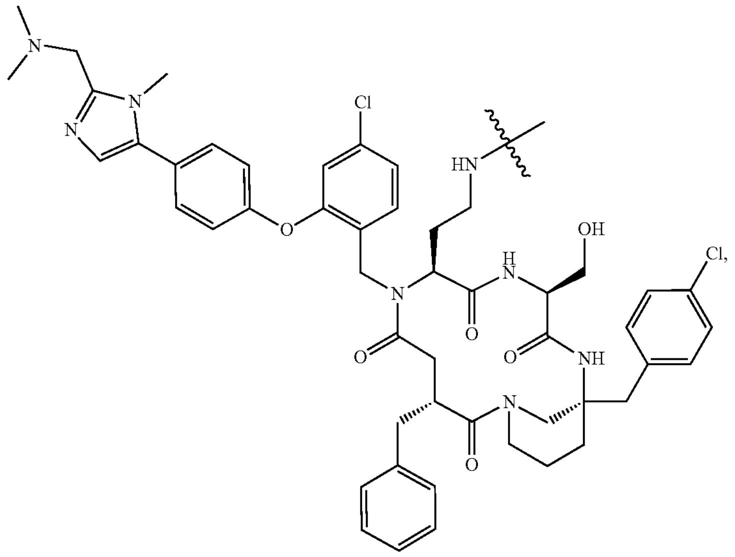 [SMILES: *NCC[C@H]1C(=O)N[C@@H](CO)C(=O)N[C@@]2(Cc3ccc(Cl)cc3)CCCN(C2)C(=O)[C@H](Cc2ccccc2)CC(=O)N1Cc1ccc(Cl)cc1Oc1ccc(-c2cnc(CN(C)C)n2C)cc1]

or a pharmaceutically acceptable salt or stereoisomer thereof.

Embodiment 56. The bifunctional compound of Formula (I), or any one of Embodiments 1 to 2, having the structure of Formula (Ib):

$$R_L\text{-}L_A\text{-}FHR3_L \quad \text{(Ib)}$$

wherein:

$R_L$ is a moiety that binds to a cell surface receptor associated with receptor mediated endocytosis;

$L_A$ is a linker, and $FHR3_L$ is a moiety that binds to FHR3.

Embodiment 57. The bifunctional compound of Formula (I), Formula (Ib), or any one of Embodiments 1 to 2, wherein the moiety that binds to FHR3 and is a compound selected from:
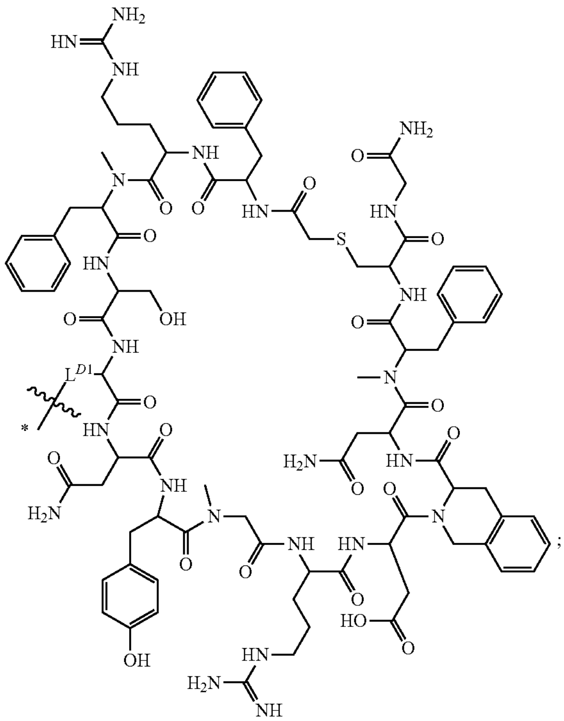
;
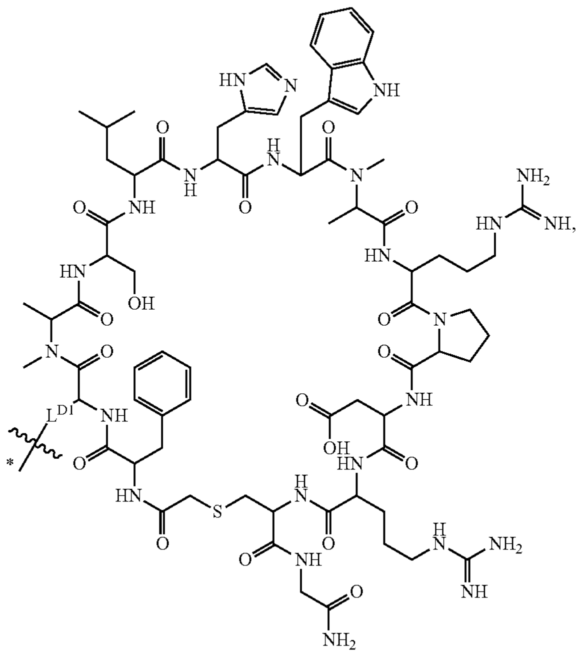
, -continued
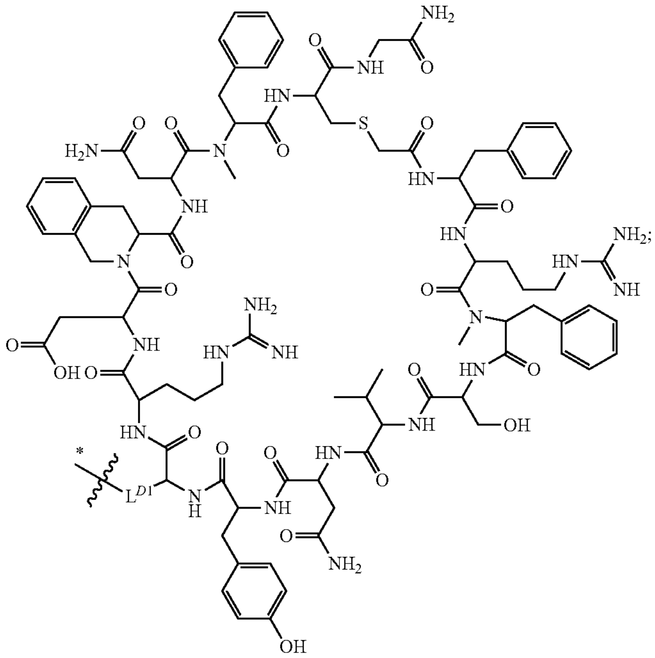
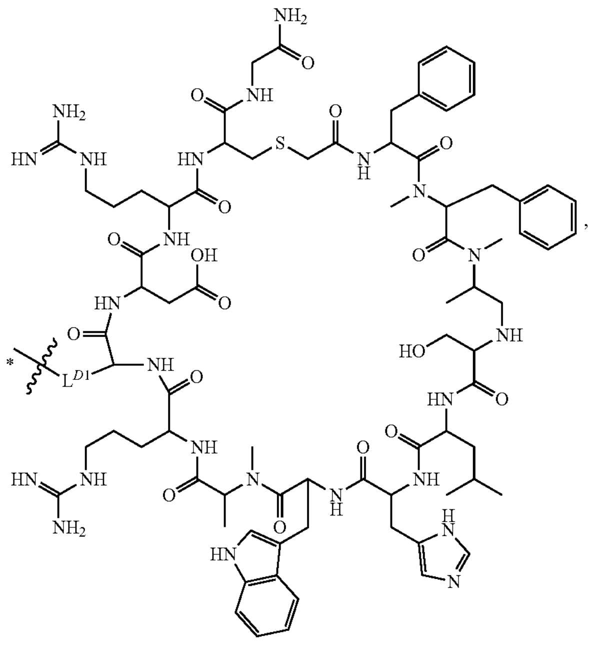
, and -continued
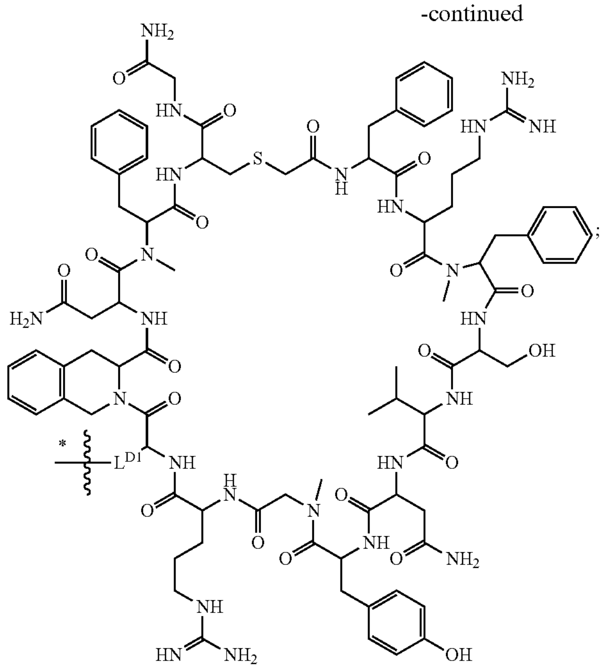
where $L^{D1}$ is —$(CH_2)_p$NH—*, p is 1, 2, 3, 4, 5 or 6, and where the * of $L^{D1}$ indicates the point of attachment to Linker ($L_A$).
Embodiment 58. The bifunctional compound of Embodiment 56 or Embodiment 57, wherein the moiety that binds to FHR3 is a compound or pharmaceutically acceptable salts or stereoisomers, selected from:
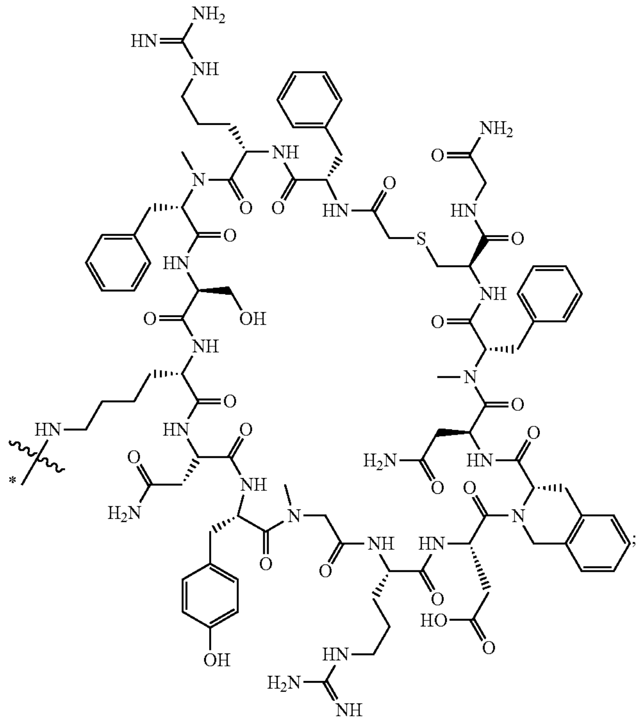

-continued
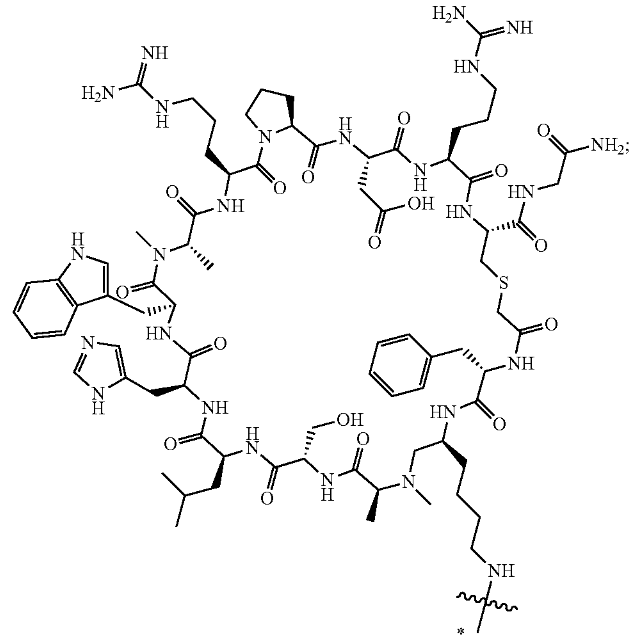
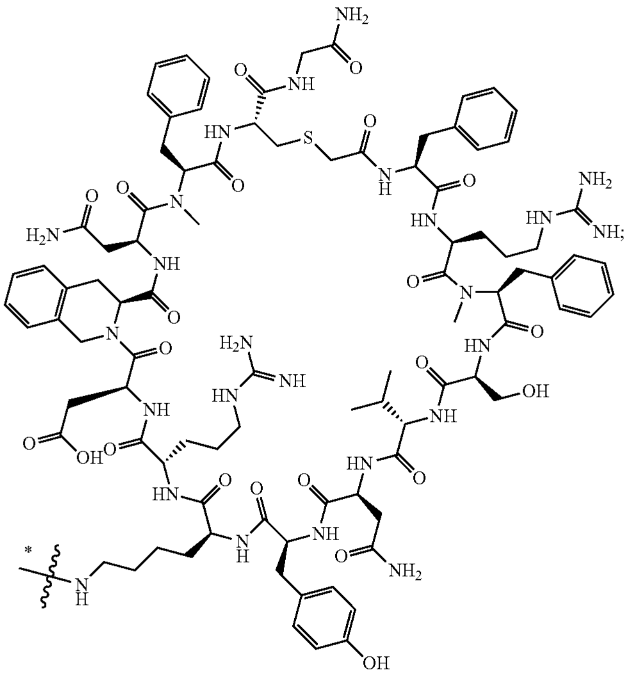

-continued

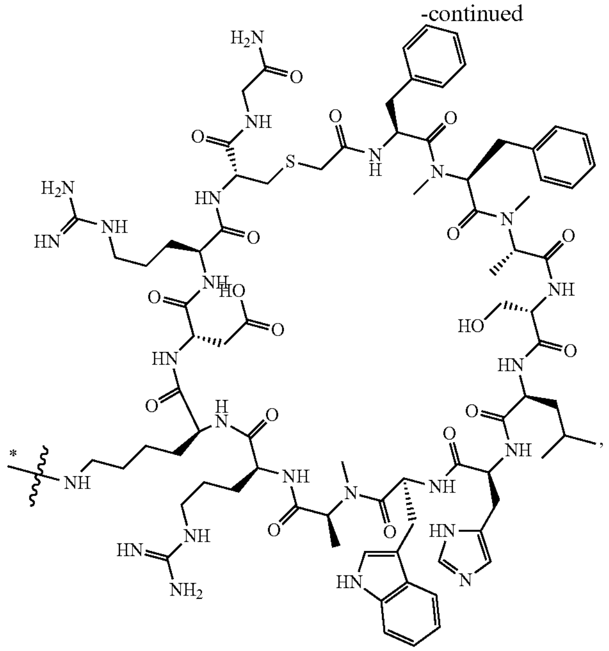

, and

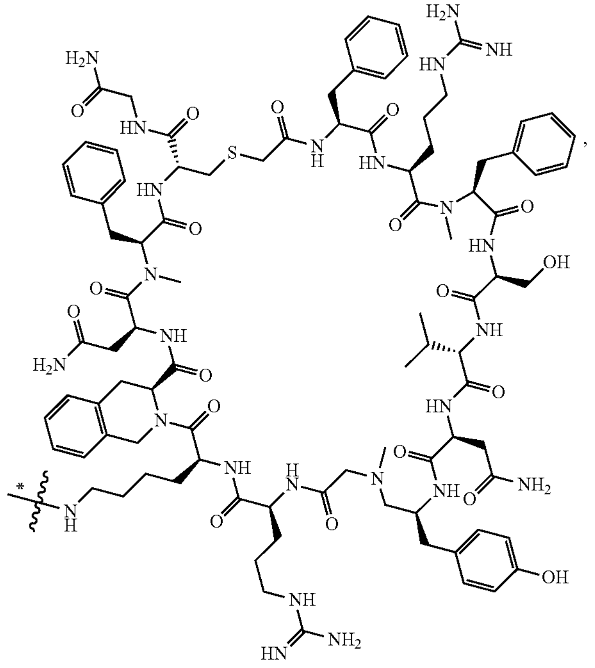 [SMILES: *NCCCC[C@@H]1NC(=O)[C@H](CCCNC(=N)N)NC(=O)CN(C)C[C@H](Cc2ccc(O)cc2)NC(=O)[C@H](CC(N)=O)NC(=O)[C@H](C(C)C)NC(=O)[C@H](CO)NC(=O)[C@H](Cc2ccccc2)N(C)C(=O)[C@H](CCCNC(=N)N)NC(=O)[C@H](Cc2ccccc2)NC(=O)CSC[C@@H](C(=O)NCC(N)=O)NC(=O)[C@H](Cc2ccccc2)N(C)C(=O)[C@H](CC(N)=O)NC(=O)[C@@H]2Cc3ccccc3CN2C1=O]

, where the * indicates the point of attachment to Linker ($L_A$).

B. Receptor Binding Moiety ($R_L$)

The Receptor Binding moiety ($R_L$) is a moiety that binds to a cell surface receptor, where the cell surface receptor is associated with receptor mediated endocytosis. Examples of such cell surface receptors include, but is not limited to, asialoglycoprotein receptor (ASGPR), mannose-6-phosphate receptor (M6PR), the insulin-like growth factor 2 receptor, mannose receptor systems, Kupffer cell receptor, macrophage galactose lectin (MGL), scavenger receptor C-type lectin (SRCL), EGF receptor, the Fc receptor, lysosomal integral membrane protein receptor (LIMP-2), the transferrin receptor, sortilin and decoy receptors (such as CXCR7, DARC, D6 and CCX CKR).

Asialocilycoprotein Receptor (ASGPR)

The asialoglycoprotein receptor (ASGPR) is a C-type lectin expressed on the surface of hepatocytes which regulates levels of plasma glycoproteins terminated with galactose (Gal) or N-acetylgalactosamine (GalNAc) sugars. The ASGPR binds the glycoproteins terminated with galactose (Gal) or N-acetylgalactosamine (GalNAc) sugars and is internalized via receptor mediated endocytosis primarily in coated pits on the basolateral membrane of hepatocytes. Upon internalization, the ligand-receptor complex is transported to endo-lysosomal compartments. Calcium sequestration and subsequent acidification of endosomal compartments promotes dissociation of the ligand-receptor complex, and the receptor is recycled back to the plasma membrane while the cargo (ligand) is sorted to lysosomes for degradation.

Given its ability to efficiently assist in the delivery of glycoproteins terminated with galactose (Gal) or N-acetylgalactosamine (GalNAc) sugars to lysosomes, the asialoglycoprotein receptor (ASGPR) is herein utilized for the degradation of extracellular target molecules (such as growth factors, cytokines, chemokines, hormones, neurotransmitters, capsids, soluble receptors, extracellular secreted proteins, antibodies, lipoproteins, exosomes, viruses, cells and plasma membrane proteins), where the extracellular target molecule is bound to the ($T_L$) group of a bifunctional compound of the invention and the receptor binding moiety ($R_L$) of the bifunctional compound comprises one or more galactose (Gal) groups or one or more N-acetylgalactosamine (GalNAc) groups. Such receptor binding moiety ($R_L$) groups bind to the asialoglycoprotein receptor (ASGPR), whereby the extracellular target molecules are delivered to lysosomes and degraded via lysosomal degradation.

Embodiment 59. The bifunctional compound of Formula (I), or any one of Embodiments 1 to 58, wherein the receptor binding moieties ($R_L$) is selected from:

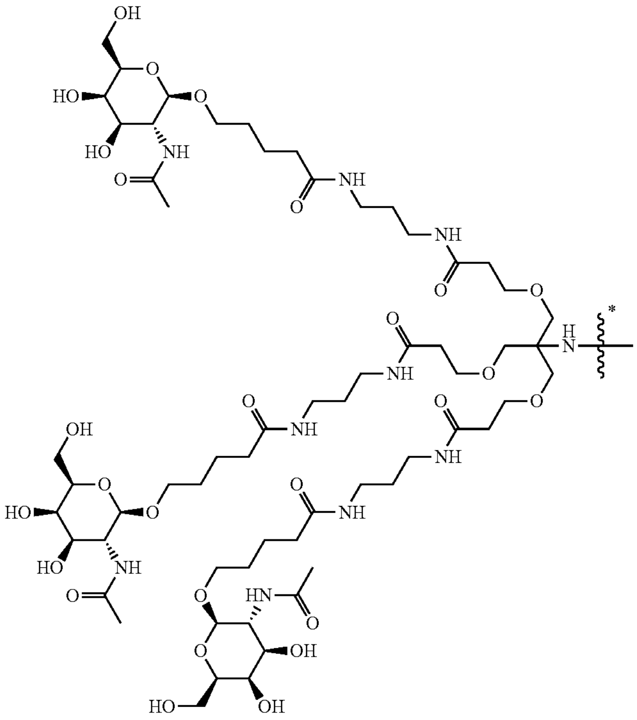
,

-continued
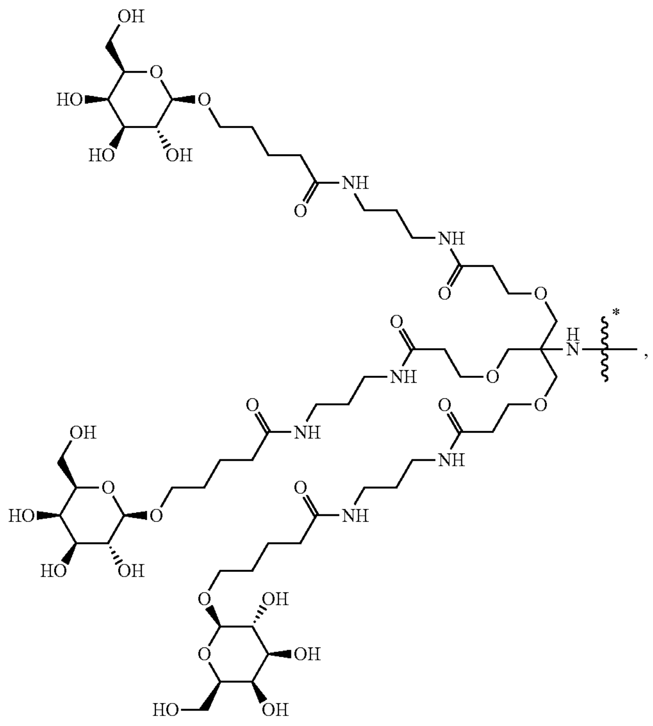
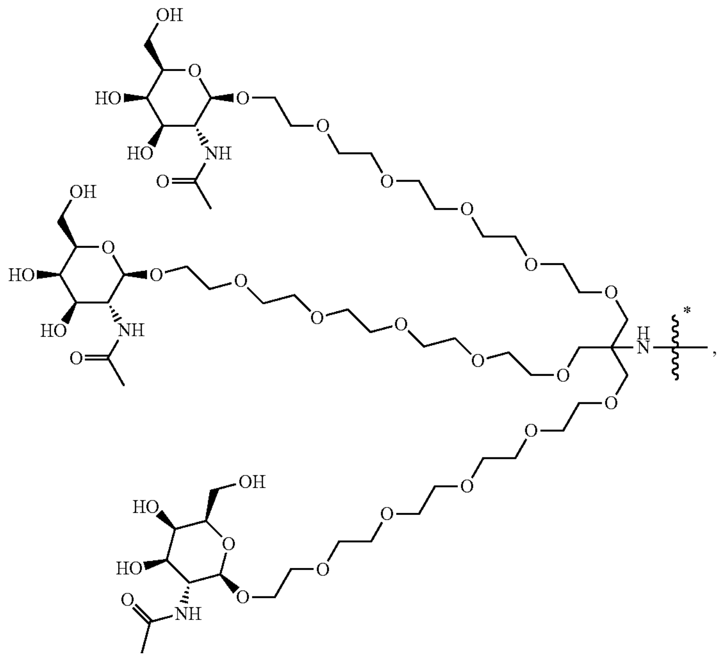

-continued
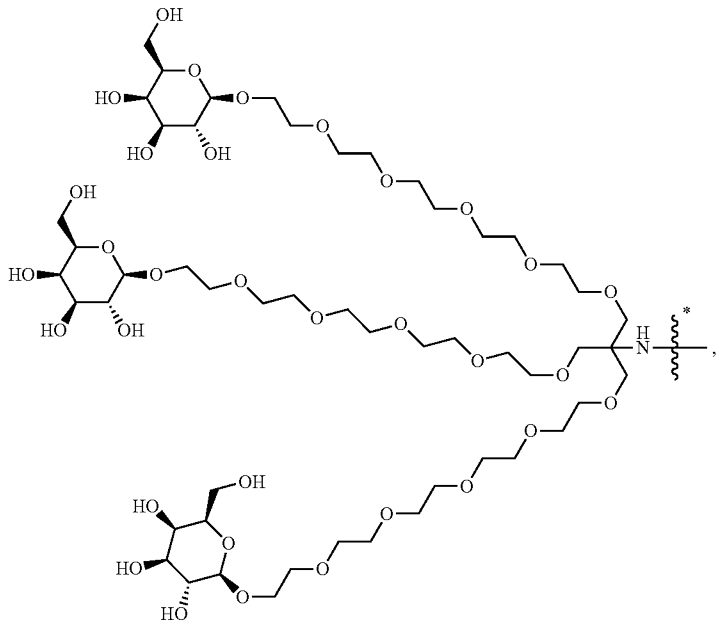
,
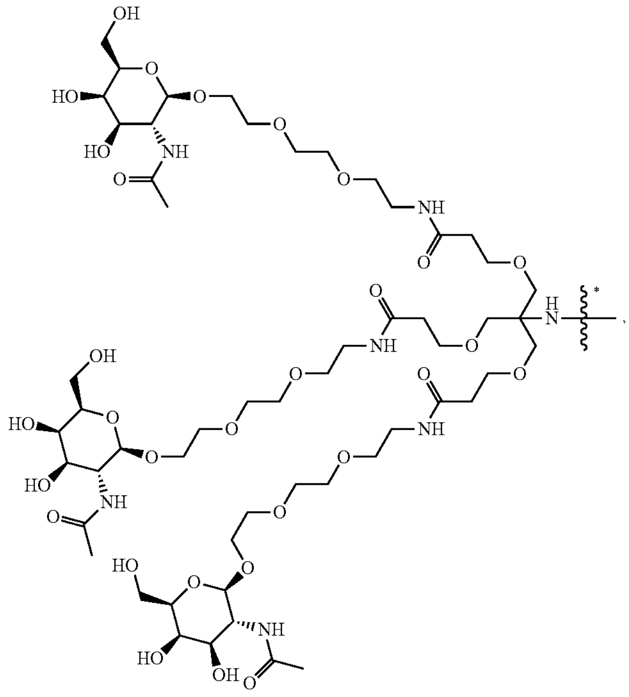
,

-continued
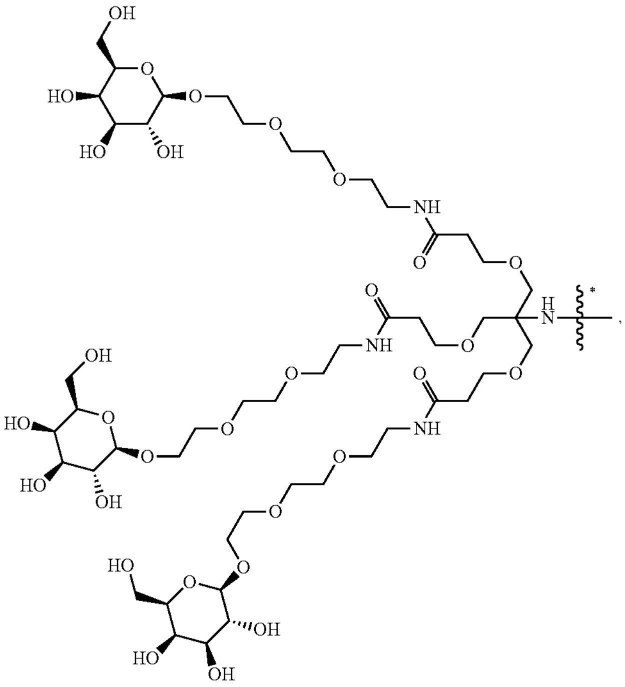
,
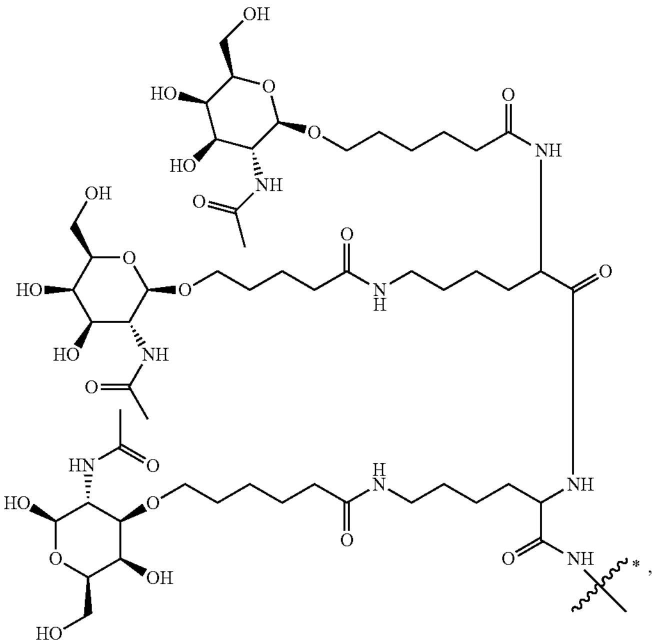
, and

-continued

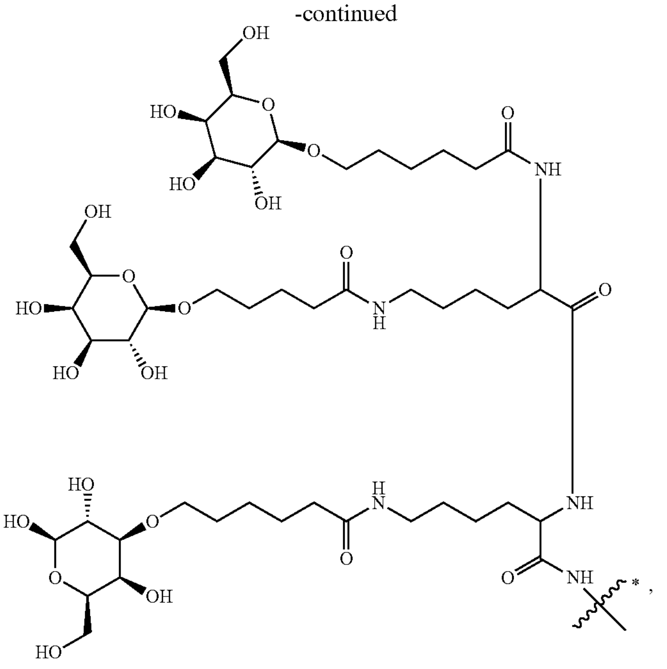

where the * of $R_L$ indicates the point of attachment to Linker ($L_A$).

In other embodiments the receptor binding moiety ($R_L$), of the bifunctional compounds of the invention, comprises one or more galactose (Gal) groups, or one or more N-acetylgalactosamine (GalNAc) groups, where the one or more galactose (Gal) groups, or one or more N-acetylgalactosamine (GalNAc) groups comprise a bridged ketal moiety.

Embodiment 60. The bifunctional compound of Formula (I), or any one of Embodiments 1 to 58, wherein the receptor binding moieties ($R_L$) is selected from:

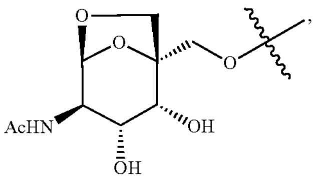

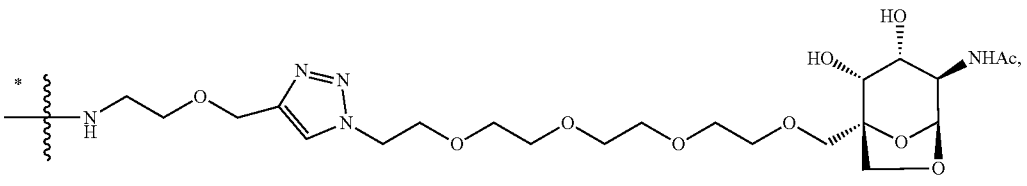

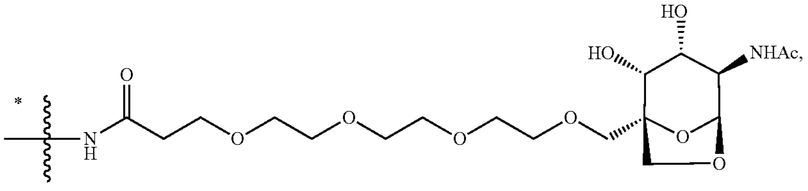

-continued

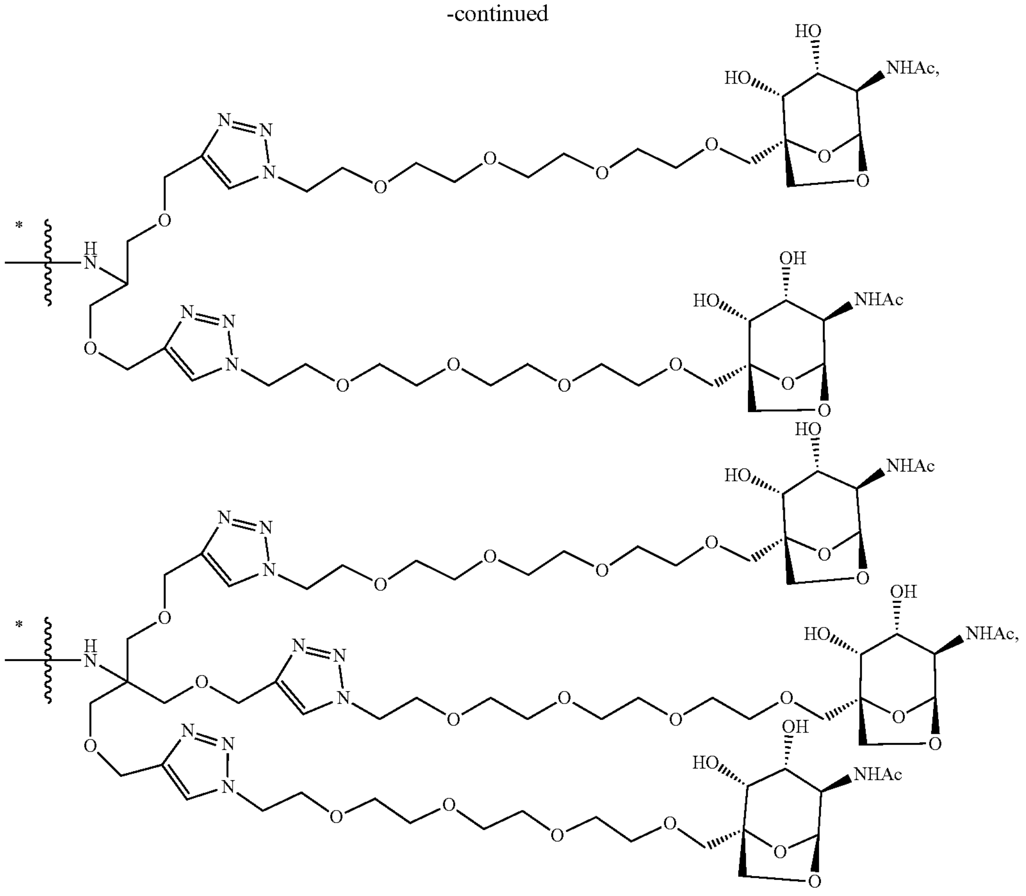

where the * of $R_L$ indicates the point of attachment to Linker ($L_A$).

Mannose-6-Phosphate Receptor (M6PR)—Also Known as Insulin-Like Growth Factor 2 Receptor Lysosomes are membrane delimited organelles with a characteristic acidic pH that are responsible for the degradation of many different substrates in the cell. This catabolic process is carried out by over 60 soluble enzymes that are contained inside the organelle, many of which belong to broad classes of hydrolytic enzymes known as glycosidases, proteases, phosphatases, sulfatases, and lipases. These lysosomal hydrolases are initially synthesized in the rough endoplasmic reticulum and specifically transported through the Golgi apparatus to the trans-Golgi network, and then delivered to the lysosome by transport vesicles.

In order to ensure that the lysosomal hydrolases are concentrated and delivered to the lysosome, the lysosomal hydrolases are tagged with a unique marker: the mannose-6 phosphate (M6P) group. The M6P group is added exclusively to the N-linked oligosaccharides of lysosomal hydrolases, as they move through the cis-Golgi network. The M6P groups are then recognized by two independent transmembrane M6P receptors (MPRs), present in the trans-Golgi network: the cation-independent M6P receptor (CI-MPR, also known as the Insulin-like growth factor 2 receptor (IGF2R)) and/or the cation-dependent M6P receptor (CD-MPR). In the trans-Golgi network, the M6P receptors bind the M6P groups on the tagged lysosomal hydrolases at pH 6.5-6.7 and then help package the hydrolases into transport vesicles for their delivery to late endosomes. The the cation-independent M6P receptor (CI-MPR, also known as the Insulin-like growth factor 2 receptor (IGF2R)) also exists on the cell surface, where it can bind lysosomal enzymes that have escaped the cell, delivering them to the late endosome. Once inside the endosomes, which is typically pH 6, the lysosomal hydrolases dissociate from the MPRs and during endosomal maturation into lysosomes the pH drops to pH 5 where hydrolases begin to digest endocytosed material delivered from early endosomes. Subsequently, the MPRs recycle from the endosome to the cell surface and then back to the Golgi complex.

Given its ability to efficiently assist in the delivery of M6P tagged proteins to lysosomes, the M6P receptors are herein utilized for the degradation of extracellular target molecules (such as growth factors, cytokines, chemokines, hormones, neurotransmitters, capsids, soluble receptors, extracellular secreted proteins, antibodies, lipoproteins, exosomes, viruses, cells and plasma membrane proteins), where the extracellular target molecule is bound to the ($T_L$) group of a bifunctional compound of the invention and the receptor binding moiety ($R_L$) of the bifunctional compound comprises one or more high affinity ligands for the M6P receptor. Such receptor binding moiety ($R_L$) groups bind to the M6P receptor, whereby extracellular target molecules are delivered to lysosomes and degraded via lysosomal degradation.

Embodiment 61. The bifunctional compound of Formula (I), or any one of Embodiments 1 to 58, wherein the receptor binding moieties ($R_L$) is selected from:

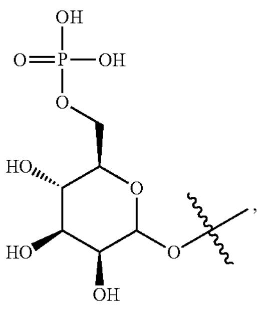,
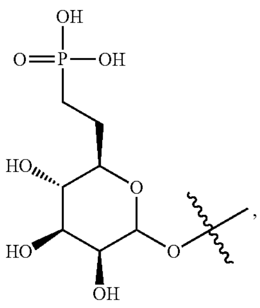,
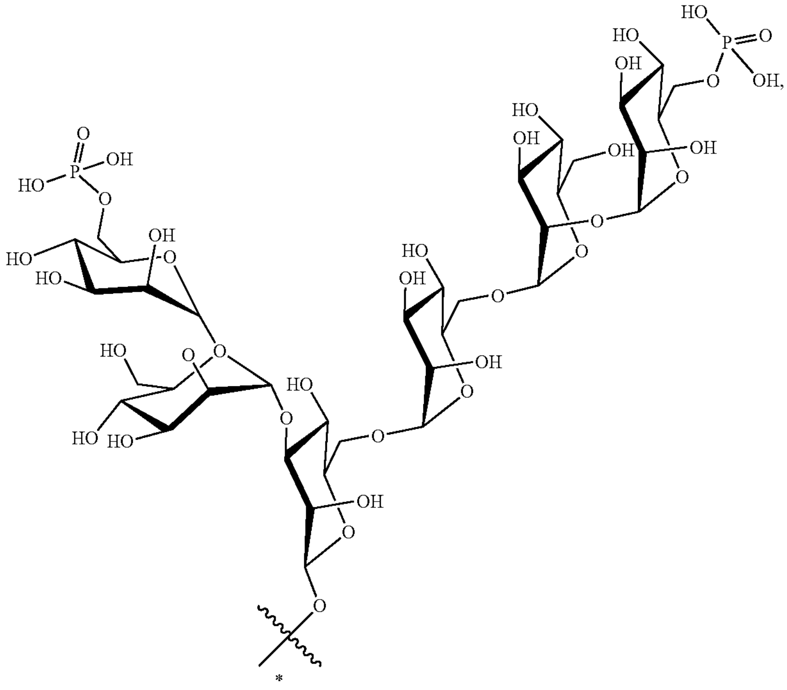,
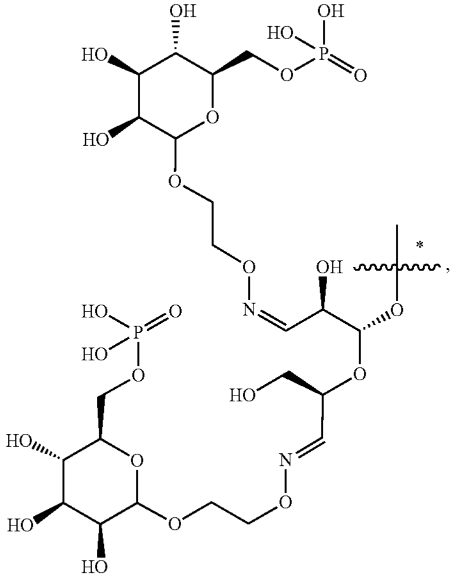,

-continued
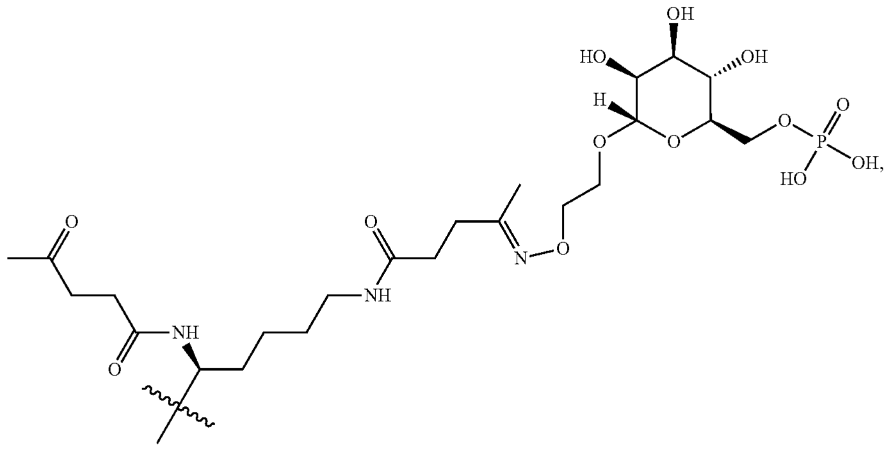
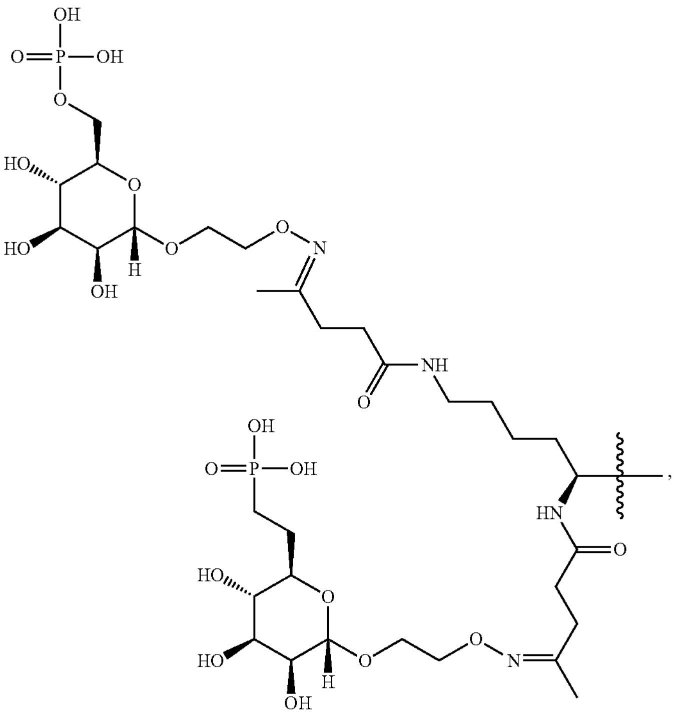
,

-continued
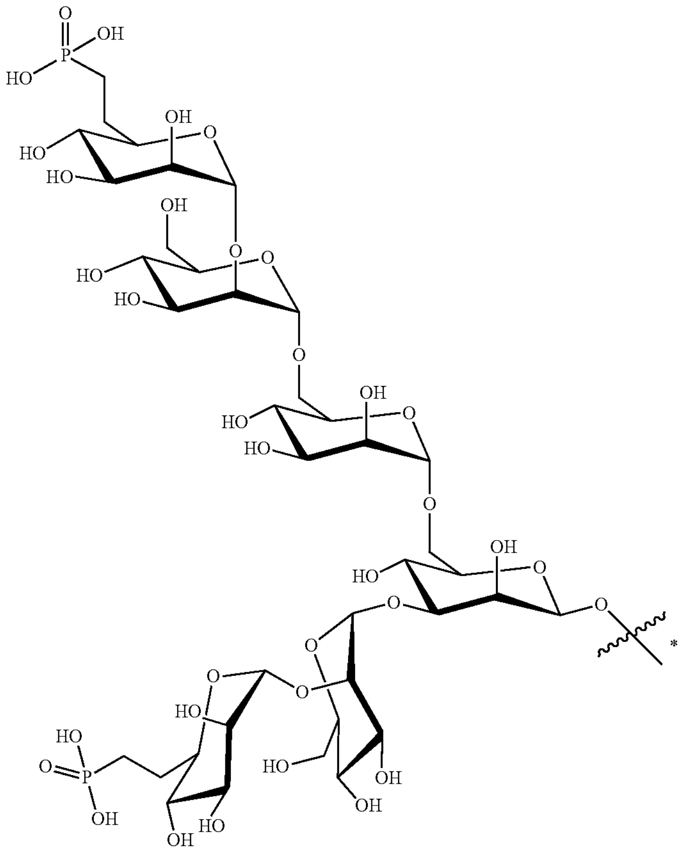
,
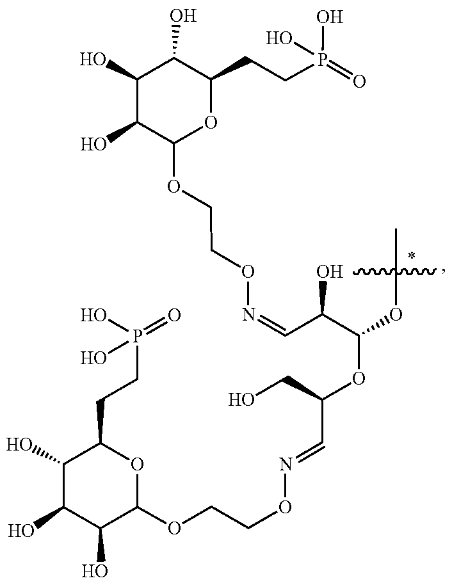
,

-continued

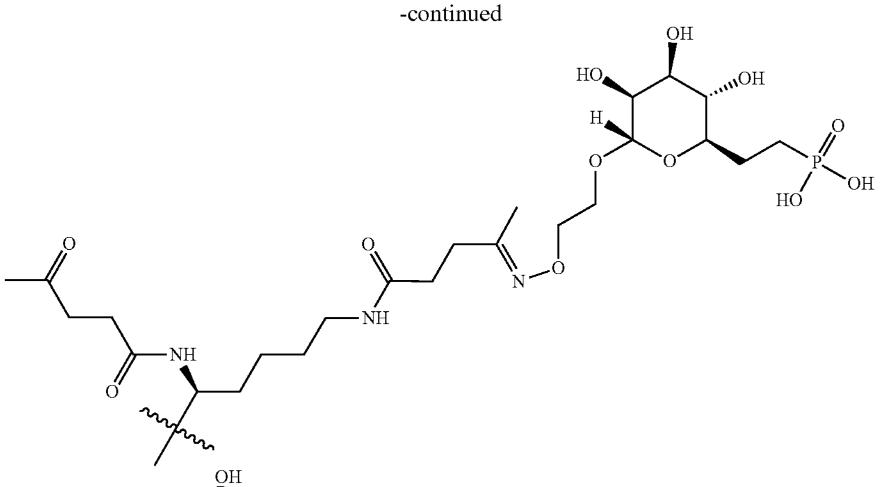

and

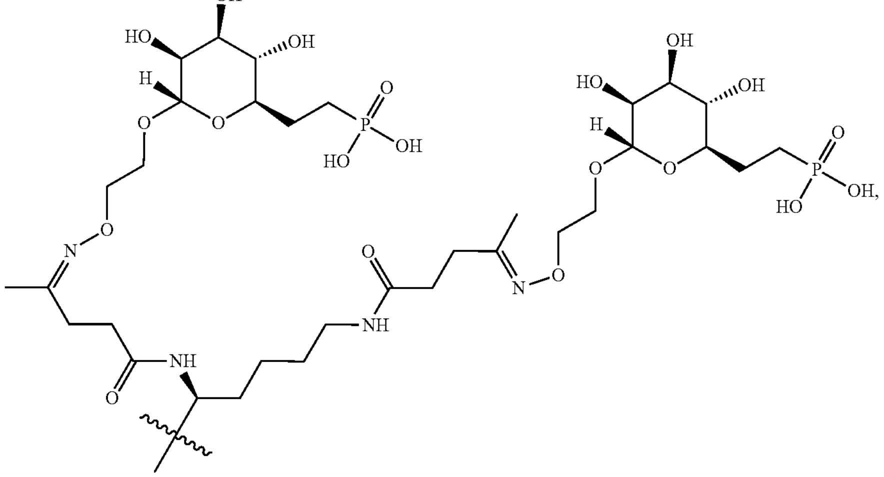

where the * of $R_L$ indicates the point of attachment to Linker ($L_A$).

C. Linker ($L_A$)

The linker moiety, ($L_A$) of the bifunctional compounds of the invention is a non-cleavable linker comprising one or more linker components selected from the following:

a) an alkylene group: $—(CH_2)_n—$ which can either be linear or branched (where in this instance n is 1-18);
b) an alkenylene group;
c) an alkynylene group;
d) an alkenyl group;
e) an alkynyl group;
f) an ethylene glycol unit: $—OCH_2CH_2$ or $—CH_2CH_2O$;
g) an polyethylene glycol unit: $(—CH_2CH_2O—)_x$ (where x in this instance is 2-20);
h) —O;
i) —S;
j) a carbonyl: —C(═O);
k) an ester: —C(═O)—O— or —O—C(═O);
l) a carbonate: —OC(═O)O;
m) an amine: —NH;
n) an tertiary amine
o) an amides: —C(═O)—NH—, —NH—C(═O)— or $—C(═O)N(C_{1-6}alkyl)$;
p) a carbamate: —OC(═O)NH— or —NHC(═O)O;
q) a urea: —NHC(═O)NH;
r) a sulphonamide: $—S(O)_2NH—$ or $—NHS(O)_2$;
s) an ether: $—CH_2O—$ or $—OCH_2$;
t) an alkylene substituted with one or more groups independently selected from carboxy, sulfonate, hydroxyl, amine, amino acid, saccharide, phosphate and phosphonate);
u) an alkenylene substituted with one or more groups independently selected from carboxy, sulfonate, hydroxyl, amine, amino acid, saccharide, phosphate and phosphonate);
v) an alkynylene substituted with one or more groups independently selected from carboxy, sulfonate, hydroxyl, amine, amino acid, saccharide, phosphate and phosphonate);
w) a $C_1$-$C_{10}$alkylene in which one or more methylene groups is replace by one or more —S—, —NH— or —O— moieties; and
x) a ring systems having two available points of attachment such as a divalent ring selected from phenyl (including 1,2-1,3- and 1,4-di-substituted phenyls), a $C_5$-$C_6$ heteroaryl, a $C_3$-$C_8$ cycloalkyl (including 1,1-disubstituted cyclopropyl, cyclobutyl, cyclopentyl or cyclohexyl, and 1,4-disubstituted cyclohexyl), and a $C_4$-$C_8$ heterocycloalkyl.

In addition, a linker component of Linker ($L_A$) can be a chemical moiety which is readily formed by reaction between two reactive groups. Non-limiting examples of such chemical moieties are given in Table 1.

TABLE 1
| Reactive Group 1 (RG1) | Reactive Group 2 (RG2) | Chemical Moiety |
|---|---|---|
| a thiol | a thiol | —S—S— |
| a thiol | a maleimide | 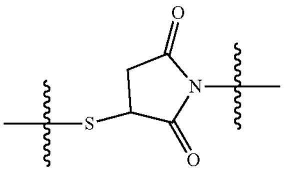 [SMILES: *SC1CC(=O)N(*)C1=O] |
| a thiol | a haloacetamide | 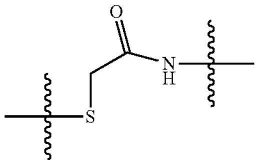 [SMILES: *NC(=O)CS*] |
| an azide | an alkyne | 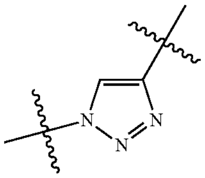 [SMILES: *c1cn(*)nn1] |
| an azide | a triaryl phosphine | 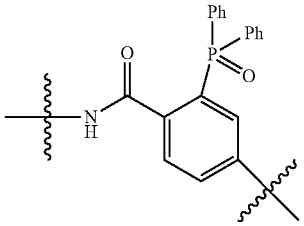 [SMILES: *NC(=O)c1ccc(*)cc1P(=O)(c1ccccc1)c1ccccc1] |
| an azide | a cyclooctyne | 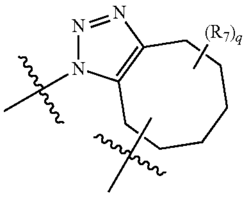<br>or<br>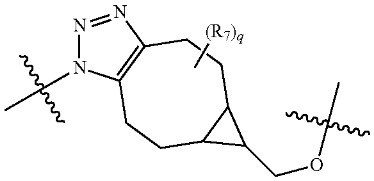<br>or<br>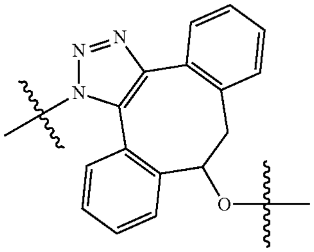 [SMILES: *OC1Cc2ccccc2-c2nnn(*)c2-c2ccccc21] |

TABLE 1-continued
| Reactive Group 1 (RG1) | Reactive Group 2 (RG2) | Chemical Moiety |
| --- | --- | --- |
| an azide | an oxanobornadiene | 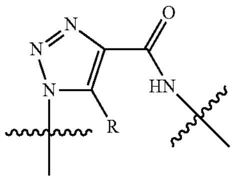 |
| a triaryl phosphine | an azide | 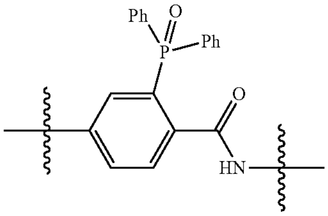 [SMILES: *NC(=O)c1ccc(*)cc1P(=O)(c1ccccc1)c1ccccc1] |
| an oxanobornadiene | an azide | 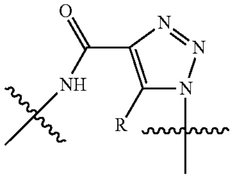 |
| an alkyne | an azide | 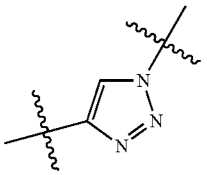 [SMILES: *c1cn(*)nn1] |
| a cyclooctyne | azide | 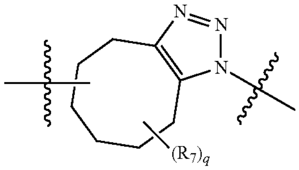 or 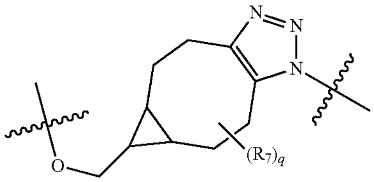 or 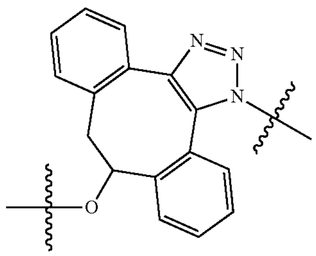 [SMILES: *OC1Cc2ccccc2-c2nnn(*)c2-c2ccccc21] |

TABLE 1-continued
| Reactive Group 1 (RG1) | Reactive Group 2 (RG2) | Chemical Moiety |
|---|---|---|
| a cyclooctene | a diaryl tetrazine | 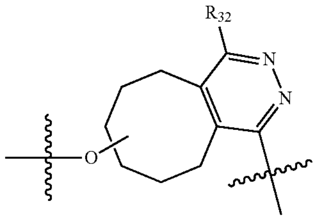<br>or<br>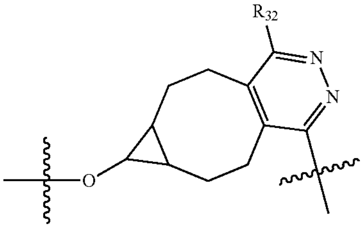 |
| a diaryl tetrazine | a cyclooctene | 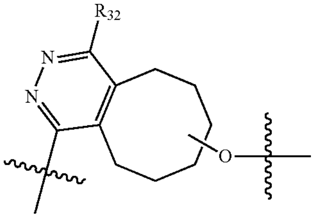<br>or<br>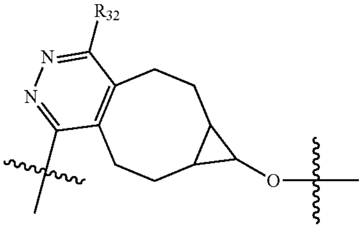 |
| a monoaryl tetrazine | a norbornene | 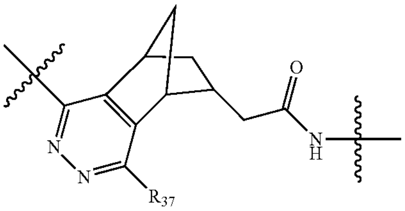 |
| a norbornene | a monoaryl tetrazine | 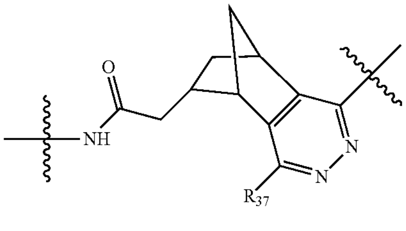 |

TABLE 1-continued
| Reactive Group 1 (RG1) | Reactive Group 2 (RG2) | Chemical Moiety |
|---|---|---|
| an aldehyde | a hydroxylamine | 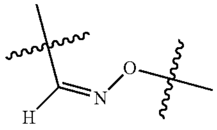 [SMILES: */C=N\O*] |
| an aldehyde | a hydrazine | 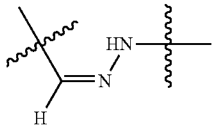 [SMILES: */C=N\N*] |
| an aldehyde | $NH_2$—NH—C(═O)— | 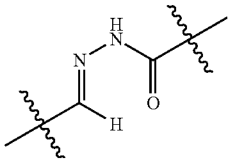 [SMILES: */C=N/NC(*)=O] |
| a ketone | a hydroxylamine | 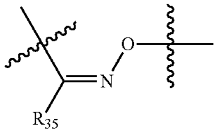 |
| a ketone | a hydrazine | 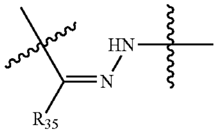 |
| a ketone | $NH_2$—NH—C(═O)— | 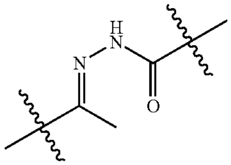 [SMILES: *C(=O)N/N=C(/*)C] |
| a hydroxylamine | an aldehyde | 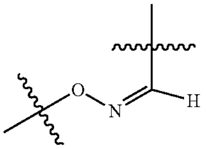 [SMILES: */C=N\O*] |
| a hydroxylamine | a ketone | 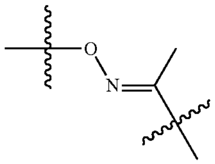 [SMILES: *O/N=C(/*)C] |
| a hydrazine | an aldehyde | 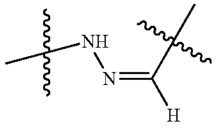 [SMILES: */C=N\N*] |
| a hydrazine | a ketone | 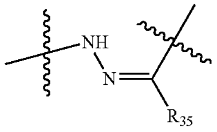 |

TABLE 1-continued
| Reactive Group 1 (RG1) | Reactive Group 2 (RG2) | Chemical Moiety |
|---|---|---|
| $NH_2$—NH—C(=O)— | an aldehyde | 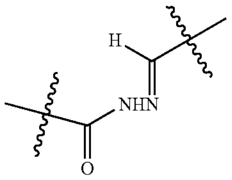 |
| $NH_2$—NH—C(=O)— | a ketone | 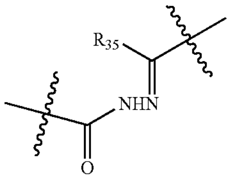 |
| a haloacetamide | a thiol | 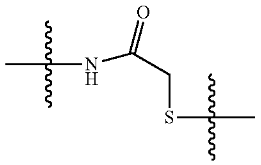 [SMILES: *NC(=O)CS*] |
| a maleimide | a thiol | 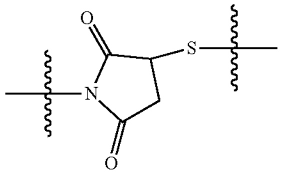 [SMILES: *SC1CC(=O)N(*)C1=O] |
| a vinyl sulfone | a thiol | 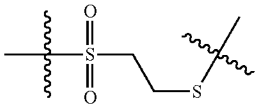 [SMILES: *SCCS(*)(=O)=O] |
| a thiol | a vinyl sulfone | 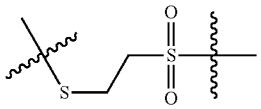 [SMILES: *SCCS(*)(=O)=O] |
| an aziridine | a thiol | 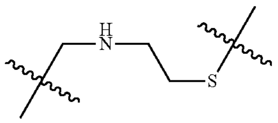 [SMILES: *CNCCS*] or 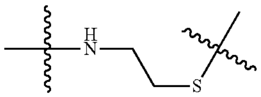 [SMILES: *NCCS*] |
| a thiol | an aziridine | 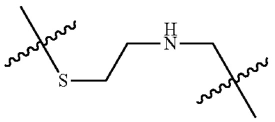 [SMILES: *CNCCS*] or |

TABLE 1-continued
| Reactive Group 1 (RG1) | Reactive Group 2 (RG2) | Chemical Moiety |
|---|---|---|
| | | 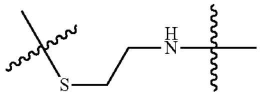 [SMILES: *NCCS*] |
| 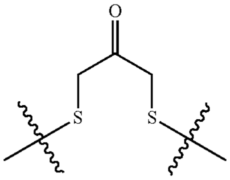 [SMILES: *SCC(=O)CS*] | hydroxylamine | 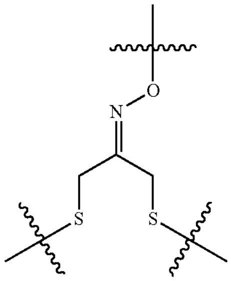 [SMILES: *ON=C(CS*)CS*] |
| 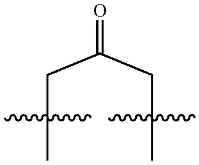 [SMILES: *CC(=O)C*] | hydroxylamine | 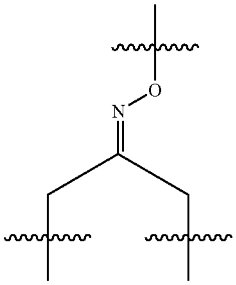 [SMILES: *CC(C*)=NO*] |
| 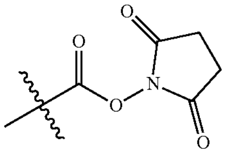 [SMILES: *C(=O)ON1C(=O)CCC1=O] | —$NH_2$, | amide |
| 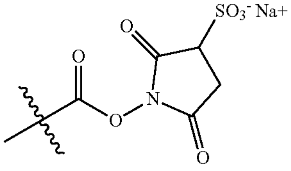 | | |
| 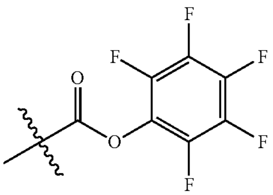 [SMILES: *C(=O)Oc1c(F)c(F)c(F)c(F)c1F] | | |
| 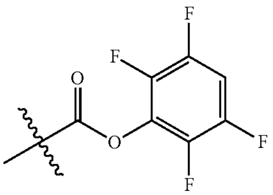 [SMILES: *C(=O)Oc1c(F)c(F)cc(F)c1F] | | |

TABLE 1-continued

| Reactive Group 1 (RG1) | Reactive Group 2 (RG2) | Chemical Moiety |
|---|---|---|
| 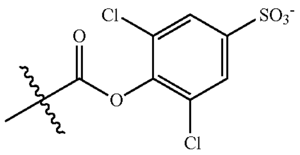 | | |
| —$NH_2$, | 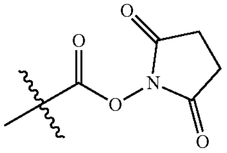 [SMILES: *C(=O)ON1C(=O)CCC1=O] 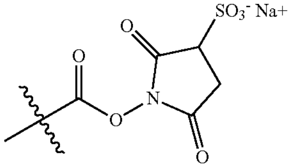 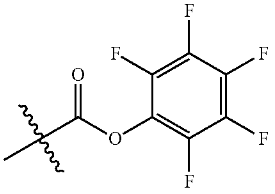 [SMILES: *C(=O)Oc1c(F)c(F)c(F)c(F)c1F] 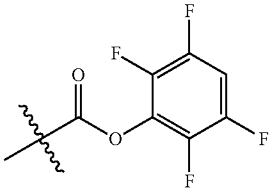 [SMILES: *C(=O)Oc1c(F)c(F)cc(F)c1F] 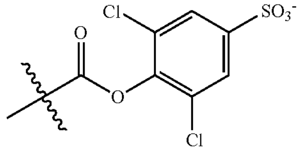 | amide |
| pyridyldithiol | thiol | disulfide |

where: $R^{32}$ in Table 1 is H, $C_{1-4}$ alkyl, phenyl, pyrimidine or pyridine; $R^{31}$ in Table 1 is H, $C_{1-6}$ alkyl, phenyl or $C_{1-4}$alkyl substituted with 1 to 3 —OH groups; each $R^7$ in Table 1 is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH; $R^{3'}$ in Table 1 is independently selected from H, phenyl and pyridine; and q in Table 1 is 0, 1, 2 or 3.

In addition, a linker component of Linker ($L_A$) can be a group given in Table 2 below.

TABLE 2

| | |
|---|---|
| 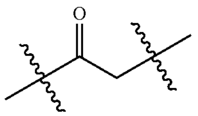 [SMILES: *CC(*)=O] | 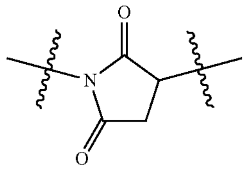 [SMILES: *C1CC(=O)N(*)C1=O] |

TABLE 2-continued
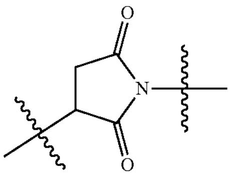 [SMILES: *C1CC(=O)N(*)C1=O]
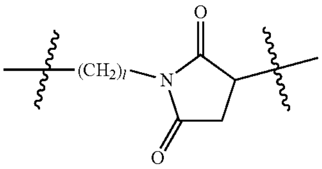
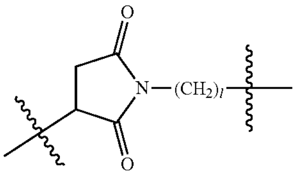
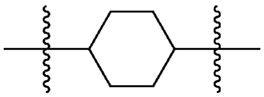 [SMILES: *C1CCC(*)CC1]
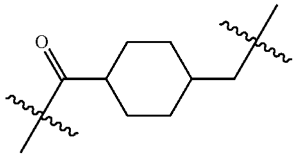 [SMILES: *CC1CCC(C(*)=O)CC1]
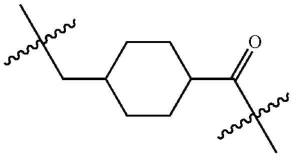 [SMILES: *CC1CCC(C(*)=O)CC1]
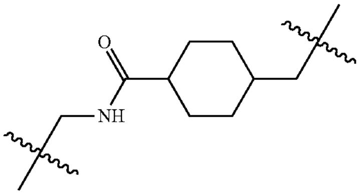 [SMILES: *CNC(=O)C1CCC(C*)CC1]
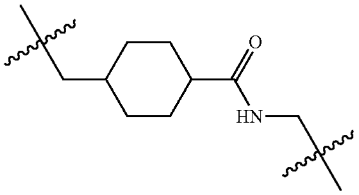 [SMILES: *CNC(=O)C1CCC(C*)CC1]
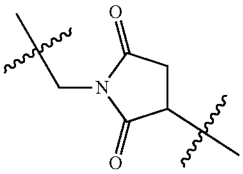 [SMILES: *CN1C(=O)CC(*)C1=O]
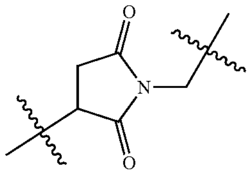 [SMILES: *CN1C(=O)CC(*)C1=O]
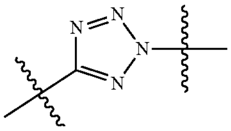 [SMILES: *c1nnn(*)n1]
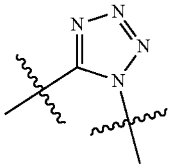 [SMILES: *c1nnnn1*]
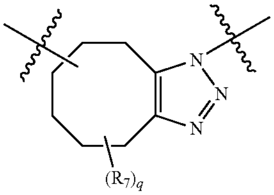
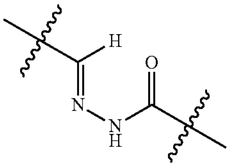 [SMILES: */C=N/NC(*)=O]
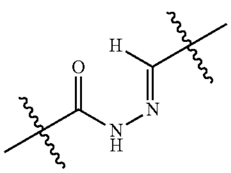 [SMILES: */C=N/NC(*)=O]
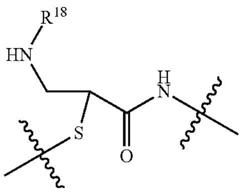

TABLE 2-continued
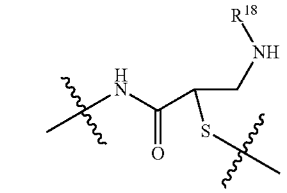
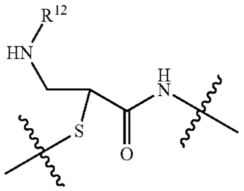
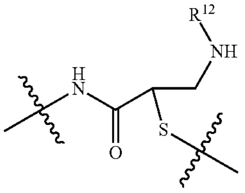
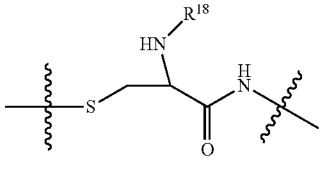
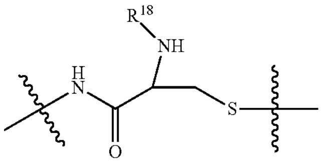
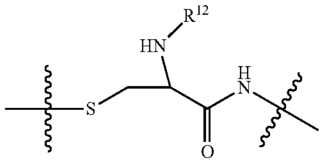
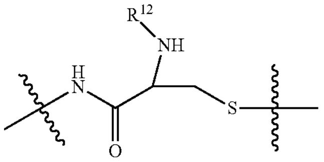
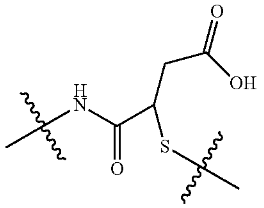 [SMILES: *NC(=O)C(CC(=O)O)S*]
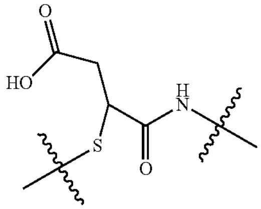 [SMILES: *NC(=O)C(CC(=O)O)S*]
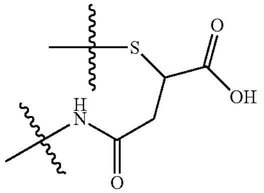 [SMILES: *NC(=O)CC(S*)C(=O)O]
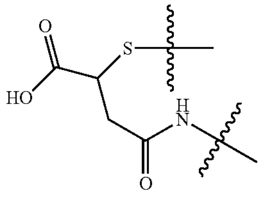 [SMILES: *NC(=O)CC(S*)C(=O)O]
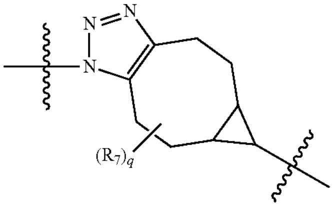
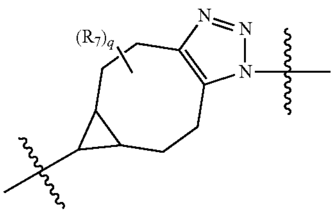
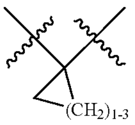

TABLE 2-continued
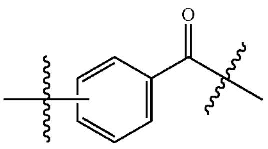
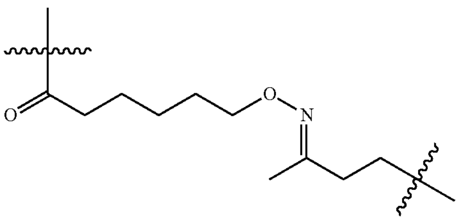 [SMILES: *CC/C(C)=N/OCCCCCC(*)=O]
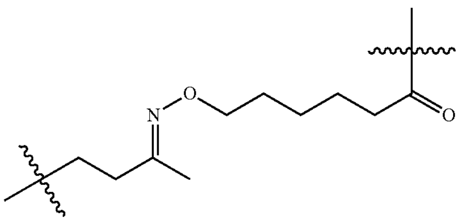 [SMILES: *CC/C(C)=N/OCCCCCC(*)=O]
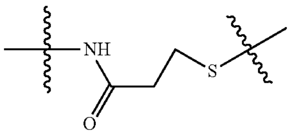 [SMILES: *NC(=O)CCS*]
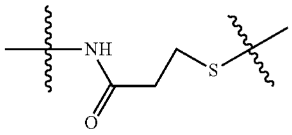 [SMILES: *NC(=O)CCS*]
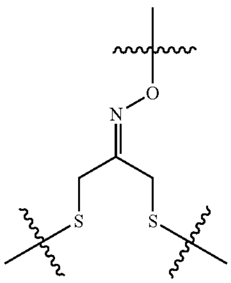 [SMILES: *ON=C(CS*)CS*]
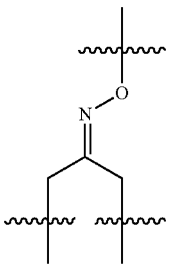 [SMILES: *CC(C*)=NO*]
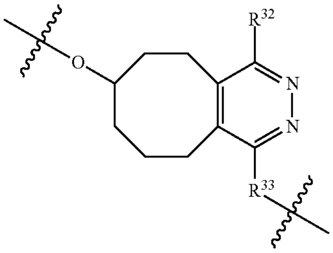
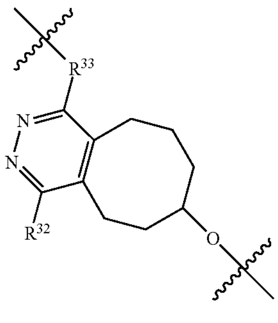
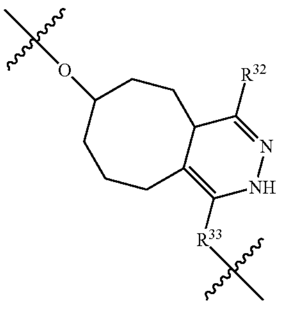

TABLE 2-continued

| | |
|---|---|
| 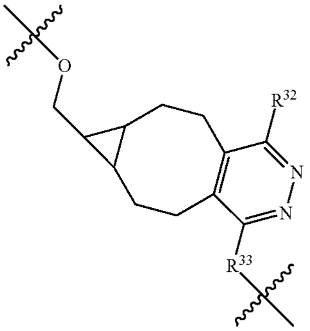 | 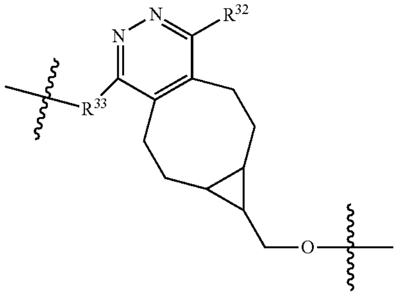 |
| 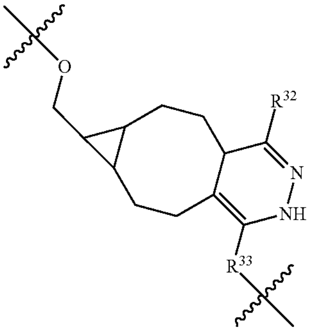 | 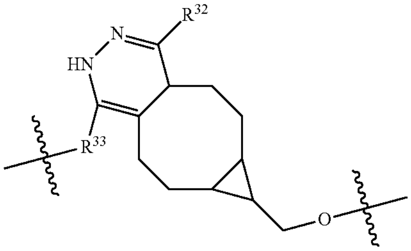 |
| 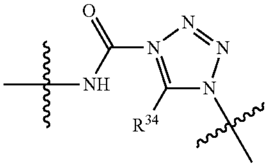 | 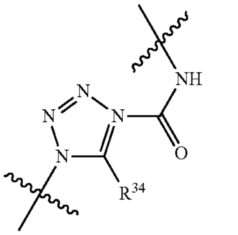 |
| 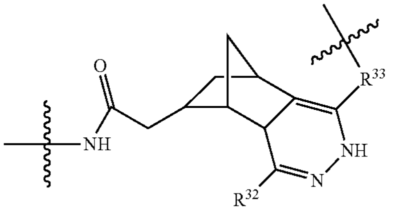 | 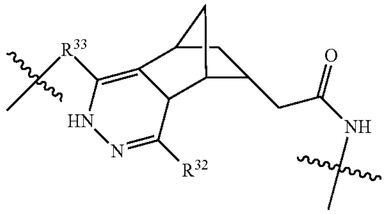 |
| 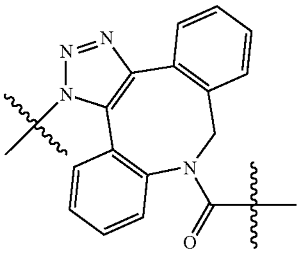 [SMILES: *C(=O)N1Cc2ccccc2-c2nnn(*)c2-c2ccccc21] | 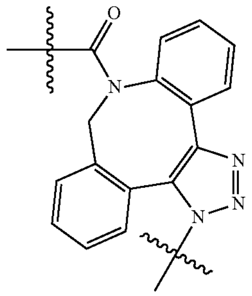 [SMILES: *C(=O)N1Cc2ccccc2-c2c(nnn2*)-c2ccccc21] |

each $R^7$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{12}$ is independently selected from H and $C_1$-$C_6$alkyl each $R^{25}$ is independently selected from H or $C_{1-4}$ alkyl;

each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;

q is 0, 1, 2 or 3;

l is 1, 2, 3, 4, 5 or 6;

$R^{32}$ is independently selected from H, $C_{1-4}$ alkyl, phenyl, pyrimidine and pyridine;

$R^{33}$ is independently selected from

TABLE 2-continued

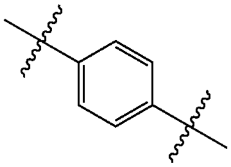
,
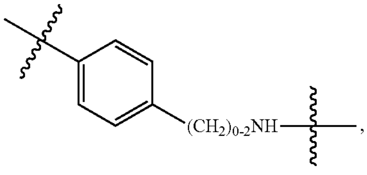
,
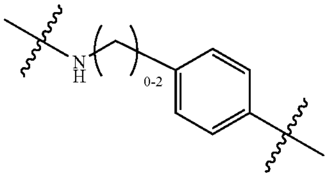
,
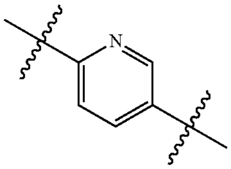
,
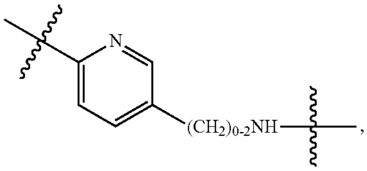
,
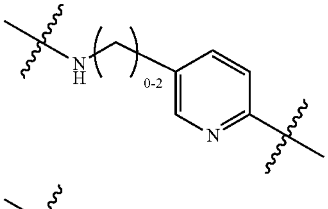
,
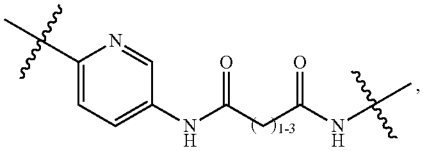
,
and
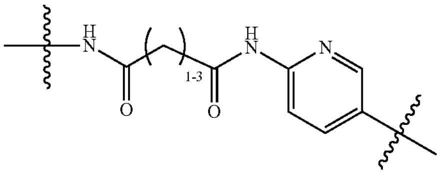
;
and
$R^{34}$ is independently selected from H, $C_{1-4}$ alkyl, and $C_{1-6}$ haloalkyl, Embodiment 62. The bifunctional compound of Formula (I), or any one of Embodiments 1 to 61, wherein the Linker ($L_A$) is selected from: *—$(CH_2)_n$C(═O)NHNHC(═O)$(CH_2)_n$ON═$CH_2X_1$C(═O)—**; *—$(CH_2)_nX_3$C(═O)—**; *—$(CH_2)_n$C(═O)—**; *—$(CH_2)_n$C(═O)NHNHC(═O)$(CH_2)_n$ON═$CH_2X_1$C(═O)NH$(CH_2)_n$CH(C═(O)$NH_2$)—**; *—$(CH_2)_nX_3$C(═O)NH$(CH_2)_n$CH(C═(O)$NH_2$)—**; *—$(CH_2)_n$C(═O)NH$(CH_2)_n$CH(C═(O)$NH_2$)—**, *—$((CH_2)_nO)_t(CH_2)_m$C(═O)—**; *—$((CH_2)_nO)_t(CH_2)_m$—**; *—$(CH_2)_n$C(═O)NH$((CH_2)_nO)_t(CH_2)_m$—**; —$(CH_2)_n$—; *—$(CH_2)_n$NHC(═O)$(CH_2)_m$—**; *—$(CH_2)_n$NHC(═O)$(CH_2)_n$C(═O)NH$(CH_2)_m$—**; *—$((CH_2)_nO)_t(CH_2)_n$NHC(═O)$(CH_2)_m$—**; *—$((CH_2)_nO)_tCH_2)_m$C(═O)NH$(CH_2)_m$—**; *$((CH_2)_nO)_t(CH_2)_n$NHC(═O)$(CH_2)_m$—**; *—$(CH_2)_n$O$(CH_2)_m$—**; *—$(CH_2)_n$NH$(CH_2)_n$—**; *—$(CH_2)_n$NH$(CH_2)_m$C(═O)—**; *—$(CH_2)_nX_3(CH_2)_m$—**; *—$((CH_2)_nO)_t(CH_2)_nX_3(CH_2)_m$—**; *—$(CH_2)_n$NHC(═O)$(CH_2)_nX_3(CH_2)_m$—**; *—$((CH_2)_nO)_t(CH_2)_n$NHC(═O)$(CH_2)_nX_3(CH_2)_m$—**; *—$((CH_2)_nO)_t(CH_2)_n$C(═O)

$NH(CH_2)_m-**$; $*-(CH_2)_mNHC(=O)((CH_2)_nO)_t(CH_2)_m-**$; $*-(CH_2)_nC(=O)NH(CH_2)_m-**$; $*-(CH_2)_nNHC(=O)((CH_2)_nO)_t(CH_2)_m-**$; $*-(CH_2)_nNHC(=O)(CH_2)_nO(CH_2)_m-**$; $*-(CH_2)_nNH(CH_2)_m-**$; $*-((CH_2)_nO)_tCH_2)_nC(=O)NH(CH_2)_m-**$; $*-(CH_2)_nNHC(=O(CH_2)_nX_3(CH_2)_m-**$; $-C(=O)-$; $*-C(=O)(CH_2)_nC(=O)-**$; $*-C(=O)((CH_2)_nO)_t(CH_2)_mC(=O)-**$; $*-C(=O)((CH_2)_nO)_t(CH_2)_m-**$; $*-((CH_2)_nO)_t(CH_2)_mX_3(CH_2)_nO(CH_2)_nNHC(=O)((CH_2)_nO)_t(CH_2)_mC(=O)-**$, $*-C(=O)(CH_2)_nC(=O)NH((CH_2)_nO)_t(CH_2)_m-**$; $*-C(=O)NHNHC(=O)(CH_2)_nON=CH_2X_1C(=O)NH(CH_2)_nCH(C=(O)NH_2)-**$; $*-X_3C(=O)NH(CH_2)_nCH(C=(O)NH_2)-**$; $*-C(=O)(CH_2)_nC(=O)NHNHC(=O)(CH_2)_nON=CH_2X_1C(=O)-**$; $*-C(=O)(CH_2)_nX_3C(=O)-**$; $*-C(=O)(CH_2)_nNHC(=O)(CH_2)_nC(=O)NH(CH_2)_m-**$; $*-C(=O)((CH_2)_nO)_t(CH_2)_nNHC(=O)(CH_2)_m-**$; $*-C(=O)((CH_2)_nO)_tCH_2)_mC(=O)NH(CH_2)_m-**$; $*-C(=O)(CH_2)_nO(CH_2)_m-**$; $*-C(=O)(CH_2)_n-**$; $*-C(=O)NH((CH_2)_nO)_t(CH_2)_m-**$; $*-C(=O)(CH_2)_nNH(CH_2)_n-**$; $*-C(=O)(CH_2)_nNH(CH_2)_mC(=O)-**$; $*-C(=O)(CH_2)_nX_3(CH_2)_m-**$; $*-C(=O)((CH_2)_nO)_t(CH_2)_nX_3(CH_2)_m-**$; $*-C(=O)(CH_2)_nNHC(=O)(CH_2)_m-**$; $*-C(=O)(CH_2)_nNHC(=O)((CH_2)_nO)_t(CH_2)_m-**$; $*-C(=O)(CH_2)_nNHC(=O)(CH_2)_nO(CH_2)_m-**$; $*-C(=O)(CH_2)_nNH(CH_2)_m-**$; $*-C(=O)((CH_2)_nO)_tCH_2)_nC(=O)NH(CH_2)_m-**$; $*-C(=O)(CH_2)_nNHC(=O(CH_2)_nX_3(CH_2)_m-**$; $*-C(=O)NH(CH_2)_nX_3(CH_2)_m-**$; $*-C(=O)NH(CH_2)_nNHC(=O)(CH_2)_m-**$; $*-C(=O)NH(CH_2)_nNHC(=O)(CH_2)_nO(CH_2)_m-**$; $*-C(=O)NH(CH_2)_nNHC(=O)(CH_2)_nX_3(CH_2)_m-**$; $*-C(=O)NH(CH_2)_nNHC(=O)-**$; $*-C(=O)NH((CH_2)_nO)_t(CH_2)_nX_3(CH_2)_m-**$; $*-C(=O)(CH_2)_nNHC(=O)(CH_2)_nX_3(CH_2)_m-**$; $*-C(=O)((CH_2)_nO)_t(CH_2)_nNHC(=O)(CH_2)_nX_3(CH_2)_m-**$; $*-C(=O)((CH_2)_nO)_t(CH_2)_nC(=O)NH(CH_2)_m-**$; $*-C(=O)(CH_2)_mNHC(=O)((CH_2)_nO)_t(CH_2)_m-**$, or $*-C(=O)(CH_2)_nC(=O)NH(CH_2)_m-**$;

wherein $X_1$ is

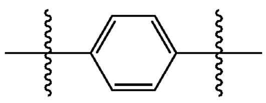 [SMILES: *c1ccc(*)cc1]

and $X_3$ is

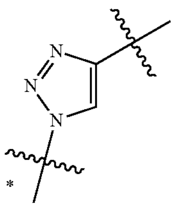

,

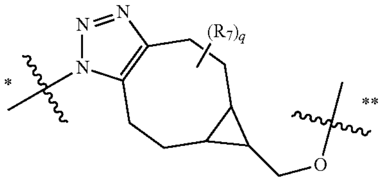

or

-continued

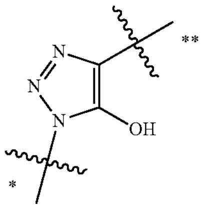

, where the * of $X_3$ indicates point of attachment is toward $R_L$ and the ** of $X_3$ indicates point of attachment is toward $L_A$, and where the * of $L_A$ indicates the point of attachment to $R_L$, and the ** of $L_A$ indicates the point of attachment to $T_L$.

Embodiment 63. The bifunctional compound of Formula (I), or any one of Embodiments 1 to 62, wherein the Linker ($L_A$) is: $*-(CH_2)_nC(=O)NHNHC(=O)(CH_2)_nON=CH_2X_1C(=O)-**$; $*-(CH_2)_nX_3C(=O)-**$; $*-((CH_2)_nO)_t(CH_2)_mC(=O)-**$; $*-(CH_2)_nC(=O)-**$; $*-(CH_2)_nC(=O)NHNHC(=O)(CH_2)_nON=CH_2X_1C(=O)NH(CH_2)_nCH(C=(O)NH_2)-**$; $*-(CH_2)_nX_3C(=O)NH(CH_2)_nCH(C=(O)NH_2)-**$; $-C(=O)-$; $*-C(=O)(CH_2)_nC(=O)-**$; $*-C(=O)((CH_2)O)_t(CH_2)_mC(=O)-**$; $*-((CH_2)_nO)_t(CH_2)_mX_3(CH_2)_nO(CH_2)_nNHC(=O)((CH_2)_nO)_t(CH_2)_mC(=O)-**$; $*-C(=O)((CH_2)_nO)_t(CH_2)_m-**$; or $*-C(=O)(CH_2)C(=O)NH((CH_2)_nO)_t(CH_2)_m-**$;

wherein $X_1$ is

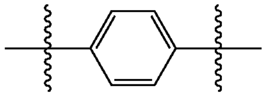 [SMILES: *c1ccc(*)cc1]

and $X_3$ is

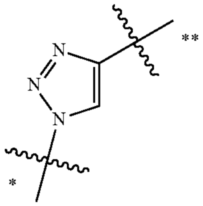

or

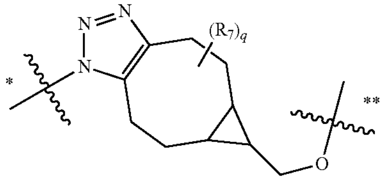

, where the * of $X_3$ indicates point of attachment is toward $R_L$ and the ** of $X_3$ indicates point of attachment is toward $L_A$, and where the * of $L_A$ indicates the point of attachment to $R_L$, and the ** of $L_A$ indicates the point of attachment to $T_L$.

Embodiment 64. The bifunctional compound of Formula (I) or Formula (Ia) selected from:

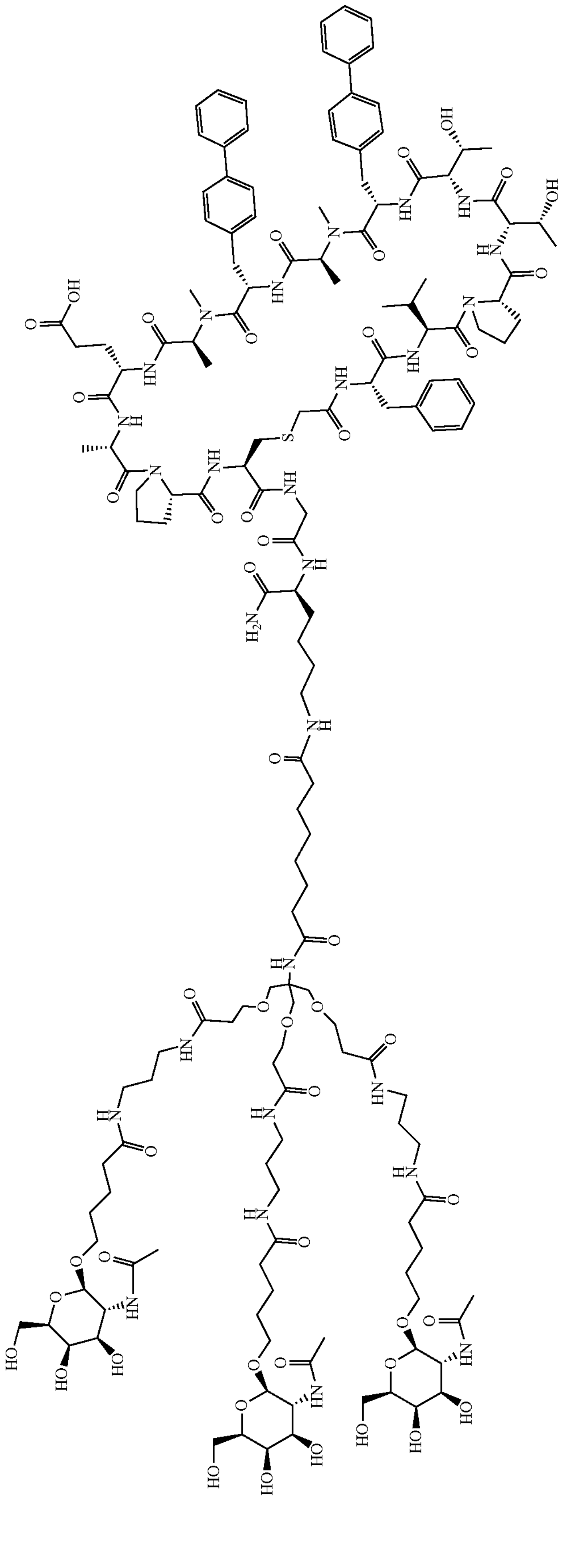

-continued
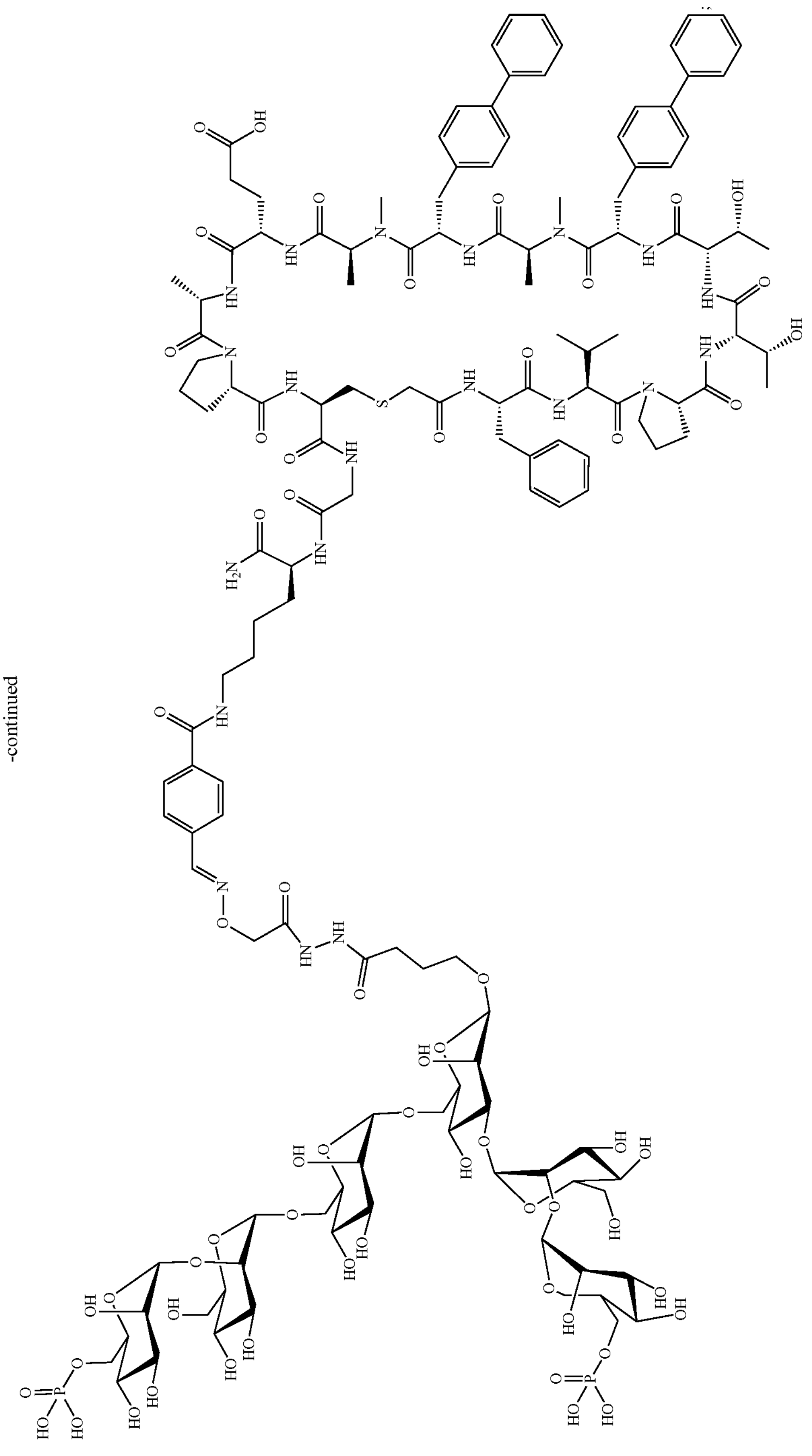

-continued
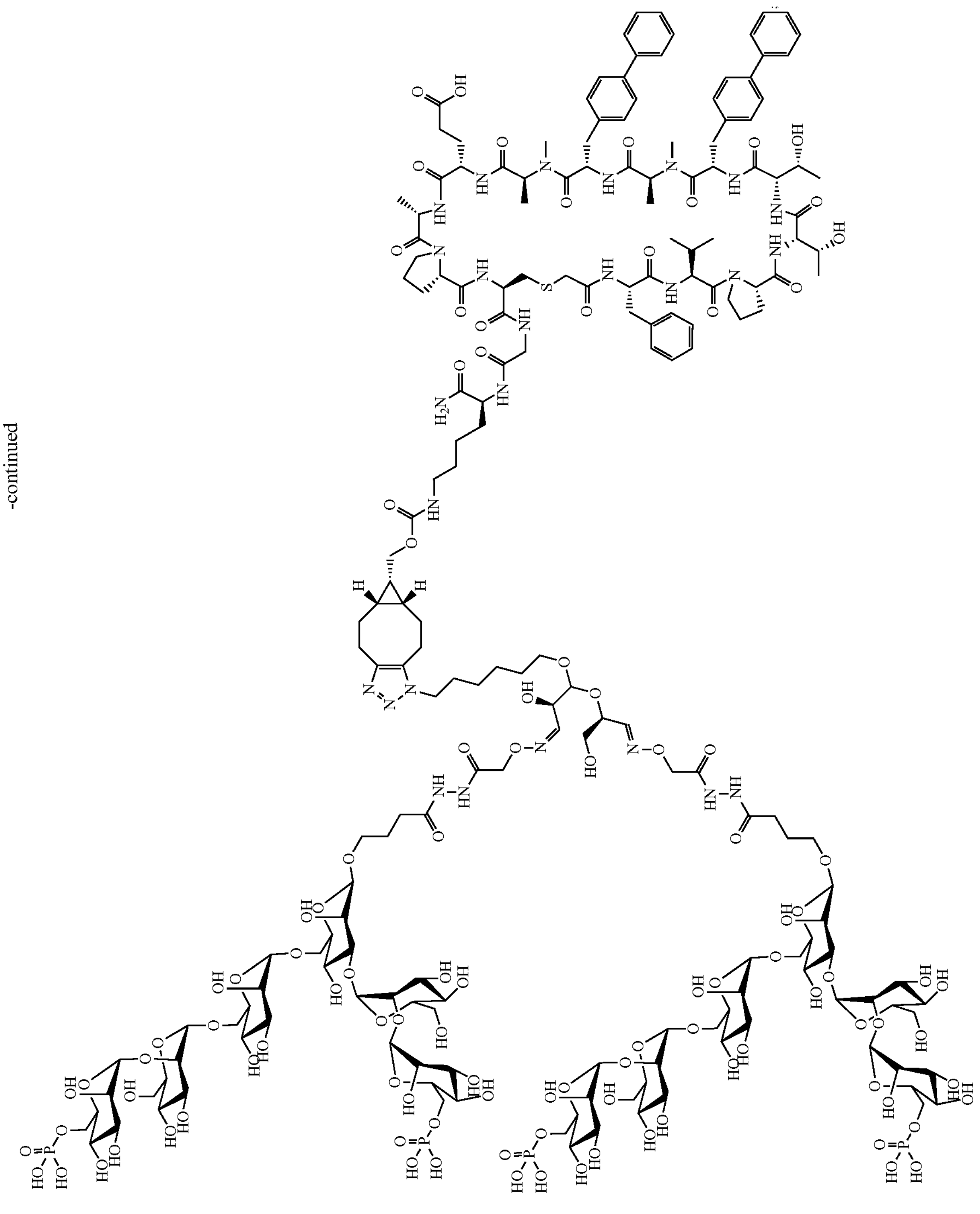

-continued
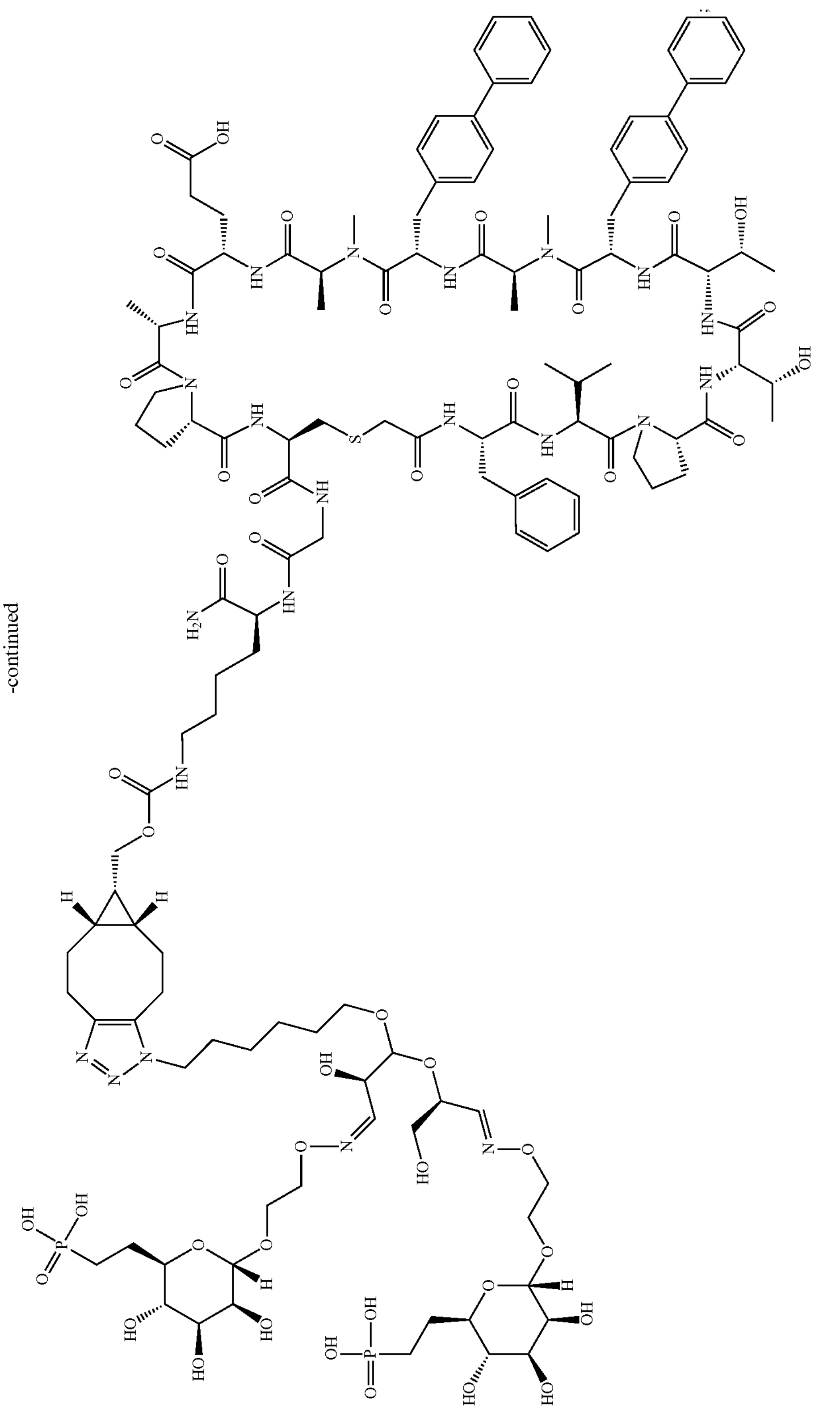

-continued
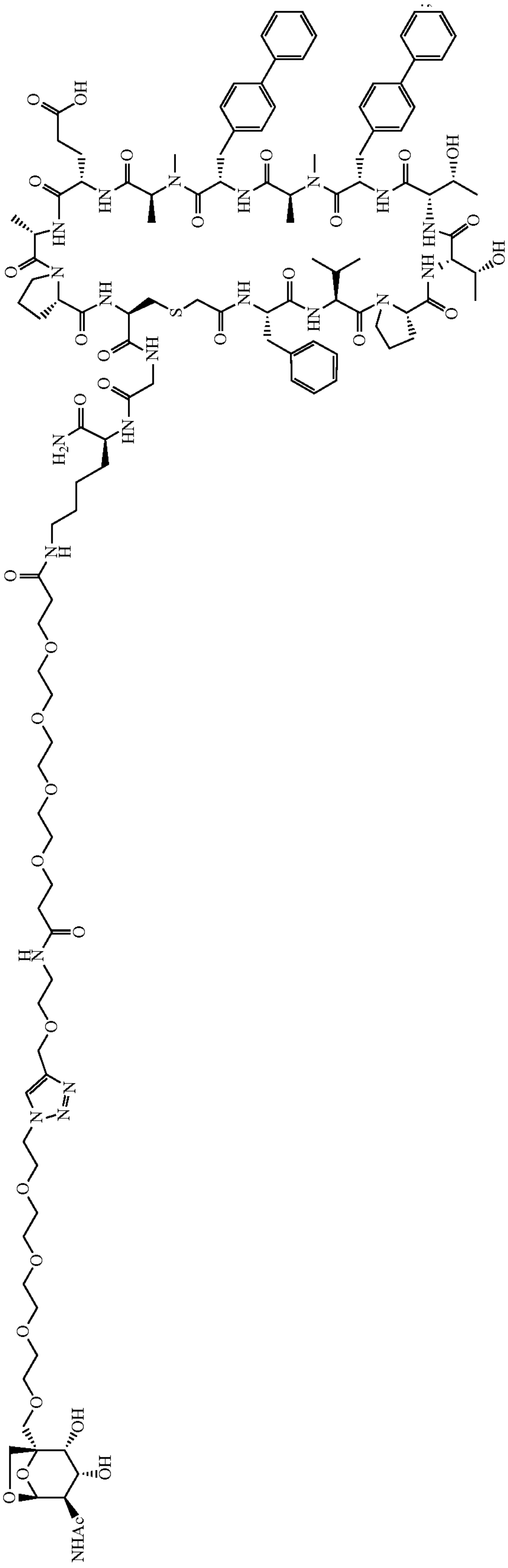

-continued
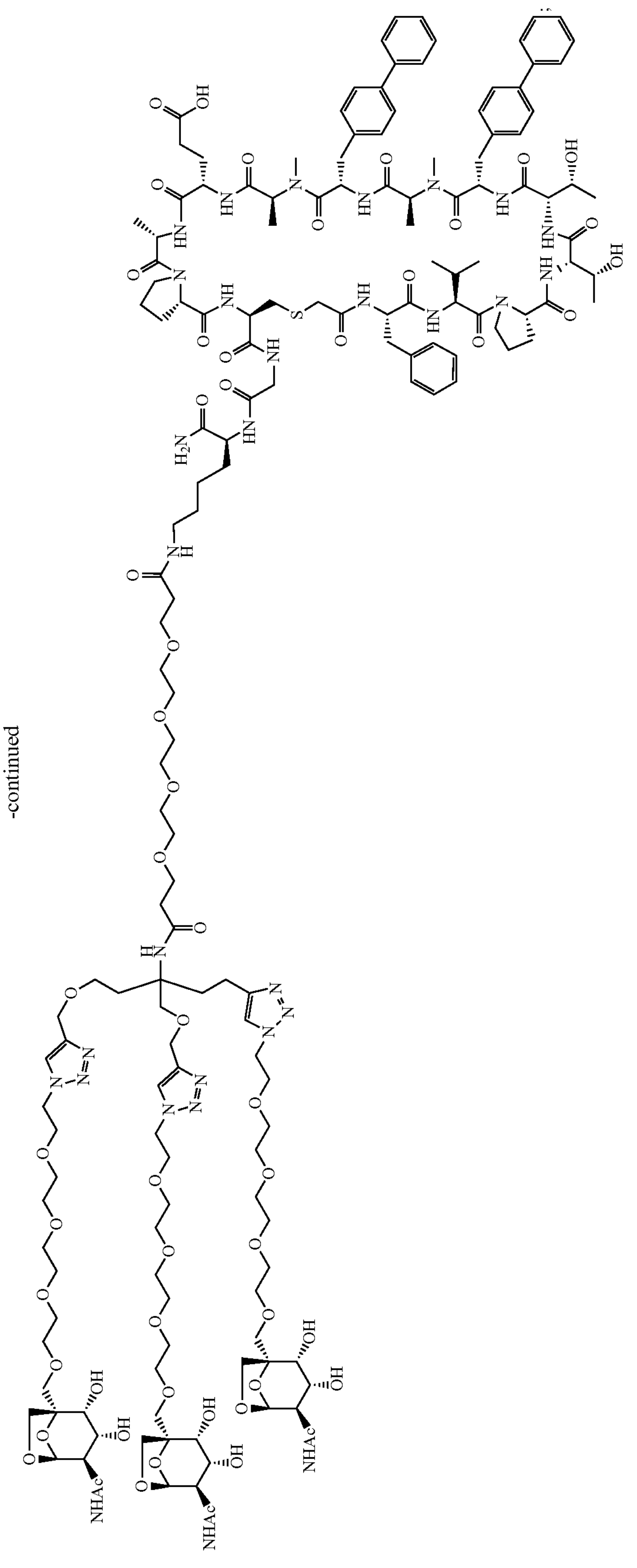

-continued
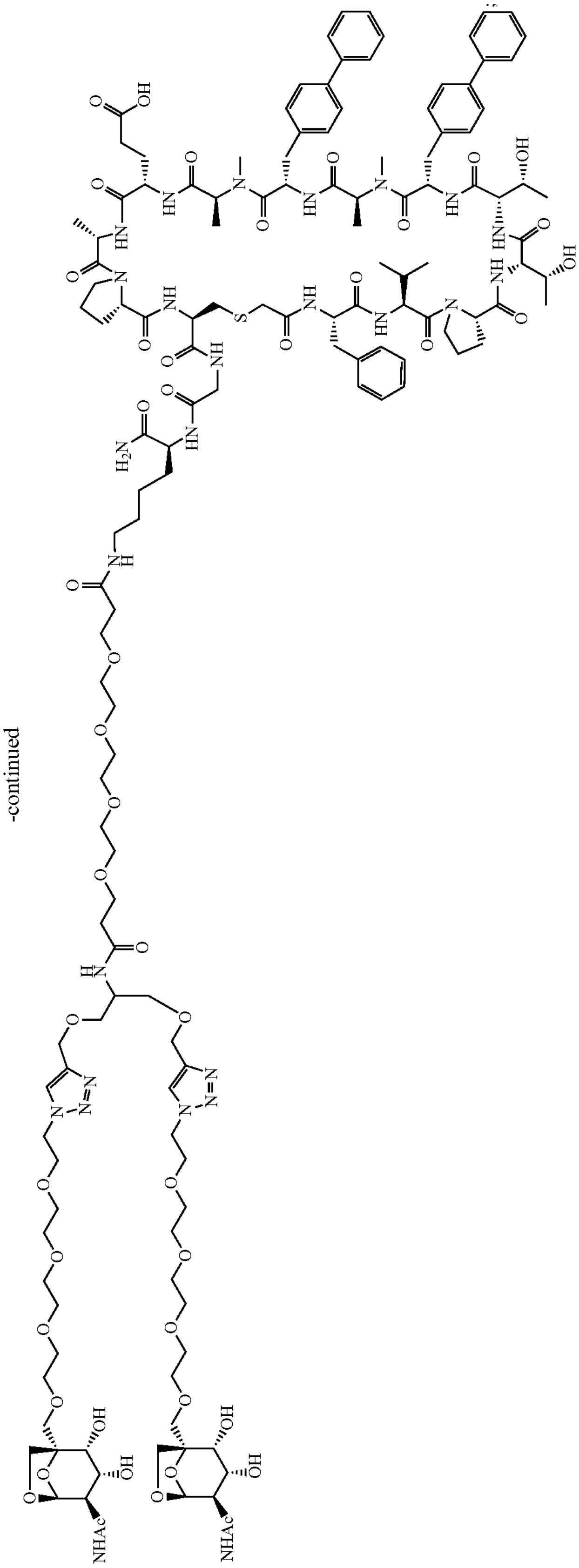

-continued
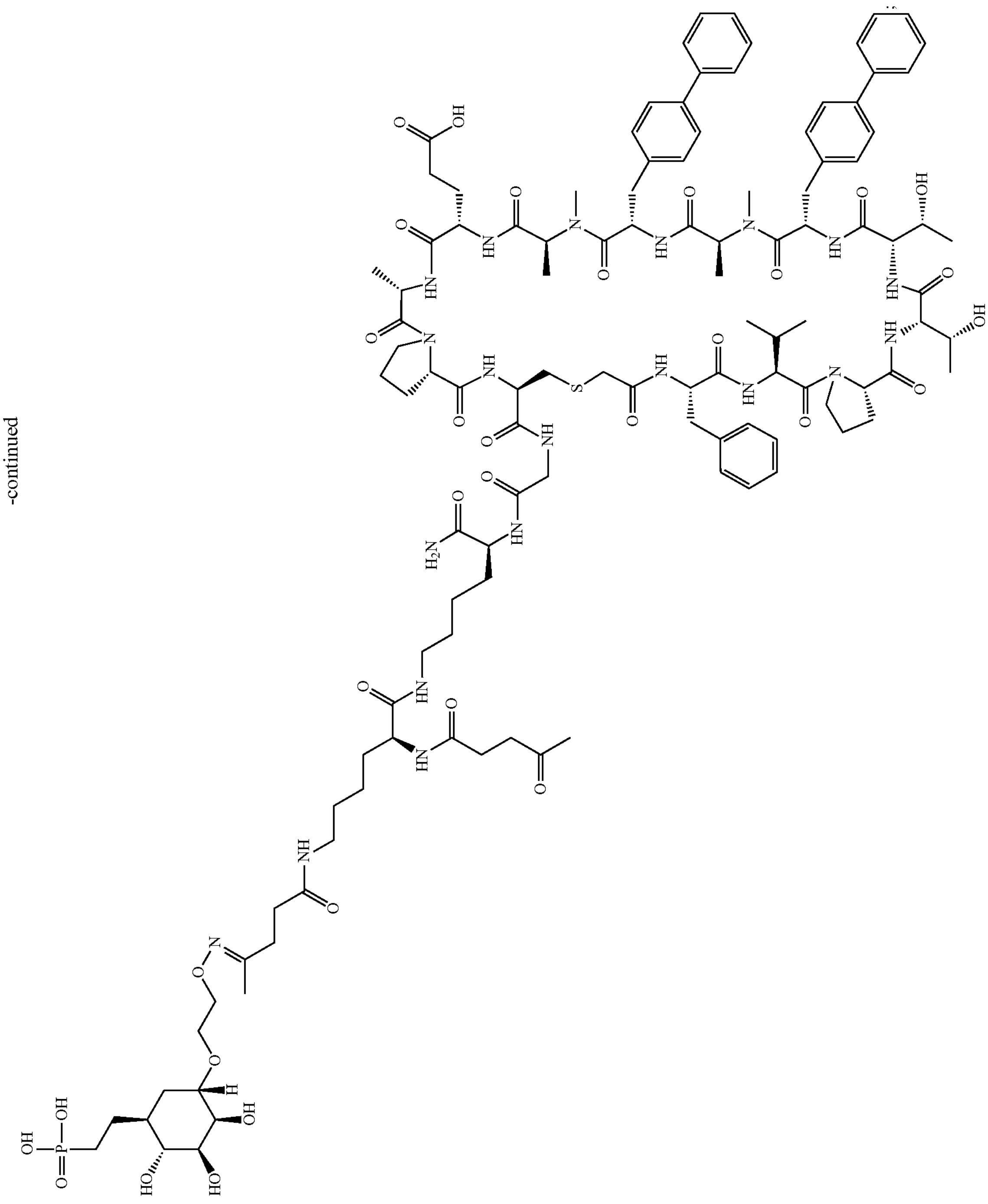

-continued
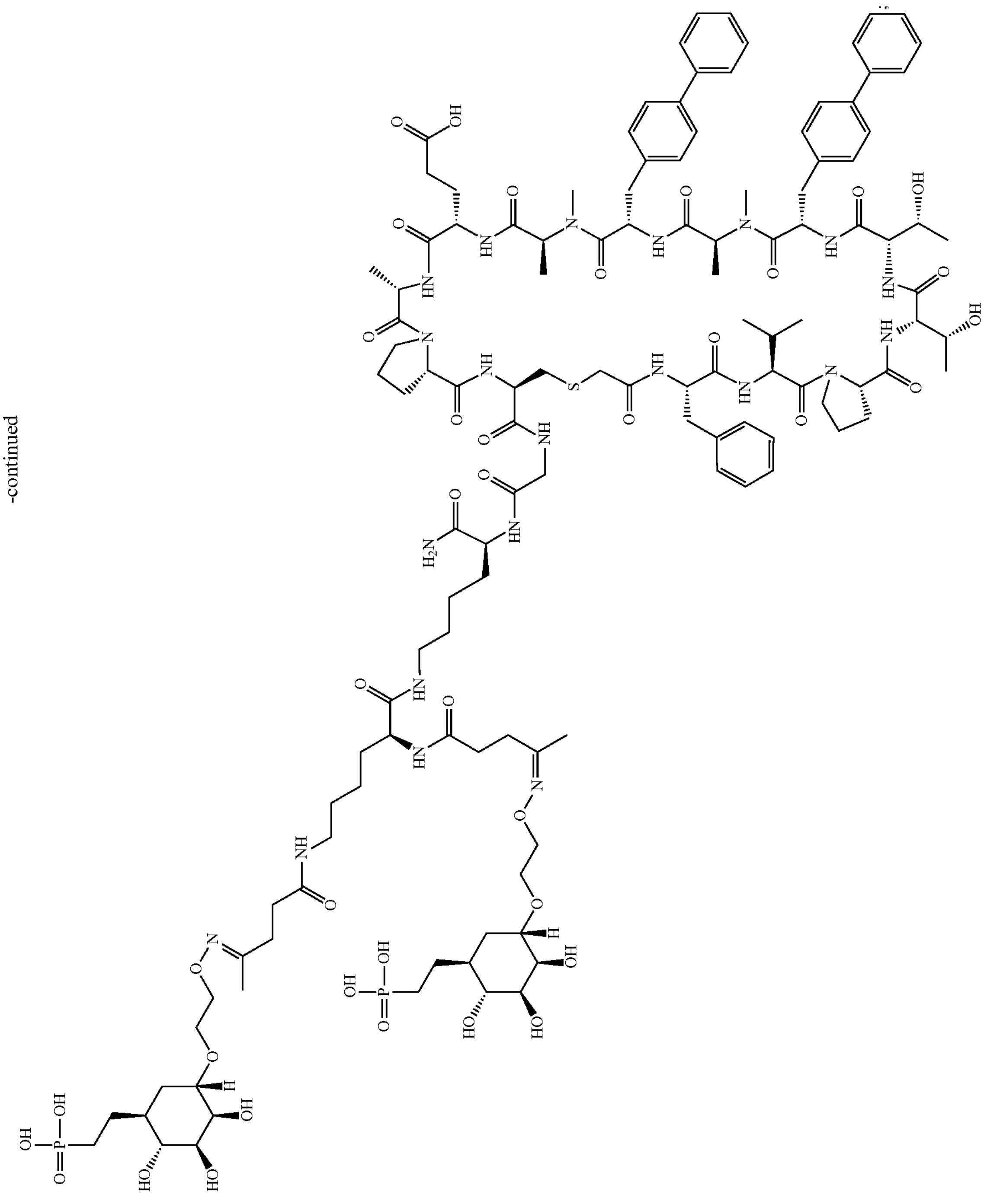

-continued
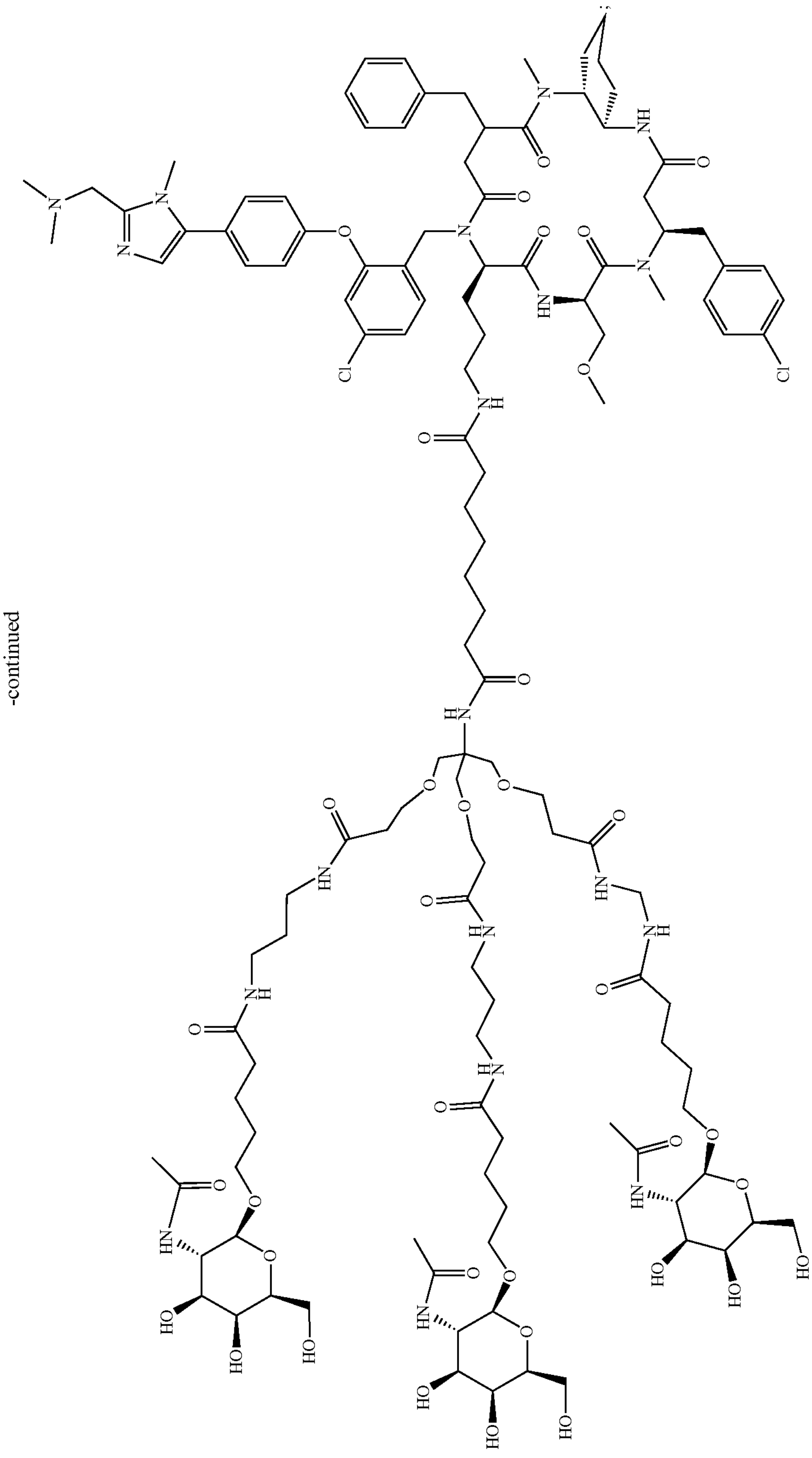

-continued
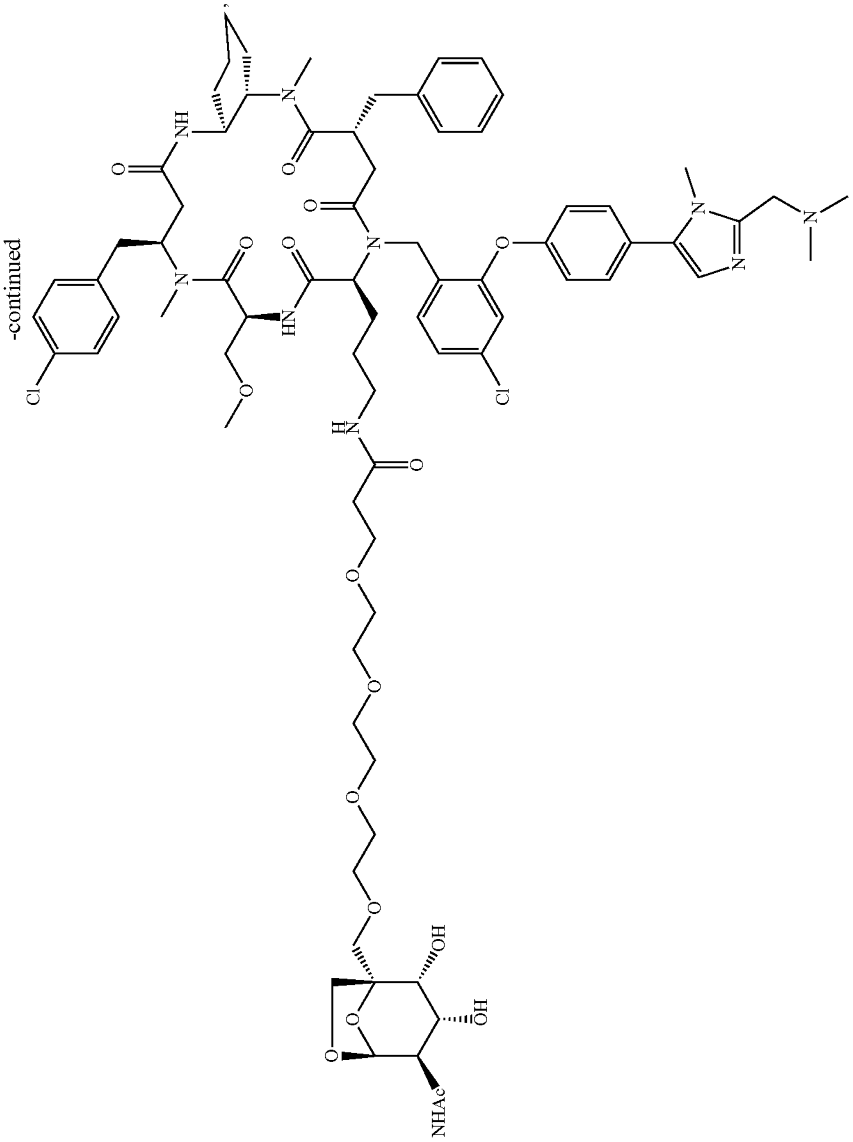
, and

-continued
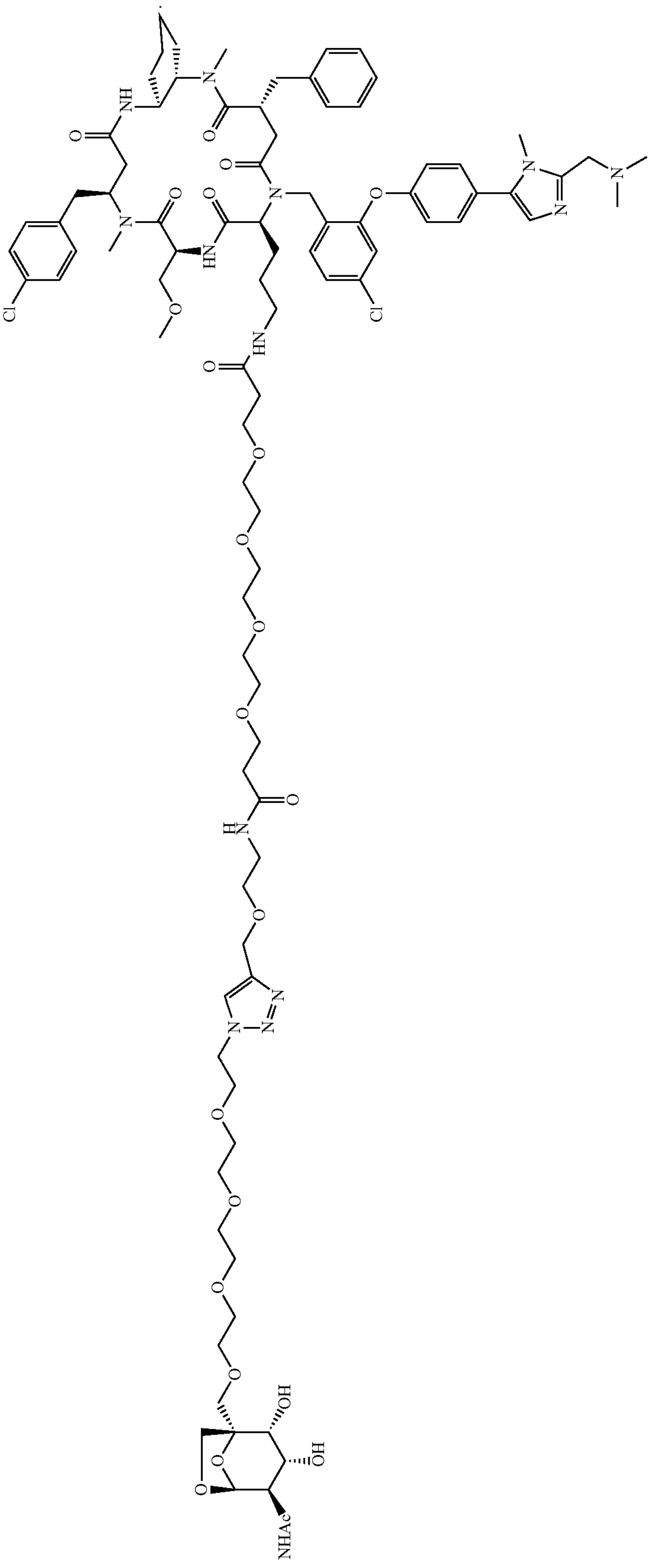

Embodiment 65. The bifunctional compound of Formula (I) or Formula (Ib) selected from:

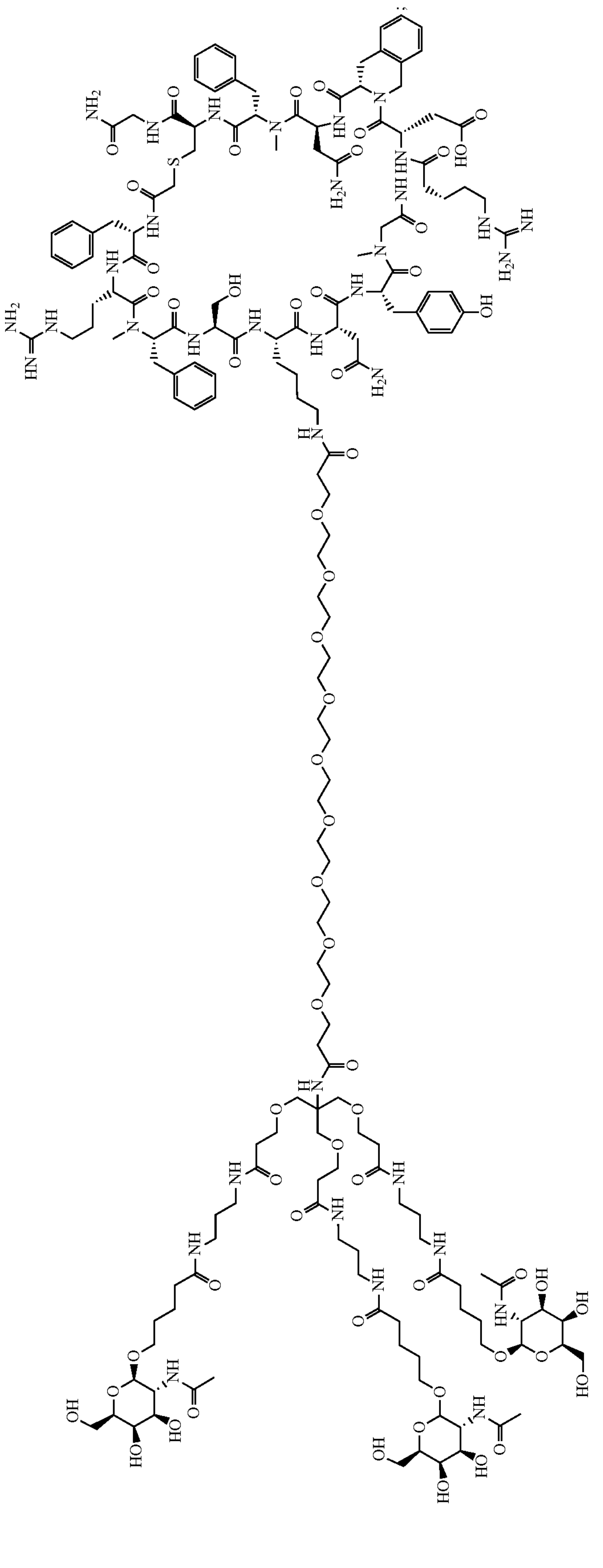

-continued
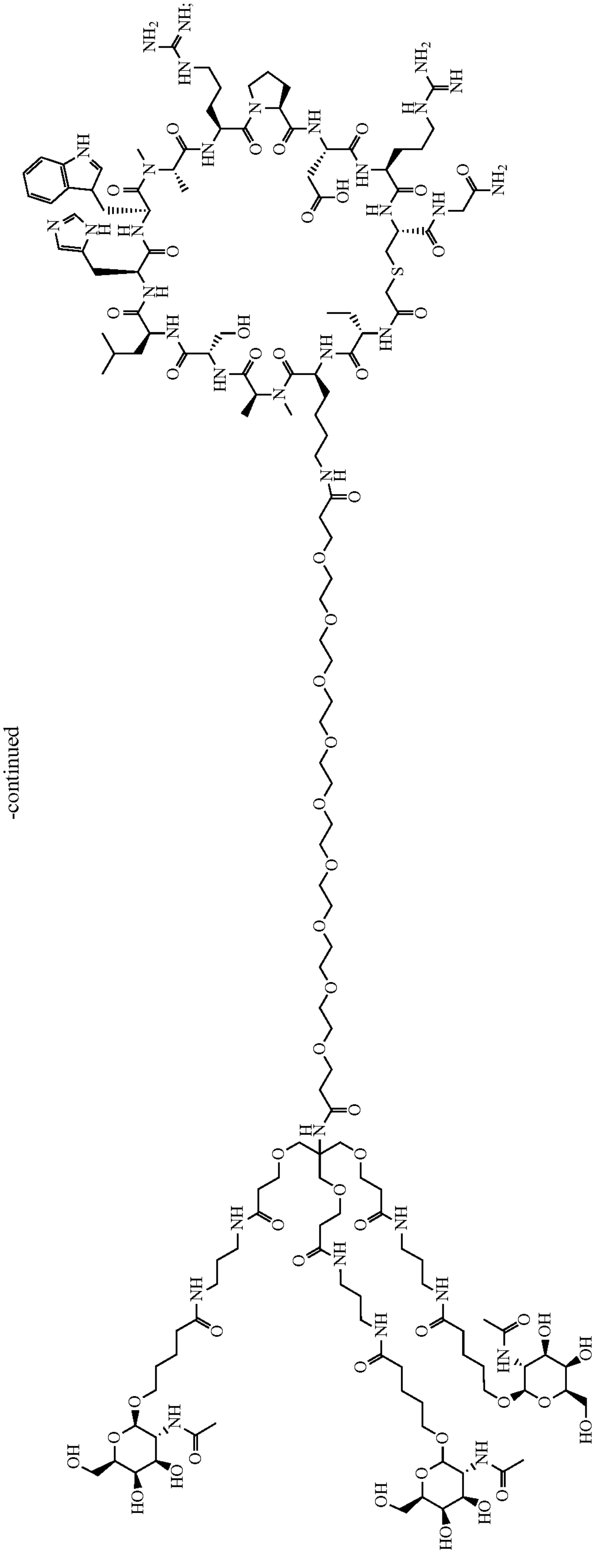

-continued
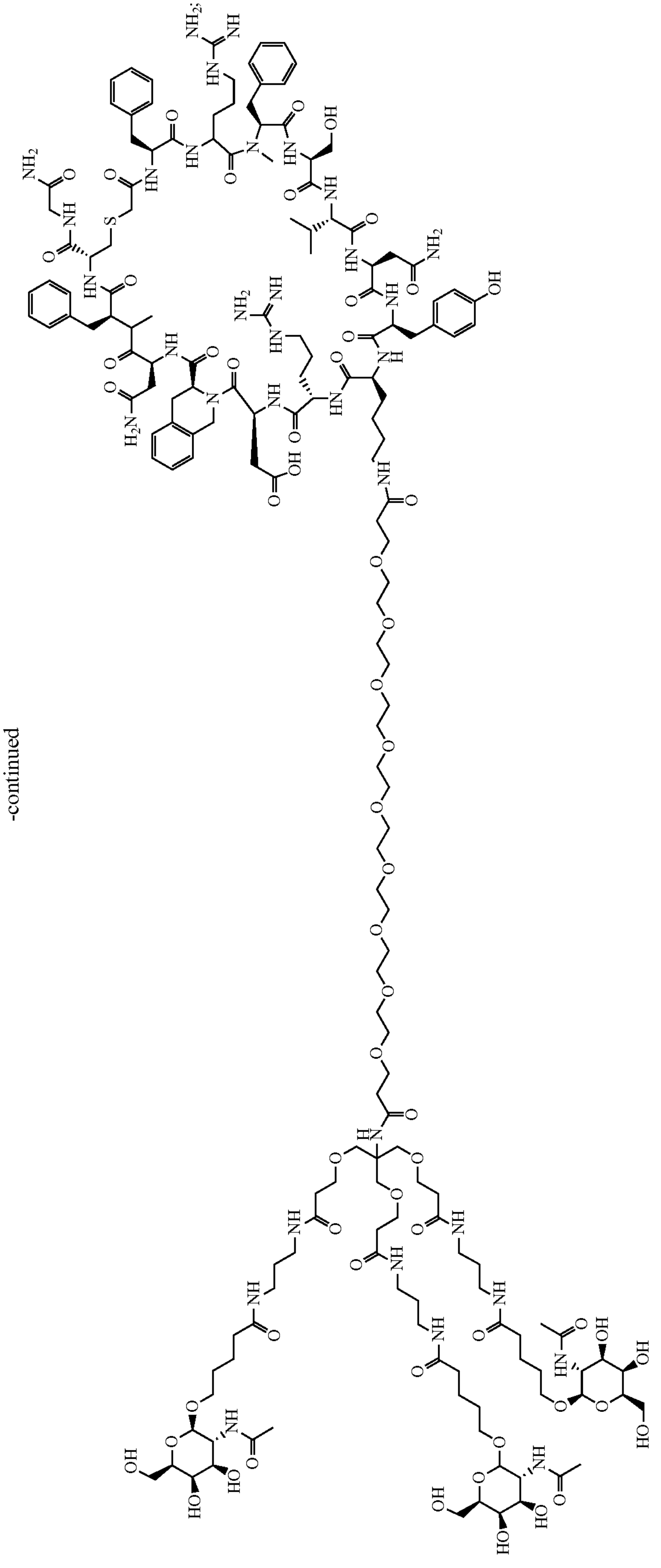

-continued
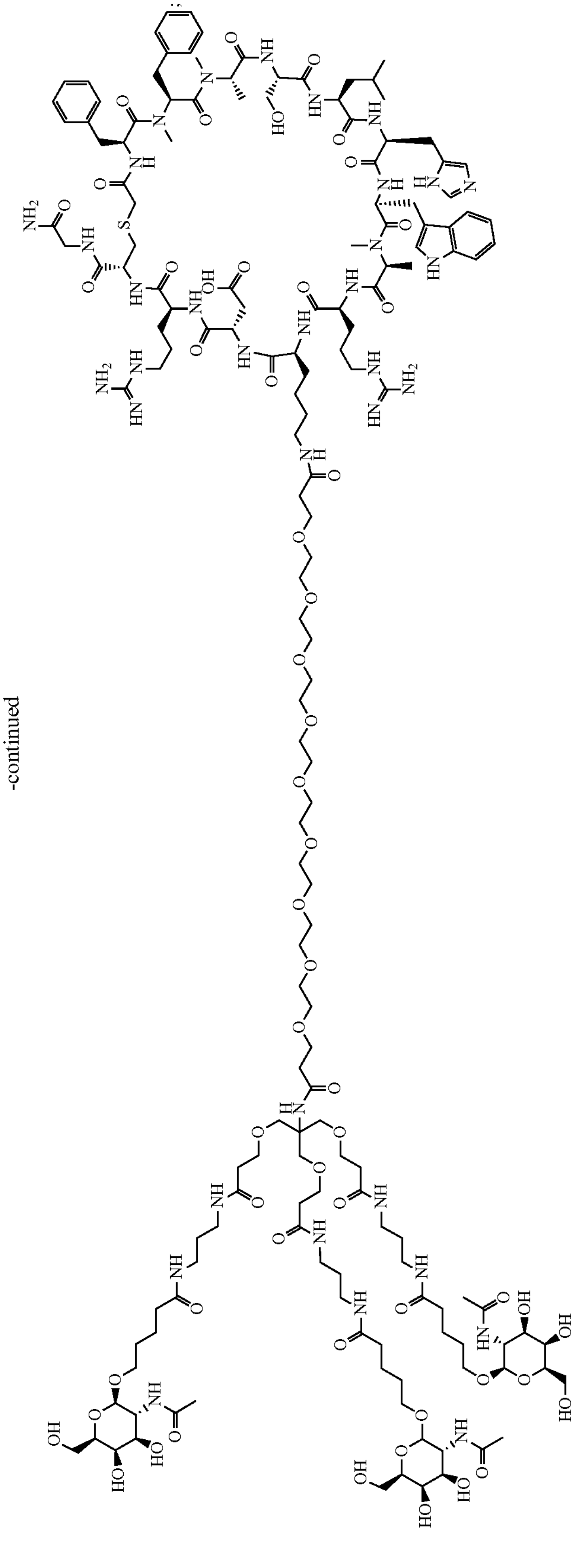
; and

-continued
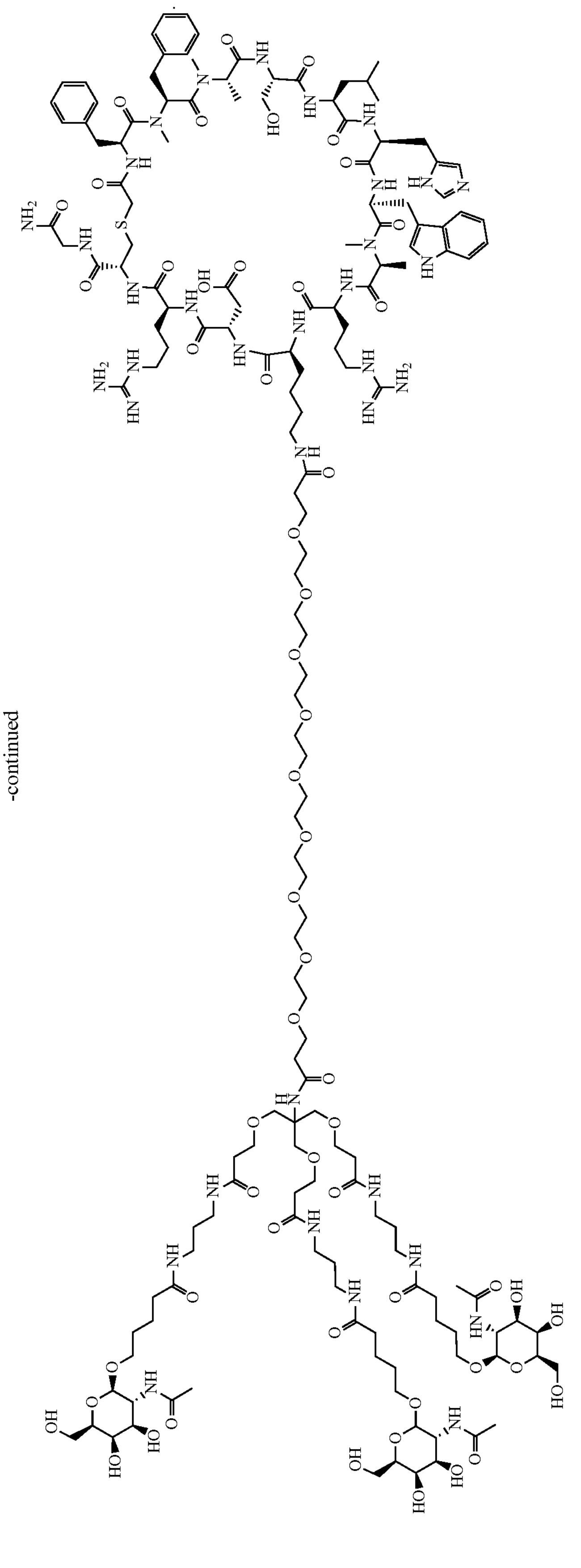

Processes for Making Compounds of Formula (I)

For illustrative purposes, the general reaction schemes depicted herein provide potential routes for synthesizing the compounds of the present invention. For a more detailed description of the individual reaction steps, see the Examples section below. In addition, many of the compounds prepared by the methods described below can be further modified in light of this disclosure using conventional chemistry well known to those skilled in the art. In the general schemes below, $R_L$, $L_A$ and $T_L$ are as defined herein.

By way of example, a general synthesis for compounds of Formula (I) is shown below in Scheme 1, wherein the receptor ligand ($R_L$) has an attached reactive group (e.g. $RG_1$) and the target ligand is attached to a linker moiety ($L_A$') which has a pendant reactive group (e.g. $RG_2$) that is capable of reacting with the reactive group on the receptor ligand, and thereby form a linker ($L_A$) which couples the receptor ligand to the target ligand, forming a compound of Formula (I).

Scheme I

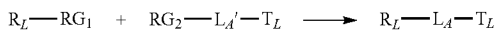

In scheme I, $RG_1$ is a reactive group 1 from Table 1 and $RG_2$ is a reactive group 1 from Table 1, wherein and the reaction product of the respective groups (as seen in Table 1) becomes a linker component of linker $L_A$.

Another general synthesis for compounds of Formula (I) is shown below in Scheme II, wherein the receptor ligand ($R_L$) is attached to a linker moiety ($L_A$') which has a pendant reactive group (e.g. $RG_1$) and the target ligand has an attached reactive group that is capable of reacting with the reactive group off of the receptor ligand, and thereby form a linker ($L_A$) which couples the receptor ligand to the target ligand, forming a compound of Formula (I).

Scheme II

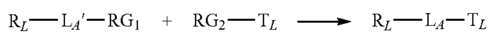

In scheme II, $RG_1$ is a reactive group 1 from Table 1 and $RG_2$ is a reactive group 1 from Table 1, wherein and the reaction product of the respective groups (as seen in Table 1) becomes a linker component of linker $L_A$.

Another general synthesis for compounds of Formula (I) is shown below in Scheme III, wherein the receptor ligand ($R_L$) is attached to a linker moiety ($L_A$") which has a pendant reactive group (e.g. $RG_1$) and the target ligand is attached to a linker moiety ($L_A$') which has a pendant reactive group (e.g. $RG_2$) that is capable of reacting with the reactive group off of the receptor ligand, and thereby form a linker ($L_A$) which couples the receptor ligand to the target ligand, forming a compound of Formula (I).

Scheme III

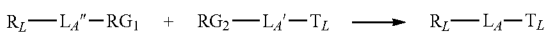

In scheme II, $RG_1$ is a reactive group 1 from Table 1 and $RG_2$ is a reactive group 1 from Table 1, wherein and the reaction product of the respective groups (as seen in Table 1) becomes a linker component of linker $L_A$.

Another general synthesis for compounds of Formula (I) is shown below in Scheme IV, wherein the receptor ligand ($R_L$) has an attached reactive group (e.g. $RG_1$) that is capable of reacting with a reactive group (e.g. $RG_2$) on a linker moiety ($L_A$"), thereby attaching the linker moiety ($L_A$") to the receptor ligand ($R_L$). The linker moiety ($L_A$") also has a protected reactive group (e.g. $RG_1$-Prot), which upon deprotection is capable of reacting with a reactive group on the target ligand (e.g. $RG_2$), thereby coupling the receptor ligand to the target ligand and forming a compound of Formula (I).

Scheme IV

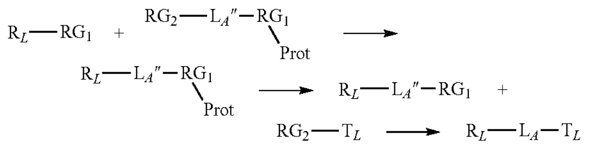

In scheme IV, $RG_1$ is a reactive group 1 from Table 1 and $RG_2$ is a reactive group 1 from Table 1, wherein and the reaction product of the respective groups (as seen in Table 1) becomes a linker component of linker $L_A$.

Another general synthesis for compounds of Formula (I) is shown below in Scheme V, wherein the target ligand ($T_L$) has an attached reactive group (e.g. $RG_1$) that is capable of reacting with a reactive group (e.g. $RG_2$) on a linker moiety ($L_A$"), thereby attaching the linker moiety ($L_A$") to the target ligand ($T_L$). The linker moiety ($L_A$") also has a protected reactive group (e.g. $RG_1$-Prot), which upon deprotection is capable of reacting with a reactive group on the receptor ligand (e.g. $RG_2$), thereby coupling the receptor ligand to the target ligand and forming a compound of Formula (I).

Scheme V

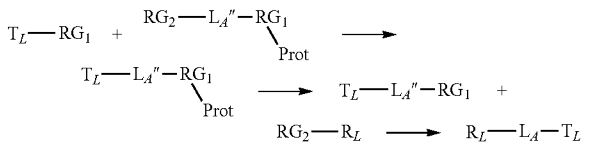

In scheme V, $RG_1$ is a reactive group 1 from Table 1 and $RG_2$ is a reactive group 1 from Table 1, wherein and the reaction product of the respective groups (as seen in Table 1) becomes a linker component of linker $L_A$.

Pharmaceutical Compositions and Routes of Administration

For the therapeutic uses of the bifunctional compounds of the invention, such compounds are administered either alone or as part of a pharmaceutical composition. Furthermore, for the therapeutic uses of the bifunctional compounds of the invention, such compounds are administered in therapeutically effective amounts either alone or as part of a pharmaceutical composition. Accordingly, in another aspect, the present invention provides a pharmaceutical composition, which comprises a bifunctional compound of the invention and a pharmaceutically acceptable carrier. In a further embodiment, the composition comprises at least two pharmaceutically acceptable carriers, such as those described herein.

The pharmaceutical compositions of the invention can be prepared using processes which include admixing a bifunctional compound of the invention with one or more pharmaceutically acceptable carriers. By way of example, the pharmaceutical compositions of the inventions are manufactured by mixing, granulating and/or coating using a bifunctional compound of the invention in free form in association with at least one pharmaceutically acceptable carrier.

The pharmaceutical composition or combination of the present invention can be in unit dosage of about 0.1-100 mg of active ingredient(s) for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, subcutaneously, intravenously, e.g., as a suspension or in aqueous solution. The dosage in vitro may range between about $10^{-12}$ molar and $10^{-6}$ molar concentrations. A therapeutically effective amount in vivo may range between about 0.01-10 mg/kg.

The activity of a compound of the present invention can be assessed by the in vitro and in vivo methods described in the examples herein.

The bifunctional compounds of the invention can the active ingredient of a pharmaceutical composition formulated for a particular route of enteral or parenteral administration.

Oral Administration Dosage Forms

The pharmaceutical compositions of the invention can be administered orally as discrete dosage forms, wherein such dosage forms include, but are not limited to, capsules, gelatin capsules, caplets, tablets, chewable tablets, lozenges, dispersible powders, granules, syrups, flavored syrups, solutions or suspensions in aqueous or non-aqueous liquids, edible foams or whips, and oil-in-water liquid emulsions or water-in-oil liquid emulsions.

Accordingly, for oral administration the pharmaceutical compositions of the invention comprising an effective amount of a compound of the invention can be made up in a solid form (including without limitation capsules, gelatin capsules, hard or soft capsules, tablets, chewable tablets, lozenges, caplets, pills, granules or dispersible powders), or in a liquid form (including without limitation, solutions, aqueous or oily suspensions, syrups, elixirs, foams, whips or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethylene glycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. Tablets may be either film coated or enteric coated according to methods known in the art. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Parenteral Dosage Forms

In certain embodiments pharmaceutical compositions of the invention are administered parenterally by various routes including, but not limited to, by subcutaneous, intravenous (including bolus injection), intramuscular, and intravitreal administration.

Certain injectable compositions are aqueous isotonic solutions or suspensions comprising a bifunctional compound of the invention. Such compositions may contain excipients, such as preserving, stabilizing, wetting or emulsifying agents, solution promoters, salts for regulating the osmotic pressure and/or buffers. Such compositions compositions may be prepared according to conventional methods known in the art, and such compositions may be sterilized.

Combination Treatment

Compounds of the invention and pharmaceutical compositions provided herein are administered singly or in combination with one or more additional therapeutic agents.

In certain embodiments, the pharmaceutical compositions of the invention optionally further comprise one or more additional therapeutic agents. Alternatively, a bifunctional compound of the invention may be administered to a patient in need thereof in combination with the administration of one or more other therapeutic agents.

The bifunctional compound of the present invention may be administered either simultaneously with, or before or after, one or more other therapeutic agent. The bifunctional compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a bifunctional compound of the present invention.

In one embodiment, the invention provides a product comprising a bifunctional compound of the present invention and at least one other therapeutic agent as a combined preparation for simultaneous, separate or sequential use in therapy, where the therapy is the treatment of a disease or condition, as described herein, by the targeted lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells or plasma membrane proteins. Products provided as a combined preparation include a composition comprising the bifunctional compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical composition comprising a bifunctional compound of the present invention and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a bifunctional compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the bifunctional compound of the present invention and the other therapeutic agent may be manufactured and/or formulated by the same or different manufacturers. Moreover, the bifunctional compound of the present invention and the other therapeutic may be brought together into a combination therapy: (i) prior to release of the combination product to physicians (e.g. in the case of a kit comprising the compound of the present invention and the other therapeutic agent); (ii) by the physician themselves (or under the guidance of the physician) shortly before administration; (iii) in the patient themselves, e.g. during sequential administration of the compound of the present invention and the other therapeutic agent.

Pharmacology and Utility

The bifunctional compounds of the present invention exhibit valuable pharmacological properties based upon depression of the levels of extracelluar target molecules by lysosomal degradation, and are therefore indicated for therapy or for use as research chemicals (e.g. as tool compounds).

Conventional therapeutics, for instance protein-directed therapeutics, treat diseases by obstructing protein function, for example by inhibiting enzymes and receptors, or by recruiting immune effectors, as in the case of many monoclonal antibody drugs. Typically, because of the reversible nature of conventional drug/target interaction, the efficacy of such conventional therapies require a superstoichiometric drug concentration to maintain inhibition, which can be lost over time as drug concentrations decrease. However, the methods described herein, which use a bifunctional compounds of the present invention, may show improved efficacy at stoichiometric or substoichiometric concentrations, where efficacy is limited by the resynthesis of target molecule (e.g. protein) rather than on drug concentration.

Accordingly, the invention provides bifunctional compounds for use in therapy by the targeted lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells or plasma membrane proteins. In certain embodiments, the invention also provides bifunctional compounds for use in therapy by the targeted asialoglycoprotein receptor (ASGPR) mediated lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins. In certain embodiments, the invention also provides bifunctional compounds for use in therapy by the targeted mannose-6-phosphate (M6PR) mediated lysosomal degradation of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins. In certain embodiments such therapies include the treatment of a cardiovascular disease, a liver disease, a renal disease, an autoimmune disease, a neurological disease, a hematological disease, a skin disease, medicinal poisoning or vasculitis. In certain embodiments such therapies include the treatment of hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning or Kawasaki disease. In other embodiments, such therapies include the treatment of nephropathy, age-related macular degeneration, atypical hemolytic uremic syndrome or hepatocellular carcinoma (HCC).

In addition, the invention provides bifunctional compounds for use in therapy, wherein such therapies include the treatment of a cardiovascular disease, a liver disease, a renal disease, an autoimmune disease, a neurological disease, a hematological disease, a skin disease, medicinal poisoning or vasculitis. In certain embodiments such therapies include the treatment of hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning or Kawasaki disease. In other embodiments, such therapies include the treatment of nephropathy, age-related macular degeneration, atypical hemolytic uremic syndrome or hepatocellular carcinoma (HCC).

The invention further provides the use of bifunctional compounds of the invention for use in therapy, wherein such therapies include the treatment of a cardiovascular disease, a liver disease, a renal disease, an autoimmune disease, a neurological disease, a hematological disease, a skin disease, medicinal poisoning or vasculitis. In certain embodiments such therapies include the treatment of hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning or Kawasaki disease. In other embodiments, such therapies include the treatment of nephropathy, age-related macular degeneration, atypical hemolytic uremic syndrome or hepatocellular carcinoma (HCC).

In another aspect, the invention provides methods for the treatment of diseases associated with elevated levels of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, wherein the method uses targeted lysosomal degradation of such extracellular target molecules. In certain embodiments, the invention also provides methods for the treatment of diseases associated with elevated levels of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, wherein the method uses targeted asialoglycoprotein receptor (ASGPR) mediated lysosomal degradation of extracellular target molecules. In certain embodiments, the invention also provides methods for the treatment of diseases associated with elevated levels of extracellular target molecules, such as growth factors, cytokines, chemokines, hormones, neurotransmitters, capsids, soluble receptors, extracellular secreted proteins, antibodies, lipoproteins, exosomes, viruses, cells and plasma membrane proteins, wherein the method uses targeted mannose-6-phosphate (M6PR) mediated lysosomal degradation of extracellular target molecules. These methods may be useful in the treatment of a variety of diseases, conditions or clinical situations that are often treated via therapeutic apheresis, such as cardiovascular diseases, liver diseases, renal diseases, autoimmune diseases, neurological diseases, hematological diseases, skin diseases, medicinal poisoning and vasculitis. By way of example such diseases include, but are not limited to, hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease. These methods may also be useful in the treatment of nephropathy, age-related macular degeneration, atypical hemolytic uremic syndrome and hepatocellular carcinoma (HCC).

In a further aspect, the invention provides a method of treating a cardiovascular disease, a liver disease, a renal disease, an autoimmune disease, a neurological disease, a hematological disease, a skin disease, medicinal poisoning and vasculitis, wherein the method comprises administration of a therapeutically effective amount of a bifunctional compound of the invention to a subject in need thereof. In a certain embodiments, such diseases include, but are not limited to, hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease. As a further embodiment, such diseases include nephropathy, age-related macular degeneration, atypical hemolytic uremic syndrome and hepatocellular carcinoma (HCC).

In a further aspect, the invention provides a method of treating a cardiovascular disease, a liver disease, a renal disease, an autoimmune disease, a neurological disease, a hematological disease, a skin disease, medicinal poisoning and vasculitis, wherein the method comprises administration of a bifunctional compound of the invention to a subject in need thereof. In a certain embodiments, such diseases include, but are not limited to, hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease. As a further embodiment, such diseases include nephropathy, age-related macular degeneration, atypical hemolytic uremic syndrome and hepatocellular carcinoma (HCC).

In another aspect, the invention provides the use of a bifunctional compound of the invention in the manufacture of a medicament for the treatment of a cardiovascular disease, a liver disease, a renal disease, an autoimmune disease, a neurological disease, a hematological disease, a skin disease, medicinal poisoning and vasculitis, wherein the method comprises administration of a therapeutically effective amount of a bifunctional compound of the invention to a subject in need thereof. In a certain embodiments, such diseases include, but are not limited to, hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease. As a further embodiment, such diseases include nephropathy, age-related macular degeneration, atypical hemolytic uremic syndrome and hepatocellular carcinoma (HCC).

The invention also provides an intracorporeal therapeutic plasmapheresis method, wherein the method comprises administering to a subject a bifunctional compound of the invention. The invention also provides a method for performing intracorporeal therapeutic plasmapheresis, wherein the method comprises administering to a subject a bifunctional compound of the invention.

The invention also provides an intracorporeal therapeutic plasmapheresis method for the treatment of a cardiovascular disease, a liver disease, a renal disease, an autoimmune disease, a neurological disease, a hematological disease, a skin disease, medicinal poisoning or vasculitis, wherein the method comprises administering to a subject a bifunctional compound of the invention. In certain embodiments such diseases are hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease.

The invention also provides an intracorporeal therapeutic plasmapheresis method, wherein the method comprises administering to a subject a bifunctional compound of Formula (I). The invention also provides a method for performing intracorporeal therapeutic plasmapheresis, wherein the method comprises administering to a subject a bifunctional compound of the invention.

The invention also provides an intracorporeal therapeutic plasmapheresis method for the treatment of a cardiovascular disease, a liver disease, a renal disease, an autoimmune disease, a neurological disease, a hematological disease, a skin disease, medicinal poisoning or vasculitis, wherein the method comprises administering to a subject a bifunctional compound of Formula (I). In certain embodiments such diseases are hypercholesterolemia, familial hypercholesterolemia, arteriosclerosis, arteriosclerosis obliterans, fulminant hepatic failure, postoperative hepatic failure, acute liver failure, hepatitis C, hepatitis B, chronic hepatitis C, chronic hepatitis B, liver allotransplantation, focal glomerulosclerosis, renal allotransplantation, malignant rheumatoid arthritis, systemic lupus erythematosus, myasthenia gravis, Guillain-Barre syndrome, chronic inflammatory demyelinating polyneuropathy, multiple sclerosis, multiple myeloma, macroglobulinemia, thrombic thrombopenic purpura, hemolytic-uremic syndrome, pregnancy blood group incompatibility, hemophilia, pemphigus, bullous pemphigoid, toxic epidermal necrosis, Steven-Johnson syndrome, medicinal poisoning and Kawasaki disease.

In one aspect of the present invention are bifunctional molecules that utilize receptor mediated endocytosis to either eliminate proprotein convertase subtilisin/kexin type 9 (PCSK9) from the plasma or decrease the level of PCSK9 in the plasma.

PCSK9 has pronounced effects on plasma low density lipoprotein cholesterol (LDL-C) levels via its modulation of hepatic low density lipoprotein receptors (LDLR), the main route by which cholesterol is removed from the circulation. PCSK9 binds the LDLR and directs it to lysosomal degradation, thereby increasing plasma LDL-C levels and, in turn, coronary heart disease risk. (Maxwell K. N., Proc. Natl. Acad. Sci., 101, 2004, 7100-7105; Park, S. W., J. Biol. Chem. 279, 2004, 50630-50638; Lagace T. A., et. al. J. Clin. Invest. 2006, 116(11):2995-3005). Overexpression of mouse or human PCSK9 in mice has been shown to elevate total and LDL-C levels and dramatically reduce hepatic LDLR protein, without an observed effect on the levels of mRNA, SREBP, or SREBP protein nuclear to cytoplasmic ratio. (Maxwell K. N., Proc. Natl. Acad. Sci. 101, 2004, 7100-7105). Moreover, mutations in PCSK9 that cause loss of PCSK9 function in mouse models have also been shown to lower total and LDL-C levels. (Cohen, J. C., et al., N. Engl. J. Med., 354, 2006, 1264-1272). Thus, indicating that modulation of PCSK9 results in a reduction of LDLR protein levels.

Furthermore, gene deletion of PCSK9 has also been conducted in mice. PCSK9 knockout mice show an approximate 50% reduction in plasma cholesterol levels and enhanced sensitivity to statins in reducing plasma cholesterol (Rashid. S., et al., (2005) Proc Natl Acad Sci 102: 5374-5379). Human genetic data strongly support the role of PCSK9 in LDL homeostasis. The link between PCSK9 and plasma LDL-C levels was first established by the discovery of PCSK9 missense mutations in patients with an autosomal dominant form of familial hypercholesterolemia (Abifadel M., et al., Nature Genetics, 2003; 34:154-156). Patients carrying PCSK9 gain-of-function alleles have increased plasma LDL-C levels and premature coronary heart disease, whereas those with PCSK9 loss-of-function alleles have markedly reduced plasma LDL-C and are protected from coronary heart disease.

PCSK9 also plays a role in Lipoprotein (a) (Lp(a)) metabolism. Lp(a) is a proatherogenic lipoprotein comprised of an LDL particle covalently linked to apoLp(a). Human genetic studies indicate that Lp(a) is causally associated with coronary heart disease risk. PCSK9 therapeutic antibodies have been shown to significantly reduce Lp(a) levels in patients with hypercholesterolemia. (Desai, N. R., et. al., Circulation. 2013; 128(9):962-969; Lambert, G. et. al., Clinical Science, 2017, 131, 261-268). Patients receiving statin therapy treated with a monoclonal antibody against PCSK9 have shown up to 32% reduction in Lp(a) levels compared to placebo. (Desai N. R., et. al. Circulation. 2013; 128(9):962-969).

In addition to having cardiovascular effects, PCSK9 plays an important role in sepsis, a life-threatening condition caused by a body's response to infection. Overexpression of PCSK9 in septic mice has been shown to aggravate sepsis by increasing inflammation, while inhibition of PCSK9 has been shown to reduce mortality. (Dwivedi, D. J., et al., Shock, 2016, 46(6), 672-680). Moreover, flow cytometry studies in human HepG2 cells have shown that PCSK9 negatively regulates gram-negative lipopolysaccharide (LPS) uptake by hepatocytes through the regulation of the LDLR mediated bacterial lipid uptake of lipoteichoic acid (LTA) and LPS through an LDL-dependent mechanism. (Grin, P. M., et al., Nature, 2018, 8(1):10496) Thus, inhibition of PCSK9 has the potential to treat sepsis by reducing the body's immune response to an infection.

Atherosclerotic cardiovascular disease is the leading cause of mortality worldwide, resulting in an estimated 7.4 million global deaths in 2015. LDL, the major carrier of cholesterol in the bloodstream, is the most extensively studied modifiable risk factor associated with ASCVD [Ference B A, et al 2017]. Prospective cohort studies, Mendelian randomization studies, and randomized clinical trials demonstrate a log-linear association between the absolute exposure of LDL cholesterol and the risk of ASCVD [Baigent C, et al 2005, Ference B A, et al 2017].

PCSK9 is a 692-amino acid serine protease that has pronounced effects on LDL-C levels via its modulation of hepatic LDLR receptors, the main route by which cholesterol is removed from the circulation [Brown M S and Goldstein J L 1986]. PCSK9 binds the LDLR and directs it to lysosomal degradation, thereby increasing plasma LDL-C levels and, in turn, ASCVD risk. PCSK9 has exceptional target validation. Mice lacking PCSK9 have reduced plasma cholesterol and increased hepatic LDLR expression versus littermate controls. Mice in which PCSK9 has been selectively inactivated in the liver have no detectable PCSK9 in the blood, suggesting that the liver is the main source of circulating PCSK9 [Zaid et al, 2008]. Patients carrying PCSK9 gain-of-function alleles have increased plasma LDL-C levels and premature ASCVD, whereas those with PCSK9 loss-of-function alleles have markedly reduced plasma LDL-C and are protected from ASCVD [Cohen J, et al 2006]. Thus, there is great interest in identifying novel therapies that mimic PCSK9 loss-of-function.

Clinical studies with PCSK9 blocking antibodies have demonstrated significant LDL-lowering in healthy volunteers and in hypercholesterolemic patients, with and without statins [Banerjee et al, 2012; Dias et al, 2012; Roth et al, 2012; Stein et al, 2012; Sullivan et al, 2012]. Statins increase PCSK9 levels, which limits the utility of dose escalation [Careskey et al, 2008; Welder et al, 2010]. Data from several clinical studies conducted with inclisiran demonstrate that reducing plasma PCSK9 via the inhibition of its protein synthesis in hepatocytes significantly lowers circulating LDL-C levels [Fitzgerald et al, 2017; Ray et al, 2017; Nishikido and Ray, 2018; Ray et al, 2019].

The present invention relates to bifunctional compounds and compositions that are capable of decreasing plasma levels of PCSK9 or eliminating PCSK9 circulating in the plasma. The disclosure features methods of treating, preventing or ameliorating a disease or disorder in which PCSK9 plays a role by administering to a patient in need thereof a therapeutically effective amount of a bifunctional compound of Formula (Ia). The methods of the present invention can be used in the treatment of a variety of PCSK9 dependent diseases and disorders by decreasing plasma levels of PCSK9 or eliminating PCSK9 circulating in the plasma. Decreasing plasma levels of PCSK9 or eliminating PCSK9 circulating in the plasma provides a novel approach to the treatment, prevention, or amelioration of diseases including, but not limited to, hypercholesterolemia, hyperlipidemia, hypertriglyceridemia, sitosterolemia, atherosclerosis, arteriosclerosis, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, and xanthoma.

The bifunctional compounds of Formula (Ia) of the invention, by decreasing plasma levels of PCSK9 or eliminating PCSK9 circulating in the plasma, have utility in the treatment of hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

For example, the bifunctional compounds of Formula (Ia) of the invention bind to PCSK9 and direct it for elimination via receptor mediated endocytosis, thereby either decreasing plasma levels of PCSK9 or eliminating PCSK9 circulating in the plasma. Consequently, PCSK9 is not available to bind to the low density lipoprotein receptors (LDLR) or any other target receptors, resulting in more LDLRs present on the surface of cells to remove LDL-particles from the extracellular fluid. Therefore, decreasing plasma levels of PCSK9 or eliminating PCSK9 circulating in the plasma can lower blood LDL-particle concentrations.

Accordingly, bifunctional compounds of Formula (Ia) of the invention may therefore be potentially useful in the treatment, prevention, amelioration or delay of progression of a PCSK9 mediated disease or disorder, or a disease or disorder in which PCSK9 plays a role, as well as conditions, diseases and disorders benefitting from decreased plasma levels of PCSK9 or elimination of PCSK9 circulating in the plasma. Such diseases and disorders include diseases or disorders selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

In addition, bifunctional compounds of Formula (Ia) of the invention may therefore be potentially useful in the treatment, prevention, amelioration or delay of progression of a disease or disorder requiring decreased plasma levels of PCSK9 or elimination of PCSK9 circulating in the plasma. Such diseases and disorders include diseases or disorders selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

Another aspect of the present invention are bifunctional molecules that utilize receptor mediated endocytosis to eliminate or decrease level of complement factor H-related protein 3 (FHR3) from the plasma.

Complement mediated immune responses are tightly regulated by a number of endogenously produced proteins to regulate activity and discriminate between healthy self (non-activating) and damaged or non-self, pathogenic activating cells. These complement control proteins range from cell surface bound (i.e. CR1, MCP, DAF) to circulating proteins (i.e. factor H and $C_4BP$) that are recruited to self-surfaces by binding to polysaccharides such as glycosaminoglycans on host self-surfaces to inactivate complement (Mol Immuno 47(13): 2187-2197). Complement regulation is tightly controlled to maintain homeostasis and whose dysregulation and deficiency causing it to target host cells, have been implicated in many diseases.

Factor H (FH), a major negative regulator of alternative complement pathway activation, belongs to a family that also includes five other related family members thought to have arisen from nonallelic homologous recombination and interlocus gene conversion: complement factor H-related protein 1 (FHR1), complement factor H-related protein 2 (FHR2), complement factor H-related protein 3 (FHR3), complement factor H-related protein 4 with isoforms 4A and 4B (FHR4A and FHR4B) and complement factor H-related protein 5 (FHR5).

Due to the central role that factor H plays in the regulation of complement, there are many clinical implications arising from aberrant FH activity. Loss of function mutations in factor H increase susceptibility to the renal diseases, atypical haemolytic uraemic syndrome (aHUS) and dense deposit disease (DDD), whilst polymorphic variation of complement factor H has been strongly associated with important human diseases, including age-related macular degeneration (AMD) and meningococcal sepsis (Clin Exp Immunol 151 (2):210-230; Immunobiology 217(11):1034-1046).

FHR3, unlike factor H, lacks the complement regulatory domains essential for complement inactivation and also competes with factor H, resulting in complement over-activation. Thus the present invention provides bifunctional compounds for use in modulating the concentration of complement factor H-proteins, specifically FHR3, to remove factor H's competitor and thereby restore factor H-mediated regulation to treat disorders caused by excessive complement activation.

The present invention also relates to bifunctional compounds and compositions that are capable of decreasing plasma levels of FHR3 or eliminating FHR3 circulating in the plasma. The disclosure features methods of treating, preventing or ameliorating a disease or disorder associated with FHR3 by administering to a patient in need thereof a therapeutically effective amount of a bifunctional compound of Formula (Ib). The methods of the present invention can be used in the treatment of a variety of disease or disorder associated with FHR3 by decreasing plasma levels of FHR3 or eliminating FHR3 circulating in the plasma. Decreasing plasma levels of FHR3 or eliminating FHR3 circulating in the plasma provides a novel approach to the treatment, prevention, or amelioration of diseases including, but not limited to, nephropathy, age-related macular degeneration, atypical hemolytic uremic syndrome and hepatocellular carcinoma (HCC).

The bifunctional compounds of Formula (Ib) of the invention, by decreasing plasma levels of FHR3 or eliminating FHR3 circulating in the plasma, have utility in the treatment of nephropathy, age-related macular degeneration, atypical hemolytic uremic syndrome and hepatocellular carcinoma (HCC).

For example, the bifunctional compounds of Formula (Ib) of the invention bind to FHR3 and direct it for elimination via receptor mediated endocytosis, thereby either decreasing plasma levels of FHR3 or eliminating FHR3 circulating in the plasma. Accordingly, bifunctional compounds of Formula (Ib) of the invention may therefore be potentially useful in the treatment, prevention, amelioration or delay of progression of a disease or disorder mediated by compliment activity, such as nephropathy, age-related macular degeneration, atypical hemolytic uremic syndrome and hepatocellular carcinoma (HCC).

EXAMPLES

The invention is further described in the following examples, which are not intended to limit the scope of the invention described in the claims.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art or can be produced by organic synthesis methods as described herein.

Abbreviations Used in the Following Examples and Elsewhere Herein are

AA: amino acid
Ac: acetyl
$Ac_2O$: acetic anhydride
ACN: acetonitrile
aq.: aqueous
AM: aminomethyl
Boc: tert-butoxycarbonyl
BnOH: Benzyl alcohol
BSA: bovine serum albumin
DBU: 1,8-Diazabicyclo[5.4.0]undec-7-ene
DCM: dichloromethane
DIC: N,N'-Diisopropylcarbodiimide
DTT: dithiothreitol
DMA: dimethylacetamide
DMAP: 4-Dimethylaminopyridine
DMF: N,N-dimethylformamide
DMSO: dimethylsulfoxide
DIEA or DIPEA: N,N-diisopropylethylamine
EA: Ethyl acetate
EDCI: 1-Ethyl-3-(3-dimethylaminopropyl)carbodiimide
EDT: ethanedithiol
eq.: equivalent
ESI-MS: electrospray ionization mass spectrometry
Et and EtOAc: ethyl and ethyl acetate
Fmoc: fluorenylmethyloxycarbonyl
FRET: Fluorescence Resonance Energy Transfer
HATU: O-(7-azobenzotriazol-1-yl)-1,1,3,3-tetramethyluroniumhexafluorophosphate
HCTU: O-(1H-6-chlorobenzotriazole-1-yl)-1,1,3,3-tetramethyluronium hexafluorophosphate
HEPES: 4-(2-hydroxyethyl)-1-piperazineethanesulfonic acid
HFIP: Hexafluoroisopropanol
HILIC: (hydrophilic interaction liquid chromatography
HOAt: 1-Hydroxy-7-azabenzotriazole
HOBt: Hydroxybenzotriazole
HPLC: high pressure liquid chromatography
h, hr: hour(s)
HRMS: high resolution mass spectrometry IC50: half maximal inhibitory concentration
LC and LCMS: liquid chromatography and liquid chromatography-mass spectrometry
LDLR: low density lipoprotein receptor
min: minute(s)
Me: methyl
MS: mass
m/z: mass to charge ratio
M and mM: molar and millimolar
mg: milligram
µL, mL and L: microliter(s), milliliter(s) and liter(s)
N: equivalent per liter
NMP: N-methyl-2-pyrrolidone
Oxima pure: 2-Cyano-2-(hydroxyimino)acetic acid ethyl ester, potassium salt, Ethyl (hydroxyimino)cyanoacetate potassium salt
PBS: Phosphate-buffered saline
PD: Pharmacodynamics
PE: Petroleum ether
PG: protecting group
PS: Polystyrene resin
PyOxim: [Ethyl cyano(hydroxyimino)acetato-O2]tri-1-pyrrolidinylphosphonium hexafluorophosphate
Pbf: 2,2,4,6,7-pentamethyldihydrobenzofuran-5-sulfonyl
PCSK9: Proprotein convertase subtilisin/kexin type 9
Ph: phenyl
RP: reverse phase
rpm: revolutions per minute
rt: room temperature
RU: Resonance unit
SPPS: solid phase peptide synthesis
sat.: saturated
tBu: tertiary butyl
TBAI: Tetrabutylammonium iodide
TBTU: 2-(1H-Benzotriazole-1-yl)-1,1,3,3-tetramethyluronium tetrafluoroborate
TEA: triethylamine
THF: tetrahydrofuran
TentaGel™ S RAM resin: N-Fmoc-4'-[poly(oxyethylene) carbamoylmethoxy]-2,4-dimethoxy-benzhydrylamine polymer bound, poly(oxyethylene)-RAM polymer bound
TFA: trifluoroacetic acid
THPTA: tris-hydroxypropyltriazolylmethylamine
TIS: triisopropylsilane
TLC: Thin-layer chromatography
TMSOTF or TMSOTf: trimethylsilyl trifluoromethanesulfonate
$t_r$: retention time
TR: time resolved
TMSCI: Trimethylsilyl chloride
Trt: trityl
TsOH:
UPLC: ultra performance liquid chromatography
UV: ultraviolet
wt: weight Analytical Methods, Materials, and Instrumentation Unless otherwise noted, reagents and solvents were used as received from commercial suppliers. Proton nuclear magnetic resonance (NMR) spectra were obtained with a Varian spectrometer at 400 MHz, a Bruker spectrometer at 300 MHz or 400 MHz. Spectra are given in ppm (δ) and coupling constants, J, are reported in Hertz. Tetramethylsilane (TMS) or the solvent peak was used as an internal standard. If not otherwise specified, purity and low resolution mass spectral data were measured using a Thermo Finnigan Surveyor HPLC system with Surveyor photo diode array (PDA) detection and a Thermo LCQ Fleet™ ion trap mass spectrometer. Column: Synergi 4 micron, hydro-RP80A, 30×2.0 mm, Flow rate: 0.500 mL/min; Solvent A (water+0.1% formic acid), Solvent B (acetonitrile+0.1% formic acid); Gradient: 2% B at t=0 to 95% B at 3 min to 95% B at 3.3 min.

General Preparative HPLC Purification Procedure and Mass Spectra

The crude peptides were purified by preparative reverse phase C18-HPLC, using columns of different sizes and with varying flow rates, depending on the amount of crude peptide to be purified. For example, 0.1% TFA in water (A) and 0.1% TFA in acetonitrile (B) were employed as eluents. Product-containing fractions were collected and lyophilized to obtain the purified product.

Condition E-1 (LCMS)—Column: Acquity UPLC® BEH C18, 300 Å, 1.7 µm 2.1×50 mm, 80° C.; Flow rate: 1.0 mL/min; Mobile phase: (A) 0.5% TFA in water/(B) 0.4% TFA in acetonitrile; Gradient: 5% to 98% in 4.4 min; Electrospray mass spectra (+), DAD-UV chromatogram 214 nm.

Analytical Method 1

Agilent 1100/1200 ALS system/Waters ZQD MS system
Eluent A: 0.05% Trifluoroacetic acid in $H_2O$
Eluent B: Acetonitrile
Column temperature: 40° C.
Flow: 2.0 mL/min
Column: SunFire C18, 3.5 µm, 3.0×30 mm
Gradient:

| Time | Eluent A [%] | Eluent B [%] |
|---|---|---|
| 0.00 | 95 | 5 |
| 1.70 | 5 | 95 |
| 2.00 | 5 | 95 |
| 2.10 | 95 | 5 |

Analytical Method 2

Waters Acquity UPLC system/Waters SQD MS system
Eluent A: 5 mM Ammonium hydroxide in $H_2O$
Eluent B: 5 mM Ammonium hydroxide in acetonitrile
Column temperature: 50° C.
Flow: 1.0 mL/min
Column: Acquity UPLC BEH C18, 1.7 µm, 2.1×50 mm
Gradient:

| Time | Eluent A [%] | Eluent B [%] |
|---|---|---|
| 0.00 | 98 | 2 |
| 4.40 | 2 | 98 |
| 5.15 | 2 | 98 |
| 5.19 | 98 | 2 |

Analytical Method 3

Waters Acquity UPLC system/Waters Xevo G2 Qtof MS system
Eluent A: 0.1% Formic acid in $H_2O$
Eluent B: 0.1% Formic acid in acetonitrile
Column temperature: 50° C.
Flow: 1.0 mL/min
Column: Acquity UPLC BEH C18, 1.7 µm, 2.1×50 mm Gradient:

| Time | Eluent A [%] | Eluent B [%] |
|---|---|---|
| 0.00 | 98 | 2 |
| 0.06 | 98 | 2 |
| 1.76 | 2 | 98 |
| 2.00 | 2 | 98 |
| 2.16 | 98 | 2 |

Analytical Method 5

Waters Acquity UPLC system/Waters SQD MS system

Eluent A: 5 mM Ammonium hydroxide in $H_2O$

Eluent B: 5 mM Ammonium hydroxide in acetonitrile

Column temperature: 50° C.

Flow: 1.0 mL/min

Column: Acquity UPLC BEH C18, 1.7 μm, 2.1×30 mm

Gradient:

| Time | Eluent A [%] | Eluent B [%] |
|---|---|---|
| 0.00 | 98 | 2 |
| 0.10 | 98 | 2 |
| 1.50 | 2 | 98 |
| 1.80 | 2 | 98 |
| 1.90 | 98 | 2 |
| 2.00 | 98 | 2 |

Analytical Method 7

Waters Acquity UPLC system/Waters SQD MS system

Eluent A: 0.1% Formic acid in $H_2O$

Eluent B: 0.1% Formic acid in acetonitrile

Column temperature: 50° C.

Flow: 1.0 mL/min

Column: Acquity UPLC BEH C18, 1.7 μm, 2.1×30 mm

Gradient:

| Time | Eluent A [%] | Eluent B [%] |
|---|---|---|
| 0.00 | 98 | 2 |
| 0.10 | 98 | 2 |
| 1.50 | 2 | 98 |
| 1.80 | 2 | 98 |
| 1.90 | 98 | 2 |
| 2.00 | 98 | 2 |

Analytical Method 9

Waters Acquity UPLC/Waters QTof MS system

Eluent A: 0.05% Trifluoroacetic acid in $H_2O$

Eluent B: 0.04% Trifluoroacetic acid in acetonitrile

Column temperature: 80° C.

Flow: 0.5 mL/min

Column: Acquity UPLC CSH C18, 1.7 μm, 2.1 mm×100 mm

Gradient:

| Time | Eluent A [%] | Eluent B [%] |
|---|---|---|
| 0.00 | 95 | 5 |
| 0.20 | 95 | 5 |
| 9.40 | 2 | 98 |

-continued

| Time | Eluent A [%] | Eluent B [%] |
|---|---|---|
| 9.80 | 2 | 98 |
| 9.90 | 95 | 5 |
| 10.00 | 95 | 5 |

Analytical Method 10

Waters Acquity UPLC/SQD MS system

Eluent A: 0.05% Formic acid and 3.75 mM ammonium acetate in $H_2O$

Eluent B: 0.04% Formic acid in acetonitrile

Column temperature: 60° C.

Flow: 1.0 mL/min

Column: Acquity UPLC HSS T3, 1.8 μm, 2.1 mm×50 mm

Gradient:

| Time | Eluent A [%] | Eluent B [%] |
|---|---|---|
| 0.00 | 95 | 5 |
| 1.40 | 2 | 98 |
| 1.80 | 2 | 98 |
| 1.90 | 95 | 5 |
| 2.00 | 95 | 5 |

Analytical Method 11

Waters Acquity UPLC/SQD MS system

Eluent A: 0.05% Formic acid and 3.75 mM ammonium acetate in $H_2O$

Eluent B: 0.04% Formic acid in acetonitrile

Column temperature: 60° C.

Flow: 1.0 mL/min

Column: Acquity UPLC HSS T3, 1.8 μm, 2.1 mm×50 mm

Gradient:

| Time | Eluent A [%] | Eluent B [%] |
|---|---|---|
| 0.00 | 99 | 1 |
| 1.40 | 2 | 98 |
| 1.80 | 2 | 98 |
| 1.90 | 99 | 1 |
| 2.00 | 99 | 1 |

Analytical Method 12

Waters Acquity UPLC/SQD MS system

Eluent A: 0.05% Formic acid and 3.75 mM ammonium acetate in $H_2O$

Eluent B: 0.04% Formic acid in acetonitrile

Column temperature: 60° C.

Flow: 1.0 mL/min

Column: Acquity UPLC HSS T3, 1.8 μm, 2.1 mm×50 mm

Gradient:

| Time | Eluent A [%] | Eluent B [%] |
|---|---|---|
| 0.00 | 95 | 5 |
| 9.40 | 2 | 98 |
| 9.80 | 2 | 98 |
| 9.90 | 95 | 5 |
| 10.00 | 95 | 5 |

General Procedure for Cyclic Peptides

Synthesis:

The following general scheme can be used to obtain compounds cyclic peptides, such as compounds (C1) to (C4).

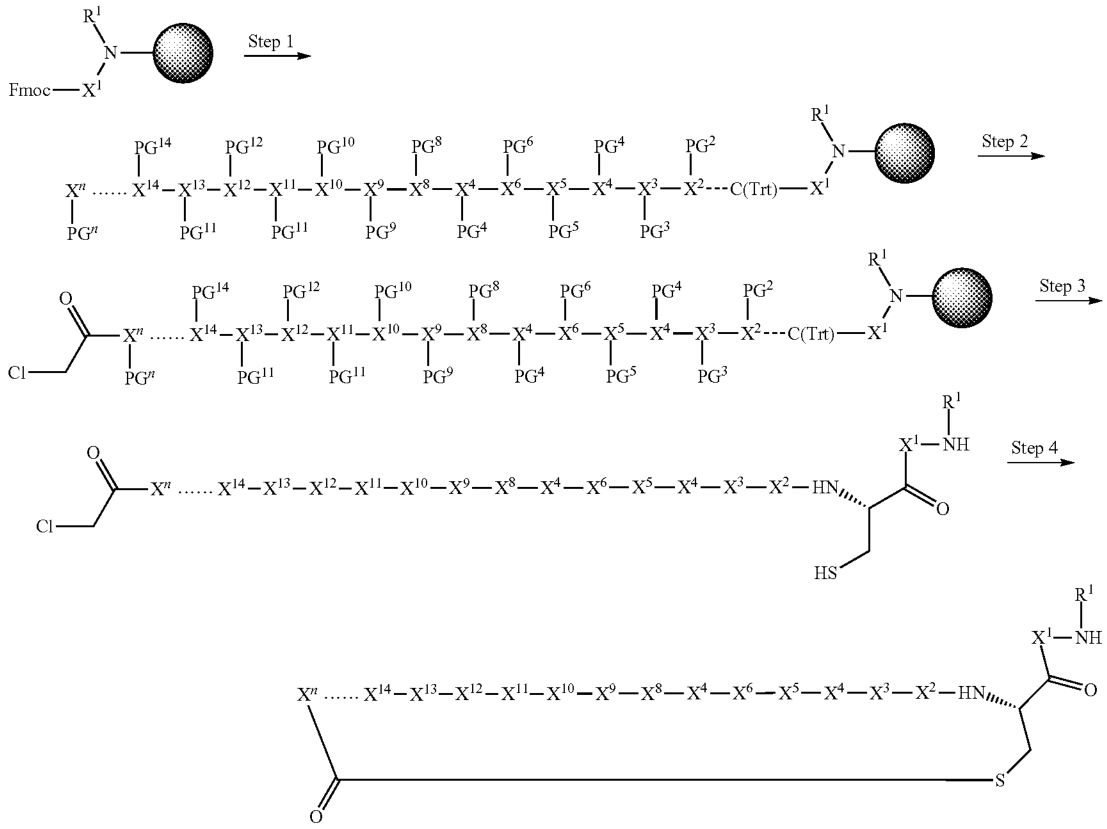

Step 1: Peptide Synthesis

Solid Phase Peptide Synthesis on the Liberty® Peptide Synthesizer from CEM. Inc.

Synthesis Cycle A-1

The resin was washed with DMF and then deprotected in two cycles by treatment with 4-methylpiperidine/DMF (1:4)—the first cycle for 30 seconds, and the second cycle for 3 minutes. Coupling was accomplished by addition of the Fmoc-amino acid (4-5 eq.; 0.2 M solution in DMF), HATU (4-5 eq.; 0.5 M solution in DMF) and DIPEA (4-6 eq.; 2 M solution in NMP). The coupling and deprotection steps were repeated until the desired cyclic polypeptide was obtained. All Fmoc amino acids were coupled for 5 min at 75° C., except for the amino acids shown in Table 3 below. After the final coupling was completed, Fmoc was removed by repetitive treatment with 4-methylpiperidine/DMA (1:4) to provide the deprotected peptide.

TABLE 3

AA coupling condition for Synthesis Cycle A -1

| AA | Temperature (° C.) | Time (min) |
|---|---|---|
| Fmoc-N-methyl AA | 75 | 10 |
| Any Fmoc-AA coupled to an N-methyl AA | 75 | 10 |
| Fmoc-C(Trt) | 50 | 10 |

Solid Phase Peptide Synthesis on the Prelude® Peptide Synthesizer from Gyros Protein Technologies AB.

Alternatively, the peptide was synthesized on the Prelude® Peptide Synthesizer as described in Synthesis Cycle B-1 or in Synthesis Cycle B-2.

Synthesis Cycle B-1

The resin was washed with DMA. Fmoc was then removed by repetitive treatment of the resin with piperidine/DMA (1:4). Coupling was accomplished by addition of the Fmoc-amino acid (3 eq.; 0.2 M solution in NMP), HCTU (3 eq.; 0.3 M solution in NMP), and DIPEA (3-6 eq.; 0.66-0.9 M solution in NMP) followed by mixing of the suspension with nitrogen at rt for typically 15 min to 4 h depending on the specific requirements. After washing with DMA, the coupling step was repeated. After washing with DMA, capping was performed by addition of a mixture of $Ac_2O$/pyridine/DMA (1:1:8) and subsequent mixing of the suspension at rt. After the final coupling was completed, Fmoc was removed as described above in Synthesis Cycle A-1 to provide the peptide.

Synthesis Cycle B-2

The resin was washed with DMA. Fmoc was removed by repetitive treatment with 4-methylpiperidine/DMA (1:4). Coupling was accomplished by addition of a mixture of the Fmoc-amino acid (3 eq.; 0.2 M solution in NMP), Oxyma Pure (3 eq. 0.3 M solution in NMP) and DIPEA (6-7 eq.; 0.66 M solution in NMP) followed by mixing of the suspension with nitrogen at rt for 15 min to 4 h depending on the specific requirements. After washing with DMA, the coupling step was repeated. After washing with DMA capping was performed by addition of a mixture of $Ac_2O$/pyridine/DMA (1:1:8) and subsequent mixing of the suspension at rt. After the final coupling was completed, Fmoc was removed as described above in Synthesis Cycle A-1 to provide the peptide.

Step 2: Peptide Acylation

The resin product obtained from Step 1 was suspended in N-methylpyrrolidine, and N-succinimidyl 2-chloroacetate (5 equivalents) was added. The resulting resin mixture was shaken at room temperature overnight. The resin was then filtered and washed three times each with dimethylformamide and dichloromethane to provide the acylated peptide product.

Step 3: Cleavage from Resin with or without Concomitant Removal of Protecting Groups (PGs)

The resin product obtained from Step 2 was shaken for 1-3 h with one of the cleavage solutions listed herein below (1-5 mL for 0.1 mmol scale). The resin was filtered and treated again with fresh cleavage solution for 0.5-1.5 h. The cleavage cycle was repeated as needed.

The resin was then filtered and the combined filtrates were poured slowly onto a mixture of cold heptane/diethyl ether (1:1) to provide a precipitate. The suspension containing the precipitate was centrifuged and the supernatant was poured off. The precipitate was suspended in cold ether, vortexed briefly, and then centrifuged. This washing process was repeated two more times. The crude peptide product was dried in high vacuum.

The following cleavage solutions were used:

Cleavage Method 1: TFA/$H_2O$/TIS/DTT (92.5:2.5:2.5:2.5)

Cleavage Method 2: 95% aq. TFA/EDT/TIS (95:2.5:2.5)

Step 4: Peptide Cyclization

The crude peptide product obtained from Step 3 was dissolved in DMSO or DMA and treated with TEA or DIPEA. The reaction mixture was then shaken overnight at room temperature. The resulting reaction mixture containing the cyclized peptide was concentrated on a centrifugal evaporator to provide the desired cyclic polypeptide.

Example 1: Synthesis of PCSK9 Receptor Ligands Compounds (C1) to (C11)

Example 1-1: Synthesis of 3-((6S,9S,12S,15S, 18S, 21S,24S,27S,29aS,35S,38S,44R,46aS)-15,21-bis([1, 1'-biphenyl]-4-ylmethyl)-38-benzyl-44-((2-(((S)-1,6-diamino-1-oxohexan-2-yl)amino)-2-oxoethyl) carbamoyl)-24,27-bis((R)-1-hydroxyethyl)-35-isopropyl-6,12,13,18,19-pentamethyl-5,8,11,14,17, 20,23,26,29,34,37,40,46-tridecaoxotetratetracontahydro-5H-dipyrrolo[2,1-f: 2',1'-g1][1]thia[4,7,10,13,16,19,22,25,28,31,34,37, 40]tridecaazacyclodotetracontin-9-yl)propanoic acid (C1)

(C1)

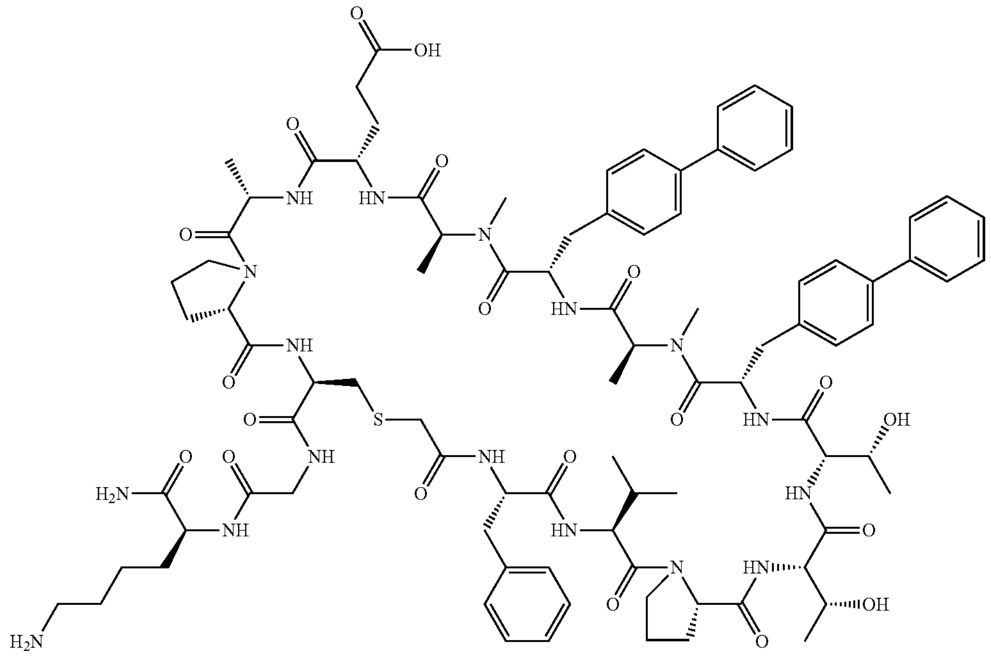

Note: Compound (C1) has the following amino acid sequence:

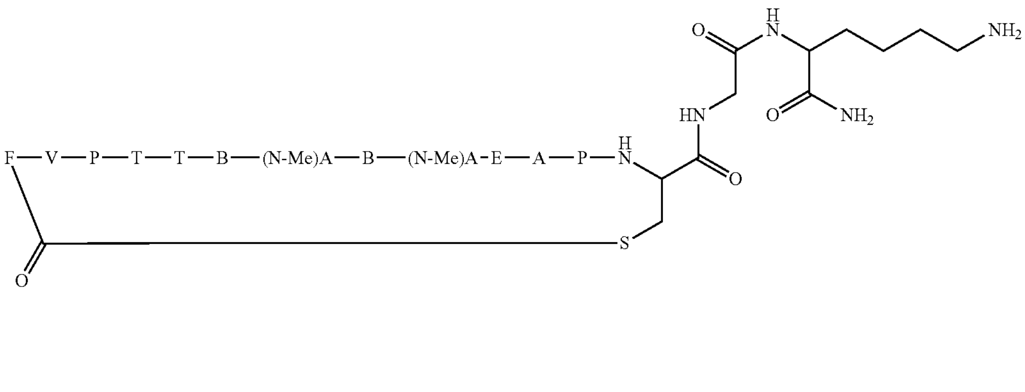

-continued

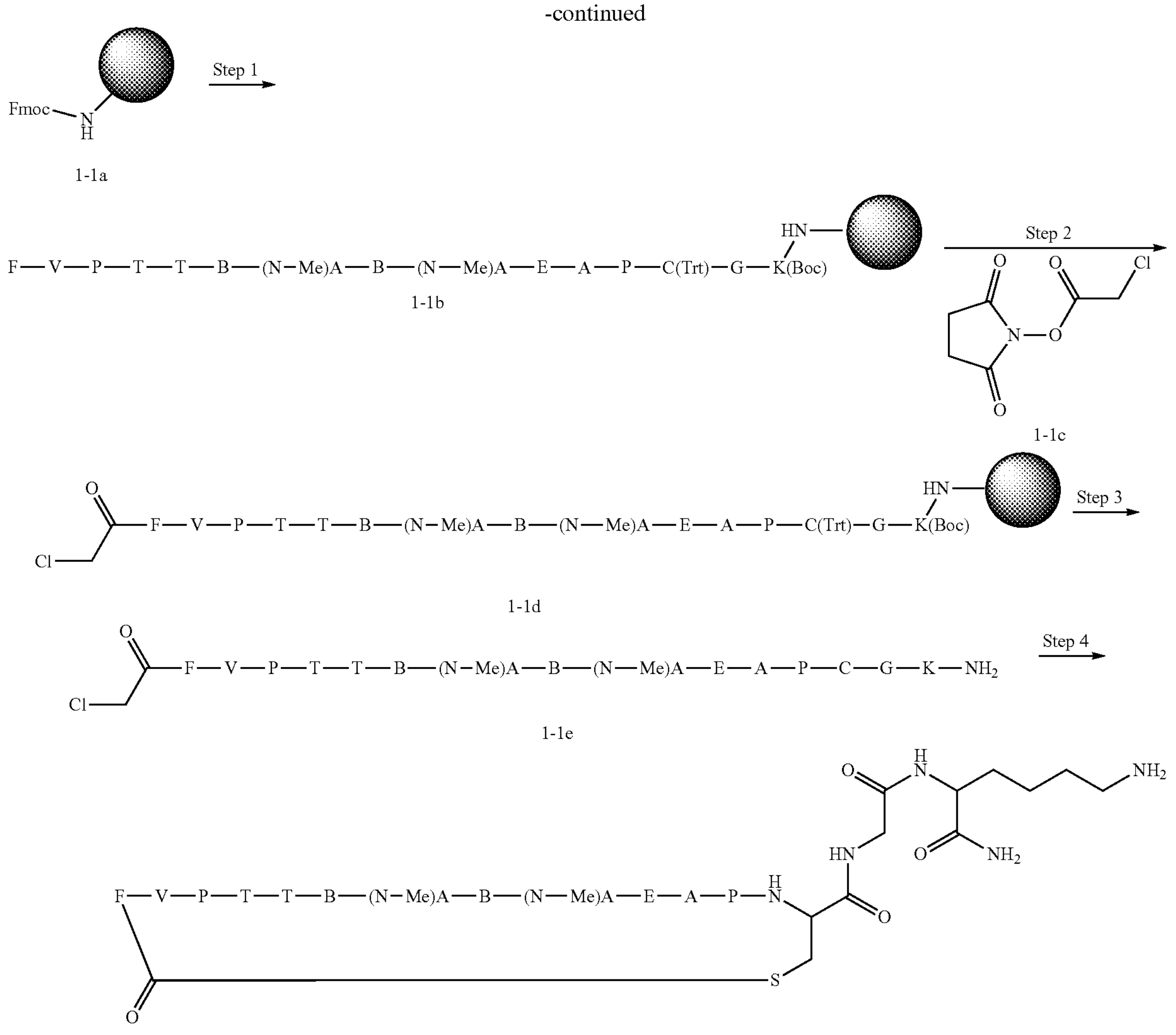

1-1a 1-1b 1-1c 1-1d 1-1e (C1)

Step 1: The peptide sequence F-V-P-T-T-B-(N-Me)A-B-(N-Me)A-E-A-P-C(Trt)-G-K-NH-resin (1-1b) was synthesized on Fmoc-RAM TentaGel™ Resin (1-1a, 0.22 mmol/g loading, 0.25 mmol scale) on a Liberty® Peptide Synthesizer following general peptide Synthesis Cycle A-1 (Fmoc-amino acid (4 eq.; 0.2 M solution in DMF), HATU (4 eq.; 0.5 M solution in DMF) and DIPEA (4.4 eq.; 2 M solution in NMP)). The resin was then filtered and washed with DMF (2×) and DCM (3×) to provide F-V-P-T-T-B-(N-Me)A-B-(N-Me)A-E-A-P-C(Trt)-G-K-NHresin (1-1b).

Step 2: A solution of N-succinimidyl 2-chloroacetate (1-1c, 287 mg, 1.5 mmol) in NMP (8 mL) was added to the peptide resin 1-1b from Step 1 (0.25 mmol) and the resulting mixture was shaken at room temperature overnight. The resin was then drained, washed with DMF (3×) and DCM (4×), and dried to provide tClCH$_2$C(═O)—F-V-P-T-T-B-(N-Me)A-B-(N-Me)A-E-A-P-C(Trt)-G-K-NHresin (1-1d).

Step 3: The peptide resin product 1-1d from Step 2 was cleaved from the resin and simultaneously deprotected using Cleavage Method 1 described herein above to provide the crude peptide ClCH$_2$C(O)—F-V-P-T-T-B-(N-Me)A-B-(N-Me)A-E-A-P-C-G-K-NH$_2$ (1-1e) (266 mg). Analytical method 1: $t_R$=1.22 min.; M+H+2/2 921.8.

Step 4: The crude peptide 1-1e from Step 3 460 mg, 0.25 mmol) was dissolved in DMSO (25.4 mL). A few drops of TEA were added to adjust to pH 8-9. The resulting mixture was stirred at rt overnight. The reaction mixture was then concentrated down to a few mL of DMSO on a centrifugal evaporator. The crude cyclic peptide was purified by preparative HPLC (Sunfire™ Prep C18 Column, 130 Å, 5 μm, 30×50 mm, 15-40% in 6 min, 75 mL/min, ACN in water with 0.1% TFA) and then lyophilized to provide cyclic peptide compound 3-((6S,9S,12S,15S,18S,21S,24S,27S,29aS,35S,38S,44R,46aS)-15,21-bis([1,1'-biphenyl]-4-ylmethyl)-38-benzyl-44-((2-(((S)-1,6-diamino-1-oxohexan-2-yl)amino)-2-oxoethyl)carbamoyl)-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (C1) (SEQ ID NO:1). Analytical method 3: $t_R$=0.45 min, M+2/2 903.7

Example 1-2: Synthesis of 2-((3R,9S,12S,15S,18S,21S,24S,27S,30S,33S,36S,39S,44aS)-30-([1,1'-biphenyl]-4-ylmethyl)-3-((2-amino-2-oxoethyl)carbamoyl)-36-(4-aminobutyl)-9-benzyl-18,21-bis((R)-1-hydroxyethyl)-24,39-bis(hydroxymethyl)-12-isopropyl-26,27,32,33-tetramethyl-1,7,10,13,16,19,22,25,28,31,34,37,40-tridecaoxodotetracontahydro-6H-pyrrolo[2,1-f][1]thia[4,7,10,13,16,19,22,25,28,31,34,37,40]tridecaazacyclodotetracontin-15-yl)acetic acid (C2)
(C2)
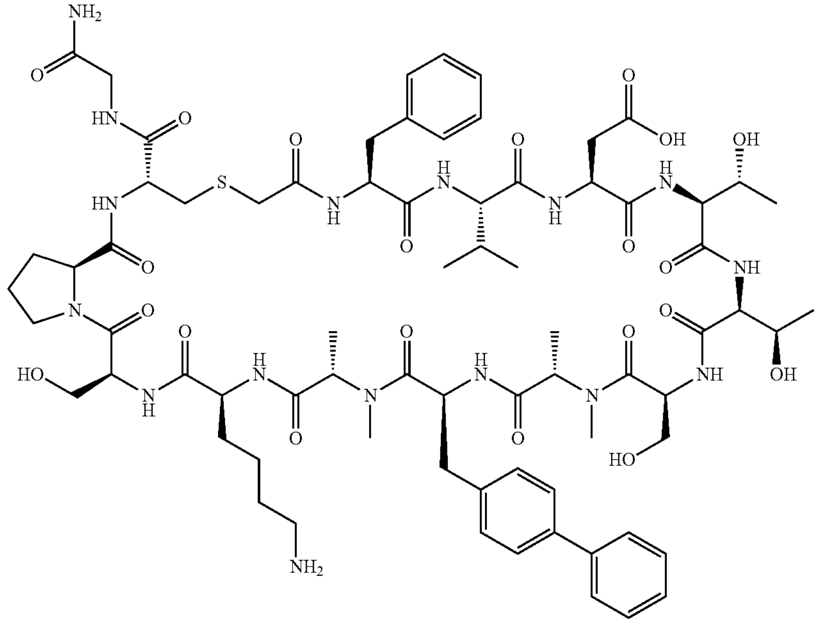
Note: Compound (C2) has the following amino acid sequence:
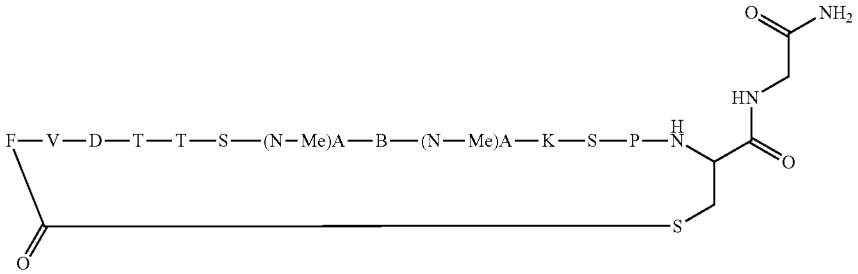
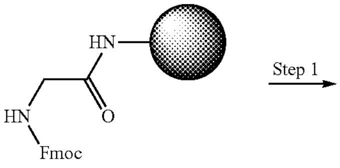
1-2a -continued

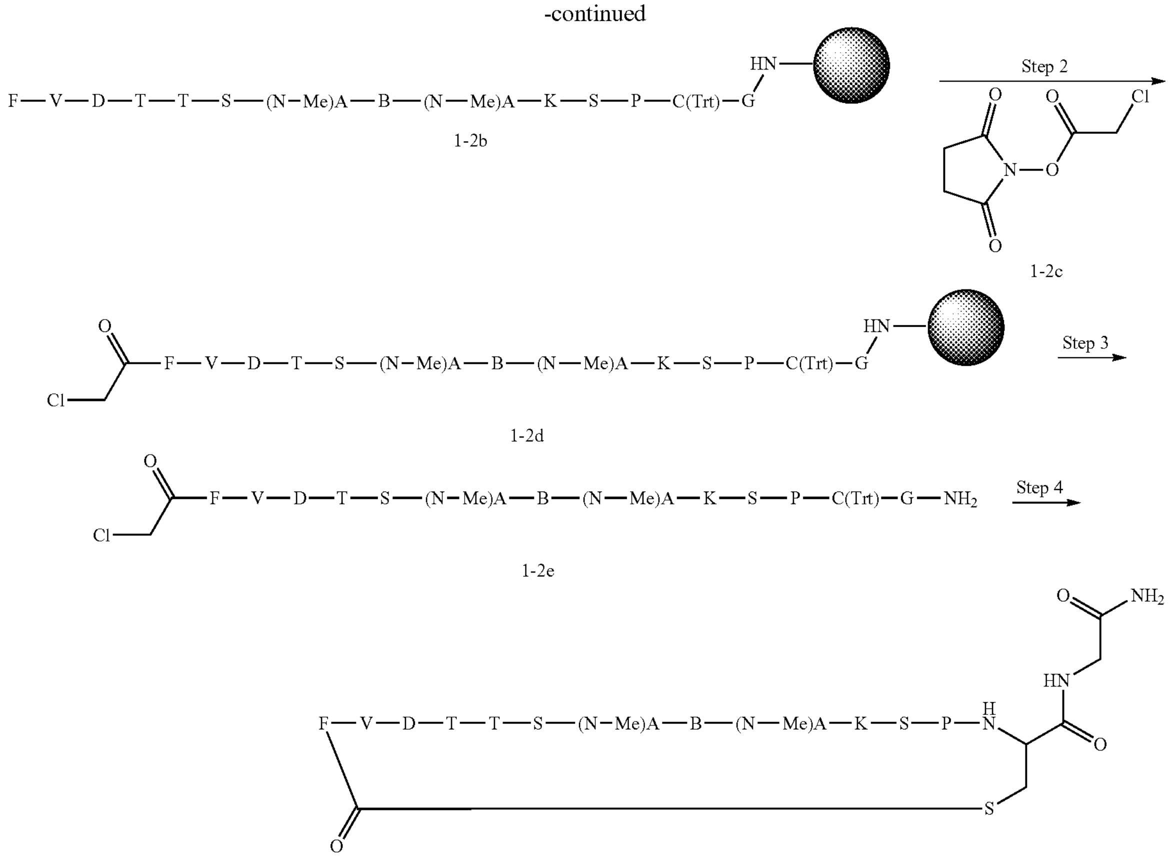

1-2b 1-2c 1-2d 1-2e (C1)

Step 1: The peptide sequence F-V-D-T-T-S-(N-Me)A-B-(N-Me)A-K-S-P-C(Trt)-G-NH-resin (1-2b) was synthesized on Fmoc-Gly-RAM TentaGel™ Resin (1-2a, 0.22 mmol/g loading, 0.25 mmol scale) on a Liberty® Peptide Synthesizer following general peptide Synthesis Cycle A-1 (Fmoc-amino acid (4 eq.; 0.2 M solution in DMF), HATU (4 eq.; 0.5 M solution in DMF) and DIPEA (4.4 eq.; 2 M solution in NMP)). The resin was then filtered and washed with DMF (2×) and DCM (3×) to provide F-V-D-T-T-S-(N-Me)A-B-(N-Me)A-K-S-P-C(Trt)-G-NHresin (1-2b).

Step 2: A solution of N-succinimidyl 2-chloroacetate (1-2c, 287 mg, 1.5 mmol) in NMP (8 mL) was added to the peptide resin 1-2b from Step 1 (0.25 mmol) and the resulting mixture was shaken at room temperature overnight. The resin was then drained, washed with DMF (3×) and DCM (4×), and dried to provide $ClCH_2C(=O)$—F-V-D-T-T-S-(N-Me)A-B-(N-Me)A-K-S-P-C(Trt)-G-NHresin (1-2d).

Step 3: The peptide resin product 1-2d from Step 2 was cleaved from the resin and simultaneously deprotected using Cleavage Method 1 described herein above to provide the crude peptide $ClCH_2C(O)$—F-V-D-T-T-S-(N-Me)A-B-(N-Me)A-K-S-P-C-G-$NH_2$ (1-2e) (266 mg).

Step 4: The crude peptide 1-2e from Step 3 (266 mg) was dissolved in DMSO (20.5 mL). A few drops of TEA were added to adjust to pH 8-9. The resulting mixture was stirred at rt overnight. The reaction mixture was then concentrated down to a few mL of DMSO on a centrifugal evaporator. The crude cyclic peptide was purified by preparative HPLC (Sunfire™ Prep C18 Column, 130 Å, 5 μm, 30×50 mm, 15-40% in 6 min, 75 mL/min, ACN in water with 0.1% TFA) and then lyophilized to provide the cyclic peptide compound 2-((3R,9S,12S,15S,18S,21S,24S,27S,30S,33S,36S,39S,44aS)-30-([1,1'-biphenyl]-4-ylmethyl)-3-((2-amino-2-oxoethyl)carbamoyl)-36-(4-aminobutyl)-9-benzyl-18,21-bis((R)-1-hydroxyethyl)-24,39-bis(hydroxymethyl)-12-isopropyl-26,27,32,33-tetramethyl-1,7,10,13,16,19,22,25,28,31,34,37,40-tridecaoxodotetracontahydro-6H-pyrrolo[2,1-f][1]thia[4,7,10,13,16,19,22,25,28,31,34,37,40]tridecaazacyclodotetracontin-15-yl)acetic acid (C2) (SEQ ID NO:2). Analytical method 9: $t_R$=7.88, m+1=1573.8; (m+2)/2=787.3.

Cyclic peptide compounds (C3) and (C4) in the table 4 below were obtained using an analogous method as described in Example 1-2, however instead of peptide sequence (1-2b) being synthesized in step 1, the respective peptide sequences synthesized in step 1 for cyclic peptide compounds (C3) and (C4) are also given in the table 4.

TABLE 4
| Compound Number | PCSK9 Ligand Structure | Peptide attached to resin synthesized in step 1 |
| --- | --- | --- |
| C3 | 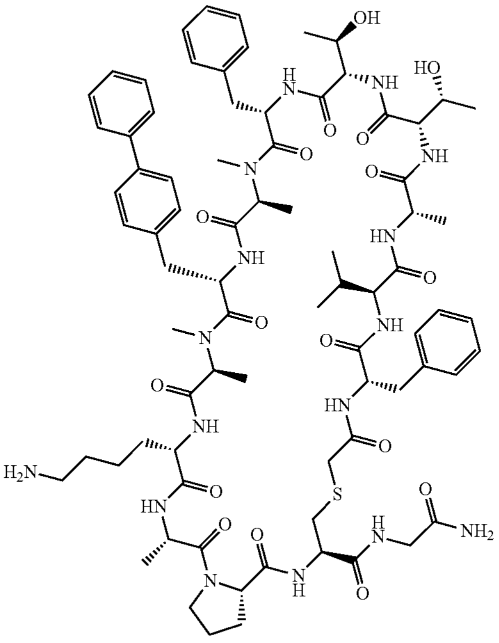 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCCCN)NC(=O)[C@H](C)N(C)C(=O)[C@H](Cc2ccc(-c3ccccc3)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](C)NC1=O]<br>(SEQ ID NO: 3) | F-V-A-T-T-F-(N-Me)A-B-(N-Me)A-K-A-P-C(Trt)-G-NH-resin |
| C4 | 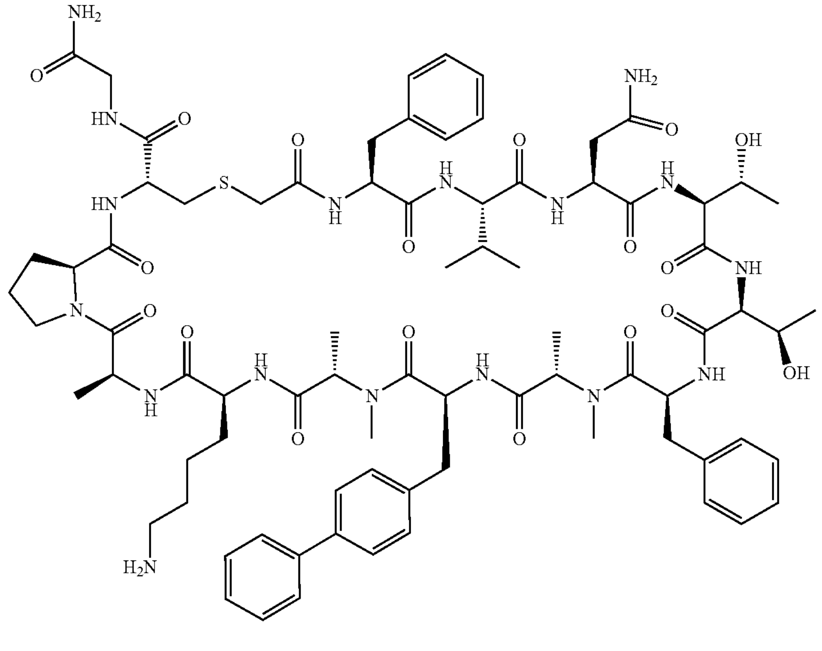 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCCCN)NC(=O)[C@H](C)N(C)C(=O)[C@H](Cc2ccc(-c3ccccc3)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](CC(N)=O)NC1=O]<br>(SEQ ID NO: 4) | F-V-N-T-T-F-(N-Me)A-B-(N-Me)A-K-A-P-C(Trt)-G-NH-resin |

The analytical data for cyclic peptide compounds (C3) and (C4) are summarized in Table 5 below and were obtained using Analytical method E-1 described herein.

TABLE 5

| Ex. No. | Measured $[M + H]^+$ | Measured $[M + 2H]^{2+}$ | Retention time (min) |
|---|---|---|---|
| (C3) | 1573.6 | 787.3 | 2.05 |
| (C4) | 1616.6 | 808.7 | 1.98 |

Example 1-3: Synthesis of 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-1-oxo-6-(4-oxopentanamido)hexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (C5)

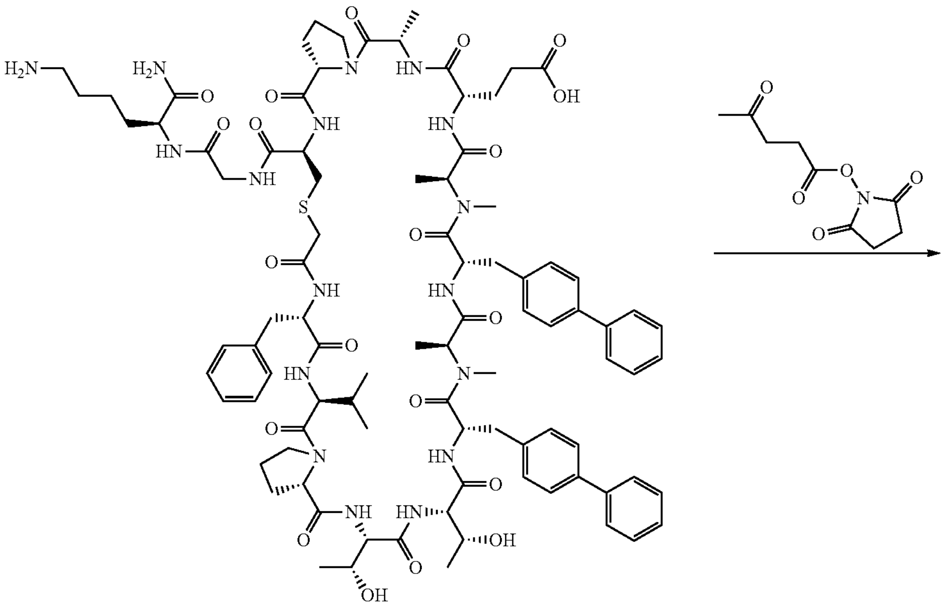

(C1)

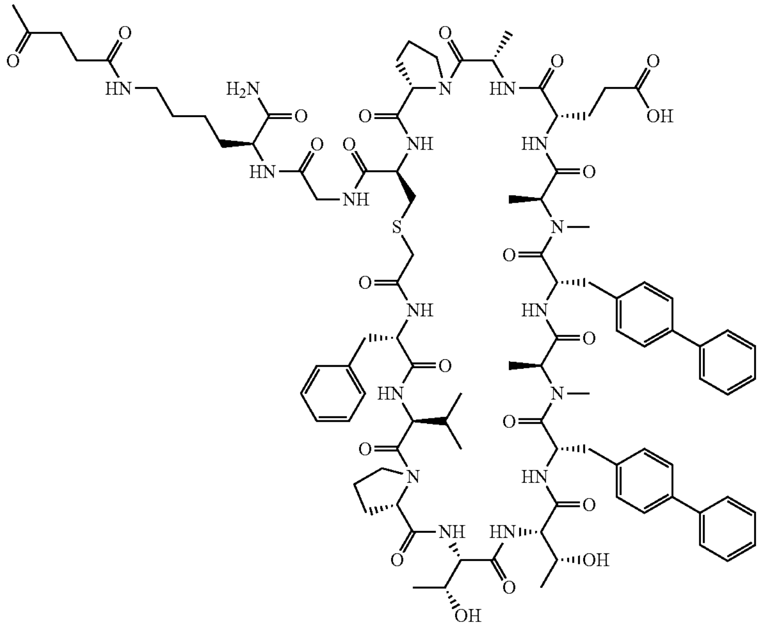

(C5)

To a room temperature solution of cyclic peptide (C1) (75 mg, 0.039 mmol) in DMSO (1 mL) was added DIPEA (0.020 mL, 0.117 mmol) and 2,5-dioxopyrrolidin-1-yl 4-oxopentanoate (0.130 mL, 0.117 mmol) in DMSO (1 mL). The reaction was purified directly C18 flash chromatography (30 g column, 0-80% ACN/water over 15 min) and pure fractions were dried by Genevac to provide cyclic peptide (C5). Analytical method 7: $t_R$=1.07 min, M−1=951.3

Synthesis of Intermediates

Synthesis of (R)-2-benzyl-4-(tert-butoxy)-4-oxobutanoic acid (int-A1)

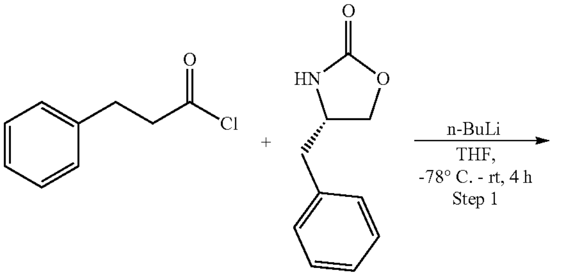

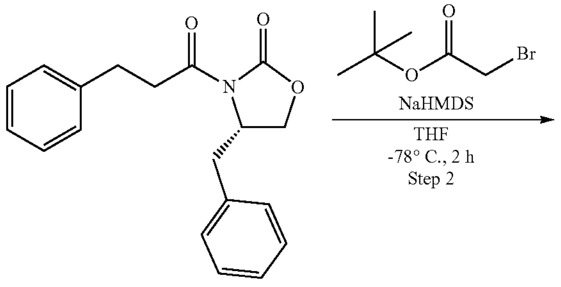

int-A1-1

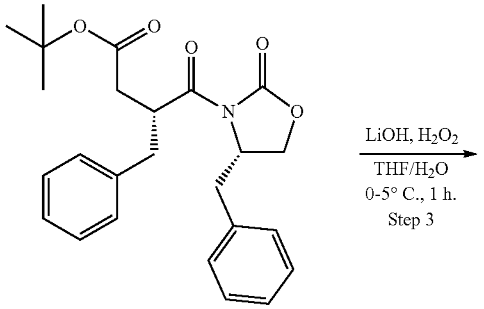

int-A1-2

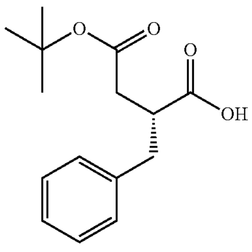

int-A1

Step 1. To a cold stirred solution of (S)-4-benzyloxazolidin-2-one (500 g, 2.821 mol) in THF (9 L) was added n-BuLi (2.5M in hexane) (1.24 L, 3.103 mol) slowly over a period of 30 minutes at −78° C. and the resulting mixture was stirred for 30 minutes at −78° C. A solution of 3-phenylpropanoyl chloride (571 g, 3.38 mol) in THF (1 L) was then slowly added over a period of 1 h at −78 to −60° C. and the reaction mixture was slowly warmed to room temperature for 2 h. The reaction mixture was cooled to 0° C., quenched with sat. $NH_4Cl$ (500 mL) and extracted with dichloromethane (2×1.5 L). The combined organic layers were washed with 0.5 N NaOH (1 L) and brine (1 L), dried over anhydrous sodium sulfate, filtered, and evaporated under reduced pressure. Crude (S)-4-benzyl-3-(3-phenylpropanoyl)oxazolidin-2-one (int-A1-1) was triturated with petroleum ether (5 L) for 1 h. The solid product was filtered, washed with petroleum ether (500 mL), and dried under vacuum to afford (S)-4-benzyl-3-(3-phenylpropanoyl)oxazolidin-2-one (int-A1-1). Analytical method 7; $t_R$=1.53 min; $[M+H]^+$=310.2.

Step 2. To a cold stirred solution of (S)-4-benzyl-3-(3-phenylpropanoyl)oxazolidin-2-one (int-A1-1) (500 g, 1.616 mol) in THF (7 L), was added 1.0 M NaHMDS in THF (1.94 L, 1.939 mol) slowly over a period of 30 minutes at −78° C. The resulting mixture was stirred for 1 h at −78° C. and a solution of tert-butyl-2-bromo acetate (472.8 g, 2.424 mol) in THF (500 mL) was then added drop wise over a period of 30 min at −78° C. The mixture was stirred for 2 h, then quenched with sat. $NH_4Cl$ (500 mL), and extracted with ethyl acetate (2×1.5 L). The combined organic layers were washed with brine solution (2 L), dried over anhydrous sodium sulfate, filtered, and concentrated under reduced pressure. The crude material was triturated with methanol (800 mL) for 1 h, after which the solid product was filtered, washed with methanol (200 mL) and dried under vacuum to afford (R)-tert-butyl 3-benzyl-4-((S)-4-benzyl-2-oxooxazolidin-3-yl)-4-oxobutanoate (int-A1-2). Analytical method 7; $t_R$=1.78 min; $[M-tBu]^+$=368.3.

Step 3. To a cold stirred solution of (R)-tert-butyl 3-benzyl-4-((S)-4-benzyl-2-oxooxazolidin-3-yl)-4-oxobutanoate (int-A1-2) (250 g, 0.59 mol) in THF (9 L) was added 30% $H_2O_2$ (267 mL, 2.37 mol) at 0-5° C. and the reaction was stirred for 30 min at same temperature. Then a solution of $LiOH·H_2O$ (49.5 g, 1.18 mol) in water (3 L) was added to the above reaction mixture at 0-5° C. and the mixture was stirred for 1 h. The reaction mixture was quenched with sat. sodium sulfite (1.6 L) and sat. sodium bicarbonate (1.6 L). Then solvent was concentrated under reduced pressure, diluted with water (3 L) and washed with DCM (2×1 L) to remove the impurities. Then the aqueous layer was cooled to 5° C. and acidified to pH ~1.5 with 6 M HCl (1 L). Product was extracted with ethyl acetate (3×1 L). The combined organic layer was washed with brine solution (1 L), dried over anhydrous sodium sulfate, and concentrated under vacuum to afford (R)-2-benzyl-4-(tert-butoxy)-4-oxobutanoic acid (int-A1). Analytical method 7; $t_R$=1.78 min; $[M-H]^-$=263.5. $^1H$ NMR (400 MHz, Chloroform-d) δ 1.42 (s, 9H), 2.36 (dd, J=16.93, 4.58 Hz, 1H), 2.48-2.62 (m, 1H), 2.71-2.83 (m, 1H), 3.00-3.18 (m, 2H), 7.12-7.35 (m, 6H).

Synthesis of tert-butyl ((1S,2S)-2-(methylamino)cyclohexyl)carbamate (int-B1)

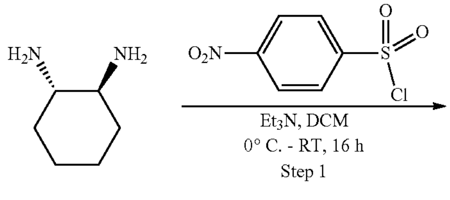

-continued

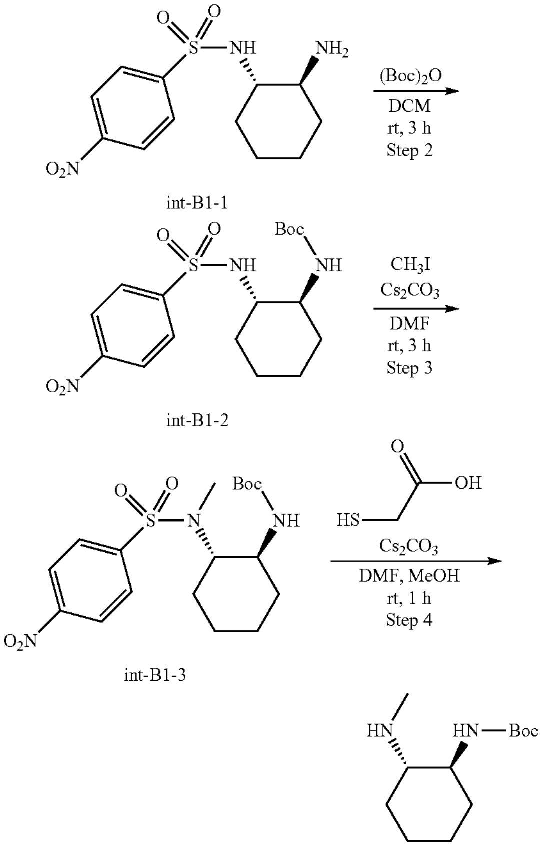

int-B1-1 int-B1-2 int-B1-3 int-B1

Step 1. 4-Nitrobenzenesulfonyl chloride (23.29 g, 105 mmol) was added to a solution of (1S,2S)-(+)-1,2-diaminocyclohexane (12 g, 105 mmol) and triethylamine (21.97 mL, 158 mmol) in DCM (200 mL) at 0° C. and stirred at the same temperature for 30 min. The reaction was slowly warmed to room temperature and stirred for 16 h. The progress of the reaction was monitored by TLC (80% ethyl acetate in petroleum ether). The reaction mixture was concentrated and diluted with water and solid was precipitated. The precipitate was filtered and washed with an excess amount of water and EtOAc and dried under vacuum to afford N-((1S,2S)-2-Aminocyclohexyl)-4-nitrobenzenesulfonamide (int-B1-1). Analytical method 7; $t_R$=0.74 min; $[M+H]^+$=300.2. $^1$HNMR (300 MHz, $CDCl_3$): δ 8.33-8.31 (d, J=8.8 Hz, 2H), 8.05-8.02 (d, J=8.8 Hz, 2H), 6.19-6.18 (d, J=4.8 Hz, 1H), 4.40-4.38 (d, J=7.6 Hz, 1H), 3.35-3.33 (d, J=10.4 Hz, 1H), 2.97-2.91 (m, 1H), 2.01-1.93 (m, 2H), 1.73-1.68 (m, 2H), 1.67-1.65 (d, J=6.8 Hz, 1H), 1.52-1.47 (m, 9H), 1.29-1.16 (m, 4H).

Step 2. Boc-anhydride (13.70 mL, 59.0 mmol) was added to a stirred solution of N-((1S,2S)-2-Aminocyclohexyl)-4-nitrobenzenesulfonamide (int-B1-1) (17.66 g, 59.0 mmol) in DCM (200 mL) and stirred for 3 h. The progress of the reaction was monitored by TLC (50% ethyl acetate in petroleum ether). The reaction mixture was concentrated under reduced pressure to give tert-Butyl ((1S,2S)-2-((4-nitrophenyl)sulfonamido)cyclohexyl)carbamate (int-B1-2). Analytical method 7; $t_R$=1.14 min; $[M-Boc+H]^+$=299.9. $^1$HNMR (400 MHz, $CDCl_3$): δ 8.33-8.31 (d, J=9.2 Hz, 2H), 8.04-8.02 (d, J=8.8 Hz, 2H), 6.17-6.16 (d, J=4.8 Hz, 1H), 4.38-4.36 (d, J=7.2 Hz, 1H), 3.35-3.32 (m, 1H), 2.96-2.91 (m, 1H), 2.02-1.92 (m, 2H), 1.73-1.65 (m, 2H), 1.52-1.46 (m, 6H), 1.36-1.27 (m, 9H), 1.28-1.21 (m, 4H).

Step 3. Methyl iodide (18.19 mL, 294 mmol) was added to a stirred solution of tert-Butyl ((1S,2S)-2-((4-nitrophenyl)sulfonamido)cyclohexyl)carbamate (int-B1-2) (23.5 g, 58.8 mmol) and $Cs_2CO_3$ (47.9 g, 147 mmol) in DMF (200 mL) and stirred at the same temperature for 3 h. The progress of the reaction was monitored by TLC (40% ethyl acetate in petroleum ether). The reaction mixture was diluted with water (300 mL) and extracted with ethyl acetate (300 mL). The organic layer was washed with water and brine and dried over anhydrous $Na_2SO_4$. The organic layer was concentrated under reduced pressure to get crude compound. The crude compound was purified via normal phase chromatography using silica gel (100-200 mesh) column chromatography eluting with 0-30% ethyl acetate in petroleum ether as a solvent to afford tert-Butyl ((1S,2S)-2-((N-methyl-4-nitrophenyl)sulfonamido)cyclohexyl)carbamate (int-B1-3). Analytical method 7; $t_R$=1.22 min $[M-Boc]^+$=313.9. $^1$HNMR (300 MHz, $CDCl_3$): δ 8.36-8.35 (d, J=6.8 Hz, 2H), 8.00-7.97 (d, J=8.8 Hz, 2H), 4.48 (s, 1H), 4.14-4.09 (m, 1H), 3.56-3.54 (d, J=6.4 Hz, 2H), 2.88 (s, 3H), 2.12-2.10 (m, 1H), 2.04 (s, 1H), 1.72-1.70 (d, J=7.6 Hz, 2H), 1.41 (s, 9H), 1.27-1.23 (m, 4H).

Step 4. A mixture of tert-Butyl ((1S,2S)-2-((N-methyl-4-nitrophenyl)sulfonamido)cyclohexyl)carbamate (int-B1-3) (1.55 g, 3.75 mmol), $Cs_2CO_3$ (8.55 g, 26.2 mmol) and 2-mercaptoacetic acid (1.524 mL, 14.99 mmol) in a mixture of DMF:MeOH (1:1, 12 mL) was stirred at rt for 1 h. The progress of the reaction was monitored by TLC (10% MeOH in DCM). The reaction mixture was diluted with water (100 mL) and ethyl acetate (100 mL). The aqueous layer was extracted with ethyl acetate (100 mL). The organic layers were combined, washed with brine and dried over $Na_2SO_4$. The organic layer was concentrated under reduced pressure to get crude product. The crude product was purified via normal phase chromatography by silica gel (100-200 mesh) column chromatography eluting with 0-5% MeOH in DCM as an eluent to afford tert-Butyl ((1S,2S)-2-(methylamino)cyclohexyl)carbamate (int-B1). Analytical method 7; $t_R$=0.75 min; $[M+H]^+$=229.3. $^1$H NMR (300 MHz, DMSO-$d_6$): δ 6.26-6.18 (m, 1H), 3.08-3.06 (m, 1H), 2.35 (s, 3H), 2.15-2.12 (m, 1H), 1.93-1.86 (m, 1H), 1.77 (m, 1H), 1.61-1.58 (m, 2H), 1.37 (s, 9H), 1.23-0.96 (m, 5H).

Synthesis of (S)—N-(2-(methylamino)propyl)-4-nitrobenzenesulfonamide (int-B2)

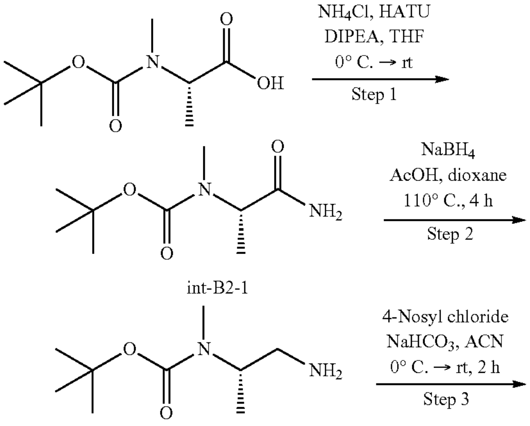

int-B2-1 int-B2-2

-continued

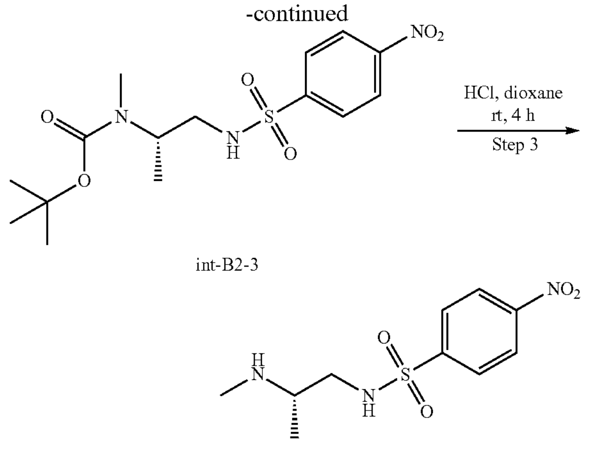

int-B2-3 int-B2

Step 1. To a stirred solution of N-Me-Boc-Ala-OH (1000.0 g, 4.92 mol) in THF (6 L) was added DIEA (3179.0 g, 24.6 mol) at 0° C. After 5 min HATU (2058.0 g, 294 mmol) was added in one portion and stirring was continued at the same temperature for 15 min. Solid ammonium chloride (1316.0 g, 24.6 mol) was then added and the mixture was stirred overnight at room temperature. A large amount of precipitate was formed which was filtered through a disposable frit, washing multiple times with THF until most of the solid dissolved. The filtrate was evaporated under reduced pressure to get crude product. The crude mass was diluted with water (2 L) and extracted by petroleum ether (2×2.5 L) to remove the non-polar impurities. The water part was then extracted with 40% EtOAc in petroleum ether several times. Then all organic parts were combined, dried over anhydrous $Na_2SO_4$, filtered & evaporated under reduced pressure to give tert-Butyl (S)-(1-amino-1-oxopropan-2-yl)(methyl)carbamate (int-B2-1). $^1H$ NMR (400 MHz, DMSO-$d_6$) δ ppm 6.70-7.47 (m, 2H), 4.48-4.49 (m, 1H), 4.11-4.82 (m, 1H), 3.08 (s, 1H), 2.72 (s, 3H), 1.39 (br. s., 9H), 1.18-1.29 (m, 3H), 1.11 (s, 1H).

Step 2. To a stirred solution of tert-Butyl (S)-(1-amino-1-oxopropan-2-yl)(methyl)carbamate (int-B2-1) (100 g, 0.49 mol.) in 1,4-dioxane (500 mL) was added $NaBH_4$ (56.4 g, 1.48 mol) under argon. Acetic acid (90 mL) in dioxane (200 mL) was added drop wise to the mixture so as to maintain a gentle effervescence, with a bubbler attached as a vent. Upon complete addition of the acid, a reflux condenser was attached, and the mixture was heated to 110° C. for 4 h. The mixture was removed from heat and allowed to come to room temperature. The reaction mass was quenched by ice & acidified with 2 N HCl. The solution was extracted with EtOAc and the aqueous part was basified up to pH 13-14 with 50% NaOH. The solution was then extracted with diethyl ether, dried over anhydrous $Na_2SO_4$, filtered & evaporated under reduced pressure to give tert-butyl (S)-(1-aminopropan-2-yl)(methyl)carbamate (int-B2-2). The crude compound was used for the next step without purification.

Step 3. To a stirred solution of crude tert-butyl (S)-(1-aminopropan-2-yl)(methyl)carbamate (int-B2-2) (300.0 g, 1.59 mol) in ACN (1500 mL) was added $NaHCO_3$ (406.9 g, 4.78 mol), followed by nosyl chloride (388.9 g, 1.75 mol) at 0° C. The mixture was stirred at room temperature for 2 h. The reaction solution was slowly quenched with ice water (2000 mL) and stirred for 2 h until white precipitate formed. Solids were filtered, washed with water and petroleum ether and dried under vacuum to give tert-butyl (S)-methyl(1-((4-nitrophenyl)sulfonamido)propan-2-yl)carbamate (int-B2-3). The crude compound was used for next step without purification.

Step 4. To a stirred solution of crude tert-butyl (S)-methyl (1-((4-nitrophenyl)sulfonamido)propan-2-yl)carbamate (int-B2-3) (450.0 g, 1.2 mol) in 1,4-dioxane (2000 mL) was added HCl (4 M in 1,4-dioxane, 2000 mL) and the reaction mixture was stirred at rt for 4 h. Solids precipitated during the reaction, which was filtered, washed with diethyl ether and dried under vacuum to get the amine as an HCl-salt. The crude solid mass was washed several times by n-pentane and dried to give (S)—N-(2-(methylamino)propyl)-4-nitrobenzenesulfonamide (int-B2). Analytical method 7; $t_R$=0.69 min; $[M+H]^+$=274.2. $^1H$ NMR (400 MHz, DMSO-$d_6$) δ ppm 1.18 (d, J=6.57 Hz, 3H) 2.47-2.55 (m, 4H) 2.89-3.13 (m, 2H) 3.14-3.26 (m, 1H) 8.03-8.16 (m, 2H) 8.37-8.52 (m, 2H).

Synthesis of tert-butyl (S)-(2-(methylamino)-6-((2-nitrophenyl)sulfonamido) hexyl)carbamate (int-B3)

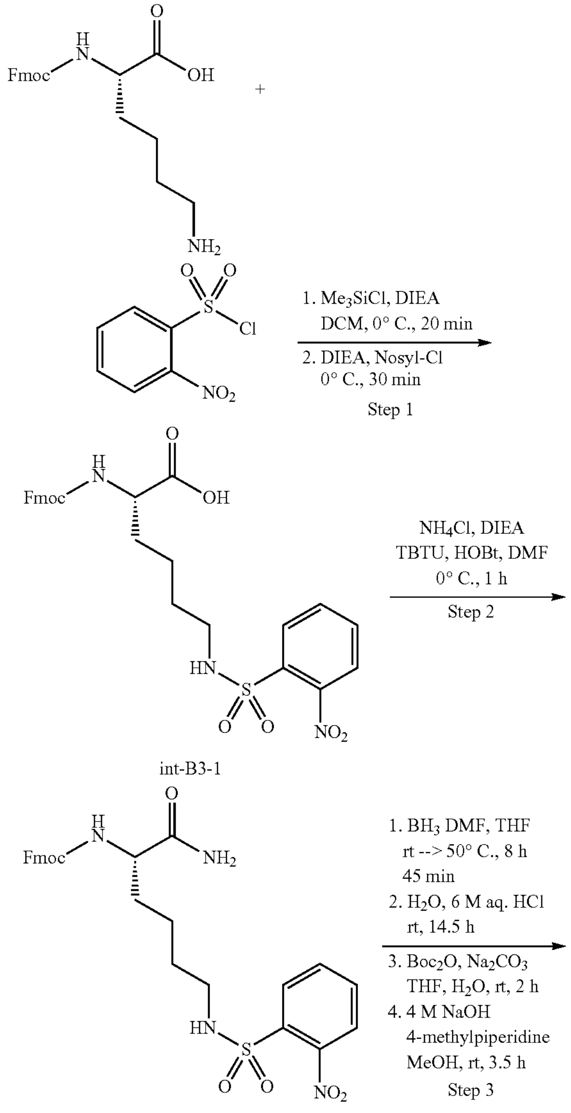

int-B3-1 int-B3-2

-continued

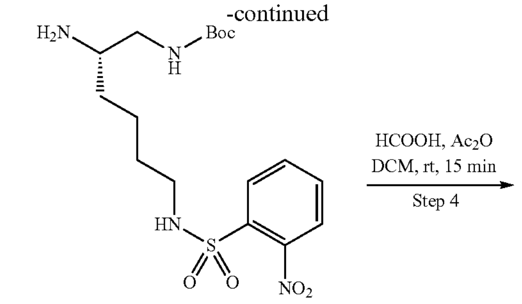

int-B3-3

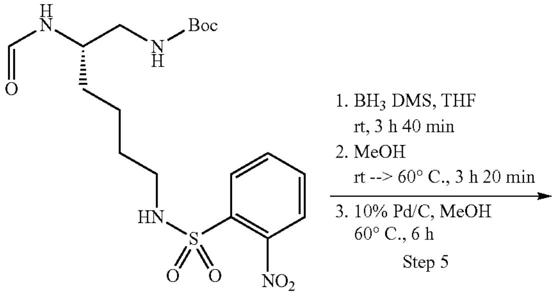

int-B3-4

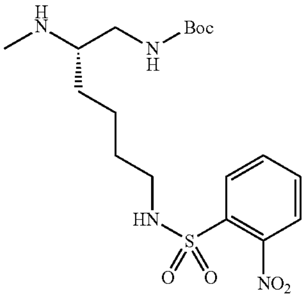

int-B3

Step 1. To a suspension of Fmoc-Lys-OH HCl (4.05 g, 10 mmol) in DCM (80 mL) at 0° C. was added $Me_3SiCl$ (3.83 mL, 30.0 mmol) and DIEA (8.73 mL, 50.0 mmol) and the resulting mixture was stirred for 20 min at 0° C. and became a clear solution. DIEA (1.747 mL, 10.00 mmol) and 2-nitrobenzene-1-sulfonyl chloride (2.327 g, 10.50 mmol) were added and the reaction mixture was stirred for 30 min at 0° C., and then concentrated to dryness in vacuo. The resulting residue was partitioned between EtOAc (150 mL) and 5% aq. $KHSO_4$ (50 mL). The organic layer was washed with 5% aq. $KHSO_4$ (3×50 mL) and brine (50 mL), dried over $Na_2SO_4$, filtered, and concentrated to dryness in vacuo to afford $N^2$-(((9H-Fluoren-9-yl)methoxy)carbonyl)-$N^6$-((2-nitrophenyl)sulfonyl)-L-lysine (int-B3-1). The crude product was used in the next step without purification. Analytical method 10; $t_R$=1.08 min; $[M+NH4]^+$=571.3.

Step 2. To a suspension of $N^2$-(((9H-Fluoren-9-yl)methoxy)carbonyl)-$N^6$-((2-nitrophenyl)sulfonyl)-L-lysine (int-B3-1) (5.36 g, 9.68 mmol), $NH_4Cl$ (1.036 g, 19.36 mmol) and HOBt (1.483 g, 9.68 mmol) in DMF (80 mL) at 0° C. was added DIEA (6.76 mL, 38.7 mmol). The resulting suspension was stirred for 5 min at 0° C., and then TBTU (3.42 g, 10.65 mmol) was added. After stirring at 0° C. for 1 h, the reaction mixture was partitioned between EtOAc (250 mL) and 5% aq. $NaHCO_3$ (100 mL). The organic layer was washed with 5% aq. $NaHCO_3$ (3×50 mL) and brine (25 mL), dried over $Na_2SO_4$, filtered, and concentrated to dryness in vacuo to afford (9H-Fluoren-9-yl)methyl (S)-(1-amino-6-((2-nitrophenyl)sulfonamido)-1-oxohexan-2-yl) carbamate (int-B3-2). The crude product was used in the next step without purification. Analytical method 19; $t_R$=1.04 min; $[M+H]^+$=553.3.

Step 3-1: To (9H-Fluoren-9-yl)methyl (S)-(1-amino-6-((2-nitrophenyl)sulfonamido)-1-oxohexan-2-yl)carbamate (int-B3-2) (9.66 mmol) dissolved in THF (60 mL) was added and $BH_3$—$S(CH_3)_2$ (5.50 mL, 58.0 mmol) and the resulting mixture was stirred for 2 h 15 min at rt, and then for 6.5 h at 50° C. The reaction mixture was allowed to cool to rt.

Step 3-2: $H_2O$ (1 mL) and 6 M aq. HCl (2 mL) were added and the reaction mixture was stirred for 14.5 h at rt.

Step 3-3: 0.5 M aq. $Na_2CO_3$ (48.3 mL, 24.15 mmol) and a solution of $Boc_2O$ (2.243 mL, 9.66 mmol) in THF (20 mL) were added. The resulting mixture was stirred for 2 h at rt, quenched with 8 M $MeNH_2$ in EtOH (1 mL), and stirred at rt for 30 min.

Step 3-4: 4 M aq. NaOH (9.66 mL, 38.6 mmol) was added and the reaction mixture was stirred for 85 min at rt. 4-Methylpiperidine (4 mL) was then added and the reaction mixture was stirred for 40 min at rt. Additional 4-methylpiperidine (8 mL) was added and stirring at rt was continued for 30 min. MeOH (10 mL) was then added with stirring for 25 min at rt. Additional MeOH (20 mL) and 4-methylpiperidine (10 mL) were added and stirred for 30 min. The reaction mixture was then concentrated in vacuo and the crude product was purified by flash chromatography on silica gel (eluent A: EtOAc/DIEA (98:2), eluent B: EtOAc/MeOH/DIEA (95:5:2)) Pure fractions were combined and concentrated to dryness in vacuo to afford tert-Butyl (S)-(2-amino-6-((2-nitrophenyl)sulfonamido)hexyl)carbamate (int-B3-3). Analytical method 10; $t_R$=0.69 min; $[M+H]^+$ =417.2.

Step 4. A mixture of formic acid (0.611 mL, 15.92 mmol) and $Ac_2O$ (1.502 mL, 15.92 mmol) was stirred for 40 min at rt, and then added to a solution of tert-Butyl (S)-(2-amino-6-((2-nitrophenyl)sulfonamido)hexyl)carbamate (int-B3-3) (1.326 g, 3.18 mmol) in DCM (15 mL). The reaction mixture was stirred for 15 min at rt, and then concentrated to dryness in vacuo. The obtained residue was partitioned between EtOAc (80 mL) and 5% aq. $NaHCO_3$ (10 mL) The organic layer was washed with 5% aq. $NaHCO_3$ (4×10 mL) and brine (10 mL), dried over $Na_2SO_4$, filtered, and concentrated to dryness in vacuo to afford tert-Butyl (S)-(2-formamido-6-((2-nitrophenyl)sulfonamido)hexyl)carbamate (int-B3-4) (1.217 g, 2.74 mmol, 86% yield) as a yellow foam. The crude product was used in the next step without purification. Analytical method 10; $t_R$=0.87 min; $[M+H]^+$=445.2.

Step 5-1: To tert-Butyl (S)-(2-formamido-6-((2-nitrophenyl)sulfonamido)hexyl)carbamate (int-B3-4) (1.217 g, 2.74 mmol) dissolved in THF (20 mL) was added $BH_3$—$S(CH_3)_2$ (1.300 mL, 13.69 mmol) and the resulting mixture was stirred for 3 h 40 min at rt.

Step 5-2: The reaction was quenched by the addition of MeOH (2 mL) and the resulting solution was stirred for 125 min at rt. MeOH (3 mL) was added and stirring was continued at 60° C. for 75 min. The reaction mixture was then concentrated to dryness in vacuo.

Step 5-3: The obtained residue was dissolved in MeOH (20 mL) and a suspension of 10% Pd/C (0.087 g, 0.082 mmol) in $H_2O$ (1 mL) was added. The resulting mixture was stirred for 3.5 h at 60° C. Additional 10% Pd/C (0.087 g, 0.082 mmol) in $H_2O$ (1 mL) was added and stirring at 60° C. was continued for 2.5 h. The reaction mixture was filtered over Hyflo (CAS No: 61790-53-2) and the filtrate was concentrated to dryness in vacuo to afford tert-Butyl (S)-(2-(methylamino)-6-((2-nitrophenyl)sulfonamido)hexyl)carbamate (int-B3). The crude product was used in the next step without purification. Analytical method 10; $t_R$=0.71 min; $[M+H]^+$=431.3.

Synthesis of (S)-3-((((9H-Fluoren-9-yl)methoxy)carbonyl)(methyl)amino)-4-(4-chlorophenyl)butanoic acid (int-C1)

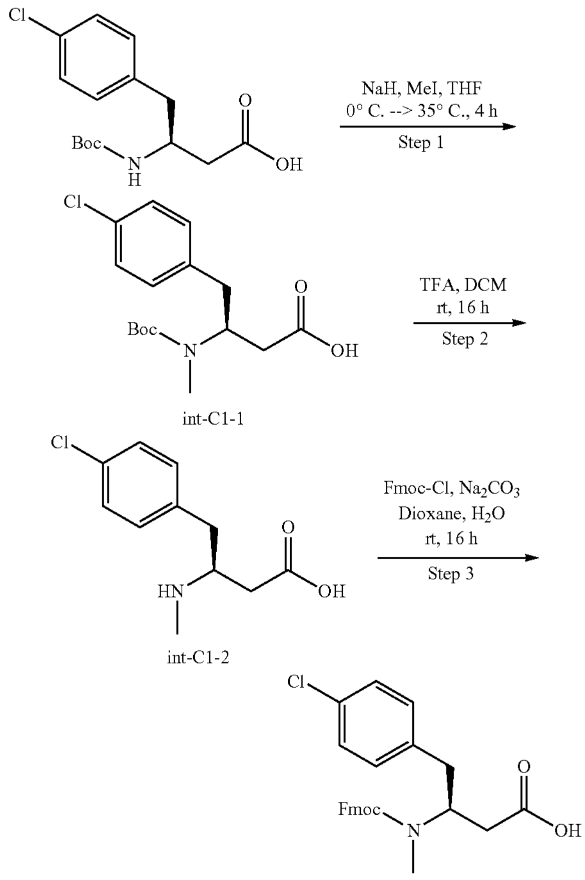

int-C1-1 int-C1-2 int-C1

Step 1. To a 20 L 4-necked round-bottom flask, purged and maintained with an inert atmosphere of nitrogen, containing a solution of (3S)-3-[[(tert-butoxy)carbonyl]amino]-4-(4-chlorophenyl)butanoic acid (360 g, 1.15 mol) in THF (8 L) was added by sodium hydride (212 g, 5.74 mol, 65%), in portions at 0° C. and the resulting mixture was stirred at 0° C. for 1 h. MeI was then added (1633 g, 11.5 mol) dropwise with stirring at 0° C. and the resulting solution was stirred for 4 h at 35° C. The reaction mixture was then quenched by the addition of 300 g of water/ice at −10° C., concentrated under vacuum and then diluted with 3 L of water. The aqueous phase was extracted with 3×1 L of ether. The pH value of the aqueous phase was adjusted to pH 3 with HCl (2 N) at 0° C. and the resulting solution was extracted with 3×2 L of ethyl acetate. The combined organic phases were washed with brine (1×2 L), dried over anhydrous sodium sulfate, filtered, and concentrated under vacuum to provide (S)-3-((tert-Butoxycarbonyl)(methyl)amino)-4-(4-chlorophenyl)butanoic acid (int-C1-1). Analytical method 7; $t_R$=1.01 min; $[M+H]^+$=328.1.

Step 2. To a 5 L 4-necked round-bottom flask, purged and maintained with an inert atmosphere of nitrogen containing a solution of (S)-3-((tert-Butoxycarbonyl)(methyl)amino)-4-(4-chlorophenyl)butanoic acid (int-C1-1) (284.2 g, 866.98 mmol) in DCM (3 L) was added TFA (990.8 g, 8.77 mol) dropwise with stirring at 0° C. The resulting solution was stirred overnight at room temperature and then concentrated under vacuum to provide (S)-4-(4-Chlorophenyl)-3-(methylamino)butanoic acid (int-C1-2). Analytical method 1; $t_R$=0.66 min; $[M+H]^+$=228.2.

Step 3. To a 5 L 4-necked round-bottom flask, purged and maintained with an inert atmosphere of nitrogen containing a solution of (S)-4-(4-chlorophenyl)-3-(methylamino)butanoic acid trifluoroacetic acid salt (int-C1-2) (320 g crude) in dioxane:$H_2O$ (5:1) (3.6 L) was added sodium carbonate (249.1 g, 2.35 mol) in several batches. Fmoc-Cl (242 g, 935.45 mmol) was then added in several batches at 0° C. The resulting mixture was stirred overnight at room temperature, concentrated under vacuum and then diluted with 3 L of water. The pH value of the aqueous solution was adjusted to pH 5 with HCl (1 N). The aqueous phase was extracted with 3×1 L of ethyl acetate. The combined organic phases were washed brine (1×1 L), dried over anhydrous sodium sulfate, filtered, and concentrated under vacuum. The crude residue was purified by silica gel column chromatography eluting with ethyl acetate/petroleum ether (1:5-1:3) to provide (S)-3-((((9H-Fluoren-9-yl)methoxy)carbonyl)(methyl)amino)-4-(4-chlorophenyl)butanoic acid (int-C1). Analytical method 1; $t_R$=1.60 min; $[M+H]^+$=450.3. $^1H$ NMR (300 MHz, DMSO-$d_6$, ppm): δ 12.09-12.45 (br, 1H), 7.89 (m, 2H), 7.21-7.69 (m, 8H), 7.13-7.20 (m, 1H), 6.85-7.08 (br, 1H), 4.04-4.55 (m, 4H), 2.73-2.8 (m, 1H), 2.11-2.85 (m, 6H).

Synthesis of tert-butyl (R)-3-amino-3-(4-chlorobenzyl)piperidine-1-carboxylate (int-C2)

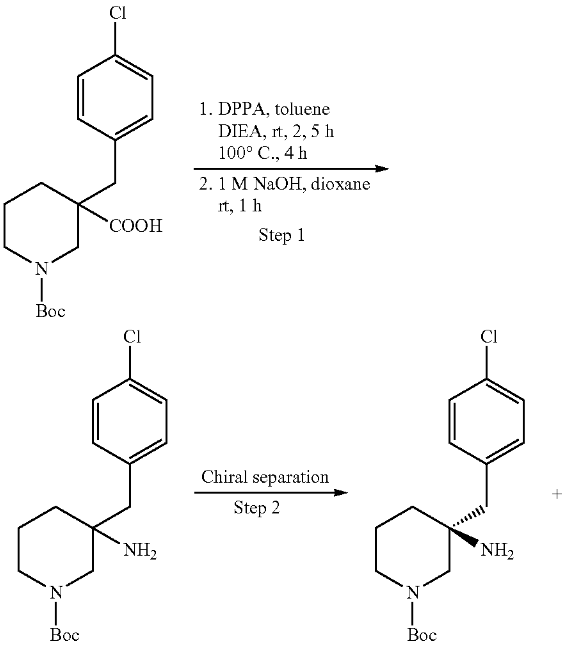

+

-continued

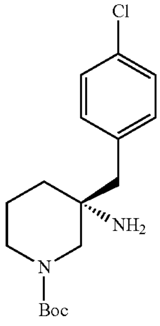

int-C2

Step 1-1: To 1-(tert-Butoxycarbonyl)-3-(4-chlorobenzyl)piperidine-3-carboxylic acid (6.905 g, 19.51 mmol) dissolved in toluene (100 mL) and DIEA (5.11 ml, 29.3 mmol) was added diphenyl phosphoryl azide (5.48 ml, 25.4 mmol) and the reaction was stirred for 2.5 h at rt, and then for 4 h at 100° C. The reaction mixture was partitioned between EtOAc (300 mL) and 5% aq. $NaHCO_3$ (60 mL). The organic phase was washed with 5% aq. $NaHCO_3$ (3×60 mL) and brine (50 mL), dried over $Na_2SO_4$, filtered, and concentrated to dryness in vacuo.

Step 1-2: To the residue from Step 1-1 dissolved in dioxane (200 mL) was added 1 M NaOH (195 ml, 195 mmol). The resulting mixture was stirred for 1 h at rt, and then concentrated to dryness in vacuo. The resulting residue was partitioned between EtOAc (250 mL) and 5% aq. $Na_2CO_3$ (20 mL) and aqueous phase was extracted with EtOAc (70 mL). The combined organic phases were washed with 5% aq. $Na_2CO_3$ (40 mL) and brine (40 mL) dried over $Na_2SO_4$, filtered, and concentrated to dryness in vacuo to afford the racemate tert-butyl 3-amino-3-(4-chlorobenzyl)piperidine-1-carboxylate which was used in the next step without further purification. Analytical method 10; $t_R$=0.80 min; $[M+H]^+$=325.2.

Step 2. The racemate tert-butyl 3-amino-3-(4-chlorobenzyl)piperidine-1-carboxylate (19.5 mmol) was separated by preparative SFC (Instrument: Thar 200 preparative SFC) using the following conditions: Column: ChiralPak AD, 300×50 mm I.D., 10 μm; eluent A: $CO_2$; eluent B: EtOH (0.1% $NH_4OH$); gradient: B 45%; flow rate: 200 mL/min; back pressure: 100 bar; column temperature: 38° C.; cycle time: ~9 min; compound was dissolved in ~130 mL MeOH; injection: 10 mL per injection. tert-Butyl (R)-3-amino-3-(4-chlorobenzyl)piperidine-1-carboxylate (int-C2) (slower eluting isomer) and partial crystallization occurred upon storage allowing for the structural confirmation by X-ray crystallography. Analytical method 10; $t_R$=0.77 min; $[M+H]^+$=325.3.

Synthesis of (R)-3-(4-chlorobenzyl)piperidin-3-amine hydrochloride (int-C3)

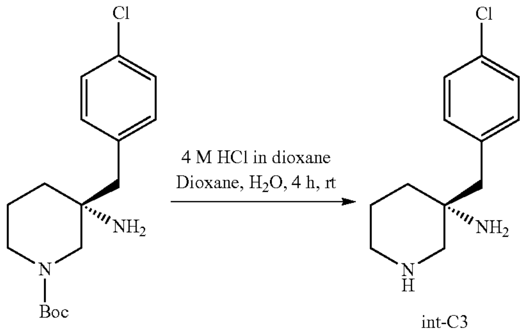

int-C2 int-C3 tert-Butyl (R)-3-amino-3-(4-chlorobenzyl)piperidine-1-carboxylate (int-C2) (2.09 g, 6.43 mmol) was dissolved in dioxane (10 mL). 4 M HCl in dioxane (50 mL) and $H_2O$ (5 mL) were added and the solution was stirred for 4 h at rt. The reaction was concentrated to dryness in vacuo to afford (R)-3-(4-chlorobenzyl)piperidin-3-amine hydrochloride (int-C3). Analytical method 10; $t_R$=0.40 min; $[M+H]^+$=225.1.

Synthesis of 4-chloro-2-(4-(2-((dimethylamino)methyl)-1-methyl-1H-imidazol-5-yl)phenoxy)benzaldehyde (int-F1)

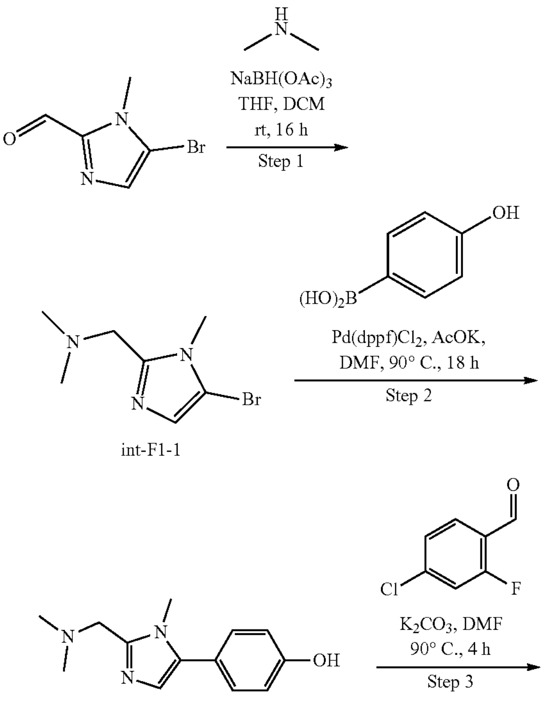

int-F1-1 int-F1-2

-continued

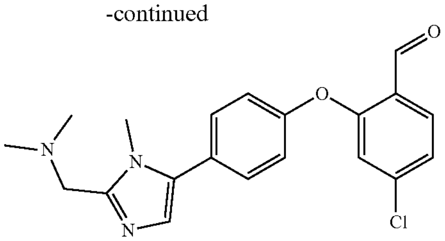

int-F1

Step 1. Into a 5-L 3-necked round-bottom flask, purged and maintained under an inert atmosphere of nitrogen, were placed 5-bromo-1-methyl-1H-imidazole-2-carbaldehyde (216 g, 1.14 mol, 1.00 equiv) and 4 Å molecular sieves in dichloromethane (3 L) and THF (1 L), followed by dimethylamine (862.5 mL, 1.50 equiv). The resulting mixture was stirred for 30 min at rt and $NaBH(OAc)_3$ (292.6 g, 1.38 mol, 1.20 equiv) was added batchwise at 0° C. The reaction mixture was stirred overnight at rt and then quenched with water (1 L). The organic phase was separated and washed with $H_2O$ (2x2 L). The aqueous phase was then extracted with DCM (2x1 L). The combined organic phases were dried over anhydrous sodium sulfate, filtered, and concentrated under vacuum. The residue was purified via silica gel column chromatography eluting with dichloromethane/ethyl acetate (2:1) to afford [(5-bromo-1-methyl-1H-imidazol-2-yl)methyl]dimethylamine (int-F1-1). Analytical method 5; $t_R$=0.60 min; $[M+H]^+$=220.1.

Step 2. Into a 3-L 4-necked round-bottom flask, purged and maintained under an inert atmosphere of nitrogen, were placed [(5-bromo-1-methyl-1H-imidazol-2-yl)methyl]dimethylamine (int-F1-1) (53.675 g, 246.11 mmol, 1.00 equiv), (4-hydroxyphenyl)boronic acid (66.55 g, 482.49 mmol, 1.50 equiv), $Pd(dppf)Cl_2$ (11.75 g, 16.06 mmol, 0.05 equiv), and potassium acetate (189.05 g, 1.93 mol, 6.00 equiv) in N,N-dimethylformamide (1.3 L). The resulting solution was stirred for 18 h at 90° C. in an oil bath. The reaction was repeated three times on the same scale. The batches were combined and the mixture was cooled to rt and then poured into 3.5 L of water/ice. The resulting solution was extracted with EtOAc (3x1.5 L) and the organic layers were combined. The mixture was diluted with water (1 L) and the pH value of the solution was adjusted to 4-5 with 2 M aq. HCl. The aqueous phase was extracted with EtOAc (2x1 L) and the aqueous layers were combined. The pH value of the solution was then adjusted to 11 with $NH_4OH$. The resulting solution was extracted with DCM (6x1 L) and the organic layers were combined and concentrated under vacuum. The crude product was purified via silica gel column chromatography eluting with dichloromethane/methanol (8:1) to afford 4-[2-[(dimethylamino)methyl]-1-methyl-1H-imidazol-5-yl]phenol (int-F1-2) (120 g, 53%) as a purple oil. Analytical method 5; $t_R$=0.55 min; $[M+H]^+$=232.1.

Step 3. Into a 3-L 4-necked round-bottom flask were placed 4-[2-[(dimethylamino)methyl]-1-methyl-1H-imidazol-5-yl]phenol (int-F1-2) (120 g, 518.82 mmol, 1.00 equiv) and potassium carbonate (214.9 g, 1.55 mol, 3.00 equiv) in N,N-dimethylformamide (2 L). The resulting mixture was stirred for 30 min at rt and 4-chloro-2-fluorobenzaldehyde (98.5 g, 621.23 mmol, 1.20 equiv). The reaction mixture was stirred for 4 h at 90° C. in an oil bath and then cooled to rt and diluted with water (3 L). The resulting solution was extracted with EtOAc (3x2 L) and the organic layers were combined. The mixture was diluted with water (1 L) and the pH value of the solution was adjusted to 2 with 2 M aq. HCl. The aqueous phase was extracted with EtOAc (3x2 L) and the aqueous layers were combined. The pH value of the solution was adjusted to 11 with $NH_4OH$ and then extracted with DCM (2x2 L). The combined organic phases were concentrated under vacuum and then purified via silica gel column chromatography eluting with dichloromethane/ethyl acetate (7:3) to afford 4-chloro-2-(4-[2-[(dimethylamino) methyl]-1-methyl-1H-imidazol-5-yl]phenoxy)benzaldehyde (int-F1). $^1H$ NMR: (300 MHz, $CDCl_3$, ppm): δ 10.47 (s, 1H), 7.90 (d, J=8.4 Hz, 1H), 7.44 (d, J=8.6 Hz, 1H), 7.25-7.10 (m, 3H), 7.02 (s, 1H), 6.94 (d, J=1.9 Hz, 1H), 3.71 (s, 3H), 3.60 (s, 2H). Analytical method 5; $t_R$=1.00 min; $[M+H]^+$=370.2.

Synthesis of 4-chloro-2-(4-(1-methyl-2-(pyrrolidin-1-ylmethyl)-1H-imidazol-5-yl)phenoxy)benzaldehyde (int-F2)

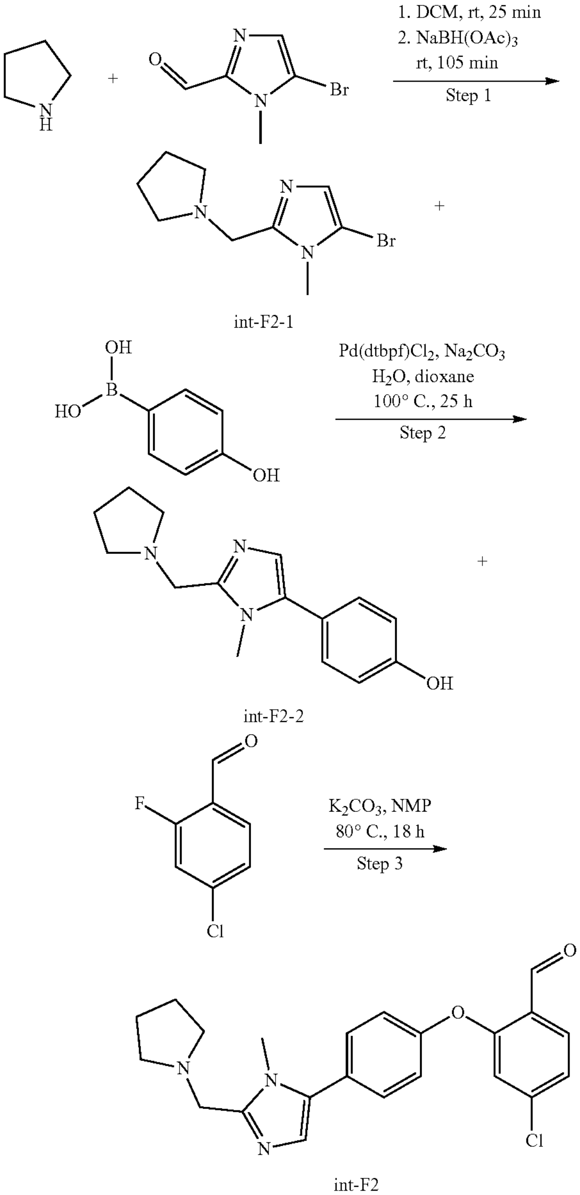

int-F2

Step 1. To a solution of 5-bromo-1-methyl-1H-imidazole-2-carbaldehyde (1.890 g, 10.0 mmol) in DCM (70 mL) was added pyrrolidine (1.643 mL, 20.0 mmol). After stirring for 25 min at rt $NaBH(OAc)_3$ (8.48 g, 40.0 mmol) was added. The resulting mixture was stirred for 105 min at rt, then concentrated to dryness in vacuo, and partitioned between EtOAc (250 mL) and 1 M aq. NaOH (50 mL). The organic layer was washed with 1 M NaOH (2×40 mL) and brine (20 mL), dried over $Na_2SO_4$, filtered, and concentrated to dryness in vacuo to afford 5-bromo-1-methyl-2-(pyrrolidin-1-ylmethyl)-1H-imidazole (int-F2-1). The crude product was used in the next step without purification. Analytical method 11; $t_R$=0.66 min; $[M+H]^+$=244.1.

Step 2. To 5-bromo-1-methyl-2-(pyrrolidin-1-ylmethyl)-1H-imidazole (int-F2-1) (10 mmol), (4-hydroxyphenyl)boronic acid (2.76 g, 20.0 mmol) and [1,1'-bis(di-tert-butylphosphino)ferrocene]dichloropalladium(II) (0.978 g, 1.50 mmol) were added dioxane (30 mL) and 1 M aq. $Na_2CO_3$ (30 mL). The reaction mixture was stirred for 4 h at 100° C. under a $N_2$ atmosphere. An additional amount of (4-hydroxyphenyl)boronic acid (1.379 g, 10.0 mmol) was added and stirring at 100° C. was continued for 135 min. More (4-hydroxyphenyl)boronic acid (1.379 g, 10.0 mmol) and [1,1'-bis(di-tert-butylphosphino)ferrocene]dichloropalladium(II) (0.244 g, 0.375 mmol) were added and stirring at 100° C. was continued for 18.75 h. EtOAc (250 mL) and $H_2O$ (50 mL) were added and the mixture was filtered over Hyflo. The layers were separated and the organic layer was washed with 5% aq. $NaHCO_3$ (3×40 mL) and brine (40 mL), dried over $Na_2SO_4$, filtered, and concentrated to dryness in vacuo. The crude product was purified by silica gel flash chromatography (eluent A: EtOAc/MeOH/DIEA (95:5:2), eluent B: EtOAc/MeOH/DIEA (85:15:2)) to give 4-(1-methyl-2-(pyrrolidin-1-ylmethyl)-1H-imidazol-5-yl)phenol (int-F2-2). Analytical method 11; $t_R$=0.76 min; $[M+H]^+$=258.1.

Step 3. 4-(1-Methyl-2-(pyrrolidin-1-ylmethyl)-1H-imidazol-5-yl)phenol (int-F2-2) (1.029 g, 4 mmol) and 4-chloro-2-fluorobenzaldehyde (0.824 g, 5.20 mmol) were dissolved in NMP (20 mL) and $K_2CO_3$ (1.437 g, 10.40 mmol) was added. The reaction mixture was stirred for 18 h at 80° C., and then partitioned between EtOAc (125 mL) and $H_2O$ (20 mL). The organic layer was washed with 5% aq. $NaHCO_3$ solution (3×10 mL) and brine (10 mL), dried with $Na_2SO_4$, filtered, and concentrated to dryness in vacuo. The crude product was purified by silica gel flash chromatography (eluent A: EtOAc/DIEA (98:2), eluent B: EtOAc/MeOH/DIEA (90:10:2)) to give 4-chloro-2-(4-(1-methyl-2-(pyrrolidin-1-ylmethyl)-1H-imidazol-5-yl)phenoxy)benzaldehyde (int-F2). Analytical method 10; $t_R$=0.79 min; $[M+H]^+$=396.2.

Synthesis of methyl (R)-4-((R)-3-amino-3-(4-chlorobenzyl)piperidin-1-yl)-3-benzyl-4-oxobutanoate (int-F3)

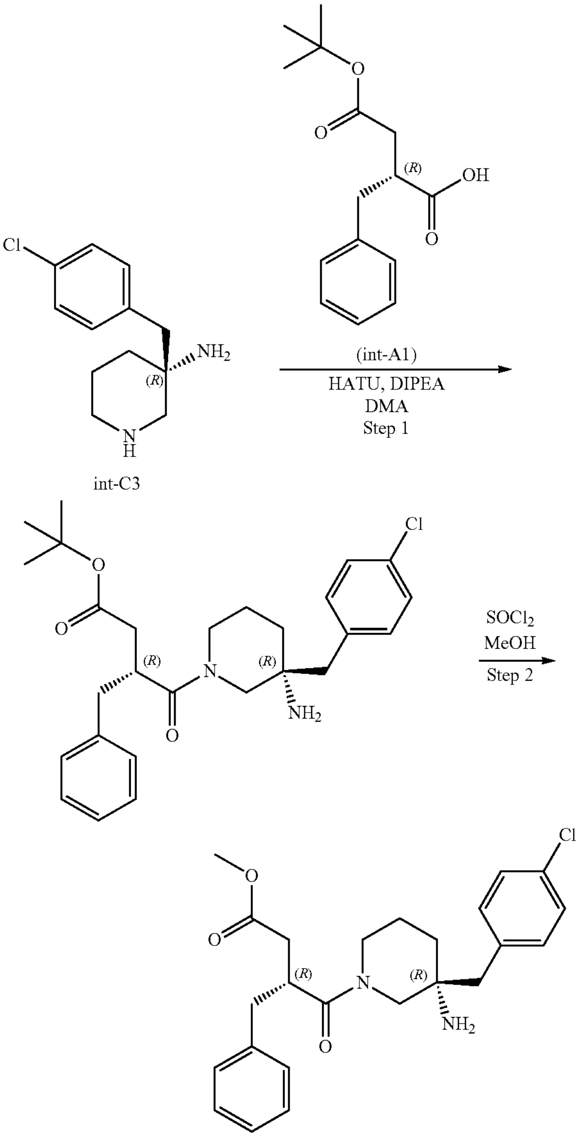

int-C3 int-F3

Step 1. To a vial containing (R)-2-benzyl-4-(tert-butoxy)-4-oxobutanoic acid (int-A1) (244 mg, 0.924 mmol) in DMA (4 mL) at room temperature was added DIPEA (0.323 mL, 1.848 mmol) and HATU (358 mg, 0.942 mmol) in several portions. Once the addition was complete, the resulting mixture was stirred at room temperature for another 15 min and then added dropwise to another vial containing (R)-3-(4-chlorobenzyl)piperidin-3-amine (int-C3) (275 mg, 0.924 mmol) in DMA (1.5 mL) and DIPEA (0.807 mL, 4.62 mmol). The reaction mixture was stirred at room temperature overnight, then transferred to a separatory funnel, diluted with EtOAc, and washed with saturated aq. sodium bicarbonate and brine (×3). The organic phase was dried over sodium sulfate, filtered, and concentrated to afford tert-butyl (R)-4-((R)-3-amino-3-(4-chlorobenzyl)piperidin- 1-yl)-3-benzyl-4-oxobutanoate, which was carried to the next step without purification.

Step 2. To a round bottom flask containing tert-butyl (R)-4-((R)-3-amino-3-(4-chlorobenzyl)piperidin-1-yl)-3-benzyl-4-oxobutanoate (435 mg, 0.924 mmol) in anhydrous methanol (18 mL) and cooled in an ice bath was added thionyl chloride (1.35 mL, 18.47 mmol) dropwise. When the addition was complete, the resulting mixture was warmed to room temperature gradually and then stirred overnight to complete the reaction. The reaction mixture was concentrated to dryness under reduced pressure with heating in a water bath at 30° C. The crude oil was dissolved in EtOAc, washed with a half-saturated aqueous solution of sodium bicarbonate, and then washed with brine. The separated organic phase was dried over sodium sulfate, filtered, and concentrated to afford methyl (R)-4-((R)-3-amino-3-(4-chlorobenzyl)piperidin-1-yl)-3-benzyl-4-oxobutanoate (int-F3).

Synthesis of (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1)

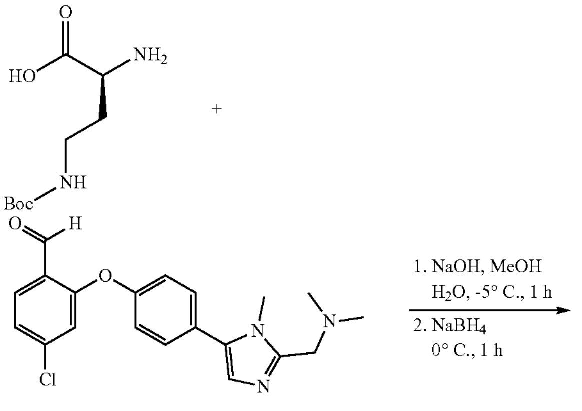

int-F1

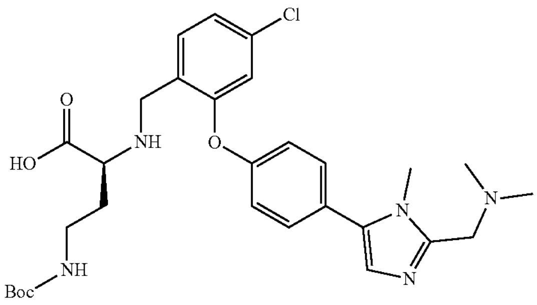

int-G1

To a suspension of (S)-2-amino-4-((tert-butoxycarbonyl)amino)butanoic acid (1.04 mg, 4.77 mmol) in MeOH (10 mL) and water (0.46 mL) at rt was added NaOH (4.67 mL, 4.67 mmol). The resulting mixture was allowed to stir for 1 hr at rt and then 4-chloro-2-(4-(2-((dimethylamino)methyl)-1-methyl-1H-imidazol-5-yl)phenoxy)benzaldehyde (int-F1) (1.6 g, 4.33 mmol) was added and the reaction mixture was stirred for 15 min., cooled to −5° C. and then stirred for 1 h. $NaBH_4$ (65 mg, 1.73 mmol) was added in portions maintaining the internal reaction temperature below 0° C. The reaction mixture was stirred at −5° C. for 30 min. and then at rt for 2 hrs. The reaction mixture was quenched by adding water dropwise until gas evolution stopped. The reaction mixture was then concentrated to remove the MeOH and 60 mL water was added. The aqueous mixture was extracted with EtOAc (150 mL) and the organic layer washed with 40 mL $NaHCO_3$ solution, cooled and 1.0N HCl was added to adjust pH~8. The resulting precipitate was filtered, washed with water and dried. The filtrate was extracted with DCM (4×200 mL). The organics were concentrated and the residue was combined with the precipitate. The solid was dried under vacuum to give (S)-4-((tert-butoxycarbonyl)amino)-2-((4-chloro-2-(4-(2-((dimethylamino)ethyl)-1-methyl-1H-imidazol-5-yl)phenoxy)benzyl)amino)butanoic acid (int-G1). Analytical method 7: $t_R$=0.66 min; $[M+H]^+$=572.0

Synthesis of (S)-5-((tert-butoxycarbonyl)amino)-2-((4-chloro-2-(4-(2-((dimethylamino)methyl)-1-methyl-1H-imidazol-5-yl)phenoxy)benzyl)amino)pentanoic acid (int-G2)

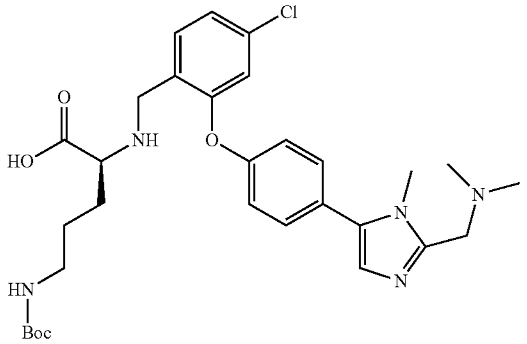

int-G2

(S)-5-((tert-butoxycarbonyl)amino)-2-((4-chloro-2-(4-(2-((dimethylamino)methyl)-1-methyl-1H-imidazol-5-yl)phenoxy)benzyl)amino)pentanoic acid (int-G2) was obtained using a method similar to the procedure used in the synthesis of (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1), except (S)-2-amino-4-((tert-butoxycarbonyl)amino)butanoic acid was replaced with (S)-2-amino-5-((tert-butoxycarbonyl)amino)pentanoic acid. Analytical method 7: $t_R$=0.67 min; $[M+H]^+$=586.2.

Synthesis of (S)-5-((tert-butoxycarbonyl)amino)-2-((4-chloro-2-(4-(1-methyl-2-(pyrrolidin-1-ylmethyl)-1H-imidazol-5-yl)phenoxy)benzyl)amino)pentanoic acid (int-G3)

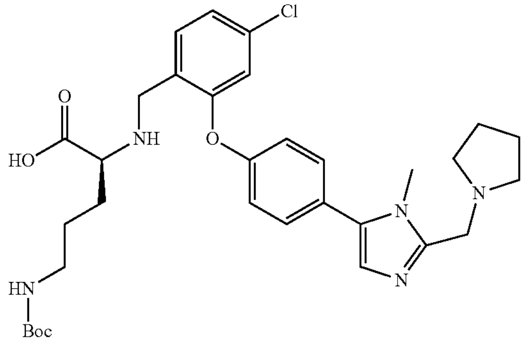

int-G3

(S)-5-((tert-butoxycarbonyl)amino)-2-((4-chloro-2-(4-(1-methyl-2-(pyrrolidin-1-ylmethyl)-1H-imidazol-5-yl)phenoxy)benzyl)amino)pentanoic acid (int-G3) was obtained using a method similar to the procedure used in the synthesis of (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1), except (S)-2-amino-4-((tert-butoxycarbonyl)amino)butanoic acid was replaced with (S)-2-amino-5-((tert-butoxycarbonyl)amino)pentanoic acid and 4-chloro-2-(4-(2-((dimethylamino)methyl)-1-methyl-1H-imidazol-5-yl)phenoxy)benzaldehyde (int-F1) was replaced with 4-chloro-2-(4-(1-methyl-2-(pyrrolidin-1-ylmethyl)-1H-imidazol-5-yl)phenoxy)benzaldehyde (int-F2). Analytical method 7: $t_R$=1.46 min; $[M+H]^+$=612.6.

Synthesis of PS-(2-Chlorotrityl) (R)-4-(((S)-1-aminopropan-2-yl)(methyl)amino)-3-benzyl-4-oxobutanoate (AB1)

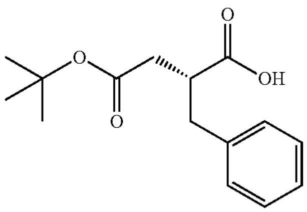

int-A1

+

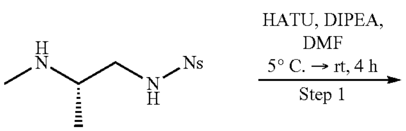

int-B2

-continued

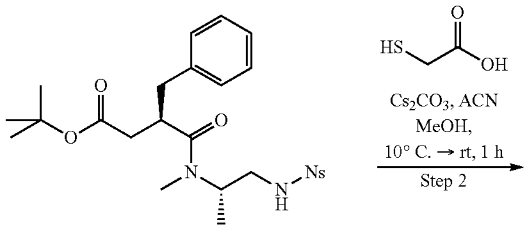

AB1-1

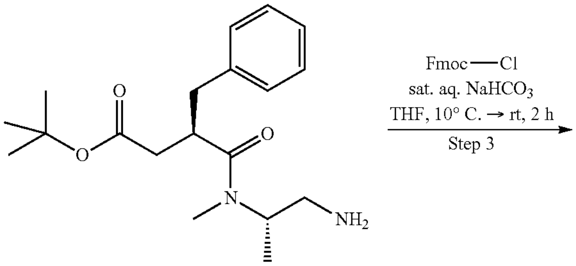

AB1-2

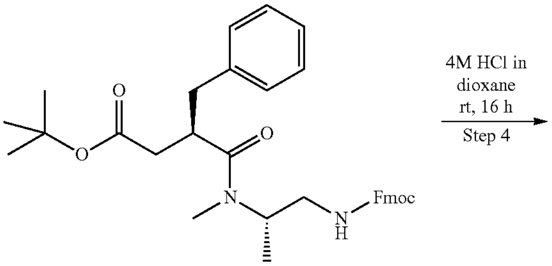

AB1-3

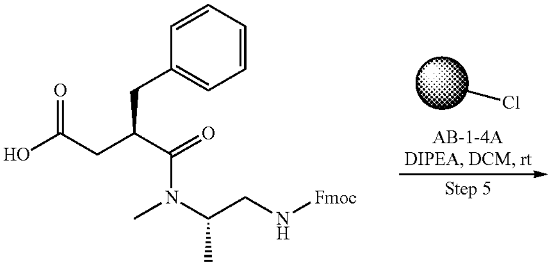

AB1-4

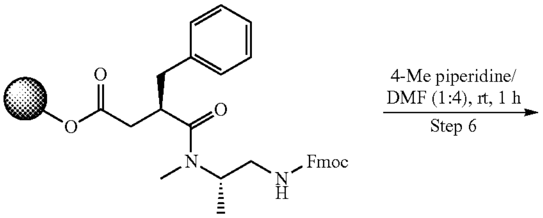

AB1-5

-continued

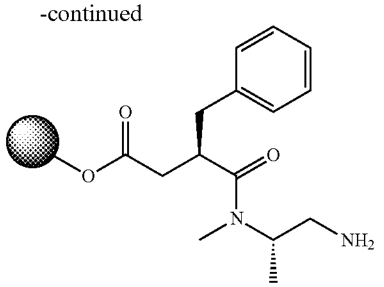

AB1

Step 1. To a cold stirred solution of (S)—N-(2-(methylamino)propyl)-4-nitrobenzenesulfonamide (int-B2) (230 g, 0.742 mol) and (R)-2-benzyl-4-(tert-butoxy)-4-oxobutanoic acid (int-A1) (186.4 g, 0.705 mol) in DMF (460 mL) was added DIPEA (388 mL, 2.227 mol) followed by HATU (310.3 g, 0.816 mol) at 5-10° C. The resulting mixture was removed from the cold bath and stirred at rt for 4 h. The reaction mixture was then poured into ice-cold water (5 L) and extracted with ethyl acetate (2×2 L). The combined organic layers were washed with brine solution (2 L), dried over anhydrous $Na_2SO_4$ and concentrated under vacuum. The crude product was purified by 230-400-mesh silica gel column chromatography eluting with 20% ethyl acetate in petroleum ether to afford tert-butyl (R)-3-benzyl-4-(methyl((S)-1-((4-nitrophenyl)sulfonamido)propan-2-yl)amino)-4-oxobutanoate (AB1-1). Analytical method 7; $t_R$=1.40 min; $[M+H]^+$=520.3.

Step 2. To a cold stirred solution of tert-butyl (R)-3-benzyl-4-(methyl((S)-1-((4-nitrophenyl)sulfonamido)propan-2-yl)amino)-4-oxobutanoate (AB1-1) (455 g, 0.875 mol) in acetonitrile (3.5 L) and methanol (3.5 L) below 10° C. was added cesium carbonate (1.995 kg, 6.125 mol) and the resulting mixture was stirred for 15 minutes. 2-Mercaptoacetic acid (322.7 g, 3.50 mol) was then added to at the same temperature. The resulting mixture was stirred at room temperature for 1 h and concentrated under reduced pressure to remove the solvent. The crude product was dissolved in water (3 L) and the aqueous phase was extracted with dichloromethane (2×2 L). The combined organic layers were washed with sat. sodium bicarbonate (3 L) and brine solution (2 L), dried over anhydrous $Na_2SO_4$, filtered, and concentrated under vacuum to afford tert-butyl (R)-4-(((S)-1-aminopropan-2-yl)(methyl)amino)-3-benzyl-4-oxobutanoate (AB1-2) which used in the next step without purification.

Step 3. To a cold stirred solution of tert-butyl (R)-4-(((S)-1-aminopropan-2-yl)(methyl)amino)-3-benzyl-4-oxobutanoate (AB1-2) (270 g, 0.807 mol) in THF (1.5 L) was added Fmoc-Cl (209.1 g, 0.807 mol) portion wise over 30 min at 10° C., followed by sat. sodium bicarbonate solution (3.3 L) over a period of 30 minutes at the same temperature. The mixture was then stirred at room temperature for 2 h. The reaction mixture was diluted with water (2 L) and extracted with ethyl acetate (2×1 L). The combined organic layers were washed with brine solution (2 L), dried over anhydrous $Na_2SO_4$, filtered, and concentrated under vacuum. The crude material was purified on a 230-400-mesh silica gel column eluting with 20% ethyl acetate in petroleum ether to afford tert-butyl (R)-4-(((S)-1-((((9H-fluoren-9-yl)methoxy)carbonyl)amino)propan-2-yl)(methyl)amino)-3-benzyl-4-oxobutanoate (AB1-3). Analytical method 7; $t_R$=1.49 min; $[M+H]^+$=557.3.

Step 4. To a solution of tert-butyl (R)-4-(((S)-1-((((9H-fluoren-9-yl)methoxy)carbonyl)amino)propan-2-yl)(methyl) amino)-3-benzyl-4-oxobutanoate (AB1-3) (265 g, 0.476 mol) in 1,4-dioxane (530 mL) was added 4 M HCl in dioxane (2.65 L) at room temperature. The resulting mixture was stirred for 16 h and then concentrated under reduced pressure. The crude product was purified on a 230-400-mesh silica gel column eluting with 30% ethyl acetate in petroleum ether to give (R)-4-(((S)-1-((((9H-fluoren-9-yl)methoxy)carbonyl)amino)propan-2-yl)(methyl)amino)-3-benzyl-4-oxobutanoic acid (AB1-4). Analytical method 7; $t_R$=1.48 min; $[M+H]^+$=501.4.

Step 5. 2-Chlorotrityl chloride resin (AB-1-4A), 4.27 g, 4.27 mmol) was pre-washed with DCM (3×20 mL). (R)-4-(((S)-1-((((9H-fluoren-9-yl)methoxy)carbonyl)amino)propan-2-yl)(methyl)amino)-3-benzyl-4-oxobutanoic acid (AB1-4) (1.9 g, 3.80 mmol) dissolved in DCM (20 mL) and DIPEA (1.5 mL, 8.59 mmol) were added to the resin. The resulting mixture was shaken at rt for 16 h, then washed with DCM (3×40 mL), and shaken in DCM/MeOH (50 mL/20 mL) for 30 min to cap the resin. The resin was then filtered, washed with DMF (2×50 mL), and DCM (2×50 mL) and dried under vacuum to give PS-(2-chlorotrityl) (R)-4-(((S)-1-((((9H-fluoren-9-yl)methoxy)carbonyl)amino)propan-2-yl)(methyl)amino)-3-benzyl-4-oxobutanoic acid (AB1-5) resin (6.13 g, crude). The resin was taken onto the next step without purification.

Step 6. To PS-(2-chlorotrityl) (R)-4-(((S)-1-((((9H-fluoren-9-yl)methoxy)carbonyl)amino)propan-2-yl)(methyl) amino)-3-benzyl-4-oxobutanoic acid (AB1-5) (285 mg, 1.283 mmol) was added 20% 4-methylpiperidine in DMF (10 mL) and the resulting mixture was shaken at rt for 2 h. The resin was then filtered, washed with DMF (2×10 mL) and DCM (2×10 mL), and dried under vacuum. This provided resin PS-(2-chlorotrityl) (R)-4-(((S)-1-aminopropan-2-yl)(methyl)amino)-3-benzyl-4-oxobutanoic acid (AB1), which was used without purification.

Synthesis of PS-(2-Chlorotrityl) (R)-4-(((1S,2S)-2-aminocyclohexyl)(methyl)amino)-3-benzyl-4-oxobutanoate (AB2)

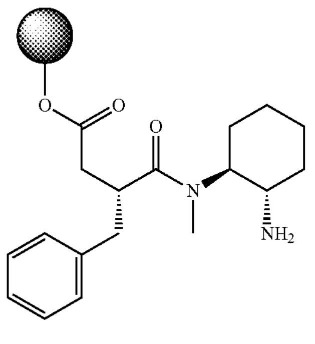

AB2

PS-(2-Chlorotrityl) (R)-4-(((1S,2S)-2-aminocyclohexyl)(methyl)amino)-3-benzyl-4-oxobutanoate (AB2) was obtained using a method similar to the procedure used in the synthesis of PS-(2-Chlorotrityl) (R)-4-(((S)-1-aminopropan-2-yl)(methyl)amino)-3-benzyl-4-oxobutanoate (AB1), except (S)—N-(2-(methylamino)propyl)-4-nitrobenzenesulfonamide (int-B2) was replaced with tert-butyl ((1S,2S)-2-(methylamino)cyclohexyl)carbamate (int-B1).

Synthesis of PS-(2-Chlorotrityl) (R)-4-(((S)-1-amino-6-((2-nitrophenyl)sulfonamido)hexan-2-yl)(methyl)amino)-3-benzyl-4-oxobutanoate (AB3)

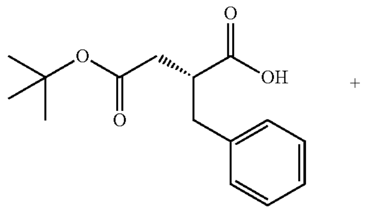

int-A1

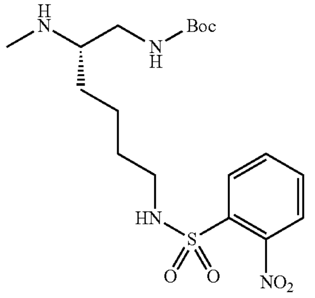

int-B3

TBTU, DIPEA,
DMF, DCM
Step 1

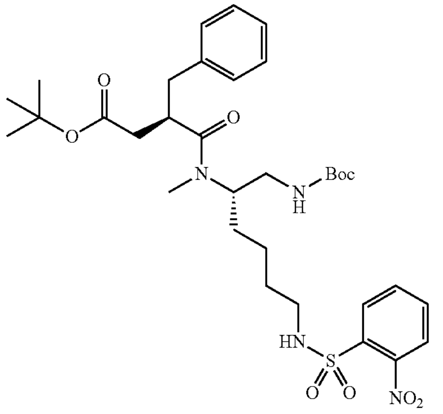

AB3-1

TEA,
DCM,
rt, 1 h
Step 2

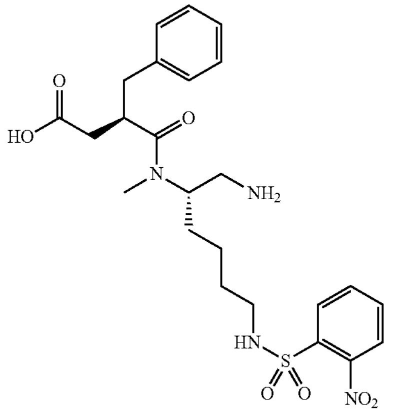

AB3-2

Fmoc—NCS,
THF
sat. aq. NaHCO$_3$
Step 3

-continued

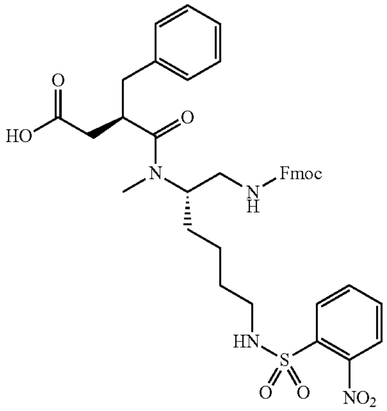

AB3-3

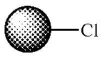

PS-2-Chlorotrityl
chloride, DIEA
Step 4

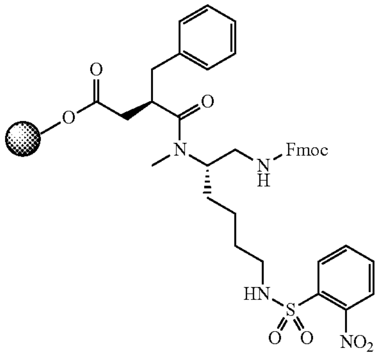

AB3-4

4-Me-piperidine/
DMF (1:4), rt, 1 h
Step 5

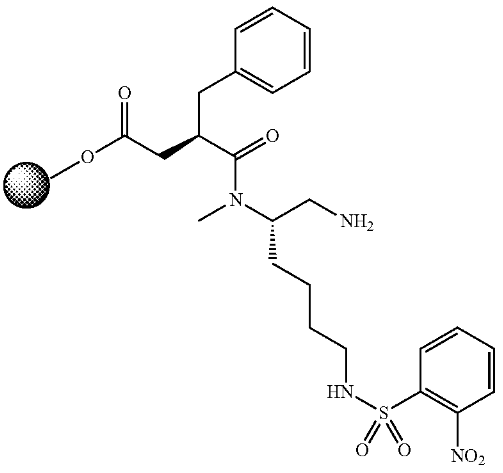

AB3

Step 1. (R)-2-benzyl-4-(tert-butoxy)-4-oxobutanoic acid (0.537 g, 2.03 mmol) and TBTU (0.717 g, 2.233 mmol) were suspended in DCM/DMF (3:1) (20 mL) and DIEA (0.390 mL, 2.233 mmol) was added. The mixture was stirred for 25 min at room temperature. A solution of tert-butyl (S)-(2-(methylamino)-6-((2-nitrophenyl)sulfonamido)hexyl)carbamate (1.049 g, 2.436 mmol) in DCM (20 mL) was added and the reaction was stirred for 2 h 10 min at room temperature. Additional DIEA (0.390 mL, 2.233 mmol) was added and stirring was continued for 44 h. $H_2O$ (1 mL) was added and DCM was removed in vacuo. The residue was partitioned between EtOAc (60 mL) and 5% aq. $NaHCO_3$ (15 mL). The organic layer was washed with 5% aq. $NaHCO_3$ (3×10 mL) and brine (10 mL), dried over $Na_2SO_4$, filtered and concentrated to dryness in vacuo to afford (1.535 g, 2.030 mmol, 100% yield) as a brown oil. The crude tert-butyl (R)-3-benzyl-4-(((S)-1-((tert-butoxycarbonyl) amino)-6-((2-nitrophenyl)sulfonamido)hexan-2-yl)(methyl) amino)-4-oxobutanoate was used in the next step without purification. Analytical method 11; $t_R$=1.31 min; $[M+H]^+$=677.5.

Step 2. tert-butyl (R)-3-benzyl-4-(((S)-1-((tert-butoxycarbonyl)amino)-6-((2-nitrophenyl)sulfonamido)hexan-2-yl)(methyl)amino)-4-oxobutanoate (1.535 g, 2.020 mmol) was dissolved in TFA (95% aq., 20 mL), stirred for 1 h at room temperature, then concentrated to dryness to provide (R)-4-(((S)-1-amino-6-((2-nitrophenyl)sulfonamido)hexan-2-yl)(methyl)amino)-3-benzyl-4-oxobutanoic acid, which was used directly in the next reaction.

Step 3. The crude (R)-4-(((S)-1-amino-6-((2-nitrophenyl)sulfonamido)hexan-2-yl)(methyl)amino)-3-benzyl-4-oxobutanoic acid obtained from step 2 was dissolved in dioxane (20 mL), then treated with 0.5 M aq. $Na_2CO_3$ (12.18 mL, 6.09 mmol) and a solution of (9H-fluoren-9-yl)methyl (2,5-dioxopyrrolidin-1-yl) carbonate (0.685 g, 2.030 mmol) in dioxane (20 mL). The reaction was maintained at room temperature for 90 min, then quenched by addition of 2.0 M aq. HCl (15 mL) and concentrated to about half the volume in vacuo. The residue was partitioned between EtOAc (100 mL) and 5% $KHSO_4$ (15 mL). The organic layer was washed with 5% aq. $KHSO_4$ (3x15 mL) and brine (15 mL), dried over $Na_2SO_4$, filtered and concentrated to dryness in vacuo. The crude product was purified by flash chromatography over silica gel. Pure fractions were combined and concentrated to dryness in vacuo. The residue was partitioned between EtOAc (80 mL) and 5% aq. $NaHCO_3$ (7 mL). The organic layer was washed with 5% aq. $NaHCO_3$ (3x7 mL), 5% aq. $KHSO_4$ (15 mL) and brine (10 mL), dried over $Na_2SO_4$, filtered and concentrated to dryness in vacuo to afford (R)-4-(((S)-1-((((9H-fluoren-9-yl)methoxy)carbonyl) amino)-6-((2-nitrophenyl)sulfonamido)hexan-2-yl)(methyl) amino)-3-benzyl-4-oxobutanoic acid (900 mg, 1.212 mmol, 60% yield) as a white foam Analytical method 11; $t_R$=1.21 min; $[M+H]^+$=743.15.

Step 4. 2-Chlorotrityl chloride resin (1.250 mg, 2.00 mmol) was pre-washed with DCM (3x30 mL). tert-butyl (R)-4-(((S)-1-((((9H-fluoren-9-yl)methoxy)carbonyl) amino)-6-((2-nitrophenyl)sulfonamido)hexan-2-yl)(methyl) amino)-3-benzyl-4-oxobutanoate (AB3-3) (900 mg, 1.21 mmol) in DCM (30 mL) and DIEA (1.69 mL, 9.69 mmol) were added to the resin. The resulting mixture was shaken at rt for 16 h, washed with DCM (3x50 mL), and then shaken in DCM/MeOH (5:2) (20 mL) to cap the resin for 30 min. The resin was then filtered, washed with DCM/MeOH/DIEA (17:2:1) (3x15 mL) and dried under vacuum. This provided resin PS-(2-chlorotrityl)-(R)-4-(((S)-1-((((9H-fluoren-9-yl)methoxy)carbonyl)amino)-6-((2-nitrophenyl) sulfonamido)hexan-2-yl)(methyl)amino)-3-benzyl-4-oxobutanoate (AB3-4), which was carried onto the next step without purification.

Step 5. To PS-(2-chlorotrityl)-(R)-4-(((S)-1-((((9H-fluoren-9-yl)methoxy)carbonyl)amino)-6-((2-nitrophenyl)sulfonamido)hexan-2-yl)(methyl)amino)-3-benzyl-4-oxobutanoate (AB3-4) (266 mg, 0.336 mmol) was added 20% 4-methylpiperidine in DMF (10 mL) and the resulting mixture was shaken at rt for 2 h. The resin was then filtered, washed with DMF (2x10 mL) and DCM (2x10 mL), and dried under vacuum. This provided resin PS-(2-chlorotrityl)-(R)-4-(((S)-1-amino-6-((2-nitrophenyl)sulfonamido)hexan-2-yl)(methyl)amino)-3-benzyl-4-oxobutanoate (AB3), which was used without purification.

Synthesis of PS-(2-Chlorotrityl) (4S,7S,12S,15R)-4-amino-15-benzyl-7-(4-chlorobenzyl)-6,12,13-trimethyl-5,9,14-trioxo-2-oxa-6,10,13-triazaheptadecan-17-oate (AB4)

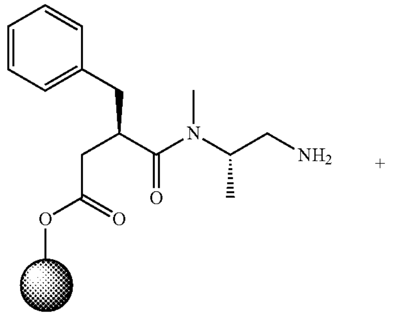

AB1

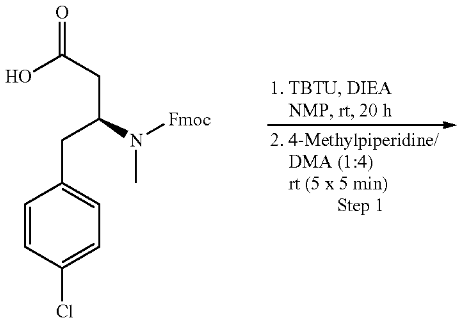

int-C1

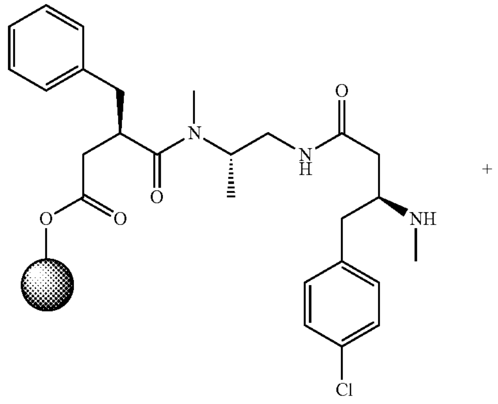

AB4-1

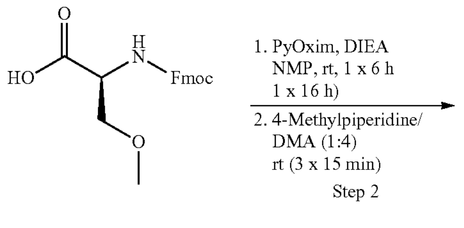

-continued

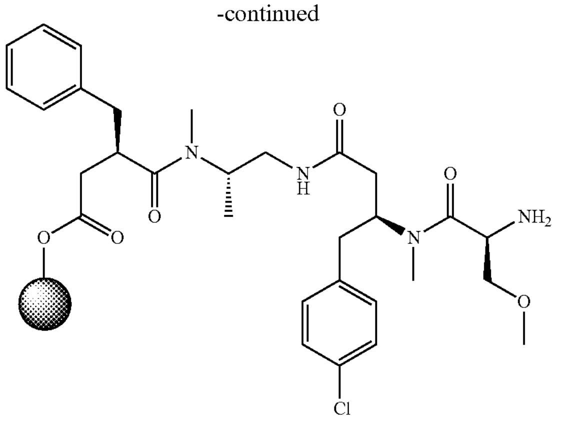

AB4

Step 1-1. A solution of (S)-3-((((9H-Fluoren-9-yl)methoxy)carbonyl)(methyl)amino)-4-(4-chlorophenyl)butanoic acid (int-C1) (4.05 g, 9.00 mmol), TBTU (2.89 g, 9.00 mmol) and DIEA (1.729 mL, 9.90 mmol) in NMP (70 mL) was shaken for 2 min at rt, and was then added to PS-(2-Chlorotrityl) (R)-4-(((S)-1-aminopropan-2-yl)(methyl)amino)-3-benzyl-4-oxobutanoate (AB1) (6.00 mmol) that had been washed with NMP (3×). The resulting suspension was shaken for 20 h at rt, then filtered and the resin was washed with DMA (3×). For capping, $Ac_2O$/pyridine/DMA (1:1:8) (70 mL) was added and the resulting suspension was shaken for 15 min at rt. The resin was drained, and then washed with DMA (3×).

Step 1-2. Fmoc-deprotection was done by repetitive treatment with 4-methylpiperidine/DMA (1:4) (5×70 mL, each time shaking for 5 min at rt). The cleavage solutions were collected and used to determine the loading of the resin via UV spectra. After Fmoc removal, the resin was washed with DMA (3×), DCM (3×), DMA (3×) and DCM (5×) and dried in vacuo to provide PS-(2-chlorotrityl) (R)-3-benzyl-4-(((S)-1-((S)-4-(4-chlorophenyl)-3-(methylamino)butanamido)-propan-2-yl)(methyl)amino)-4-oxobutanoate (AB4-1).

Step 2-1. A solution of Fmoc-O-methyl-L-serine (2.292 g, 6.72 mmol), PyOxim (3.54 g, 6.72 mmol), and DIEA (2.346 mL, 13.43 mmol) in NMP (55 mL) was shaken for 2 min at rt, and was then added to PS-(2-chlorotrityl) (R)-3-benzyl-4-(((S)-1-((S)-4-(4-chlorophenyl)-3-(methylamino)butanamido)-propan-2-yl)(methyl)amino)-4-oxobutanoate (AB4-1) (4.477 mmol) that had been washed with NMP (3×). The resulting suspension was shaken for 6 h at rt, and then filtered. A solution of Fmoc-O-methyl-L-serine (1.528 g, 4.48 mmol), PyOxim (2.361 g, 4.48 mmol) and DIEA (1.564 mL, 8.95 mmol) in NMP (35 mL) was stirred for 2 min at rt, and then added to the resin. The resulting suspension was shaken for 16 h at rt and filtered and the resin was washed with DMA (3×). For capping, $Ac_2O$/pyridine/DMA (1:1:8) (40 mL) was added and the resulting suspension was shaken for 15 min at rt. The resin was drained, and then washed with DMA (3×).

Step 2-2. Fmoc-deprotection was done by repetitive treatment with 4-methylpiperidine/DMA (1:4) (3×30 mL, each time shaking for 15 min at rt). After Fmoc-removal, the resin was washed with DMA (3×) and DCM (5×) to give PS-(2-Chlorotrityl) (4S,7S,12S,15R)-4-amino-15-benzyl-7-(4-chlorobenzyl)-6,12,13-trimethyl-5,9,14-trioxo-2-oxa-6,10,13-triazaheptadecan-17-oate (AB4).

Synthesis of PS-(2-Chlorotrityl) (R)-4-(((1S,2S)-2-((S)-3-((S)-2-amino-3-methoxy-N-methylpropanamido)-4-(4-chlorophenyl)butanamido)cyclohexyl)(methyl)amino)-3-benzyl-4-oxobutanoate (AB5)

AB5

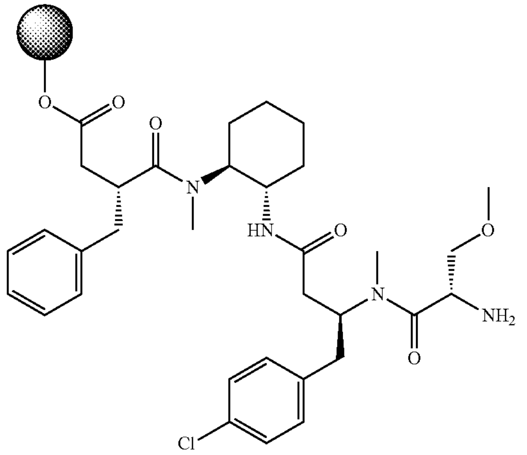

PS-(2-Chlorotrityl) (R)-4-(((1S,2S)-2-((S)-3-((S)-2-amino-3-methoxy-N-methylpropanamido)-4-(4-chlorophenyl)butanamido)cyclohexyl)(methyl)amino)-3-benzyl-4-oxobutanoate (AB5) was obtained using a method similar to the procedure used in the synthesis of PS-(2-chlorotrityl) (4S,7S,12S,15R)-4-amino-15-benzyl-7-(4-chlorobenzyl)-6,12,13-trimethyl-5,9,14-trioxo-2-oxa-6,10,13-triazaheptadecan-17-oate (AB4), except PS-(2-chlorotrityl) (R)-4-(((S)-1-aminopropan-2-yl)(methyl)amino)-3-benzyl-4-oxobutanoate (AB1) was replaced with PS-(2-chlorotrityl) (R)-4-(((1S,2S)-2-aminocyclohexyl)(methyl)amino)-3-benzyl-4-oxobutanoate (AB2).

Synthesis of N-(4-((2S,5S,8S,13S,16R)-16-benzyl-1-(4-choro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7,14-trimethyl-3,6,10,15,18-pentaoxo-1,4,7,11,14-pentaazacyclooctadecan-13-yl)butyl)-2-nitrobenzenesulfonamide (AB6)
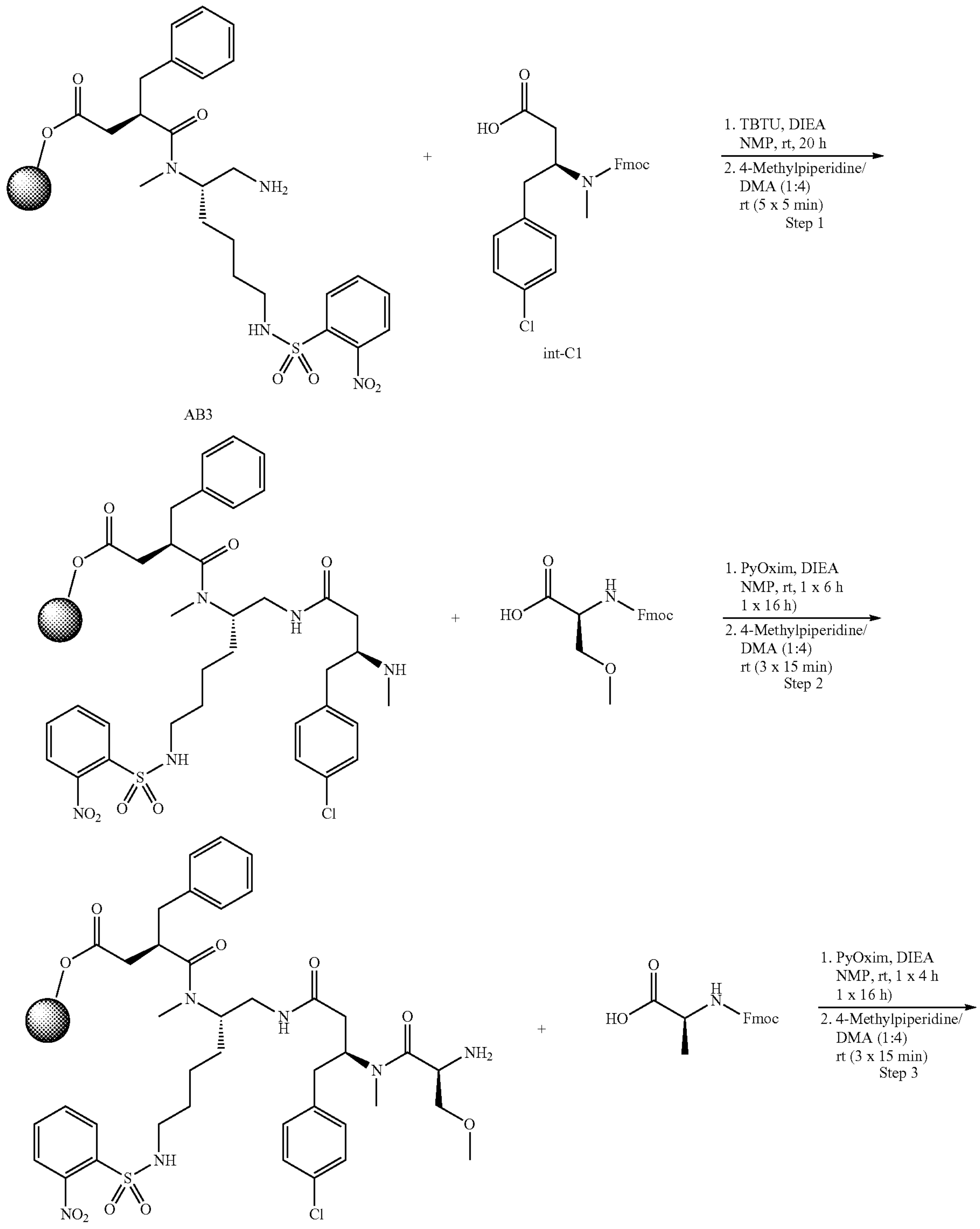

-continued
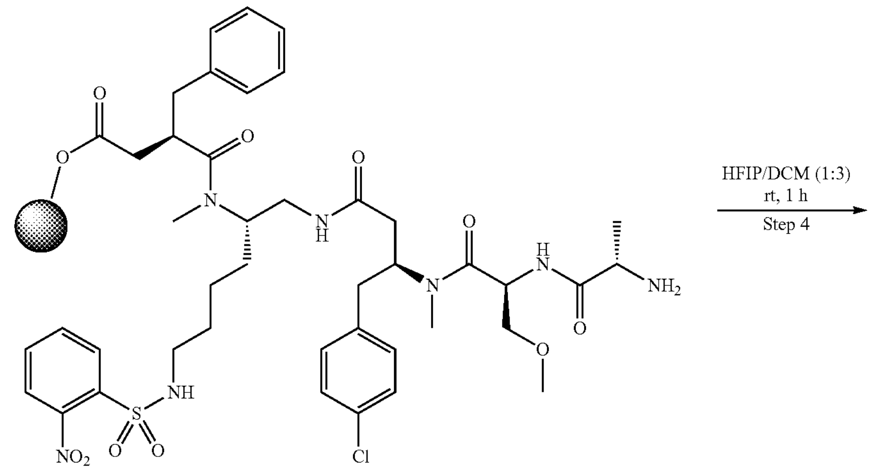
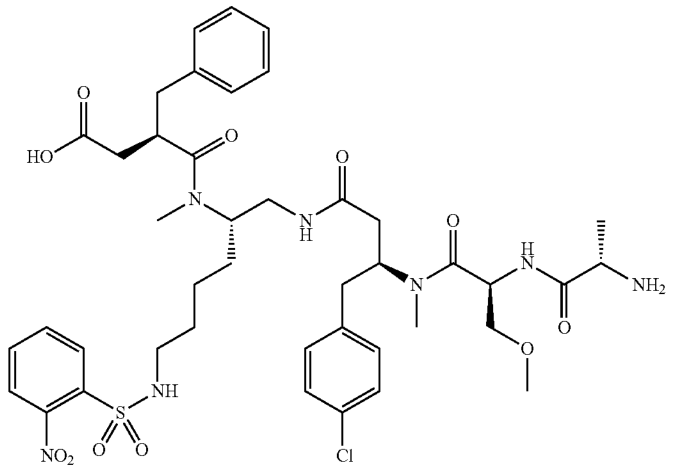
+
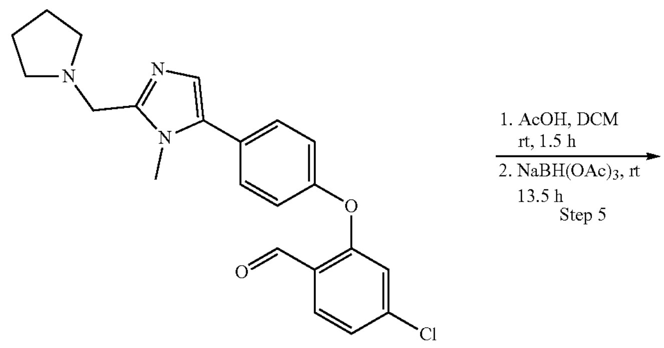
int-F2

-continued

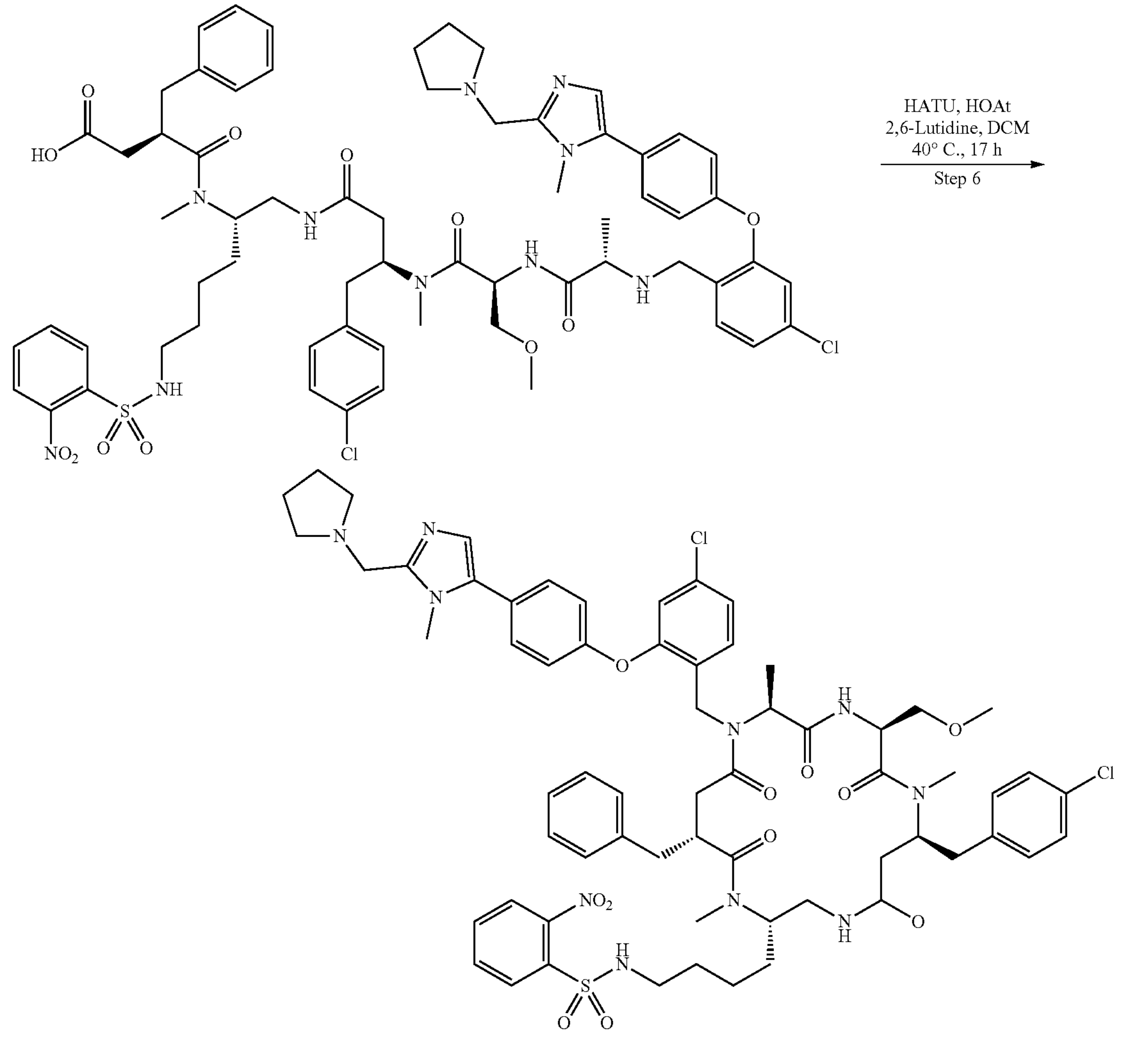

AB6

Step 1-1. A solution of (S)-3-((((9H-Fluoren-9-yl) methoxy)carbonyl)(methyl)amino)-4-(4-chlorophenyl)butanoic acid (int-C1) (0.601 g, 1.336 mmol), TBTU (0.429 g, 1.339 mmol) and DIEA (0.257 mL, 1.4690 mmol) in NMP (20 mL) was shaken for 2 min at rt, and was then added to PS-(2-chlorotrityl)-(R)-4-(((S)-1-amino-6-((2-nitrophenyl) sulfonamido)hexan-2-yl)(methyl)amino)-3-benzyl-4-oxobutanoate (AB3) (1.113 mmol) that had been washed with NMP (3×). The resulting suspension was shaken for 20 h at rt, then filtered and the resin was washed with DMA (3×). For capping, $Ac_2O$/pyridine/DMA (1:1:8) (70 mL) was added and the resulting suspension was shaken for 20 h at rt. The resin was drained, and then washed with DMA (3×).

Step 1-2. Fmoc-deprotection was done by repetitive treatment with 4-methylpiperidine/DMA (1:4) (5×20 mL, each time shaking for 15 min at rt). The cleavage solutions were collected and used to determine the loading of the resin via UV spectra. After Fmoc removal, the resin was washed with DMA (3×), DCM (3×), DMA (3×) and DCM (5×) and dried in vacuo to provide PS-(2-Chlorotrityl) (R)-3-benzyl-4-(((S)-1-((S)-4-(4-chlorophenyl)-3-(methylamino)butanamido)-6-((2-nitrophenyl)sulfonamido)hexan-2-yl)(methyl) amino)-4-oxobutanoate.

Step 2-1. A solution of Fmoc-O-methyl-L-serine (0.57 g, 1.67 mmol), PyOxim (0.88 g, 1.67 mmol), and DIEA (0.583 mL, 3.339 mmol) in NMP (15 mL) was shaken for 2 min at rt, and was then added to PS-(2-Chlorotrityl) (R)-3-benzyl-4-(((S)-1-((S)-4-(4-chlorophenyl)-3-(methylamino)butanamido)-6-((2-nitrophenyl)sulfonamido)hexan-2-yl)(methyl) amino)-4-oxobutanoate (1.113 mmol) that had been washed with NMP (3×). The resulting suspension was shaken for 3 h at rt, filtered and the resin was washed with DMA (3×). For capping, $Ac_2O$/pyridine/DMA (1:1:8) (40 mL) was added and the resulting suspension was shaken for 15 min at rt. The resin was drained, and then washed with DMA (3×).

Step 2-2. Fmoc-deprotection was done by repetitive treatment with 4-methylpiperidine/DMA (1:4) (3×15 mL, each time shaking for 15 min at rt). After Fmoc-removal, the resin was washed with DMA (3×) and DCM (5×) to give PS-(2-Chlorotrityl) (4S,7S,12S,15R)-4-amino-15-benzyl-7-(4-chlorobenzyl)-6,13-dimethyl-12-(4-((2-nitrophenyl)sulfonamido)butyl)-5,9,14-trioxo-2-oxa-6,10,13-triazaheptadecan-17-oate which was taken to the next step.

Step 3-1. A solution of Fmoc-Ala-OH (1.04 g, 3.339 mmol), PyOxim (1.761 g, 3.339 mmol), and DIEA (1.166 mL, 6.678 mmol) in NMP (25 mL) was shaken at rt for 2 min, and was then added to PS-(2-Chlorotrityl) (4S,7S,12S,15R)-4-amino-15-benzyl-7-(4-chlorobenzyl)-6,13-dimethyl-12-(4-((2-nitrophenyl)sulfonamido)butyl)-5,9,14-trioxo-2-oxa-6,10,13-triazaheptadecan-17-oate (1.113 mmol) that had been washed with NMP (3×). The resulting suspension was shaken for 3 h at rt, then filtered and the resin was washed with DMA (3×). For capping, $Ac_2O$/pyridine/DMA (1:1:8) (20 mL) was added and the resulting suspension was shaken for 15 min at rt. The resin was drained and then washed with DMA (3×).

Step 3-2. Fmoc-deprotection was done by repetitive treatment with 4-methylpiperidine/DMA (1:4) (3×20 mL, each time shaking for 15 min at rt). After Fmoc-removal the resin was washed with DMA (3×) and DCM (5×) to give PS-(2-chlorotrityl) (2S,5S,8S,13S,16R)-2-amino-16-benzyl-8-(4-chlorobenzyl)-5-(methoxymethyl)-7,14-dimethyl-13-(4-((2-nitrophenyl)sulfonamido)butyl)-3,6,10,15-tetraoxo-4,7,11,14-tetraazaoctadecan-18-oate which was taken to the next step.

Step 4. To PS-(2-Chlorotrityl) (2S,5S,8S,13S,16R)-2-amino-16-benzyl-8-(4-chlorobenzyl)-5-(methoxymethyl)-7,14-dimethyl-13-(4-((2-nitrophenyl)sulfonamido)butyl)-3,6,10,15-tetraoxo-4,7,11,14-tetraazaoctadecan-18-oate (1.113 mmol) was added HFIP/DCM (1:3) (20 mL) and the resulting suspension was shaken for 20 min at rt. The cleavage solution was then filtered off and collected (3×). The resin was washed with DCM (2×) and the wash solutions were collected. The combined cleavage and wash solutions were concentrated to dryness in vacuo. The crude residue was lyophilized from tBuOH/$H_2O$ (4:1) to yield (2S,5S,8S,13S,16R)-2-amino-16-benzyl-8-(4-chlorobenzyl)-5-(methoxymethyl)-7,14-dimethyl-13-(4-((2-nitrophenyl)sulfonamido)butyl)-3,6,10,15-tetraoxo-4,7,11,14-tetraazaoctadecan-18-oic acid. Analytical method 12: $t_R$=0.87 min.; $[M+H]^+$=902.7

Step 5. (2S,5S,8S,13S,16R)-2-amino-16-benzyl-8-(4-chlorobenzyl)-5-(methoxymethyl)-7,14-dimethyl-13-(4-((2-nitrophenyl)sulfonamido)butyl)-3,6,10,15-tetraoxo-4,7,11,14-tetraazaoctadecan-18-oic acid (456 mg, 0.5 mmol) and 4-chloro-2-(4-(1-methyl-2-(pyrrolidin-1-ylmethyl)-1H-imidazol-5-yl)phenoxy)benzaldehyde (int-F2) (238 mg, 0.6 mmol) were dissolved in DCM (30 mL) and AcOH (0.114 mL, 2 mmol), and the resulting solution was stirred for 1.5 h at rt. $NaBH(OAc)_3$ (530 mg, 2.5 mmol) was then added and the reaction mixture was stirred for 18 h at rt. MeOH (2 mL) was added and the reaction mixture was concentrated to dryness in vacuo. The crude product was purified by preparative reverse-phase HPLC (eluent A: 0.1% TFA in $H_2O$ and eluent B: ACN). The pure fractions were combined and lyophilized to afford (3S,6S,9S,14S,17R)-17-benzyl-1-(4-chloro-2-(4-(1-methyl-2-(pyrrolidin-1-ylmethyl)-1H-imidazol-5-yl)phenoxy)phenyl)-9-(4-chlorobenzyl)-6-(methoxymethyl)-3,8,15-trimethyl-14-(4-((2-nitrophenyl)sulfonamido)butyl)-4,7,11,16-tetraoxo-2,5,8,12,15-pentaazanonadecan-19-oic acid. Analytical method 9: $t_R$=4.05 min.; $[M+H]^+$=1281.5

Step 6. To a solution of (3S,6S,9S,14S,17R)-17-benzyl-1-(4-chloro-2-(4-(1-methyl-2-(pyrrolidin-1-ylmethyl)-1H-imidazol-5-yl)phenoxy)phenyl)-9-(4-chlorobenzyl)-6-(methoxymethyl)-3,8,15-trimethyl-14-(4-((2-nitrophenyl)sulfonamido)butyl)-4,7,11,16-tetraoxo-2,5,8,12,15-pentaazanonadecan-19-oic acid (440 mg, 271 μmol), HATU (412 mg, 1.083 mmol) and HOAt (55.3 mg, 0.406 mmol) in DCM (100 mL) was added 2,6-lutidine (0.946 mL, 8.13 mmol) and the resulting mixture was stirred for 18.5 h at rt. The reaction mixture was concentrated to dryness in vacuo and the resulting residue was partitioned between EtOAc (100 mL) and 5% aq. $NaHCO_3$ (15 mL). The organic layer was washed with 5% aq. $NaHCO_3$ (3×15 mL) and brine (10 mL), dried over $Na_2SO_4$, filtered, and evaporated to dryness to afford N-(4-((2S,5S,8S,13S,16R)-16-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7,14-trimethyl-3,6,10,15,18-pentaoxo-1,4,7,11,14-pentaazacyclooctadecan-13-yl)butyl)-2-nitrobenzenesulfonamide (AB6). Analytical method 10: $t_R$=1.1 min; $[M+2H]^2$+=633.6.

Example 1-4: Synthesis of (4S,7S,10S,14R,16aS,20aS)-10-(2-aminoethyl)-14-benzyl-11-(4-chloro-2-(4-(2-((dimethylamino)methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone (C6)

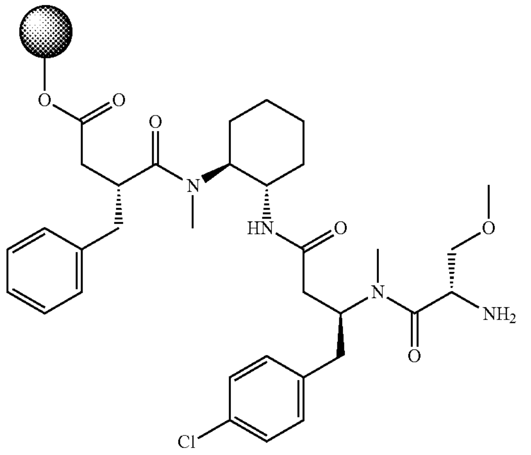

AB5

+

-continued
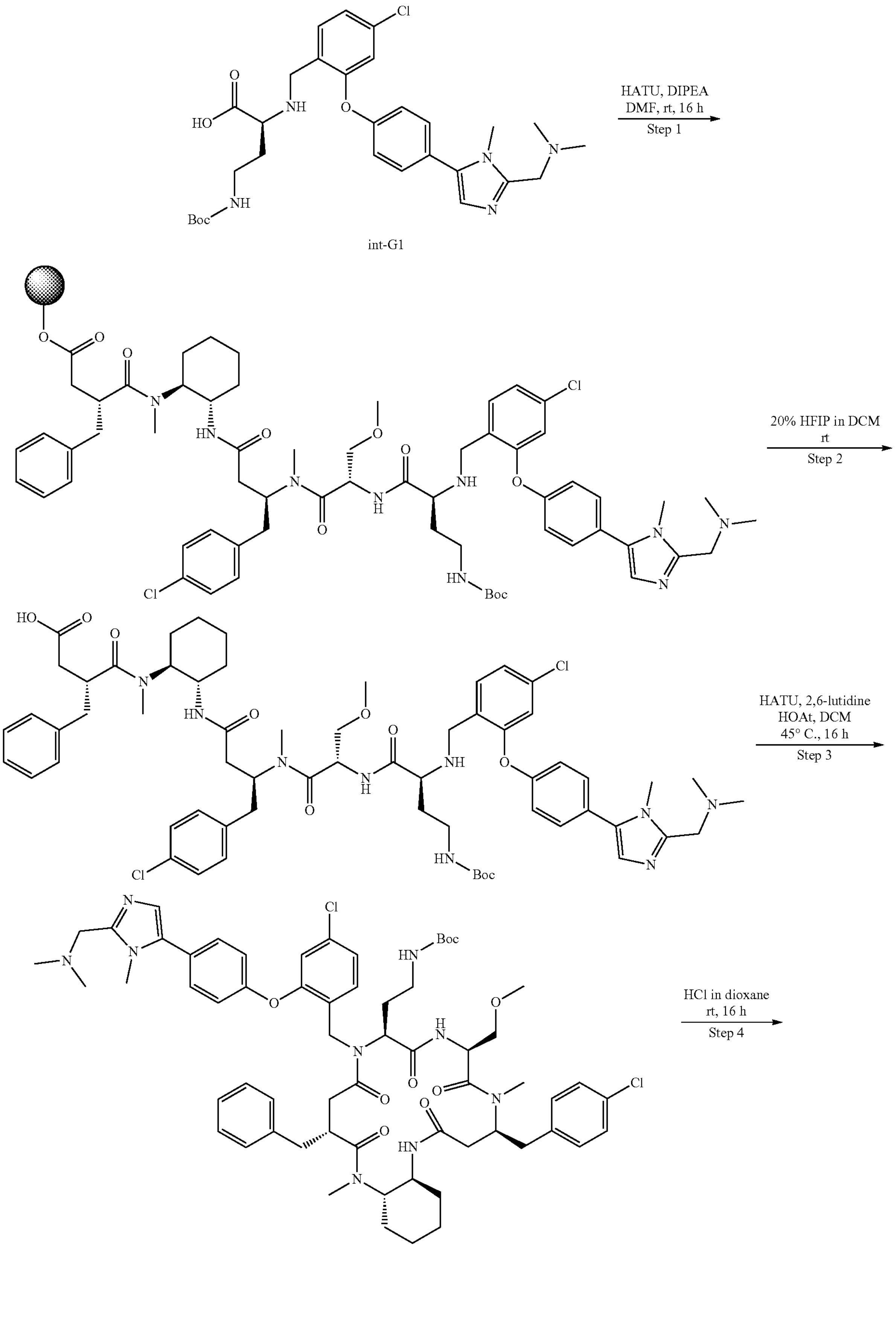

-continued

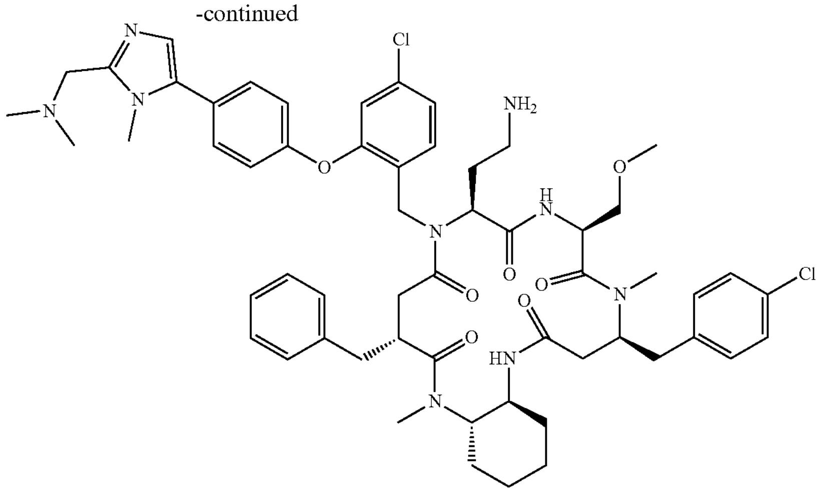

(C6)

Step 1. To (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1) (1.000 g, 1.680 mmol) in DMF (20 mL) was added DIPEA (0.587 mL, 3.36 mmol) followed by HATU (0.639 g, 1.680 mmol) and the resulting mixture was stirred until completely homogenous. This solution was then added to PS-(2-Chlorotrityl) (R)-4-(((1S,2S)-2-((S)-3-((S)-2-amino-3-methoxy-N-methylpropanamido)-4-(4-chlorophenyl)butanamido)cyclohexyl)(methyl)amino)-3-benzyl-4-oxobutanoate (AB5) (2.8 g, 0.840 mmol) in 10 mL of DMF in a shaker flask. The reaction mixture was allowed to shake o/n at rt. The resin was filtered, washed with DMF (3×) and DCM (3×), and dried under vacuum to give PS-2-chlorotrityl (R)-3-benzyl-4-(((1S,2S)-2-((8S,11S,14S)-8-((4-chloro-2-(4-(2-((dimethylamino)-methyl)-1-methyl-1H-imidazol-5-yl)phenoxy) benzyl)amino)-14-(4-chlorobenzyl)-11-(methoxymethyl)-2,2,13-trimethyl-4,9,12-trioxo-3-oxa-5,10,13-triazahexadecan-16-amido)cyclohexyl)(methyl)amino)-4-oxobutanoate which was taken onto the next step without purification.

Step 2. PS-2-chlorotrityl (R)-3-benzyl-4-(((1S,2S)-2-((8S,11S,14S)-8-((4-chloro-2-(4-(2-((dimethylamino)-methyl)-1-methyl-1H-imidazol-5-yl)phenoxy)benzyl) amino)-14-(4-chlorobenzyl)-11-(methoxymethyl)-2,2,13-trimethyl-4,9,12-trioxo-3-oxa-5,10,13-triazahexadecan-16-amido)cyclohexyl)(methyl)amino)-4-oxobutanoate (2.9 g, 0.87 mmol) was cleaved from the resin by shaking with 75 mL of 20% HFIP/DCM for 20 min at rt. The resin was filtered and the filtrate was collected. Both steps were repeated three more times to ensure all of the product was cleaved from the resin. The combined filtrates were concentrated to provide a crude oil (1.8 g) which was purified via reversed-phase chromatography (eluting with $MeCN/H_2O$ with 0.1% $NH_4OH$) to afford 1(R)-3-benzyl-4-(((1S,2S)-2-((8S,11S,14S)-8-((4-chloro-2-(4-(2-((dimethylamino) methyl)-1-methyl-1H-imidazol-5-yl)phenoxy)benzyl) amino)-14-(4-chlorobenzyl)-11-(methoxymethyl)-2,2,13-trimethyl-4,9,12-trioxo-3-oxa-5,10,13-triazahexadecan-16-amido)cyclohexyl)(methyl)amino)-4-oxobutanoic acid. Analytical method 7; $t_R$=1.77 min; $[M+H]^+$=1182.7.

Step 3. To (R)-3-benzyl-4-(((1S,2S)-2-((8S,11S,14S)-8-((4-chloro-2-(4-(2-((dimethylamino)methyl)-1-methyl-1H-imidazol-5-yl)phenoxy)benzyl)amino)-14-(4-chlorobenzyl)-11-(methoxymethyl)-2,2,13-trimethyl-4,9,12-trioxo-3-oxa-5,10,13-triazahexadecan-16-amido)cyclohexyl) (methyl)amino)-4-oxobutanoic acid (115 mg, 0.097 mmol) dissolved in DCM (100 mL) was added HATU (148 mg, 0.389 mmol), 2,6-lutidine (0.340 mL, 2.92 mmol) and HOAt (13.23 mg, 0.097 mmol) and the resulting mixture was stirred for overnight at 45° C. The reaction mixture was then concentrated to dryness and then partitioned between EtOAc (100 mL) and 5% aq. $NaHCO_q$(100 mL). The organic layer was washed with 5% aq. $NaHCO_3$ (2×50 mL) and brine (50 mL), dried over $Na_2SO_4$ filtered and concentrated to dryness via rotovap. The residue was then taken up in EtOAc and washed with 1 M HCl (×2). Brine was added to the combined 1 M HCl layers and back extracted with EtOAc (×2). The combined EtOAc layers were dried with sodium sulphate, filtered and concentrated in vacuo. The product was purified via reversed-phase chromatography (eluting with $MeCN/H_2O$, a gradient 20-65% with 0.1% $NH_4OH$) to afford tert-butyl (2-((4S,7S,10S,14R,16aS,20aS)-14-benzyl-11-(4-chloro-2-(4-(2-((dimethylamino)-methyl)-1-methyl-1H-imidazol-5-yl)phenoxy)benzyl)-4-(4-chlorobenzyl)-7-(methoxymethyl)-5,16-dimethyl-2,6,9,12,15-pentaoxodocosahydrobenzo[1][1,4,7,11,14] pentaazacyclooctadecin-10-yl)ethyl)carbamate trifluoroacetate. Analytical method 2; $t_R$=3.17 min; $[M+H]^+$=1163.6.

Step 4. To a solution of tert-butyl (2-((4S,7S,10S,14R,16aS,20aS)-14-benzyl-11-(4-chloro-2-(4-(2-((dimethylamino)-methyl)-1-methyl-1H-imidazol-5-yl)phenoxy)benzyl)-4-(4-chlorobenzyl)-7-(methoxymethyl)-5,16-dimethyl-2,6,9,12,15-pentaoxodocosahydrobenzo[1][1,4,7,11,14] pentaazacyclooctadecin-10-yl)ethyl)carbamate trifluoroacetate (40 mg, 0.034 mmol) in anhydrous dioxane (1.72 mL) at 0° C. was added HCl (4 M in dioxane) (0.67 mL, 2.40 mmol) dropwise. The reaction mixture turned cloudy. After 15 min the ice bath was removed and the mixture was then stirred at rt for 1 hr. The reaction mixture was then concentrated and the resulting residue was dried under vacuum. The crude material was dissolved in EtOAc and washed with sat. aq. sodium bicarbonate. The aq. layer was then extracted with fresh EtOAc. The combined organics were dried over sodium sulfate, filtered, and concentrated in vacuo to yield (4S,7S,10S,14R,16aS,20aS)-10-(2-aminoethyl)-14-benzyl-11-(4-chloro-2-(4-(2-((dimethylamino) methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14] pentaazacyclooctadecine-2,6,9,12,15 (3H)-pentaone (C6). Analytical method 7; $t_R$=2.36 min; $[M+H]^+$=1063.7.

Example 1-5: Synthesis of (2S,5S,8S,13S,16R)-2-(3-aminopropyl)-16-benzyl-1-(4-chloro-2-(4-(2-((dimethylamino)methyl)-1-methyl-1H-imidazol-5-yl)phenoxy)benzyl)-8-(4-chlorobenzyl)-5-(methoxymethyl)-7,13,14-trimethyl-1,4,7,11,14-pentaazacyclooctadecane-3,6,10,15,18-pentaone (C7)

(C7)

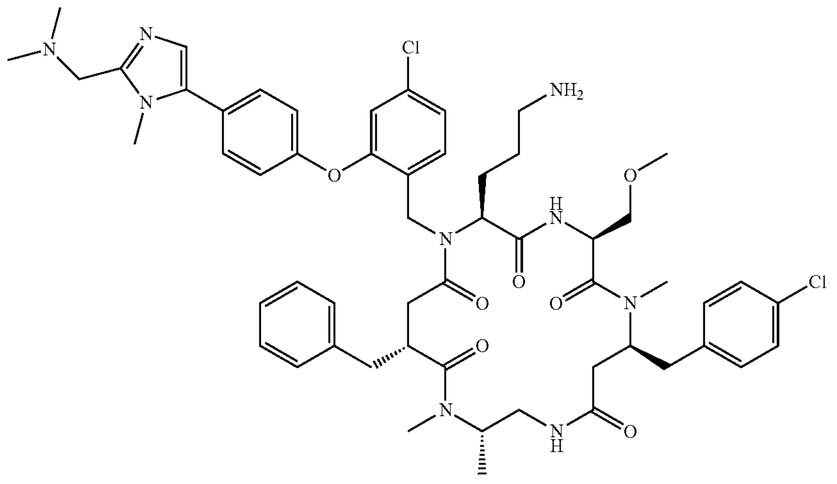

(2S,5S,8S,13S,16R)-2-(3-aminopropyl)-16-benzyl-1-(4-chloro-2-(4-(2-((dimethylamino)methyl)-1-methyl-1H-imidazol-5-yl)phenoxy)benzyl)-8-(4-chlorobenzyl)-5-(methoxymethyl)-7,13,14-trimethyl-1,4,7,11,14-pentaazacyclooctadecane-3,6,10,15,18-pentaone (C7) was obtained using a method similar to the procedure used in the synthesis of (4S,7S,10S,14R,16aS,20aS)-10-(2-aminoethyl)-14-benzyl-11-(4-chloro-2-(4-(2-((dimethylamino) methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14] pentaazacyclooctadecine-2,6,9,12,15 (3H)-pentaone (C6), except PS-(2-Chlorotrityl) (R)-4-(((1S,2S)-2-((S)-3-((S)-2-amino-3-methoxy-N-methylpropanamido)-4-(4-chlorophenyl)butanamido)cyclohexyl)(methyl)amino)-3-benzyl-4-oxobutanoate (AB5) was replaced with PS-(2-Chlorotrityl) (4S,7S,12S,15R)-4-amino-15-benzyl-7-(4-chlorobenzyl)-6,12,13-trimethyl-5,9,14-trioxo-2-oxa-6,10,13-triazaheptadecan-17-oate (AB4) and (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1) was replaced with (S)-5-((tert-butoxycarbonyl) amino)-2-((4-chloro-2-(4-(2-((dimethylamino)methyl)-1-methyl-1H-imidazol-5-yl)phenoxy)benzyl)amino)pentanoic acid (int-G2). Analytical method 7; $t_R$=1.18 min; $[M+H]^+$=1038.4.

Example 1-6: Synthesis of (4S,7S,10S,14R,16aS, 20aS)-10-(3-aminopropyl)-14-benzyl-11-(4-chloro-2-(4-(1-methyl-2-(pyrrolidin-1-ylmethyl)-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone (C8)

(C8)

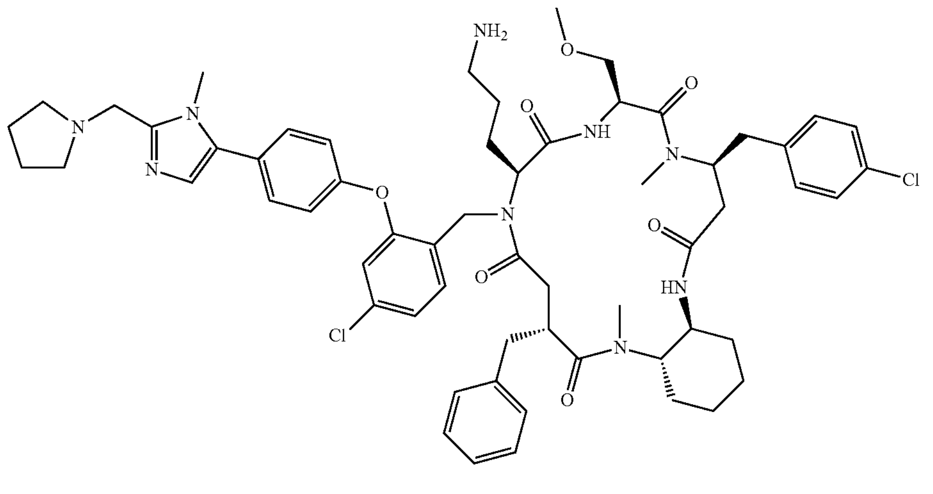

(4S,7S,10S,14R,16aS,20aS)-10-(3-aminopropyl)-14-benzyl-11-(4-chloro-2-(4-(1-methyl-2-(pyrrolidin-1-ylmethyl)-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone (C8) was obtained using a method similar to the procedure used in the synthesis of (4S,7S,10S,14R,16aS,20aS)-10-(2-aminoethyl)-14-benzyl-11-(4-chloro-2-(4-(2-((dimethylamino)methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone ($C_6$), except (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1) was replaced with (S)-5-((tert-butoxycarbonyl)amino)-2-((4-chloro-2-(4-(1-methyl-2-(pyrrolidin-1-ylmethyl)-1H-imidazol-5-yl)phenoxy)benzyl)amino)pentanoic acid (int-G3). Analytical method 7; $t_R$=1.35 min; $[M+H]^+$=1102.2.

Example 1-7: Synthesis of (4S,7S,10S,14R,16aS, 20aS)-10-(3-aminopropyl)-14-benzyl-11-(4-chloro-2-(4-(2-((dimethylamino)methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone (C9)

(C9)

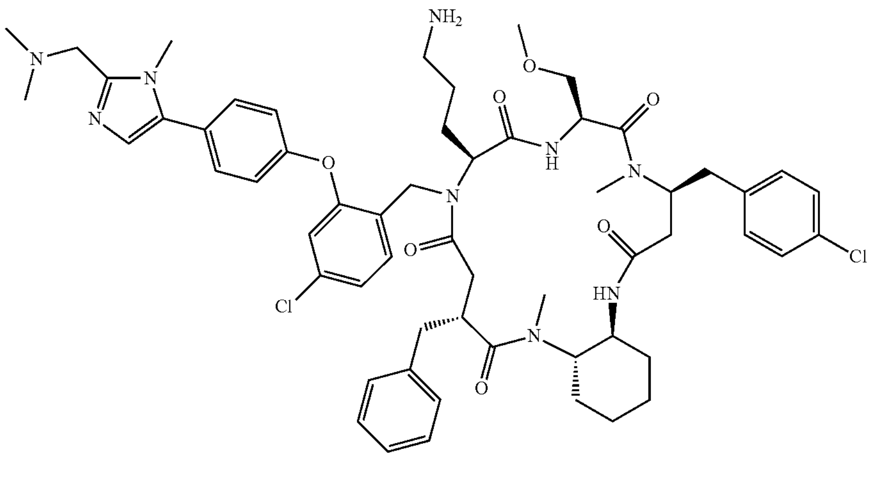

((4S,7S,10S,14R,16aS,20aS)-10-(3-aminopropyl)-14-benzyl-11-(4-chloro-2-(4-(2-((dimethylamino)methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone (C9) was obtained using a method similar to the procedure used in the synthesis of (4S,7S,10S,14R,16aS,20aS)-10-(2-aminoethyl)-14-benzyl-11-(4-chloro-2-(4-(2-((dimethylamino)methyl)-1-methyl-1H-imidazol-5-yl)phenoxy)benzyl)-4-(4-chlorobenzyl)-7-(methoxymethyl)-5,16-dimethylhexadecahydrobenzo[1][1,4,7,11,14]pentaazacyclooctadecine-2,6,9,12,15 (3H)-pentaone (C6), except (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1) was replaced with (S)-5-((tert-butoxycarbonyl)amino)-2-((4-chloro-2-(4-(2-((dimethylamino)methyl)-1-methyl-1H-imidazol-5-yl)phenoxy)benzyl)amino)pentanoic acid (int-G2). Analytical method 7; $t_R$=1.23 min; $[M+H]^+$=1078.7.

Example 1-8: Synthesis of (2S,5S,8S,13S,16R)-13-(4-aminobutyl)-16-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7,14-trimethyl-1,4,7,11,14-pentaazacyclooctadecane-3,6,10,15,18-pentaone trifluoroacetate (C10)

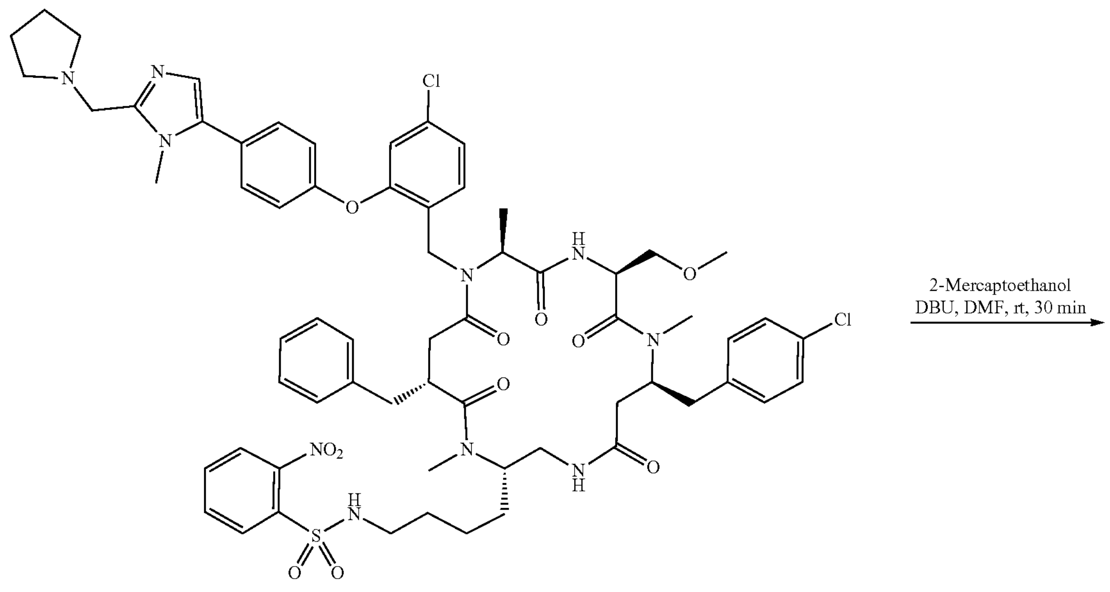

AB6

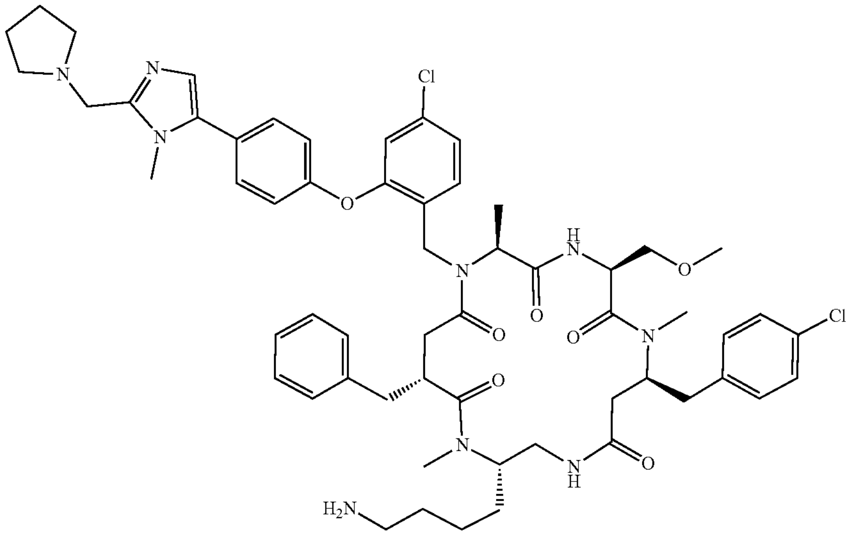

(C10)

To a solution of N-(4-((2S,5S,8S,13S,16R)-16-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7,14-trimethyl-3,6,10,15,18-pentaoxo-1,4,7,11,14-pentaazacyclooctadecan-13-yl)butyl)-2-nitrobenzenesulfonamide (AB6) (532 mg, 0.271 mmol, 64.5%) in DMF (15 mL) was added 2-mercaptoethanol (0.115 mL, 1.628 mmol) and DBU (0.082 mL, 0.543 mmol) and the resulting mixture was stirred for 30 min at rt, then quenched by the addition of AcOH (0.4 mL), and concentrated to dryness in vacuo. The crude product was purified by preparative reversed-phase HPLC (eluent A: 0.1% TFA in $H_2O$ and eluent B: ACN). Pure fractions were combined and lyophilized to afford (2S,5S,8S,13S,16R)-13-(4-aminobutyl)-16-benzyl-1-(4-chloro-2-(4-(1-methyl-2-(pyrrolidin-1-ylmethyl)-1H-imidazol-5-yl)phenoxy)benzyl)-8-(4-chlorobenzyl)-5-(methoxymethyl)-2,7,14-trimethyl-1,4,7,11,14-pentaazacyclooctadecane-3,6,10,15,18-pentaone trifluoroacetate (C10). Analytical method 9; $t_R$=3.85 min; $[M+H]^+$=1078.5.

Example 1-9: Synthesis of (3R,7S,10S,13R)-7-(2-aminoethyl)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-1,6,9,12-tetraazabicyclo[11.3.1]heptadecane-2,5,8,11-tetraone (C11)

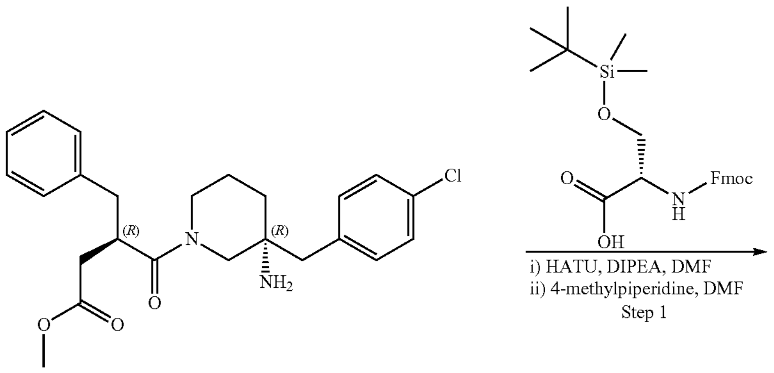

int-F3

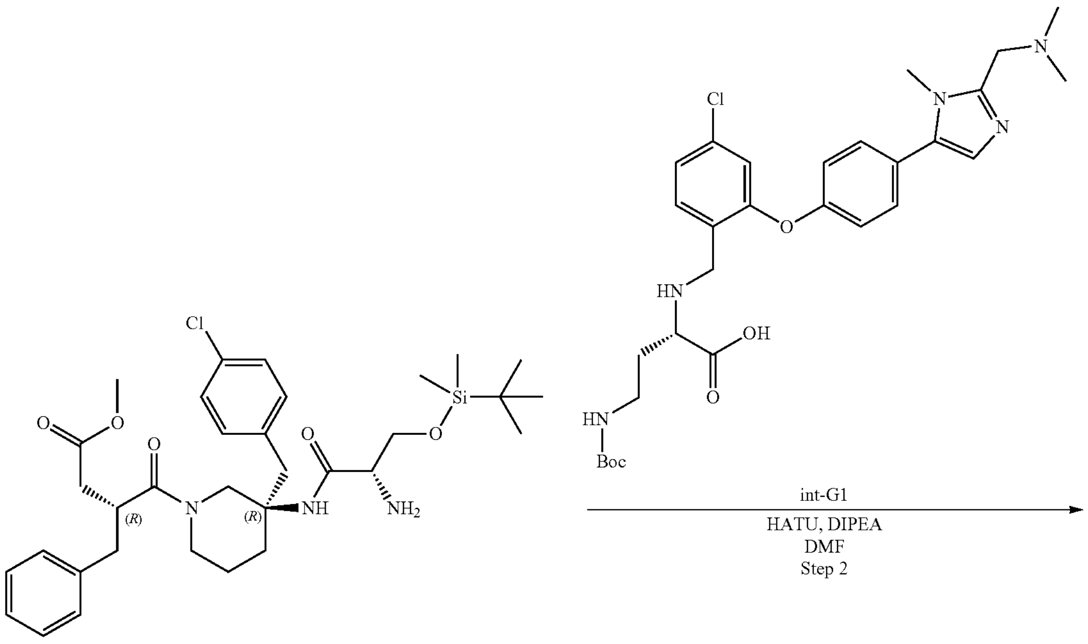

-continued
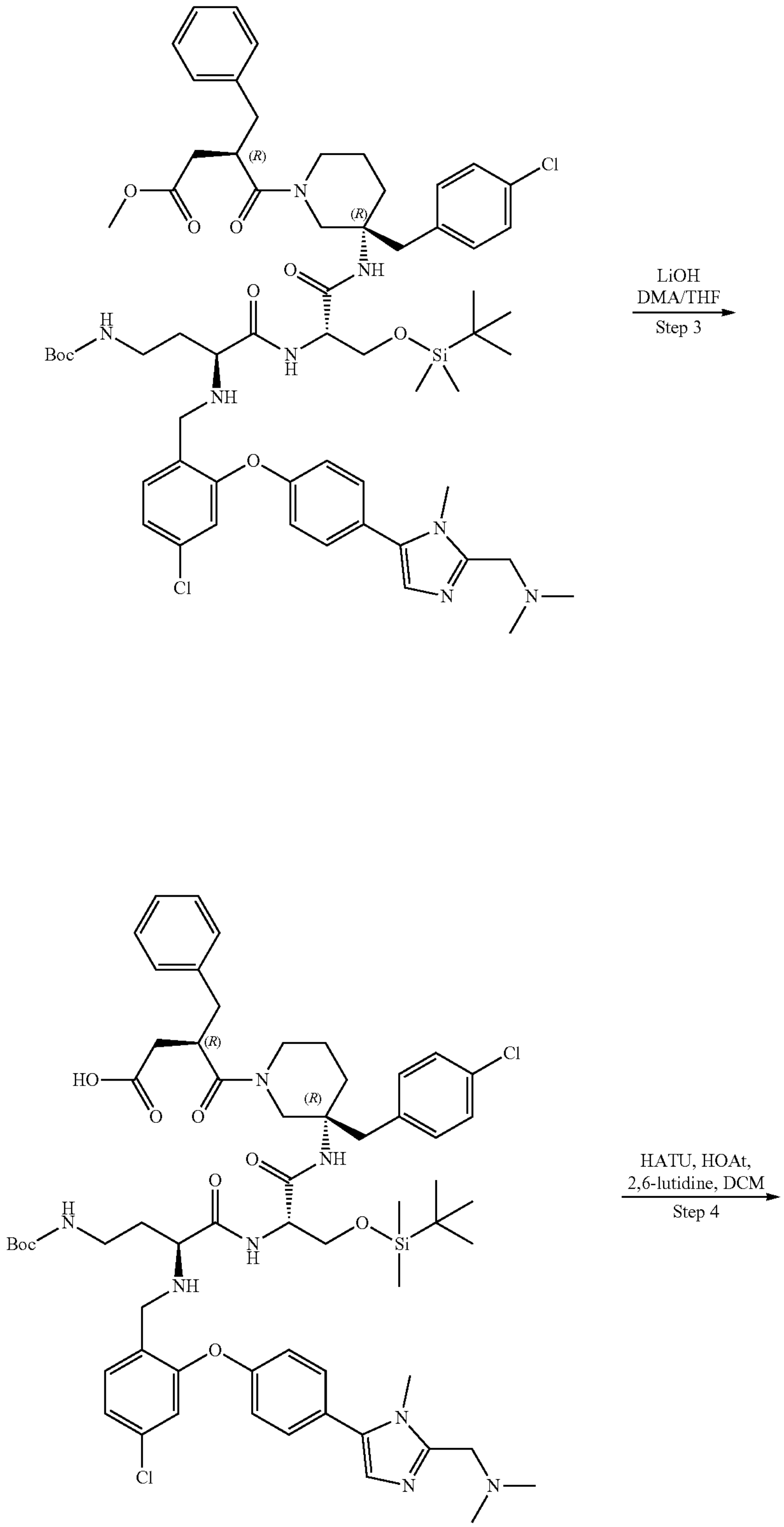

-continued
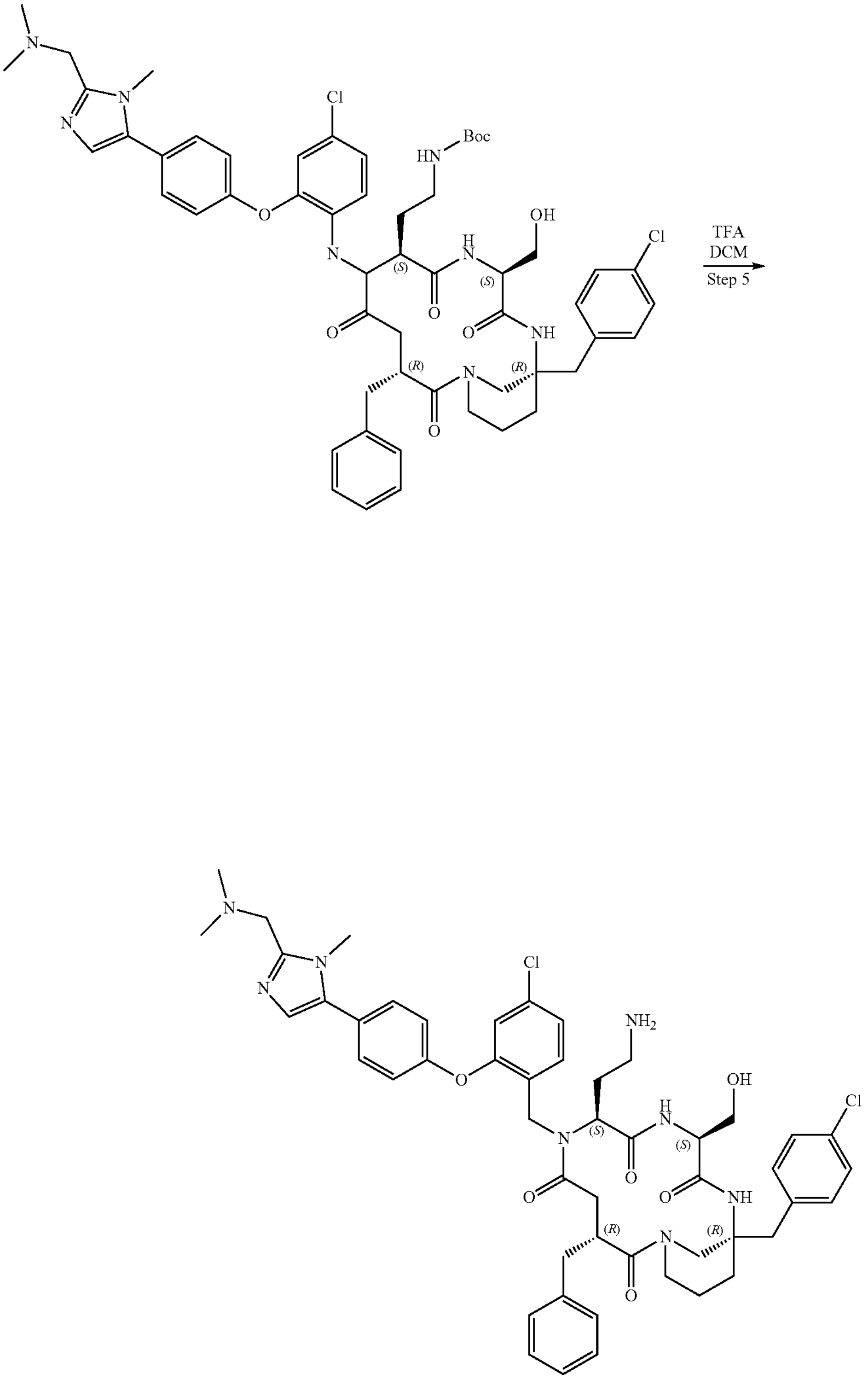
(C11)

Step 1: To a solution of Fmoc-Ser($OtBMe_2Si$)OH (548 mg, 1.242 mmol) in DMA (5 ml) was added HATU (455 mg, 1.197 mmol) and DIPEA (0.789 mL, 4.52 mmol). The resulting mixture was stirred for 2 mmn at room temperature and then added to a solution of methyl (R)-4-((R)-3-amino-3-(4-chlorobenzyl)piperidin-1-yl)-3-benzyl-4-oxobutanoate (int-F3) (484 mg, 1.129 mmol) in DMA (3 mL. The reaction mixture was stirred at room temperature for 6 h. Additional Fmoc-Ser($OtBMe_2Si$)OH (88 mg, 0.200 mmol) and HATU (76 mg, 0.20 mmol) were added and stirring was continued overnight at room temperature. 4-methylpiperidine (0.8 mL, 6.77 mmol) was added and stirring was continued for 30 min. at room temperature. The reaction mixture was concentrated under reduced pressure (bath temperature 50° C.) and the residue was purified by reverse flash column chromatography (eluting with 5-90% water/ACN with 0.1% $NH_4OH$) to afford methyl (R)-4-((R)-3-((S)-2-amino-3-((tert-butyldimethylsilyl)oxy)propanamido)-3-(4-chlorobenzyl)piperidin-1-yl)-3-benzyl-4-oxobutanoate. Analytical method 7, $t_R$=1.41 min, $[M+H]^+$=630.5.

Step 2: To a solution of (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1) (449 mg, 0.785 mmol) and methyl (R)-4-((R)-3-((S)-2-amino-3-((tert-butyldimethylsilyl)oxy)propanamido)-3-(4-chlorobenzyl)piperidin-1-yl)-3-benzyl-4-oxobutanoate (450 mg, 0.714 mmol) in DMA (5 mL) was added DIPEA (0.374 mL, 2.142 mmol). The resulting solution was stirred for 2 min at room temperature and then a solution of HATU (299 mg, 0.785 mmol) in DMA (3 mL) was added. The reaction mixture was stirred at room temperature for 3 h. Additional (S)-4-((tert-butoxycarbonyl)amino)-2-((4-chloro-2-(4-(2-((dimethylamino)methyl)-1-methyl-1H-imidazol-5-yl)phenoxy)benzyl)amino)butanoic acid (int-G1) (88 mg, 0.14 mmol) and HATU (76 mg, 0.20 mmol) were added and stirring was continued at room temperature overnight. The resulting mixture was concentrated under reduced pressure and the residue was purified by flash column chromatography (eluting with 98/2 to 85/15 DCM/MeOH with 0.3% triethylamine) to afford methyl (R)-3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-((tert-butyldimethylsilyl)oxy)propanamido)-3-(4-chlorobenzyl)piperidin-1-yl)-4-oxobutanoate. Analytical method 7, $t_R$=1.55 min, $[M+H]^+$=1184.1.

Step 3: To a solution of methyl (R)-3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-((tert-butyldimethylsilyl)oxy)propanamido)-3-(4-chlorobenzyl)piperidin-1-yl)-4-oxobutanoate (770 mg, 0.65 mmol) in DMA (5 mL) was added water (1 mL) and THF (4 mL). The resulting mixture was stirred at room temperature and then a solution of LiOH (1.300 mL, 1.300 mmol) was added. The reaction mixture was stirred at room temperature for 3 h. Additional LiOH (1.300 mL, 1.300 mmol) was added and stirring was continued at room temperature overnight (LCMS indicated a mixture of desire product as well as the de-silyl alcohol R═H). The reaction mixture was cooled in an ice bath, the pH was neutralized (pH=7) by the addition of 1 N HCl, and then concentrated under reduced pressure (bath maintained at 30° C.). The residue was taken up in 250 mL of EtOAc. The organic phase was washed with water and brine, dried over $Na_2SO_4$, filtered, and concentrated to afford (R)-3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-((tert-butyldimethylsilyl)oxy)propanamido)-3-(4-chlorobenzyl)piperidin-1-yl)-4-oxobutanoic acid. Analytical method 5, $t_R$=1.97 min, $[M+H]^+$=1055.1.

Step 4: To a 1 L round bottom flask containing a solution of (R)-3-benzyl-4-((R)-3-((S)-2-((S)-4-((tert-butoxycarbonyl)amino)-2-((4-chloro-2-(4-(2-((dimethylamino)methyl)-1-methyl-1H-imidazol-5-yl)phenoxy)benzyl)amino)butanamido)-3-((tert-butyldimethylsilyl)oxy)propanamido)-3-(4-chlorobenzyl)piperidin-1-yl)-4-oxobutanoic acid (770 mg, 0.658 mmol) in DCM (700 mL) was added 2,6-lutidine (2.3 mL, 19.74 mmol), HOAt (107 mg, 0.790 mmol) and HATU (1001 mg, 2.63 mmol). The resulting mixture was stirred for 16 hr at 38° C. The reaction mixture was then concentrated to dryness under reduced pressure and the residue was partitioned between EtOAc (400 mL) and 5% aq. $NaHCO_3$ (30 mL). The organic phase was washed with 5% aq. $NaHCO_3$ (2×25 mL) and brine (30 mL), dried over $Na_2SO_4$, filtered, and concentrated. The crude material was purified by reverse flash column chromatography (eluting with 5-60% water/AcN with 0.1% trifluoroacetic acid) to afford tert-butyl (2-((3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-2,5,8,11-tetraoxo-1,6,9,12-tetraazabicyclo[11.3.1]heptadecan-7-yl)ethyl)carbamate. Analytical method 2, $t_R$=3.22 min, $[M+H]^+$=1039.4).

Step 5: To a round bottom flask containing tert-butyl (2-((3R,7S,10S,13R)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-2,5,8,11-tetraoxo-1,6,9,12-tetraazabicyclo[11.3.1]heptadecan-7-yl)ethyl)carbamate (320 mg, 0.308 mmol) in anhydrous dioxane (6 mL) and cooled in an ice bath was added 4.0 N hydrogen chloride in dioxane (2 mL, 8.00 mmol). The ice bath was then removed and the resulting mixture was stirred overnight at room temperature. The reaction mixture was concentrated under reduced pressure to afford an off-white solid which was purified by reverse flash column chromatography (eluting with 5-50% water/ACN with 0.1% trifluoroacetic acid) to afford (3R,7S,10S,13R)-7-(2-aminoethyl)-3-benzyl-6-(4-chloro-2-(4-(2-((dimethylamino)methyl)-1-methyl-1H-imidazol-5-yl)phenoxy)benzyl)-13-(4-chlorobenzyl)-10-(hydroxymethyl)-1,6,9,12-tetraazabicyclo[11.3.1]heptadecane-2,5,8,11-tetraone ($C_{11}$). Analytical method 3, $t_R$=1.23 min., $[M+H]^+$=937.6.

Example 2: Synthesis of FHR3 receptor ligands Compounds (C12) to (C16)
Example 2-1: Synthesis of 2-((3S,6S,9R,15S,18S,21S,24S,27S,30S,33S,39S,42S,50aS)-3,30-bis(2-amino-2-oxoethyl)-9-((2-amino-2-oxoethyl)carbamoyl)-27-(4-aminobutyl)-6,15,21-tribenzyl-18,39-bis(3-guanidinopropyl)-33-(4-hydroxybenzyl)-24-(hydroxymethyl)-5,20,35-trimethyl-1,4,7,13,16,19,22,25,28,31,34,37,40,43-tetradecaoxo-1,3,4,5,6,7,8,9,10,12,13,14,15,16,17,18,19,20,21,22,23,24,25,26,27,28,29,30, 31,32,33,34,35,36,37,38,39,40,41,42,43,45,50,50a-tetratetracontahydro-2H-[1]thia[4,7,10,13,16,19,22,25,28,31,34,37,40,43]tetradecaazacyclopentatetracontino[13,12-b]isoquinolin-42-yl)acetic acid (C12)
(C12)
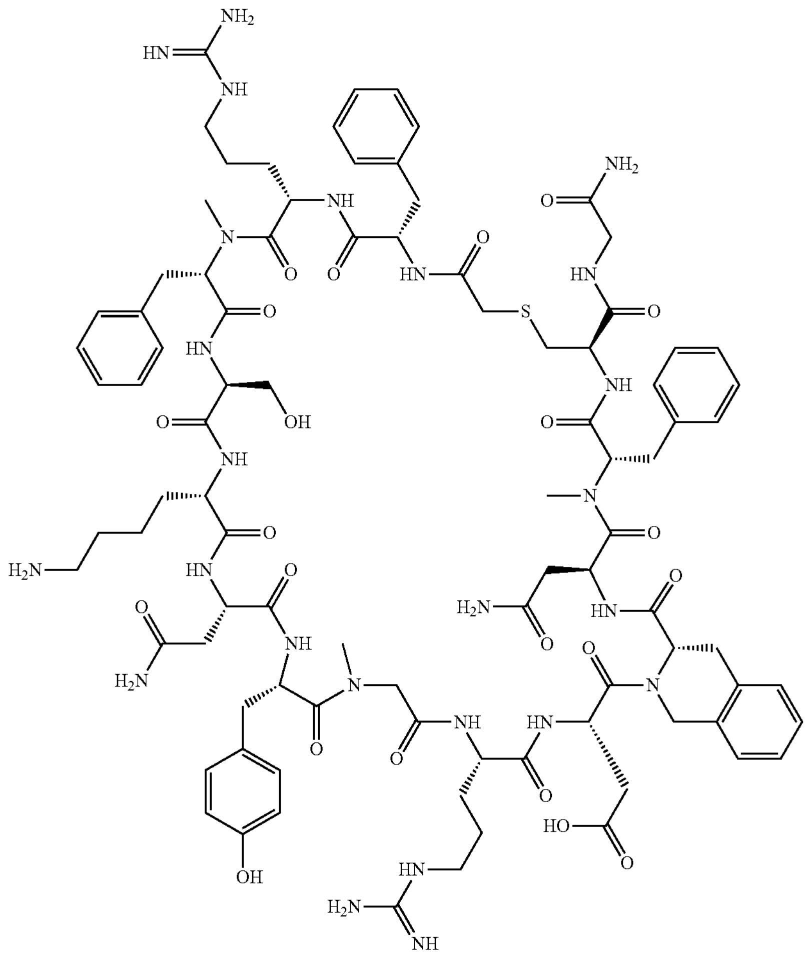

Note: Compound (C12) has the following amino acid sequence:

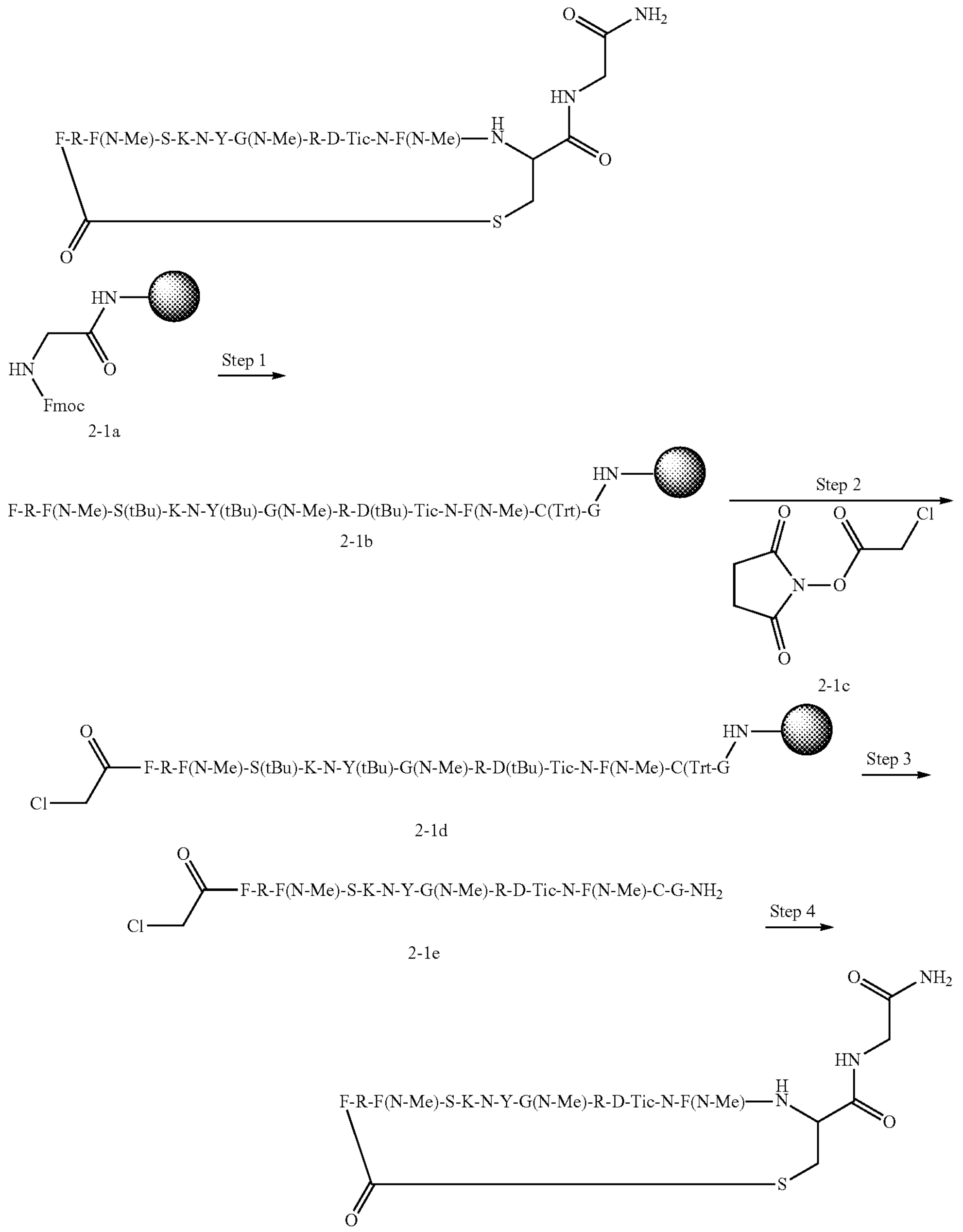

2-1a 2-1b 2-1c 2-1d 2-1e (C12)

Step 1: F-R-F(N-Me)-S(tBu)-K-N-Y(tBu)-G(N-Me)-R-D(tBu)-Tic-N-F(N-Me)-C(Trt)-G-NHresin (1-1 b)

The peptide sequence 2-1b was synthesized on Fmoc-Gly-RAM TentaGel™ Resin (2-1a, 0.22 mmol/g loading, 0.25 mmol scale) on a Liberty® Peptide Synthesizer following general peptide Synthesis Cycle A-1 (Fmoc-amino acid (4 eq.; 0.2 M solution in DMF), HATU (4 eq.; 0.5 M solution in DMF) and DIPEA (4.4 eq.; 2 M solution in NMP)). The resin was then filtered and washed with DMF (2×) and DCM (3×) to provide the desired product 2-1b.

Step 2: $ClCH_2C(=O)$—F-R-F(N-Me)-S(tBu)-K-N-Y(tBu)-G(N-Me)-R-D(tBu)-Tic-N-F(N-Me)-C(Trt)-G-NHresin (1-1d)

A solution of N-succinimidyl 2-chloroacetate (2-1c, 287 mg, 1.5 mmol) in NMP (8 mL) was added to the peptide resin 2-1b from Step 1 (0.25 mmol) and the resulting mixture was shaken at room temperature overnight. The resin was then drained, washed with DMF (3×) and DCM (4×), and dried to provide the desired product 2-1d.

Step 3: $ClCH_2C(O)$—F-R-F(N-Me)-S—K-N-Y-G (N-Me)-R-D-Tic-N-F(N-Me)-C-G-$NH_2$ (1-1e)

The peptide resin product 2-1d from Step 2 was cleaved from the resin and simultaneously deprotected using Cleavage Method 1 described herein above to provide the crude peptide 2-1e.

Step 4: 2-((3S,6S,9R,15S,18S,21S,24S,27S,30S, 33S,39S,42S,50aS)-3,30-bis(2-amino-2-oxoethyl)-9-((2-amino-2-oxoethyl)carbamoyl)-27-(4-aminobutyl)-6,15,21-tribenzyl-18,39-bis(3-guanidinopropyl)-33-(4-hydroxybenzyl)-24-(hydroxymethyl)-5,20,35-trimethyl-1,4,7,13,16,19, 22,25,28,31,34,37,40,43-tetradecaoxo-1,3,4,5,6,7,8, 9,10,12,13,14,15,16,17,18,19,20,21,22,23,24,25,26, 27,28,29,30,31,32, 33,34,35,36,37,38,39,40,41,42, 43,45,50,50a-tetratetracontahydro-2H-[1]thia[4,7,10, 13,16,19,22,25,28,31,34,37,40,43] tetradecaazacyclopentatetracontino[13,12-b] isoquinolin-42-yl)acetic acid (C12)

The crude peptide 1-2e from Step 3 (266 mg) was dissolved in DMSO (20.5 mL). A few drops of TEA were added to get to pH 8-9. The resulting mixture was stirred at rt overnight. The reaction mixture was then concentrated down to a few mL of DMSO on a centrifugal evaporator. The crude cyclic peptide was purified by preparative HPLC (Sunfire™ Prep C18 Column, 130 Å, 5 μm, 30×50 mm, 15-40% in 6 min, 75 mL/min, ACN in water with 0.1% TFA) and then lyophilized to provide the title cyclic peptide compound (C12) (SEQ ID NO: 5). Analytical method 9: $t_R$=3.24, m+1=1951.20

Example 2-2: Synthesis of 2-((3S,6S,9R,15S,18S, 21S,24S,27S,30S,33S,36S,39S,44aS)-30-((1H-imidazol-5-yl)methyl)-33-((1H-indol-3-yl)methyl)-9-((2-amino-2-oxoethyl)carbamoyl)-18-(4-aminobutyl)-15-benzyl-6,39-bis(3-guanidinopropyl)-24-(hydroxymethyl)-27-isobutyl-20,21,35,36-tetramethyl-1,4,7,13,16,19,22,25,28,31,34,37,40-tridecaoxodotetracontahydro-12H-pyrrolo[1,2-e1][1] thia[4,7,10,13,16,19,22,25,28,31,34,37,40] tridecaazacyclodotetracontin-3-yl)acetic acid (C13)

(C13)

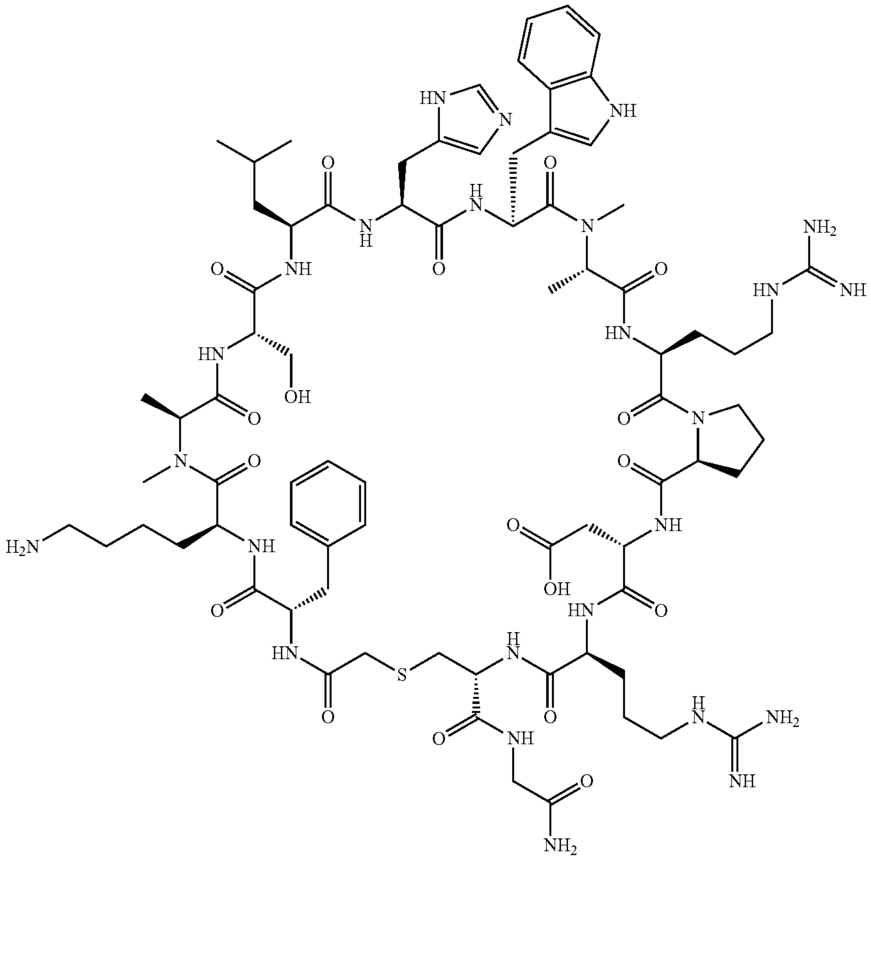

Note: Compound (C13) has the following amino acid sequence:

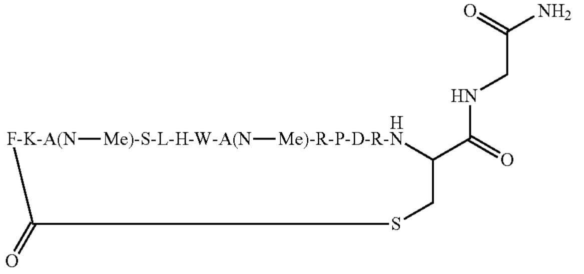

Cyclic peptide compound (C13) (SEQ ID NO: 6) was obtained using an analogous method as described in Example 2-1, however in step 1 the peptide sequence attached to the resin

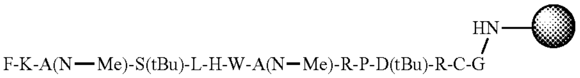

was synthesized instead of peptide sequence 2-4b. Analytical method 9: $t_R$=3.01, m+1=1710.98

Example 2-3: Synthesis of 2-((3S,6S,9R,15S,18S,21S,24S,27S,30S,33S,36S,39S,42S,50aS)-3,30-bis(2-amino-2-oxoethyl)-9-((2-amino-2-oxoethyl)carbamoyl)-36-(4-aminobutyl)-6,15,21-tribenzyl-18,39-bis(3-guanidinopropyl)-33-(4-hydroxybenzyl)-24-(hydroxymethyl)-27-isopropyl-5,20-dimethyl-1,4,7,13,16,19,22,25,28,31,34,37,40,43-tetradecaoxo-1,3,4,5,6,7,8,9,10,12,13,14,15,16,17,18,19,20,21,22,23,24,25,26,27,28,29,30, 31,32,33,34,35,36,37,38,39,40,41,42,43,45,50,50a-tetratetracontahydro-2H-[1]thia[4,7,10,13,16,19,22,25,28,31,34,37,40,43]tetradecaazacyclopentatetracontino[13,12-b]isoquinolin-42-yl)acetic acid (C14)

(14)

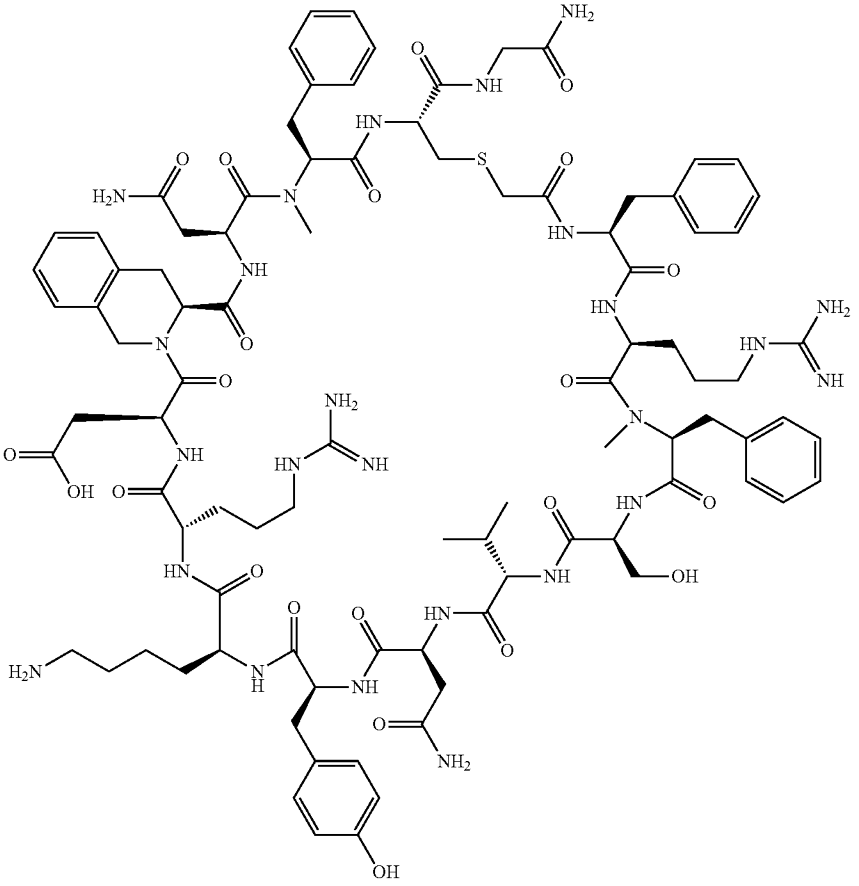

Note: Compound (C14) has the following amino acid sequence:
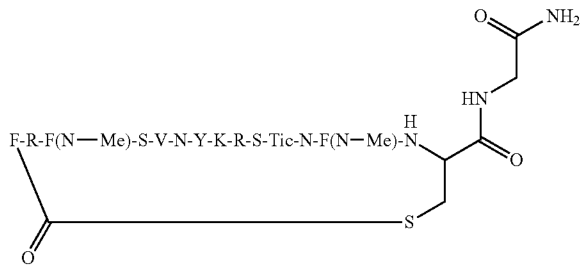
Cyclic peptide compound (C14) (SEQ ID NO: 7) was obtained using an analogous method as described in Example 2-1, however in step 1 the peptide sequence attached to the resin
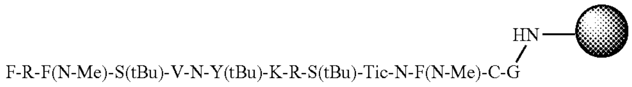
was synthesized instead of peptide sequence 2-4b. Analytical method 9: $t_R$=3.35, m+1=1979.25

Example 2-4: Synthesis of 2-((3R,6S,9S,12S,15S,18S,21S,24S,27S,30S,33S,36S,39S)-24-((1H-imidazol-5-yl)methyl)-21-((1H-indol-3-yl)methyl)-3-((2-amino-2-oxoethyl)carbamoyl)-12-(4-aminobutyl)-36,39-dibenzyl-6,15-bis(3-guanidinopropyl)-30-(hydroxymethyl)-27-isobutyl-18,19,33,34,37-pentamethyl-5,8,11,14,17,20,23,26,29,32,35,38,41-tridecaoxo-1-thia-4,7,10,13,16,19,22,25,28,31,34,37,40-tridecaazacyclodotetracontan-9-yl)acetic acid (C15)

(C15)

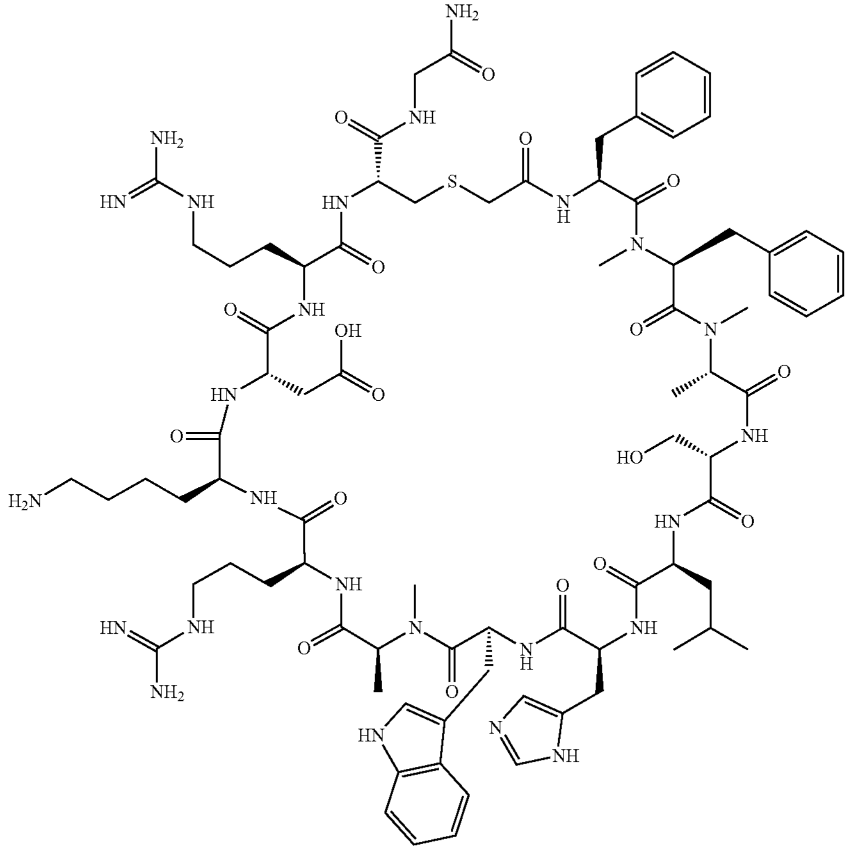

Note: Compound (C15) has the following amino acid sequence:

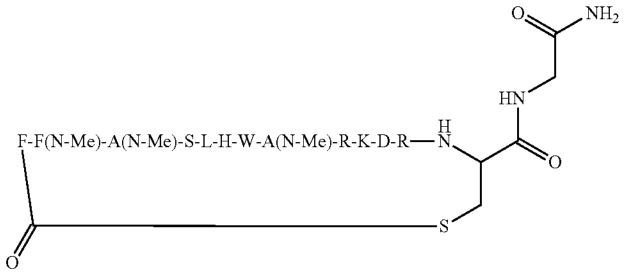

Cyclic peptide compound (C15) (SEQ ID NO: 8) was obtained using an analogous method as described in Example 2-1, however in step 1 the peptide sequence attached to the resin

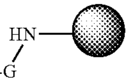

F-F(N-Me)-A(N-Me)-S(tBu)-L-H-W-A(N-Me)-R-K-D(tBu)-R-C-G was synthesized instead of peptide sequence 2-4b. Analytical method 9: $t_R$=3.35, m+1=1775.07

Example 2-5: Synthesis of 2,2'-((3S,6S,9R,15S,18S,21S,24S,27S,30S,33S,39S,42S,50aS)-9-((2-amino-2-oxoethyl)carbamoyl)-42-(4-aminobutyl)-6,15,21-tribenzyl-18,39-bis(3-guanidinopropyl)-33-(4-hydroxybenzyl)-24-(hydroxymethyl)-27-isopropyl-5,20,35-trimethyl-1,4,7,13,16,19,22,25,28,31,34,37,40,43-tetradecaoxo-1,3,4,5,6,7,8,9,10,12,13,14,15,16,17,18,19,20,21,22,23,24,25,26,27,28,29,30, 31,32,33,34,35,36,37,38,39,40,41,42,43,45,50,50a-tetratetracontahydro-2H-[1]thia[4,7,10,13,16,19,22,25,28,31,34,37,40,43]tetradecaazacyclopentatetracontino[13,12-b]isoquinoline-3,30-diyl)diacetamide (C16)

(C16)

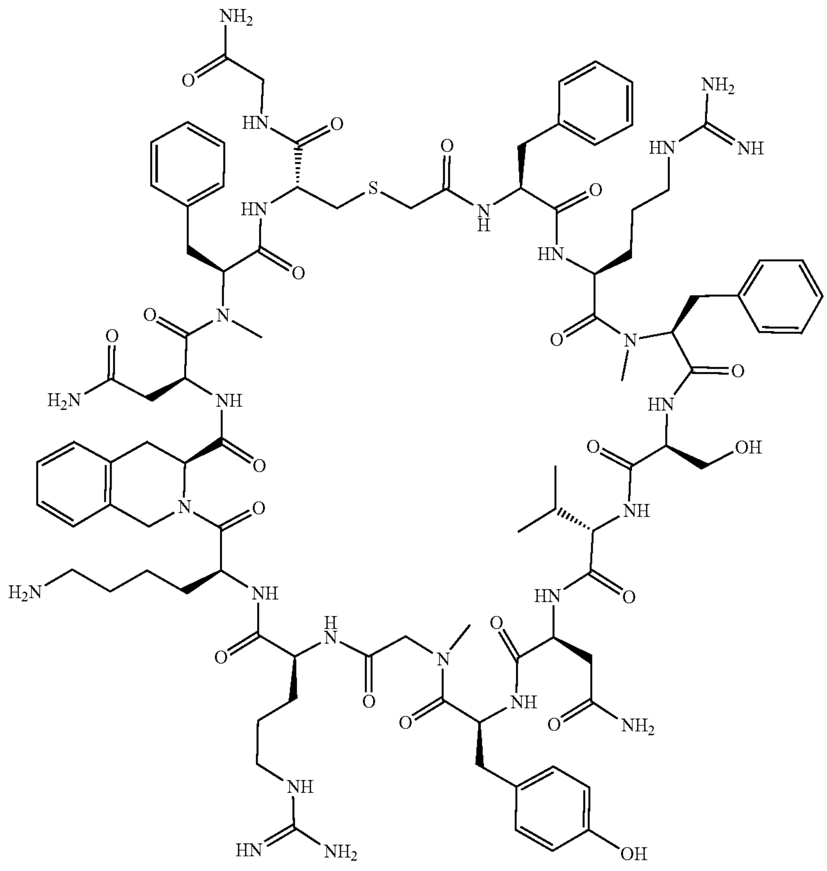

Note: Compound (C16) has the following amino acid sequence:

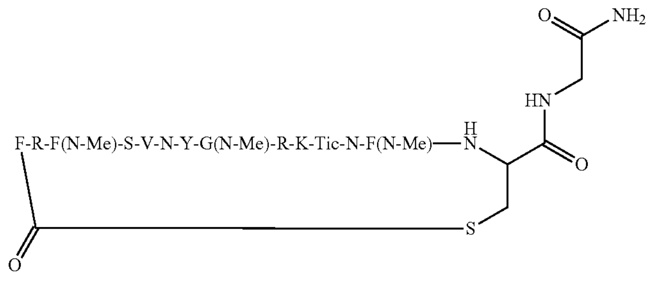

Cyclic peptide compound (C16) (SEQ ID NO: 9) was obtained using an analogous method as described in Example 2-1, however in step 1 the peptide sequence attached to the resin

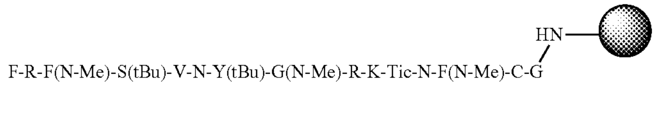

was synthesized instead of peptide sequence 2-4b. Analytical method 9: $t_R$=3.45, m+1=1935.24

Example 3: Synthesis of ASGPR Receptor Ligands and M6P Receptor Ligands

Synthesis of Intermediates

Type AA:

Synthesis of benzyl 5-hydroxypentanoate (int-AA1)

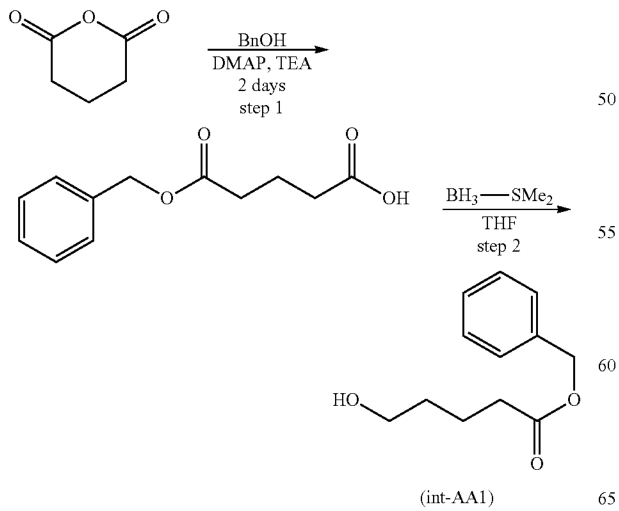

(int-AA1)

Step 1: To a solution of dihydro-2H-pyran-2,6 (3H)-dione (20 g, 175.44 mmol) and BnOH (20.8 g, 192.98 mmol) in DCM (150 mL) were added DMAP (0.32 g, 2.62 mmol) and $Et_3N$ (29 mL, 210.5 mmol) at 0° C. The reaction mixture was allowed to warm to room temperature and continued to stir for two days. The reaction mixture was evaporated to dryness and the resulting residue was dissolved in DCM (200 mL), washed with 3M HCl (100 mL×2). The organic layer was dried over anhydrous $Na_2SO_4$ and concentrated. The residue was purified by silica gel column chromatography (elute: PE:EA=20:1-10:1) to obtain 5-(benzyloxy)-5-oxopentanoic acid as a colorless oil. $^1$H NMR (400 MHz, $CDCl_3$) δ ppm 7.38-7.28 (m, 5H), 5.12 (s, 2H), 2.46-2.40 (m, 4H), 2.00-1.93 (m, 2H).

Step 2: To a solution of 5-(benzyloxy)-5-oxopentanoic acid (30 g, 135.1 mmol) in THF (200 mL) $BH_3$—$S(CH_3)_2$ (20.2 ml, 202.7 mmol) was added dropwise at 0° C. under $N_2$ protection. The mixture was allowed to warm to room temperature and stirred for 16 hours. TLC showed the start material was completely consumed. The reaction was quenched with $H_2O$ (8 mL) carefully. The resulting mixture was filtered and the filtrate was concentrated. The residue was purified by silica gel column chromatography (elute: PE:EA=20:1-2:1) to afford benzyl 5-hydroxypentanoate (int-AA1). $^1$H NMR (400 MHz, $CDCl_3$) δ ppm 7.41-7.33 (m, 5H), 5.14 (s, 2H), 3.66 (t, 2H, J=6 Hz), 2.43 (t, 2H, J=7.2 Hz), 1.80-1.73 (m, 2H), 1.65-1.58 (m, 2H).

Synthesis of 3-((6-azidohexyl)oxy)-2-hydroxy-3-((1-hydroxy-3-oxopropan-2-yl)oxy)propanal (int-AA2)

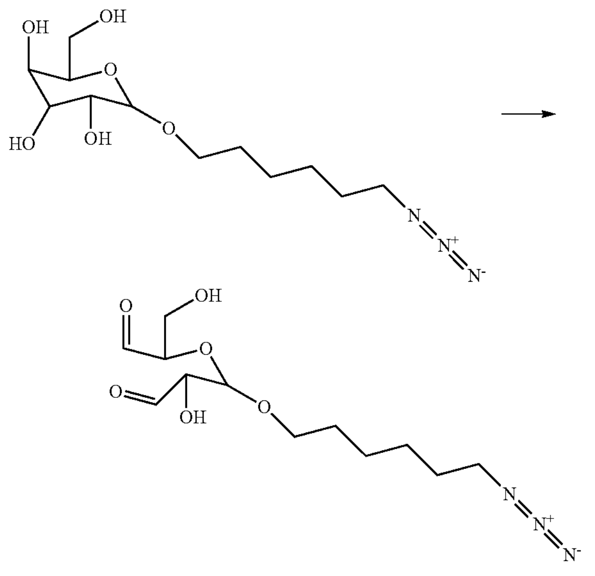

(int-AA2)

To (3R,4R,5R,6R)-2-((6-azidohexyl)oxy)-6-(hydroxymethyl)tetrahydro-2H-pyran-3,4,5-triol (see Hwu, Jih Ru; Hsu, Chuan-I; Hsu, Ming-Hua; Liang, Yu-Chuan; Huang, Ru Chih C.; Lee, Yuan C. Bioorganic and Medicinal Chemistry Letters, 2011, vol. 21, #1, p. 380-382) (40 mg, 0.131 mmol) in acetonitrile (2 mL) and water (0.5 mL) was added sodium periodate on silica (420 mg, 0.197 mmol). The mixture was stirred at room temperature for 4 h, filtered and then purified by reverse phase flash chromatography to give 3-((6-azidohexyl)oxy)-2-hydroxy-3-((1-hydroxy-3-oxopropan-2-yl)oxy)propanal (int-AA2). Analytical method 7: $t_r$=0.80 min, MS m/z 326.2 [M+Na]$^+$.

Type BB:

Synthesis of (2R,3R,4R,5R,6R)-5-acetamido-2-(acetoxymethyl)-6-((5-((2,5-dioxopyrrolidin-1-yl)oxy)-5-oxopentyl)oxy)tetrahydro-2H-pyran-3,4-diyldiacetate (int-BB1)

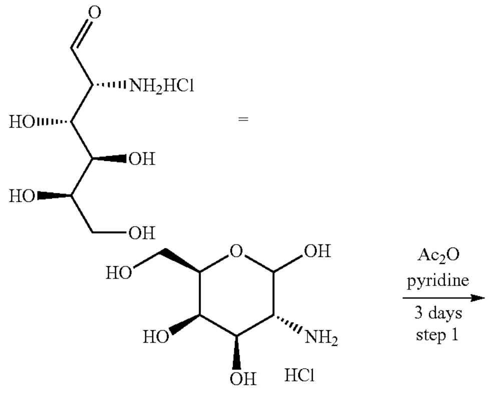

-continued

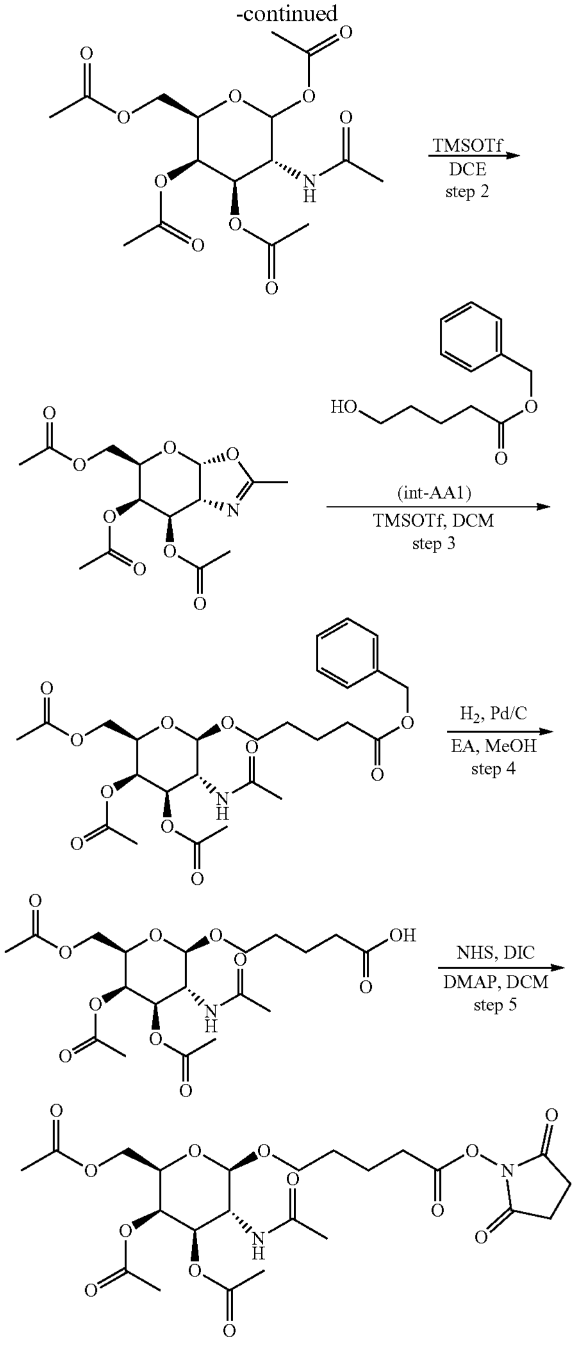

int-BB1

Step 1: To a solution of (2R,3R,4R,5R)-2-amino-3,4,5,6-tetrahydroxyhexanal hydrochloride (100.0 g, 0.132 mol) in pyridine (1 L) was added acetic anhydride (473 g, 4.64 mol) at 0° C. The reaction mixture was stirred for 72 hours at room temperature. The resultant precipitate was collected and washed with $H_2O$ (200 mL×2), dried in vacuum to give (3R,4R,5R,6R)-3-acetamido-6-(acetoxymethyl)tetrahydro-2H-pyran-2,4,5-triyl triacetate. $^1H$ NMR (400 MHz, $CDCl_3$) δ ppm 5.68 (d, 1H, J=8.8 Hz), 5.46 (d, 1H, J=9.2 Hz), 5.35 (d, 1H, J=3.2 Hz), 5.07 (dd, 1H, J1=11.2 Hz, J2=3.2 Hz), 4.47-4.39 (m, 1H), 4.18-4.07 (m, 2H), 4.02-3.98 (m, 1H), 2.16 (s, 3H), 2.11 (s, 3H), 2.03 (s, 3H), 2.00 (s, 3H), 1.93 (s, 3H).

Step 2: To a solution of (3R,4R,5R,6R)-3-acetamido-6-(acetoxymethyl)tetrahydro-2H-pyran-2,4,5-triyl triacetate (100 g, 0.257 mol) in 1,2-dichloroethane (500 mL) cooled to 0° C. was added TMSOTF (85.5 g, 0.385 mol), the mixture was stirred for 10 min, then heated to 50° C. and stirred for 3 hours. TLC showed the start material was completely consumed. After cooling, the resultant mixture was treated with sat. aqueous $NaHCO_3$ (1000 mL) at 0° C., extracted with DCM (500 mL×2). The combined organic layers were dried over $Na_2SO_4$ and concentrated. The residue was dried under high vacuum overnight to give (3aR,5R,6R,7R,7aR)-5-(acetoxymethyl)-2-methyl-3a, 6,7,7a-tetrahydro-5H-pyrano[3,2-d]oxazole-6,7-diyl diacetatel. $^1H$ NMR (400 MHz, $CDCl_3$) δ ppm 6.00 (d, 1H, J=2.8 Hz), 5.47-5.46 (m, 1H), 4.93-4.90 (m, 1H), 4.27-4.18 (m, 2H), 4.13-4.09 (m, 1H), 4.02-3.98 (m, 1H), 2.13 (s, 3H), 2.07 (s, 6H), 2.06 (s, 3H).

Step 3: (3aR,5R,6R,7R,7aR)-5-(acetoxymethyl)-2-methyl-3a, 6,7,7a-tetrahydro-5H-pyrano[3,2-d]oxazole-6,7-diyl diacetate (65 g, 197.4 mmol) and benzyl 5-hydroxy-pentanoate (int-AA1) (41 g, 197.4 mmol) were dissolved in DCM (600 mL). Molecular sieves (50 g) were added, the reaction was stirred for 30 min, and TMSOTF (6.5 g, 29.6 mmol) was added. The reaction mixture was then stirred at room temperature overnight. TLC showed the starting material was completely consumed. The reaction mixture was filtered to remove the molecular sieves. The filtrate was treated with saturated aqueous $NaHCO_3$ (500 ml) and extracted with DCM (500 mL×2). The combined organic layer was dried over anhydrous $Na_2SO_4$ and concentrated. The residue was purified by silica gel column chromatography (elute: PE:EA=2:1-1:2) to obtain (2R,3R,4R,5R,6R)-5-acetamido-2-(acetoxymethyl)-6-((5-(benzyloxy)-5-oxo-pentyl)oxy)tetrahydro-2H-pyran-3,4-diyl diacetate. $^1H$ NMR (400 MHz, $CDCl_3$) δ ppm 7.37-7.32 (m, 5H), 5.60 (d, 1H, J=8.4 Hz), 5.35 (d, 1H, J=2.4 Hz), 5.25 (dd, 1H, J1=11.6 Hz, J2=3.6 Hz), 5.11 (s, 2H), 4.63 (d, 1H, J1=8.4 Hz), 4.15-4.11 (m, 2H), 3.98-3.86 (m, 3H), 3.55-3.45 (m, 1H), 2.41-2.36 (m, 2H), 2.14 (s, 3H), 2.03 (s, 3H), 2.00 (s, 3H), 1.91 (s, 3H), 1.72-1.55 (m, 4H).

Step 4: (2R,3R,4R,5R,6R)-5-acetamido-2-(acetoxymethyl)-6-((5-(benzyloxy)-5-oxopentyl)oxy)tetrahydro-2H-pyran-3,4-diyl diacetate (90 g, 167.4 mmol) was dissolved in a mixture of EtOAc (250 mL) and MeOH (250 mL), then wet Pd/C (4.5 g, 10%) was added. The reaction mixture was degassed and refilled $H_2$ with balloon, then stirred overnight. TLC showed the starting material was completely consumed. The reaction mixture was filtered and the filtrate was concentrated to dryness to give 5-(((2R,3R,4R,5R,6R)-3-acetamido-4,5-diacetoxy-6-(acetoxymethyl)tetrahydro-2H-pyran-2-yl)oxy)pentanoic acid. $^1H$ NMR (400 MHz, $CDCl_3$) δ ppm 5.95 (d, 1H, J=8.4 Hz), 5.35 (d, 1H, J=2.4 Hz), 5.25 (dd, 1H, J1=11.6 Hz, J2=3.6 Hz), 4.66 (d, 1H, J1=8 Hz), 4.16-4.11 (m, 2H), 4.01-3.90 (m, 3H), 3.56-3.49 (m, 1H), 2.40-2.34 (m, 2H), 2.16 (s, 3H), 2.06 (s, 3H), 2.01 (s, 3H), 1.98 (s, 3H), 1.72-1.55 (m, 4H).

Step 5: To a solution of 5-(((2R,3R,4R,5R,6R)-3-acetamido-4,5-diacetoxy-6-(acetoxymethyl)tetrahydro-2H-pyran-2-yl)oxy)pentanoic acid (69 g, 154.2 mmol) and NHS—OH (19.5 g, 169.62 mmol) in DCM (600 mL) was added DIC (19.4 g, 154.2 mmol) and DMAP (36 mg, 0.29 mmol). The reaction mixture was stirred at room temperature for 3 hours. TLC showed the starting material was completely consumed. The resultant mixture was filtered and the filtrate was concentrated. The residue was purified by silica gel column chromatography (elute: PE:EA=2:1-1:4) to obtain (2R,3R,4R,5R,6R)-5-acetamido-2-(acetoxymethyl)-6-((5-((2,5-dioxopyrrolidin-1-yl)oxy)-5-oxopentyl)oxy)tetrahydro-2H-pyran-3,4-diyl diacetate (int-BB1). $^1H$ NMR (400 MHz, $CDCl_3$) δ ppm 5.83 (d, 1H, J=8.4 Hz), 5.33 (d, 1H, J=2.4 Hz), 5.25 (dd, 1H, J1=11.6 Hz, J2=3.6 Hz), 4.67 (d, 1H, J1=8 Hz), 4.13-4.07 (m, 2H), 4.00-3.87 (m, 3H), 2.86-2.82 (m, 4H), 2.73-2.55 (m, 2H), 2.14 (s, 3H), 2.02 (s, 3H), 1.97 (s, 3H), 1.91 (s, 3H), 1.72-1.55 (m, 4H).

Synthesis of (1S,2R,3R,4R,5S)-4-amino-1-(hydroxymethyl)-6,8-dioxabicyclo[3.2.1]octane-2,3-diol (int-BB2)

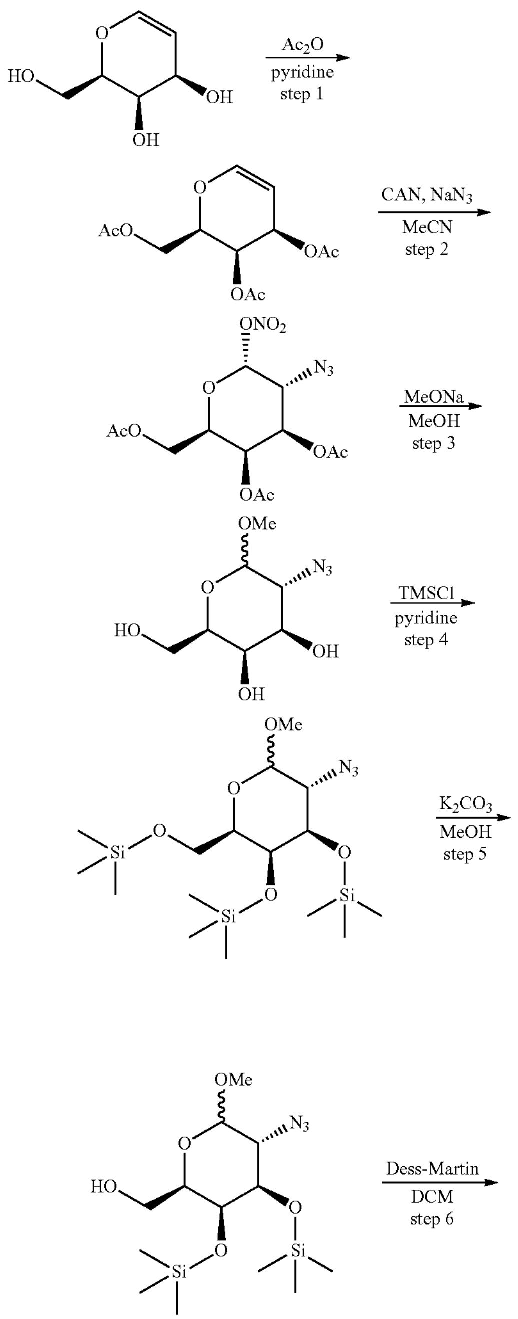

-continued

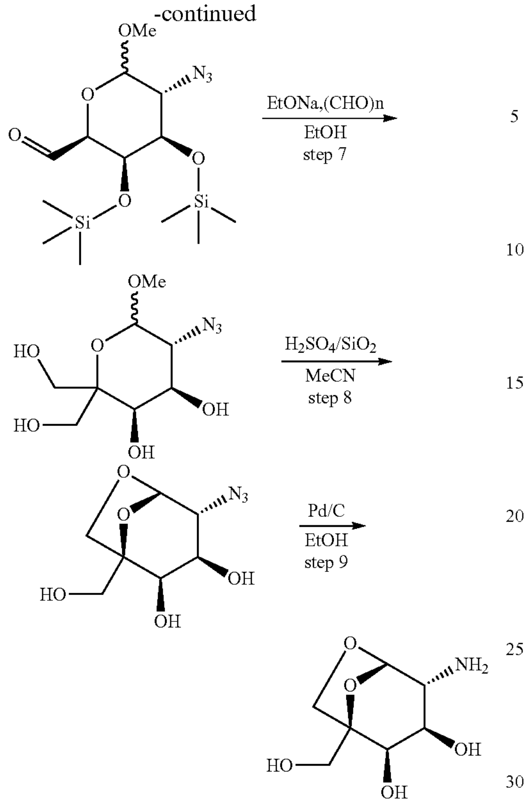

(int-BB2)

Step 1: A mixture of (2R,3R,4R)-2-(hydroxymethyl)-3,4-dihydro-2H-pyran-3,4-diol (500 g, 3.42 mol) and pyridine (1.93 L, 23.95 mol) was stirred at 20° C. for 30 min. then cooled to 0° C. before adding $Ac_2O$ (1.12 L, 11.97 mol) dropwise while maintaining the temperature between 5° C. and 15° C. The reaction mixture was further stirred at 20° C. for 2 hours under $N_2$, cooled to 0° C., quenched with ice-water (1 L) and then extracted first with MTBE (3×1.2 L) and then with EA (2×1 L). The combined organic layers were washed with 0.5 N HCl (3×1 L), sat·$NaHCO_3$ (1 L), and then brine (1 L). The combined aqueous layers were then extracted with EtOAc (3 L) and the organic layer was washed with 0.5 N HCl (3×1 L), sat·$NaHCO_3$ (1 L), and then brine (1 L). All organic layers were combined and dried over $Na_2SO_4$, filter and concentrate under vacuum at 35° C. to give (2R,3R,4R)-2-(acetoxymethyl)-3,4-dihydro-2H-pyran-3,4-diyl diacetate. $^1H$ NMR: ($CDCl_3$ 400 MHz) δ 1.98-2.14 (m, 9H) 4.17-4.33 (m, 3H) 4.71 (ddt, J=5.00, 2.61, 1.27, 1.27 Hz, 1H) 5.41 (dd, J=4.34, 1.65 Hz, 1H) 5.51-5.57 (m, 1H) 6.45 (d, J=6.24 Hz, 1H).

Step 2: A solution of (2R,3R,4R)-2-(acetoxymethyl)-3,4-dihydro-2H-pyran-3,4-diyl diacetate (900 g, 3.31 mol, 1 eq) dissolved in MeCN (2 L) was added to MeCN (16 L) with agitation (300 rpm) under $N_2$ flow and the mixture then cooled to −15° C. under $N_2$. $NaN_3$ (429.82 g, 6.61 mol, 2 eq) was added to the reaction mixture in portions while maintaining the temperature between −15° C. and −10° C., again under a gentle $N_2$ flow. Cerric ammonium nitrate (5.44 kg, 9.92 mol) was added to the reaction mixture with agitation (350 rpm) in 6 portions over 3 hours while maintaining the temperature between −15° C. and −10° C. under a gentle $N_2$ flow. The reaction mixture was then stirred under $N_2$ at a temperature between −15° C. and −10° C. for 4 hr and then MTBE (10 L) was added in in two portions. $H_2O$ (10 L) was carefully added to the reaction mixture under a $N_2$ flow at a temperature between −5° C. and 0° C. and the mixture was stirred for 30 min at 0° C. and then let stand at room temperature (25° C.) for 16 hours. The mixture was separated and the organic layer washed with $H_2O$ (8×10 L and then dried over $Na_2SO_4$, filtered and concentrated under vacuum at 20-25° C. to give (2R,3R,4R,5R,6R)-2-(acetoxymethyl)-5-azido-6-(nitrooxy)tetrahydro-2H-pyran-3,4-diyl diacetate which was used directly in the next step.

Step 3: A solution of (2R,3R,4R,5R,6R)-2-(acetoxymethyl)-5-azido-6-(nitrooxy)tetrahydro-2H-pyran-3,4-diyl diacetate (1140 g, 3.03 mol.) in MeOH (8 L) was cooled to 0° C. and then NaOMe (1.1 M, 1.60 L) was added while maintain the temperature between 0° C. and 5° C. The reaction mixture was then stirred for 2 hours at a temperature between 0° C. and 5° C. Resin (H+) (500 g) was then added and the reaction mixture further stirred for 30 min. The reaction mixture was filtered and the filter cake rinsed with MeOH (2 L). Triturated with MeOH (2 L) for 30 min at room temperature (25° C.) and filtered (repeat 4×). All filtrates were combined and concentrated under vacuum at 35° C. to give a residue which was purified by column chromatography on silica gel (DCM:MeOH=50:1~30:1) to give (2R,3R,4R,5R)-5-azido-2-(hydroxymethyl)-6-methoxytetrahydro-2H-pyran-3,4-diol.

Step 4: (2R,3R,4R,5R)-5-azido-2-(hydroxymethyl)-6-methoxytetrahydro-2H-pyran-3,4-diol (320 g, 1.46 mol) in pyridine (589.17 mL, 7.30 mol) was added to DCM (3.2 L) at 25° C. The mixture was cooled to 0° C. and stirred for 30 min. at a temperature between 0° C. and 5° C. TMSCl (634.42 g, 5.84 mol, 741.14 mL, 4 eq) was then added dropwise and the resulting white suspension was stirred for 1 hour at a temperature between 5° C. and 10° C. The slurry was quenched with sat·$NH_4Cl$ (1.5 L), stirred for 10 min., let stand for 5 min. and then separated. The DCM layer was washed with $NH_4Cl$ (1.5 L×4) and $H_2O$ (1.5 L×5), dried over $Na_2SO_4$, filtered and concentrated under vacuum at 35° C. to give (((2R,3S,4R,5R)-5-azido-6-methoxy-2-(((trimethylsilyl)oxy)methyl)tetrahydro-2H-pyran-3,4-diyl)bis(oxy))bis(trimethylsilane), which was used directly for next step.

Step 5: To (((2R,3S,4R,5R)-5-azido-6-methoxy-2-(((trimethylsilyl)oxy)methyl)tetrahydro-2H-pyran-3,4-diyl)bis(oxy))bis(trimethylsilane) (580.00 g, 1.33 mol) in MeOH (3.5 L) under $N_2$, was added dropwise $K_2CO_3$ (1.84 g, 13.31 mmol, 0.01 eq) dissolved in MeOH (160 mL) at a temperature between −10° C. and −5° C. and the reaction mixture was stirred for 30 min. The reaction mixture was then acidified with AcOH (1.84 g) to pH~6, concentrated and then EtOAc (6 L) was added. The mixture was washed with $H_2O$ (3 L×2), brine (3 L), dried over $Na_2SO_4$, filtered and concentrated to give the crude product which was purified by column chromatography on silica gel (Petroleum ether: EtOAc=30:1~5:1) to give ((2R,3S,4R,5R)-5-azido-6-methoxy-3,4-bis((trimethylsilyl)oxy)tetrahydro-2H-pyran-2-yl)methanol.

Step 6: Dess-Martin reagent (CAS Number: 87413-09-0) (346.49 g, 816.93 mmol) was added in portions over 3 hours to a solution of ((2R,3S,4R,5R)-5-azido-6-methoxy-3,4-bis((trimethylsilyl)oxy)tetrahydro-2H-pyran-2-yl)methanol (270 g, 742.66 mmol) in DCM (6 L). The reaction mixture was stirred for 1 hour at 8° C., poured into stirring sat·$NaHCO_3$ (4 L) and then separated. The aqueous layer was extracted with DCM (1 L) and the organic layer washed with sat·$NaHCO_3$ (4 Lx 2), $H_2O$ (4 L×2), dried over $Na_2SO_4$, filtered and concentrated to give (2S,3S,4R,5R)-5-azido-6-methoxy-3,4-bis((trimethylsilyl)oxy)tetrahydro-2H-pyran-2-carbaldehyde.

Step 7: To a solution of (2S,3S,4R,5R)-5-azido-6-methoxy-3,4-bis((trimethylsilyl)oxy)tetrahydro-2H-pyran-2-carbaldehyde (200 g, 553.19 mmol) in EtOH (1.5 L) was added $(CHO)_n$ (497.87 g, 16.60 mol, 30 eq) at room temperature (25° C.). The reaction mixture was cooled to 0° C., NaOEt (2 M, 553.19 mL, 2 eq) in EtOH was added and the reaction mixture stirred at room temperature for 18 hours. The reaction mixture was then concentrated and purified by column chromatography on silica gel (DCM:MeOH=50:1~20:1) to give (3R,4R,5R)-5-azido-2,2-bis(hydroxymethyl)-6-methoxytetrahydro-2H-pyran-3,4-diol.

Step 8: $H_2SO_4$ (10.27 mL, 192.60 mmol) on silica gel (38 g) was added to (3R,4R,5R)-5-azido-2,2-bis(hydroxymethyl)-6-methoxytetrahydro-2H-pyran-3,4-diol (60 g, 240.75 mmol) in MeCN (600 mL) and the reaction mixture was heated to 60° C. for 1 hour. The mixture was then cooled to room temperature, the pH adjusted to pH 7~8 with $NH_4OH$, concentrated and purified by column chromatography on silica gel (DCM:MeOH=30:1~20:1) to give (1S,2R,3R,4R,5S)-4-azido-1-(hydroxymethyl)-6,8-dioxabicyclo[3.2.1]octane-2,3-diol. $^1H$ NMR: (MeOD 400 MHz) δ 3.35-3.40 (m, 1H) 3.68-3.74 (m, 1H) 3.77-3.85 (m, 2H) 3.86-3.95 (m, 3H) 5.35 (d, J=1.00 Hz, 1H).

Step 9: At room temperature Pd/C (3.63 g, 3.41 mmol, 10% purity) (1S,2R,3R,4R,5S)-4-azido-1-(hydroxymethyl)-6,8-dioxabicyclo[3.2.1]octane-2,3-diol (37 g, 170.37 mmol) in EtOH (1.2 L) under Ar. The reaction mixture was degassed (5×) with $H_2$ and then stirred for 16 hours under $H_2$ (20 psi) at 25° C. The reaction mixture was filtered and the filter cake triturated with MeOH:$H_2O$ (200 mL×3, 1:1) at room temperature (25° C.) for 10 min. and filtered again. The filtrates were combined and concentrated to give (1S,2R,3R,4R,5S)-4-amino-1-(hydroxymethyl)-6,8-dioxabicyclo[3.2.1]octane-2,3-diol (int-BB2). $^1H$ NMR: (MeOD 400 MHz) δ: 2.75 (dd, J=9.29, 1.51 Hz, 1H) 3.50 (dd, J=9.16, 4.39 Hz, 1H) 3.72 (q, J=8.03 Hz, 2H) 3.79-3.85 (m, 2H) 3.89-3.95 (m, 1H) 5.24 (d, J=1.25 Hz, 1H).

Synthesis of Synthesis of N-((3aR,4S,7S,8R,8aR)-4-(hydroxymethyl)-2,2-dimethylhexahydro-4,7-epoxy[1,3]dioxolo[4,5-d]oxepin-8-yl)acetamide (int-BB3)

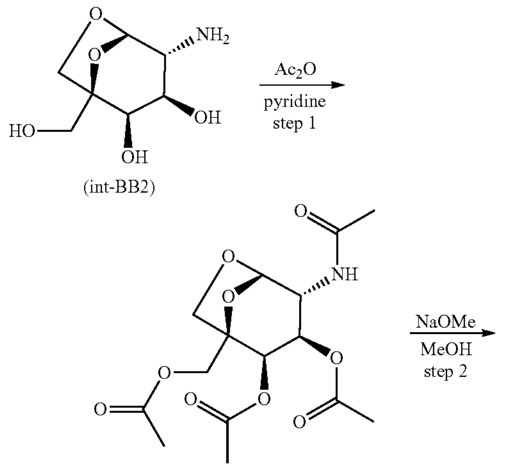

(int-BB2)

-continued

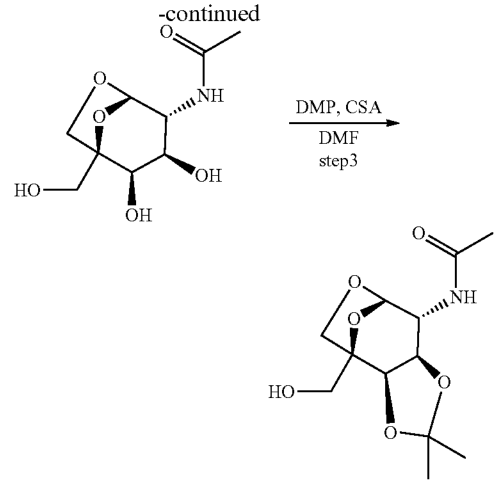

(int-BB3)

Step 1: (1S,2R,3R,4R,5S)-4-amino-1-(hydroxymethyl)-6,8-dioxabicyclo[3.2.1]octane-2,3-diol (int-BB2) (17.7 g, 92.58 mmol) in pyridine (280 mL) was cooled to 0° C. with ice-$H_2O$, $Ac_2O$ (89.79 g, 879.53 mmol) was added dropwise and then allowed to warm to room temperature while stirring for 16 hours. The reaction mixture was concentrated, diluted with EtOAc (800 mL), poured into sat·$NaHCO_3$ (800 mL), and separated. The aqueous layer was extracted with EtOAc (500 mL×2), the combined organic layers washed with brine (800 mL), dried over $Na_2SO_4$, filtered and concentrated to give (1R,2R,3R,4R,5S)-4-acetamido-1-(acetoxymethyl)-6,8-dioxabicyclo[3.2.1]octane-2,3-diyl diacetate, which was used directly for next step.

Step 2: (1R,2R,3R,4R,5S)-4-acetamido-1-(acetoxymethyl)-6,8-dioxabicyclo[3.2.1]octane-2,3-diyl diacetate (30 g, 83.49 mmol) dissolved in THF (200 mL) and MeOH (200 mL) was cooled to 0° C., NaOMe (3 M, 27.83 mL) was add dropwise and the reaction mixture warmed to room temperate while stirring under $N_2$ for 30 min. The reaction mixture was cooled to 0° C., resin (H+) IR 120 (20 g, Aldrich:CAS Number: 39389-20-3) was added in portions and then warmed to room temperate while stirring for 1 hour. The mixture was filtered and the filter cake washed with MeOH (500 mL×3). The combined filtrates were concentrated and the crude product purified by column chromatography on silica gel (DCM:MeOH=30:1~10:1) to give N-((1S,2R,3R,4R,5S)-2,3-dihydroxy-1-(hydroxymethyl)-6,8-dioxabicyclo[3.2.1]octan-4-yl)acetamide. $^1H$ NMR: (MeOD 400 MHz) δ 2.01 (s, 3H) 3.35-3.41 (m, 1H) 3.68-3.85 (m, 4H) 3.88-3.99 (m, 3H) 5.24 (d, J=1.51 Hz, 1H).

Step 3: DMP (26.79 g, 257.27 mmol, 31.52 mL, 6 eq) and CSA (3.98 g, 17.15 mmol, 0.4 eq) were added to N-((1S,2R,3R,4R,5S)-2,3-dihydroxy-1-(hydroxymethyl)-6,8-dioxabicyclo[3.2.1]octan-4-yl)acetamide (10 g, 42.88 mmol, 1 eq) in DMF (150 mL) and the mixture heated to 60° C. and stirred for 20 hours under $N_2$. The reaction mixture was allowed to cool to room temperature, dry MeOH (20 mL) was added, the mixture stirred for 30.min. and then $Et_3N$ (5 mL) was added. The reaction mixture was concentrated and the crude product purified by column chromatography (DCM:MeOH=50:1~20:1) to give N-((3aR,4S,7S,8R,8aR)-4-(hydroxymethyl)-2,2-dimethylhexahydro-4,7-epoxy[1,3]dioxolo[4,5-d]oxepin-8-yl)acetamide (int-BB3). $^1H$ NMR:

(MeOD 400 MHz) δ 1.36 (s, 3H) 1.50 (s, 3H) 2.00 (s, 3H) 3.77-3.96 (m, 5H) 4.15-4.22 (m, 1H) 4.32 (d, J=5.77 Hz, 1H) 5.25 (d, J=2.01 Hz, 1H).

Synthesis of 1,3-bis(prop-2-yn-1-yloxy)-2-((prop-2-yn-1-yloxy)methyl)propan-2-amine (int-BB4)

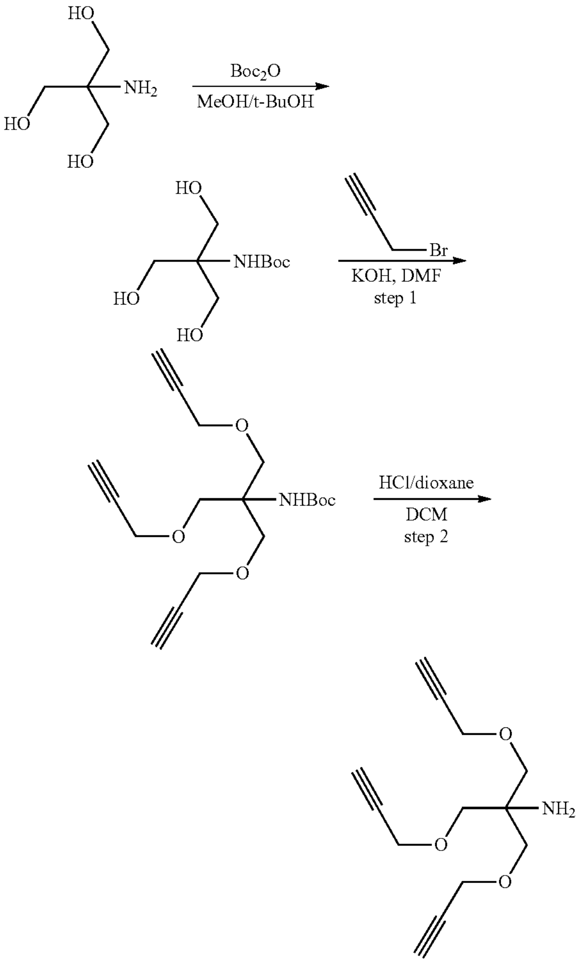

(int-BB4)

Step 1: To a suspension of 2-amino-2-(hydroxymethyl) propane-1,3-diol (15 g, 123.83 mmol) in MeOH (75 mL) and t-BuOH (75 mL) was added a solution of $Boc_2O$ (35.13 g, 160.98 mmol, 36.98 mL, 1.3 eq) in t-BuOH (25 mL) over 30 min and the mixture was stirred for 3 hours. The mixture was added Petroleum ether (500 mL) at 25° C., stirred for 30 min and filtered. The filter cake was washed with Petroleum ether (200 mL×3) and then dried under vacuum to give tert-butyl (1,3-dihydroxy-2-(hydroxymethyl)propan-2-yl) carbamate. $^1$H NMR: (DMSO 400 MHz) δ 1.38 (s, 9H) 3.52 (d, J=5.75 Hz, 6H) 4.51 (t, J=5.62 Hz, 3H) 5.78 (br s, 1H) Step 2: To a solution of tert-butyl (1,3-dihydroxy-2-(hydroxymethyl)propan-2-yl)carbamate (17 g, 76.84 mmol, 1 eq) in DMF (150 mL) was added 3-bromoprop-1-yne (45.70 g, 307.34 mmol), and KOH (22.42 g, 399.55 mmol). The reaction mixture was stirred at 25° C. for 16 hours. The mixture was diluted with MTBE (200 mL) and $H_2O$ (200 mL) then separated, and the aqueous layer extracted with MTBE (100 mL×2). The combined organics were washed with brine (150 mL×2), dried over $Na_2SO_4$, filtered and concentrated and the crude product. was purified by column chromatography (Petroleum ether:EtOAc=15:1~10:1) to give compound tert-butyl (1,3-bis(prop-2-yn-1-yloxy)-2-((prop-2-yn-1-yloxy)methyl)propan-2-yl)carbamate. $^1$H NMR: ($CDCl_3$ 400 MHz) δ 1.41 (s, 9H) 2.42 (t, J=2.38 Hz, 3H) 3.77 (s, 6H) 4.14 (d, J=2.51 Hz, 6H) 4.92 (br s, 1H).

Step 3: To a solution of tert-butyl (1,3-bis(prop-2-yn-1-yloxy)-2-((prop-2-yn-1-yloxy)methyl)propan-2-yl)carbamate (10 g, 29.82 mmol) in DCM (450 mL) was added dropwise HCl/dioxane (4 M, 52.18 mL) and the resulting solution was stirred at room temperature (30° C.) for 18 hours. The mixture was concentrated under vacuum to give a residual solid which was triturated with DCM:EA:PE (10 mL:70 mL:70 mL) at room temperature (30° C.) for 2 hours and filtered. The filter cake was rinsed with EtOAc (40 mL) and Petroleum ether (40 mL×2), then dried under vacuum at 45° C. for 2 hours to give 1,3-bis(prop-2-yn-1-yloxy)-2-((prop-2-yn-1-yloxy)methyl)propan-2-amine (int-BB4). $^1$H NMR: (MeOD 400 MHz) δ 2.99 (t, J=2.38 Hz, 3H) 3.75 (s, 6H) 4.28 (d, J=2.51 Hz, 6H). MS: (ESI) m/z=236.1 $[M+H]^+$.

Synthesis of 1,3-bis(prop-2-yn-1-yloxy)propan-2-amine (int-BB5)

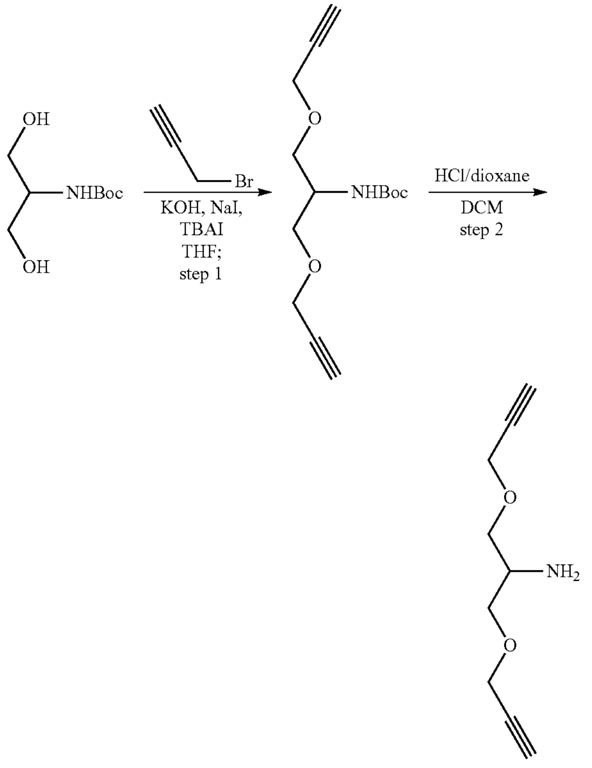

(int-BB5)

Step 1: To a solution of tert-butyl (1,3-dihydroxypropan-2-yl)carbamate (25 g, 130.74 mmol) in THF (200 mL) was added TBAI (7.24 g, 19.61 mmol), NaI (3.92 g, 26.15 mmol) and 3-bromoprop-1-yne (68.04 g, 457.58 mmol) at room temperature (25° C.). The mixture was cooled to 10° C., KOH (14.67 g, 261.47 mmol, 2 eq) was added in portions over 30 min., and then the mixture was stirred at room temperature for 16 hours. The reaction mixture was diluted with EtOAc (200 mL) and $H_2O$ (250 mL), separated and the aqueous layer extracted with EtOAc (200 mL×2). The combined organics were washed with brine (300 mL×2), dried over $Na_2SO_4$, filtered and concentrated to give a crude product which was purified by column chromatography (Petroleum ether:EtOAc=15:1~10:1) to give tert-butyl (1,3-bis(prop-2-yn-1-yloxy)propan-2-yl)carbamate. $^1H$ NMR: ($CDCl_3$ 400 MHz) δ 1.40-1.49 (m, 9H) 2.45 (t, J=2.38 Hz, 2H) 3.53-3.67 (m, 4H) 3.87-3.99 (m, 1H) 4.16 (d, J=2.32 Hz, 4H) 4.93 (br d, J=6.36 Hz, 1H).

Step 2: To a solution of tert-butyl (1,3-bis(prop-2-yn-1-yloxy)propan-2-yl)carbamate (10 g, 37.41 mmol) in DCM (45 mL) was added dropwise HCl/dioxane (4 M, 66.67 mL) under $N_2$ at 0-5° C. and the solution stirred at room temperature for 18 hours. The mixture was concentrated to give a residual solid which was triturated with DCM:EtOAc: Petroleum ether (10 mL:70 mL:70 mL) at room temperature (30° C.) for 2 hour and filtered. The filter cake was rinsed with EtOAc (40 mL) and Petroleum ether (40 mL×2), then dried under vacuum at 45° C. for 2 hours to give 1,3-bis(prop-2-yn-1-yloxy)propan-2-amine (int-BB5). $^1H$ NMR: (MeOD 400 MHz) δ 2.99 (t, J=2.38 Hz, 2H) 3.58-3.65 (m, 1H) 3.67-3.77 (m, 2H) 3.78-3.84 (m, 2H) 4.28 (d, J=2.26 Hz, 4H). MS: (ESI) m/z=168.1 $[M+H]^+$.

Type CC:

Synthesis of Intermediate (int-CC1)

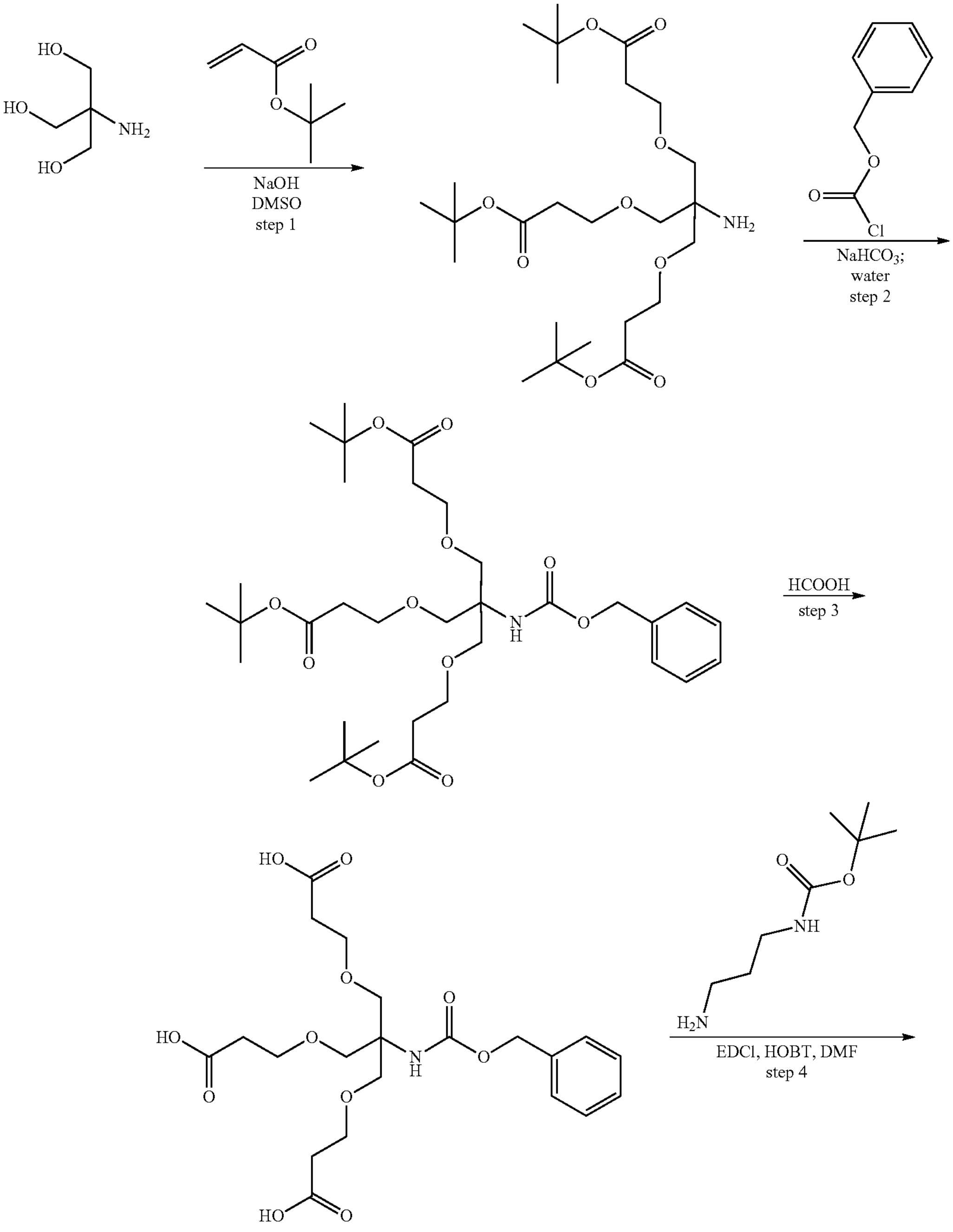

-continued
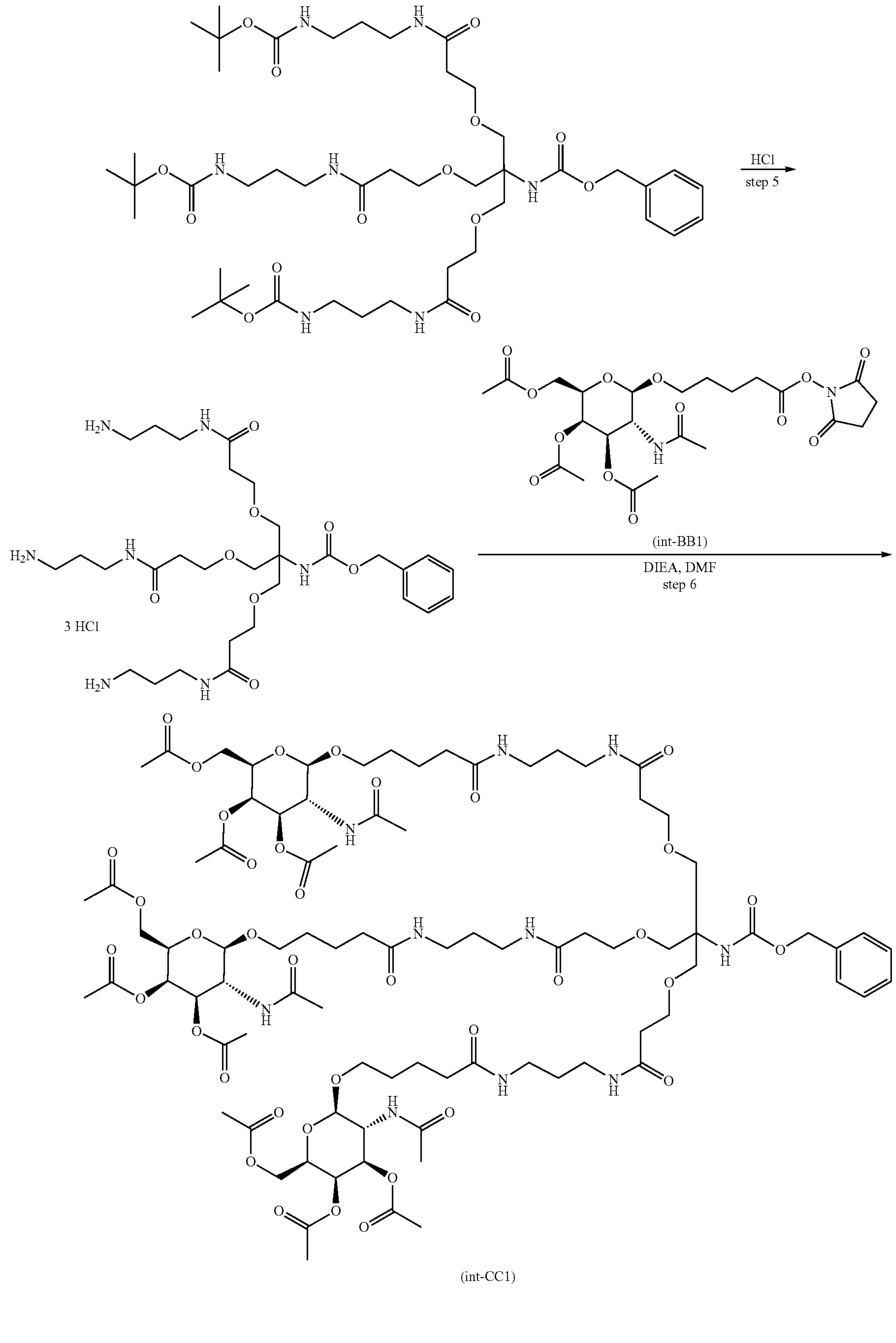
(int-CC1)

Step 1: Aqueous NaOH (3.2 mL, 5 M) was added to a mixture of 2-amino-2-(hydroxymethyl)propane-1,3-diol (20 g, 165.28 mmol) in DMSO (32 mL) at 20° C., then tert-butyl acrylate (74 g, 578.48 mmol) was added dropwise. The mixture was stirred at 20° C. for 24 hours. The resulting mixture was diluted with EtOAc (1 L), washed with $H_2O$ (800 ml). The organic layer was dried over $Na_2SO_4$ and concentrated to give crude di-tert-butyl 3,3'-((2-amino-2-((3-(tert-butoxy)-3-oxopropoxy)methyl)propane-1,3-diyl)bis(oxy))dipropionate, which was used in next step directly. $t_R$=1.308 min, $[M+H]^+$ 506.3 Step 2: Aqueous $NaHCO_3$ (1 L) was added to a solution of di-tert-butyl 3,3'-((2-amino-2-((3-(tert-butoxy)-3-oxopropoxy)methyl)propane-1,3-diyl)bis(oxy))dipropionate (160 g, 316.20 mmol, crude) in EtOAc (1 L), then benzyl carbonochloridate (53.9 g, 316.20 mmol) was added dropwise. The reaction mixture was stirred at room temperature for 3 hours. TLC showed the reaction was completed. The organic layer was separated, washed with $H_2O$ (500 ml), dried over $Na_2SO_4$ and concentrated. The residue was purified by silica gel column chromatography (elute: PE:EA=20:1 to 5:1) to give di-tert-butyl 3,3'-((2-(((benzyloxy)carbonyl)amino)-2-((3-(tert-butoxy)-3-oxopropoxy)methyl)propane-1,3-diyl)bis(oxy))dipropionate. $^1H$ NMR (400 MHz, $CDCl_3$) δ ppm 7.36-7.26 (m, 5H), 5.29 (brs, 1H), 5.02 (s, 2H), 3.65-3.61 (m, 12H), 2.43 (t, 6H, J=6.4 Hz), 1.43 (s, 27H).

Step 3: A solution of di-tert-butyl 3,3'-((2-(((benzyloxy)carbonyl)amino)-2-((3-(tert-butoxy)-3-oxopropoxy)methyl)propane-1,3-diyl)bis(oxy))dipropionate (37 g, 57.83 mmol) in formic acid (100 mL) was stirred for 8 hours at room temperature. The resultant mixture was concentrated to dryness to give 3,3'-((2-(((benzyloxy)carbonyl)amino)-2-((2-carboxyethoxy)methyl)propane-1,3-diyl)bis(oxy))dipropionic acid. $^1H$ NMR (400 MHz, $CDCl_3$) δ ppm 7.39-7.30 (m, 5H), 5.35 (brs, 1H), 5.06 (s, 2H), 3.71-3.65 (m, 12H), 2.59 (t, 6H, J=6.8 Hz).

Step 4: To a mixture of 3,3'-((2-(((benzyloxy)carbonyl)amino)-2-((2-carboxyethoxy)methyl)propane-1,3-diyl)bis(oxy))dipropionic acid (27 g, 57.27 mmol) and tert-butyl (3-aminopropyl)carbamate (49.8 g, 286.34 mmol) in DMF (600 mL), HOBT (38.6 g, 286.34 mmol), EDCI (54.9 g, 286.34 mmol) and $Et_3N$ (28.9 g, 286.34 mmol) were added. The reaction mixture was stirred at room temperature for 6 hours. TLC showed the reaction was completed. The resulting mixture was diluted with $H_2O$ (1 L), extracted with DCM (800 mL×3). The combined organic layer was washed with aqueous $NH_4Cl$ (1 L), dried over $Na_2SO_4$ and concentrated. The residue was purified by silica gel column chromatography (elute: DCM:MeOH=50:1-20:1) to obtain benzyl di-tert-butyl (10-(13,13-dimethyl-5,11-dioxo-2,12-dioxa-6,10-diazatetradecyl)-5,15-dioxo-8,12-dioxa-4,16-diazanonadecane-1,10,19-triyl)tricarbamate. $^1H$ NMR (400 MHz, $CDCl_3$) δ ppm 7.37-7.29 (m, 5H), 6.85 (brs, 3H), 5.55 (brs, 1H), 5.14 (brs, 3H), 5.02 (s, 2H), 3.69-3.64 (m, 12H), 3.31-3.23 (m, 6H), 3.15-3.08 (m, 6H), 2.43-2.36 (m, 6H), 1.65-1.56 (m, 6H), 1.42 (s, 27H).

Step 5: To a solution of benzyl di-tert-butyl (10-(13,13-dimethyl-5,11-dioxo-2,12-dioxa-6,10-diazatetradecyl)-5,15-dioxo-8,12-dioxa-4,16-diazanonadecane-1,10,19-triyl)tricarbamate (35 g, 37.23 mmol) in MeOH (500 mL) was added a solution of HCl in 1,4-dioxane (46 ml, 186.17 mmol, 4M). The reaction mixture was stirred at room temperature for 3 hours. The resultant mixture was concentrated to dryness to give the HCl salt of benzyl (1,19-diamino-10-((3-((3-aminopropyl)amino)-3-oxopropoxy)methyl)-5,15-dioxo-8,12-dioxa-4,16-diazanonadecan-10-yl)carbamate. $^1H$ NMR (400 MHz, MeOD) δ ppm 7.41-7.32 (m, 5H), 5.06 (s, 2H), 3.70-3.64 (m, 12H), 3.33-3.29 (m, 6H), 2.97-2.93 (m, 6H), 2.48-2.45 (m, 6H), 1.88-1.82 (m, 6H).

Step 6: To a mixture of benzyl (1,19-diamino-10-((3-((3-aminopropyl)amino)-3-oxopropoxy)methyl)-5,15-dioxo-8,12-dioxa-4,16-diazanonadecan-10-yl)carbamate (10 g, 13.35 mmol) and DIPEA (17.2 g, 133.5 mmol) in DMF (250 mL), a solution of (2R,3R,4R,5R,6R)-5-acetamido-2-(acetoxymethyl)-6-((5-((2,5-dioxopyrrolidin-1-yl)oxy)-5-oxopentyl)oxy)tetrahydro-2H-pyran-3,4-diyl diacetate (int-BB1) (24 g, 44.05 mmol) was added. The reaction mixture was stirred at room temperature for 12 hours. TLC showed the reaction was completed. The resulting mixture was diluted with $H_2O$ (500 mL), extracted with DCM (300 mL×3). The combined organic layer was washed with aqueous HCl (300 mL, 4M), dried over $Na_2SO_4$ and concentrated. The residue was purified by silica gel column chromatography (elute: DCM:MeOH=30:1-15:1) to give Intermediate (int-CC1). $^1H$ NMR (400 MHz, DMSO-d6) δ ppm 7.85-7.80 (m, 6H), 7.72 (brs, 3H), 7.34-7.30 (m, 5H), 6.52 (s, 1H), 5.19 (d, 3H, J=3.2 Hz), 4.95-4.92 (m, 5H), 4.46 (d, 3H, J=8.4 Hz), 4.00 (brs, 9H), 3.86-3.84 (m, 3H), 3.69-3.67 (m, 3H), 3.54-3.41 (m, 15H), 3.01 (brs, 12H), 2.27-2.24 (m, 6H), 2.08

Synthesis of N,N'-(10-((3-((3-(5-(((3R,4R,5R,6R)-3-acetamido-4,5-dihydroxy-6-(hydroxymethyl)tetrahydro-2H-pyran-2-yl)oxy)pentanamido)propyl)amino)-3-oxopropoxy)methyl)-10-amino-5,15-dioxo-8,12-dioxa-4,16-diazanonadecane-1,19-diyl)bis(5-(((2R,3R,4R,5R,6R)-3-acetamido-4,5-dihydroxy-6-(hydroxymethyl)tetrahydro-2H-pyran-2-yl)oxy)pentanamide) (int-CC2)

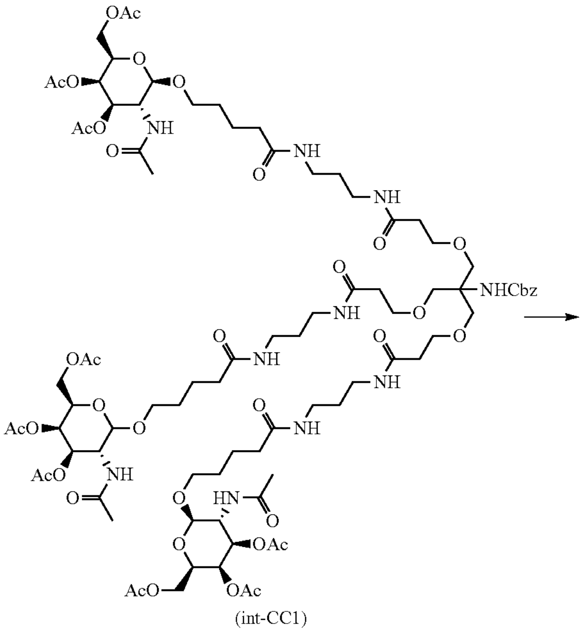

(int-CC1)

-continued

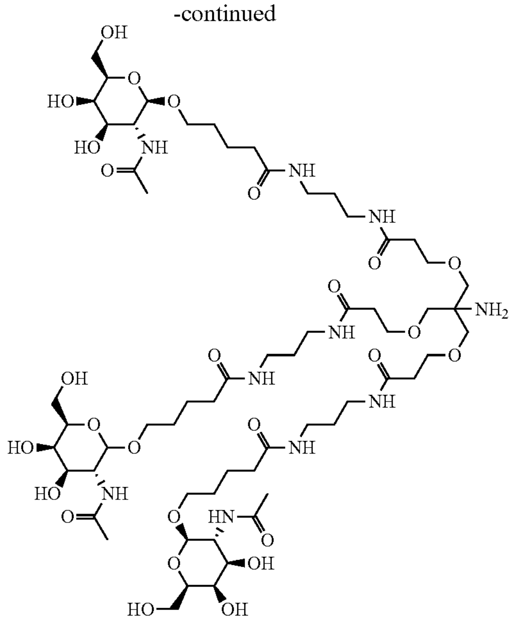

(int-CC2)

To Intermediate (int-CC1) (500 mg, 0.259 mmol) at room temperature in ethanol (3 mL) was added Pd/C (27.6 mg, 0.259 mmol) and the mixture was stirred under 1 atm of hydrogen for 16 h. The mixture was filtered, and then methylamine 2M in methanol (2 mL, 4.00 mmol) was added. The mixture was stirred at room temperature for 16 h, and then concentrated in vacuo to yield Intermediate (int-CC2). Analytical method 7: $t_R$=0.53 min.; MS m/z 1414.1 $[M-H]^-$.

Synthesis of N-((1S,2R,3R,4R,5S)-1-(13-(4-((2-aminoethoxy)methyl)-1H-1,2,3-triazol-1-yl)-2,5,8,11-tetraoxatridecyl)-2,3-dihydroxy-6,8-dioxabicyclo[3.2.1]octan-4-yl)acetamide (int-CC3)

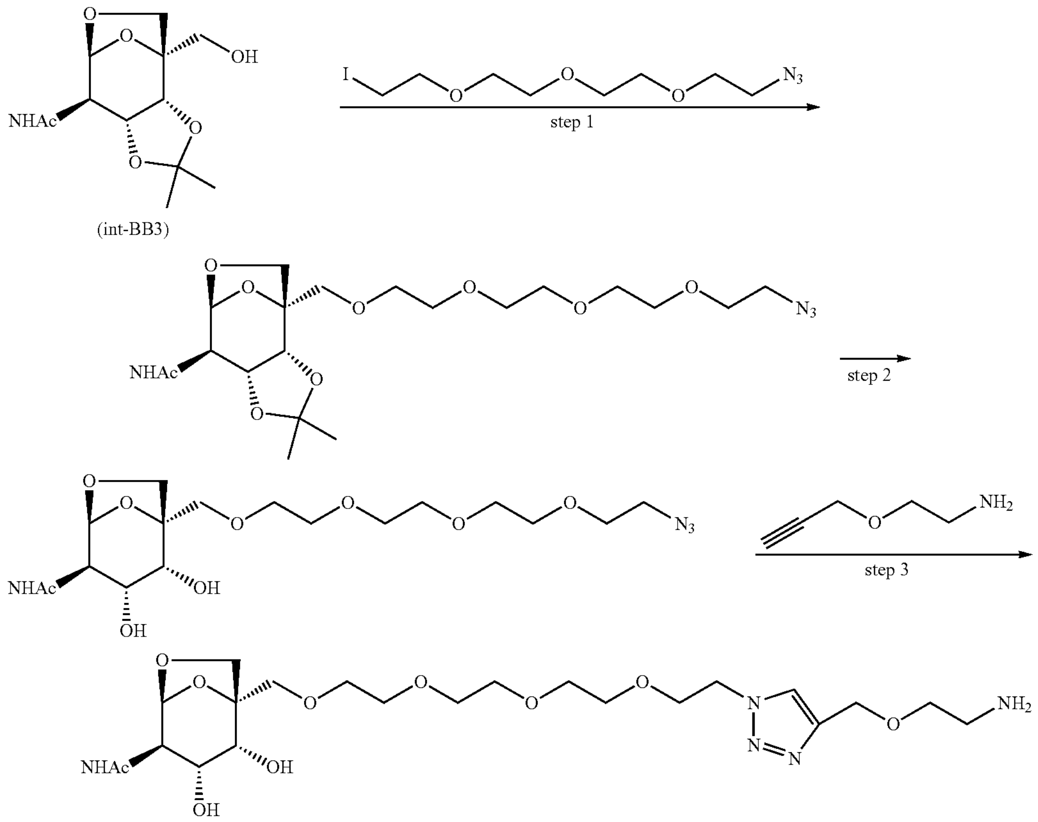

(int-CC3)

Step 1: To N-((3aR,4S,7S,8R,8aR)-4-(hydroxymethyl)-2,2-dimethylhexahydro-4,7-epoxy[1,3]dioxolo[4,5-d]oxepin-8-yl)acetamide (int-BB3) (623 mg, 2.279 mmol) in $CH_2Cl_2$ (4 mL) at room temperature was added iodo-PEG3-azide (750 mg, 2.279 mmol), followed by 1,4,7,10,13-Pentaoxacyclopentadecane (15-crown-5) (30 μL, 2.279 mmol) and NaOH 12M (1 mL, 2.279 mmol). The mixture was stirred at 50° C. for 16 h, and then purified by reverse phase silica gel chromatography to yield N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)acetamide. Analytical Method 7: $t_R$=0.73 min, MS m/z 475.4 $[M+H]^+$.

Step 2: To N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)acetamide (608 mg, 1.281 mmol) in MeOH (3 mL) at room temperature was added acetic acid (1 mL) and water (1 mL). The mixture was stirred at 70° C. for 16 h. TsOH (441 mg, 2.56 mmol) was then added, and the mixture was stirred at room temperature for another 2 h. The mixture was purified by reverse phase silica gel chromatography to obtain N-((1S,2R,3R,4R,5S)-1-(13-azido-2,5,8,11-tetraoxatridecyl)-2,3-dihydroxy-6,8-dioxabicyclo[3.2.1]octan-4-yl)acetamide. Analytical Method 7: $t_R$=0.57 min, MS m/z 435.3 $[M+H]^+$.

Step 3: To a solution of N-((1S,2R,3R,4R,5S)-1-(13-azido-2,5,8,11-tetraoxatridecyl)-2,3-dihydroxy-6,8-dioxabicyclo[3.2.1]octan-4-yl)acetamide (0.017 mL, 0.161 mmol) in MeOH (2 mL) at room temperature was added a solution of THPTA (3 mg, 0.115 mmol) and copper(II) sulfate (1.5 mg, 9.40 μmol) in 75 μL water. Then a solution of sodium ascorbate (2.7 mg, 0.115 mmol) in 45 μL water was added, and the mixture was stirred at room temperature for 16 h. The mixture was concentrated in vacuo, and then purified by reverse phase C18 silica gel chromatography to obtain N-((1S,2R,3R,4R,5S)-1-(13-(4-((2-aminoethoxy)methyl)-1H-1,2,3-triazol-1-yl)-2,5,8,11-tetraoxatridecyl)-2,3-dihydroxy-6,8-dioxabicyclo[3.2.1]octan-4-yl)acetamide (int-CC3). Analytical Method 7: $t_R$=0.47 min, MS m/z 534.4 $[M+H]^+$.

Synthesis of N,N'-((1S,1'S,2R,2'R,3R,3'R,4R,4'R,5S,5'S)-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(2,3-dihydroxy-6,8-dioxabicyclo[3.2.1]octane-1,4-diyl))diacetamide (int-CC4)

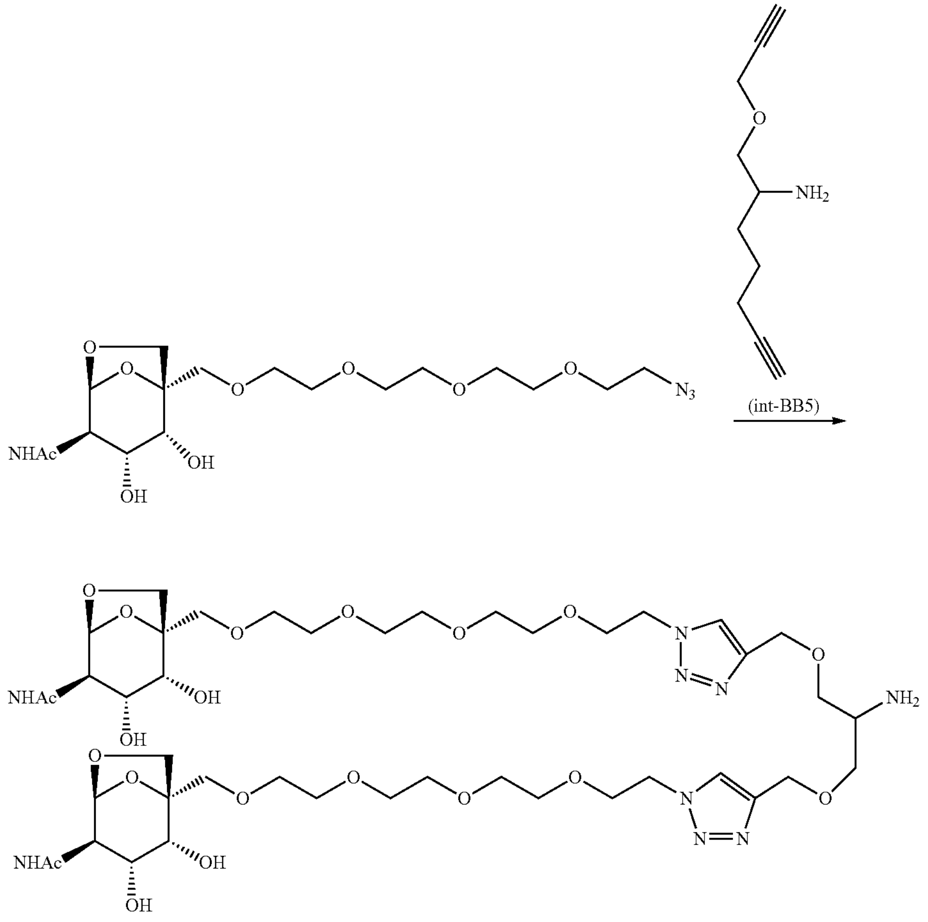

(int-CC4)

To a solution of N-((1S,2R,3R,4R,5S)-1-(13-azido-2,5,8,11-tetraoxatridecyl)-2,3-dihydroxy-6,8-dioxabicyclo[3.2.1]octan-4-yl)acetamide (see step 2 in synthesis of (int-CC3) (62.4 mg, 0.144 mmol) and 1,3-bis(prop-2-yn-1-yloxy)propan-2-amine (int-BB5) (12 mg, 0.072 mmol) in MeOH (2 mL) at room temperature was added a solution of THPTA (6 mg, 0.072 mmol) and copper(II) sulfate (3 mg, 0.019 mmol) in 75 μL water. Then a solution of sodium ascorbate (5.4 mg, 0.072 mmol) in 45 μL water was added, and the mixture was stirred at room temperature for 16 h. The mixture was concentrated in vacuo, and then left at −20 C until purification by reverse phase C18 silica gel chromatography to obtain N,N'-((1S,1'S,2R,2'R,3R,3'R,4R,4'R,5S,5'S)-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(2,3-dihydroxy-6,8-dioxabicyclo[3.2.1]octane-1,4-diyl))diacetamide (int-CC4). Analytical Method 7: $t_R$=0.49 min, MS m/z 1036.8 [M+H].

Synthesis of Intermediate (int-CC5)

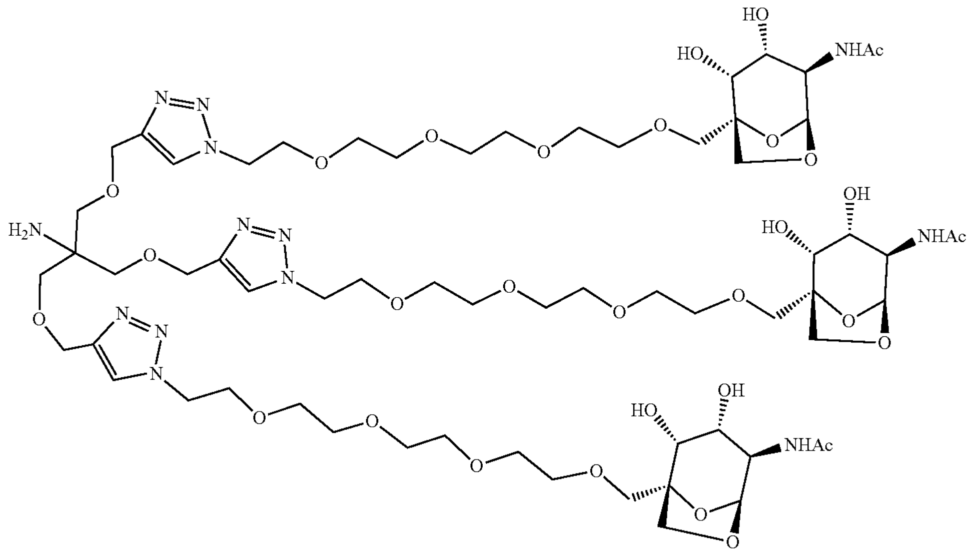

(int-CC5)

To a solution of N-((1S,2R,3R,4R,5S)-1-(13-azido-2,5,8,11-tetraoxatridecyl)-2,3-dihydroxy-6,8-dioxabicyclo[3.2.1]octan-4-yl)acetamide (see step 2 in synthesis of int-CC3) (62.6 mg, 0.144 mmol) and 1,3-bis(prop-2-yn-1-yloxy)-2-((prop-2-yn-1-yloxy)methyl)propan-2-amine (int-BB4) (11.29 mg, 0.048 mmol) in MeOH (2 mL) at room temperature was added a solution of THPTA (9 mg, 0.048 mmol) and copper(II) sulfate (4.5 mg, 0.028 mmol) in 75 μL water. Then a solution of sodium ascorbate (8.1 mg, 0.048 mmol) in 45 μL water was added, and the mixture was stirred at room temperature for 16 h. The mixture was concentrated in vacuo, and then left at −20 C until purification by reverse phase C18 silica gel chromatography to obtain Intermediate (int-CC5). Analytical Method 7: $t_R$=0.53 min, MS m/z 1539.9 $[M+H]^+$.

Synthesis of (((2S,3S,4S,5S,6S)-6-(((2R,3S,4S,5S,6R)-2-(((2R,3S,4S,5R,6R)-2-(4-(2-(2-(aminooxy)acetyl)hydrazineyl)-4-oxobutoxy)-6-((((2S,3S,4S,5S,6R)-6-((((2S,3S,4S,5S,6R)-4,5-dihydroxy-6-(hydroxymethyl)-3-(((2R,3S,4S,5S,6R)-3,4,5-trihydroxy-6-((phosphonooxy)methyl)tetrahydro-2H-pyran-2-yl)oxy)tetrahydro-2H-pyran-2-yl)oxy)methyl)-3,4,5-trihydroxytetrahydro-2H-pyran-2-yl)oxy)methyl)-3,5-dihydroxytetrahydro-2H-pyran-4-yl)oxy)-4,5-dihydroxy-6-(hydroxymethyl)tetrahydro-2H-pyran-3-yl)oxy)-3,4,5-trihydroxytetrahydro-2H-pyran-2-yl)methyl)phosphonoperoxoic acid (int-CC6)

(int-CC6)

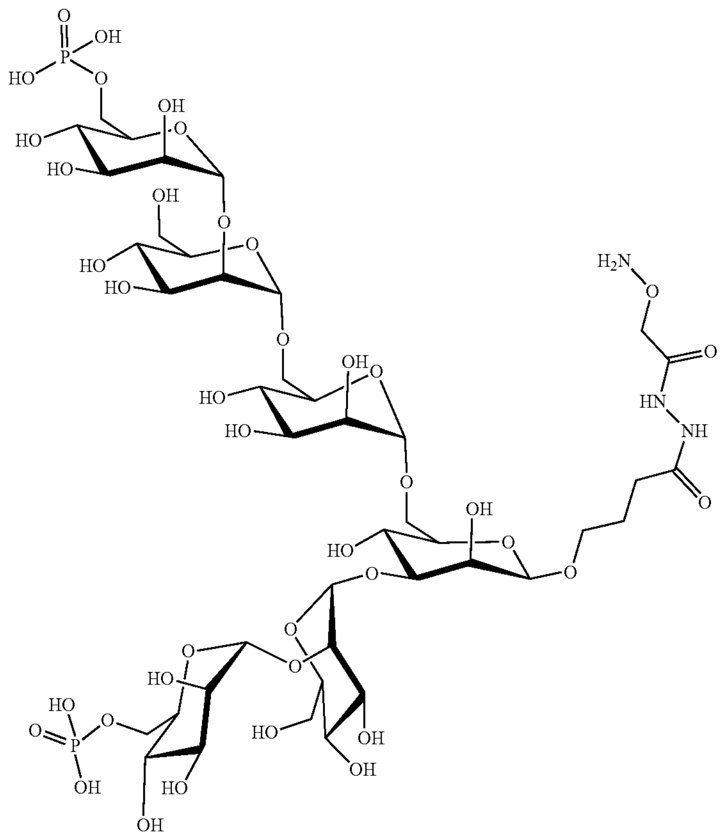

Intermediate (int-CC6) was obtained using the synthetic methods described in WO2008089403A2.

Synthesis of (2-((2R,3S,4S,5S,6S)-6-(2-(aminooxy)ethoxy)-3,4,5-trihydroxytetrahydro-2H-pyran-2-yl)ethyl)phosphonic acid (int-CC7)

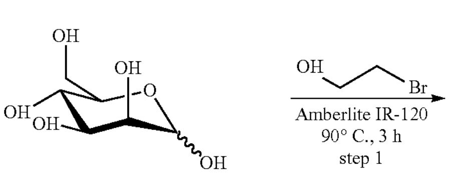

-continued

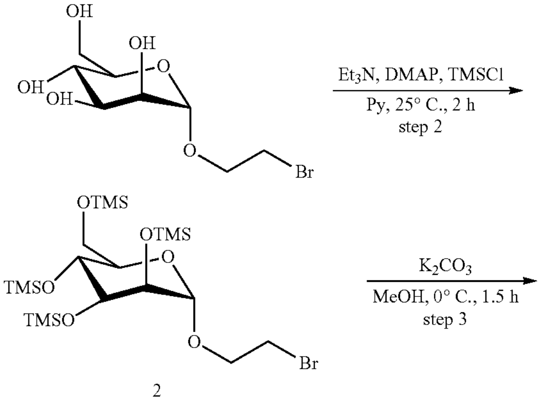

2

-continued

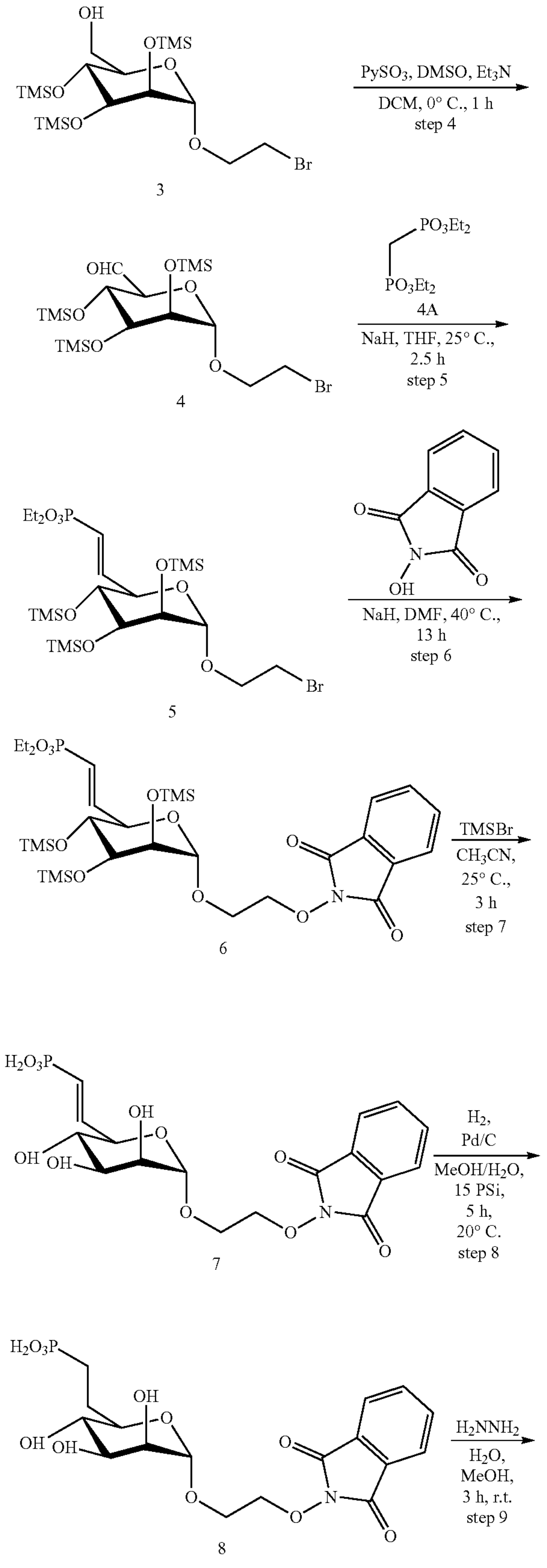

3

4

5

6

7

8

-continued

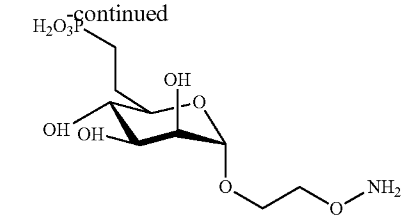

(int-CC7)

Step 1: Amberlite IR-120 (90.0 g, 499.6 mmol, 1.0 eq) was added to 2-bromoethanol (600.0 g, 4.8 mol, 340.9 mL, 9.6 eq) and stirred at 90° C. for 0.5 h. D-(+)-mannose (90.0 g, 499.6 mmol, 1.0 eq) was then added and the mixture was stirred at 90° C. for 2.5 h., then filtered and concentrated. The residue was purified by column chromatography ($SiO_2$, Ethyl acetate/MeOH=20/1 to 7/1) to give (2S,3S,4S,5S,6R)-2-(2-bromoethoxy)-6-(hydroxymethyl)tetrahydro-2H-pyran-3,4,5-triol. TLC: Ethyl acetate/MeOH=5/1, Rt=0.41

Step 2: To a solution of (2S,3S,4S,5S,6R)-2-(2-bromoethoxy)-6-(hydroxymethyl)tetrahydro-2H-pyran-3,4,5-triol (50.0 g, 174.2 mmol, 1.0 eq) in pyridine (400 mL) was added TMSCI (113.5 g, 1.04 mol, 132.6 mL, 6.0 eq) at 0° C. The mixture was stirred at 30° C. for 2 hr. and then concentrated. The residue was diluted with ethyl acetate (1000 mL) and extracted with $H_2O$ (1000 mL). The organic layers were concentrated under reduced pressure to give a residue. The crude compound 2 which was used into the next step without further purification. TLC: Petroleum ether/Ethyl acetate=5/1, $R_f$=0.58

Step 3: To a solution of compound 2 (75.0 g, 130.3 mmol, 1.0 eq) in MeOH (300 mL) was added $K_2CO_3$ (2.40 g, 17.4 mmol, 75.0 mL, 0.032M in MeOH). The mixture was stirred at 0° C. for 1.5 hr. AcOH (0.1 mL) was added and the mixture was then concentrated under reduced pressure to give a residue. The residue was purified by column chromatography ($SiO_2$, Petroleum ether/Ethyl acetate=20/1 to 10/1) to give compound 3. TLC: Petroleum ether/ethyl acetate=5/1, $R_f$=0.48

Step 4: To a solution of compound 3 (55.0 g, 109.2 mmol, 1.0 eq) in DCM (400 mL) was added DMSO (68.3 g, 873.6 mmol, 68.3 mL, 8.0 eq), $Et_3N$ (33.2 g, 327.6 mmol, 45.6 mL, 3.0 eq), and $PySO_3$ (52.1 g, 327.6 mmol, 3.0 eq). The mixture was stirred at 0° C. for 1 hr. and then extracted with ethyl acetate (800 mL×2) and $H_2O$ (1000 mL). The combined organic layers were dried over $Na_2SO_4$, filtered and concentrated under reduced pressure to give crude product 4 which was used into the next step without further purification. $^1H$ NMR: (400 MHz $CDCl_3$) δ ppm 9.62 (s, 1H), 4.79 (s, 1H), 3.55-4.13 (m, 8H), 3.33-3.53 (m, 4H), 3.09 (m, 1H), 0.03-0.18 (m, 27H).

Step 5: To a solution of NaH (8.77 g, 219.3 mmol, 60% purity, 2.0 eq) in THF (350 mL) was added 4A (63.2 g, 219.3 mmol, 2.0 eq) stirred for 1 h, and compound 4 (55.0 g, 109.6 mmol, 1.0 eq) was added. The mixture was stirred at 25° C. for 1.5 h. and then concentrated under reduced pressure to remove solvent. The residue was diluted with DCM (1000 mL) and extracted with $H_2O$ (1000 mL). The organic layers were concentrated under reduced pressure to give a residue. The residue was purified by column chromatography ($SiO_2$, Petroleum ether/ethyl acetate=20/1 to 5/1) to give compound 5. TLC: Petroleum ether/ethyl acetate=2/1, $R_f$=0.11. $^1H$ NMR: (400 MHz $CDCl_3$) δ ppm 6.60-6.83 (m, 1H), 5.77-6.03 (m, 1H), 4.54 (d, J=2.00 Hz, 1H), 3.87-4.12 (m, 5H), 3.71-3.84 (m, 1H), 3.45-3.71 (m, 4H), 3.22-3.40 (m, 2H), 1.07-1.27 (m, 6H), 0.00-0.10 (m, 27H).

Step 6: To a solution of NaH (2.46 g, 61.5 mmol, 60% purity, 1.7 eq) in DMF (250 mL) was added 2-hydroxyisoindoline-1,3-dione (8.85 g, 54.27 mmol, 1.5 eq), after 1 h, compound 5 (23.0 g, 36.2 mmol, 1.0 eq) was added. The mixture was stirred at 40° C. for 12 hr. and the reaction mixture was then concentrated and residue diluted with $CH_3CN$ 500 mL and filtered. The filter cake washed with $CH_3CN$ (200 mL), then organic layers concentrated under reduced pressure to give crude product 6 which was used into the next step without further purification. LC-MS: $t_R$=1.60 min, MS cal.: 717.9, $[M+1]^+$=718.3

Step 7: To a solution of compound 6 (15.0 g, 20.9 mmol, 1.0 eq) in $CH_3CN$ (150 mL) was added pyridine (4.13 g, 52.2 mmol, 4.22 mL, 2.5 eq) and TMSBr (31.9 g, 208.9 mmol, 27.1 mL, 10 eq). The mixture was stirred at 20° C. for 3 hr. and then concentrated under reduced pressure to give a residue. The residue was purified by prep-HPLC (neutral condition). Column: Phenomenex luna (2) C18 250*50 10u; mobile phase: [water (0.1% TFA)-ACN]; B %: 5%-30%, 20 min; to give compound 7. LC-MS: $t_R$=0.51 min, MS cal.: 445.1, $[M+1]^+$=446.1, $^1$H NMR: (400 MHz MeOD) δ ppm 7.81-7.94 (m, 4H), 6.76-6.95 (m, 1H), 6.09-6.29 (m, 1H), 4.88 (s, 1H), 4.38 (t, J=4.00 Hz, 2H), 4.12-4.20 (m, 1H), 3.99 (m, 1H), 3.81-3.89 (m, 1H), 3.77 (dd, J=3.20, 1.60 Hz, 1H), 3.64 (dd, J=9.20, 3.20 Hz, 1H), 3.44-3.54 (m, 1H).

Step 8: To a solution of compound 7 (4.00 g, 8.9 mmol, 1.0 eq) in MeOH (40 mL) and $H_2O$ (20 mL) was added Pd/C (2.00 g, 10% purity) under $N_2$ atmosphere. The suspension was degassed and purged with $H_2$ for 3 times. The mixture was stirred under $H_2$ (15 Psi) at 20° C. for 5 hr. The reaction mixture was then filtered and concentrated under reduced pressure to give a residue. The residue was purified by prep-HPLC (TFA condition). Column: Phenomenex luna (2) C18 250*50 10u; mobile phase: [water (0.1% TFA)-ACN]; B %: 5%-30%, 20 min. to give compound 8. LC-MS: $t_R$=0.91 min, MS cal.: 447.1, $[M+1]^+$=448.1.

Step 9: To a solution of compound 8 (1.30 g, 2.9 mmol, 1.0 eq) in $H_2O$ (5 mL) and MeOH (5 mL) was added $H_2NNH_2$ (436.5 mg, 8.7 mmol, 423.7 uL, 3 eq). The mixture was stirred at 25° C. for 3 hr. The reaction mixture was then concentrated under reduced pressure to give a residue and the residue was purified by prep-HPLC (HCl condition). Column: Phenomenex luna (2) C18 250*50 10 μm; mobile phase: [water(0.05% HCl)-ACN]; B %: 0%-0%, 10 min. to give (2-((2R,3S,4S,5S,6S)-6-(2-(aminooxy)ethoxy)-3,4,5-trihydroxytetrahydro-2H-pyran-2-yl)ethyl)phosphonic acid (int-CC7). LC-MS: $t_R$=0.16 min, MS cal.: 317.1, $[M+1]^+$=318.1 $^1$H NMR: (400 MHz $D_2O$) δ ppm 4.79 (s, 2H), 4.10 (t, J=4.00 Hz, 2H), 3.81-3.96 (m, 2H), 3.72 (m, 2H), 3.36-3.57 (m, 2H), 1.92-2.10 (m, 1H), 1.69-1.87 (m, 1H), 1.40-1.67 (m, 2H).

Synthesis of (1-((1S,2R,3R,4R,5S)-4-acetamido-2,3-dihydroxy-6,8-dioxabicyclo[3.2.1]octan-1-yl)-2,5,8,11-tetraoxatetradecan-14-oic acid (int-CC8)

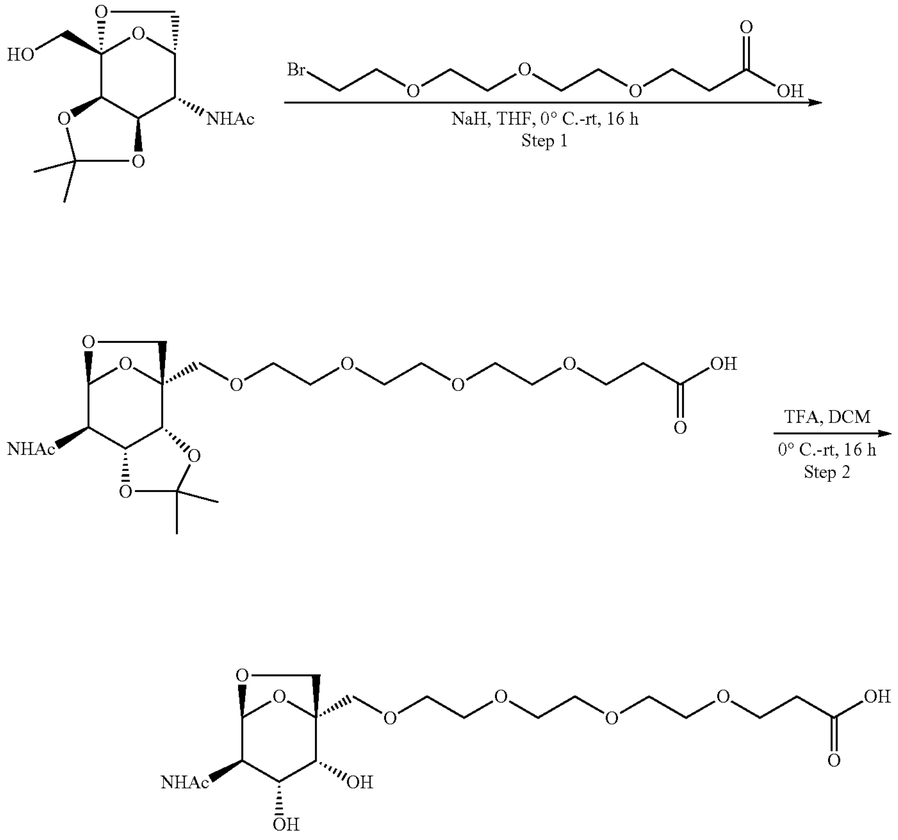

(int-CC8)

Step 1: A stirred solution of N-((3aR,4S,7S,8R,8aR)-4-(hydroxymethyl)-2,2-dimethylhexahydro-4,7-epoxy[1,3]dioxolo[4,5-d]oxepin-8-yl)acetamide (int-BB3) (315 mg, 1.15 mmol) in THF (5 mL) was cooled to 0° C. and 60% sodium hydride (80 mg, 2.3 mmol) was added and the reaction mixture was stirred for 1 hour. (3-(2-(2-(2-bromoethoxy) ethoxy) ethoxy)propanoic acid (650 mg, 1.95 mmol, 1.7 eq) in THF (3 mL) was then added dropwise at 0° C. and the reaction mixture stirred at room temperature for 16 h. The reaction was concentrated under reduced pressure to give crude 1-((3aR,4S,7S,8R,8aR)-8-acetamido-2,2-dimethyltetrahydro-4,7-epoxy[1,3]dioxolo[4,5-d]oxepin-4 (5H)-yl)-2,5,8,11-tetraoxatetradecan-14-oic acid which was triturated with ethyl acetate (2×10 ml), then methanol (10 ml) was added and the mixture was filtered. The filtrate was concentrated under reduced pressure to 1-((3aR,4S,7S,8R,8aR)-8-acetamido-2,2-dimethyltetrahydro-4,7-epoxy[1,3]dioxolo[4,5-d]oxepin-4 (5H)-yl)-2,5,8,11-tetraoxatetradecan-14-oic acid. LC-MS: [M+1]=495.25 Step 2: To a stirred solution of 1-((3aR,4S,7S,8R,8aR)-8-acetamido-2,2-dimethyltetrahydro-4,7-epoxy[1,3]dioxolo[4,5-d]oxepin-4 (5H)-yl)-2,5,8,11-tetraoxatetradecan-14-oic acid (600 mg, 1.25 mmol, 1.0 eq) in dichloromethane (10 mL) was cooled to 0° C. and was added trifluoro acetic acid (1 mL) dropwise at 0° C. and was stirred at rt for 16 h. The reaction was concentrated under reduced pressure to give crude 1-((1S,2R,3R,4R,5S)-4-acetamido-2,3-dihydroxy-6,8-dioxabicyclo[3.2.1]octan-1-yl)-2,5,8,11-tetraoxatetradecan-14-oic acid, which was triturated with 20% ethyl acetate and hexane (3×10 ml), the gummy liquid was lyophilized to give 1-((1S,2R,3R,4R,5S)-4-acetamido-2,3-dihydroxy-6,8-dioxabicyclo[3.2.1]octan-1-yl)-2,5,8,11-tetraoxatetradecan-14-oic acid (int-CC8). LC-MS: [M−1]=436.15.

Synthesis of 2,3,5,6-tetrafluorophenyl-1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)-6-oxo-2,9,12,15,18-pentaoxa-5-azahenicosan-21-oate (int-CC9)

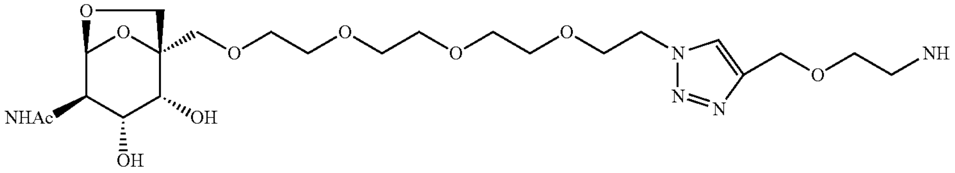

(int-CC3)

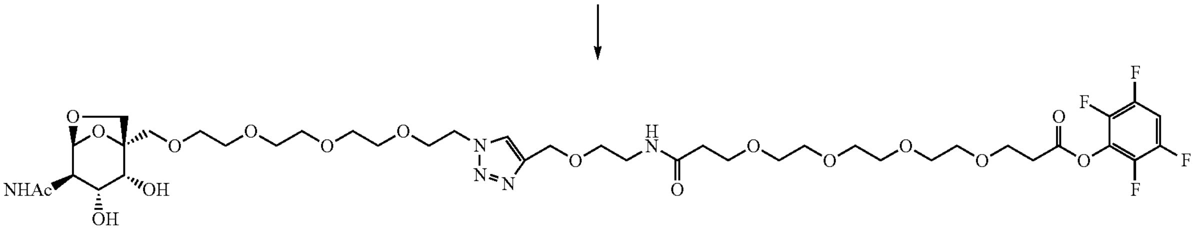

(int-CC9)

To N-((1S,2R,3R,4R,5S)-1-(13-(4-((2-aminoethoxy) methyl)-1H-1,2,3-triazol-1-yl)-2,5,8,11-tetraoxatridecyl)-2,3-dihydroxy-6,8-dioxabicyclo[3.2.1]octan-4-yl)acetamide (int-CC3) (44 mg, 0.082 mmol) in DMF (2 mL) at room temperature was added Bis-dPEG4-TFP ester (CAS Number: 1446282-42-3) (53.6 mg, 0.091 mmol) and DIPEA (0.043 mL, 0.247 mmol). The mixture was stirred at room temperature for 2 h, and then purified by reverse phase silica gel chromatography to give 2,3,5,6-tetrafluorophenyl 1-(1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)-6-oxo-2,9,12,15,18-pentaoxa-5-azahenicosan-21-oate (int-CC9). Analytical method 7: $t_R$=0.87 min.; MS m/z 958.7 $[M+H]^+$.

Type DD:

Synthesis of Intermediate (int-DD1b)

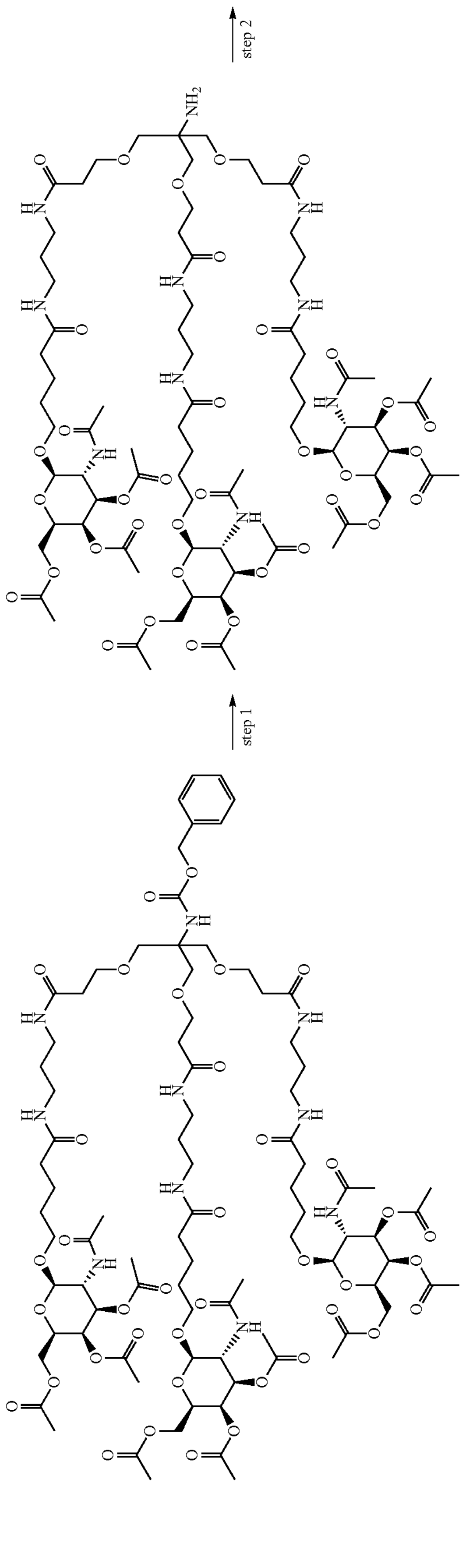
(int-CC1)
(int-DD1a)

-continued
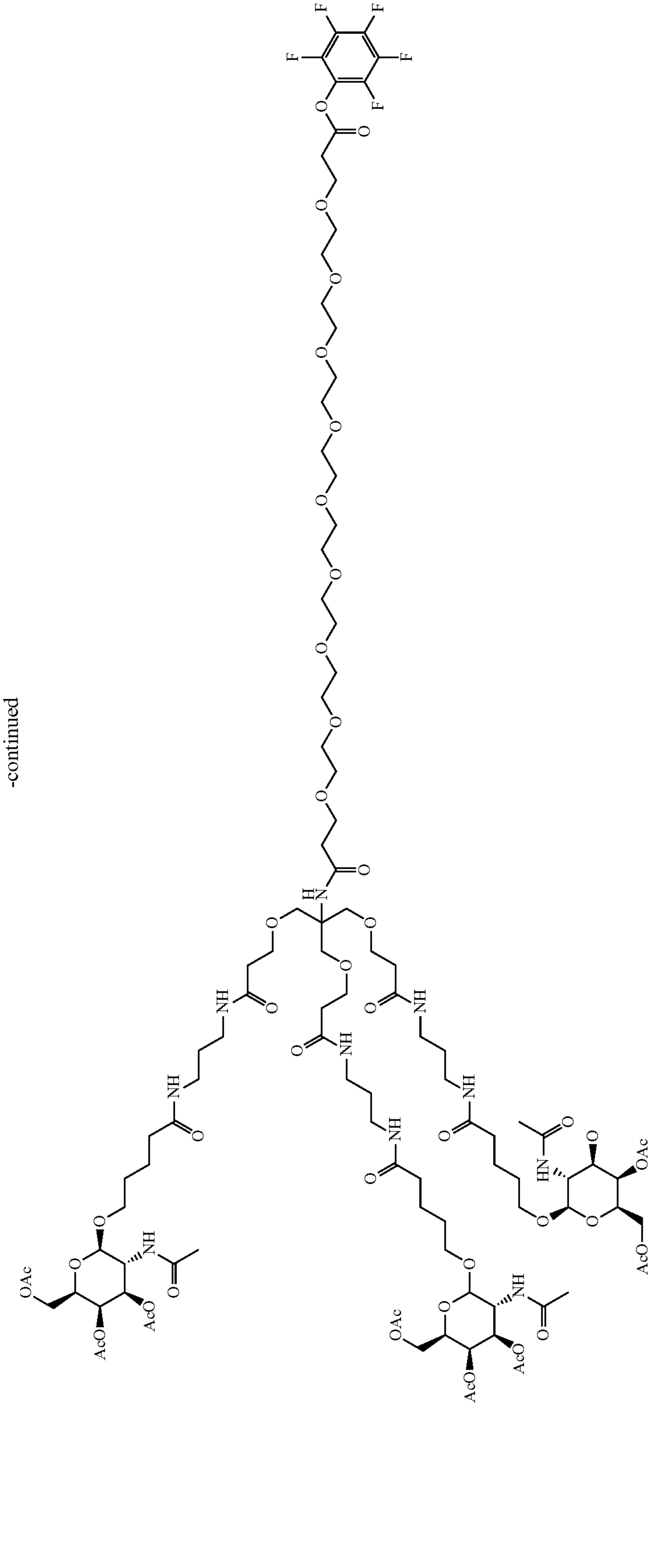
(int-DD1b)

Step 1: Pd/C 50% in water (60.7 mg, 0.057 mmol) was added to Intermediate (int-CC1) (550 mg, 0.285 mmol) in methanol (2 mL) at room temperature and the mixture was then put under 1 atm of $H_2$. The mixture was then stirred for 16 hours, and then filtered and concentrated in vacuo to give Intermediate (int-DD1a). Analytical method 7: Rt.=0.79 min, MS m/z 898.0 $[(M+H)/2]^+$.

Step 2: To a solution of Intermediate (int-DD1a) (0.511 g, 0.285 mmol) in DMF (2 mL) at room temperature was added Bis-dPEG9-PFP ester (CAS Number: 1334170-00-1) (0.290 g, 0.342 mmol) and DIPEA (0.149 mL, 0.855 mmol). The mixture was stirred at room temperature for 2 hr to give Intermediate (int-DD1b). Analytical method 7: Rt.=0.96 min.; MS m/z 1229.8.

Synthesis of 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-(((((5aS,6R,6aR)-1-(6-((1R,2R)-2-hydroxy-1-(((R)-1-hydroxy-3-oxopropan-2-yl)oxy)-3-oxopropoxy)hexyl)-1,4,5,5a,6,6a, 7,8-octahydrocyclopropa[5,6]cycloocta[1,2-d][1,2,3]triazol-6-yl)methoxy)carbonyl)amino)-1-oxohexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (int-DD2)

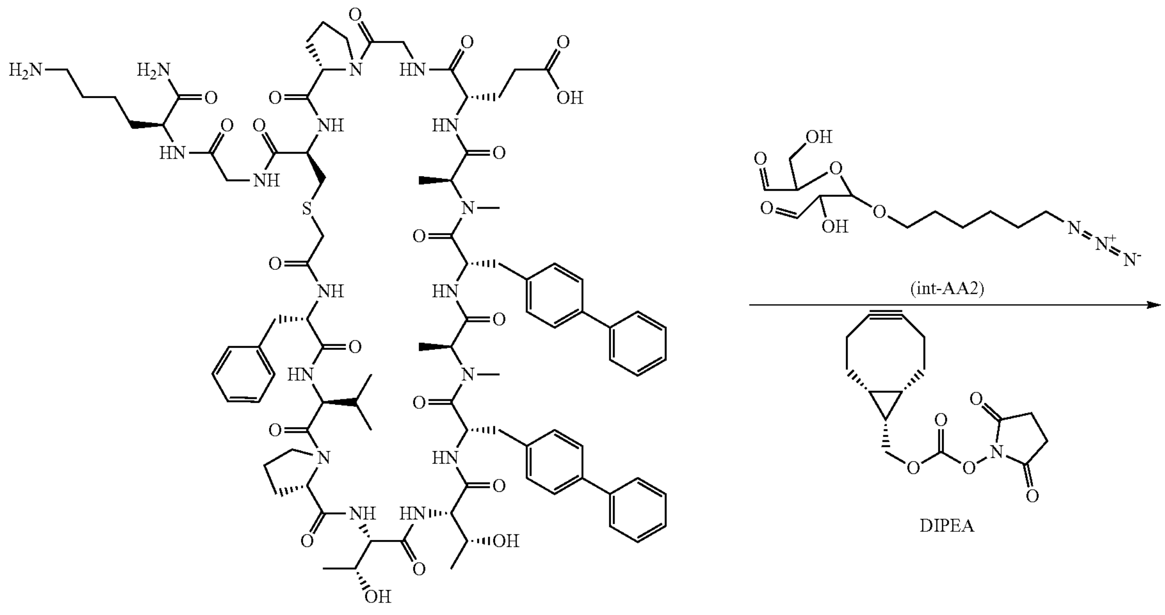

(C1)

-continued

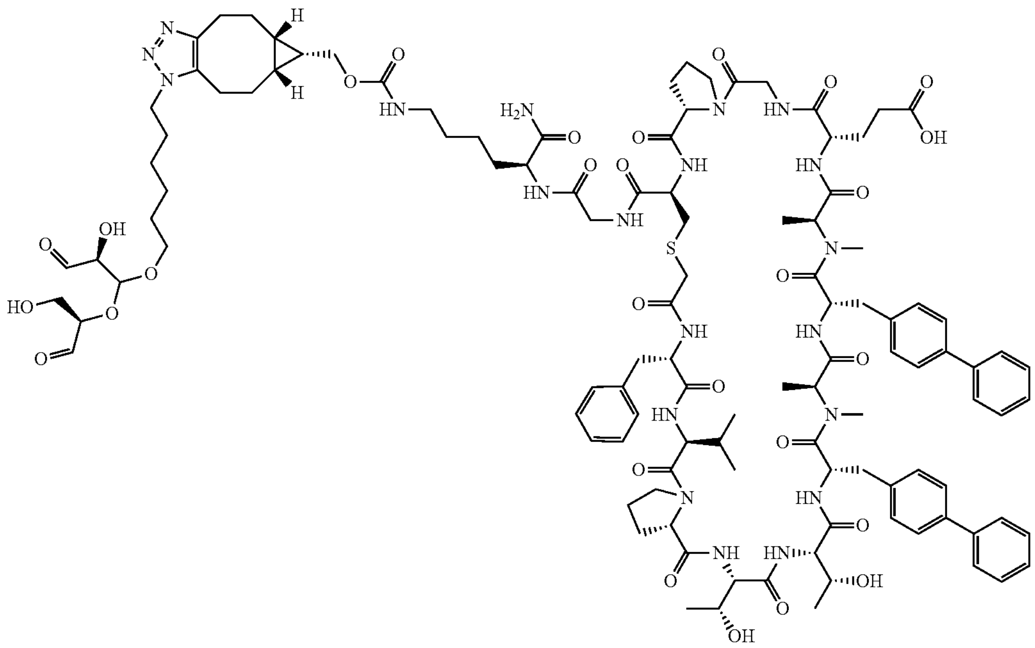

(int-DD2)

To 3-((6-azidohexyl)oxy)-2-hydroxy-3-((1-hydroxy-3-oxopropan-2-yl)oxy)propanal (int-AA2) (4.67 mg, 0.015 mmol) in acetonitrile (0.3 mL) and DMSO (0.1 mL) at room temperature was added ((1R,8S,9s)-bicyclo[6.1.0]non-4-yn-9-yl)methyl (2,5-dioxopyrrolidin-1-yl) carbonate (obtained from Chiroblock GmbH) (4.49 mg, 0.015 mmol), cyclic peptide (C1) (29.5 mg, 0.015 mmol) and DIPEA (5.38 μl, 0.031 mmol). The mixture was stirred at room temperature for 16 h, and then purified by reverse phase silica gel chromatography to obtain Intermediate (int-DD2). Analytical method 7: $t_R$=1.09 min, MS m/z 1142.9 $[(M+H)/2]^+$.

Synthesis of 3-((6S,9S,12S,15S,18S,21S,24S,27S,29aS,35S,38S,44R,46aS)-15,21-bis([1,1'-biphenyl]-4-ylmethyl)-38-benzyl-44-(((S)-4-carbamoyl-2,10,25-trioxo-25-(2,3,5,6-tetrafluorophenoxy)-13,16,19,22-tetraoxa-3,9-diazapentacosyl)carbamoyl)-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (int-DD3)

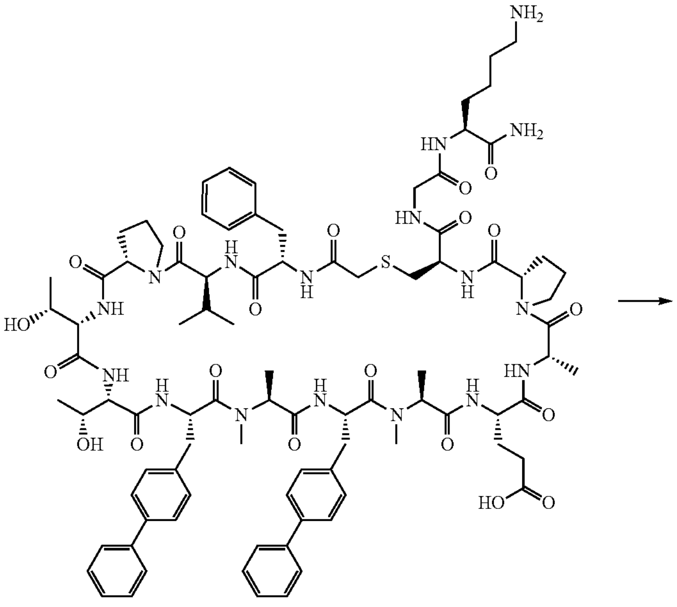

(C1)

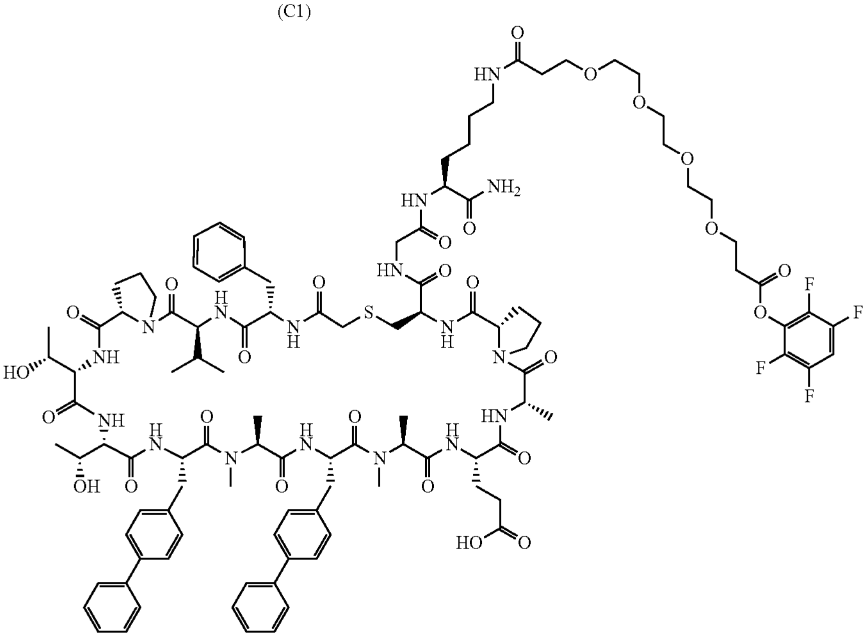

(int-DD3)

To cyclic peptide (C1) (150 mg, 0.083 mmol) in DMF (1.5 mL) at room temperature was added Bis-dPEG4-TFP ester (CAS Number: 1446282-42-3) (49.1 mg, 0.083 mmol) and DIPEA (0.058 mL, 0.332 mmol). The mixture was stirred at room temperature for 2 h, and then purified by reverse phase silica gel chromatography to obtain Intermediate (int-DD3). Analytical method 7: $t_r$=1.17 min, MS m/z 1115.4 $[(M+H)/2]^+$.

Synthesis of 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-(((((5aS,6R,6aR)-1-(6-((1R,2R)-2-hydroxy-1-(((R)-1-hydroxy-3-oxopropan-2-yl)oxy)-3-oxopropoxy)hexyl)-1,4,5,5a,6,6a, 7,8-octahydrocyclopropa[5,6]cycloocta[1,2-d][1,2,3]triazol-6-yl)methoxy)carbonyl)amino)-1-oxo-hexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (int-DD4)

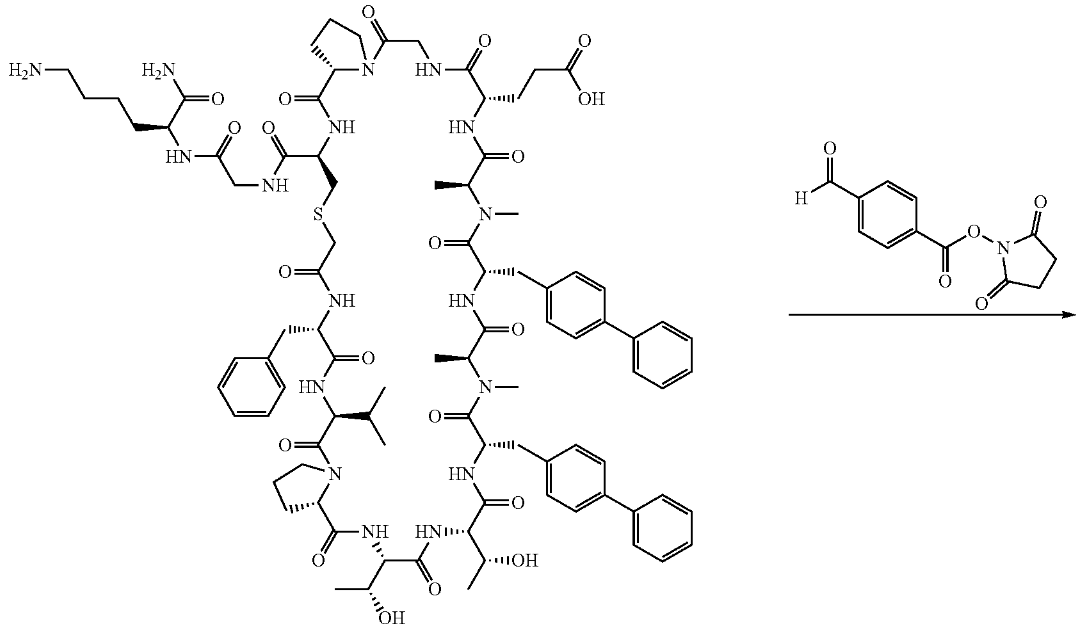

(C1)

-continued
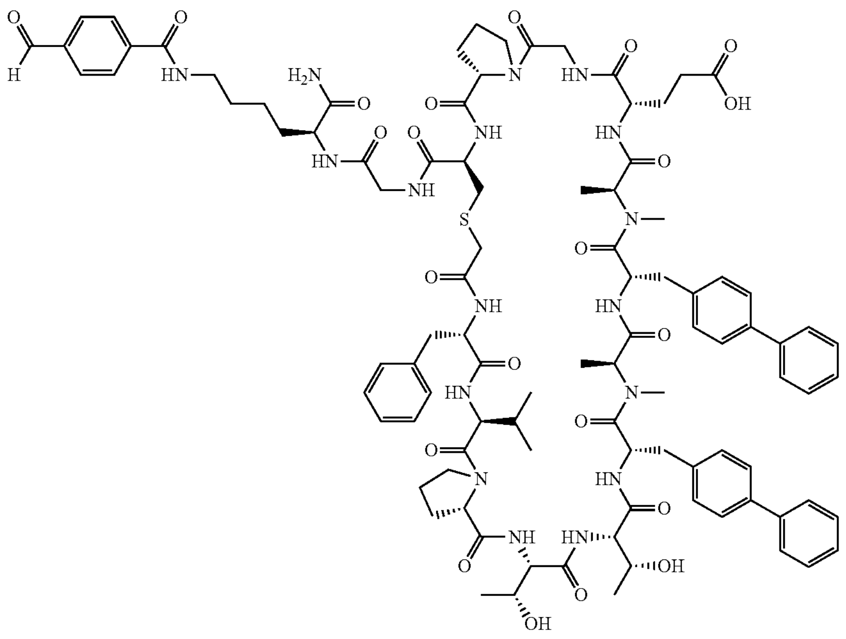
(int-DD4)
To cyclic peptide (C1) (20 mg, 10.42 μmol) at room temperature was added DMF (500 μL), 4-formylbenzoate NHS ester (3.86 mg, 0.016 mmol) and DIPEA (5.46 μL, 0.031 mmol). The mixture was stirred for 16 h at room temperature and then purified by reverse phase silica gel chromatography (5-95% acetonitrile/water with 0.1% formic acid) to give Intermediate (int-DD4). Analytical method 7: $t_R$=2.57 min, MS m/z 969.4 $[(M+H)/2]^+$ Synthesis of 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-((S)-2,6-diaminohexanamido)-1-oxohexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (int-DD5)
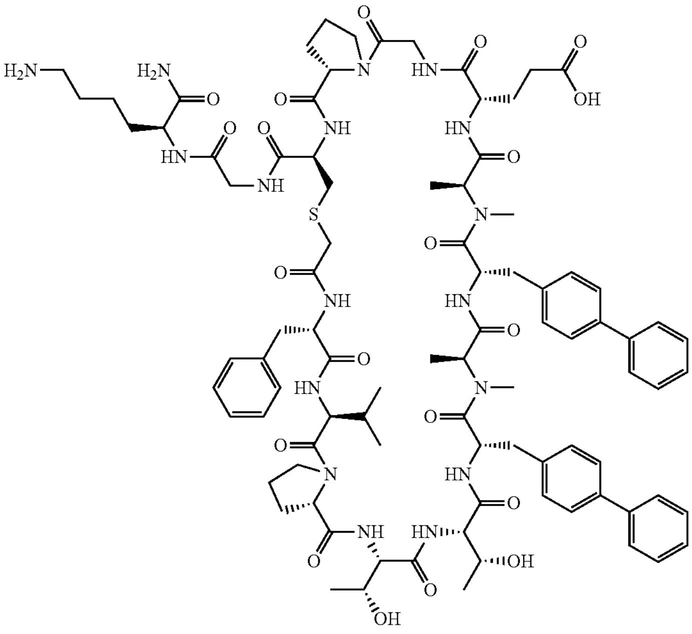
(C1)
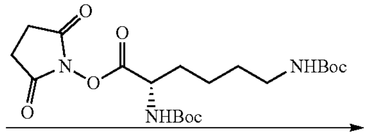
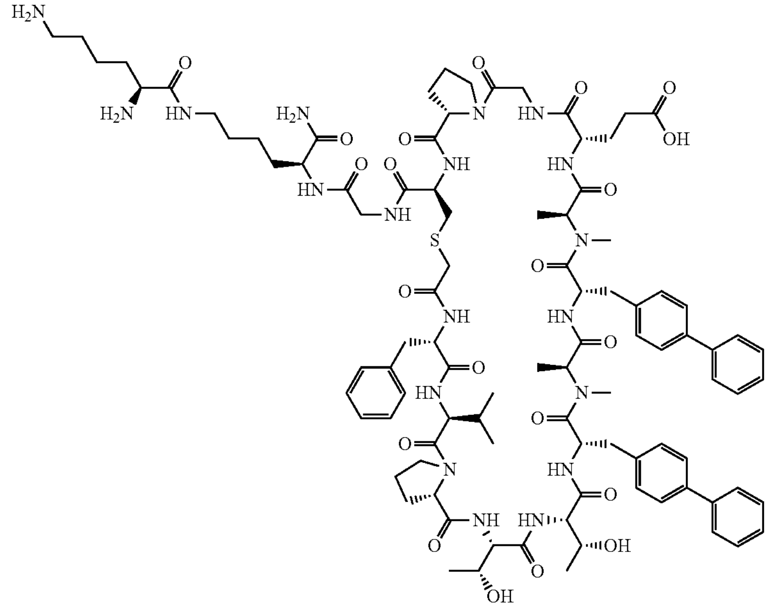
(int-DD5)

To cyclic peptide (C1) (75 mg, 0.039 mmol), Lys(Boc) NHS (17.33 mg, 0.039 mmol), DIPEA (6.83 μl, 0.039 mmol) in acetonitrile (1 mL), was add 0.1 mL water for solubility, and the mixture stirred overnight. The reaction was concentrated, treated with TFA (1 mL), stirred for 1 h, and concentrated again. The residue was dissolved in DMSO and purified by prep HPLC (25-50% ACN/water $NH_4OH$-modified on 30x50 mm C18 column). Pure fractions were combined and lyophilized to provide (int-DD5). Analytical method 2: r.t. 0.89 min ES+967.3: $[M+2H]/2^+$.

Synthesis of 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-((S)-2,6-bis(4-oxopentanamido)hexanamido)-1-oxohexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (int-DD6)

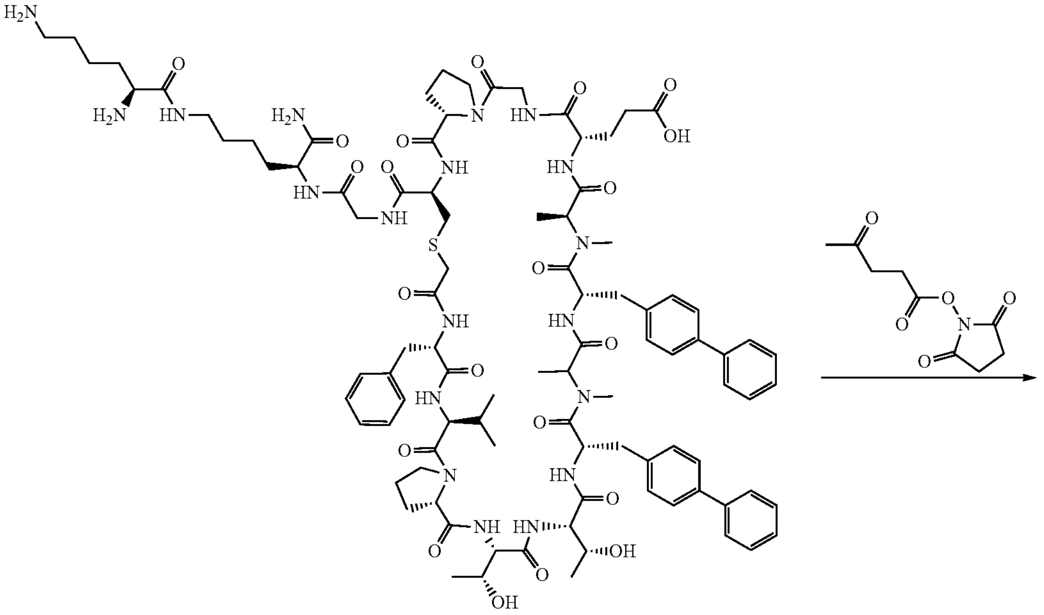

(int-DD5)

-continued
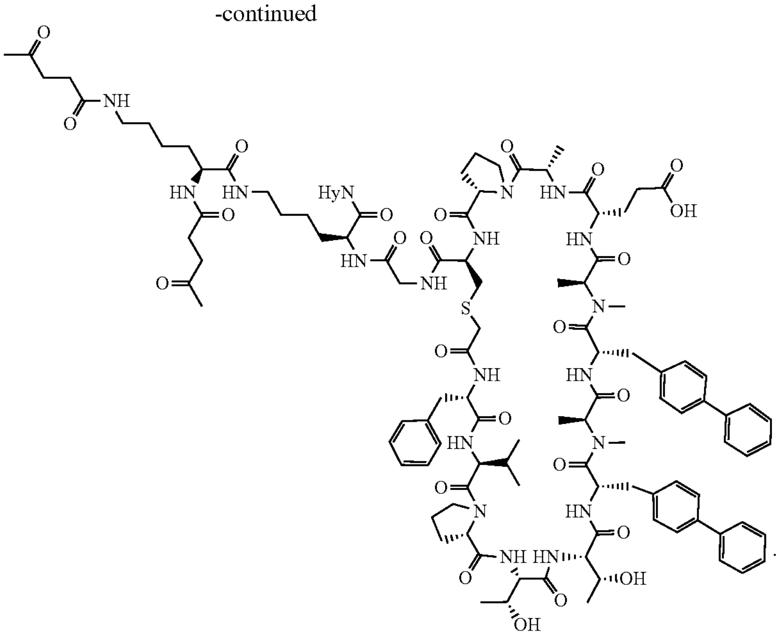
(int-DD6)
A solution of Intermediate (int-DD5) (18 mg, 9.3 μM in DMSO was treated with 2,5-dioxopyrrolidin-1-yl 4-oxopentanoate (0.9 M in DMSO, 0.021 mL, 0.019 mmol). At completion, the reaction was purified by prep HPLC (35-60% ACN/water formic acid modified on 30×50 mm 018 column) and lyophylized to provide Intermediate (int-DD6).
Synthesis of Intermediate (int-DD7)
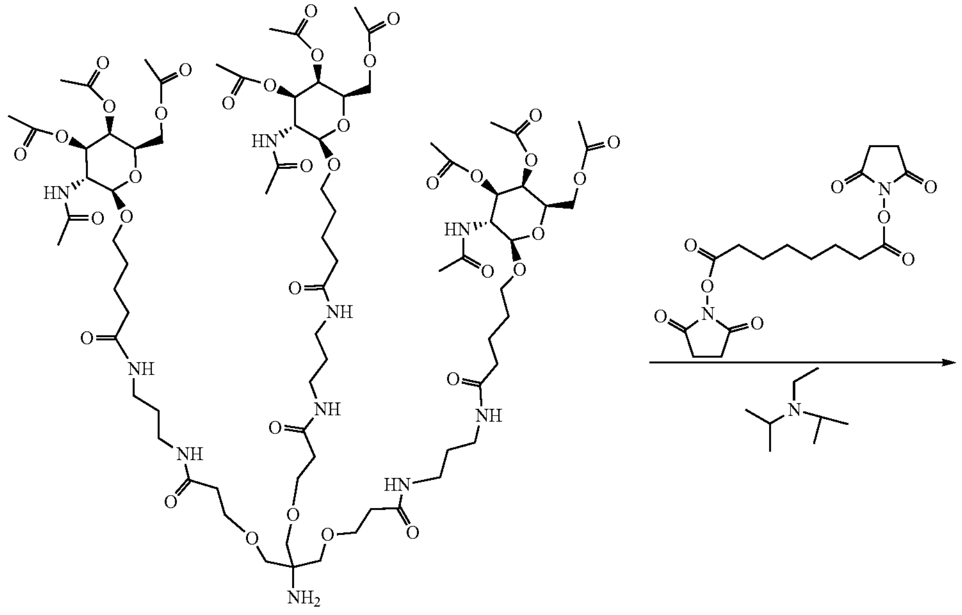
(int-DD1a)

-continued
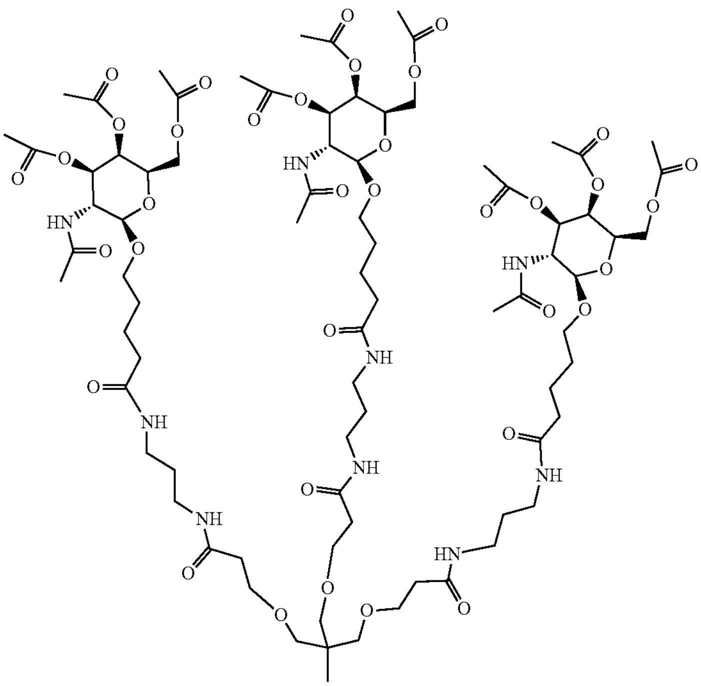
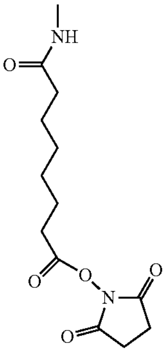
(int-DD7)

A mixture of Intermediate (int-DD1a) (136.2 mg, 0.071 mmol), bis(2,5-dioxopyrrolidin-1-yl) octanedioate (105 mg, 0.286 mmol) and DIEPA (0.050 mL, 0.286 mmol) in N,N-dimethylformamide (1.5 mL) was stirred at room temperature overnight. The reaction mixture was purified by SFC: $t_R$=4.71 min) to give Intermediate (int-DD7). Analytical method 7: $t_R$=0.78 min; m/z: 1024.0 (M+2).

Example 4: Synthesis of Exemplary Bifunctional Compounds

Example 4-1: Synthesis of Bifunctional compound 3-((6S,9S,12S,15S,18S,21S,24S,27S,29aS,35S,38S,44R,46aS)-15,21-bis([1,1'-biphenyl]-4-ylmethyl)-44-(((S)-34-(((2R,3R,4R,5R,6R)-3-acetamido-4,5-dihydroxy-6-(hydroxymethyl)tetrahydro-2H-pyran-2-yl)oxy)-19,19-bis((3-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-3-oxopropoxy)methyl)-4-carbamoyl-2,10,17,24,30-pentaoxo-21-oxa-3,9,18,25,29-pentaazatetratriacontyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (BFC-1)

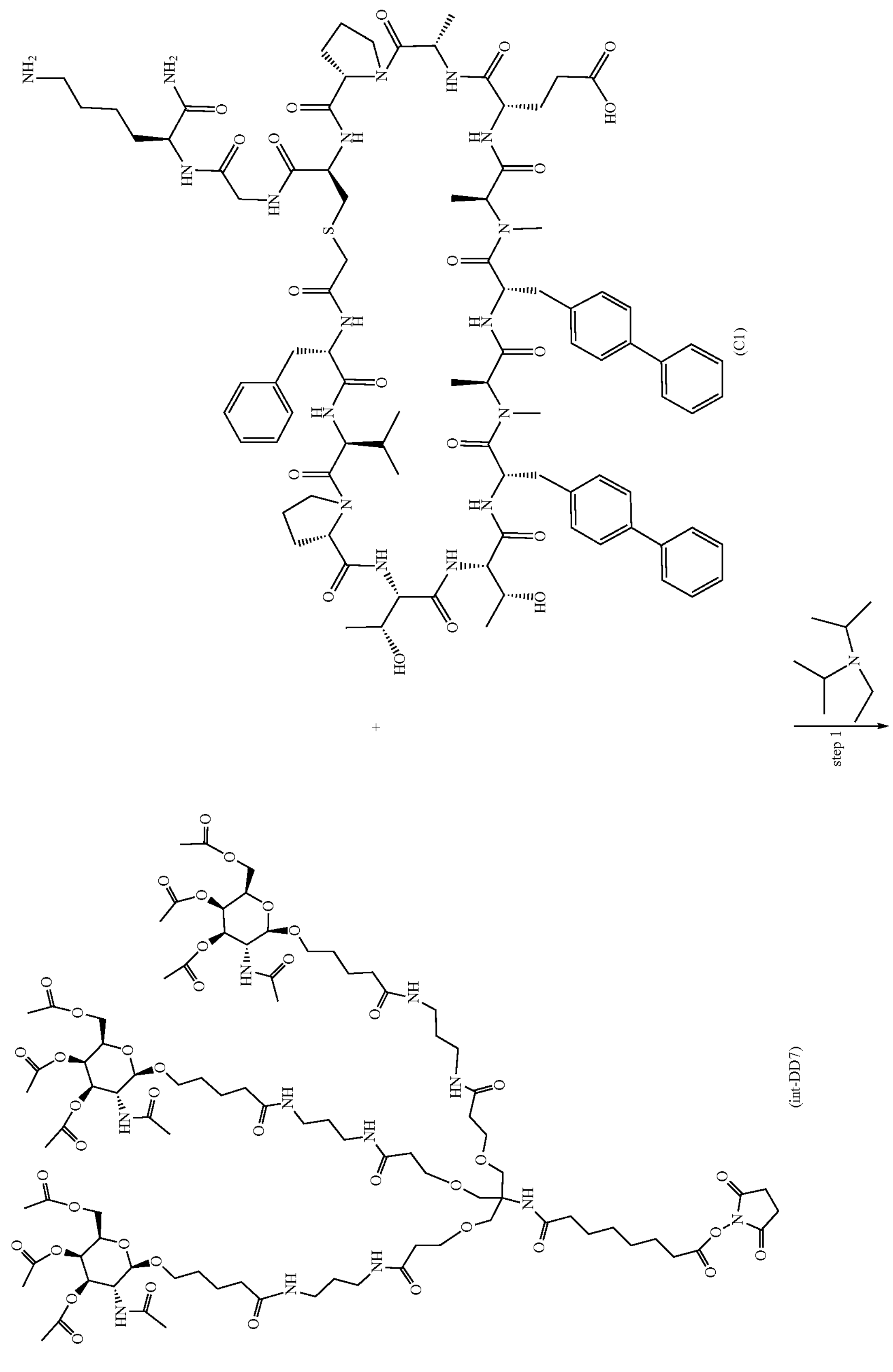
(C1)
+
(int-DD7)

-continued
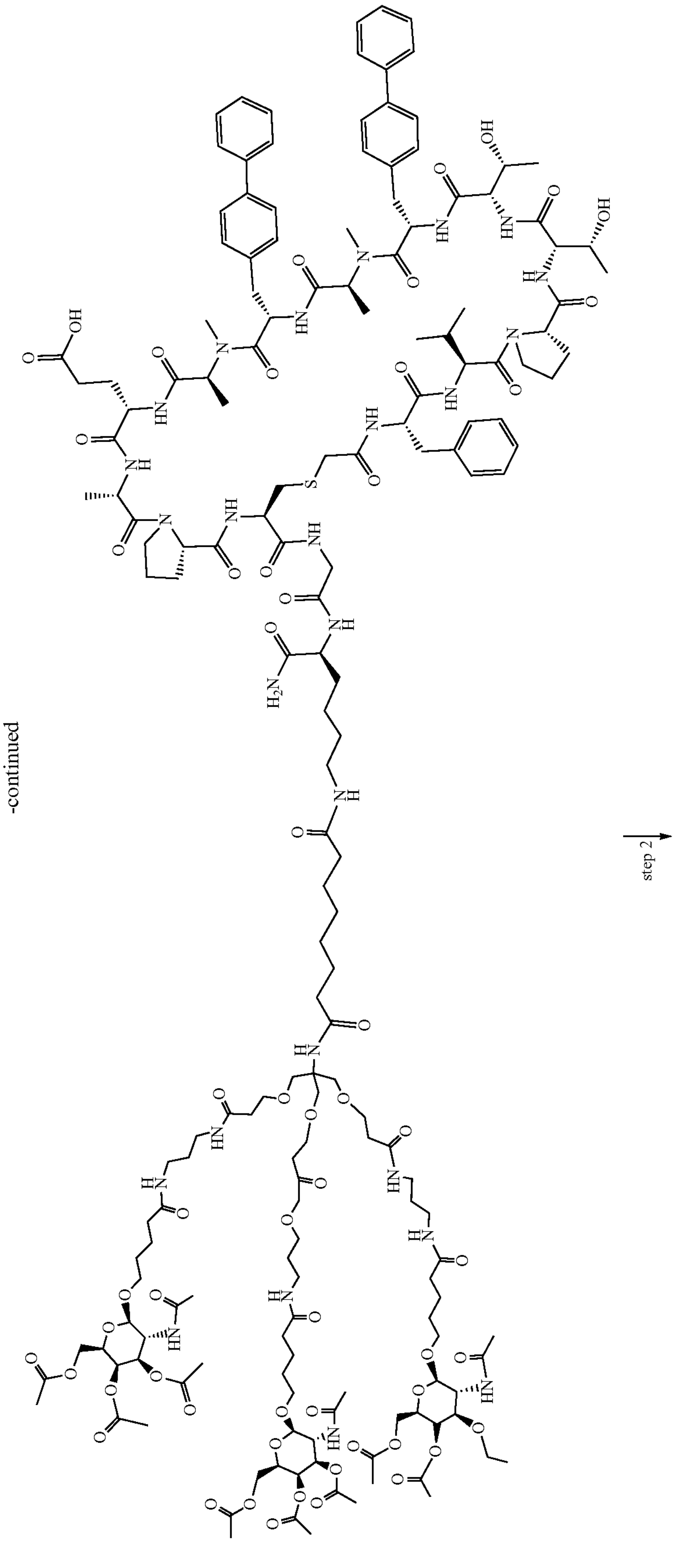

-continued
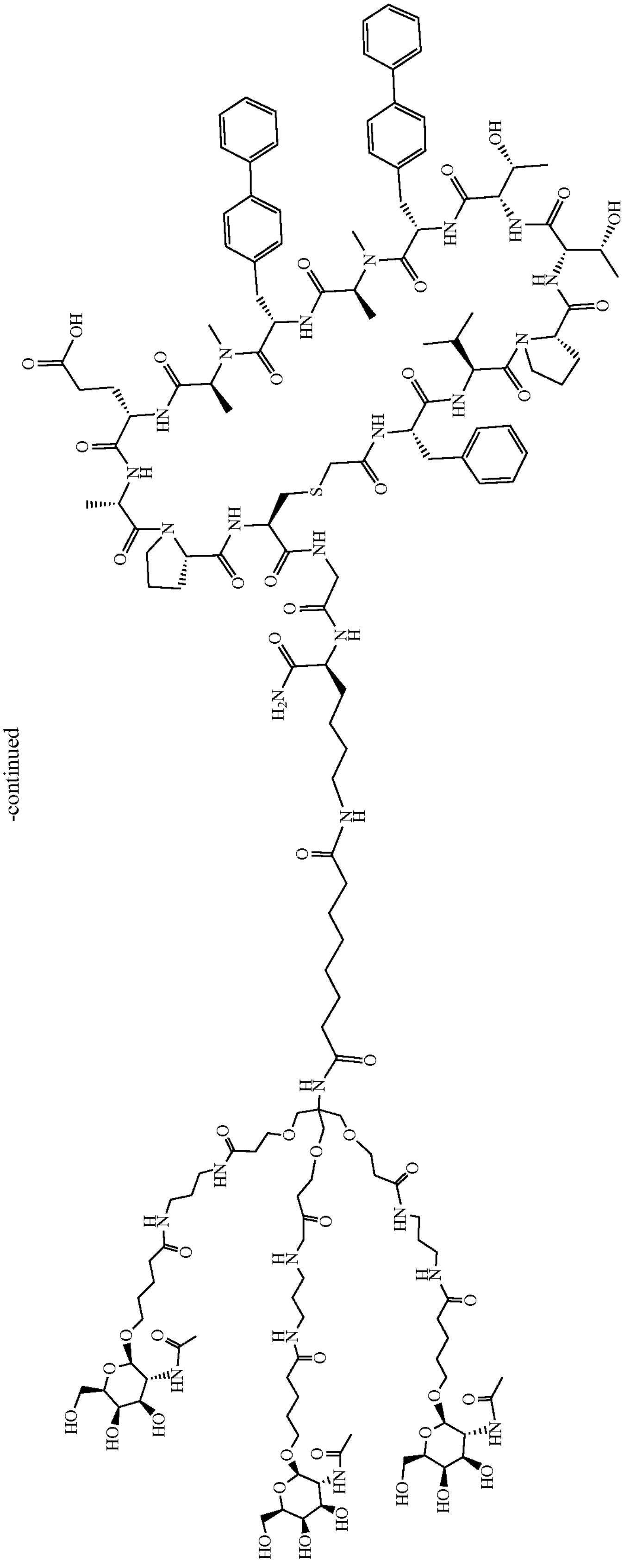
(BFC-1)

Step 1: To a solution of Intermediate (int-DD7) (4 mg, 1.954 μmol) in DMSO (300 μL) was added cyclic peptide (C1) (3.75 mg, 1.954 μmol) and DIEPA (3.41 μl, 0.020 mmol). The resultant reaction mixture was stirred at room temperature for overnight and the reaction was purified by prep HPLC. Pure fractions were collected and lyophilized to give 3-((6S,9S,12S,15S,18S,21S,24S,27S,29aS,35S,38S,44R,46aS)-15,21-bis([1,1'-biphenyl]-4-ylmethyl)-44-(((S)-34-(((2R,3R,4R,5R,6R)-3-acetamido-4,5-diacetoxy-6-(acetoxymethyl)tetrahydro-2H-pyran-2-yl)oxy)-19,19-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-4-carbamoyl-2,10,17,24,30-pentaoxo-21-oxa-3,9,18,25,29-pentaazatetratriacontyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid. Analytical method 7: $t_R$=1.05 min.; m/z: 1246.8 (M+3).

Step 2: 3-((6S,9S,12S,15S,18S,21S,24S,27S,29aS,35S,38S,44R,46aS)-15,21-bis([1,1'-biphenyl]-4-ylmethyl)-44-(((S)-34-(((2R,3R,4R,5R,6R)-3-acetamido-4,5-diacetoxy-6-(acetoxymethyl)tetrahydro-2H-pyran-2-yl)oxy)-19,19-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-4-carbamoyl-2,10,17,24,30-pentaoxo-21-oxa-3,9,18,25,29-pentaazatetratriacontyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid from step 1 (26 mg, 6.96 μmol) was dissolved in methylamine (2M) in methanol (2 ml, 4.0 mmol). The resultant mixture was stirred at room temperature for 3 hrs and then evaporated to dryness and purified by HPLC (Sunfire™ Prep 018 Column, 130 Å, 5 μm, 30×50 mm, 25-50% in 3.5 min, 75 mL/min, ACN in water with 0.1% TFA) to give (BFC-1): $t_R$=3.16 min. Analytical method 7: $t_R$=2.18 min.; m/z 1120.6 (M+3/3).

Example 4-2: Synthesis of Bifunctional compound 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-(4-((E)-((2-(2-(4-(((2R,3S,4S,5R,6R)-4-(((2R,3S,4S,5S,6R)-4,5-dihydroxy-6-(hydroxymethyl)-3-(((2R,3S,4S,5S,6R)-3,4,5-trihydroxy-6-((phosphonooxy)methyl)tetrahydro-2H-pyran-2-yl)oxy)tetrahydro-2H-pyran-2-yl)oxy)-6-((((2S,3S,4S,5S,6R)-6-((((2S,3S,4S,5S,6R)-4,5-dihydroxy-6-(hydroxymethyl)-3-(((2R,3S,4S,5S,6R)-3,4,5-trihydroxy-6-((phosphonooxy)methyl)tetrahydro-2H-pyran-2-yl)oxy)tetrahydro-2H-pyran-2-yl)oxy)methyl)-3,4,5-trihydroxytetrahydro-2H-pyran-2-yl)oxy)methyl)-3,5-dihydroxytetrahydro-2H-pyran-2-yl)oxy)butanoyl)hydrazineyl)-2-oxoethoxy)imino)methyl)benzamido)-1-oxohexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (BFC-2)

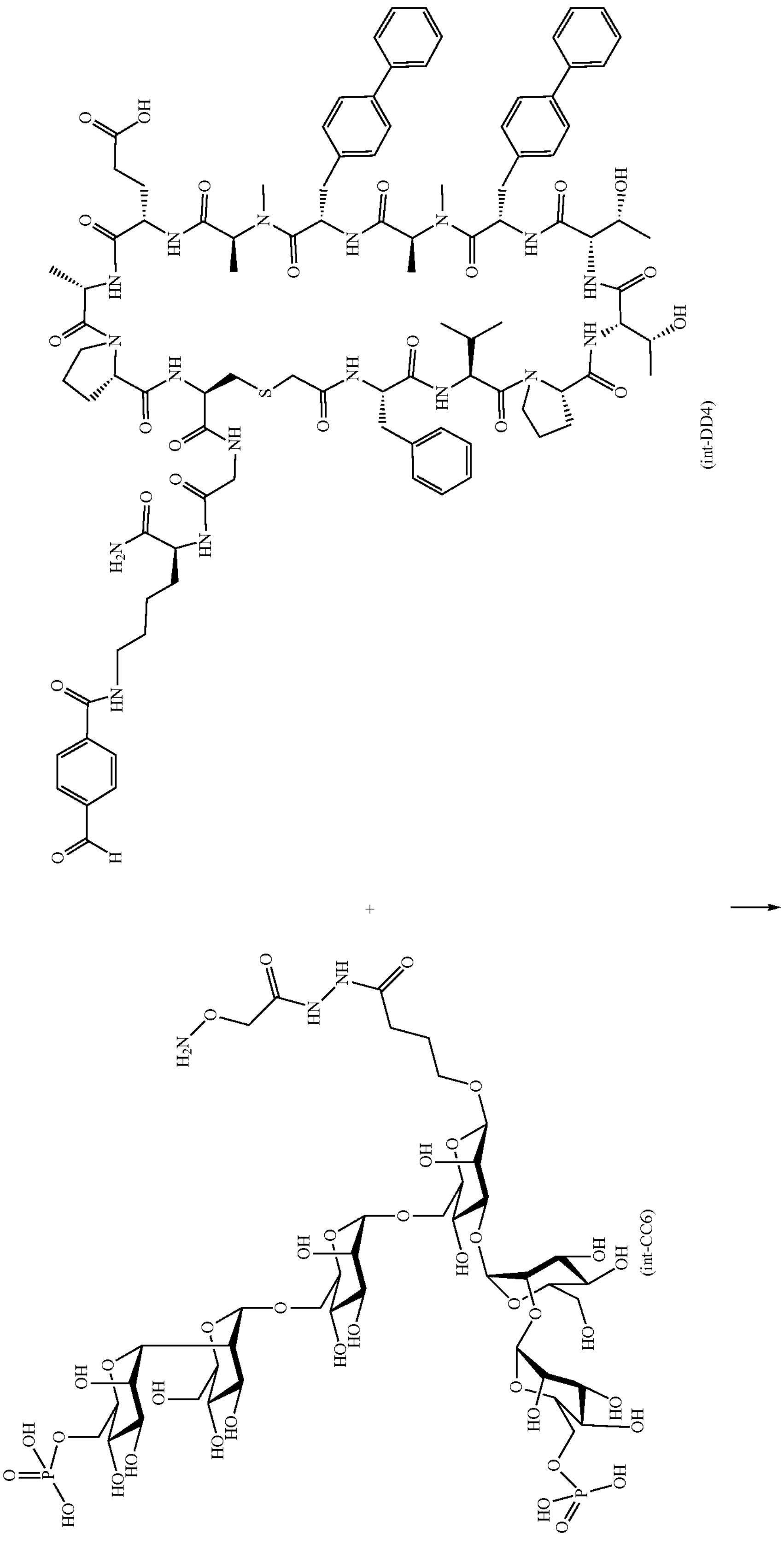
(int-DD4)
(int-CC6)

-continued
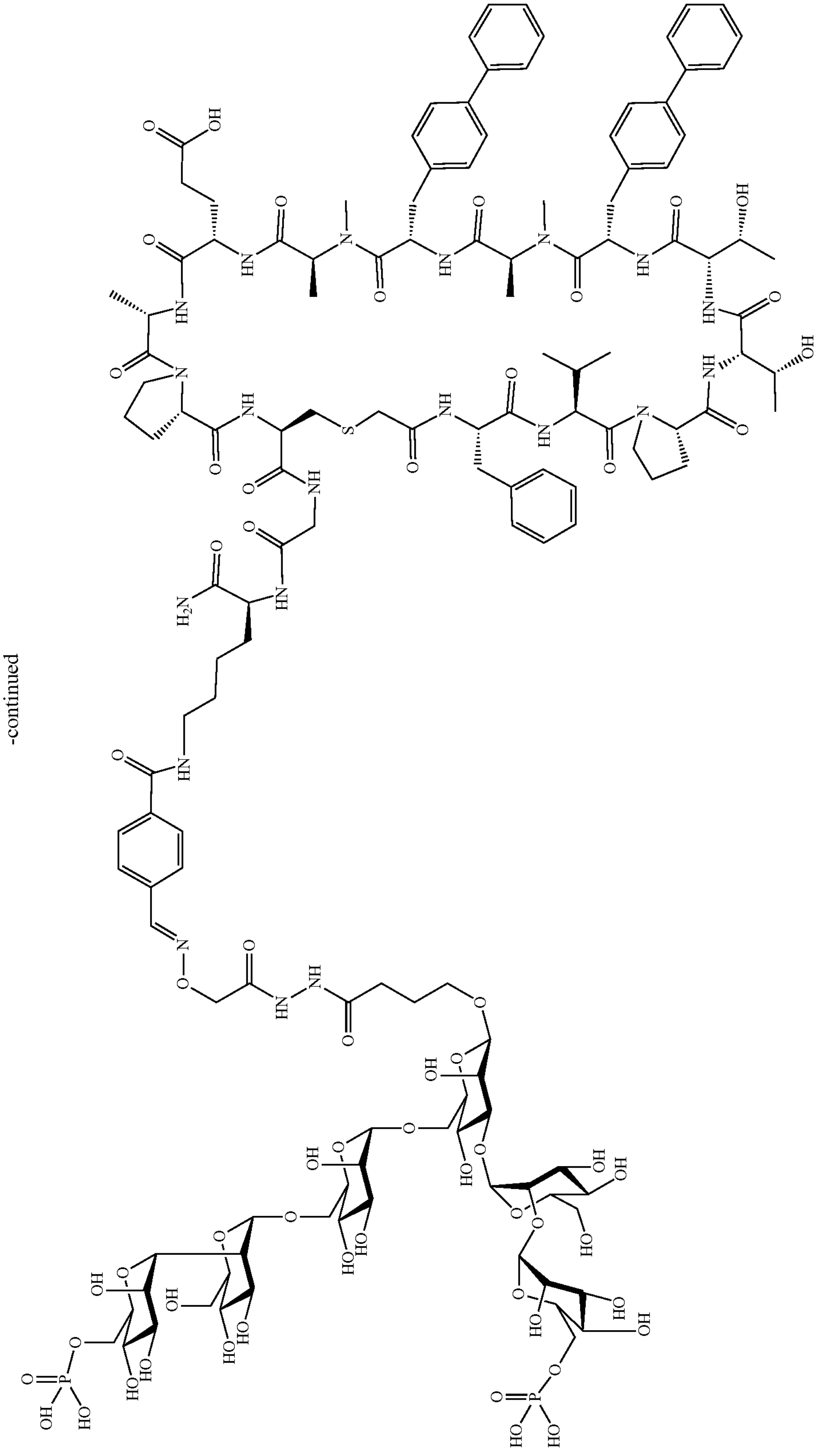
(BFC-2)

To (((2S,3S,4S,5S,6S)-6-(((2R,3S,4S,5S,6R)-2-(((2R,3S,4S,5R,6R)-2-(4-(2-(2-(aminooxy)acetyl)hydrazinyl)-4-oxobutoxy)-6-((((2S,3S,4S,5S,6R)-6-((((2S,3S,4S,5S,6R)-4,5-dihydroxy-6-(hydroxymethyl)-3-(((2R,3S,4S,5S,6R)-3,4,5-trihydroxy-6-((phosphonooxy)methyl)tetrahydro-2H-pyran-2-yl)oxy)tetrahydro-2H-pyran-2-yl)oxy)methyl)-3,4,5-trihydroxytetrahydro-2H-pyran-2-yl)oxy)methyl)-3,5-dihydroxytetrahydro-2H-pyran-4-yl)oxy)-4,5-dihydroxy-6-(hydroxymethyl)tetrahydro-2H-pyran-3-yl)oxy)-3,4,5-trihydroxytetrahydro-2H-pyran-2-yl)methyl) phosphonoperoxoic acid (int-CC6) (7.13 mg, 5.03 μmol) at room temperature was added 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-(4-formylbenzamide)-1-oxohexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1f:2,1'-g1][1]thia[4,7,10,13,1619, 22,25,28,31,34,37,40]tridecaazacyclodotetracontin-9-yl)propanoic acid (int-DD4) (6.5 mg, 3.36 μmol), water (100 μL) and DMSO (100 μL). The mixture was stirred at room temperature for 30 min. Acetic acid was added to adjust the pH to ~5, so acetic (7.68 μL, 0.134 mmol). The mixture was stirred at room temperature for 4 h. Prep-hplc HILIC purification gave Bifunctional Compound (BFC-2). Analytical method 7: $t_R$=2.74 min, MS m/z 1081.8 $[(M+H)/3]^+$.

Example 4-3: Synthesis of Bifunctional Compound (BFC-3)

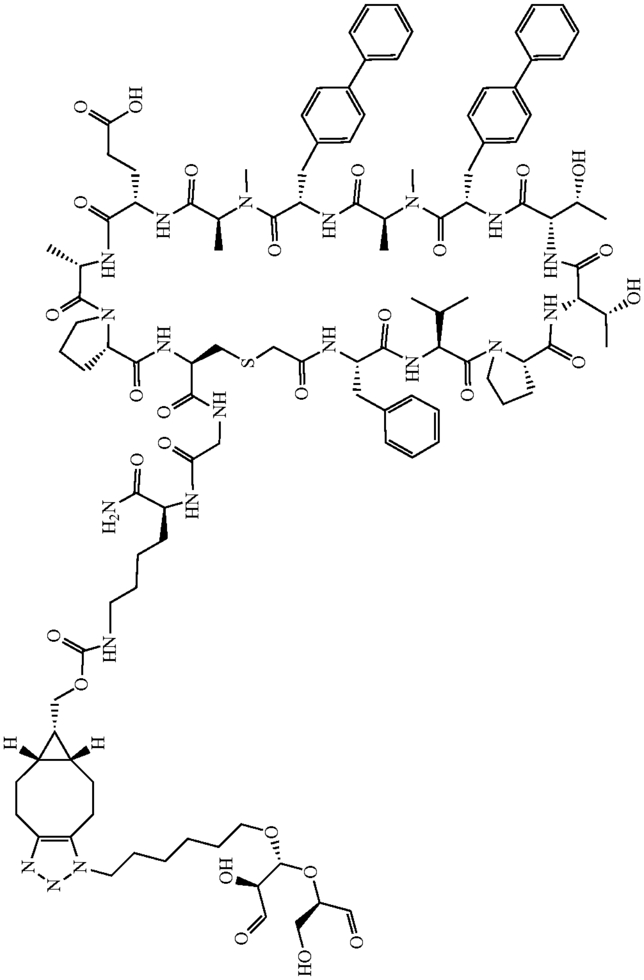
(int-DD2)
+
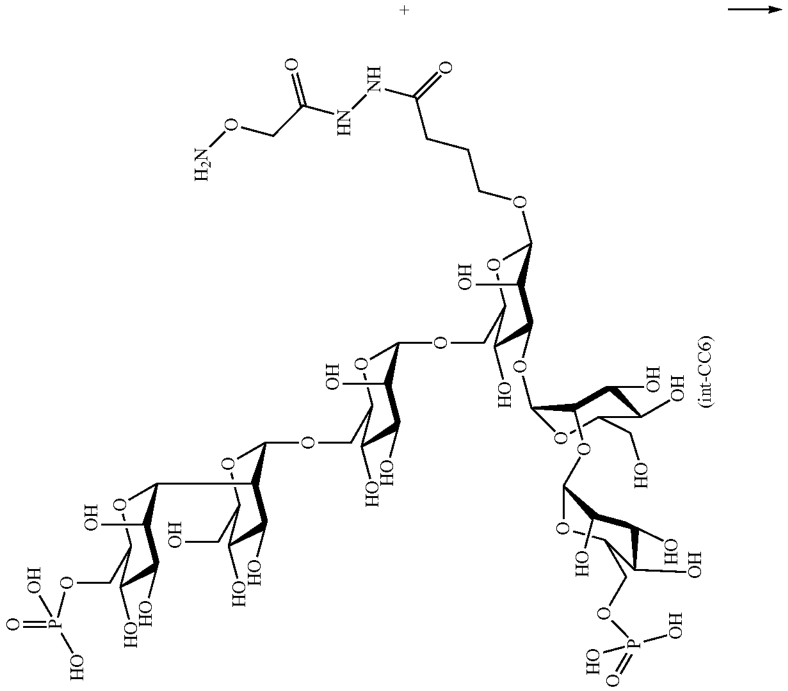
(int-CC6)

-continued
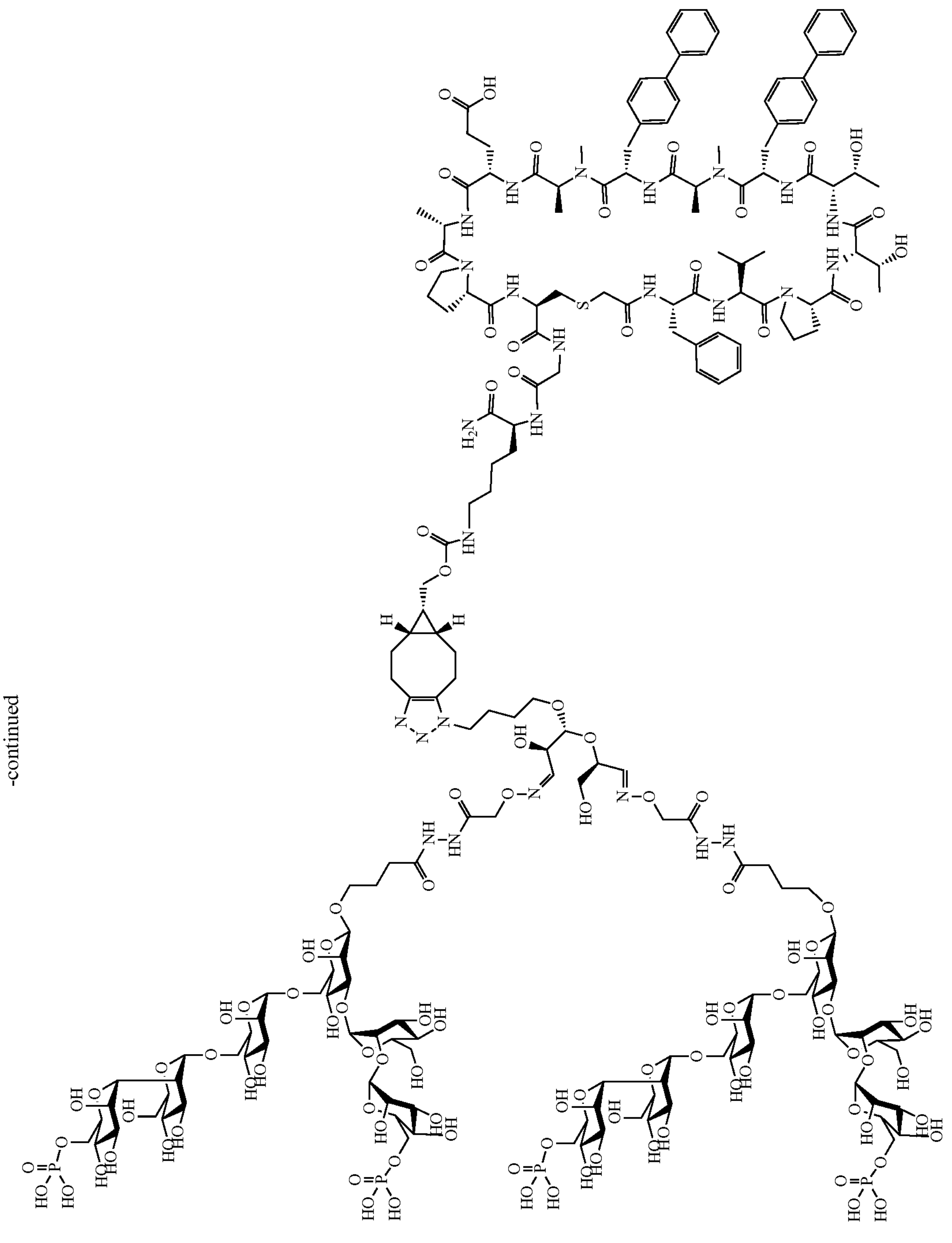
(BFC-3)

To (((2S,3S,4S,5S,6S)-6-(((2R,3S,4S,5S,6R)-2-(((2R,3S,4S,5R,6R)-2-(4-(2-(2-(aminooxy)acetyl)hydrazinyl)-4-oxobutoxy)-6-((((2S,3S,4S,5S,6R)-6-((((2S,3S,4S,5S,6R)-4,5-dihydroxy-6-(hydroxymethyl)-3-(((2R,3S,4S,5S,6R)-3,4,5-trihydroxy-6-((phosphonooxy)methyl) tetrahydro-2H-pyran-2-yl)oxy)tetrahydro-2H-pyran-2-yl)oxy)methyl)-3,4,5-trihydroxytetrahydro-2H-pyran-2-yl)oxy) methyl)-3,5-dihydroxytetrahydro-2H-pyran-4-yl)oxy)-4,5-dihydroxy-6-(hydroxymethyl) tetrahydro-2H-pyran-3-yl)oxy)-3,4,5-trihydroxytetrahydro-2H-pyran-2-yl)methyl) phosphonoperoxoic acid (int-CC6) (40.9 mg, 0.029 mmol) in water (300 μL) and DMSO (600 μL) at room temperature was added Intermediate (int-DD2) (22 mg, 9.63 μmol) and acetic acid (44.1 μl, 0.770 mmol). The mixture was stirred at room temperature for 16 h, and then purified by reverse phase HILIC prep HPLC chromatography to obtain bifunctional compound (BFC-3). Analytical method 7: $t_R$=3.32 mil, MS m/z 1225.0 $[(M+H)/4]^+$.

Example 4-4: Synthesis of Bifunctional compound 3-((6S,9S,12S,15S,18S,21S,24S,27S,29aS,35S,38S,44R,46aS)-15,21-bis([1,1'-biphenyl]-4-ylmethyl)-44-((2-(((S)-1-amino-6-(((((5aS,6R,6aR)-1-((6S,8R,E)-8-((R,Z)-1-hydroxy-2-((2-(((2S,3S,4S,5S,6R)-3,4,5-trihydroxy-6-(2-phosphonoethyl)tetrahydro-2H-pyran-2-yl)oxy)ethoxy)imino)ethyl)-6-(hydroxymethyl)-1-(((2S,3S,4S,5S,6R)-3,4,5-trihydroxy-6-(2-phosphonoethyl)tetrahydro-2H-pyran-2-yl)oxy)-3,7,9-trioxa-4-azapentadec-4-en-15-yl)-1,4,5,5a, 6,6a,7,8-octahydrocyclopropa[5,6]cycloocta[1,2-d][1,2,3]triazol-6-yl)methoxy)carbonyl)amino)-1-oxohexan-2-yl)amino)-2-oxoethyl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-gl][1]thia[4,7,10,13,16,19,22,25,28,31,34,37,40]tridecaazacyclodotetracontin-9-yl)propanoic acid (BFC-4)

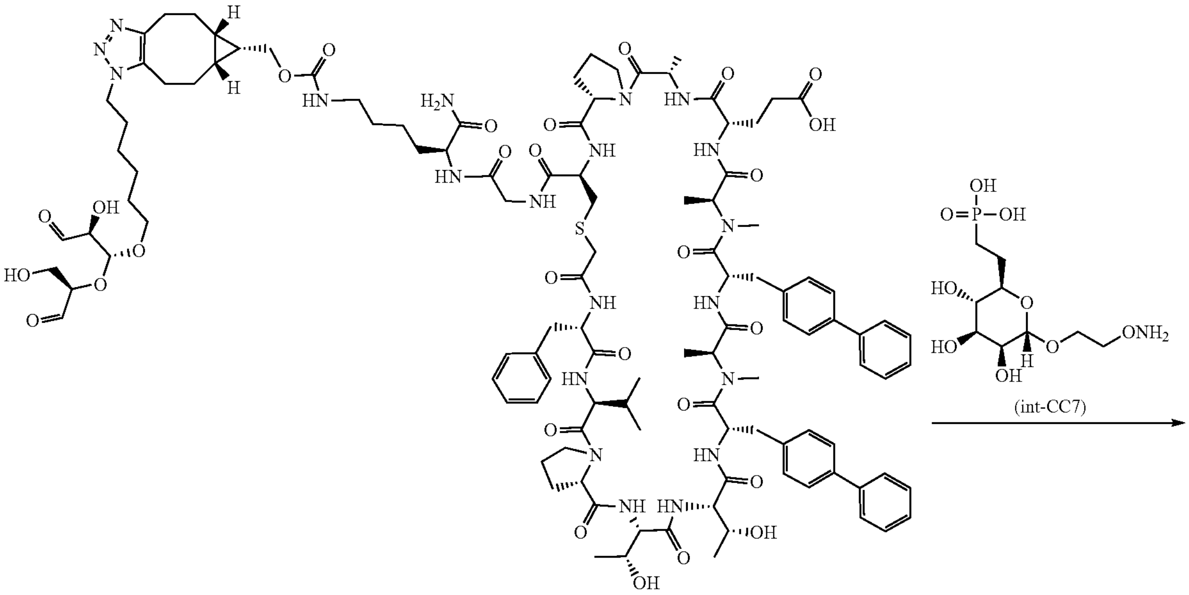

(int-DD2)

-continued

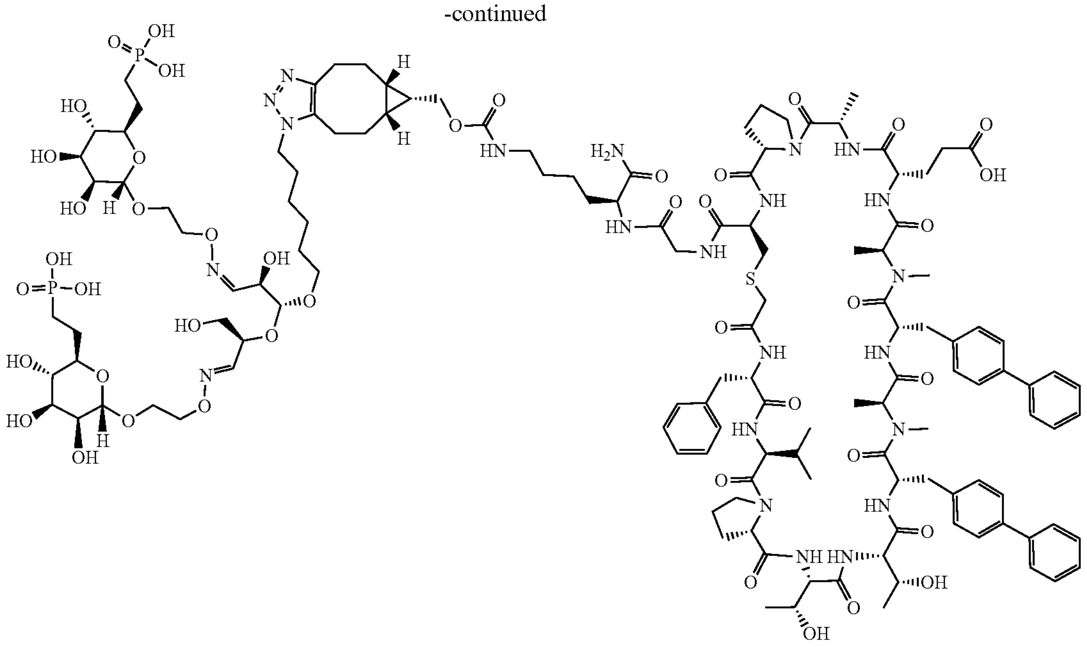

(BFC-4)

To intermediate (int-DD2) (21 mg, 9.19 μmol) in acetonitrile (200 μL), DMSO (200 μL) and water (100 μL) was added (2-((2R,3S,4S,5S,6S)-6-(2-(aminooxy)ethoxy)-3,4,5-trihydroxytetrahydro-2H-pyran-2-yl)ethyl)phosphonic acid (int-CC7) (13.02 mg, 0.037 mmol). The mixture was stirred at room temperature for 4 h, and then purified by reverse phase silica gel chromatography to obtain Bifunctional Compound (BFC-4). Analytical method 7: $t_R$=1.19 min, MS m/z 1442.3 $[(M+H)/2]^+$.

Example 4-5: Synthesis of Bifunctional compound 3-((6S,9S,12S,15S,18S,21S,24S,27S,29aS,35S,38S,44R,46aS)-15,21-bis([1,1'-biphenyl]-4-ylmethyl)-44-(((S)-1-(1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)-27-carbamoyl-6,21,29-trioxo-2,9,12,15,18-pentaoxa-5,22,28-triazatriacontan-30-yl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-gl][1]thia[4,7,10,13,16,19,22,25,28,31,34,37,40]tridecaazacyclodotetracontin-9-yl) propanoic acid (BFC-5)

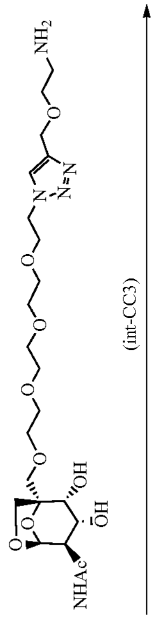
(int-CC3)
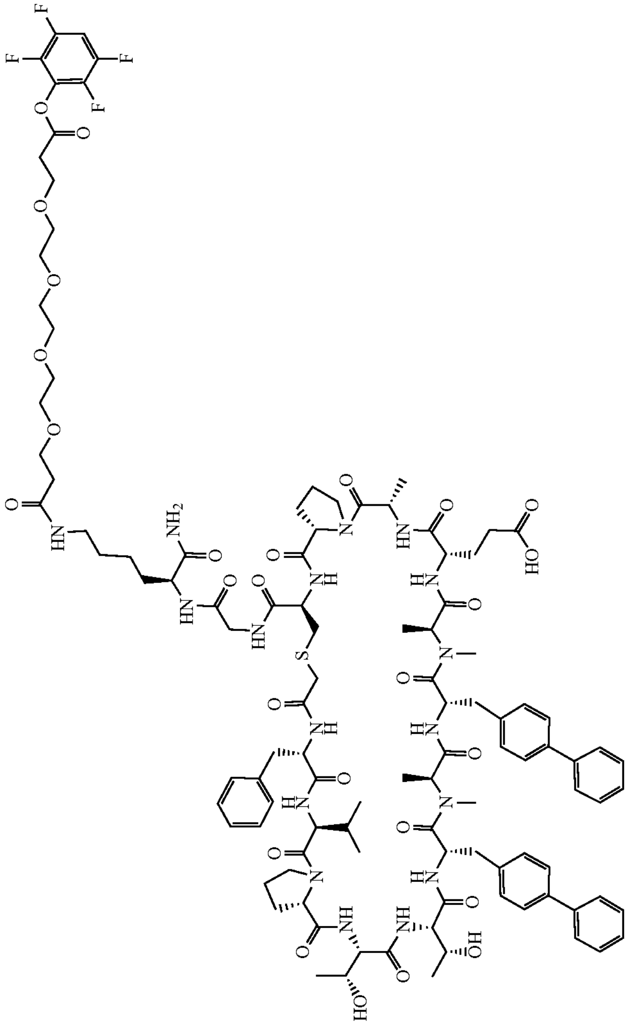
(int-DD3)

-continued
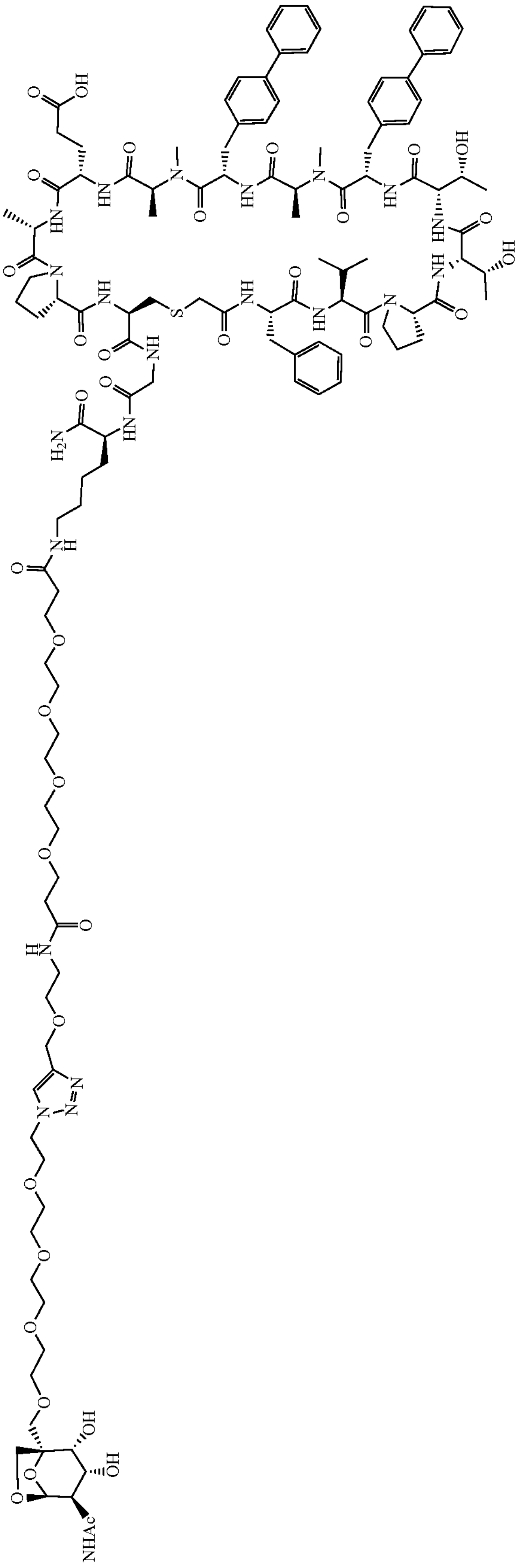
(BFC-5)

To Intermediate (int-DD3) (14 mg, 0.026 mmol) in DMF (1.5 mL) at room temperature was added N-((1S,2R,3R,4R,5S)-1-(13-(4-((2-aminoethoxy)methyl)-1H-1,2,3-triazol-1-yl)-2.5,8,11-tetraoxatridecyl)-2,3--dihydroxy-6,8-dioxabicyclo[3.2.1]octan-4-yl)acetamide (int-CC3) (58.5 mg, 0.026 mmol) and DIPEA (0.014 mL, 0.079 mmol). The mixture was stirred at room temperature for 2 h, and then purified by reverse phase prep HPLC to obtain Bifunctional Compound (BFC-5). Analytical method 7: $t_R$=2.35 min, MS m/z 1299.3 $[(M+H)/2]^+$.

Example 4-6: Synthesis of Bifunctional compound 3-((6S,9S,12S,15S,18S,21S,24S,27S,29aS,35S,38S,44R,46aS)-15,21-bis([1,1'-biphenyl]-4-ylmethyl)-44-(((S)-1-(1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)-4,4-bis(((1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)methyl)-27-carbamoyl-6,21,29-trioxo-2,9,12,15,18-pentaoxa-5,22,28-triazatriacontan-30-yl)carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (BFC-6)

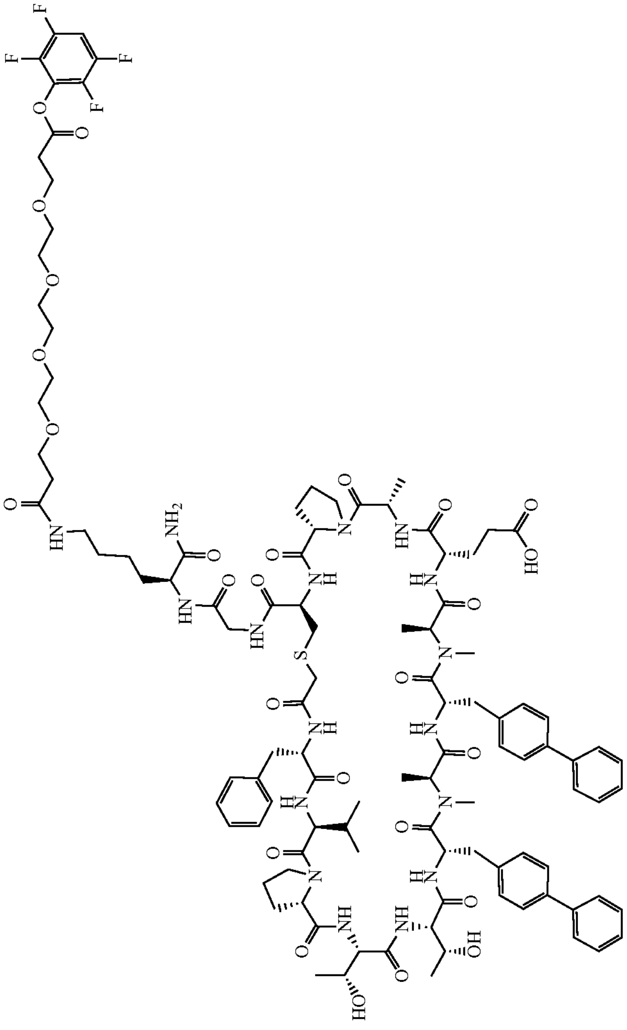
(int-DD3)
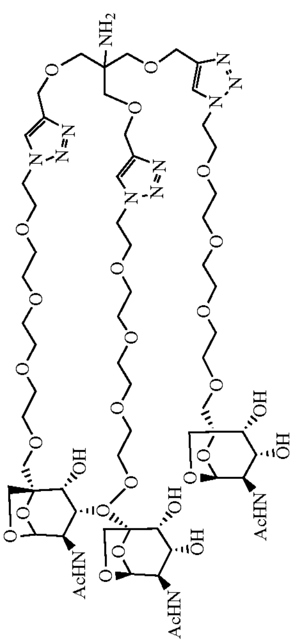
(int-CC5)

-continued
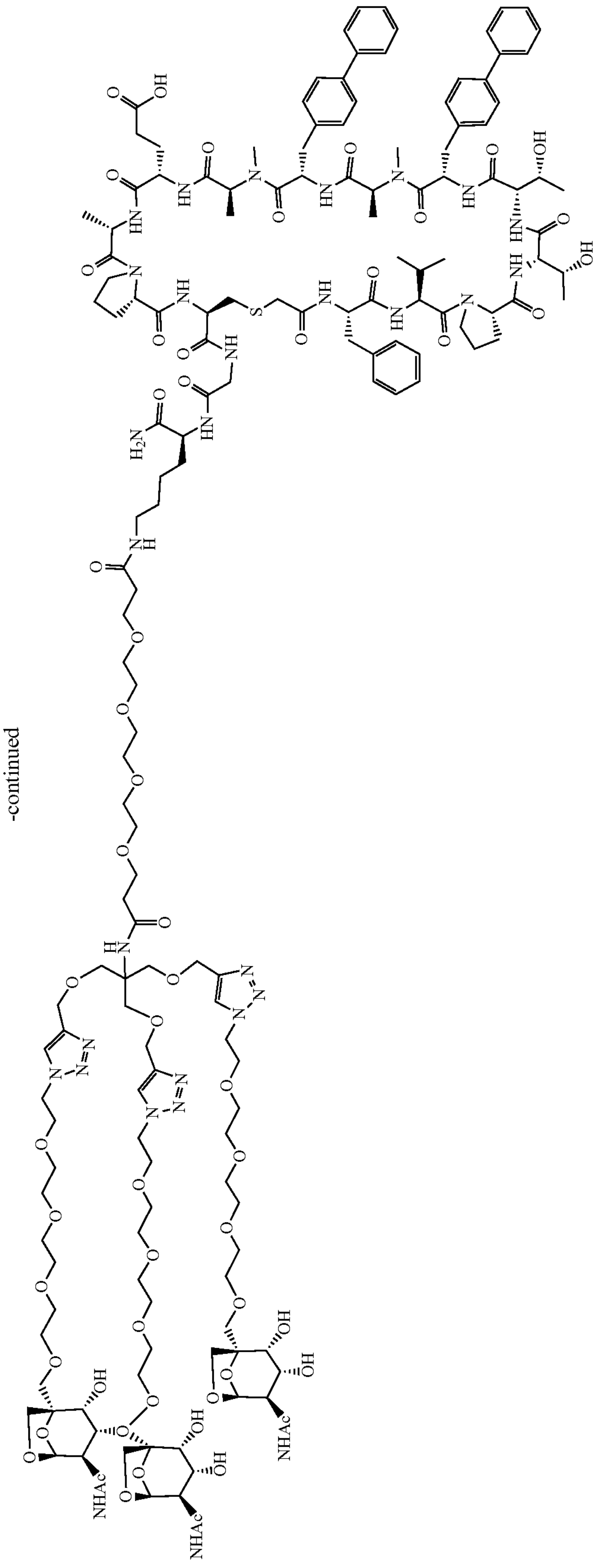
(BFC-6)

To Intermediate (int-CC5) (38.5 mg, 0.025 mmol) in DMF (1 mL) at room temperature was added Intermediate (int-DD3) (55.7 mg, 0.025 mmol) and DIPEA (0.044 mL, 0.250 mmol). The mixture was stirred at room temperature for 16 h, and then purified by prep-HPLC with formic acid modifier to obtain Bifunctional Compound (BFC-6). Analytical method 5: $t_R$=0.82 min, MS m/z 1201.7 $[(M+H)/3]^+$.

Example 4-7: Synthesis of Bifunctional compound 3-((6S,9S,12S,15S,18S,21S,24S,27S,29aS,35S,38S,44R,46a)-15,21-bis([1,1'-biphenyl]-4-ylmethyl)-44-(((S)-1-(1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-, 2,3-triazol-4-yl)-4-(((1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl) methoxy)methyl)-27-carbamoyl-6,21,29-trioxo-2,9,12,15,18-pentaoxa-5,22,28-triazatriacontan-30-yl) carbamoyl)-38-benzyl-24,27-bis((R)-1-hydroxyethyl)-35-isopropyl-6,12,13,18,19-pentamethyl-5,8,11,14,17,20,23,26,29,34,37,40,46-tridecaoxotetratetracontahydro-5H-dipyrrolo[2,1-f:2',1'-g1][1]thia[4,7,10,13,16,19,22,25,28,31,34,37,40]tridecaazacyclodotetracontin-9-yl)propanoic acid (BFC-7)

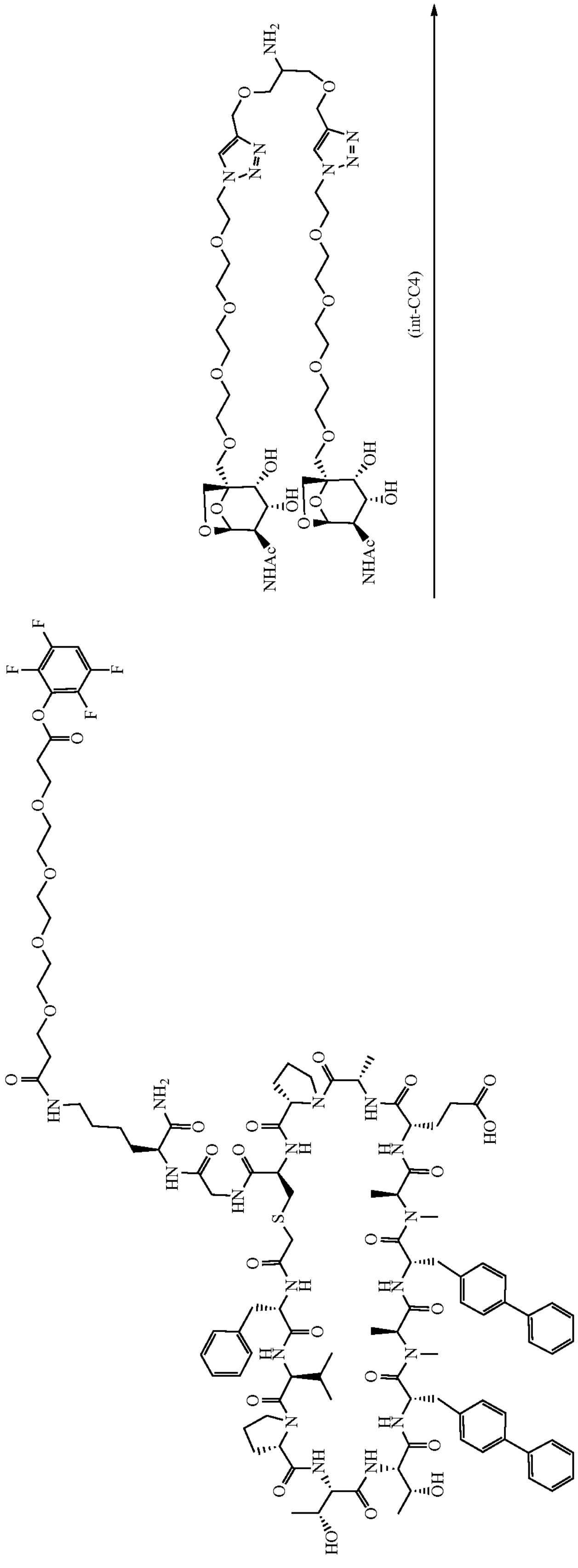
(int-DD3)
(int-CC4)

-continued
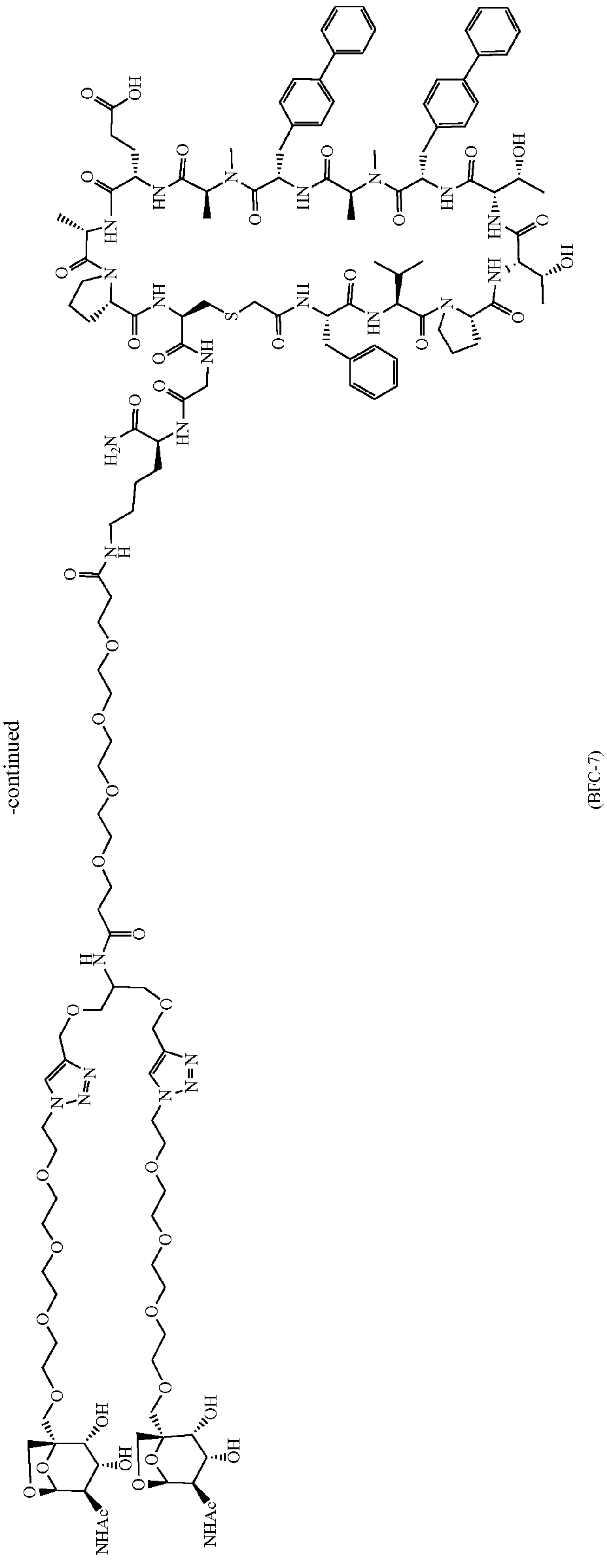
(BFC-7)

To N,N'-((1 S, 1'S,2R,2'R,3R,3'R,4R,4'R,5S,5'S)-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(2,3-dihydroxy-6,8-dioxabicyclo[3.2.1]octane-1,4-diyl))diacetamide (int-CC4) (25.9 mg, 0.025 mmol) in DMF (1 mL) at room temperature was added Intermediate (int-DD3) (55.7 mg, 0.025 mmol) and DIPEA (0.044 mL, 0.250 mmol). The mixture was stirred at room temperature for 2 h, and then purified by reverse phase silica gel chromatography with acidic modifier to obtain Bifunctional Compound (BFC-7). Analytical method 5: $t_R$=0.83 min, MS m/z 1550.6 $[(M+H)/2]^+$.

Example 4-8: Synthesis of Bifunctional compound (BFC-8) and Bifunctional compound (BFC-9)

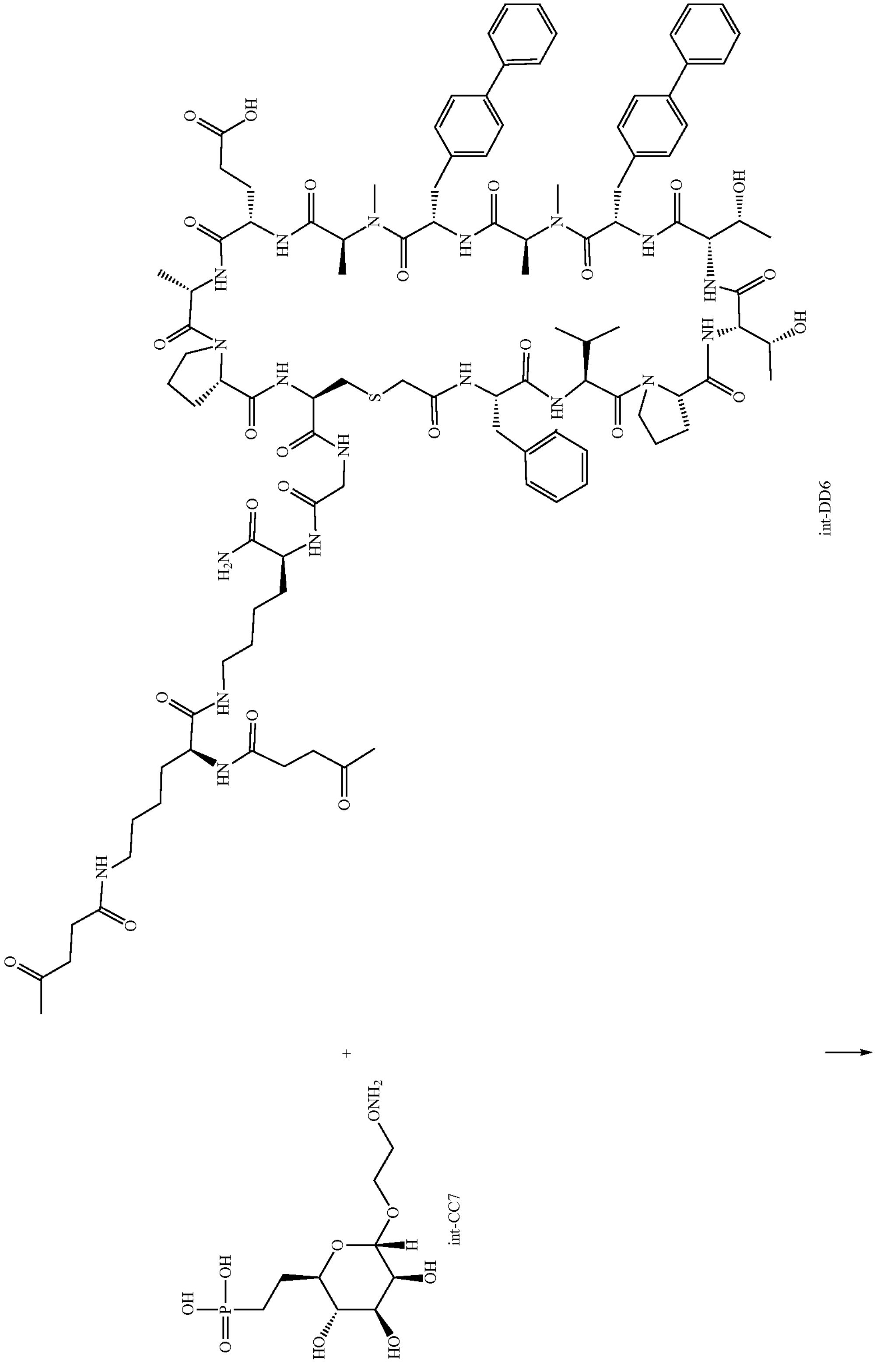
int-DD6
+
int-CC7

-continued
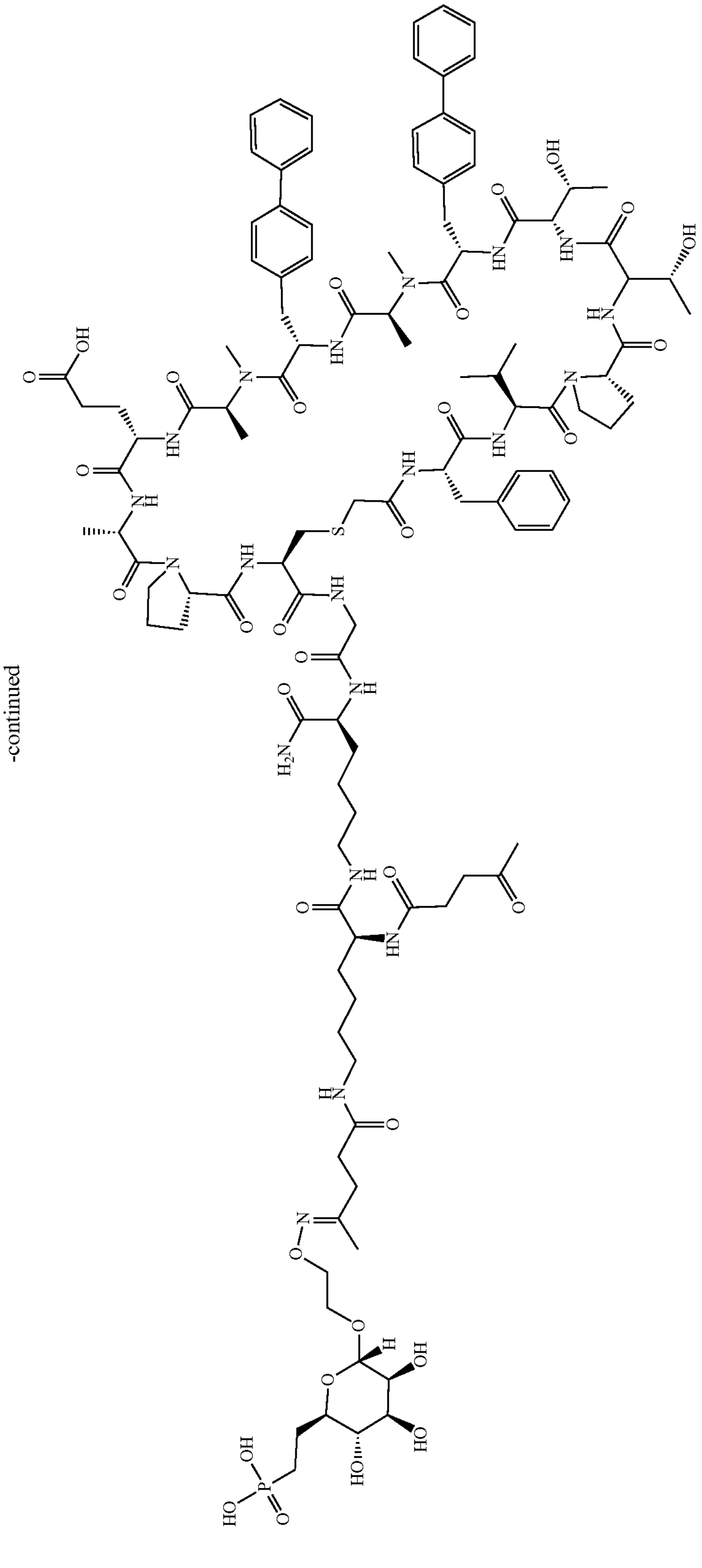
(BFC-8)

-continued
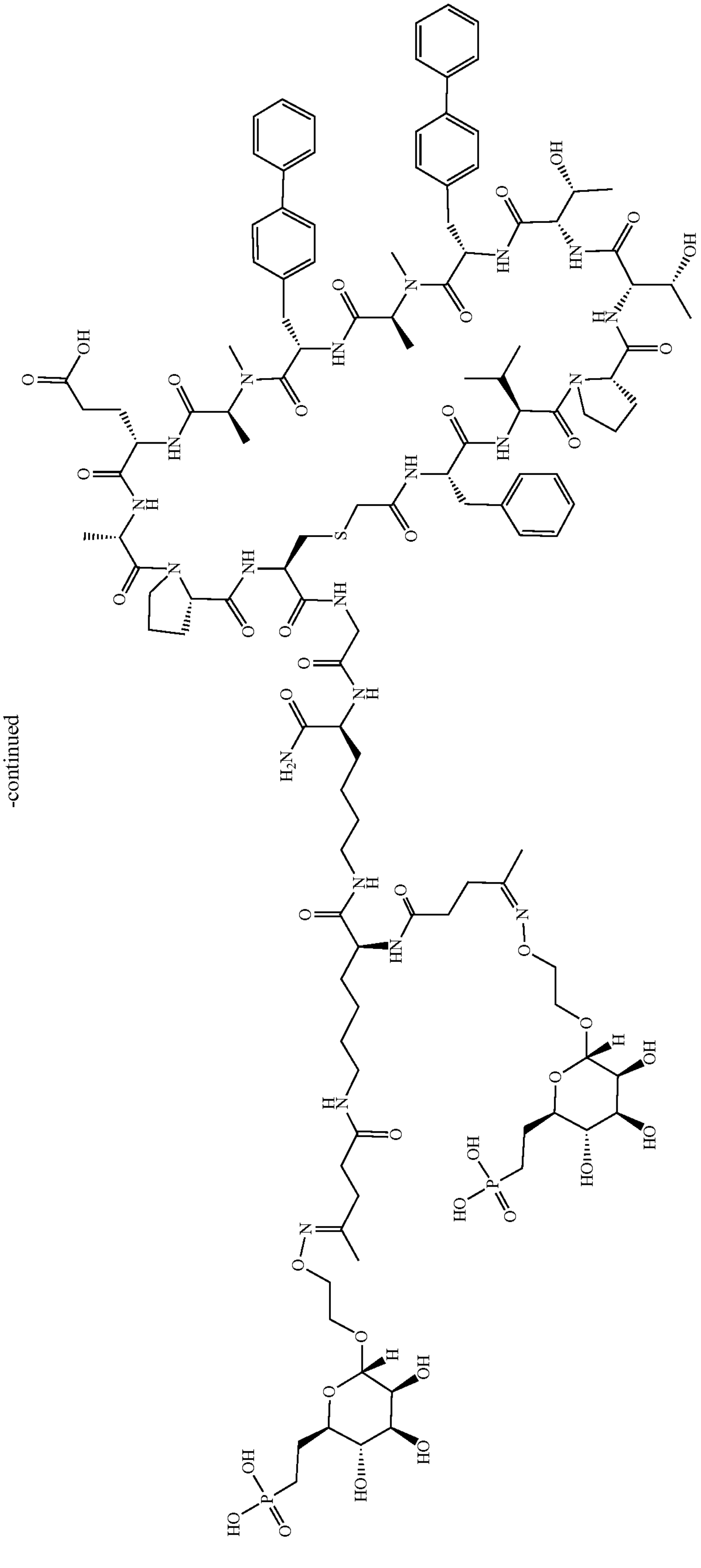
(BFC-9)

To Intermediate (int-DD6) (27.5 mg, 0.013 mmol) in acetonitrile (240 μL) and water (160 μL) at room temperature is added ((2R,3S,4S,5S)-6-(((4E,6S,8R,9R,10Z)-8,9-dihydroxy-6-(hydroxymethyl)-1-(((3S,4S,5S,6R)-3,4,5-trihydroxy-6-((phosphonooxy)methyl)tetrahydro-2H-pyran-2-yl)oxy)-3,7,12-trioxa-4,11-diazatetradeca-4,10-dien-14-yl) oxy)-3,4,5-trihydroxytetrahydro-2H-pyran-2-yl)methyl dihydrogen phosphate (int-CC7) (16.39 mg, 0.052 mmol). The mixture is stirred at room temperature for 3 days and is purified by HPLC: X-bridge BEH C18 30×100 mm 5 μm column ACN/$H_2O$ w/5 mM $NH_4OH$ 75 mL/min, 10-30% ACN/water, ammonium hydroxide modified.

Example 4-9: Synthesis of Bifunctional compound (BFC-10)

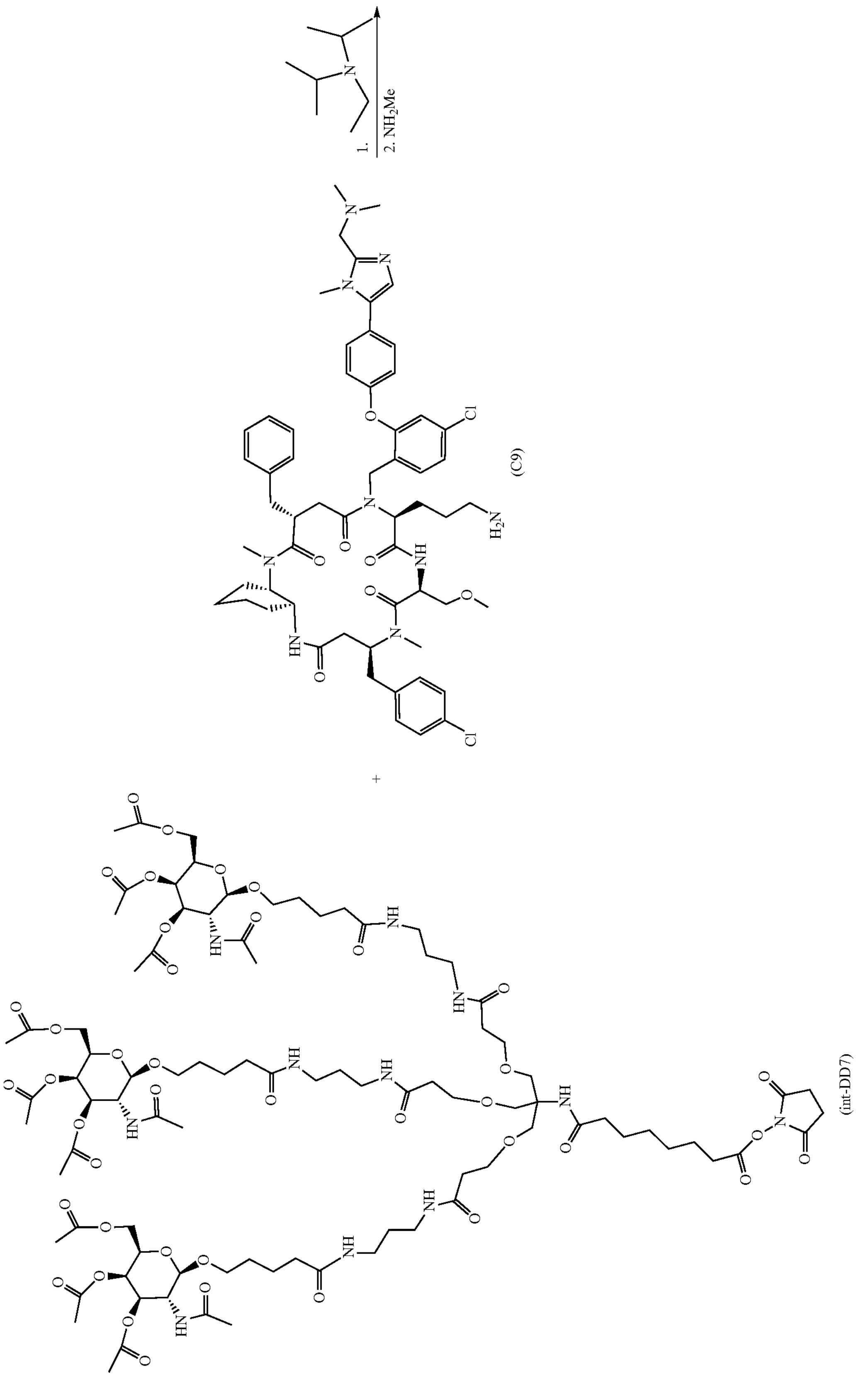
(C9)
(int-DD7)

-continued
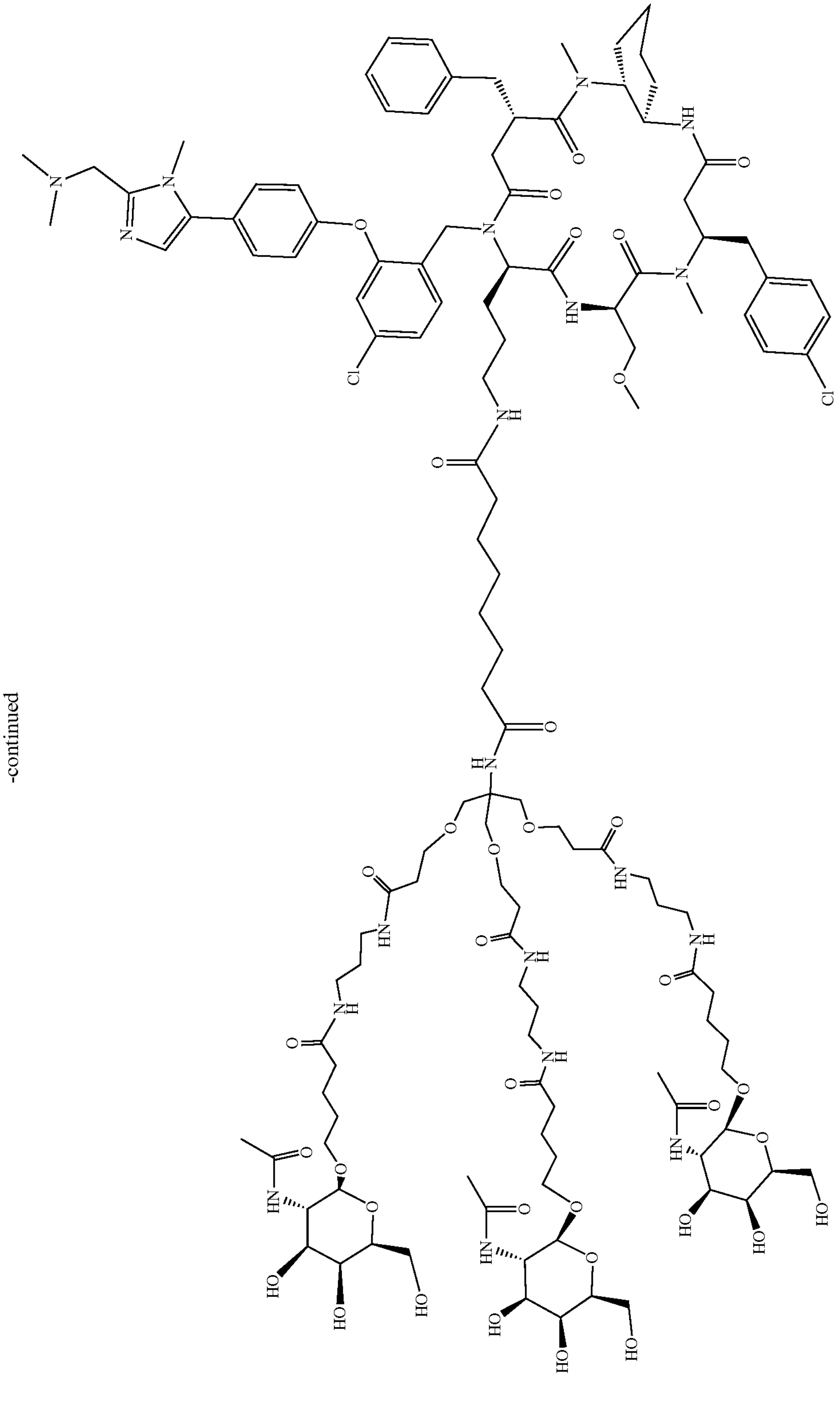
(BFC10)

To a solution of intermediate (int-DD7) (20.49 mg, 10.01 μmol) in DMSO (1 mL) was added cyclic peptide (C9) (10.8 mg, 10.01 μmol) and DIEPA (0.017 mL, 0.100 mmol). The reaction mixture was stirred at rt overnight. Methylamine in methanol (2 M, 3 mL) was then added and the reaction mixture was stirred at rt for overnight. The reaction mixture was then concentrated and purified by prepared HPLC first using X-bridge Prep C18 OBD 30×50 mm 5 μm column, ACN/$H_2O$ with 0.1% formic acid (gradient 25-50% ACN for 3.5 min, 75 mL/min: ($t_R$=2.2 min), followed by X-bridge Prep C18 OBD 30×50 mm 5 μm column, ACN/$H_2O$ with 5 mM $NH_4OH$ (gradient 35-60% ACN for 3.5 min, 75 mL/min.: ($t_R$=1.84 min) to give Bifunctional Compound (BFC10). Analytical method 7: $t_R$=1.80 min.; m/z: 1317.5 (M+2).

Example 4-10: Synthesis of Bifunctional Compound (BFC-11)

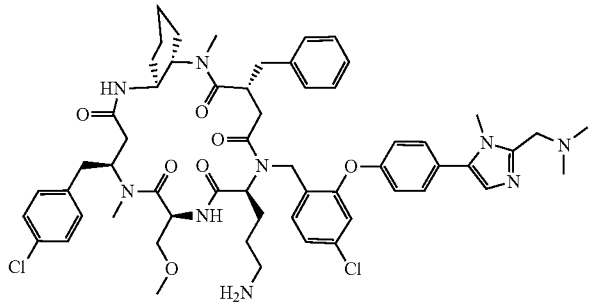

(C9)

+

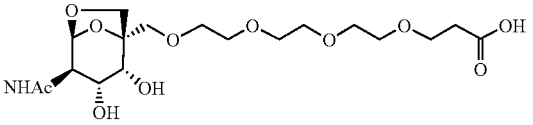

(int-CC8)

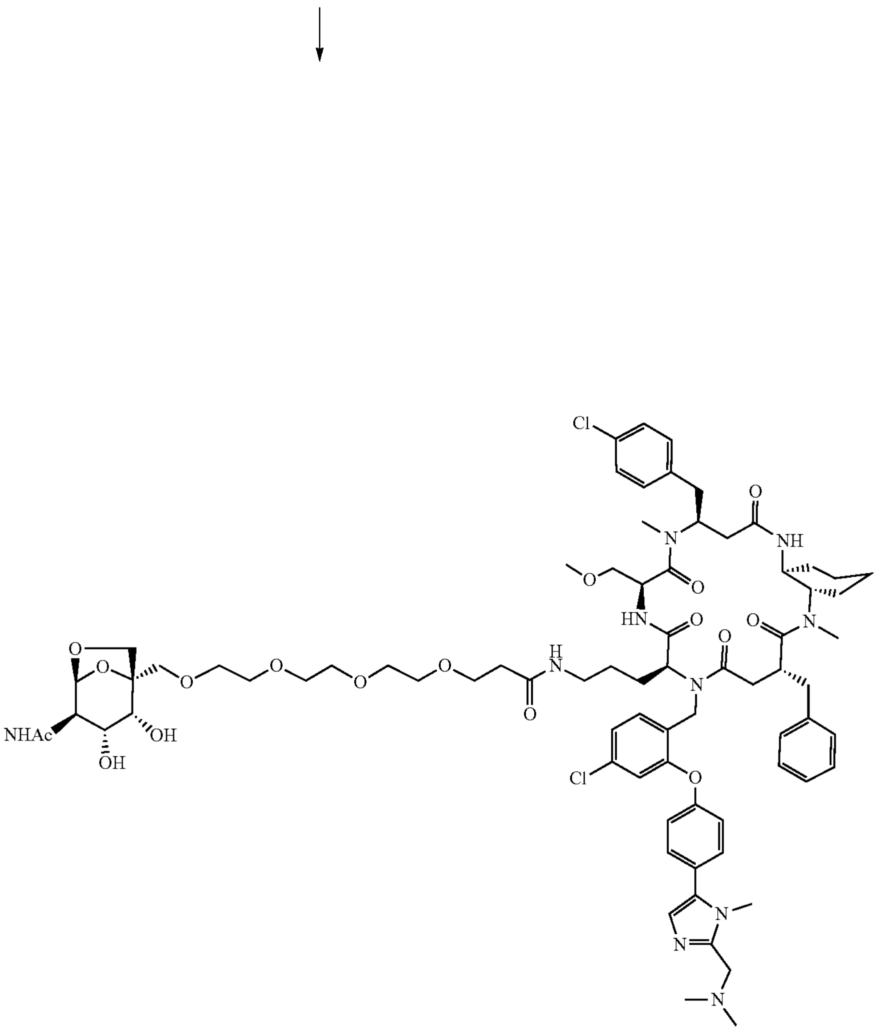

(BFC11)

To cyclic peptide (C9) (25 mg, 0.023 mmol) in DMF (1 mL) at room temperature was added 1-((1S,2R,3R,4R,5S)-4-acetamido-2,3-dihydroxy-6,8-dioxabicyclo[3.2.1]octan-1-yl)-2,5,8,11-tetraoxatetradecan-14-oic acid (int-CC8) (12.16 mg, 0.028 mmol), HATU (13.21 mg, 0.035 mmol) and DIPEA (0.016 mL, 0.093 mmol). The mixture was stirred at room temperature for 2 h, and then purified by preparative HPLC using X-bridge Prep C18 OBD 30×50 mm 5 μm column, ACN/$H_2O$ with 0.1% formic acid (gradient 25-50% ACN for 3.5 min, 75 mL/min.: ($t_R$=3.1 min) to give Bifunctional Compound (BFC11). Analytical method 7: $t_R$=0.90 min, MS m/z 1501.4 $[M+H]^+$.

Example 4-11: Synthesis of Bifunctional Compound (BFC-12)

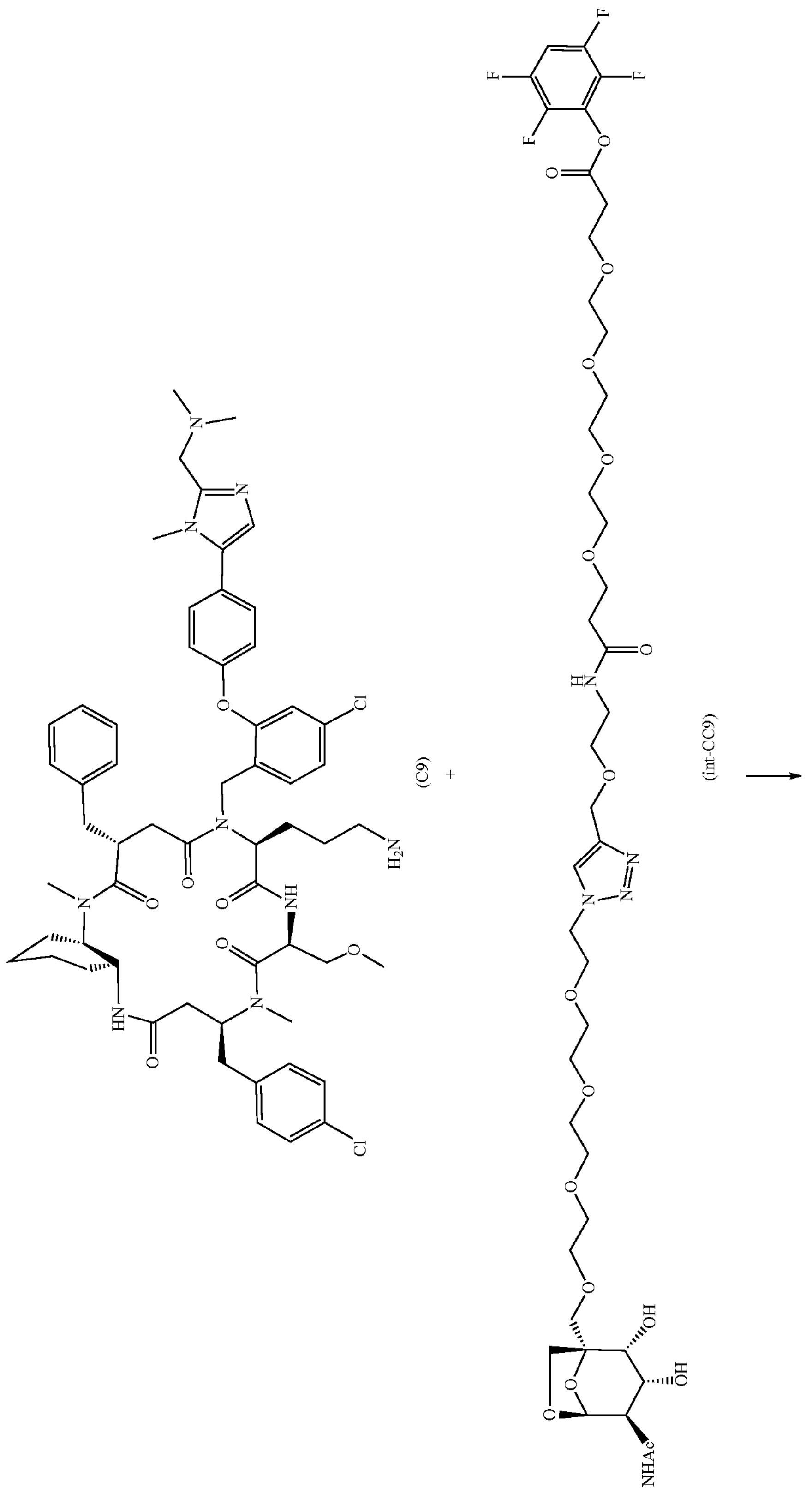
(C9)
+
(int-CC9)

-continued
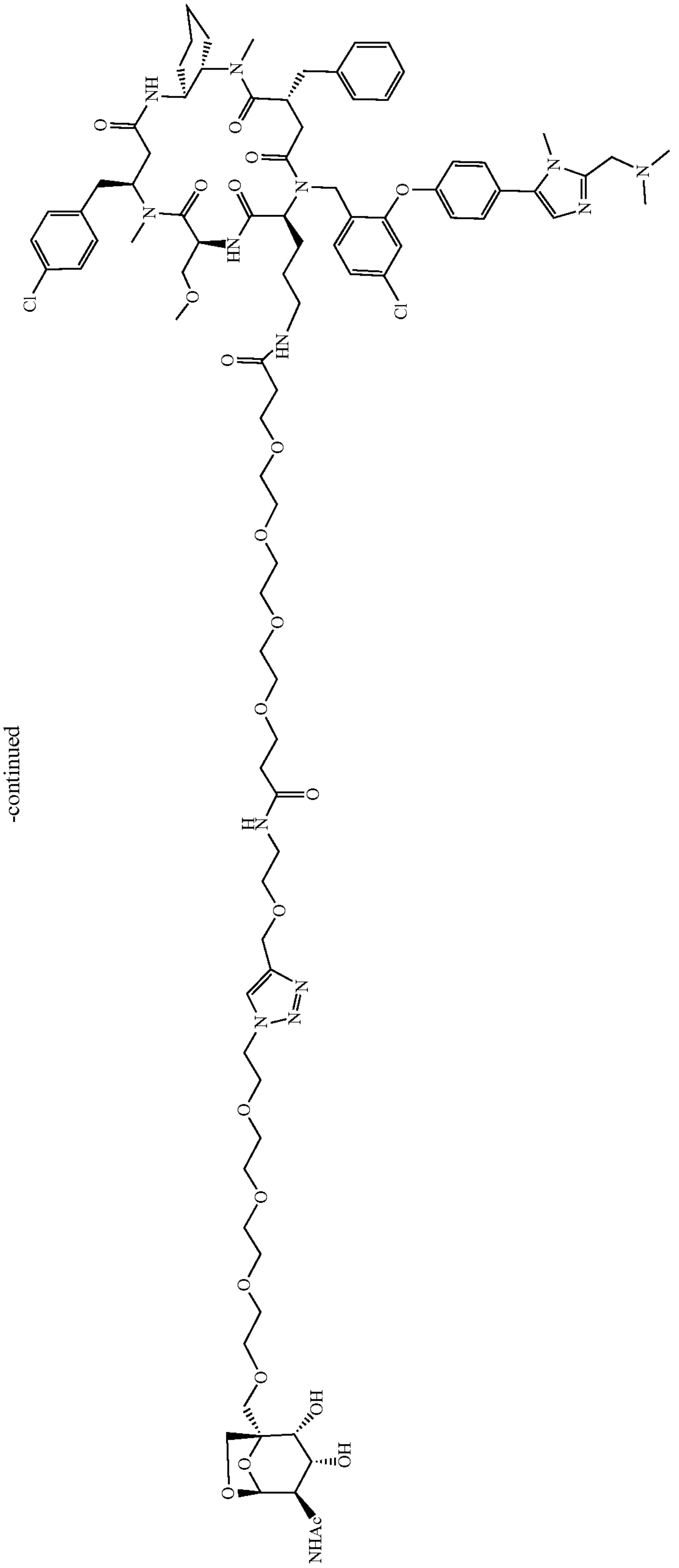
(CFC12

To cyclic peptide ($C_9$) (11.27 mg, 10.44 μmol) in DMF (1 mL) at room temperature was added 2,3,5,6-tetrafluorophenyl 1-(1-(1-((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)-6-oxo-2,9,12,15,18-pentaoxa-5-azahenicosan-21-oate (int-CC9) (10 mg, 10.44 μmol) and DIPEA (9.12 μl, 0.052 mmol). The mixture was stirred at room temperature for 2 h, and then purified by reverse phase silica gel chromatography to give Bifunctional Compound (BFC12). Analytical method 9: $t_R$=1.08 min.; MS m/z 1868.8 (M+H)+.

Example 4-12: Synthesis of Bifunctional Compound (BFC-13)

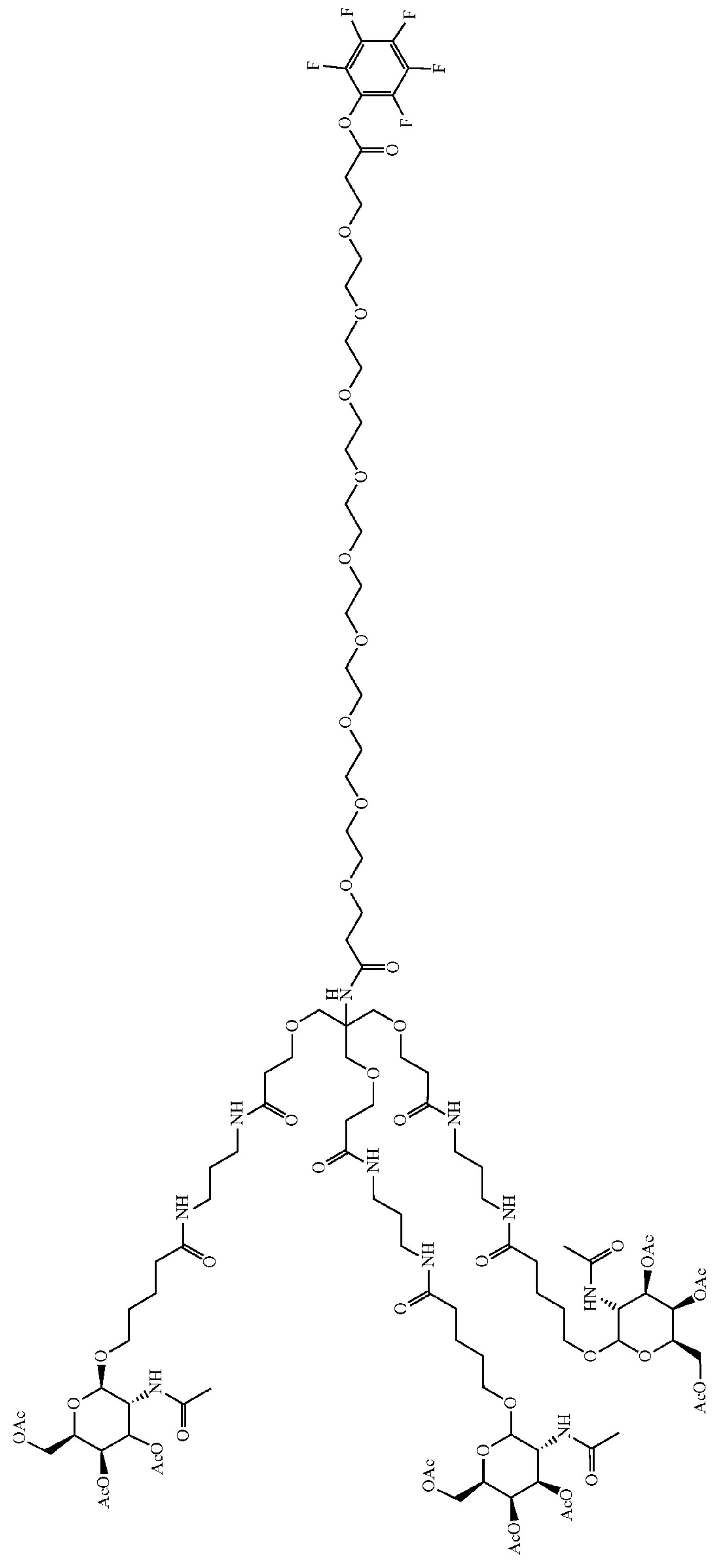
(int-DD1b)

-continued
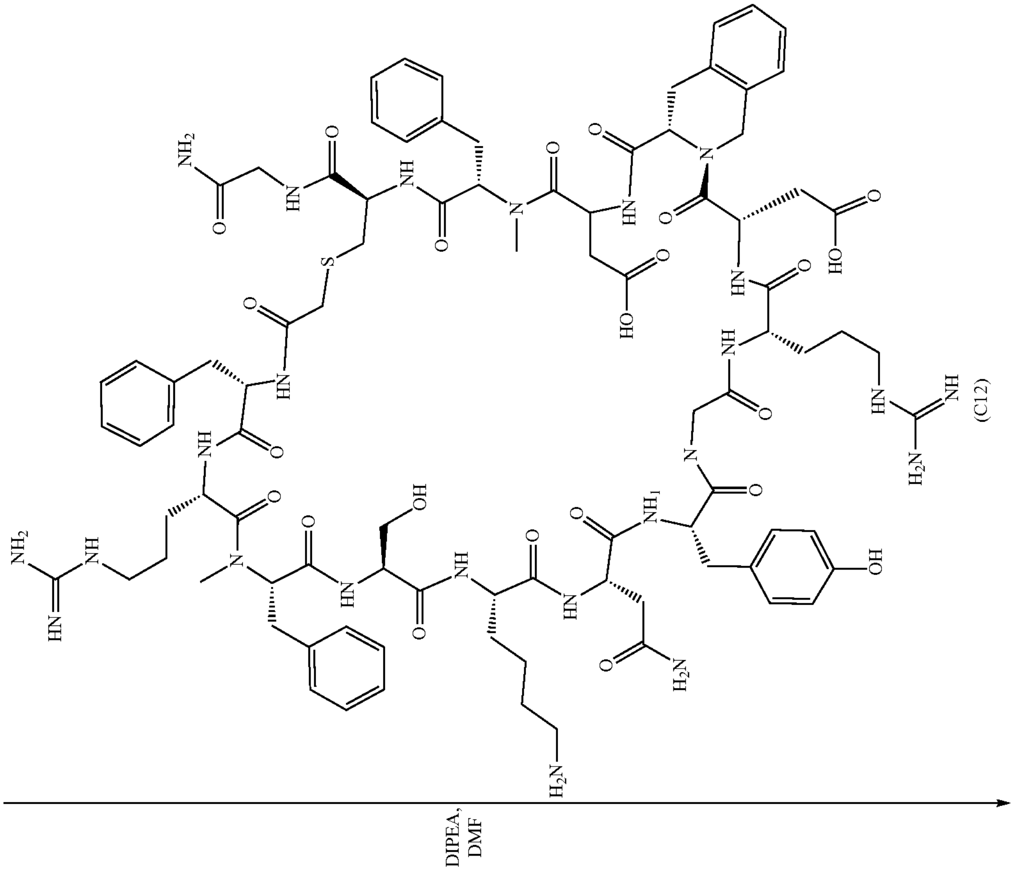
(C12)

-continued
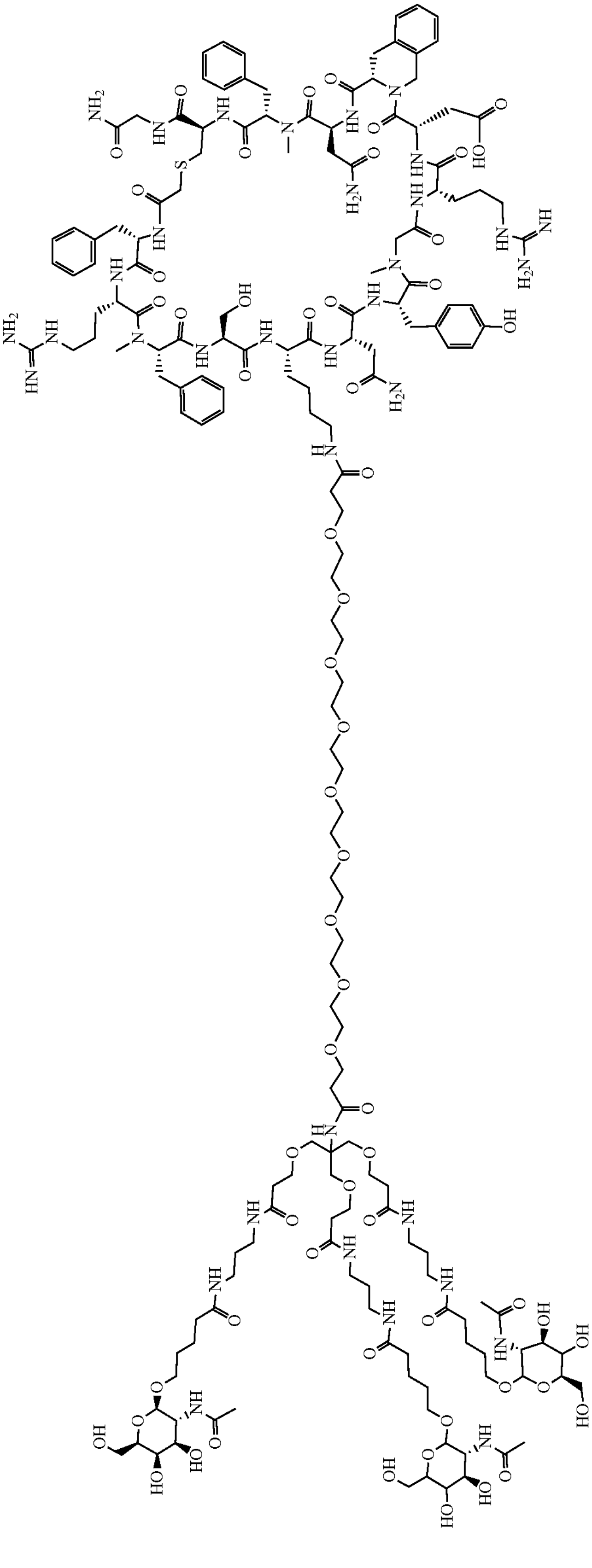
(BFC-13)

To cyclic peptide (C12) (4.84 μmol) in DMF (1 mL) at room temperature was added Intermediate (int-DD1b) (13.09 mg, 5.33 μmol) and DIPEA (8.46 μl, 0.048 mmol). The mixture was stirred at room temperature for 2 hrs., and then purified by prep HILIC reverse phase to obtain Bifunctional compound (BFC-13), which was lyophilized, and then methylamine (2M) in methanol (1 mL, 2.000 mmol) was added. The mixture was stirred at room temperature for 2 hrs, and then concentrated in vacuo and dried to give Bifunctional compound (BFC-13). Analytical method 7: $t_R$=0.77 min.; MS m/z 1922.4 $[(M-H)/2]^+$.

Example 4-13: Synthesis of Bifunctional Compound (BFC-14)

(BFC-14)

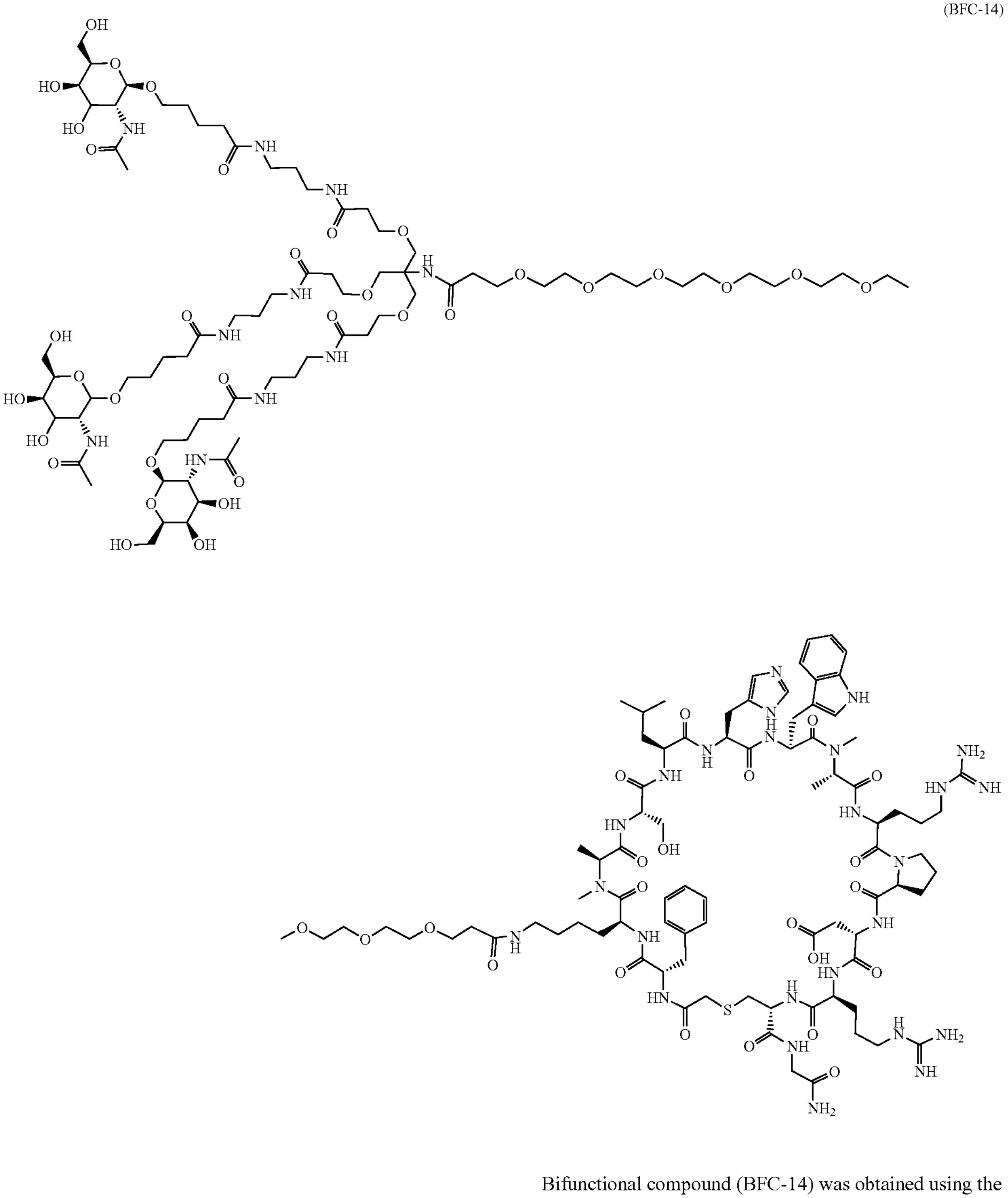

Bifunctional compound (BFC-14) was obtained using the method described in Example 4-12, except cyclic peptide (C12) was replaced with cyclic peptide (C13). Analytical method 7: $t_R$=0.74 min.; MS m/z 1901.4 $[(M-H)/2]^+$.

Example 4-14: Synthesis of Bifunctional compound (BFC-15)
(BFC-15)
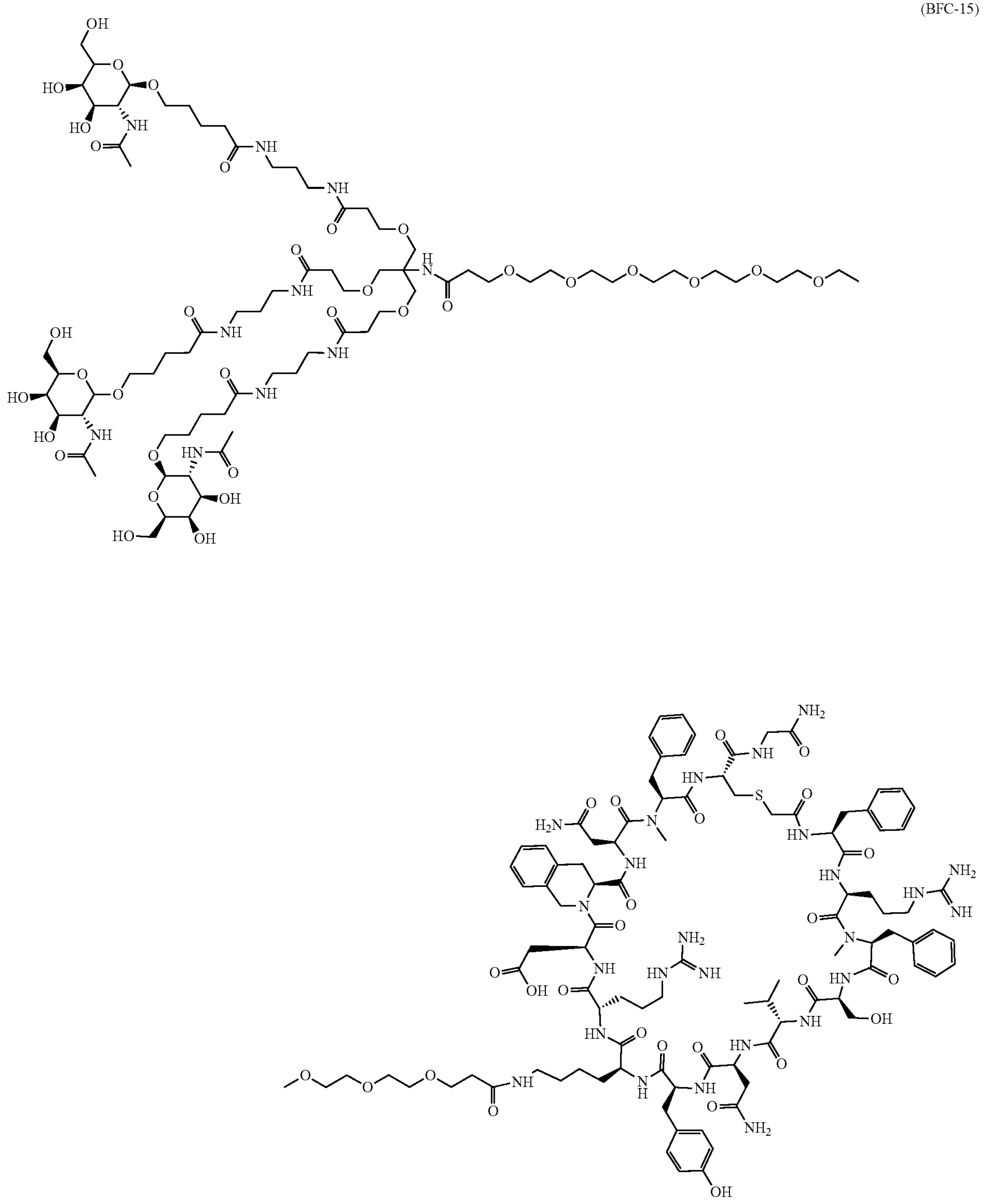
Bifunctional compound (BFC-15) was obtained using the method described in Example 4-12, except cyclic peptide (C12) was replaced with cyclic peptide (C14). Analytical method 7: $t_R$=0.80 min.; MS m/z 1935.7 $[(M-H)/2]^+$.

Example 4-15: Synthesis of Bifunctional Compound (BFC-16)
(BFC-16)
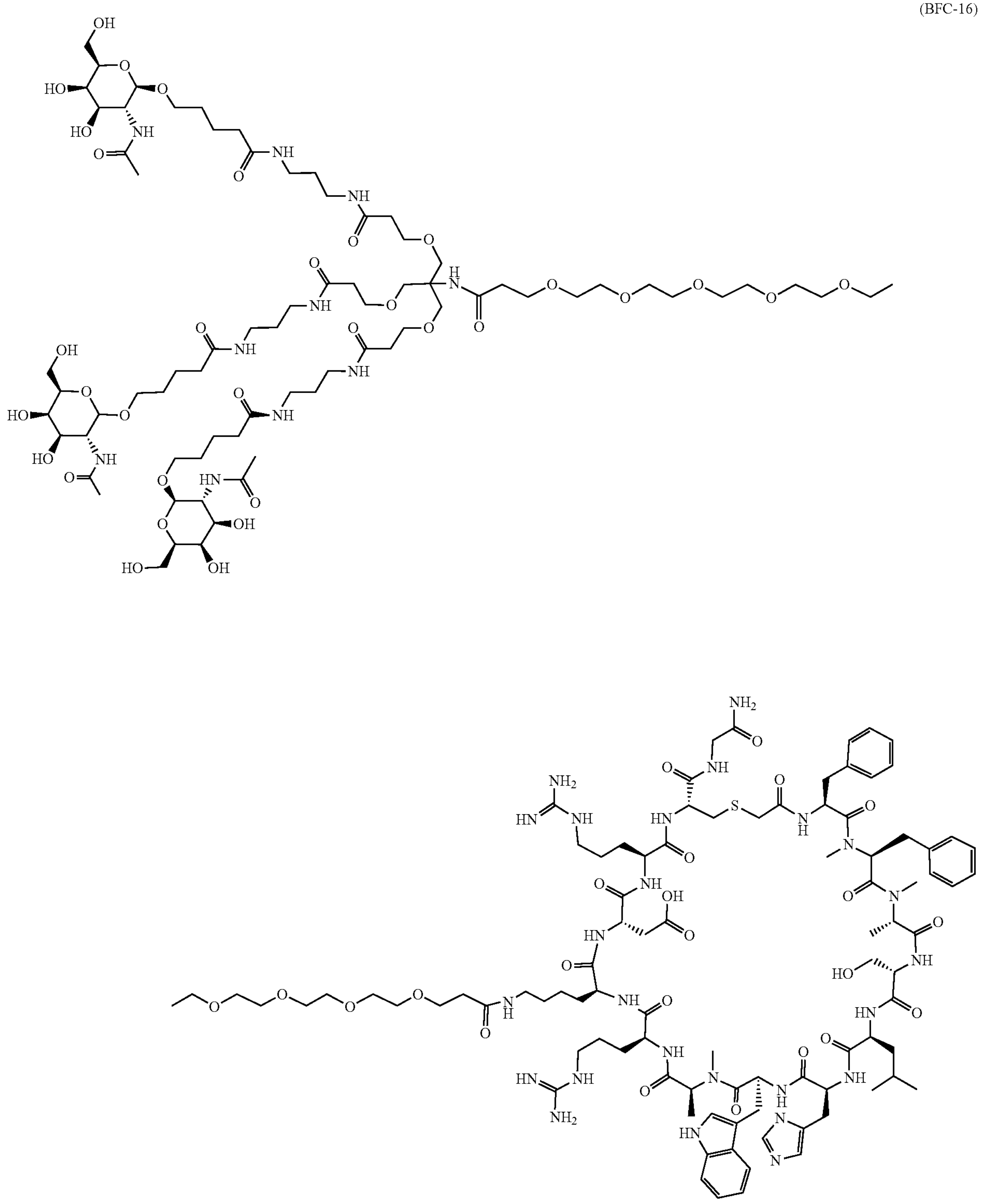
Bifunctional compound (BFC-16) was obtained using the method described in Example 4-12, except cyclic peptide (C12) was replaced with cyclic peptide (C15). Analytical method 7: $t_R$=0.81 min.; MS m/z 1834.1 $[(M-H)/2]^+$.

Example 4-16: Synthesis of Bifunctional Compound (BFC-17)

(BFC-17)

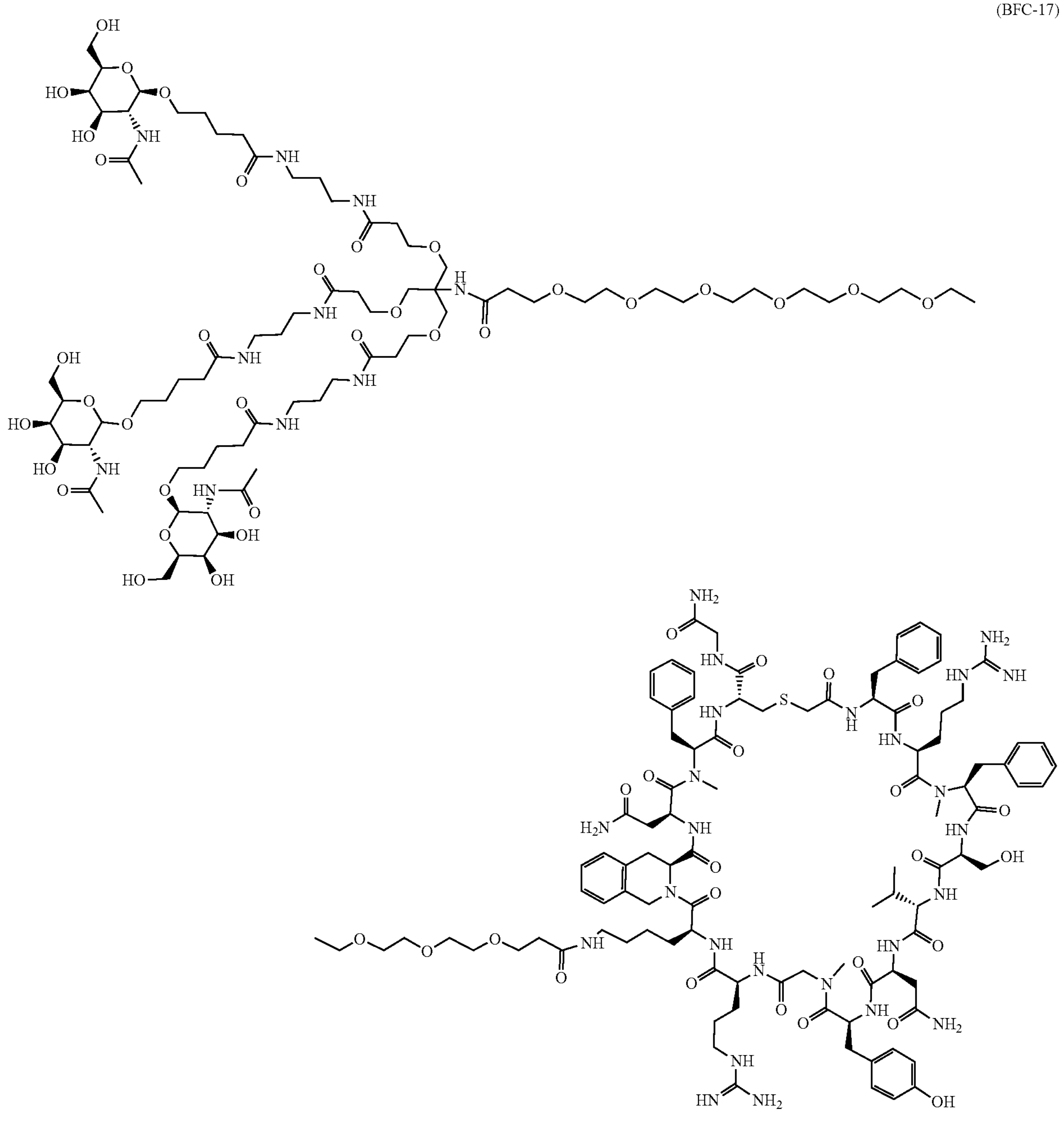

Bifunctional compound (BFC-17) was obtained using the method described in Example 4-12, except cyclic peptide (C12) was replaced with cyclic peptide (C16). Analytical method 7: $t_R$=0.81 min.; MS m/z 1913.5 [(M−H)/2]

Example 5: Bifunctional Compounds In Vitro Evaluation

Example 5-1: FHR3 Bifunctional Compounds-FHR3 Binding Data

SPR was used to obtain the binding data for FHR3 receptor ligands compounds (C12), (C13), (C14), (C15) and (C16), either alone or as part of the bifunctional compounds (BFC13), (BFC14), (BFC15), (BFC16) and (BFC17), respectively. The corresponding data is given in Table 6 below.

SPR Binding experiments were performed on a Proteon XPR36 instrument (Bio-Rad Laboratories). Purified FHR3 with C-terminal biotinylated Avitag was used for the assay. Biotinylated FHR3 was incubated with fivefold molar excess of bifunctional compounds (BFC13), (BFC14), (BFC15), (BFC16) or (BFC17), or compounds (C12), (C13), (C14), (C15) or (C16), and immobilized onto a Neutravidin coated sensor chip. (NLC chip, Bio-Rad Laboratories, Inc). After conditioning the chip by injecting running buffer (20 mM Tris pH7.5, 300 mM NaCl, 25 mM $CaCl_2$, 2 mM betamercaptoethanol, 2% DMSO and 0.05% Tween-20) at a flow rate of 0.1 mL/min for 240 s, FHR3 was injected at a protein concentration of 0.02 mg/ml in running buffer with fivefold molar excess of bifunctional compound and a flow rate of 0.03 mL/min followed by 4 washes with running buffer with 1 μM of bifunctional compound (0.1 mL/min for 60 seconds each).

To perform sandwich SPR binding assays, His-ASGPR1 (62-291) protein stocks were diluted with running buffer to a desired concentration. ASGPR were injected at a flow rate of 0.1 mL/min for 240 s and allowed to dissociate for 1200 s. Sensorgrams were recorded for association and dissociation phases. All sensorgrams were processed by subtracting the binding response recorded from a blank control surfaces (or interspot surfaces), followed by subtracting buffer blank injections from the reaction surface. Data were processed with the ProteOn Manager software (version 3.1.0.6, Bio-Rad, Inc.).

TABLE 6

| Free Ligand | FHR3 KD (nM) | Bifunctional Compound | FHR3 KD (nM) |
|---|---|---|---|
| C12 | 8 | BFC-13 | 20 |
| C13 | 48 | BFC-14 | 80 |
| C14 | 162 | BFC-15 | 301 |
| C15 | 15 | BFC-16 | 26 |
| C16 | 13 | BFC-17 | 55 |

Example 5-2: FHR3 Bifunctional Compounds-ASGPR Binding Data

SPR was used to obtain the binding data for ASGP receptor ligand compound (int-CC2), either alone or as part of the bifunctional compounds (BFC-13), (BFC-15) and (BFC16). The corresponding data is given in Table 7 below.

ASGPR1 SPR experiments were performed on either Biacore T200 or Biacore 8K. The assay was optimized for Biacore (Streptavidin) SA chip in running buffer consisting of 20 mM HEPES, 300 mM NaCl, 2 mM $CaCl_2$, 0.01% tween-20, 2% DMSO, pH 7.4. Recombinant extracellular domain of human ASGPR1 with N-terminal biotinylated Avitag was diluted to 20 μg/mL in running buffer, and immobilized onto SA chip after it was preconditioned with at least four 60-second injections at 30 uL/min of 1 M NaCl/40 mM NaOH solution. Protein immobilization level varied from 500 RU to 3500 RU dependent on analytes' molecular weight, for targeted $R_{max}$ of 30 RUs. Direct binding of analytes to ASGPR1 was observed when a dose response titration of analytes in 2% DMSO was flown over the immobilized protein. Data analysis was done on either Biacore T200 Evaluation Software or Biacore Insight Evaluation Software.

TABLE 7

| Free Ligand | ASGPR KD (nM) | Bifunctional Compound | ASGRR KD (nM) |
|---|---|---|---|
| int-CC2 | 0.9 | BFC-13 | 0.44 |
| int-CC2 | 0.9 | BFC-15 | 0.45 |
| int-CC2 | 0.9 | BFC-16 | 0.32 |

Example 5-3: PCSK9 Bifunctional Compounds-PCSK9 Binding Data

SPR was used to obtain the binding data for PCSK9 receptor ligand compound (C5), either alone or as part of the bifunctional compounds (BFC1), respectively. The corresponding data is given in Table 8 below.

SPR Binding experiments were performed on a Proteon XPR36 instrument (Bio-Rad Laboratories). Purified recombinant full length human PCSK9 with C-terminal biotinylated Avitag was used for the assay. Biotinylated human PCSK9 was incubated with fivefold molar excess of bifunctional compound (BFC1) or compound ($C_5$), and immobilized onto a Neutravidin coated sensor chip. (NLC chip, Bio-Rad Laboratories, Inc). After conditioning the chip by injecting running buffer (20 mM Tris pH7.5, 300 mM NaCl, 25 mM $CaCl_2$, 2 mM betamercaptoethanol, 2% DMSO and 0.05% Tween-20) at a flow rate of 0.1 mL/min for 240 s, PCSK9 protein was injected at a protein concentration of 0.02 mg/ml in running buffer with fivefold molar excess of bifunctional compound and a flow rate of 0.03 mL/min followed by 4 washes with running buffer with 1 μM of bifunctional compound (0.1 mL/min for 60 seconds each).

To perform sandwich SPR binding assays, His-ASGPR1 (62-291) protein stocks were diluted with running buffer to a desired concentration. ASGPR was injected at a flow rate of 0.1 mL/min for 240 s and allowed to dissociate for 1200 s. Sensorgrams were recorded for association and dissociation phases. All sensorgrams were processed by subtracting the binding response recorded from a blank control surfaces (or interspot surfaces), followed by subtracting buffer blank injections from the reaction surface. Data were processed with the ProteOn Manager software (version 3.1.0.6, Bio-Rad, Inc.).

TABLE 8

| Free Ligand | PCSK9 KD (nM) | Bifunctional Compound | PCSK9 KD (nM) |
|---|---|---|---|
| C5 | 1.2 | BFC-1 | 3.9 |
| C5 | 1.2 | BFC-2 | 9.2 |
| C5 | 1.2 | BFC-3 | 7.7 |
| C5 | 1.2 | BFC-4 | 4.1 |
| C5 | 1.2 | BFC-5 | 4.6 |
| C5 | 1.2 | BFC-6 | 5.8 |
| C5 | 1.2 | BFC-7 | 3.5 |
| C5 | 1.2 | BFC-8 | 4.9 |
| C5 | 1.2 | BFC-9 | 7.4 |
| C9 | <1 | BFC-10 | 2.3 |
| C9 | <1 | BFC-11 | n.d. |
| C9 | <1 | BFC-12 | n.d. |

Note:
n.d. indicates not determimined

Example 5-4: PCSK9 Bifunctional Compounds-ASGPR Binding Data

SPR was used to obtain the binding data for ASGP receptor ligand compounds (int-CC2), either alone or as part of the bifunctional compounds (BFC1). The corresponding data is given in Table 9 below.

ASGPR1 SPR experiments were performed on either Biacore T200 or Biacore 8K. The assay was optimized for Biacore SA chip in running buffer consisting of 20 mM HEPES, 300 mM NaCl, 2 mM $CaCl_2$, 0.01% tween-20, 2% DMSO, pH 7.4. Recombinant extracellular domain of human ASGPR1 with N-terminal biotinylated Avitag was diluted to 20 μg/mL in running buffer, and immobilized onto SA chip after it was preconditioned with at least four 60-second injections at 30 uL/min of 1 M NaCl/40 mM NaOH solution. Protein immobilization level varied from 500 RU to 3500 RU dependent on analytes' molecular weight, for targeted $R_{max}$ of 30 RUs. Direct binding of analytes to ASGPR1 was observed when a dose response titration of analytes in 2% DMSO was flown over the immobilized protein. Data analysis was done on either Biacore T200 Evaluation Software or Biacore Insight Evaluation Software.

TABLE 9

| Free Ligand | ASGPR binding KD (nM) | Bifunctional Compound | ASGPR binding KD (nM) |
|---|---|---|---|
| Int-CC2 | 0.9 | BFC1 | 0.32 |
| Int-CC3 | n.d. | BFC-5 | 90 |
| Int-CC5 | n.d. | BFC-6 | <1 |
| Int-CC4 | n.d. | BFC-7 | 7 |
| Int-CC2 | 0.9 | BFC-10 | 100 |
| Int-CC8 | n.d. | BFC-11 | n.d. |
| Int-CC9 | n.d. | BFC-12 | 22 |

Note:
n.d. indicates not determimined

Example 5-5: PCSK9 Bifunctional Compounds-M6PR Binding Data

SPR was used to obtain the binding data for M6P receptor ligands compounds (int-CC6), either alone or as part of the bifunctional compound (BFC-2). The corresponding data is given in Table 10 below.

TABLE 10

| Free Ligand | M6PR binding KD (nM) | Bifunctional Compound | M6PR binding KD (nM) |
|---|---|---|---|
| Int-CC6 | 0.327 | BFC-2 | 7.19 |
| Int-CC6 | 0.327 | BFC-3 | n.d. |
| Int-CC7 | n.d. | BFC-4 | 110 |
| Int-CC7 | n.d. | BFC-8 | 480 |
| Int-CC7 | n.d. | BFC-9 | 170 |

Note:
n.d. indicates not determimined

Example 6: Bifunctional Compounds: In Vivo Evaluation

Example 6-1: FHR3 Bifunctional Compounds: In Vivo Evaluation

The in-vivo studies described in this report were performed according to institutional ACUC approved protocol 170PH021. Transgenic mice expressing human FHR3 were generated internally. The male human FHR3 transgenic mice used in the following studies were four months old.

The test bifunctional compounds BFC-13 and BFC-15 were formulated in PBS at 30 μg/ml and 3 μg/mL to ensure that a fixed volume of 0.1 mL would deliver the desired 0.1 and 0.01 mg/kg dose based on the mean body weight of the mice (around 30 grams).

Blood samples were collected via tail snip into EDTA collection tubes (Grenier, Kremsmünster, Austria) before dosing to determine baseline levels. Animals were injected intraperitoneally with a 0.1 mL bolus containing either bifunctional compound BFC-13 or BFC-15 at 0.1 mg/kg and 0.01 mg/kg. Control mice received only PBS. At, 1, 2 and 4 hours post-dosing, 25 μL of blood was collected and stored on ice. Blood samples were centrifuged at 15,000 g, 4° C. for 10 minutes with resulting plasma aliquoted and frozen at −80° C. for later PD measurements.

To enable the determination of human FHR3 plasma protein levels in the transgenic mice, rabbits were immunized with human FHR3 protein by Covance (Princeton, NJ, USA), and polyclonal antibodies were isolated from rabbit sera using affinity purification with CNBr-activated sepharose from GE (Boston, MA, USA). Subsequently, FHR3 levels in mouse plasma was measured using immunoassays on the Mesoscale Discovery (Rockville, MD, USA) platform where the rabbit anti-FHR3 antibody was used as the capture antibody, and biotinylated rabbit anti-FHR3 was used as the detection antibody.

Figure 1A:
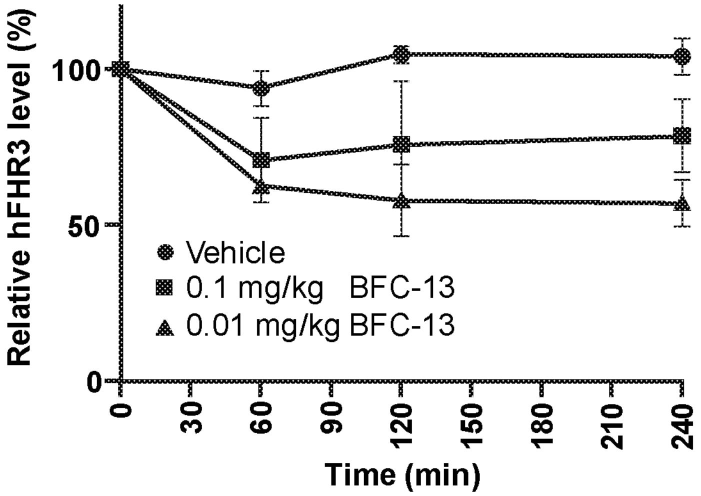
FIG. 1A: Clearance of human FHR3 from transgenic mice expressing human FHR3 after intraperitoneally bolus administration of vehicle, 0.01 mg/kg of bifunctional compound (BFC-13) and 0.1 mg/kg of bifunctional compound (BFC-13). The hFHR3 levels are relative to the level of FHR3 prior to administration.
Figure 1B:
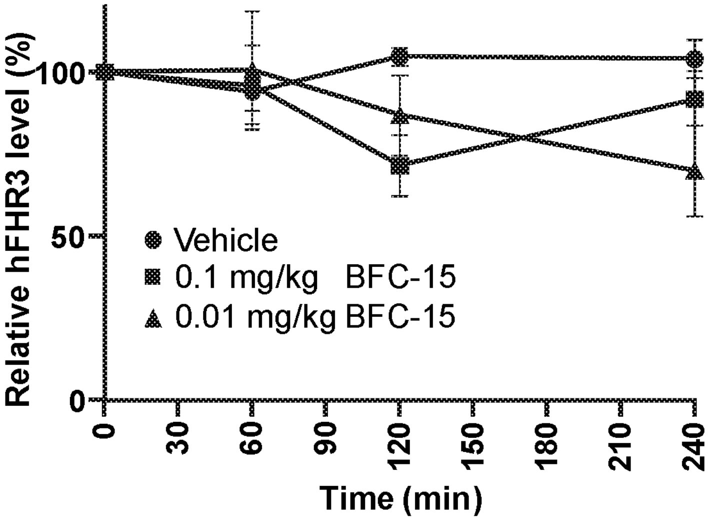
FIG. 1B: Clearance of human FHR3 from transgenic mice expressing human FRH3 after intraperitoneally bolus administration of vehicle, 0.01 mg/kg of bifunctional compound (BFC-15) and 0.1 mg/kg of bifunctional compound (BFC-15). The hFHR3 levels are relative to the level of FHR3 prior to administration.

The clearance of hFHR3 after the iv bolus administration of a bifunctional compound of BFC-13 and BFC15 is shown in FIGS. 1A and 1B, respectively. The level of hFHR3 is relative to the value obtained prior to administration of the bifunctional compound. The data illustrates that bifunctional compound BFC-13 and BFC-15 facilitate accelerated clearance of hFHR3 from the plasma relative to vehicle control.

Example 6-2: PCSK9 Bifunctional Compounds: In Vivo Evaluation

The in-vivo studies described herein were performed according to institutional ACUC approved protocols 18CVM018 and 17CVM029. Male LDLR(−/−) mice were obtained from Jackson Laboratories, Bar Harbor, ME (cat. #002207). On the morning of the study, mice were weighed and sorted into treatment groups having similar mean body weights.

Vehicle was composed of 10% polyethylene glycol 300 (Sigma-Aldrich, Saint Louis, MO), 25% Kolliphor HS 15 (20% stock solution; Sigma-Aldrich, Saint Louis, MO) and 65% PBS (Gibco/ThermoFisher, Waltham, MA).

Test compounds, such as bifunctional compounds BFC-1, BFC-2, BFC-5, BFC-7, BFC-11, BFC12, BFC-13 and BFC-15, PCSK9 ligand compounds ($C_5$) and ($C_{15}$), ASGPR ligand (int-CC2) and M6PR ligand (int-CC6), were formulated based on the mean body weight of the mice to ensure that a fixed volume of 0.1 mL would deliver a desired dose of test compound, such as 0.01 mg/kg, 0.03 mg/kg, 0.05 mg/kg, 0.1 mg/kg, 0.3 mg/kg, 1 mg/kg or 10 mg/kg. For the co-administration of test compound with hPCSK9 protein, the test compound was formulated in vehicle and then combined with human PCSK9 protein (33.3 μg/mL) in PBS immediately before dosing. Otherwise, for pre-administration of test compound without hPCSK9 the test compound was formulated with vehicle.

Using a rotating tail injector (Braintree Scientific Inc., Braintree, MA), animals were injected i.v. via the lateral tail vein with a 0.2 mL bolus containing the mixture of test compound at the desired concentration and 3.3 μg of wild type human PCSK9 protein.

Blood samples (25 μL) were obtained at 5 min., 15 min., 30 min., 60 min., 120 min. and 240 min. post-dose using EDTA collection tubes (Sarstedt AG, Sarstedt, Germany) and then stored on ice. The blood samples were centrifuged at 15,000 g, 4° C. for 10 minutes with resulting plasma aliquoted and frozen at −80° C. for later PD measurements.

Plasma concentrations of PCSK9 were assessed using a commercially available human (Human Proprotein Convertase 9/PCSK9 Quantikine ELISA Kit, DPC900; R&D Systems, Minneapolis, MN) ELISA kit. For the measurement of PCSK9 levels, plasma samples were diluted (1:25 or 1:50) and analyzed according to the manufacturer's instructions, with the exception that all incubations were performed on a Titer Plate Shaker (Lab-Line Instruments, Melrose Park, Illinois) at 300 rpm.

Example 6-2a: PCSK9 Bifunctional Compounds—In Vivo PD Evaluation: i.v. Bolus Co-Administration of a Bifunctional Compound with hPCSK9 Protein The clearance of hPCSK9 protein after the iv bolus co-administration of a bifunctional compound of the invention with hPCSK9 protein is shown in FIGS. 2-5

Figure 2A:
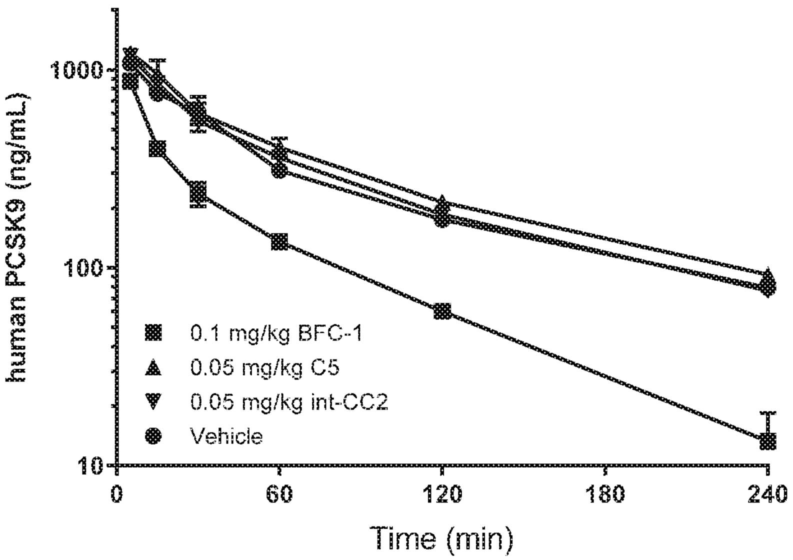
FIG. 2A: Co-administration study: clearance of human PCSK9 from LDLR(−/−) mice after intravenous bolus administration of vehicle+3.3 μg hPCSK9, 0.1 mg/kg of bifunctional compound (BFC-1)+3.3 μg hPCSK9, 0.05 mg/kg of PCSK9 ligand (C5), and 0.05 mg/kg of ASGPR ligand (int-CC2)+3.3 μg hPCSK9.
Figure 2B:
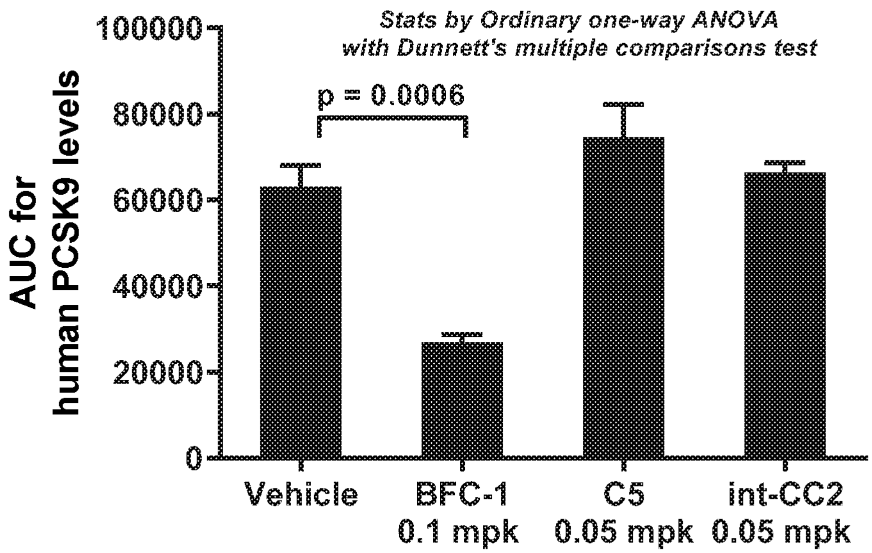
FIG. 2B: Co-administration study: AUC plot of clearance data depicted in FIG. 2A. Statistics by Ordinary one-way ANOVA with Dunnett's multiple comparison test.

FIG. 2A shows the plasma concentration of human PCSK9 over time after iv bolus administration of vehicle+hPCSK9 (3.3 μg), bifunctional compound (BFC-1) (0.1 mg/kg)+hPCSK9 (3.3 μg), a PCSK9 ligand ($C_5$) (0.05 mg/kg)+hPCSK9 (3.3 μg), or an ASGPR ligand (int-CC2) (0.05 mg/kg)+hPCSK9 (3.3 μg). The corresponding AUC plot is shown in FIG. 2B. The data shows that clearance of the wild type human PCSK9 protein from the plasma is eliminated more quickly with bifunctional compound (BFC-1) than that observed for the vehicle, the PCSK9 ligand alone ($C_5$) or the ASGPR ligand alone (int-CC2), all of which showed similar rates of elimination.

Figure 3A:
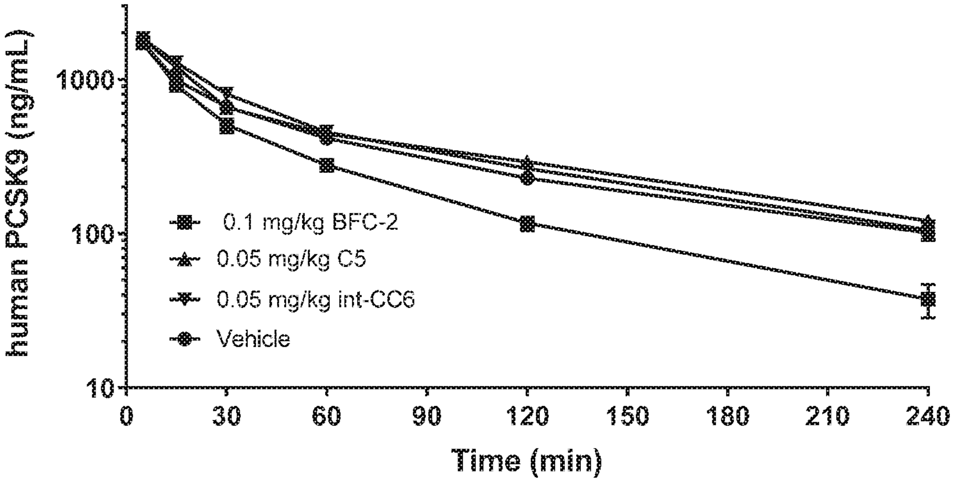
FIG. 3A: Co-administration study: clearance of human PCSK9 from LDLR(−/−) mice after intravenous bolus administration of vehicle+3.3 μg hPCSK9, 0.1 mg/kg of bifunctional compound (BFC-2)+3.3 μg hPCSK9, 0.05 mg/kg of PCSK9 ligand (C5), and 0.05 mg/kg of M6PR ligand (int-CC6)+3.3 μg hPCSK9.
Figure 3B:
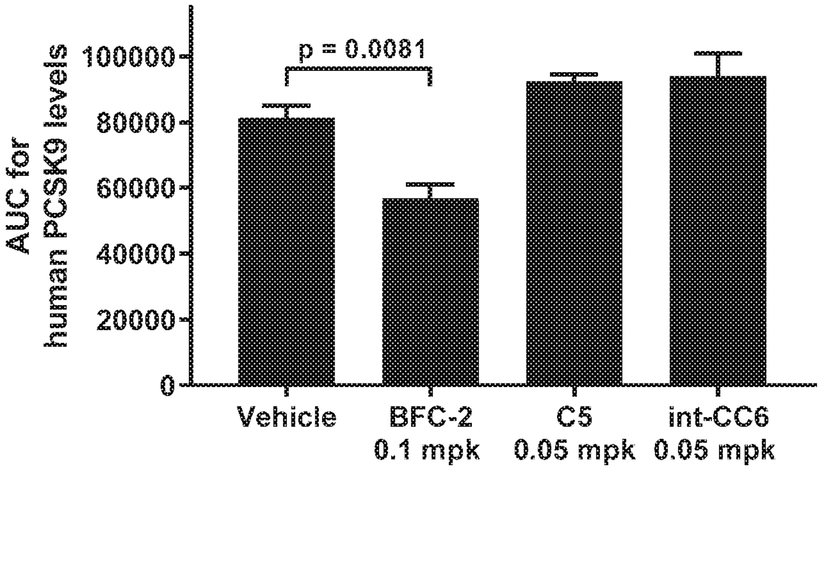
FIG. 3B: Co-administration study: AUC plot of clearance data depicted in FIG. 3A. Statistics by Ordinary one-way ANOVA with Dunnett's multiple comparison test.

A similar study is shown in FIGS. 3A and 3B, where FIG. 3A shows the plasma concentration of human PCSK9 as a function of time after iv bolus administration of either vehicle+hPCSK9 (3.3 μg), bifunctional compound (BFC-2) (0.1 mg/kg)+hPCSK9 (3.3 μg), a PCSK9 ligand ($C_5$) (0.05 mg/kg)+hPCSK9 (3.3 μg), or a M6PR ligand (int-CC6) (0.05 mg/kg)+hPCSK9 (3.3 μg). The corresponding AUC plot is shown in FIG. 3B. The data shows that clearance of the wild type human PCSK9 protein from the plasma is eliminated more quickly with bifunctional compound (BFC-2) than that observed for the vehicle, the PCSK9 ligand alone ($C_5$) or the M6PR ligand alone (int-CC6), all of which showed similar rates of elimination.

Figure 4A:
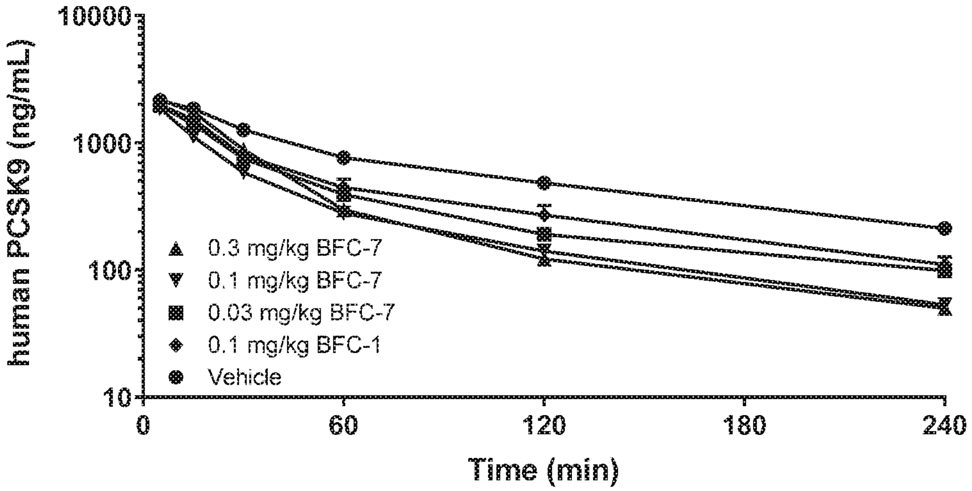
FIG. 4A: Co-administration study: clearance of human PCSK9 from LDLR(−/−) mice after intravenous bolus administration of vehicle+3.3 μg hPCSK9, 0.1 mg/kg of bifunctional compound (BFC-1)+3.3 μg hPCSK9, 0.03 mg/kg of bifunctional compound (BFC-7)+3.3 μg hPCSK9, 0.1 mg/kg of bifunctional compound (BFC-7)+3.3 μg hPCSK9, and 0.3 mg/kg of bifunctional compound (BFC-7)+3.3 μg hPCSK9.
Figure 4B:
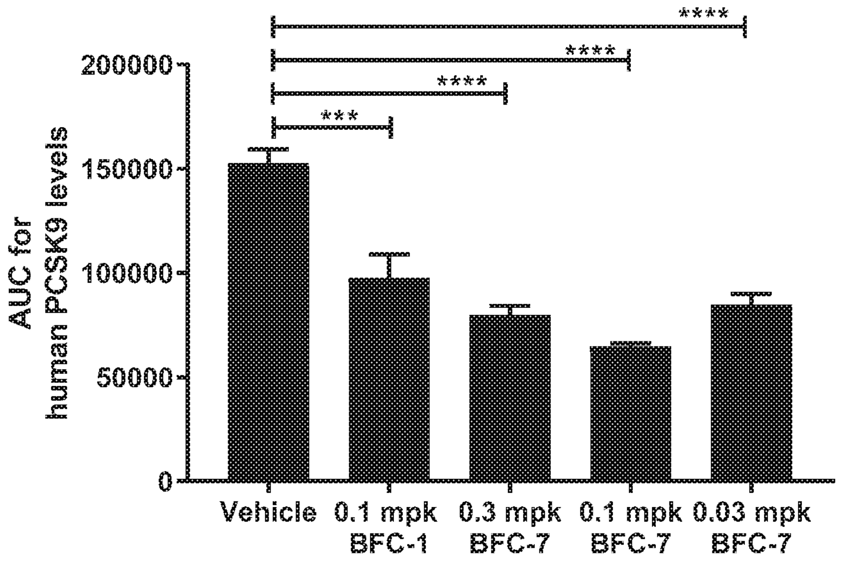
FIG. 4B: Co-administration study: AUC plot of clearance data depicted in FIG. 4A. Statistics by Ordinary one-way ANOVA versus vehicle: * p=0.0001; ** p<0.0001
Figure 5A:
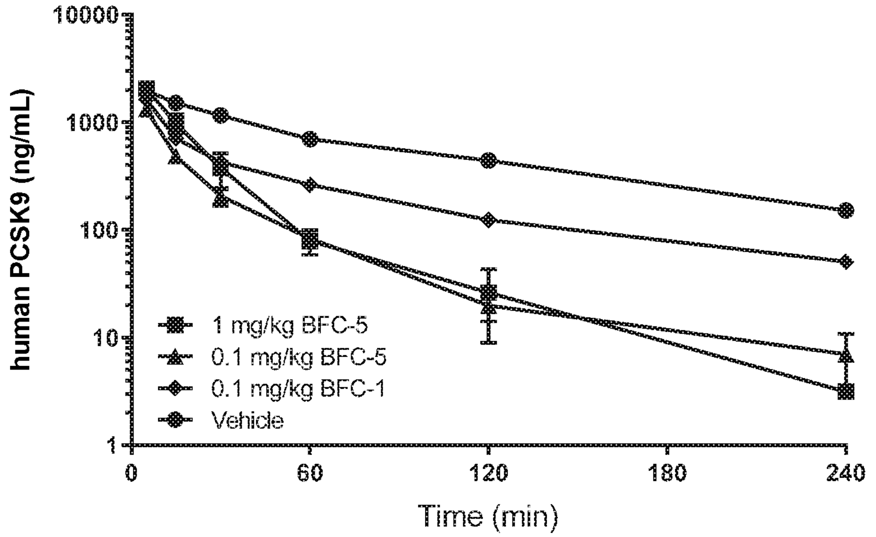
FIG. 5A: Co-administration study: clearance of human PCSK9 from LDLR(−/−) mice after intravenous bolus administration of vehicle+3.3 μg hPCSK9, 0.1 mg/kg of bifunctional compound (BFC-1)+3.3 μg hPCSK9, 0.1 mg/kg of bifunctional compound (BFC-5)+3.3 μg hPCSK9, and 1 mg/kg of bifunctional compound (BFC-5)+3.3 μg hPCSK9.
Figure 5B:
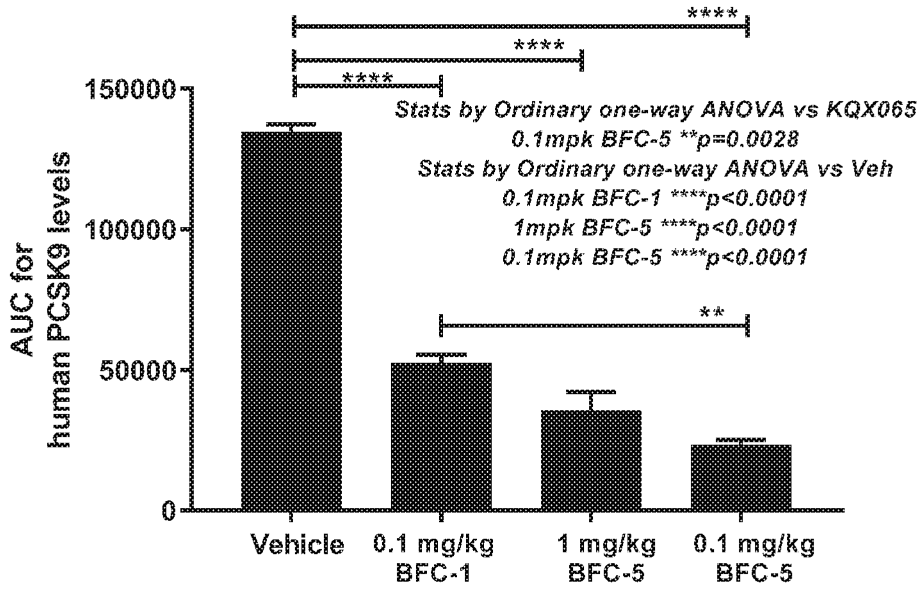
FIG. 5B: Co-administration study: AUC plot of clearance data depicted in FIG. 5A. Statistics by Ordinary one-way ANOVA vs BFC-1:  p=0.0028 Statistics by Ordinary one-way ANOVA vs vehicle: ** p<0.0001

FIG. 4A and FIG. 4B show the dose response of bifunctional compound (BFC-7) on the clearance of the plasma concentration of human PCSK9 after iv bolus administration bifunctional compound (BFC-7) (0.03 mg/kg)+hPCSK9 (3.3 μg), bifunctional compound (BFC-7) (0.1 mg/kg)+hPCSK9 (3.3 μg) and bifunctional compound (BFC-7) (0.3 mg/kg)+hPCSK9 (3.3 μg). In addition, for comparison the plasma concentration of hPCSK9 as a function of time after iv bolus administration of vehicle+hPCSK9 (3.3 μg) and bifunctional compound (BFC-1) (0.1 mg/kg)+hPCSK9 (3.3 μg) is shown in FIGS. 4A and 4B. As compared to vehicle, BFC-1 and all three doses of BFC-7 significantly accelerated PCSK9 clearance Similarly, FIG. 5A and FIG. 5B show the dose response of bifunctional compound (BFC-5) on the clearance of human PCSK9 after iv bolus administration: bifunctional compound (BFC-5) (0.1 mg/kg)+hPCSK9 (3.3 μg) and bifunctional compound (BFC-5) (1 mg/kg)+hPCSK9 (3.3 μg). In addition, for comparison the plasma concentration of hPCSK9 as a function of time after iv bolus administration of vehicle+hPCSK9 (3.3 μg) and bifunctional compound (BFC-1) (0.1 mg/kg)+hPCSK9 (3.3 μg) is shown in FIGS. 5A and 5B. As compared to vehicle, BFC-1 and BFC-5 at doses tested, significantly accelerated PCSK9 clearance. PCSK9 clearance was significantly accelerated by BFC-5 at 0.1 mg/kg as compared to vehicle or BFC-1 at the same dose.

Example 6-2b: PCSK9 Bifunctional Compounds—In Vivo Evaluation: Pre-Administration Versus Co-Administration The comparison between iv bolus co-administration of a bifunctional compound with hPCSK9 protein and the iv bolus pre-administration of a bifunctional compound prior to iv bolus administration of hPCSK9 protein is shown in FIGS. 6A and 6B.

Figure 6A:
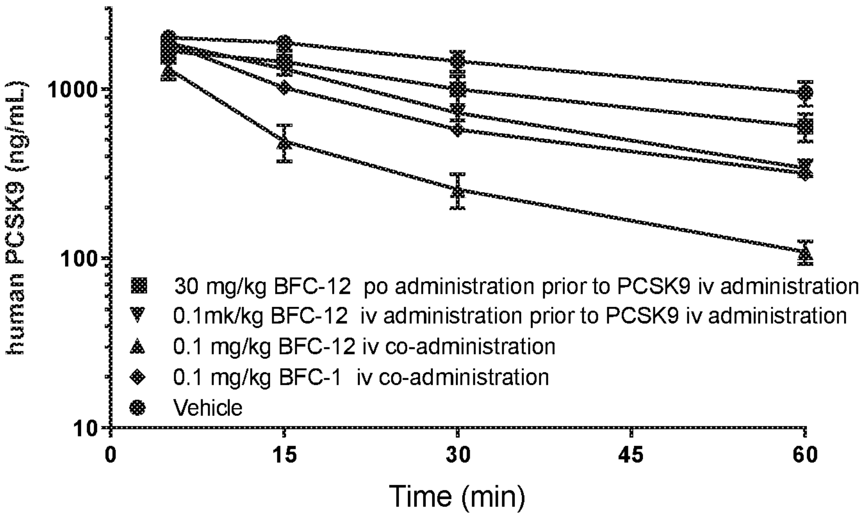
FIG. 6A: Co-administration vs pre-dosing of bifunctional compound study: clearance of human PCSK9 from LDLR (−/−) mice after.
Figure 6B:
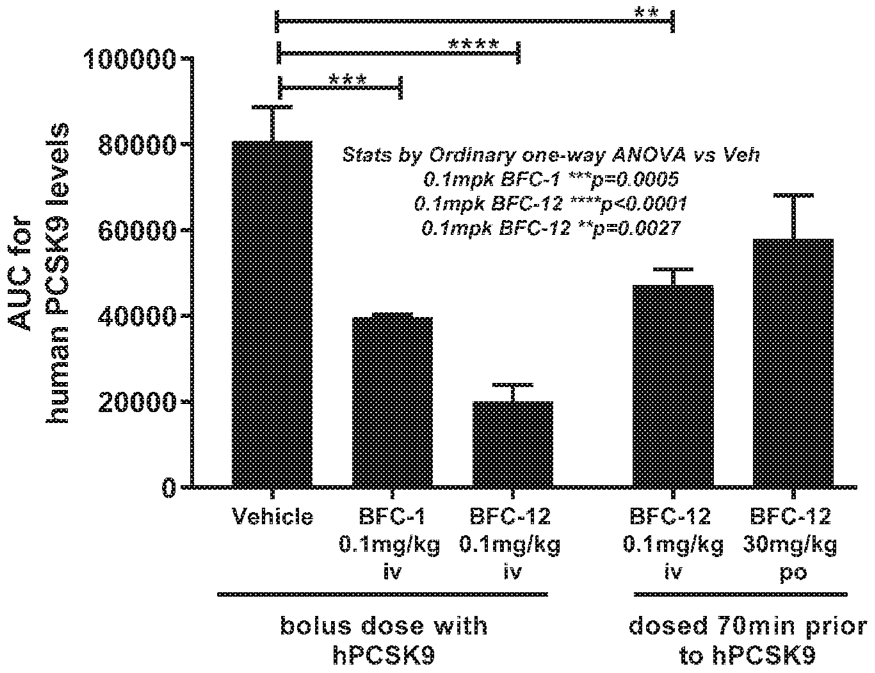
FIG. 6B: Co-administration vs pre-dosing of bifunctional compound study: AUC plot of clearance data depicted in FIG. 6A.

In particular, FIG. 6A shows the plasma concentration of hPCSK9 over time after iv bolus co-administration of 0.1 mg/kg bifunctional compound (BFC-1)+3.3 μg hPCSK9, bolus co-administration of 0.1 mg/kg bifunctional compound (BFC-12)+3.3 μg hPCSK9; iv bolus administration of 0.1 mg/kg bifunctional compound (BFC-12) followed by iv bolus administration of 3.3 μg hPCSK9 70 minutes later and iv bolus co-administration of vehicle+3.3 μg hPCSK9. In addition, FIG. 6A shows the plasma concentration of hPCSK9 over time after oral (po) administration of 30 mg/kg bifunctional compound (BFC-12) followed by iv bolus administration of 3.3 μg hPCSK9 70 minutes later. FIG. 6B shows the corresponding AUC plots of the clearance data shown in FIG. 6A.

The data shows that clearance of hPCSK9 from the plasma occurs after pre-dosing of a bunctional compound of the invention. It is also shown that bifunctional compounds of the invention, for example BFC-12, can be orally administered and effect clearance of hPCSK9.

Figure 7B:
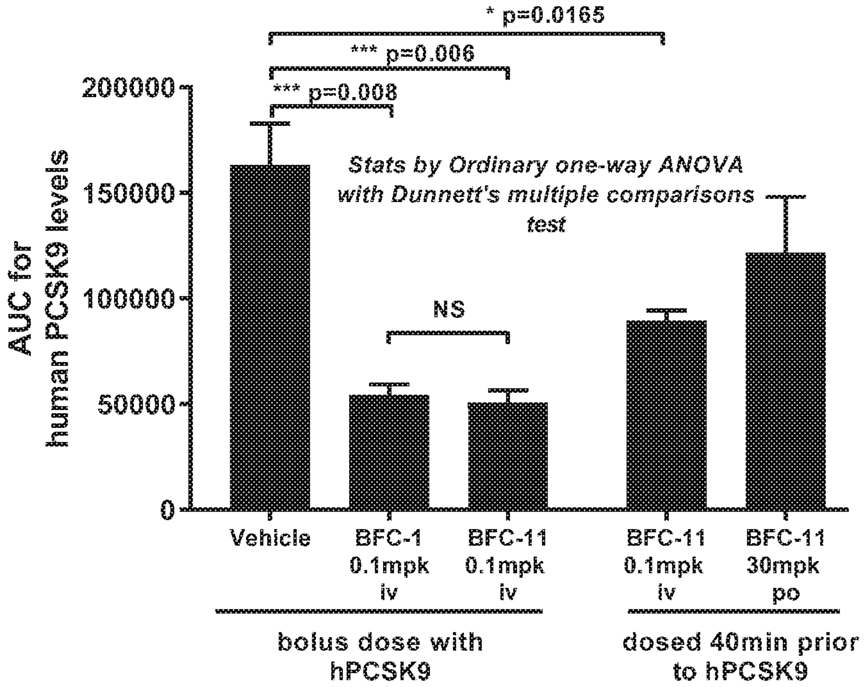

A similar study is shown in FIGS. 7A and 7B, where the plasma concentration of hPCSK9 over time after iv bolus co-administration of 0.1 mg/kg bifunctional compound (BFC-1)+3.3 μg hPCSK9, iv bolus co-administration of 0.1 mg/kg bifunctional compound (BFC-11)+3.3 μg hPCSK9; iv bolus administration of 0.1 mg/kg bifunctional compound (BFC-11) followed by iv bolus administration of 3.3 μg hPCSK9 40 minutes later and iv bolus co-administration of vehicle+3.3 μg hPCSK9.

In addition, FIG. 7A shows the plasma concentration of hPCSK9 over time after oral (po) administration of 30 mg/kg bifunctional compound (BFC-11) followed by iv bolus administration of 3.3 μg hPCSK9 40 minutes later. FIG. 6B shows the corresponding AUC plots of the clearance data shown in FIG. 6A.

The data shows that clearance of hPCSK9 from the plasma occurs after pre-dosing of a bunctional compound of the invention. It is also shown that bifunctional compounds of the invention, for example BFC-11 can be orally administered and effect clearance of hPCSK9.

Example 6-2c: PCSK9 Bifunctional Compounds—In Vivo Evaluation: Competition Assay A competition assay was used to illustrate that clearance of hPCSK9 requires binding to both PCSK9 and ASGPR. FIG. 8A shows the clearance of hPCSK9 after the iv bolus administration of vehicle+3.3 μg hPCSK9 (control), the iv bolus co-administration of 0.1 mg/kg bifunctional compound (BFC-1)+3.3 μg hPCSK9 (no competition control); the iv bolus administration of 0.1 mg/kg bifunctional compound (BFC-1)+3.3 μg hPCSK9+10 mg/kg ASGPR ligand (int-CC2) (competition with ASGPR ligand), and the iv bolus administration of 0.1 mg/kg bifunctional compound (BFC-1)+3.3 μg hPCSK9+10 mg/kg PCSK9 ligand ($C_5$) (competition with PCSK9 ligand. FIG. 8B: shows the corresponding AUC plots of the clearance data shown in FIG. 8A.

Focusing first on the AUC plot, while the bifunctional alone (BFC-1) significantly accelerated clearance as compared to vehicle control, no increased PCSK9 clearance was observed with excess PCSK9 ligand ($C_5$) or ASGPR ligand (int-CC2). Returning to the time course, excess PCSK9 ligand ($C_5$) did not differ from vehicle control at any time point. On the other hand, excess ASGPR ligand (int-CC2) most dramatically slowed clearance at the earliest time points, with the effect being lost over time, likely as int-CC2 is cleared over time through ASGPR.

It is understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A bifunctional compound of Formula (I):

$R_L$-$L_A$-$T_L$ Formula (I)

wherein:

$R_L$ is

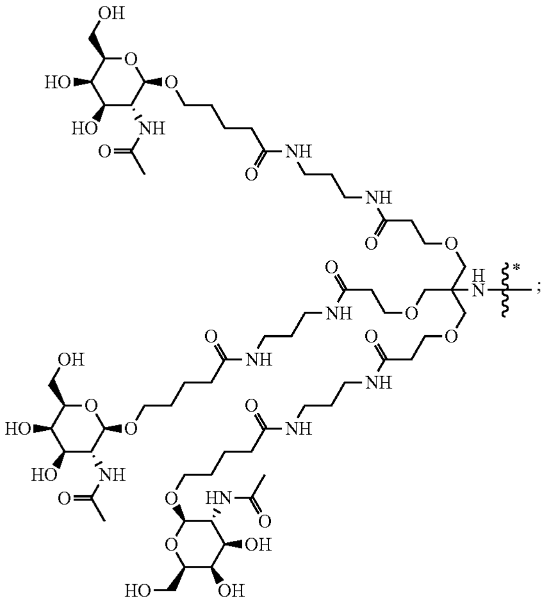

-continued

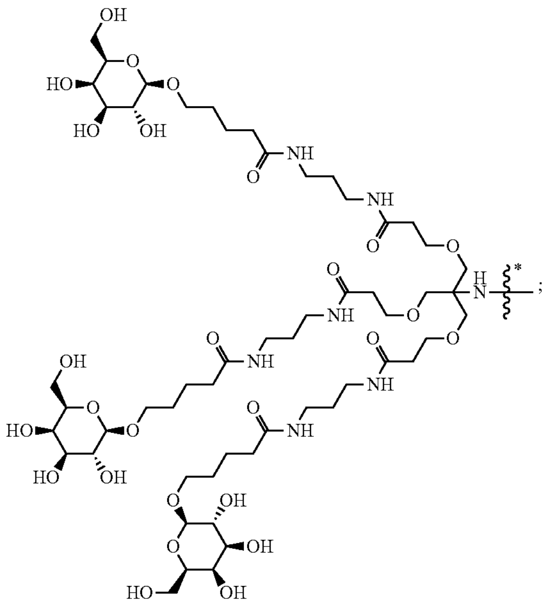

-continued
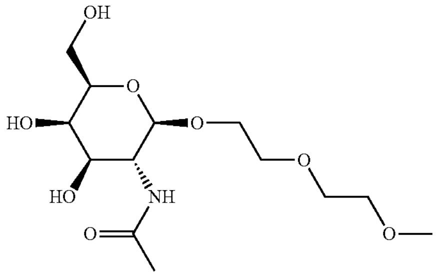
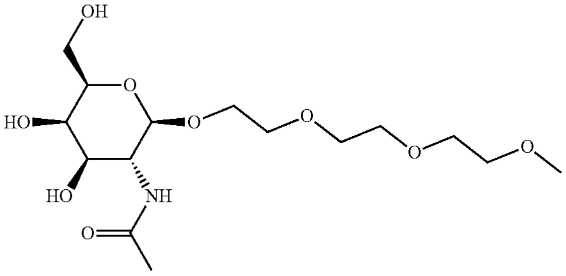
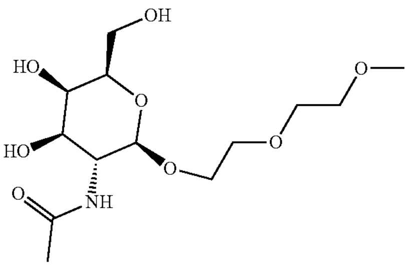
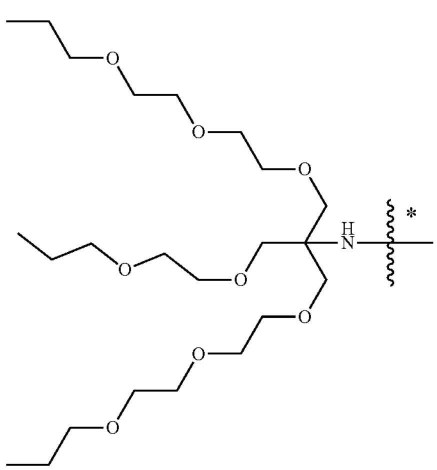
;
-continued
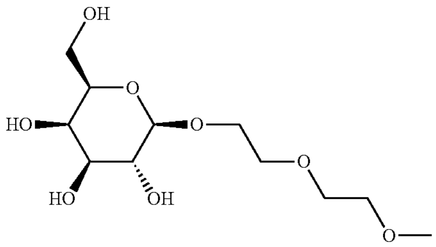
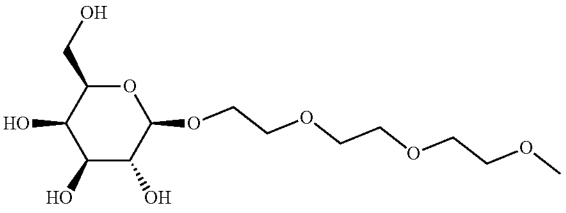
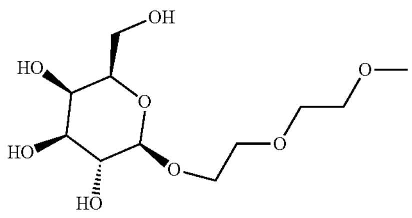
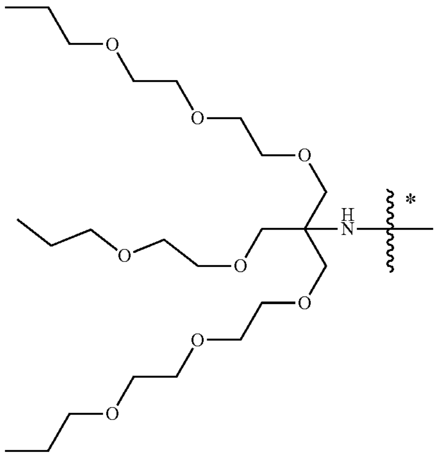
;

-continued
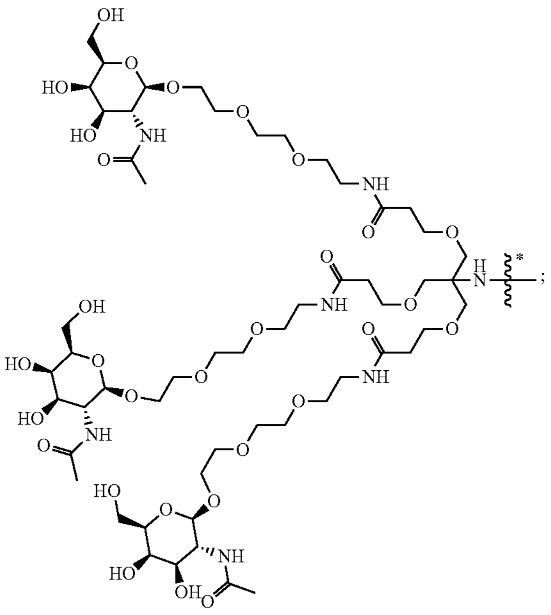
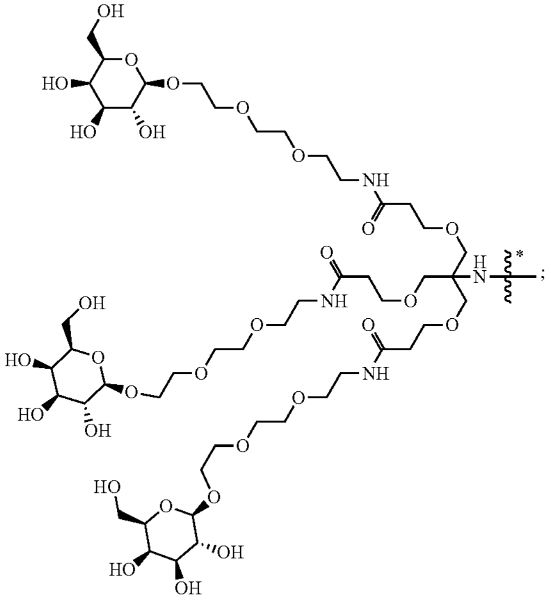
-continued
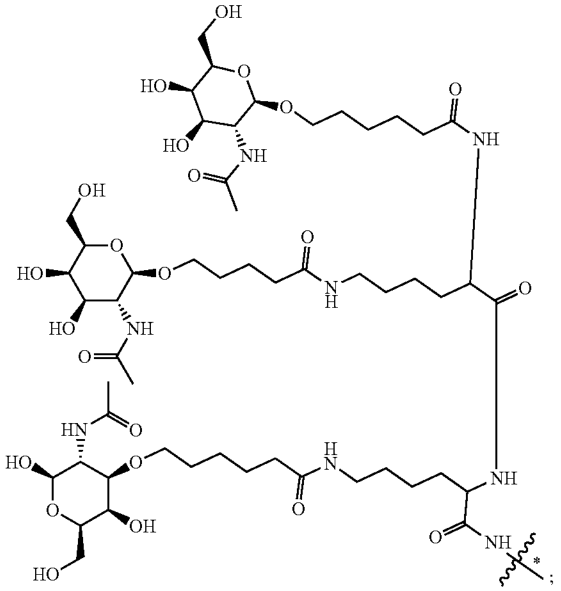
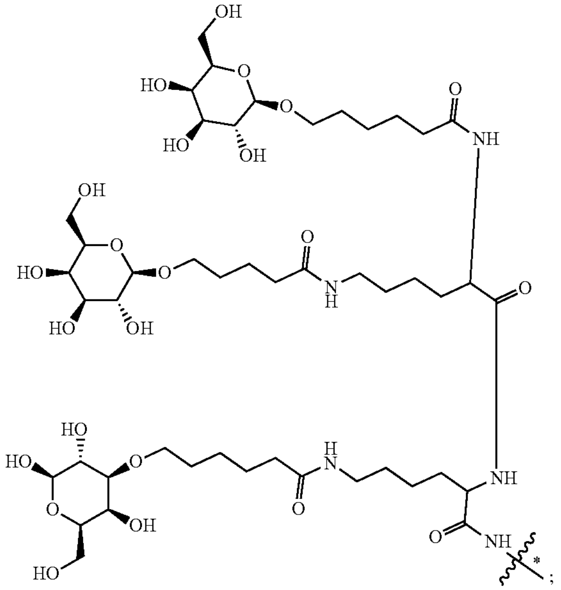
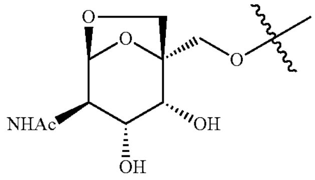
;
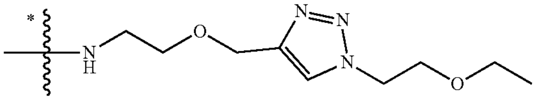
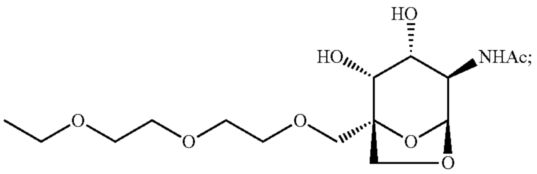

-continued
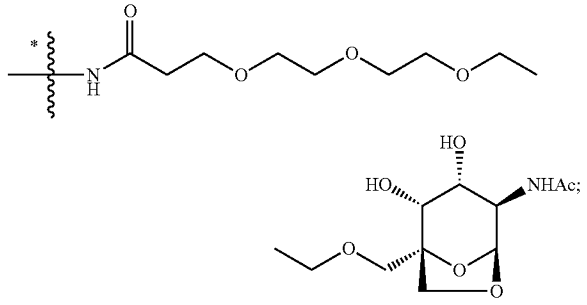
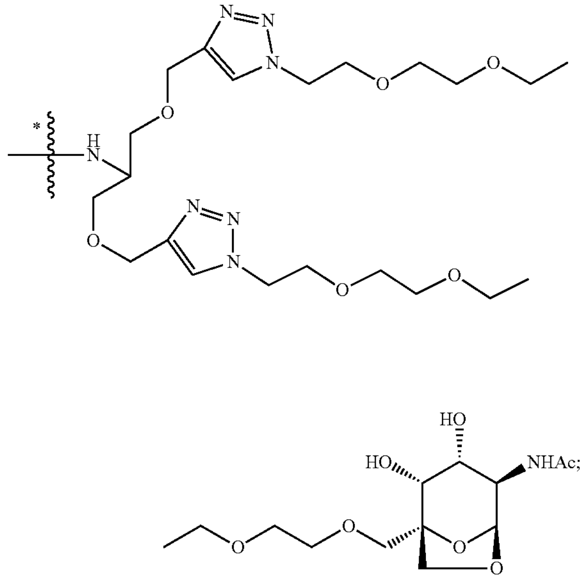
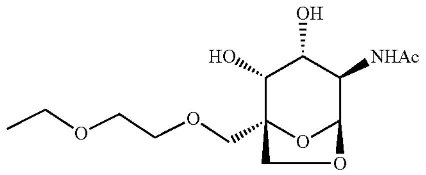
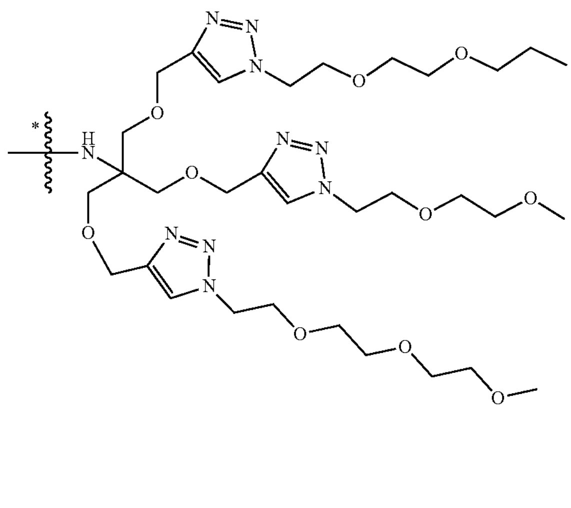
-continued
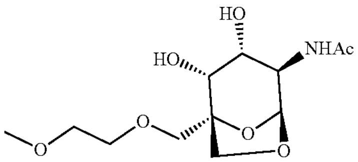
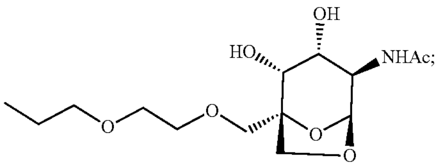
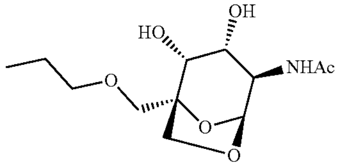
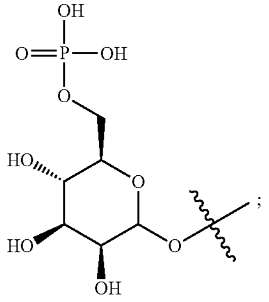
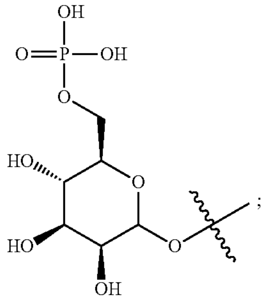
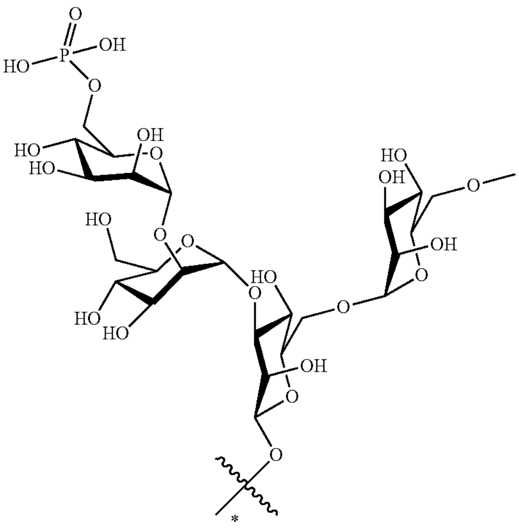

-continued
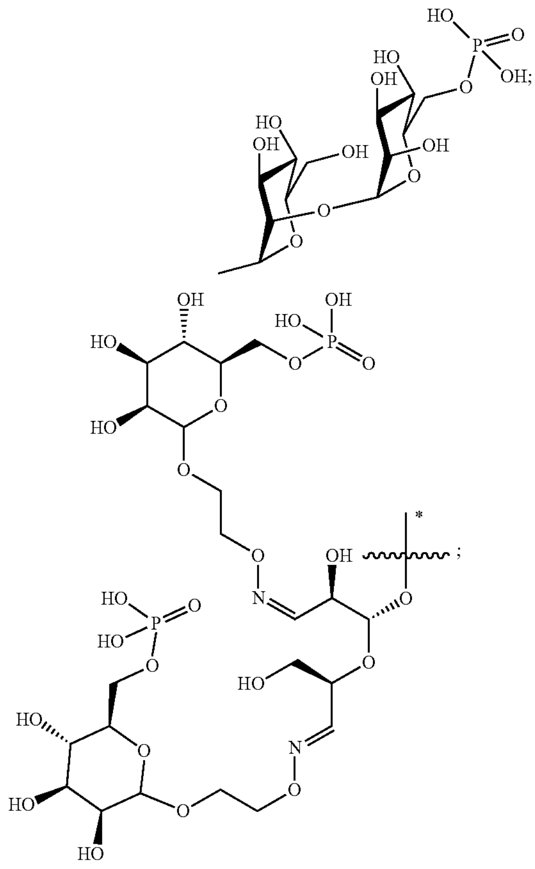
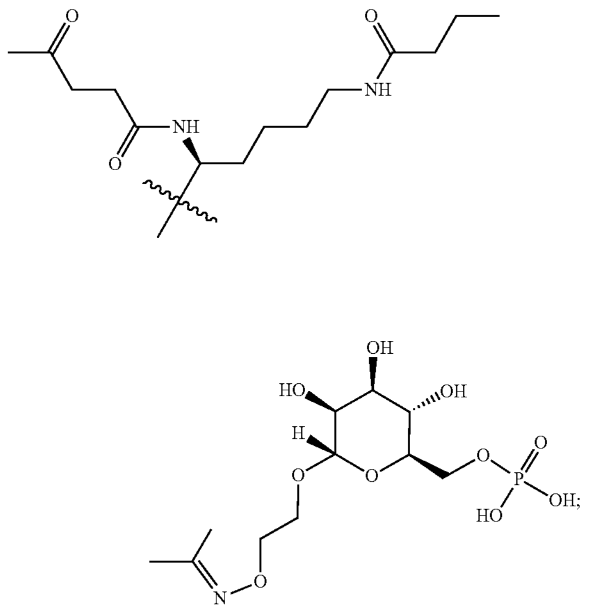
-continued
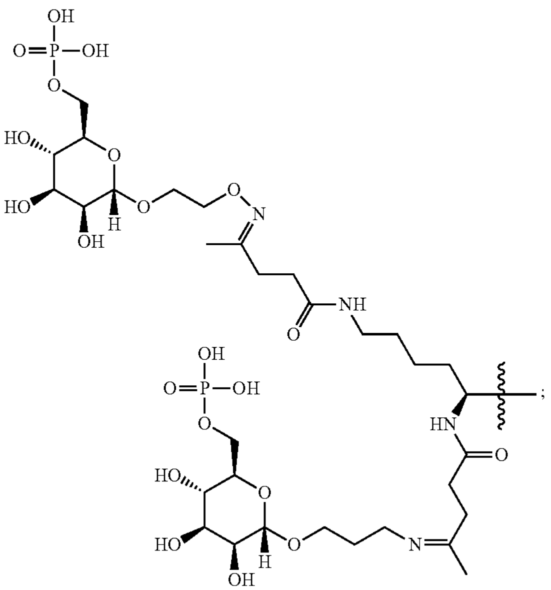
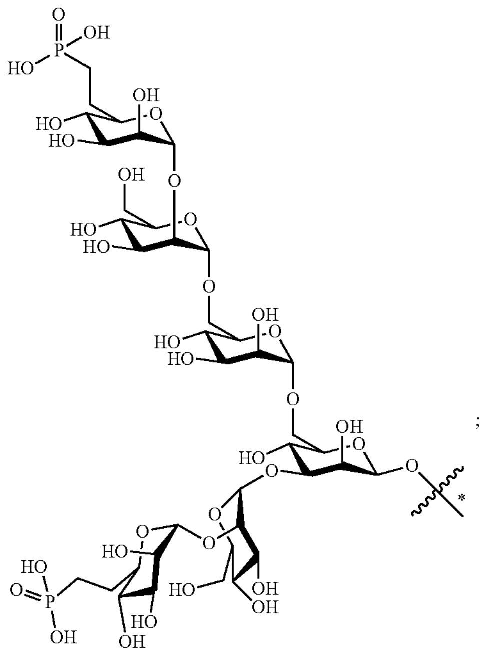

-continued
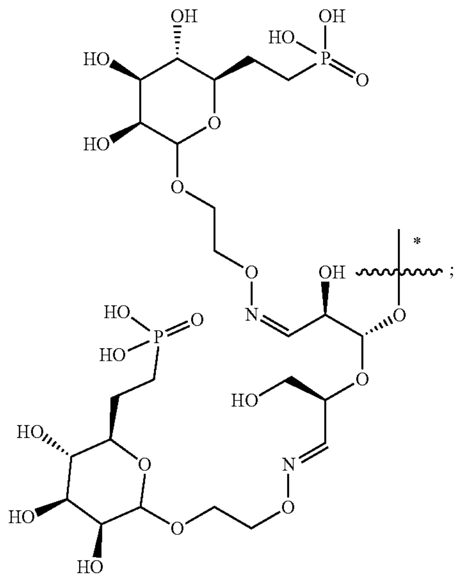
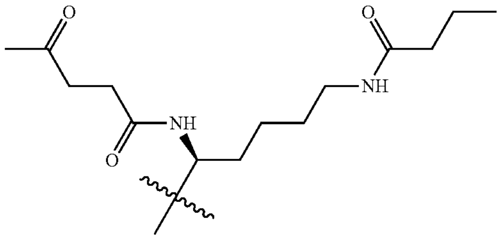
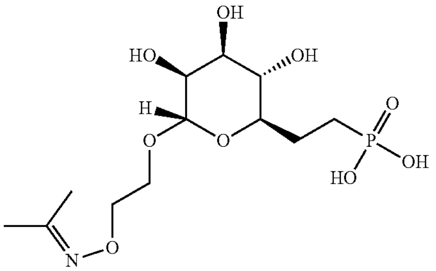
or
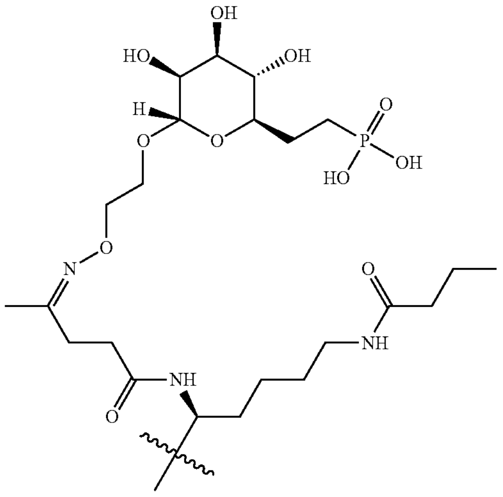
-continued
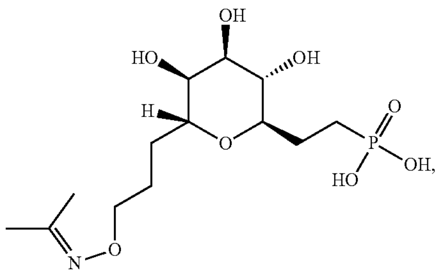
where the * of $R_L$ indicates the point of attachment to Linker ($L_A$),
$L_A$ is a linker,
and
$T_L$ is a cyclic peptide selected from:
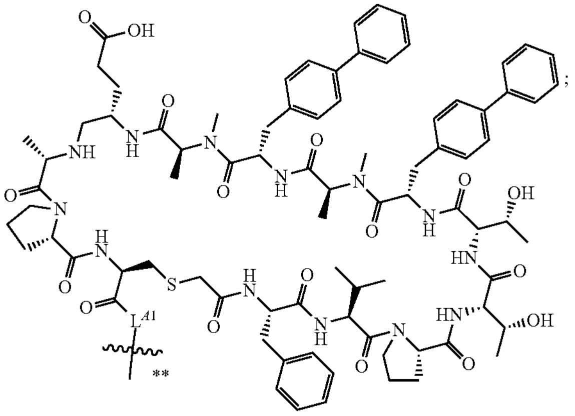
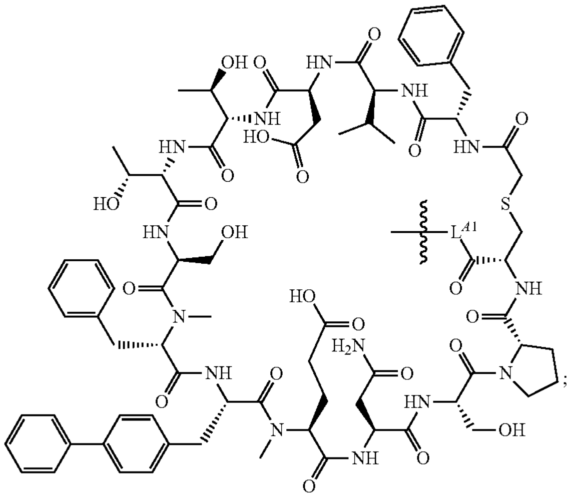

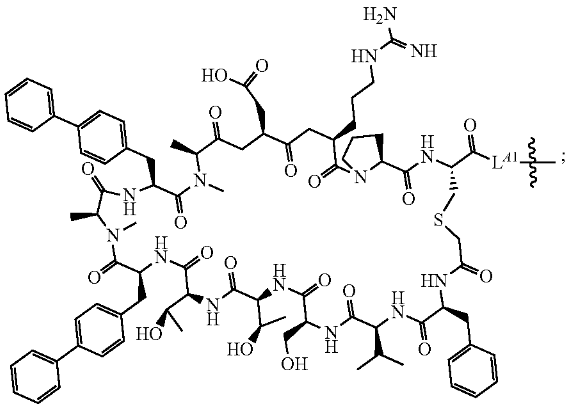
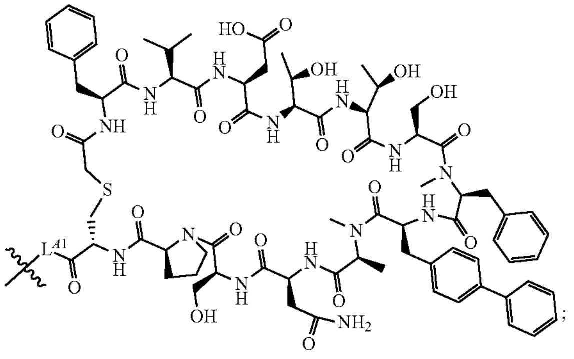
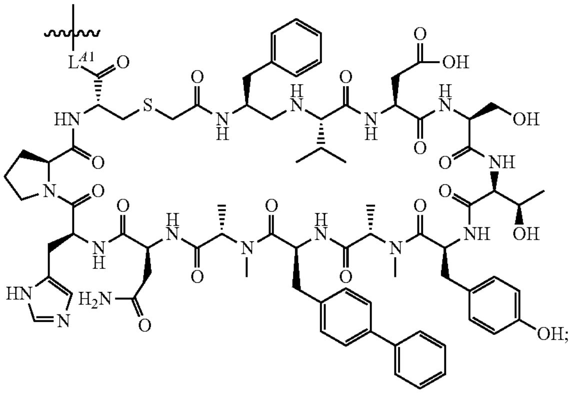
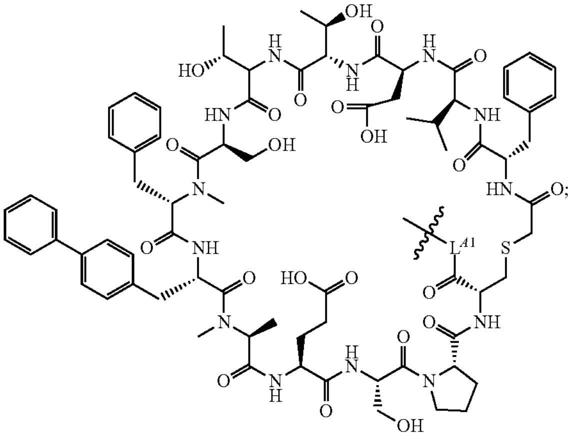
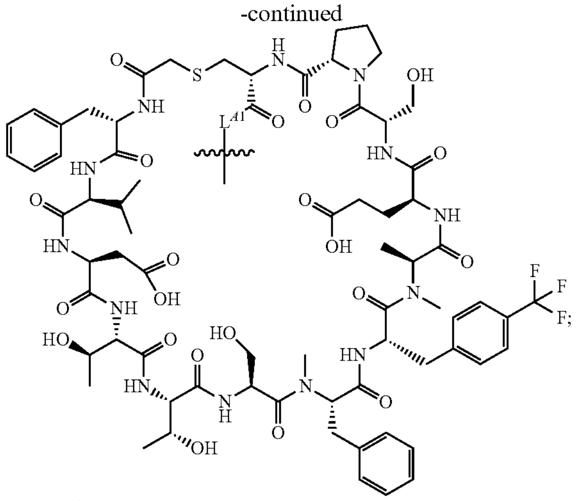
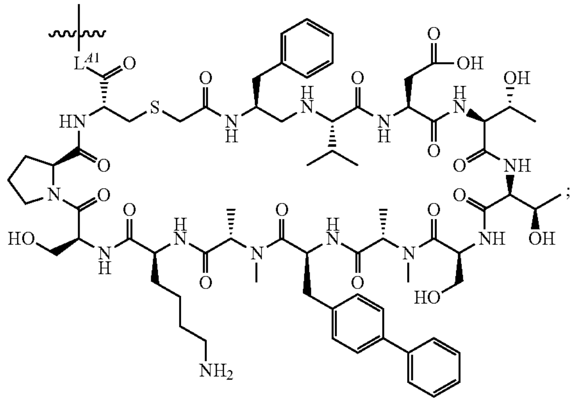
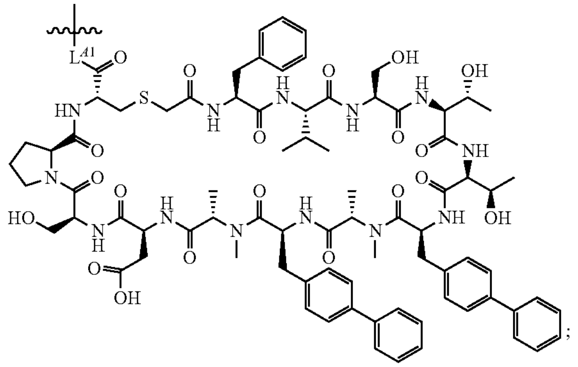
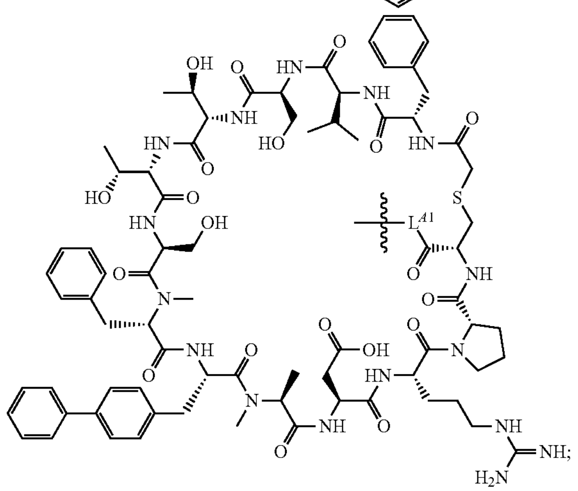

-continued
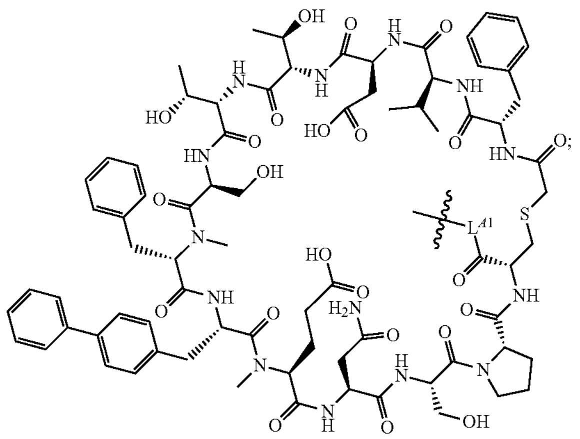
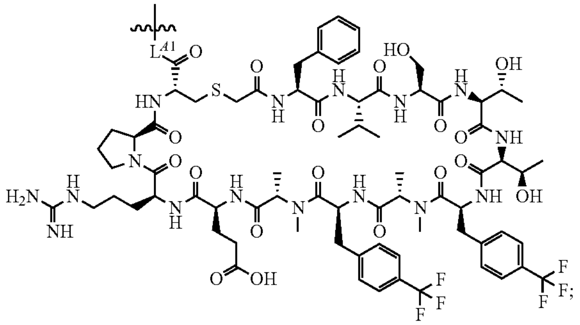
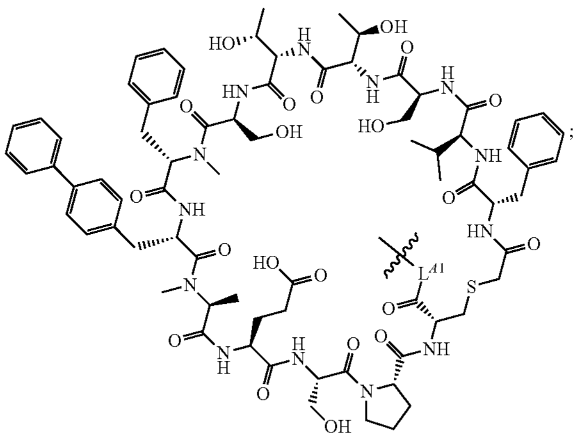
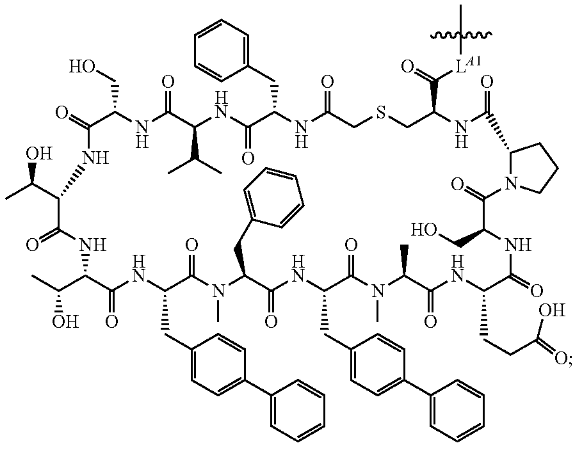
-continued
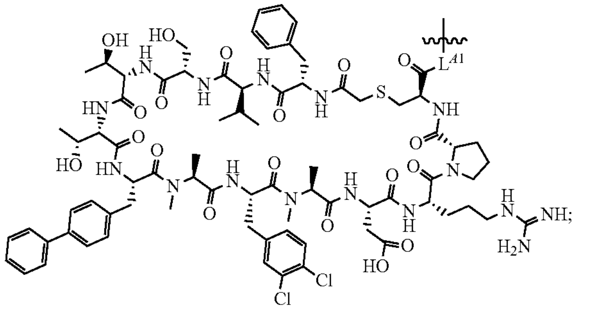
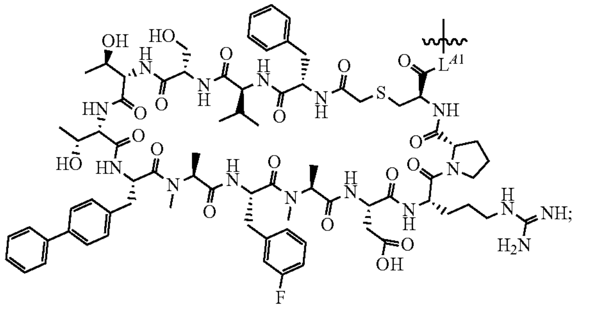
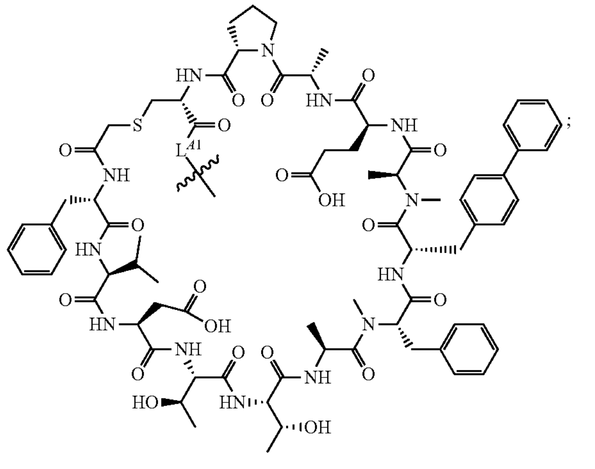
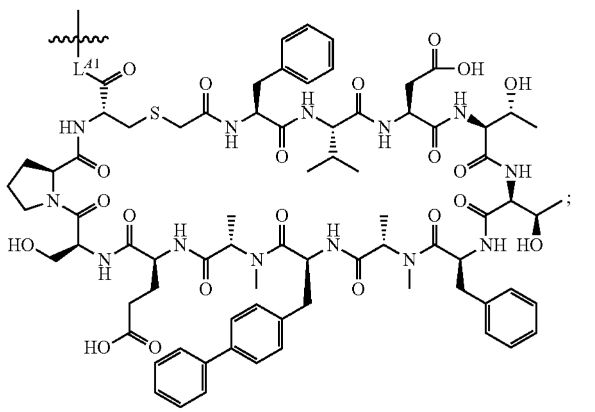

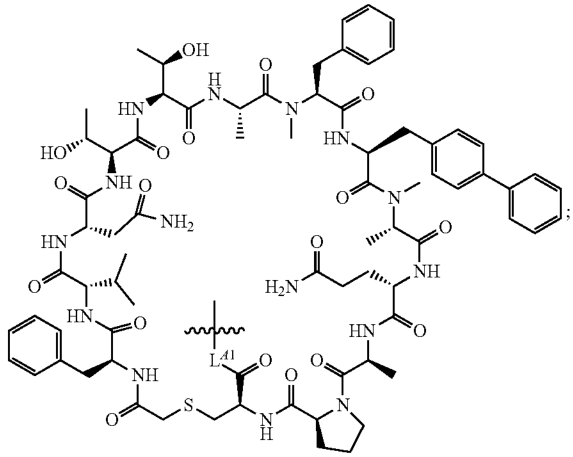
;
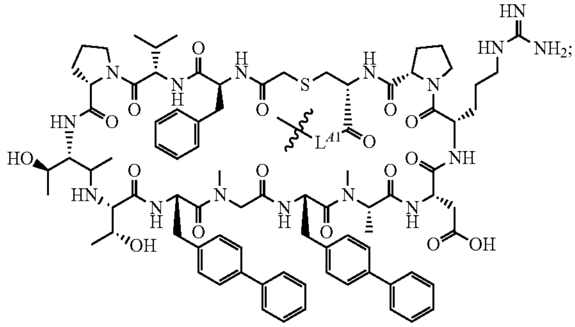
;
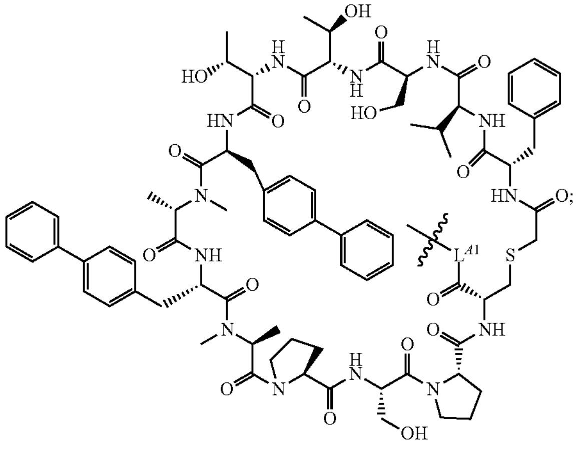
;
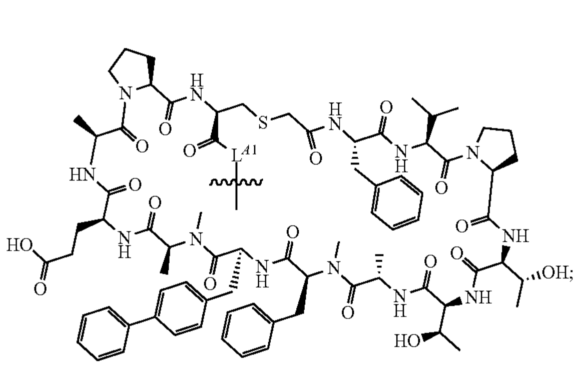
;
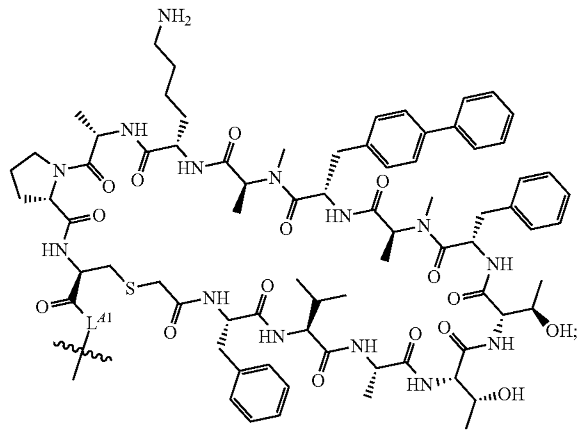
;
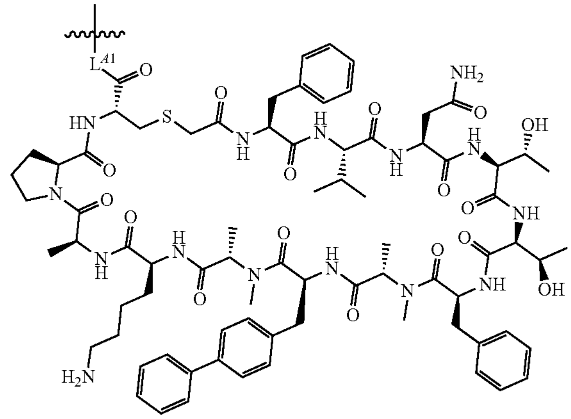
;
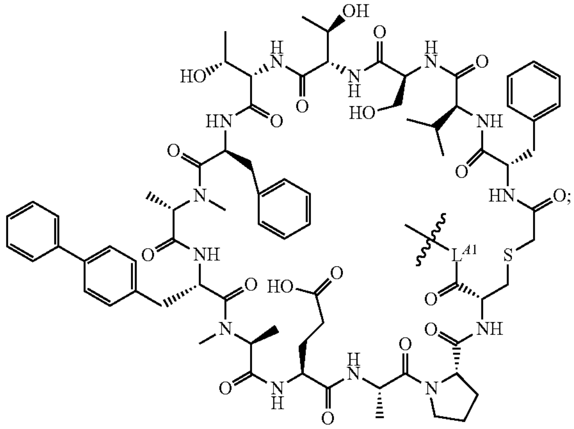
;
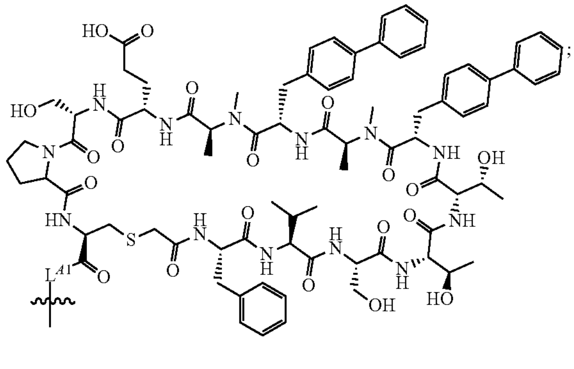
;

-continued
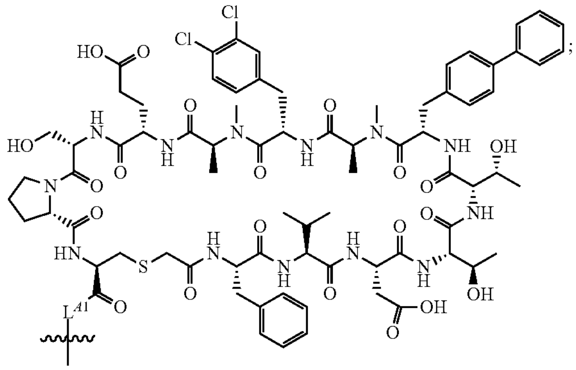
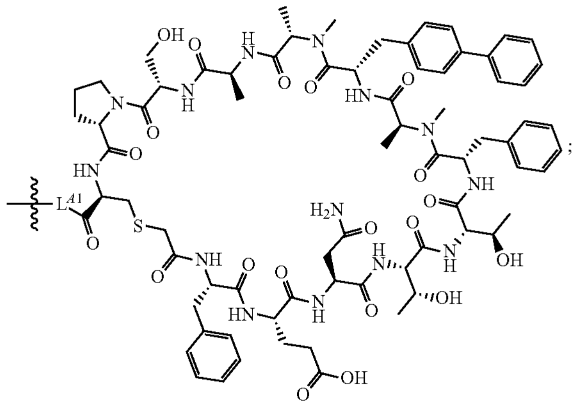
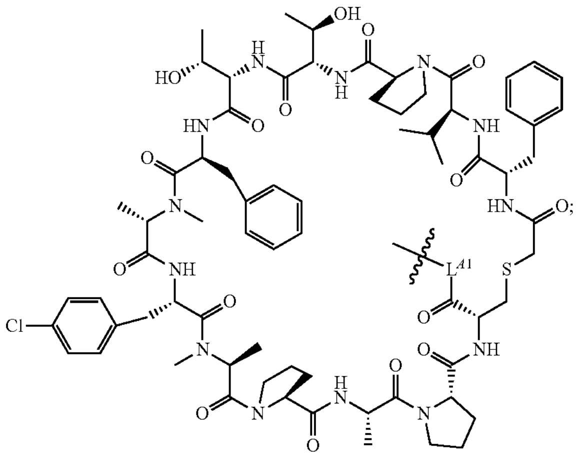
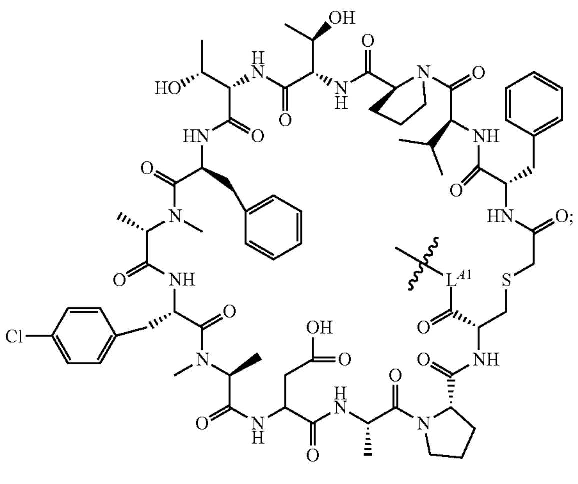
-continued
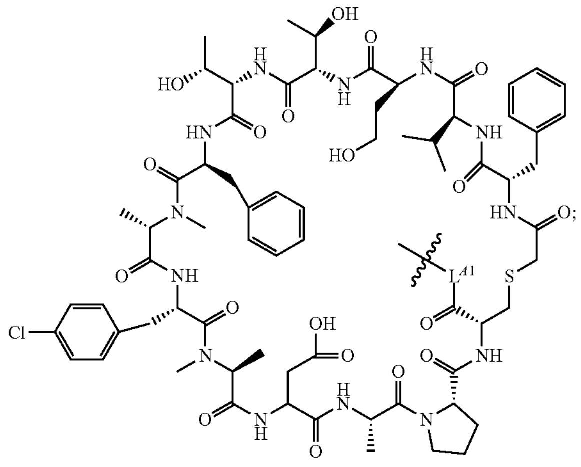
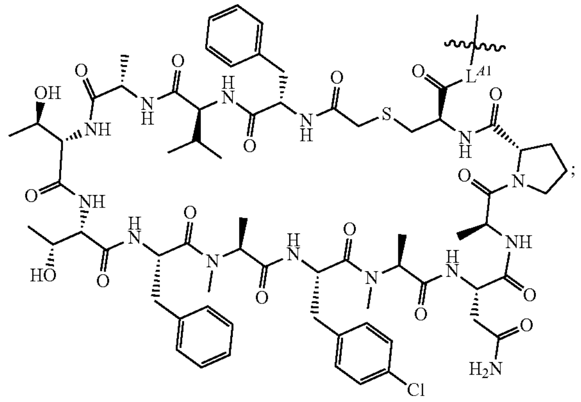
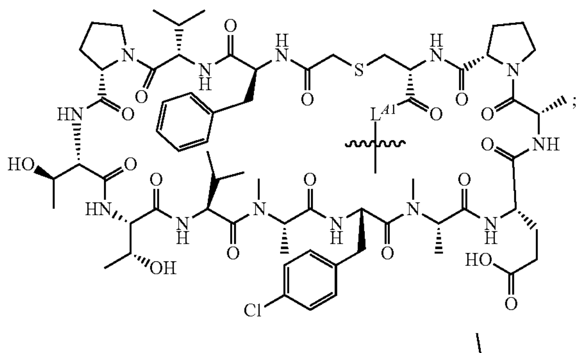
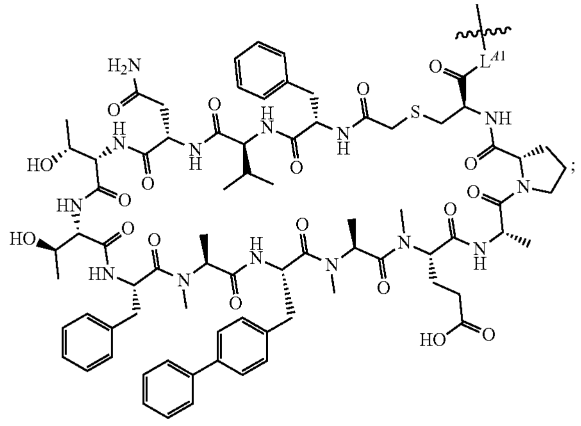

-continued
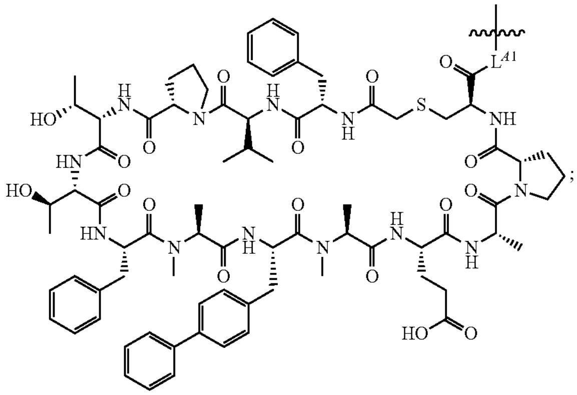
and
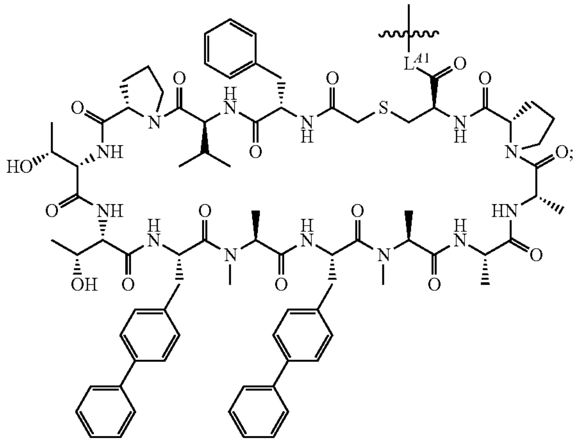
wherein:
$L^{A1}$ is selected from
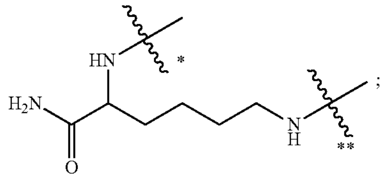
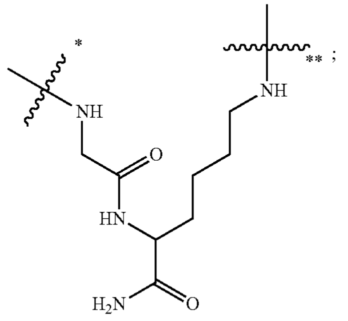
-continued
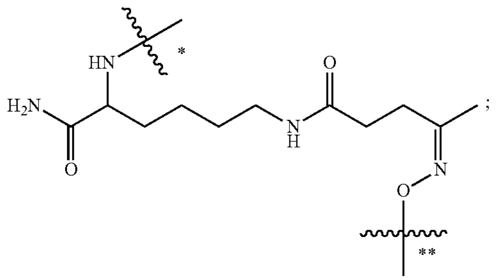
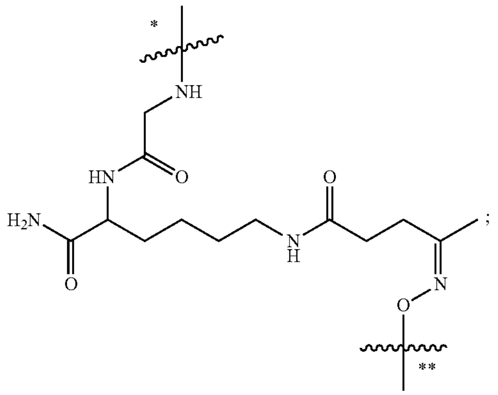
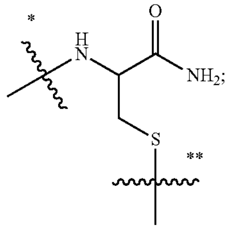
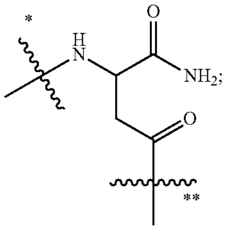
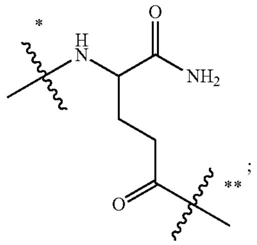
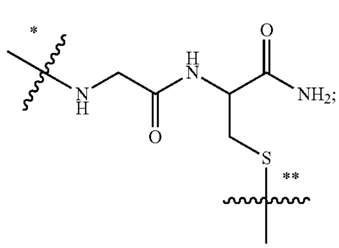

-continued
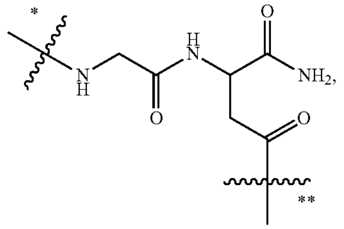
and
-continued
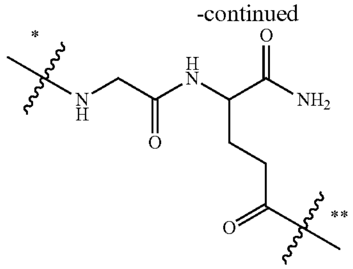
;
where the * of $L^{A1}$ indicates the point of attachment to Linker ($L_A$).
2. The bifunctional compound of claim 1, wherein $T_L$ is selected from:
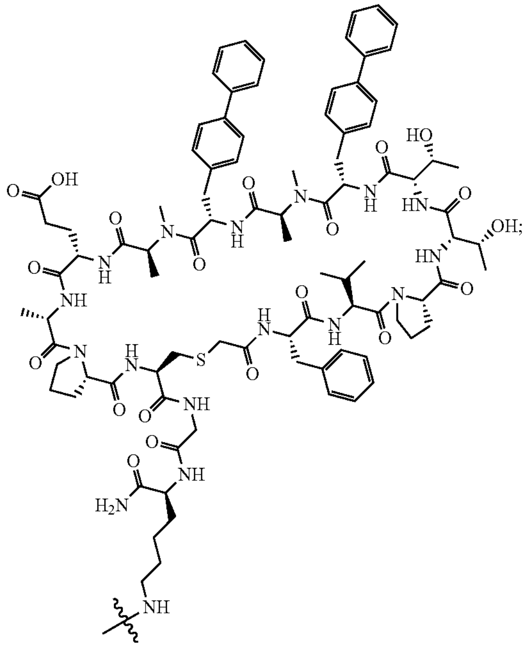
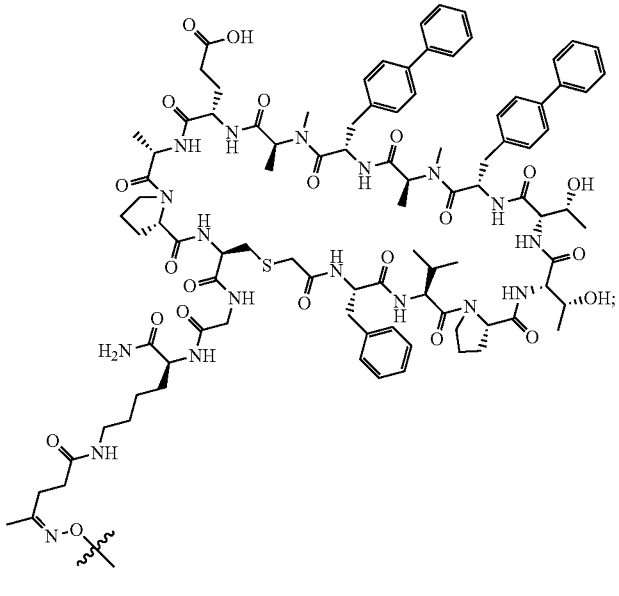

-continued
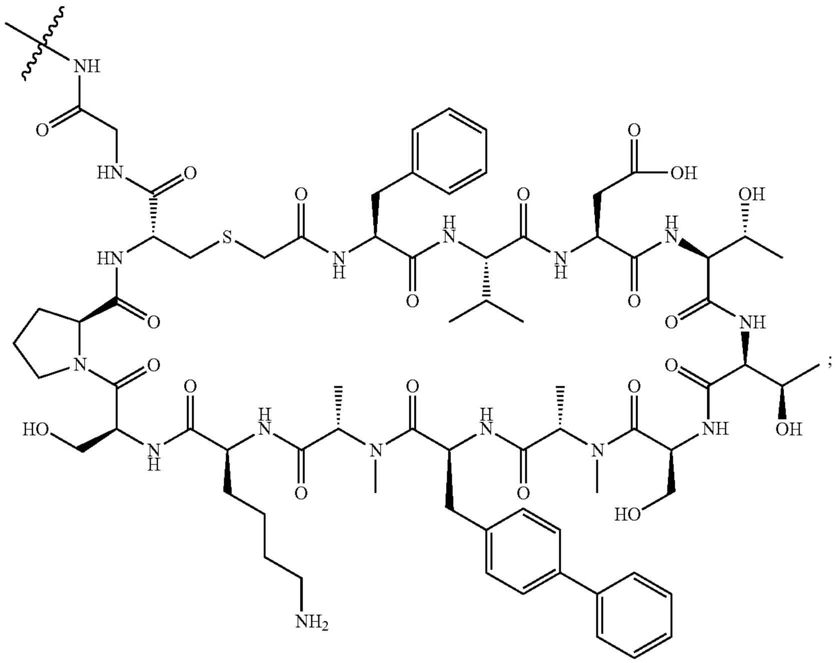
;
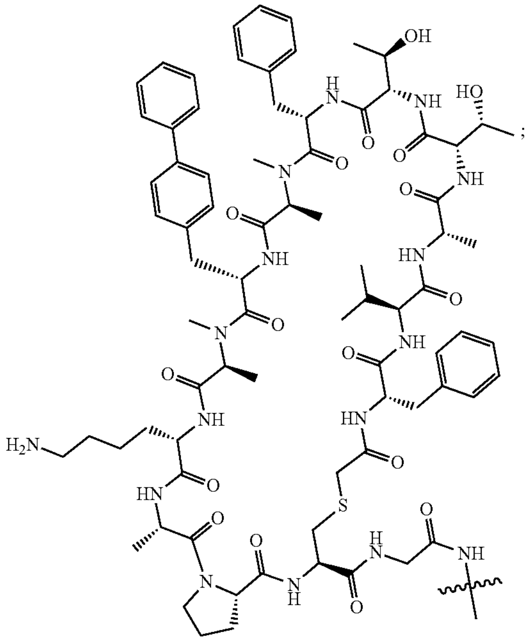
; and

-continued
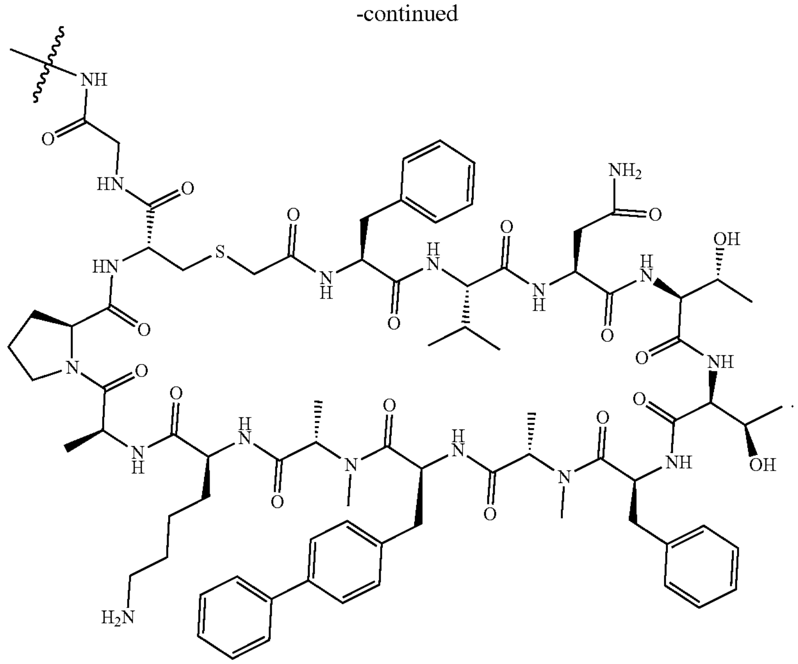
3. The bifunctional compound of claim 2, selected from:
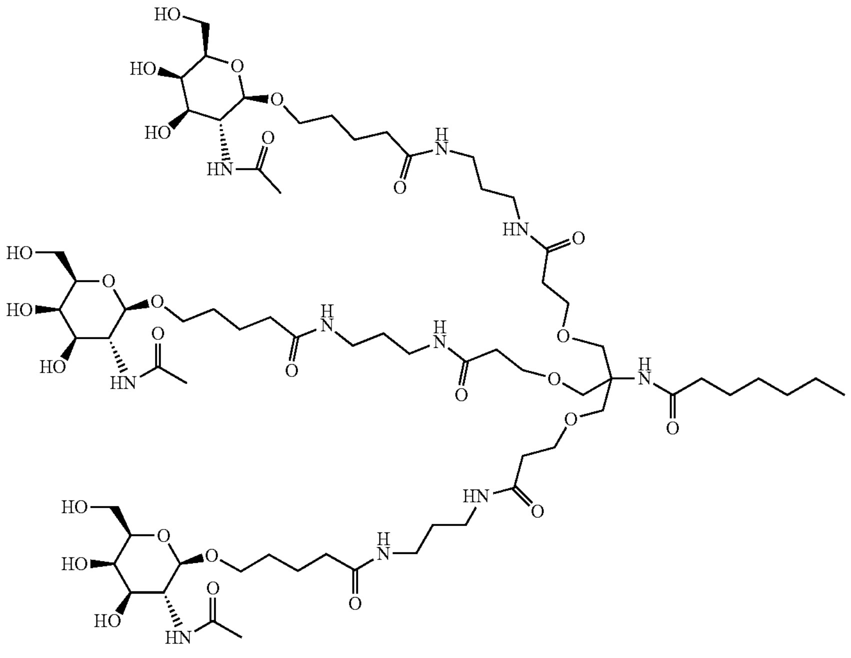

-continued
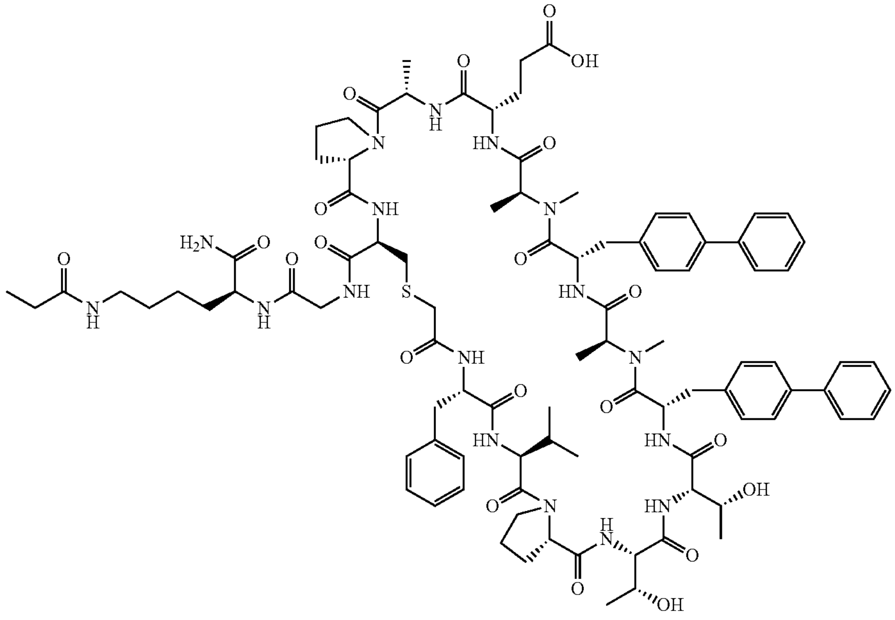
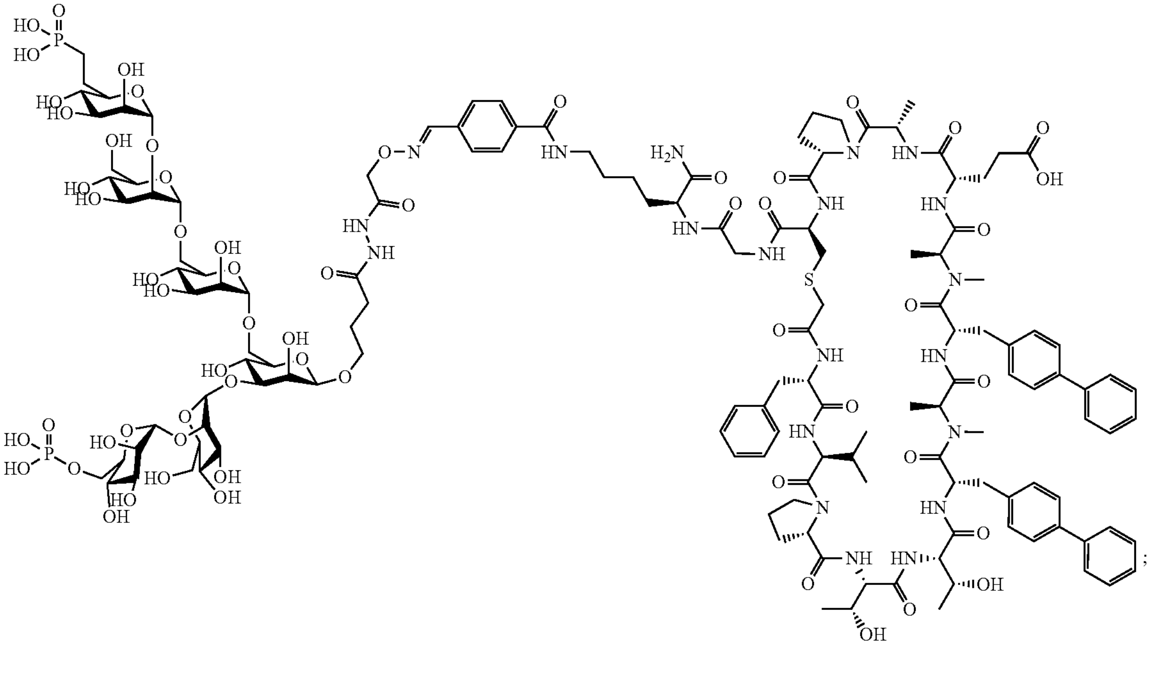
;

-continued
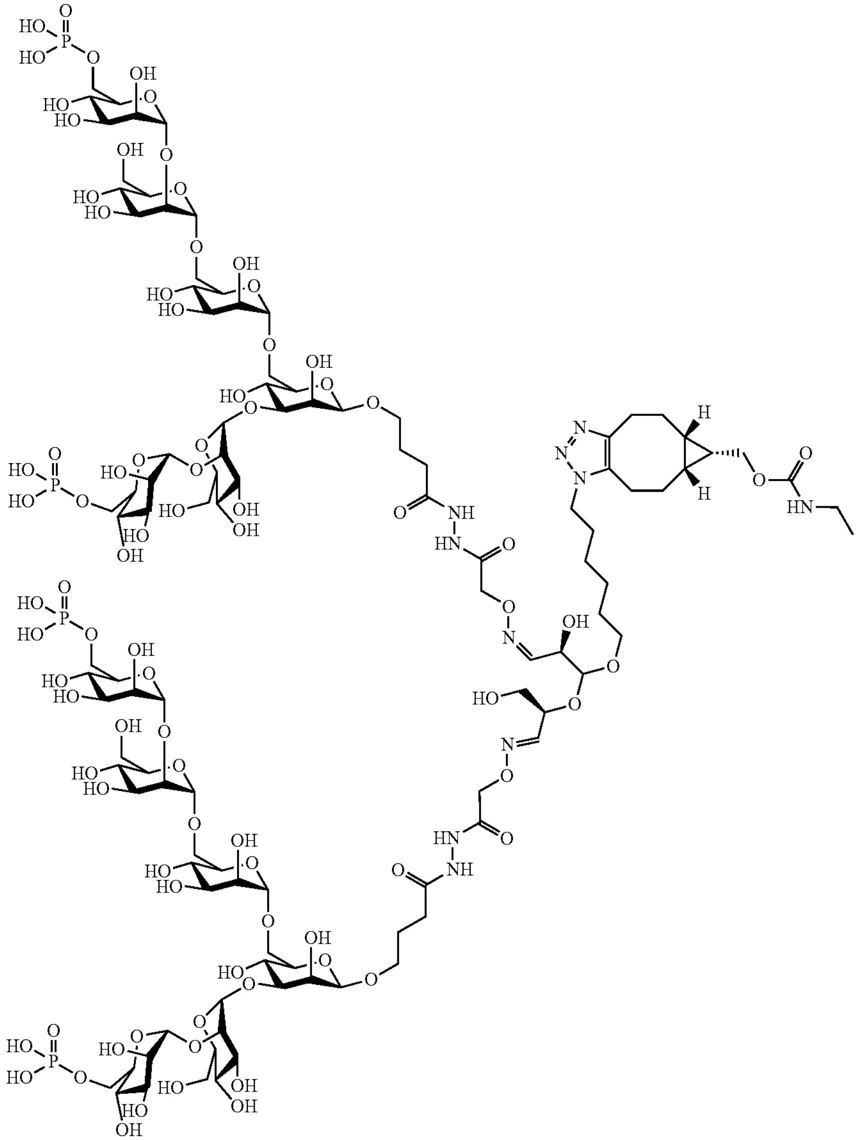

-continued
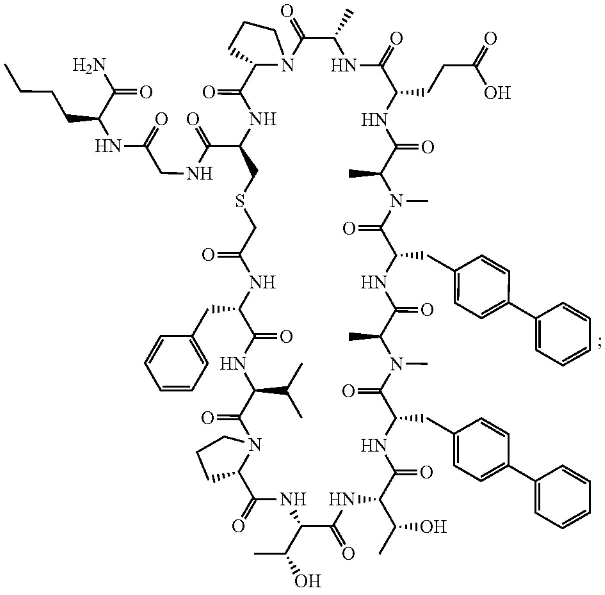
;
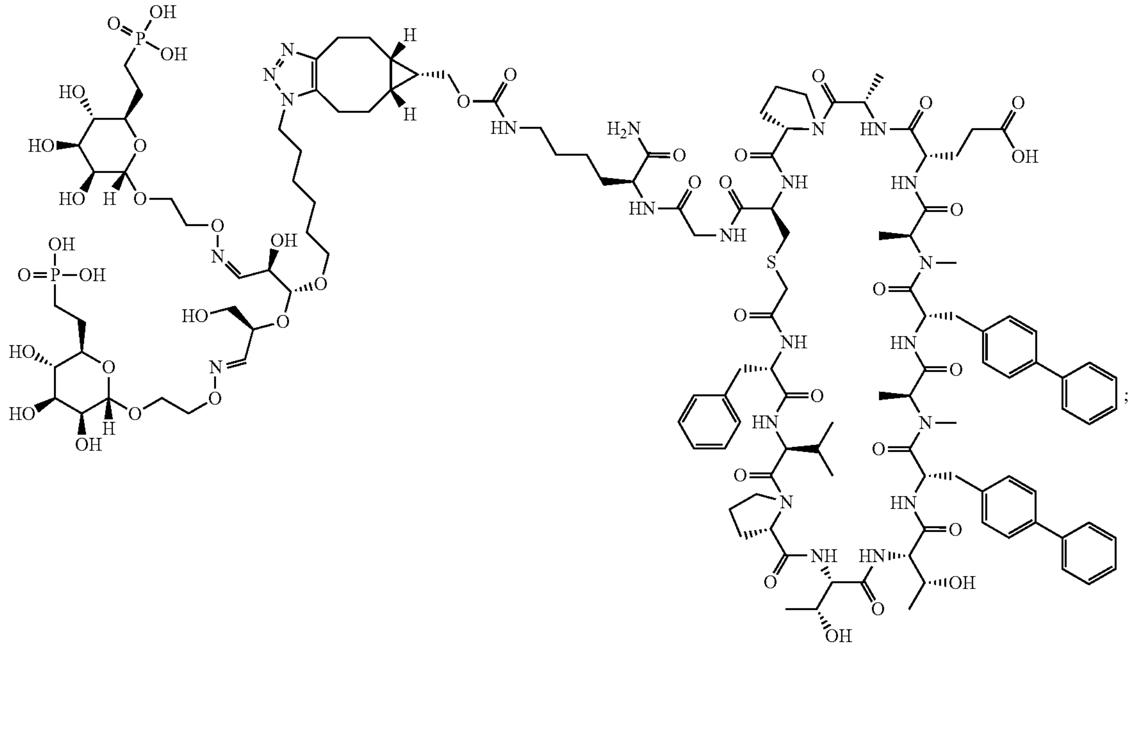 [SMILES: CC(C)[C@@H]1NC(=O)[C@H](Cc2ccccc2)NC(=O)CSC[C@@H](C(=O)NCC(=O)N[C@@H](CCCCNC(=O)OC[C@@H]2[C@@H]3CCc4c(nnn4CCCCCCO[C@H](O[C@@H](/C=N/OCCO[C@H]4O[C@H](CCP(=O)(O)O)[C@@H](O)[C@H](O)[C@@H]4O)CO)[C@H](O)/C=N\OCCO[C@H]4O[C@H](CCP(=O)(O)O)[C@@H](O)[C@H](O)[C@@H]4O)CC[C@@H]32)C(N)=O)NC(=O)[C@@H]2CCCN2C(=O)[C@H](C)NC(=O)[C@H](CCC(=O)O)NC(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@@H]2CCCN2C1=O]
;
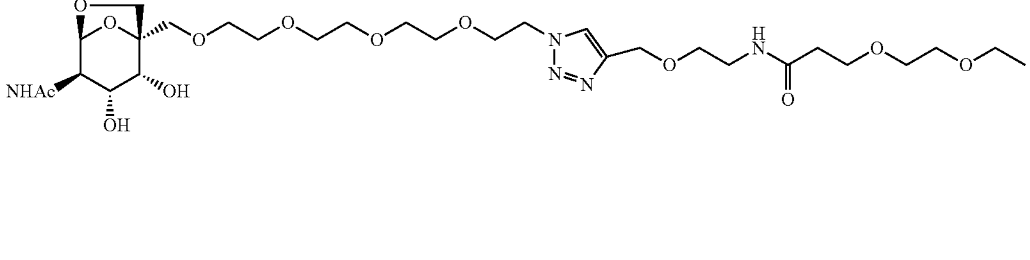

-continued
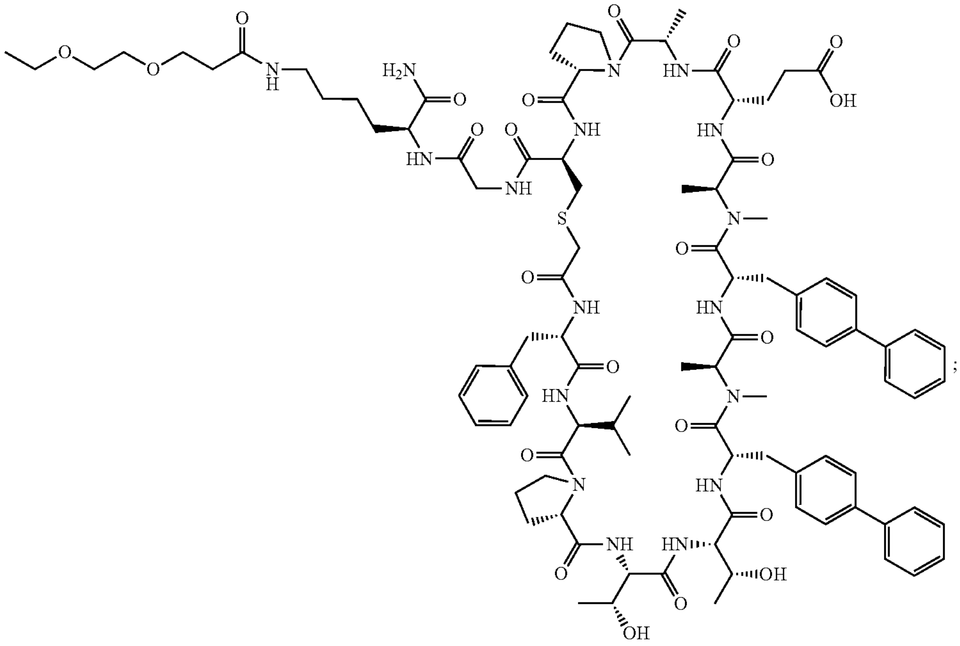
;
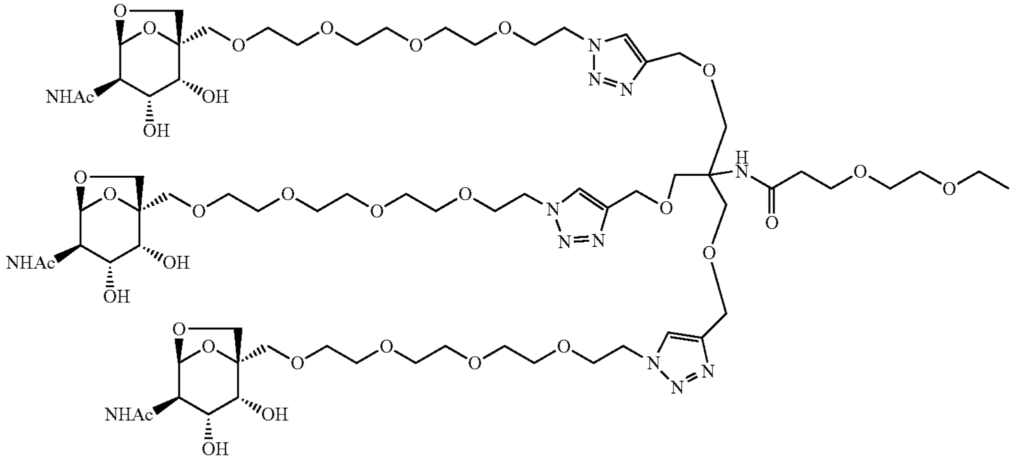

-continued
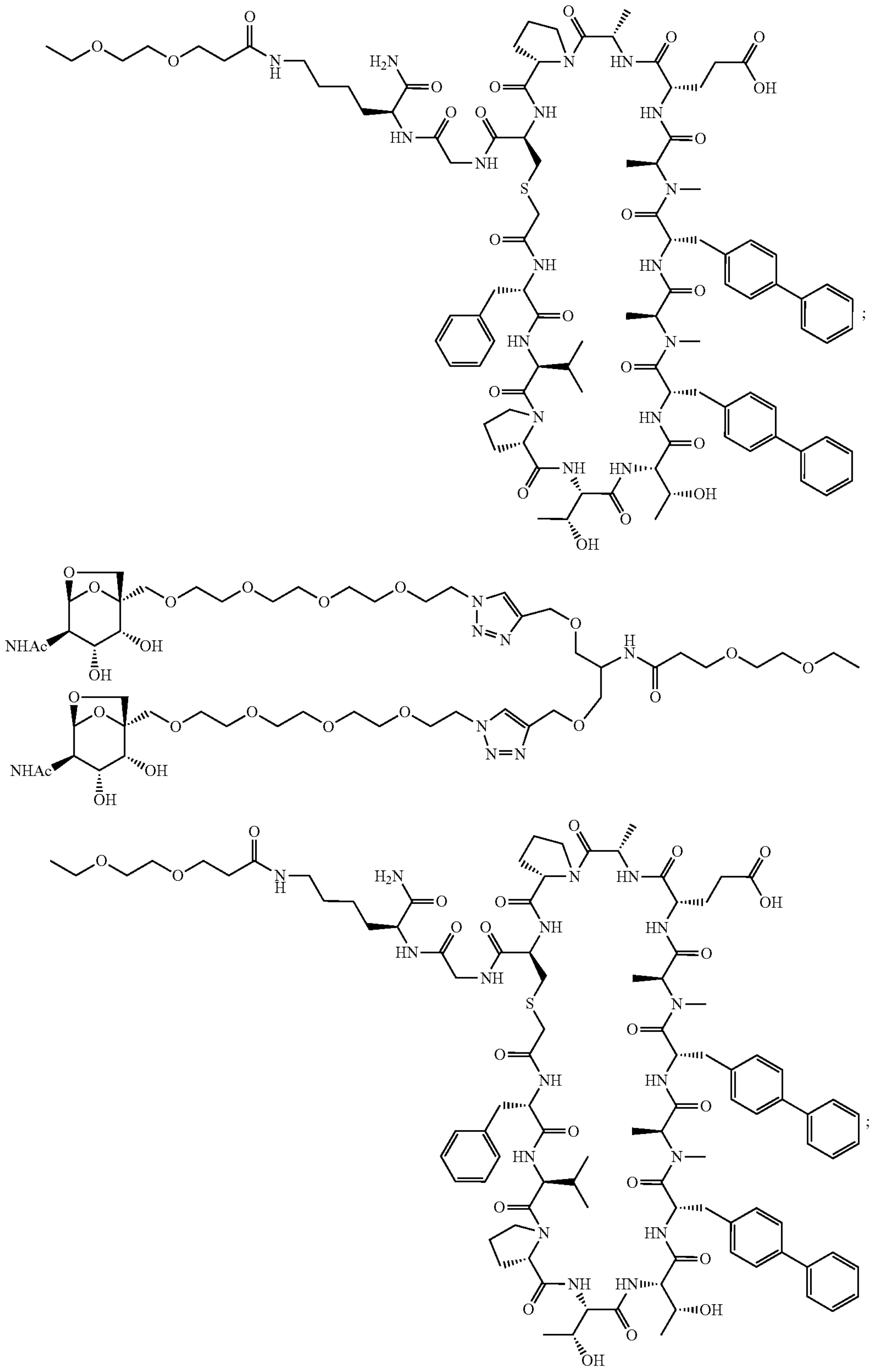
;
;

-continued
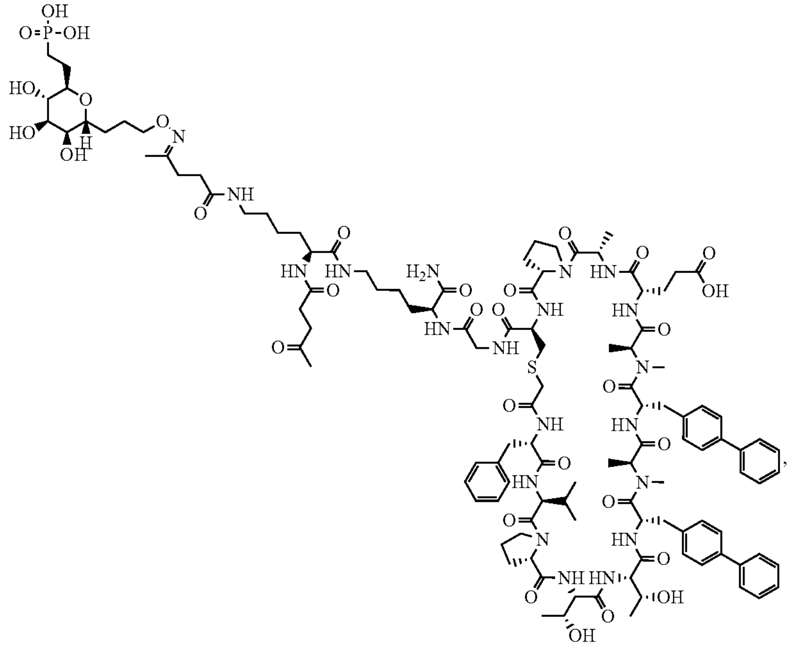
, and
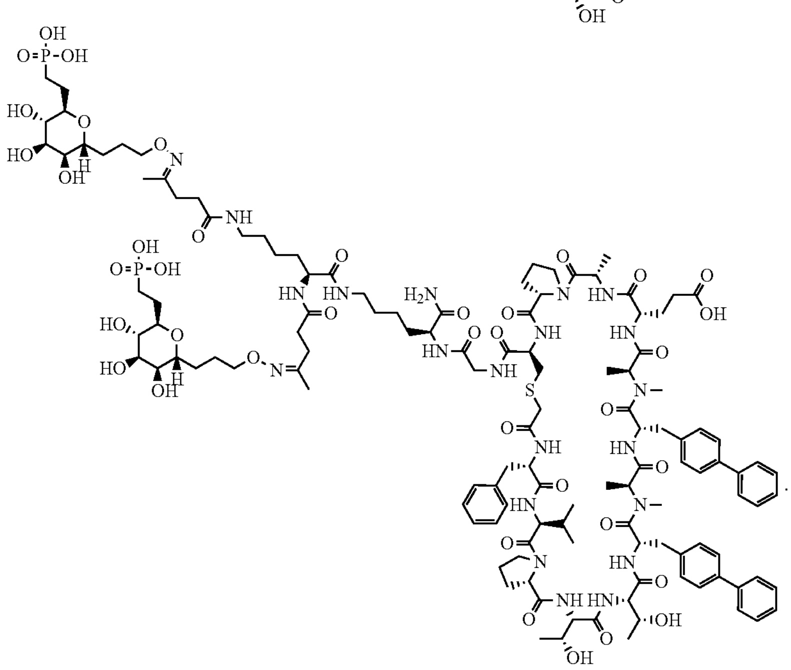
.
* * * * *

SEQUENCE LISTING

```
<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A

<400> SEQUENCE: 1

Phe Val Pro Thr Thr Xaa Xaa Xaa Xaa Glu Ala Pro Cys Gly Lys
1               5                   10                  15


<210> SEQ ID NO 2
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A

<400> SEQUENCE: 2

Phe Val Asp Thr Thr Ser Xaa Xaa Xaa Lys Ser Pro Cys Gly
1               5                   10


<210> SEQ ID NO 3
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
```

<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A

<400> SEQUENCE: 3

Phe Val Ala Thr Thr Phe Xaa Xaa Xaa Lys Ala Pro Cys Gly
1               5                   10

<210> SEQ ID NO 4
<211> LENGTH: 14
<212> TYPE: PRT
<213> ORGANISM: Artificial Sequence
<220> FEATURE:
<223> OTHER INFORMATION: /note="Description of Artificial Sequence: Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A

<400> SEQUENCE: 4

Phe Val Asn Thr Thr Phe Xaa Xaa Xaa Lys Ala Pro Cys Gly
1               5                   10

<210> SEQ ID NO 5
<211> LENGTH: 15
<212> TYPE: PRT
<213> ORGANISM: Artificial Sequence
<220> FEATURE:
<223> OTHER INFORMATION: /note="Description of Artificial Sequence: Synthetic peptide"
<220> FEATURE:
<221> NAME/KEY: MOD_RES
<222> LOCATION: (3)..(3)
<223> OTHER INFORMATION: (N-Me)F
<220> FEATURE:
<221> NAME/KEY: MOD_RES
<222> LOCATION: (8)..(8)
<223> OTHER INFORMATION: (N-Me)G
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (13)..(13)
<223> OTHER INFORMATION: (N-Me)F

<400> SEQUENCE: 5

Phe Arg Xaa Ser Lys Asn Tyr Xaa Arg Asp Xaa Asn Xaa Cys Gly
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: /note="Description of Artificial Sequence:

Synthetic peptide"
<220> FEATURE:
<221> NAME/KEY: MOD_RES
<222> LOCATION: (3)..(3)
<223> OTHER INFORMATION: (N-Me)A
<220> FEATURE:
<221> NAME/KEY: MOD_RES
<222> LOCATION: (8)..(8)
<223> OTHER INFORMATION: (N-Me)A

<400> SEQUENCE: 6

Phe Lys Xaa Ser Leu His Trp Xaa Arg Pro Asp Arg Cys Gly
1 5 10

<210> SEQ ID NO 7
<211> LENGTH: 15
<212> TYPE: PRT
<213> ORGANISM: Artificial Sequence
<220> FEATURE:
<223> OTHER INFORMATION: /note="Description of Artificial Sequence:
Synthetic peptide"
<220> FEATURE:
<221> NAME/KEY: MOD_RES
<222> LOCATION: (3)..(3)
<223> OTHER INFORMATION: (N-Me)F
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (13)..(13)
<223> OTHER INFORMATION: (N-Me)F

<400> SEQUENCE: 7

Phe Arg Xaa Ser Val Asn Tyr Lys Arg Ser Xaa Asn Xaa Cys Gly
1 5 10 15

<210> SEQ ID NO 8
<211> LENGTH: 14
<212> TYPE: PRT
<213> ORGANISM: Artificial Sequence
<220> FEATURE:
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: (N-Me)F
<220> FEATURE:
<221> NAME/KEY: MOD_RES
<222> LOCATION: (3)..(3)
<223> OTHER INFORMATION: (N-Me)A
<220> FEATURE:
<221> NAME/KEY: MOD_RES
<222> LOCATION: (8)..(8)
<223> OTHER INFORMATION: (N-Me)A

<400> SEQUENCE: 8

Phe Xaa Xaa Ser Leu His Trp Xaa Arg Lys Asp Arg Cys Gly
1 5 10

-continued

```
<210> SEQ ID NO 9
<211> LENGTH: 15
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: (N-Me)F
<220> FEATURE:
<221> NAME/KEY: MOD_RES
<222> LOCATION: (8)..(8)
<223> OTHER INFORMATION: (N-Me)G
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (13)..(13)
<223> OTHER INFORMATION: (N-Me)F

<400> SEQUENCE: 9

Phe Arg Xaa Ser Val Asn Tyr Xaa Arg Lys Xaa Asn Xaa Cys Gly
1               5                   10                  15
```